(12) United States Patent
Pavé et al.

(10) Patent No.: US 9,012,633 B2
(45) Date of Patent: *Apr. 21, 2015

(54) [1,2,4]TRIAZOLO[1,5-A]PYRIDINE AND [1,2,4]TRIAZOLO[1,5-C]PYRIMIDINE COMPOUNDS AND THEIR USE

(71) Applicant: Cancer Research Technology Limited, London (GB)

(72) Inventors: Grégoire Alexandre Pavé, London (GB); James Donald Firth, London (GB); Lorna Stewart, London (GB); Laurent Jean Martin Rigoreau, London (GB); Emma Louise Stanway, London (GB)

(73) Assignee: Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/869,374

(22) Filed: Apr. 24, 2013

(65) Prior Publication Data

US 2014/0155594 A1    Jun. 5, 2014

Related U.S. Application Data

(63) Continuation of application No. 12/679,871, filed as application No. PCT/GB2008/003428 on Oct. 10, 2008, now Pat. No. 8,431,596.

(60) Provisional application No. 60/978,792, filed on Oct. 10, 2007.

(30) Foreign Application Priority Data

Oct. 10, 2007 (GB) .................................... 0719803.9

(51) Int. Cl.
   *C07D 487/00* (2006.01)
   *C07D 487/04* (2006.01)
   *C07D 471/04* (2006.01)

(52) U.S. Cl.
   CPC ............ *C07D 487/04* (2013.01); *C07D 471/04* (2013.01)

(58) Field of Classification Search
   None
   See application file for complete search history.

(56) References Cited

U.S. PATENT DOCUMENTS

| | | | |
|---|---|---|---|
| 2,963,480 A | | 12/1960 | Taylor et al. |
| 3,046,276 A | * | 7/1962 | Rose et al. ............. 544/263 |
| 3,053,844 A | * | 9/1962 | Rose et al. ............. 544/263 |
| 4,579,848 A | * | 4/1986 | Paul et al. ........... 514/259.31 |
| 5,217,973 A | | 6/1993 | Bru-Magniez et al. |
| 5,358,950 A | | 10/1994 | Bru-Magniez et al. |
| 5,858,924 A | | 1/1999 | Johnson et al. |
| 6,514,989 B1 | | 2/2003 | Nettekoven et al. |
| 6,693,116 B2 | | 2/2004 | Nettekoven et al. |
| 8,263,595 B2 | * | 9/2012 | Swinnen et al. ......... 514/233.2 |
| 8,431,596 B2 | * | 4/2013 | Pave et al. ............. 514/303 |
| 2010/0227800 A1 | | 9/2010 | Wilson et al. |

FOREIGN PATENT DOCUMENTS

| | | |
|---|---|---|
| EP | 0132851 | 2/1985 |
| EP | 1894931 | 3/2008 |
| EP | 06119831.3 | 3/2008 |
| EP | 07108769.6 | 3/2008 |
| EP | 07115408.2 | 3/2009 |
| GB | 873223 | 7/1961 |
| GB | 874096 | 8/1961 |
| GB | 897870 | 5/1962 |
| JP | 4-204441 | 7/1992 |
| JP | 10-148903 | 6/1998 |
| JP | 2003-213152 | 7/2003 |
| WO | WO 01/17999 | 3/2001 |
| WO | WO 03/010167 | 2/2003 |
| WO | WO 03/031445 | 4/2003 |
| WO | WO 2004/072072 | 8/2004 |
| WO | WO 2004/081001 | 9/2004 |
| WO | WO 2005/012306 | 2/2005 |
| WO | WO 2005/018532 | 3/2005 |
| WO | WO 2005/019216 | 3/2005 |
| WO | WO 2005/021536 | 3/2005 |
| WO | WO 2006/038116 | 4/2006 |
| WO | WO 2006/052546 | 5/2006 |

(Continued)

OTHER PUBLICATIONS

Yamazaki, et. al., Journal of the Chemical Society, Perkin Transactions 1: Organic and Bio-Organic Chemistry (1972-1999) (1994), (7), 825-8.*

Abd Elmonem, M. E., et al., 1991, "Synthesis of 8,11-dihydro-10-methyl-8,11-diphenylpyrazolo[4',3':5,6]pyrano[3,2-e][1,2,4]triazolo[1,5-c]pyrimidine and some derivatives", Collection of Czechoslovak Chemical Communications, vol. 56, No. 9, pp. 1977-1982.

Abdel-Monem, W. R., 2004, "Synthesis and biological evaluation of some new fused heterobicyclic derivatives containing 1,2,4-triazolo/1,2,4-triazinopyridinone moieties", Egypt. Chemical Papers, vol. 58, No. 4, pp. 276-285.

Adenot, M., et al., 1997, "Interest of cluster significance analysis in structure-affinity relationships for non-xanthine heterocyclic antagonists of adenosine", Eur. J. Med. Chem., vol. 32, No. 6, pp. 493-504.

(Continued)

*Primary Examiner* — Jeffrey H Murray
(74) *Attorney, Agent, or Firm* — Swanson & Bratschun, L.L.C.

(57) ABSTRACT

The present invention pertains generally to the field of therapeutic compounds, and more specifically to certain triazolo compounds (referred to herein as TAZ compounds), and especially certain [1,2,4]triazolo[1,5-a]pyridine and [1,2,4]triazolo[1,5-c]pyrimidine compounds, which, inter alia, inhibit AXL receptor tyrosine kinase function. The present invention also pertains to pharmaceutical compositions comprising such compounds, and the use of such compounds and compositions, both in vitro and in vivo, to inhibit AXL receptor tyrosine kinase function, and in the treatment of diseases and conditions that are mediated by AXL receptor tyrosine kinase, that are ameliorated by the inhibition of AXL receptor tyrosine kinase function, etc., including proliferative conditions such as cancer, etc.

33 Claims, No Drawings

(56) References Cited

FOREIGN PATENT DOCUMENTS

| WO | WO 2006/084184 | 8/2006 |
|---|---|---|
| WO | WO 2008/025821 | 3/2008 |
| WO | WO 2008/025821 A1 | 3/2008 |
| WO | WO 2009/027283 | 3/2009 |
| WO | WO 2009/027283 A1 | 3/2009 |
| WO | WO 2009/155565 A1 | 12/2009 |

OTHER PUBLICATIONS

Ahmed, E., et al., 2006, "Heterocyclization of Orthoaminoester and Orthoamino-nitrile-thieno[2,3-c]pyridine: The FacileSynthesis of Fused Pyridothienopyrimidines", Phosphorus, Sulfur and Silicon and the Related Elements, 2006, vol. 181, No. 3, pp. 497-510.

Alessi, D.R., et al., 1996, "Mechanism of activation of protein kinase B by insulin and IGF-1", EMBO J., vol. 15, pp. 6541-6551.

Bakhite, E. A.-G., 2000, "Benzoquinolines II. Synthesis of some new benzo[h]pyrimido[4',5':4,5]thieno[2,3-b]quinoline derivatives and related fused hexacyclic systems", Phosphorus, Sulfur and Silicon and the Related Elements, vol. 159, pp. 171-194.

Baraldi, P. G., et al., 2004, "Synthesis of new pyrazolo[4,3-e]- 1,2,4-triazolo[1,5-c]pyrimidines and related heterocycles", Tetrahedron, vol. 60, No. 23, pp. 5093-5104.

Basyouni, W. M., et al., 1997, "Pyrrolo[2,3-d]pyrimidines. Part 3. Synthesis of some novel 4-substituted pyrrolo[2,3-d]pyrimidines and their related triazolo derivatives", J. Chem. Research, Synopses, No. 12, pp. 452-453.

Bellosta, P., et al., 1995, "The receptor tyrosine kinase ARK mediates cell aggregation by homophilic binding", Mol. Cell Biol., vol. 15, No. 2, pp. 614-625.

Bellosta, P., et al., 1997, "Signaling through the ARK tyrosine kinase receptor protects from apoptosis in the absence of growth stimulation", Oncogene, vol. 15, No. 20, pp. 2387-2397.

Braunger, J., et al., 1997, "Intracellular signaling of the Ufo/Axl receptor tyrosine kinase is mediated mainly by a multi-substrate docking-site", Oncogene, vol. 14, No. 22, pp. 2619-2631.

Chuiguk, V.A., et al., 1982, "Mesoionic heterocycles based on 2-amino-1,2,4-triazolo[1.5-a]pyridine", Ukrainskii Khimicheskii Zhurnal (Russian Edition), vol. 48, No. 6, pp. 647-649.

Ei-Sayed, A. M., et al., 1998, "Synthesis of some new heterocycles derived from (arylmethylene)malononitriles", Synthetic Communications, vol. 28, No. 18, pp. 3331-3343.

Fratev, F., et al., 2005, "CoMFA study of non-peptide angiotensin II receptor (AT1) antagonist", Oxidation Communications, vol. 28, No. 1, pp. 230-236.

Fridell, Y.W., et al., 1998, "GAS6 induces Axl-mediated chemotaxis of vascular smooth muscle cells", J. Biol. Chem., vol. 273, No. 12, pp. 7123-7126.

Fujimoto, Y., et al., 1965, "Pyrimidine and purine bases. II. Synthesis of adenine from malonic ester. 2", Yakugaku Zasshi, vol. 85, No. 4, pp. 367-370.

Graham, D.K., et al., 1994, "Cloning and mRNA expression analysis of a novel human protooncogene, c-mer", Cell Growth Differ., vol. 5, No. 6, pp. 647-657.

Green, J., et al., 2006, "Overexpression of the Axl tyrosine kinase receptor in cutaneous SCC-derived cell lines and tumours", Br. J. Cancer, vol. 94, No. 10, pp. 1446-1451.

Hafidh, A., et al., 1996, "Reaction of hydrazine and its derivatives on y-ketonitriles. Synthesis of diamino and triazolodihydropyridines", Journal de la Societe Chimique de Tunisie, vol. 3, No. 11, pp. 771-780.

Hafidh, A., et al., 2002, "Synthesis of novel heterocyclic polynuclear compounds: pyranopyrimidines and pyranopyrimidotriazoles", Journal de la Societe Algerienne de Chimie, vol. 12, No. 1, pp. 89-97.

Hafizi, S., et al., 2002, "Interaction of Axl receptor tyrosine kinase with C1-TEN, a novel C1 domain-containing protein with homology to tensin", Biochem. Biophys. Res. Commun., vol. 299, No. 5, pp. 793-800.

Hafizi, S., et al., 2006a, "Signalling and functional diversity within the Axl subfamily of receptor tyrosine kinases", Cytokine Growth Factor Rev., vol. 17, No. 4, pp. 295-304.

Hafizi, S., et al., 2006b, "Gas6 and protein S. Vitamin Kdependent ligands for the Axl receptor tyrosine kinase subfamily", FEBS J., vol. 273, No. 23, pp. 5231-5244.

Hanada, M., et al., 2004, "Structure, regulation and function of PKB/AKT—a major therapeutic target", Biochim. Biophys. Acta, vol. 1697, pp. 3-16.

Hassan, K. M., et al., 1989, "Synthesis of tricyclic compounds with pyridinethione rings", Assiut, Egypt. Phosphorus, Sulfur and Silicon and the Related Elements, vol. 45, No. 3-4, pp. 261-267.

Holland, S.J., et al., 2005, "Multiple roles for the receptor tyrosine kinase axl in tumor formation", Cancer Res., vol. 65, No. 20, pp. 9294-9303.

Hozien, Z. A., et al., 1997, "Synthesis of some biologically active agents derived from thieno[2,3-d]pyrimidine derivatives", Pharmazie, vol. 52, No. 10, pp. 753-758.

Hussein, A. H. M., 1999, "Pyridines as building blocks in heterocyclic synthesis. An expeditious synthesis of triazolopyridines, tetrazolopyridines, pyridotriazines, thienopyridines and isoquinolines", Assiut, Egypt. Afinidad, vol. 56, No. 484, pp. 377-382.

Isaac, Y. A., 2003, "Synthesis of annulated and substituted pyrido[2,3-d]pyrimidines as antimicrobial agents", Pigment &Resin Technology, vol. 32, No. 6, pp. 371-381.

Isaac, Y. A., et al., 2003, "A convenient synthesis of new pentaazacyclo-pentanaphthalene and penta-aza-phenanthrene derivatives", Zeitschrift fuer Naturforschung, B: Chemical Sciences, vol. 58, No. 12, pp. 1227-1233.

Isaac, Y. A., et al., 2003, "Some reactions with 2-(2-carboxyethenyl)-4-hydrazinoquinazoline: synthesis of annelated and substituted quinazolines", Egyptian Journal of Chemistry, vol. 45, No. 5, pp. 947-961.

Kurup, A., et al., 2001, "Comparative QSAR: Angiotensin II Antagonists", Chemical Reviews, vol. 101, No. 9, pp. 2727-2750.

Manfioletti, G., et al., 1993, "The protein encoded by a growth arrest-specific gene (gas6) is a new member of the vitamin Kdependent proteins related to protein S, a negative coregulator in the blood coagulation cascade", Mol. Cell Biol., vol. 13, pp. 4976-4985.

Mark, M.R., et al., 1994, "rse, a novel receptor-type tyrosine kinase with homology to Axl/Ufo, is expressed at high levels in the brain", J. Biol. Chem., vol. 269, No. 14, pp. 10720-10728.

Medwid, J.B., et al., 1990, "Preparation of triazolo[1,5-c]pyrimidines as potential antiasthma agents", J. Med. Chem., vol. 33, No. 4, pp. 1230-1241.

Meric, F., et al., 2002, "Expression profile of tyrosine kinases in breast cancer", Clin. Cancer Res., vol. 8, No. 2, pp. 361-367.

Miller, G. W., et al., 1963, "s-Triazolopyrimidines. I. Synthesis as potential therapeutic agents", J. Chem. Soc., pp. 5642-5659.

Miller, G. W., et al., 1965, "s-Triazolopyrimidines. II. Synthesis as potential therapeutic agents", J. Chem. Soc., pp. 3357-3368.

Molina, P., et al., 1983, "Fused mesoionic heterocycles: synthesis of 1,3,4-triazolo(3,2-a)pyridine derivatives", Tetrahedron Lett., vol. 24, No. 33, pp. 3523-3526.

Molina, P., et al., 1984, "Fused mesoionic heterocycles: synthesis of 1,3,4-triazolo[3,2-a]pyridine derivatives", J. Chem. Soc., Perkin Trans. 1: Organic and Bio-Organic Chemistry, vol. 8, pp. 1891-1897.

Molina, P., et al., 1986, "Heterocyclization reactions with carbodiimides: synthesis of fused 1,2,4-triazoles", Heterocycles, vol. 24, No. 12, pp. 3363-3368.

Nettekoven, M., et al., 2003, "Synthetic access to 2-amido-5-aryl-8-methoxy-triazolopyridine and 2-amido-5-morpholino-8-methoxy-triazolopyridine derivatives as potential inhibitors of the adenosine receptor subtypes", Synthesis, No. 11, pp. 1649-1652.

Nicolai, E., et al., 1994, "Synthesis and SAR Studies of Novel Triazolopyrimidine Derivatives as Potent, Orally Active Angiotensin II Receptor Antagonists", J. Med. Chem., vol. 37, No. 15, pp. 2371-2386.

O'Bryan, J.P. et al., 1991, "axl, a transforming gene isolated from primary human myeloid leukemia cells, encodes a novel receptor tyrosine kinase", Mol. Cell Biol., vol. 11, No. 10, pp. 5016-5031.

Rangnekar, D. W., et al., 1987, "Synthesis of 7H-benzo[de]-striazolo[5,1-a]isoquinolin-7-one derivatives and study of their fluorescent properties", Dyes and Pigments, vol. 8, No. 4, pp. 291-299.

(56) References Cited

OTHER PUBLICATIONS

Reid, W., et al., 1968, "Reactions with aminoguanidine. I. s-Triazolo[1,5-c]quinazoline derivatives", Chem. Ber., vol. 101, No. 6, pp. 2106-2116 (in German; with partial English language translation).
Rescigno, J., et al., 1991, "A putative receptor tyrosine kinase with unique structural topology", Oncogene, vol. 6, No. 10, pp. 1909-1913.
Said, M., et al., 2004, "Synthesis and biological evaluation of new thiazolopyrimidines", Egypt. Archives of Pharmacal Research, vol. 27, No. 5, pp. 471-477.
Sainaghi, P.P., et al., 2005, "Gas6 induces proliferation in prostate carcinoma cell lines expressing the Axl receptor", J. Cell Physiol., vol. 204, No. 1, pp. 36-44.
Sawabu, T., et al., 2007, "Growth arrest-specific gene 6 and Axl signaling enhances gastric cancer cell survival via Akt pathway", Mol. Carcinog., vol. 46, No. 2. pp. 155-164.
Shankar, S.L., et al., 2006, "Gas6/Axl signaling activates the phosphatidylinositol 3-kinase/Akt1 survival pathway to protect oligodendrocytes from tumor necrosis factor alpha-induced apoptosis", J. Neurosci., vol. 26, No. 21, pp. 5638-5648.
Shieh, Y.S., et al., 2005, "Expression of axl in lung adenocarcinoma and correlation with tumor progression", Neoplasia, vol. 7, No. 12, p. 1058-1064.
Sun, W.S., et al., 2003, "Clinical implications of coexpression of growth arrest-specific gene 6 and receptor tyrosine kinases Axl and Sky in human uterine leiomyoma", Mol. Hum. Reprod., vol. 9, No. 11, pp. 701-707.
Vajkoczy, P., et al., 2006, "Dominant-negative inhibition of the Axl receptor tyrosine kinase suppresses brain tumor cell growth and invasion and prolongs survival", Proc. Nat. Acad. Sci. USA, vol. 103, No. 15, pp. 5799-5804.
Yamazaki, C., et al., 1994, "Cyclization of isothiosemicarbazones. Part 10. A novel route to 2-amino[1,2,4]triazolo[1,5-a]pyridine derivatives", J. Chem. Soc., Perkin Trans. 1: Organic and Bio-Organic Chemistry, vol. 7, pp. 825-828.
UK Search Report for GB 0719803.9 dated Apr. 15, 2008.
International Search Report (ISR) and Written Opinion of International Searching Authority (WOISA) for PCT/GB2008/003428 mailed Jan. 29, 2009.
International Preliminary Report on Patentability (IPRP) for PCT/GB2008/003428 issued Apr. 13, 2010.
Buchler et al., Feb. 2007, "Target Therapy Using a Small Molecule Inhibitor against Angiogenic Receptors in Pancreatic Cancer", *Neoplasia*, vol. 9, No. 2, pp. 119-127.
Carlson et al., 1996, "Flavopiridol Induces G1 Arrest with Inhibition of Cyclic-dependent Kinase (CKD) 2 and CKD4 in Human Breast Carcinoma Cells", *Cancer Research*, vol. 56, pp. 2973-2978.
Declaration by Frederik Deroose dated Aug. 5, 2014, laid open to public inspection on Sep. 3, 2014 via the opposition filed in connection with European patent No. EP 2217578.
Declaration by Nathalie Joly dated Aug. 9, 2014, laid open to public inspection on Sep. 3, 2014 via the opposition filed in connection with European patent No. EP 2217578.
U.S. Appl. No. 60/966,989, filed Aug. 31, 2007.
Declaration by Philip John Dudfield dated Aug. 21, 2014, laid open to public inspection on Sep. 3, 2014 via the opposition filed in connection with European patent No. EP 2217578.
Flyer entitled "SoftFocus® SFK Directed Libraries, Library SFK®39", from BioFocus DPI, A Galapagos Company, alleged to have been published no later than Sep. 20, 2005 by the opponents in connection with the opposition of European patent No. EP 2217578.
Hu et al., May 2004, "Requirement of Src kinasese Lyn, Hck and Fgr for BCR-ALB1-induced B-lymphoblastic leukemia but not chronic myeloide leukemia", *Nature Genetics*, vol. 36, No. 5, pp. 453-461.
Notice of Opposition by Glaxo Group Limited, filed and laid open to public inspection on Sep. 4, 2014 in connection with opposition of European patent No. EP 2217578.
Notice of Opposition by Galapagos NV, filed and laid open to public inspection on Sep. 3, 2014 in connection with opposition of European patent No. EP 2217578.
Rowe et al., Editors, 2009, *Handbook of Pharmaceutical Excipients* (sixth edition), published by Pharmaceutical Press and American Pharmacists Association (table on contents pages only).
Tortora et al., 2001, "Combined Blockage of Protein Kinase A and Bcl-2 by Antisense Strategy Induces Apoptosis and Inhibits Tumor Growth and Angiogenesis", *Clinical Cancer Research*, vol. 7, pp. 2537-2544.
Watts et al., 1998, "Expression of dominant negative Erk2 inhibits AP-1 transactivation and neoplastic transformation", *Oncogene*, vol. 17, pp. 3493-3498.

\* cited by examiner

[1,2,4]TRIAZOLO[1,5-A]PYRIDINE AND [1,2,4]TRIAZOLO[1,5-C]PYRIMIDINE COMPOUNDS AND THEIR USE

RELATED APPLICATIONS

This application is a continuation of U.S. application Ser. No. 12/679,871, filed Mar. 24, 2010. U.S. application Ser. No. 12/679,871 is a 35 U.S.C. §371 national phase application of PCT/GB2008/003428 (WO 2009/047514), filed Oct. 10, 2008, entitled "[1,2,4]Triazolo[1,5-a]Pyridine and [1,2,4]Triazolo[1,5-c]Pyrimidine Compounds and Their Use". PCT/GB2008/003428 is a non-provisional application of U.S. provisional patent application No. 60/978,792 filed Oct. 10, 2007 and United Kingdom patent application number 0719803.9 filed Oct. 10, 2007. The contents of each of these applications are incorporated herein by reference in their entirety.

TECHNICAL FIELD

The present invention pertains generally to the field of therapeutic compounds, and more specifically to certain triazolo compounds (referred to herein as TAZ compounds), and especially certain [1,2,4]triazolo[1,5-a]pyridine and [1,2,4]triazolo[1,5-c]pyrimidine compounds, which, inter alia, inhibit AXL receptor tyrosine kinase function. The present invention also pertains to pharmaceutical compositions comprising such compounds, and the use of such compounds and compositions, both in vitro and in vivo, to inhibit AXL receptor tyrosine kinase function, and in the treatment of diseases and conditions that are mediated by AXL receptor tyrosine kinase, that are ameliorated by the inhibition of AXL receptor tyrosine kinase function, etc., including proliferative conditions such as cancer, etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Axl receptor tyrosine kinase (nucleotide accession numbers NM_021913 and NM_001699) is a transmembrane receptor tyrosine kinase (RTK) protein and a member of the Axl RTK subfamily. The Axl RTK gene has a chromosomal location of 19q13.2 (see, e.g., O'Bryan et al., 1991). Axl is also known as UFO, ARK and TYRO7 and has IUBMB Enzyme Nomenclature EC 2.7.10.1.

The Axl RTK subfamily comprises Axl, Mer (Stk, Nyk) and Tyro3(Rse/Dtk/Sky). This subfamily is characterised by a common protein domain structure. The Axl RTK subfamily all possess the combination of two extracellular N-terminal immunoglobulin type domains and two fibronectin III domains, a single span transmembrane region followed by C-terminal kinase domain (see, e.g., Hafizi et al., 2006a).

Gas6 acts as a ligand to all of the Axl RTK family, but exhibits differing affinities for the receptors and activates the three proteins to varying degrees. Gas6 is a member of the vitamin K-dependent family of proteins and shows a 43% sequence identity and the same domain organisation to protein S, a serum protein which has been shown to be a negative regulator of blood coagulation (see, e.g., Hafizi et al., 2006b).

Gas6 is upregulated in growth arrested cells (see, e.g., Manfioletti et al., 1993) which indicates a function in protection of the cell against cellular stresses. It has since been shown that Gas6 can cross link Axl monomers and promote cellular survival, proliferation and migration (see, e.g., Bellosta et al., 1997; Sainaghi et al., 2005; Fridell et al., 1998).

Homophilic binding of the Axl extracellular domain can result in cellular aggregation and this event is independent of the intracellular kinase activity (see, e.g., Bellosta et al., 1995).

The Axl intracellular kinase domain (ICD) is responsible for the oncogenic transforming ability of Axl RTK. The Gas6/Axl signal transduction pathway operates, although not exclusively, through activation of the phosphatidylinositol 3-kinase (PI3K) pathway (see, e.g., Shankar et al., 2006).

The PI3K/Akt signaling network is crucial to widely divergent physiological processes that include cell cycle progression, differentiation, transcription, translation and apoptosis (see, e.g., Hanada et al., 2004).

Activation of PI3K/Akt signaling results in disturbance of control of cell proliferation and apoptosis, ensuing in competitive growth advantage for tumor cells. Activation of Akt is associated with phosphorylation of Ser$^{473}$ (see, e.g., Alessi et al., 1996) and monitoring changes in levels of total and phosphorolated Akt within the cell enables an assessment of the efficacy of drugs which act upstream of Akt.

The intracellular domain of Axl kinase has been shown to associate with many proteins (p55gamma, p85alpha and beta subunits of PI3K, phospholipaseC-gamma, Grb2, c-Src, Lck, SOCS-1, Nck2, RanBMP, C1-TEN and Axl ICD itself) (see, e.g., Hafizi et al., 2006a; Braunger et al., 1997; Hafizi et al., 2002).

Axl is ubiquitously expressed at low levels and is detectable in a variety of organs (see, e.g., Rescigno et al., 1991). Expression patterns of the other two family members (Mer and Tyro3) differ from that of Axl. Expression of Tyro3 is predominantly in the brain and the CNS (see, e.g., Mark et al., 1994), and expression of Mer is almost exclusively in the monocyte cell lineage (see, e.g., Graham et al., 1994).

Overexpression of Axl has been demonstrated in numerous cancer cell lines (e.g., colon, gastric, breast, lung, AML, thyroid, ocular, prostate, ocular melanoma, ovarian, renal, and SCC) (see, e.g., Sainaghi et al., 2005; Sawaby et al., 2007;

Vajkoczy et al., 2006; Meric et al., 2002; Shieh et al., 2005). This expression has been linked to the development of oncogenic cellular phenotype (see, e.g., Shieh et al., 2005). Overexpression of Axl has been linked to stage of disease and prognosis (see, e.g., Sawabu et al., 2007; Shieh et al., 2005; Sun et al., 2003; Green et al., 2006).

Modulation of Axl levels in vivo and in vitro demonstrates the involvement of Axl in the progression of a cancer phenotype. siRNA mediated silencing demonstrates that Axl is a regulator of multiple angiogenic behaviours in vitro and Axl knockdown reduces growth of breast carcinoma cell lines in a xenograft (see, e.g., Holland et al., 2005).

There is a need for additional and better therapeutic agents for the treatment of proliferative conditions, such as cancer, etc., including, for example, additional and better therapeutic agents that inhibit AXL receptor tyrosine kinase function.

[1,2,4]Triazolo[1,5-a]Pyridines

WO 2008/025821 (Wilson—Cellzome), and its priority application, EP 1 894 931 (Wilson—Cellzome), were published in March 2008, after the priority date of this application. These documents describe certain compounds (Compounds (PP-012) to (PP-026)) which are the subject of provisos described herein.

WO 2003/010167 (Nettekoven—Hoffmann LaRoche), corresponding to U.S. Pat. No. 6,514,989 (Nettekoven), describes certain [1,2,4]triazolo[1,5-a]pyridine compounds. However, in each compound that has a substituent corresponding to —$R^{5A}$, the substituent that would correspond to —$R^{8A}$ is a group —H or —OMe, which is not permitted by the present definition of compounds.

WO 2003/031445 (Nettekoven—Hoffmann LaRoche), corresponding to U.S. Pat. No. 6,693,116 (Nettekoven), describes certain [1,2,4]triazolo[1,5-a]pyridine compounds. However, in each compound, the substituent that would correspond to —$R^{5A}$ is a group —OMe, which is not permitted by the present definition of compounds.

Nettekoven et al., 2003 (Nettekoven et al., 2003, Synthesis, Vol. 11, pp. 1649-1652) describes certain [1,2,4]triazolo[1,5-a]pyridine compounds. However, in each compound, the substituent that would correspond to —$R^{8A}$ is a group —OMe, which is not permitted by the present definition of compounds.

WO 2006/038116 (Butler—Warner Lambert) describes certain [1,2,4]triazolo[1,5-a]pyridine compounds. However, in each compound, the group what would correspond to —NH—W is a urea, which is not permitted by the present definition of compounds.

[1,2,4]Triazolo[1,5-c]Pyrimidines

U.S. Pat. No. 5,358,950 (Bru—Magniez) describes certain [1,2,4]triazolo[1,5-c]pyrimidine compounds. However, in each compound, the substituent that would correspond to —$R^{5B}$ is a group methyl, ethyl, n-propyl, n-pentyl, or n-hexyl, which is not permitted by the present definition of compounds.

U.S. Pat. No. 3,046,276 (Miller), and its priority document, GB 897,870 (Miller—ICI Limited) describe certain [1,2,4]triazolo[1,5-c]pyrimidine compounds. However, in each compound, the substituent that would correspond to —$R^{5B}$ is a group methyl, ethyl, n-propyl, n-pentyl, or n-hexyl, which is not permitted by the present definition of compounds.

WO 2005/018532 (Westman—Actar Ab.) describes certain 1H-[1,2,4]triazolo[1,5-c]quinazoline compounds (having a fused tricyclic core) which are not encompassed by the present definition of compounds.

U.S. Pat. No. 3,053,844 (Miller) and its priority document, GB 873,223 (Miller—ICI Limited) describe certain [1,2,4]triazolo[1,5-c]pyrimidine compounds. However, in all but one of the compounds, the substituent that would correspond to —$R^{5B}$ is a group methyl, ethyl, n-propyl, n-pentyl, or n-hexyl, which is not permitted by the present definition of compounds. In the one remaining compound (see col. 8, lines 34-35 of U.S. Pat. No. 3,053,844; Reg. No. 94267-11-5P), the substituent that would correspond to —$R^{5B}$ is a group ethylthio (—$SCH_2CH_3$), which is permitted by the present definition of compounds; however, in that compound, the substituent that would correspond to —$R^{WB2}$ is a group -Me, which is not permitted by the present definition of compounds.

EP 0 132 851 (Paul—American Cyanamid), and the related journal article, Medwig et al., 1990 (Medwig et al., 1990, J. Med. Chem., Vol. 33(4), pp. 1230-1241), describe certain [1,2,4]triazolo[1,5-c]pyrimidine compounds. However, in each compound, the substituent that would correspond to —NH—$W^B$ is a group which is not permitted by the present definition of compounds. For the relevant amines (where —NH—$W^B$ is —NH—$R^{WB1}$), the substituent that would correspond to —$R^{WB1}$ is a group -Me, —$CH_2CH(OH)CH_2Cl$, or —$CH_2C(=O)OEt$, which is not permitted by the present definition of compounds. For the relevant amides (where —NH—$W^B$ is —NH—C(=O)—$R^{WB2}$), the substituent that would correspond to —$R^{WB2}$ is a group -Me or —$CH_2$-oxiranyl, which is not permitted by the present definition of compounds.

SUMMARY OF THE INVENTION

One aspect of the invention pertains to certain triazolo compounds (referred to herein as TAZ compounds), as described herein.

Another aspect of the invention pertains to a composition (e.g., a pharmaceutical composition) comprising a TAZ compound, as described herein, and a pharmaceutically acceptable carrier or diluent.

Another aspect of the invention pertains to method of preparing a composition (e.g., a pharmaceutical composition) comprising the step of admixing a TAZ compound, as described herein, and a pharmaceutically acceptable carrier or diluent.

Another aspect of the present invention pertains to a method of inhibiting AXL receptor tyrosine kinase function in a cell, in vitro or in vivo, comprising contacting the cell with an effective amount of a TAZ compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a TAZ compound, as described herein.

Another aspect of the present invention pertains to a method of treatment comprising administering to a subject in need of treatment a therapeutically-effective amount of a TAZ compound, as described herein, preferably in the form of a pharmaceutical composition.

Another aspect of the present invention pertains to a TAZ compound as described herein for use in a method of treatment of the human or animal body by therapy.

Another aspect of the present invention pertains to use of a TAZ compound, as described herein, in the manufacture of a medicament for use in treatment.

In one embodiment, the treatment is treatment of a disease or condition that is mediated by AXL receptor tyrosine kinase.

In one embodiment, the treatment is treatment of a disease or condition that is ameliorated by the inhibition of AXL receptor tyrosine kinase function.

In one embodiment, the treatment is treatment of a proliferative condition.

In one embodiment, the treatment is treatment of cancer.

In one embodiment, the treatment is treatment of solid tumour cancer.

In one embodiment, the treatment is treatment of liquid tumour cancer.

In one embodiment, the treatment is treatment of hematological cancer.

In one embodiment, the treatment is treatment of: colon cancer, gastric cancer, breast cancer, lung cancer, acute myeloid leukemia, thyroid cancer, ocular cancer, prostate cancer, ocular melanoma cancer, ovarian cancer, renal cancer, skin cancer, or squamous cell carcinoma.

Another aspect of the present invention pertains to a kit comprising (a) a TAZ compound, as described herein, preferably provided as a pharmaceutical composition and in a suitable container and/or with suitable packaging; and (b) instructions for use, for example, written instructions on how to administer the compound.

Another aspect of the present invention pertains to a TAZ compound obtainable by a method of synthesis as described herein, or a method comprising a method of synthesis as described herein.

Another aspect of the present invention pertains to a TAZ compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to certain [1,2,4]triazolo[1,5-a]pyridines and [1,2,4]triazolo[1,5-c]pyrimidines (for convenience, collectively referred to herein as "triazolo compounds" or "TAZ compounds") which are 2-amines or 2-amides.

In one especially preferred embodiment, the compounds are 2-amines.

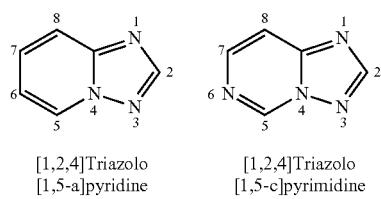

[1,2,4]Triazolo
[1,5-a]pyridine

[1,2,4]Triazolo
[1,5-c]pyrimidine

In one embodiment, the compounds are selected from compounds of the following formula, and pharmaceutically acceptable salts, hydrates, and solvates thereof:

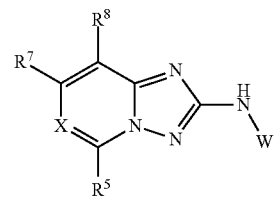

wherein:
—X= is independently —CR$^6$= or —N=;
and wherein:
  if —X= is —CR$^6$=, then:
    —R$^5$ is independently —R$^{5A}$;
    —R$^6$ is independently —R$^{6A}$;
    —R$^7$ is independently —R$^{7A}$;
    —R$^8$ is independently —R$^{8A}$; and
    —W is independently —W$^A$;
  wherein:
    —R$^{5A}$ is independently -Q$^{5A}$;
    —R$^{6A}$ is independently —H or -Q$^{6A}$;
    —R$^{7A}$ is independently —H or -Q$^{7A}$;
    —R$^{8A}$ is independently —H or -Q$^{8A}$; and
    —W$^A$ is independently —R$^{WA1}$ or —C(=O)R$^{WA2}$;
  if —X= is —N=, then:
    —R$^5$ is independently —R$^{5B}$;
    —R$^7$ is independently —R$^{7B}$;
    —R$^8$ is independently —R$^{8B}$; and
    —W is independently —W$^B$;
  wherein:
    —R$^{5B}$ is independently -Q$^{5B}$;
    —R$^{7B}$ is independently —H or -Q$^{7B}$;
    —R$^{8B}$ is independently —H or -Q$^{8B}$; and
    —W$^B$ is independently —R$^{WB1}$ or —C(=O)R$^{WB2}$.

Optional Provisos

It should be noted that the below-described provisos are relevant only in the context of definitions of the "amides" (where —W is —C(=O)R$^{WA2}$ or —C(=O)R$^{WB2}$) and so the provisos may be disregarded in the context of definitions of the "amines" (where —W is —R$^{WA1}$ or —R$^{WB1}$).

In one or more aspects of the present invention (e.g., compounds, compositions, compounds for use in therapy, use of compounds in the manufacture of a medicament, methods, methods of treatment, etc.), the compounds are optionally as defined herein, but with one or more optional provisos, as defined herein.

In one embodiment, the proviso is that the compound is not a compound selected from PP-001 through PP-011.

(Compounds PP-001 through PP-011 were obtained from a commercial source.)

| Code No. | Name and Reg. No. | Structure |
|---|---|---|
| PP-001 (WW-001) | Cyclopropanecarboxylic acid (5-phenyl-[1,2,4]triazolo[1,5-a]pyridin-2-yl)-amide 1010119-14-8 | 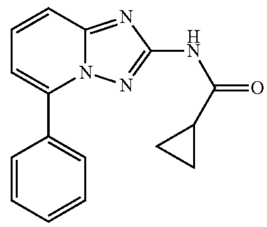 [SMILES: O=C(Nc1nc2cccc(-c3ccccc3)n2n1)C1CC1] |
| PP-002 (WW-002) | Cyclopropanecarboxylic acid [5-(3-acetylamino-phenyl)-[1,2,4]triazolo[1,5-a]pyridin-2-yl]amide | 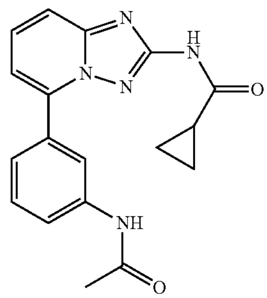 [SMILES: CC(=O)Nc1cccc(-c2cccc3nc(NC(=O)C4CC4)nn23)c1] |
| PP-003 (WW-003) | Cyclopropanecarboxylic acid {5-[4-(4-methyl-piperazin-1-yl)-phenyl]-[1,2,4]triazolo[1,5-a]pyridin-2-yl}-amide | 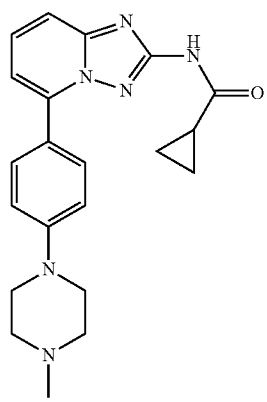 [SMILES: CN1CCN(c2ccc(-c3cccc4nc(NC(=O)C5CC5)nn34)cc2)CC1] |
| PP-004 (WW-004) | Cyclopropanecarboxylic acid [5-(3-chloro-phenyl)-[1,2,4]triazolo[1,5-a]pyridin-2-yl]amide 1010119-18-2 | 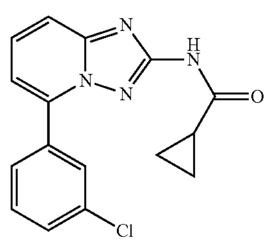 [SMILES: O=C(Nc1nc2cccc(-c3cccc(Cl)c3)n2n1)C1CC1] |
| PP-005 (WW-005) | Cyclopropanecarboxylic acid [5-(4-methoxy-phenyl)-[1,2,4]triazolo[1,5-a]pyridin-2-yl]amide 1010119-20-6 | 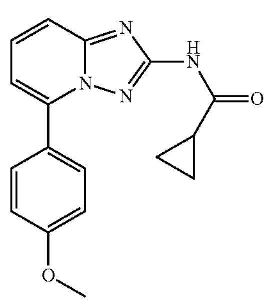 [SMILES: COc1ccc(-c2cccc3nc(NC(=O)C4CC4)nn23)cc1] |

| Code No. | Name and Reg. No. | Structure |
|---|---|---|
| PP-006 (WW-006) | Cyclopropanecarboxylic acid [5-(6-methoxy-pyridin-3-yl)-[1,2,4]triazolo[1,5-a]pyridin-2-yl]amide | 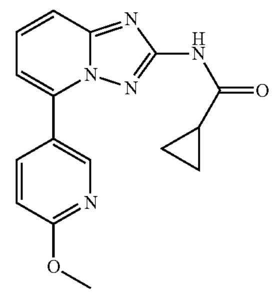 [SMILES: COc1ccc(-c2cccc3nc(NC(=O)C4CC4)nn23)cn1] |
| PP-007 (WW-007) | Cyclopropanecarboxylic acid [5-(3-fluoro-phenyl)-[1,2,4]triazolo[1,5-a]pyridin-2-yl]-amide | 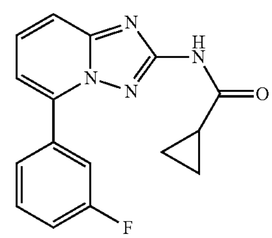 [SMILES: O=C(Nc1nc2cccc(-c3cccc(F)c3)n2n1)C1CC1] |
| PP-008 (WW-008) | Cyclopropanecarboxylic acid [5-(4-hydroxy-3,5-dimethyl-phenyl)-[1,2,4]triazolo[1,5-a]pyridin-2-yl]-amide | 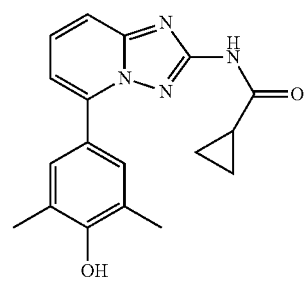 [SMILES: Cc1cc(-c2cccc3nc(NC(=O)C4CC4)nn23)cc(C)c1O] |
| PP-009 (WW-009) | 4-[2-(Cyclopropanecarbonyl-amino)-[1,2,4]triazolo[1,5-a]pyridin-5-yl]-N-(2-dimethylamino-ethyl)-benzamide 1010119-29-5 | 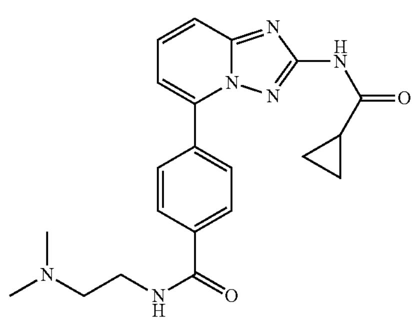 [SMILES: CN(C)CCNC(=O)c1ccc(-c2cccc3nc(NC(=O)C4CC4)nn23)cc1] |
| PP-010 (WW-010) | Cyclopropanecarboxylic acid [5-(2,4-dimethoxy-phenyl)-[1,2,4]triazolo[1,5-a]pyridin-2-yl]-amide | 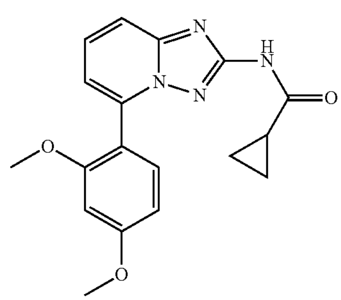 [SMILES: COc1ccc(-c2cccc3nc(NC(=O)C4CC4)nn23)c(OC)c1] |

-continued

| Code No. | Name and Reg. No. | Structure |
| --- | --- | --- |
| PP-011 (WW-011) | Cyclopropanecarboxylic acid [5-(3-methanesulfonylamino-phenyl)-[1,2,4]triazolo[1,5-a]pyridin-2-yl]-amide 1010119-33-1 | 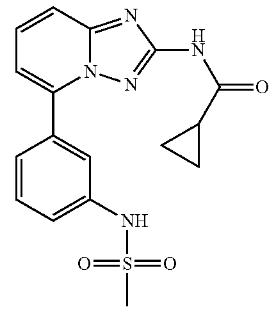 [SMILES: CS(=O)(=O)Nc1cccc(-c2cccc3nc(NC(=O)C4CC4)nn23)c1] |

In one embodiment, the proviso is that the compound is not a compound selected from PP-001 through PP-011, and salts, hydrates, and solvates thereof.

In one or more aspects of the present invention (e.g., compounds for use in therapy, use of compounds in the manufacture of a medicament, methods, methods of treatment, etc.), the compounds are optionally as defined herein, but without the above proviso.

For example, a reference to a particular group of compounds "without the recited proviso" (e.g., for use in therapy) is intended to be a reference to the compounds as defined, but wherein the definition no longer includes the indicated proviso. In such cases, it is as if the indicated proviso has been deleted from the definition of compounds, and the definition has been expanded to encompass those compounds which otherwise would have been excluded by the indicated proviso.

In one embodiment, the proviso is that the compound is not a compound selected from PP-001 through PP-026.

(Compounds PP-012 through PP-026 are shown in WO 2008/025821 and/or EP 1 894 931, both published in March 2008, after the priority date of this application.)

| Code No. | Name & Reg. No. | Structure |
| --- | --- | --- |
| PP-012 | Cyclopropanecarboxylic acid [5-(2-dimethylamino-phenyl)-[1,2,4]triazolo[1,5-a]pyridin-2-yl]-amide 1010119-12-6 | 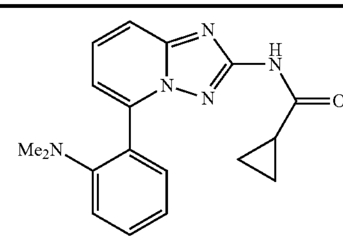 |
| PP-013 | Cyclopropanecarboxylic acid [5-(3-chloro-4-fluoro-phenyl)-[1,2,4]triazolo[1,5-a]pyridin-2-yl]-amide 1010119-13-7 | 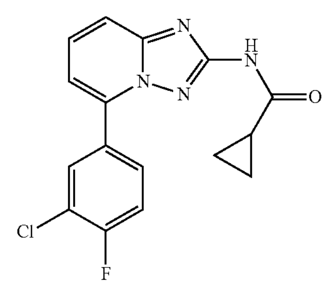 [SMILES: O=C(Nc1nc2cccc(-c3ccc(F)c(Cl)c3)n2n1)C1CC1] |
| PP-014 | Cyclopropanecarboxylic acid [5-(3-trifluoromethoxy-phenyl)-[1,2,4]triazolo[1,5-a]pyridin-2-yl]-amide 1010119-15-9 | 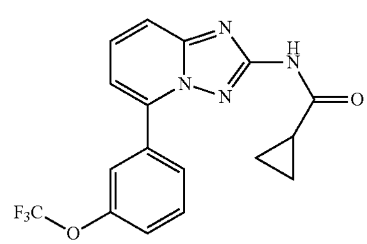 [SMILES: O=C(Nc1nc2cccc(-c3cccc(OC(F)(F)F)c3)n2n1)C1CC1] |

-continued

| Code No. | Name & Reg. No. | Structure |
|---|---|---|
| PP-015 | Cyclopropanecarboxylic acid [5-((E)-styryl)-[1,2,4]triazolo[1,5-a]pyridin-2-yl]-amide<br>1010119-17-1 | 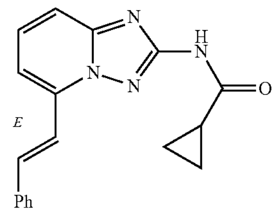 |
| PP-016 (WW-059) | Cyclopropanecarboxylic acid (5-thiophen-3-yl-[1,2,4]triazolo[1,5-a]pyridin-2-yl)-amide<br>1010119-19-3 | 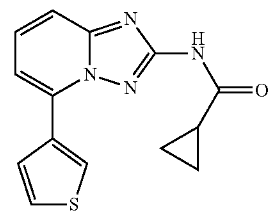 [SMILES: O=C(Nc1nc2cccc(-c3ccsc3)n2n1)C1CC1] |
| PP-017 | 3-Cyclohexyl-N-[5-(4-hydroxy-3,5-dimethyl-phenyl)-[1,2,4]triazolo[1,5-a]pyridin-2-yl]-propionamide<br>1010119-21-7 | 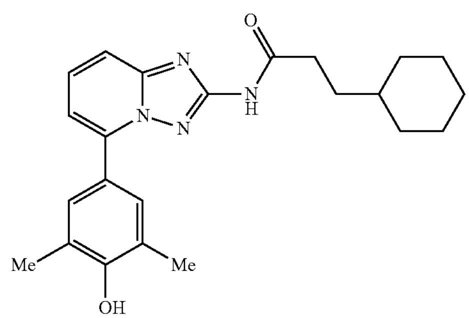 [SMILES: Cc1cc(-c2cccc3nc(NC(=O)CCC4CCCCC4)nn23)cc(C)c1O] |
| PP-018 | Cyclohexanecarboxylic acid (5-thiophen-3-yl-[1,2,4]triazolo[1,5-a]pyridin-2-yl)-amide<br>1010119-22-8 | 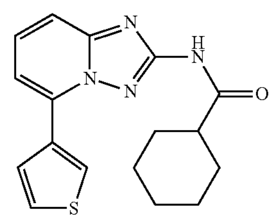 [SMILES: O=C(Nc1nc2cccc(-c3ccsc3)n2n1)C1CCCCC1] |
| PP-019 | Furan-2-carboxylic acid [5-(3-fluoro-phenyl)-[1,2,4]triazolo[1,5-a]pyridin-2-yl]-amide<br>1010119-23-9 | 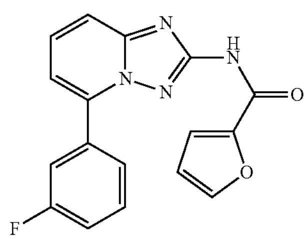 [SMILES: O=C(Nc1nc2cccc(-c3cccc(F)c3)n2n1)c1ccco1] |
| PP-020 | Furan-2-carboxylic acid [5-(4-hydroxy-3,5-dimethyl-phenyl)-[1,2,4]triazolo[1,5-a]pyridin-2-yl]-amide<br>1010119-24-0 | 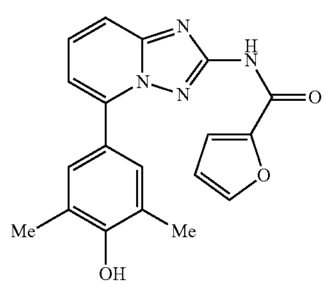 [SMILES: Cc1cc(-c2cccc3nc(NC(=O)c4ccco4)nn23)cc(C)c1O] |

-continued

| Code No. | Name & Reg. No. | Structure |
|---|---|---|
| PP-021 | 3-Methoxy-N-(5-thiophen-3-yl-[1,2,4]triazolo[1,5-a]pyridin-2-yl)-propionamide 1010119-25-1 | 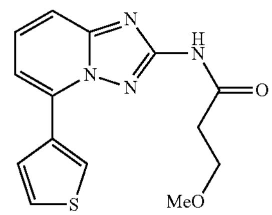 [SMILES: COCCC(=O)Nc1nc2cccc(-c3ccsc3)n2n1] |
| PP-022 | 4-[2-(Cyclopropanecarbonyl-amino)-[1,2,4]triazolo[1,5-a]pyridin-5-yl]-N-(2-hydroxy-ethyl)-benzamide 1010119-30-8 | 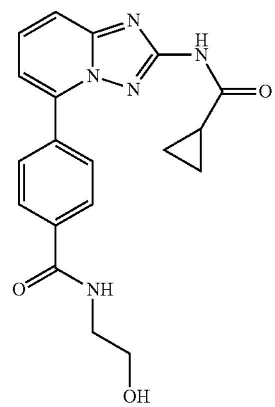 [SMILES: O=C(NCCO)c1ccc(-c2cccc3nc(NC(=O)C4CC4)nn23)cc1] |
| PP-023 (WW-056) | Cyclopropanecarboxylic acid (5-furan-3-yl-[1,2,4]triazolo[1,5-a]pyridin-2-yl)-amide 1010119-31-9 | 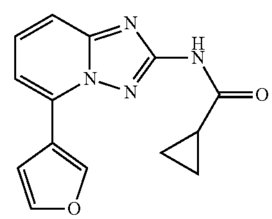 [SMILES: O=C(Nc1nc2cccc(-c3ccoc3)n2n1)C1CC1] |
| PP-024 | N-[5-(3-Amino-phenyl)-[1,2,4]triazolo[1,5-a]pyridin-2-yl]-3-pyridin-3-yl-propionamide 1010119-32-0 | 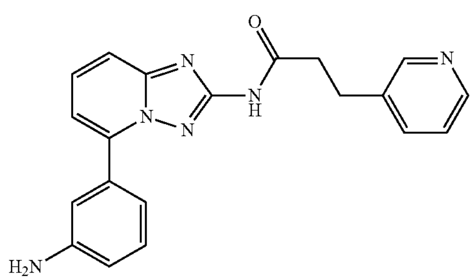 [SMILES: Nc1cccc(-c2cccc3nc(NC(=O)CCc4cccnc4)nn23)c1] |
| PP-025 | N-[6-(5-Methanesulfonyl-pyridin-3-yl)-5-methyl-[1,2,4]triazolo[1,5-a]pyridin-2-yl]acetamide 1010120-43-0 | 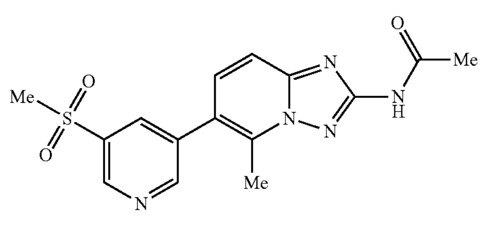 [SMILES: CC(=O)Nc1nc2ccc(-c3cncc(S(C)(=O)=O)c3)c(C)n2n1] |
| PP-026 | N-[6-(3,4-Dimethoxy-phenyl)-5-methyl-[1,2,4]triazolo[1,5-a]pyridin-2-yl]-acetamide 1010120-46-3 | 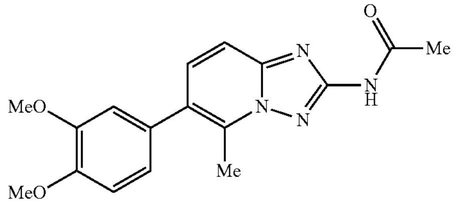 [SMILES: COc1ccc(-c2ccc3nc(NC(C)=O)nn3c2C)cc1OC] |

In one embodiment, the proviso is that the compound is not a compound selected from PP-001 through PP-026, and salts, hydrates, and solvates thereof.

In one or more aspects of the present invention (e.g., compounds for use in therapy, use of compounds in the manufacture of a medicament, methods, methods of treatment, etc.), the compounds are optionally as defined herein, but without the above proviso.

For example, a reference to a particular group of compounds "without the recited proviso" (e.g., for use in therapy) is intended to be a reference to the compounds as defined, but wherein the definition no longer includes the indicated proviso. In such cases, it is as if the indicated proviso has been deleted from the definition of compounds, and the definition has been expanded to encompass those compounds which otherwise would have been excluded by the indicated proviso.

"Amines" and "Amides"

In one embodiment ("amines"):
—$W^A$ is independently —$R^{WA1}$; and
—$W^B$ is independently —$R^{WB1}$.

In one embodiment ("amides"):
—$W^A$ is independently —$C(=O)R^{WA2}$; and
—$W^B$ is independently —$C(=O)R^{WB2}$.

The Group —X=

In one embodiment, —X= is independently —$CR^6$= or —N=.

In one embodiment:
—X= is independently —$CR^6$=;
—$R^5$ is independently —$R^{5A}$;
—$R^6$ is independently —$R^{6A}$;
—$R^7$ is independently —$R^{7A}$;
—$R^8$ is independently —$R^{8A}$; and
—W is independently —$W^A$;
as in, for example:

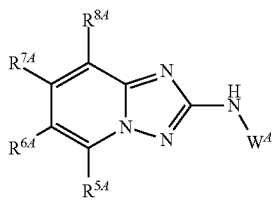

In one embodiment:
—X= is independently —N=;
—$R^5$ is independently —$R^{5B}$;
—$R^7$ is independently —$R^{7B}$;
—$R^8$ is independently —$R^{8B}$; and
—W is independently —$W^B$;
as in, for example:

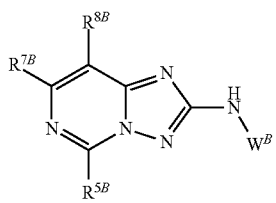

The Group —$W^A$

In one embodiment, —$W^A$ is independently —$R^{WA1}$ or —$C(=O)R^{WA2}$.

In one embodiment, —$W^A$ is independently —$R^{WA1}$.
In one embodiment, —$W^A$ is independently —$C(=O)R^{WA2}$.

The Group —$W^B$

In one embodiment, —$W^B$ is independently —$R^{WB1}$ or —$C(=O)R^{WB2}$.
In one embodiment, —$W^B$ is independently —$R^{WB1}$.
In one embodiment, —$W^B$ is independently —$C(=O)R^{WB2}$.

Combinations of the Groups —X= and —W (A) In one embodiment:
—X= is independently —$CR^6$=;
—$R^5$ is independently —$R^{5A}$;
—$R^6$ is independently —$R^{6A}$;
—$R^7$ is independently —$R^{7A}$;
—$R^8$ is independently —$R^{8A}$;
—W is independently —$W^A$; and
—$W^A$ is independently —$R^{WA1}$;
as in, for example:

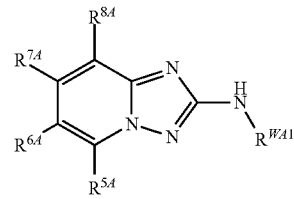

(B) In one embodiment:
—X= is independently —N=;
—$R^5$ is independently —$R^{5B}$;
—$R^7$ is independently —$R^{7B}$;
—$R^8$ is independently —$R^{8B}$;
—W is independently —$W^B$; and
—$W^B$ is independently —$R^{WB1}$;
as in, for example:

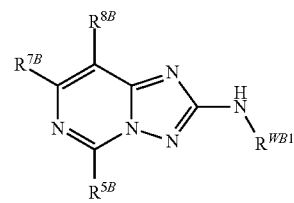

(C) In one embodiment:
—X= is independently —$CR^6$=;
—$R^5$ is independently —$R^{5A}$;
—$R^6$ is independently —$R^{6A}$;
—$R^7$ is independently —$R^{7A}$;
—$R^8$ is independently —$R^{8A}$;
—W is independently —$W^A$; and
—$W^A$ is independently —$C(=O)R^{WA2}$;
as in, for example:

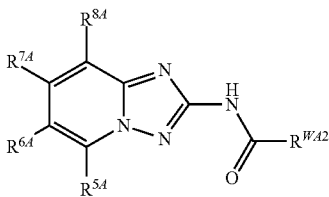

(D) In one embodiment:
—X═ is independently —N═;
—R⁵ is independently —R⁵ᴮ;
—R⁷ is independently —R⁷ᴮ;
—R⁸ is independently —R⁸ᴮ;
—W is independently —Wᴮ; and
—Wᴮ is independently —C(═O)R^{WB2};
as in, for example:

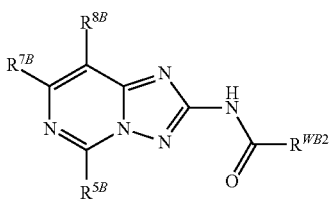

The Group —R⁶ᴬ
In one embodiment, —R⁶ᴬ, if present, is independently —H or -Q⁶ᴬ.
In one embodiment, —R⁶ᴬ, if present, is independently —H.
In one embodiment, —R⁶ᴬ, if present, is independently -Q⁶ᴬ.
The Group —R⁷ᴬ
In one embodiment, —R⁷ᴬ is independently —H or -Q⁷ᴬ.
In one embodiment, —R⁷ᴬ is independently —H.
In one embodiment, —R⁷ᴬ is independently -Q⁷ᴬ.
The Group —R⁸ᴬ
In one embodiment, —R⁸ᴬ is independently —H or -Q⁸ᴬ.
In one embodiment, —R⁸ᴬ is independently —H.
In one embodiment, —R⁸ᴬ is independently -Q⁸ᴬ.
The Group —R⁷ᴮ
In one embodiment, —R⁷ᴮ is independently —H or -Q⁷ᴮ.
In one embodiment, —R⁷ᴮ is independently —H.
In one embodiment, —R⁷ᴮ is independently -Q⁷ᴮ.
The Group —R⁸ᴮ
In one embodiment, —R⁸ᴮ is independently —H or -Q⁸ᴮ.
In one embodiment, —R⁸ᴮ is independently —H.
In one embodiment, —R⁸ᴮ is independently -Q⁸ᴮ.
The Group —R^{WA1}
In one embodiment, —R^{WA1}, if present, is independently:
—R¹ᴬ¹, —R¹ᴬ², —R¹ᴬ³, —R¹ᴬ⁴, —R¹ᴬ⁵, —R¹ᴬ⁶, —R¹ᴬ⁷, —R¹ᴬ⁸,
-L¹ᴬ-R¹ᴬ⁴, -L¹ᴬ-R¹ᴬ⁵, -L¹ᴬ-R¹ᴬ⁶, -L¹ᴬ-R¹ᴬ⁷, or -L¹ᴬ-R¹ᴬ⁸.
In one embodiment, —R^{WA1}, if present, is independently:
—R¹ᴬ¹, —R¹ᴬ⁴, —R¹ᴬ⁶, —R¹ᴬ⁷, —R¹ᴬ⁸,
-L¹ᴬ-R¹ᴬ⁴, -L¹ᴬ-R¹ᴬ⁶, -L¹ᴬ-R¹ᴬ⁷, or -L¹ᴬ-R¹ᴬ⁸.
In one embodiment, —R^{WA1}, if present, is independently:
—R¹ᴬ¹, —R¹ᴬ⁴, —R¹ᴬ⁶, —R¹ᴬ⁷, —R¹ᴬ⁸,
-L¹ᴬ-R¹ᴬ⁴, or -L¹ᴬ-R¹ᴬ⁶.
In one embodiment, —R^{WA1}, if present, is independently:
—R¹ᴬ¹, —R¹ᴬ⁴, —R¹ᴬ⁷, —R¹ᴬ⁸,
-L¹ᴬ-R¹ᴬ⁴, -L¹ᴬ-R¹ᴬ⁷, or -L¹ᴬ-R¹ᴬ⁸.

In one embodiment, —R^{WA1}, if present, is independently:
—R¹ᴬ⁴, —R¹ᴬ⁶, —R¹ᴬ⁷, —R¹ᴬ⁸,
-L¹ᴬ-R¹ᴬ⁴, -L¹ᴬ-R¹ᴬ⁶, -L¹ᴬ-R¹ᴬ⁷, or -L¹ᴬ-R¹ᴬ⁸.
In one embodiment, —R^{WA1}, if present, is independently:
—R¹ᴬ⁴, —R¹ᴬ⁶, —R¹ᴬ⁷, or —R¹ᴬ⁸.
In one embodiment, —R^{WA1}, if present, is independently:
—R¹ᴬ¹, -L¹ᴬ-R¹ᴬ⁶, —R¹ᴬ⁷, or —R¹ᴬ⁸.
In one embodiment, —R^{WA1}, if present, is independently:
-L¹ᴬ-R¹ᴬ⁴, -L¹ᴬ-R¹ᴬ⁶, —R¹ᴬ⁷, or —R¹ᴬ⁸.
In one embodiment, —R^{WA1}, if present, is independently:
—R¹ᴬ⁷, —R¹ᴬ⁸, -L¹ᴬ-R¹ᴬ⁷, or -L¹ᴬ-R¹ᴬ⁸.
In one embodiment, —R^{WA1}, if present, is independently —R¹ᴬ⁷ or —R¹ᴬ⁸.
In one embodiment, —R^{WA1}, if present, is independently —R¹ᴬ⁷.
In one embodiment, —R^{WA1}, if present, is independently —R¹ᴬ⁸.
In one embodiment, —R^{WA1}, if present, is independently selected from those groups exemplified for —R^{WA1} in the compounds shown below under the heading "Examples of Specific Embodiments".

The Group —R^{WA2}
In one embodiment, —R^{WA2}, if present, is independently:
—R¹ᴬ¹, —R¹ᴬ², —R¹ᴬ³, —R¹ᴬ⁴, —R¹ᴬ⁵, —R¹ᴬ⁶, —R¹ᴬ⁷, —R¹ᴬ⁸,
-L¹ᴬ-R¹ᴬ⁴, -L¹ᴬ-R¹ᴬ⁵, -L¹ᴬ-R¹ᴬ⁶, -L¹ᴬ-R¹ᴬ⁷, or -L¹ᴬ-R¹ᴬ⁸.
In one embodiment, —R^{WA2}, if present, is independently:
—R¹ᴬ¹, —R¹ᴬ⁴, —R¹ᴬ⁶, —R¹ᴬ⁷, —R¹ᴬ⁸,
-L¹ᴬ-R¹ᴬ⁴, -L¹ᴬ-R¹ᴬ⁶, -L¹ᴬ-R¹ᴬ⁷, or -L¹ᴬ-R¹ᴬ⁸.
In one embodiment, —R^{WA2}, if present, is independently:
—R¹ᴬ¹, —R¹ᴬ⁴, —R¹ᴬ⁶, -L¹ᴬ-R¹ᴬ⁴, or -L¹ᴬ-R¹ᴬ⁶.
In one embodiment, —R^{WA2}, if present, is independently —R¹ᴬ¹, —R¹ᴬ⁴, or —R¹ᴬ⁶.
In one embodiment, —R^{WA2}, if present, is independently —R¹ᴬ¹.
In one embodiment, —R^{WA2}, if present, is independently —R¹ᴬ⁴, —R¹ᴬ⁶, -L¹ᴬ-R¹ᴬ⁴, or -L¹ᴬ-R¹ᴬ⁶.
In one embodiment, —R^{WA2}, if present, is independently —R¹ᴬ⁴ or —R¹ᴬ⁶.
In one embodiment, —R^{WA2}, if present, is independently —R¹ᴬ⁴.
In one embodiment, —R^{WA2}, if present, is independently —R¹ᴬ⁶.
In one embodiment, —R^{WA2}, if present, is independently -L¹ᴬ-R¹ᴬ⁴, or -L¹ᴬ-R¹ᴬ⁶.
In one embodiment, —R^{WA2}, if present, is independently -L¹ᴬ-R¹ᴬ⁴.
In one embodiment, —R^{WA2}, if present, is independently -L¹ᴬ-R¹ᴬ⁶.
In one embodiment, —R^{WA2}, if present, is independently selected from those groups exemplified for —R^{WA2} in the compounds shown below under the heading "Examples of Specific Embodiments".

The Group —R^{WB1}
In one embodiment, —R^{WB1}, if present, is independently:
—R¹ᴬ², —R¹ᴬ³, —R¹ᴬ⁴, —R¹ᴬ⁵, —R¹ᴬ⁶, —R¹ᴬ⁷, —R¹ᴬ⁸,
-L¹ᴬ-R¹ᴬ⁴, -L¹ᴬ-R¹ᴬ⁵, -L¹ᴬ-R¹ᴬ⁷, or -L¹ᴬ-R¹ᴬ⁸.
In one embodiment, —R^{WB1}, if present, is independently:
—R¹ᴬ⁴, —R¹ᴬ⁶, —R¹ᴬ⁷, —R¹ᴬ⁸,
-L¹ᴬ-R¹ᴬ⁴, -L¹ᴬ-R¹ᴬ⁷, or -L¹ᴬ-R¹ᴬ⁸.
In one embodiment, —R^{WB1}, if present, is independently:
—R¹ᴬ⁴, —R¹ᴬ⁶, —R¹ᴬ⁷, —R¹ᴬ⁸, or
-L¹ᴬ-R¹ᴬ⁴.
In one embodiment, —R^{WB1}, if present, is independently:
—R¹ᴬ⁴, —R¹ᴬ⁷, —R¹ᴬ⁸, -L$^{1A}$-R$^{1A4}$, -L$^{1A}$-R$^{1A7}$, or -L$^{1A}$-R$^{1A8}$.

In one embodiment, —R$^{WB1}$, if present, is independently:
—R$^{1A4}$, —R$^{1A6}$, —R$^{1A7}$, —R$^{1A8}$,
-L$^{1A}$-R$^{1A4}$, -L$^{1A}$-R$^{1A7}$, or -L$^{1A}$-R$^{1A8}$.

In one embodiment, —R$^{WB1}$, if present, is independently:
—R$^{1A7}$, —R$^{1A8}$, or -L$^{1A}$-R$^{1A4}$.

In one embodiment, —R$^{WB1}$, if present, is independently:
—R$^{1A4}$, —R$^{1A6}$, —R$^{1A7}$, or —R$^{1A8}$.

In one embodiment, —R$^{WB1}$, if present, is independently:
—R$^{1A7}$, —R$^{1A8}$, -L$^{1A}$-R$^{1A7}$, or -L$^{1A}$-R$^{1A8}$.

In one embodiment, —R$^{WB1}$, if present, is independently —R$^{1A7}$ or —R$^{1A8}$.

In one embodiment, —R$^{WB1}$, if present, is independently —R$^{1A7}$.

In one embodiment, —R$^{WB1}$, if present, is independently —R$^{1A8}$.

In one embodiment, —R$^{WB1}$, if present, is independently selected from those groups exemplified for —R$^{WB1}$ in the compounds shown below under the heading "Examples of Specific Embodiments".

The Group —R$^{WB2}$

In one embodiment, —R$^{WB2}$, if present, is independently:
—R$^{1A2}$, —R$^{1A3}$, —R$^{1A4}$, —R$^{1A5}$, —R$^{1A6}$, —R$^{1A7}$, —R$^{1A8}$,
-L$^{1A}$-R$^{1A4}$, -L$^{1A}$-R$^{1A5}$, -L$^{1A}$-R$^{1A6}$, -L$^{1A}$-R$^{1A7}$, or -L$^{1A}$-R$^{1A8}$.

In one embodiment, —R$^{WB2}$, if present, is independently:
—R$^{1A4}$, —R$^{1A6}$, —R$^{1A7}$, —R$^{1A8}$,
-L$^{1A}$-R$^{1A4}$, -L$^{1A}$-R$^{1A6}$, -L$^{1A}$-R$^{1A7}$, or -L$^{1A}$-R$^{1A8}$.

In one embodiment, —R$^{WB2}$, if present, is independently:
—R$^{1A4}$, —R$^{1A6}$, —R$^{1A7}$, —R$^{1A8}$,
-L$^{1A}$-R$^{1A4}$, or -L$^{1A}$-R$^{1A6}$.

In one embodiment, —R$^{WB2}$, if present, is independently —R$^{1A4}$, —R$^{1A6}$, —R$^{1A7}$, or —R$^{1A8}$.

In one embodiment, —R$^{WB2}$, if present, is independently —R$^{1A4}$, —R$^{1A6}$, -L$^{1A}$-R$^{1A4}$, or -L$^{1A}$-R$^{1A6}$.

In one embodiment, —R$^{WB2}$, if present, is independently —R$^{1A4}$ or —R$^{1A6}$.

In one embodiment, —R$^{WB2}$, if present, is independently —R$^{1A4}$.

In one embodiment, —R$^{WB2}$, if present, is independently —R$^{1A6}$.

In one embodiment, —R$^{WB2}$, if present, is independently -L$^{1A}$-R$^{1A4}$ or -L$^{1A}$-R$^{1A6}$.

In one embodiment, —R$^{WB2}$, if present, is independently -L$^{1A}$-R$^{1A4}$.

In one embodiment, —R$^{WB2}$, if present, is independently -L$^{1A}$-R$^{1A6}$.

In one embodiment, —R$^{WB2}$, if present, is independently selected from those groups exemplified for —R$^{WB2}$ in the compounds shown below under the heading "Examples of Specific Embodiments".

The Groups Associated with —R$^{WA1}$, —R$^{WA2}$, —R$^{WB1}$, and —R$^{WB2}$

In one embodiment:
each —R$^{1A1}$ is independently saturated aliphatic C$_{1-6}$alkyl;
each —R$^{1A2}$ is independently aliphatic C$_{2-6}$alkenyl;
each —R$^{1A3}$ is independently aliphatic C$_{2-6}$alkynyl;
each —R$^{1A4}$ is independently saturated C$_{3-6}$cycloalkyl;
each —R$^{1A5}$ is independently C$_{3-6}$cycloalkenyl;
each —R$^{1A6}$ is independently non-aromatic C$_{3-8}$heterocyclyl;
each —R$^{1A7}$ is independently C$_{6-10}$carboaryl;
each —R$^{1A8}$ is independently C$_{5-10}$heteroaryl;
each -L$^{1A}$- is independently saturated aliphatic C$_{1-3}$alkylene;

wherein:
each —R$^{1A4}$, —R$^{1A5}$, —R$^{1A6}$, —R$^{1A7}$, and —R$^{1A8}$ is optionally substituted, for example, with one or more substituents —R$^{1B1}$ and/or one or more substituents —R$^{1B2}$, and
each —R$^{1A1}$, —R$^{1A2}$, —R$^{1A3}$, and -L$^{1A}$- is optionally substituted, for example, with one or more substituents —R$^{1B2}$, wherein:
each —R$^{1B1}$ is independently:
—R$^{1D1}$, —R$^{1D2}$, —R$^{1D3}$, —R$^{1D4}$, —R$^{1D5}$, —R$^{1D6}$, —R$^{1D7}$, —R$^{1D8}$,
-L$^{1D}$-R$^{1D4}$, -L$^{1D}$-R$^{1D5}$, -L$^{1D}$-R$^{1D6}$, -L$^{1D}$-R$^{1D7}$, or -L$^{1D}$-R$^{1D8}$;

each —R$^{1B2}$ is independently:
—F, —Cl, —Br, —I,
—CF$_3$, —OCF$_3$,
—OH, -L$^{1C}$-OH, —O-L$^{1C}$-OH,
—OR$^{1C1}$, -L$^{1C}$-OR$^{1C1}$, —O-L$^{1C}$-OR$^{1C1}$,
—SH, —SR$^{1C1}$,
—CN,
—NO$_2$,
—NH$_2$, —NHR$^{1C1}$, —NR$^{1C1}_2$, —NR$^{1C2}$R$^{1C3}$,
-L$^{1C}$-NH$_2$, -L$^{1C}$-NHR$^{1C1}$, -L$^{1C}$-NR$^{1C1}_2$, -L$^{1C}$-NR$^{1C2}$R$^{1C3}$,
—O-L$^{1C}$-NH$_2$, —O-L$^{1C}$-NHR$^{1C1}$, —O-L$^{1C}$-NR$^{1C1}_2$, —O-L$^{1C}$-NR$^{1C2}$R$^{1C3}$,
—C(=O)OH, —C(=O)OR$^{1C1}$,
—C(=O)R$^{1C1}$,
—C(=O)NH$_2$, —C(=O)NHR$^{1C1}$, —C(=O)NR$^{1C1}_2$, —C(=O)NR$^{1C2}$R$^{1C3}$,
—NHC(=O)R$^{1C1}$, —NR$^{1C1}$C(=O)R$^{1C1}$,
—NHC(=O)OR$^{1C1}$, —NR$^{1C1}$C(=O)OR$^{1C1}$,
—OC(=O)NH$_2$, —OC(=O)NHR$^{1C1}$, —OC(=O)NR$^{1C1}_2$, —OC(=O)NR$^{1C2}$R$^{1C3}$,
—NHC(=O)NH$_2$, —NHC(=O)NHR$^{1C1}$,
—NHC(=O)NR$^{1C1}_2$, —NHC(=O)NR$^{1C2}$R$^{1C3}$,
—NR$^{1C1}$C(=O)NH$_2$, —NR$^{1C1}$C(=O)NHR$^{1C1}$,
—NR$^{1C1}$C(=O)NR$^{1C1}_2$, —NR$^{1C1}$C(=O)NR$^{1C2}$R$^{1C3}$,
—NHS(=O)$_2$R$^{1C1}$, —NR$^{1C1}$S(=O)$_2$R$^{1C1}$,
—S(=O)$_2$NH$_2$, —S(=O)$_2$NHR$^{1C1}$, —S(=O)$_2$NR$^{1C1}_2$, —S(=O)$_2$NR$^{1C2}$R$^{1C3}$,
—S(=O)R$^{1C1}$, —S(=O)$_2$R$^{1C1}$, —OS(=O)$_2$R$^{1C1}$, or —S(=O)$_2$OR$^{1C1}$;

wherein:
each -L$^{1C}$- is independently saturated aliphatic C$_{1-5}$alkylene;
in each group —NR$^{1C2}$R$^{1C3}$, R$^{1C2}$ and R$^{1C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —R$^{1C1}$ is independently:
—R$^{1D1}$, —R$^{1D2}$, —R$^{1D3}$, —R$^{1D4}$, —R$^{1D5}$, —R$^{1D6}$, —R$^{1D7}$, —R$^{1D8}$,
-L$^{1D}$-R$^{1D4}$, -L$^{1D}$-R$^{1D5}$, -L$^{1D}$-R$^{1D6}$, -L$^{1D}$-R$^{1D7}$, or -L$^{1D}$-R$^{1D8}$;

each —R$^{1D1}$ is independently saturated aliphatic C$_{1-6}$alkyl;
each —R$^{1D2}$ is independently aliphatic C$_{2-6}$alkenyl;
each —R$^{1D3}$ is independently aliphatic C$_{2-6}$alkynyl;
each —R$^{1D4}$ is independently saturated C$_{3-6}$cycloalkyl;
each —R$^{1D5}$ is independently C$_{3-6}$cycloalkenyl;
each —R$^{1D6}$ is independently non-aromatic C$_{3-8}$heterocyclyl;
each —R$^{1D7}$ is independently C$_{6-10}$carboaryl;

each —$R^{1D8}$ is independently $C_{5-10}$heteroaryl;
each -$L^{1D}$- is independently saturated aliphatic $C_{1-3}$alkylene;
wherein:
  each —$R^{1D4}$, —$R^{1D5}$, —$R^{1D6}$, —$R^{1D7}$, and —$R^{1D8}$ is optionally substituted, for example, with one or more substituents —$R^{1E1}$ and/or one or more substituents —$R^{1E2}$,
  each —$R^{1D1}$, —$R^{1D2}$, —$R^{1D3}$, and -$L^{1D}$- is optionally substituted, for example, with one or more substituents —$R^{1E2}$, and
wherein:
  each —$R^{1E1}$ is independently saturated aliphatic $C_{1-4}$alkyl, phenyl, or benzyl;
  each —$R^{1E2}$ is independently:
    —F, —Cl, —Br, —I,
    —$CF_3$, —$OCF_3$,
    —OH, -$L^{1F}$-OH, —O-$L^{1F}$-OH,
    —$OR^{1F1}$, -$L^{1F}$-$OR^{1F1}$, —O-$L^{1F}$-$OR^{1F1}$,
    —SH, —$SR^{1F1}$,
    —CN,
    —$NO_2$,
    —$NH_2$, —$NHR^{1F1}$, —$NR^{1F1}{}_2$, —$NR^{1F2}R^{1F3}$,
    -$L^{1F}$-$NH_2$, -$L^{1F}$-$NHR^{1F1}$, -$L^{1F}$-$NR^{1F1}{}_2$, -$L^{1F}$-$NR^{1F2}R^{1F3}$,
    —C(=O)OH, —C(=O)$OR^{1F1}$,
    —C(=O)$NH_2$, —C(=O)$NHR^{1F1}$, —C(=O)$NR^{1F1}{}_2$, or —C(=O)$NR^{1F2}R^{1F3}$;
wherein:
  each —$R^{1F1}$ is independently saturated aliphatic $C_{1-4}$alkyl, phenyl, or benzyl;
  each -$L^{1F}$- is independently saturated aliphatic $C_{1-5}$alkylene; and
  in each group —$NR^{1F2}R^{1F3}$, $R^{1F2}$ and $R^{1F3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each -$L^{1A}$-, if present, is independently —$CH_2$—.

In one embodiment, each —$R^{1A1}$, if present, is independently saturated aliphatic $C_{1-3}$alkyl.

In one embodiment, each —$R^{1A4}$, if present, is independently saturated $C_{3-5}$cycloalkyl.

In one embodiment, each —$R^{1A4}$, if present, is independently saturated $C_3$cycloalkyl.

In one embodiment, each —$R^{1A6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{1A6}$, if present, is independently pyrrolidinyl, piperidinyl, piperazinyl, morpholinyl, tetrahydrofuranyl, or tetrahydropyranyl, and is optionally substituted.

In one embodiment, each —$R^{1A7}$, if present, is independently phenyl or naphthyl, and is optionally substituted.

In one embodiment, each —$R^{1A7}$, if present, is independently phenyl, and is optionally substituted.

In one embodiment, each —$R^{1A7}$, if present, is independently selected from groups of the following formulae, wherein each —$R^{1X}$ is independently —$R^{1B1}$ or —$R^{1B2}$:

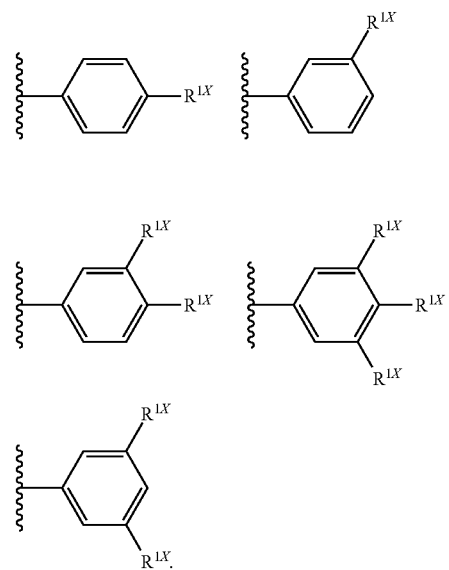

In one embodiment, each —$R^{1A7}$, if present, is independently selected from groups of the following formulae, wherein each —$R^{1X}$ is independently —$R^{1B1}$ or —$R^{1B2}$:

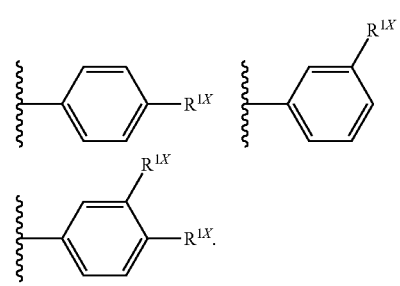

In one embodiment, each —$R^{1A7}$, if present, is independently selected from groups of the following formula, wherein each —$R^{1X}$ is independently —$R^{1B1}$ or —$R^{1B2}$:

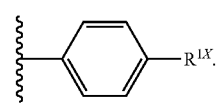

In one embodiment, each —$R^{1A7}$, if present, is independently selected from groups of the following formula, wherein each —$R^{1X}$ is independently —$R^{1B1}$ or —$R^{1B2}$:

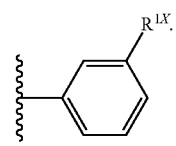

In one embodiment, each —$R^{1A7}$, if present, is independently selected from groups of the following formula, wherein each —$R^{1X}$ is independently —$R^{1B1}$ or —$R^{1B2}$:

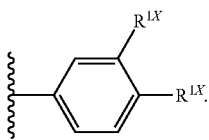

In one embodiment, each —$R^{1A8}$, if present, is independently $C_{5-6}$heteroaryl, and is optionally substituted.

In one embodiment, each —$R^{1A8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{1A8}$, if present, is independently furanyl, thienyl, pyridyl, or pyrimidinyl, and is optionally substituted.

In one embodiment, each —$R^{1A8}$, if present, is independently pyridyl, and is optionally substituted.

In one embodiment, each —$R^{1A8}$, if present, is independently pyrid-3-yl or pyrid-4-yl, and is optionally substituted.

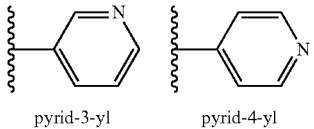

pyrid-3-yl    pyrid-4-yl

In one embodiment, each —$R^{1A8}$, if present, is independently selected from groups of the following formulae, wherein each —$R^{1X}$ is independently —$R^{1B1}$ or —$R^{1B2}$:

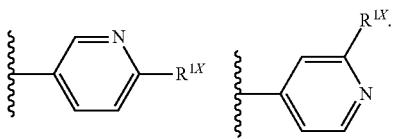

In one embodiment, each —$R^{1A8}$, if present, is independently $C_{9-10}$heteroaryl, and is optionally substituted.

In one embodiment, each —$R^{1A8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each —$R^{1B1}$ is independently:
—$R^{1D1}$, —$R^{1D2}$, —$R^{1D4}$, —$R^{1D6}$,
-$L^{1D}$-$R^{1D4}$, or -$L^{1D}$-$R^{1D6}$.

In one embodiment, each —$R^{1B1}$ is independently:
—$R^{1D4}$, —$R^{1D7}$, —$R^{1D8}$,
-$L^{1D}$-$R^{1D4}$, -$L^{1D}$-$R^{1D7}$, or -$L^{1D}$-$R^{1D8}$.

In one embodiment, each —$R^{1B1}$ is independently:
—$R^{1D7}$, —$R^{1D8}$, -$L^{1D}$-$R^{1D7}$, or -$L^{1D}$-$R^{1D8}$.

In one embodiment, each —$R^{1B1}$ is independently:
—$R^{1D1}$, —$R^{1D2}$, —$R^{1D4}$, —$R^{1D7}$, —$R^{1D8}$,
-$L^{1D}$-$R^{1D4}$, -$L^{1D}$-$R^{1D6}$, -$L^{1D}$-$R^{1D7}$, or -$L^{1D}$-$R^{1D8}$.

In one embodiment, each —$R^{1B2}$ is independently:
—F, —Cl,
—$CF_3$, —$OCF_3$,
—OH, -$L^{1C}$-OH, —O-$L^{1C}$-OH,
—$OR^{1C1}$, -$L^{1C}$-$OR^{1C1}$, —O-$L^{1C}$-$OR^{1C1}$,
—$SR^{1C1}$,
—CN,
—$NO_2$,
—$NH_2$, —$NHR^{1C1}$, —$NR^{1C1}_2$, —$NR^{1C2}R^{1C3}$,
-$L^{1C}$-$NH_2$, -$L^{1C}$-$NHR^{1C1}$, -$L^{1C}$-$NR^{1C1}_2$, -$L^{1C}$-$NR^{1C2}R^{1C3}$,
—O-$L^{1C}$-$NH_2$, —O-$L^{1C}$-$NHR^{1C1}$, —O-$L^{1C}$-$NR^{1C1}_2$, —O-$L^{1C}$-$NR^{1C2}R^{1C3}$,
—C(=O)$OR^{1C1}$,
—C(=O)$R^{1C1}$,
—C(=O)$NH_2$, —C(=O)$NHR^{1C1}$, —C(=O)$NR^{1C1}_2$, —C(=O)$NR^{1C2}R^{1C3}$,
—NHC(=O)$R^{1C1}$, —$NR^{1C1}$C(=O)$R^{1C1}$,
—NHC(=O)$NH_2$, —NHC(=O)$NHR^{1C1}$,
—NHC(=O)$NR^{1C1}_2$, —NHC(=O)$NR^{1C2}R^{1C3}$,
—$NR^{1C1}$C(=O)$NH_2$, —$NR^{1C1}$C(=O)$NHR^{1C1}$,
—$NR^{1C1}$C(=O)$NR^{1C1}_2$, —$NR^{1C1}$C(=O)$NR^{1C2}R^{1C3}$,
—NHS(=O)$_2R^{1C1}$, —$NR^{1C1}$S(=O)$_2R^{1C1}$,
—S(=O)$_2NH_2$, —S(=O)$_2NHR^{1C1}$, —S(=O)$_2NR^{1C1}_2$,
—S(=O)$_2NR^{1C2}R^{1C3}$,
—S(=O)$R^{1C1}$, or —S(=O)$_2R^{1C1}$.

In one embodiment, each —$R^{1B2}$ is independently:
—F, —Cl,
—$CF_3$, —$OCF_3$,
—OH, -$L^{1C}$-OH, —O-$L^{1C}$-OH,
—$OR^{1C1}$, -$L^{1C}$-$OR^{1C1}$, —O-$L^{1C}$-$OR^{1C1}$,
—$SR^{1C1}$,
—CN,
—$NO_2$,
—$NH_2$, —$NHR^{1C1}$, —$NR^{1C1}_2$, —$NR^{1C2}R^{1C3}$,
-$L^{1C}$-$NH_2$, -$L^{1C}$-$NHR^{1C1}$, -$L^{1C}$-$NR^{1C1}_2$, -$L^{1C}$-$NR^{1C2}R^{1C3}$,
—O-$L^{1C}$-$NH_2$, —O-$L^{1C}$-$NHR^{1C1}$, —O-$L^{1C}$-$NR^{1C1}_2$, —O-$L^{1C}$-$NR^{1C2}R^{1C3}$,
—C(=O)$R^{1C1}$,
—C(=O)$NHR^{1C1}$, —C(=O)$NR^{1C1}_2$, —C(=O)$NR^{1C2}R^{1C3}$,
—NHC(=O)$R^{1C1}$, —$NR^{1C1}$C(=O)$R^{1C1}$,
—NHC(=O)$NHR^{1C1}$,
—NHC(=O)$NR^{1C1}_2$, —NHC(=O)$NR^{1C2}R^{1C3}$,
—$NR^{1C1}$C(=O)$NHR^{1C1}$,
—$NR^{1C1}$C(=O)$NR^{1C1}_2$, —$NR^{1C1}$C(=O)$NR^{1C2}R^{1C3}$,
—NHS(=O)$_2R^{1C1}$, —$NR^{1C1}$S(=O)$_2R^{1C1}$,
—S(=O)$NHR^{1C1}$, —S(=O)$_2NR^{1C1}_2$, —S(=O)$_2NR^{1C2}R^{1C3}$,
—S(=O)$R^{1C1}$, or —S(=O)$_2R^{1C1}$.

In one embodiment, each -$L^{1C}$ is saturated aliphatic $C_{1-3}$alkylene.

In one embodiment, each —$NR^{1C2}R^{1C3}$ is independently azetidino, pyrrolidino, imidazolidino, pyrazolidino, piperidino, piperazino, morpholino, azepino, or diazepino, and is optionally substituted, for example, with one or more groups selected from saturated aliphatic $C_{1-3}$alkyl, —F, and —$CF_3$.

In one embodiment, each —$NR^{1C2}R^{1C3}$ is independently pyrrolidino, piperidino, piperazino, or morpholino, and is optionally substituted, for example, with one or more groups selected from saturated aliphatic $C_{1-3}$alkyl, —F, and —$CF_3$.

In one embodiment, each —$R^{1C1}$ is independently:
—$R^{1D1}$, —$R^{1D4}$, —$R^{1D6}$,
-$L^{1D}$-$R^{1D4}$, or -$L^{1D}$-$R^{1D6}$.

In one embodiment, each —$R^{1C1}$ is independently:
—$R^{1D1}$, —$R^{1D4}$, —$R^{1D6}$, —$R^{1D7}$, —$R^{1D8}$,
-$L^{1D}$-$R^{1D4}$, -$L^{1D}$-$R^{1D6}$, -$L^{1D}$-$R^{1D7}$, or -$L^{1D}$-$R^{1D8}$.

In one embodiment, each —$R^{1C1}$ is independently:
—$R^{1D1}$, —$R^{1D4}$, —$R^{1D7}$, —$R^{1D8}$,
-$L^{1D}$-$R^{1D4}$, -$L^{1D}$-$R^{1D7}$, or -$L^{1D}$-$R^{1D8}$.

In one embodiment, each —$R^{1C1}$ is independently:
—$R^{1D1}$, —$R^{1D7}$, —$R^{1D8}$, -$L^{1D}$-$R^{1D7}$, or -$L^{1D}$-$R^{1D8}$.

In one embodiment, each —$R^{1C1}$ is independently —$R^{1D1}$, —$R^{1D7}$, or -$L^{1D}$-$R^{1D7}$.

In one embodiment, each —$R^{1C1}$ is independently —$R^{1D7}$ or -$L^{1D}$-$R^{1D7}$.

In one embodiment, each —$R^{1C1}$ is independently —$R^{1D1}$.

In one embodiment, each -$L^{1D}$-, if present, is independently —$CH_2$—.

In one embodiment, each —$R^{1D1}$, if present, is independently saturated aliphatic $C_{1-3}$alkyl.

In one embodiment, each —$R^{1D4}$, if present, is independently saturated $C_{5-6}$cycloalkyl.

In one embodiment, each —$R^{1D6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{1D6}$, if present, is independently pyrrolidinyl, piperidinyl, piperazinyl, morpholinyl, tetrahydrofuranyl, or tetrahydropyranyl, and is optionally substituted.

In one embodiment, each —$R^{1D7}$, if present, is independently phenyl or naphthyl, and is optionally substituted.

In one embodiment, each —$R^{1D7}$, if present, is independently phenyl, and is optionally substituted.

In one embodiment, each —$R^{1D8}$, if present, is independently $C_{5-6}$heteroaryl, and is optionally substituted.

In one embodiment, each —$R^{1D8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{1D8}$, if present, is independently $C_{9-10}$heteroaryl, and is optionally substituted.

In one embodiment, each —$R^{1D8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each —$R^{1E1}$ is independently saturated aliphatic $C_{1-4}$alkyl.

In one embodiment, each —$R^{1E2}$ is independently:
- —F, —Cl, —Br,
- —$CF_3$, —$OCF_3$,
- —OH, -$L^{1F}$-OH, —O-$L^{1F}$-OH,
- —$OR^{1F1}$, -$L^{1F}$-$OR^{1F1}$, —O-$L^{1F}$-$OR^{1F1}$,
- —$SR^{1F1}$,
- —CN,
- —$NO_2$,
- —$NH_2$, —$NHR^{1F1}$, —$NR^{1F1}{}_2$, —$NR^{1F2}R^{1F3}$,
- -$L^{1F}$-$NH_2$, -$L^{1F}$-$NHR^{1F1}$, -$L^{1F}$-$NR^{1F1}{}_2$, -$L^{1F}$-$NR^{1F2}R^{1F3}$,
- —C(=O)$OR^{1F1}$,
- —C(=O)$NHR^{1F1}$, —C(=O)$NR^{1F1}{}_2$, or —C(=O)$NR^{1F2}R^{1F3}$.

In one embodiment, each —$R^{1E2}$ is independently:
- —F, —Cl,
- —$CF_3$, —$OCF_3$,
- —CN,
- —OH, -$L^{1F}$-OH, —O-$L^{1F}$-OH,
- —$OR^{1F1}$, -$L^{1F}$-$OR^{1F1}$, —O-$L^{1F}$-$OR^{1F1}$,
- —$NH_2$, —$NHR^{1F1}$, —$NR^{1F1}{}_2$, —$NR^{1F2}R^{1F3}$,
- -$L^{1F}$-$NH_2$, -$L^{1F}$-$NHR^{1F1}$, -$L^{1F}$-$NR^{1F1}{}_2$, -$L^{1F}$-$NR^{1F2}R^{1F3}$,
- —C(=O)$NHR^{1F1}$, —C(=O)$NR^{1F1}{}_2$, or —C(=O)$NR^{1F2}R^{1F3}$.

In one embodiment, each —$R^{1F1}$ is independently saturated aliphatic $C_{1-4}$alkyl.

In one embodiment, each -$L^{1F}$ is saturated aliphatic $C_{1-3}$alkylene.

In one embodiment, each —$NR^{1F2}R^{1F3}$ is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —F, and —$CF_3$.

In one embodiment, each —$NR^{1F2}R^{1F3}$ is independently pyrrolidino, piperidino, piperazino, or morpholino, and is optionally substituted, for example, with one or more groups selected from $C_{1-3}$alkyl, —F, and —$CF_3$.

The Group -$Q^{5A}$

In one embodiment, -$Q^{5A}$, if present, is independently:
- —$R^{2A1}$, —$R^{2A2}$, —$R^{2A3}$, —$R^{2A4}$, —$R^{2A5}$, —$R^{2A6}$, —$R^{2A7}$, —$R^{2A8}$,
- -$L^{2A}$-$R^{2A4}$, -$L^{2A}$-$R^{2A5}$, -$L^{2A}$-$R^{2A6}$, -$L^{2A}$-$R^{2A7}$, -$L^{2A}$-$R^{1A8}$,
- —F, —Cl, —Br, —I,
- —$CF_3$, —$OCF_3$,
- —OH, -$L^{2C}$-OH, —O-$L^{2C}$-OH,
- -$L^{2C}$-$OR^{2C1}$, —O-$L^{2C}$-$OR^{2C1}$,
- —O—$R^{2D4}$, —O—$R^{2D6}$, —O—$R^{2D7}$, —O—$R^{2D8}$,
- —O-$L^{2D}$-$R^{2D4}$, —O-$L^{2D}$-$R^{2D6}$, —O-$L^{2D}$-$R^{2D7}$, —O-$L^{2D}$-$R^{2D8}$,
- —SH, —$SR^{2C1}$,
- —CN,
- —$NO_2$,
- —$NH_2$, —$NHR^{2C1}$, —$NR^{2C1}{}_2$, —$NR^{2C2}R^{2C3}$,
- -$L^{2C}$-$NH_2$, -$L^{2C}$-$NHR^{2C1}$, -$L^{2C}$-$NR^{2C1}{}_2$, -$L^{2C}$-$NR^{2C2}R^{2C3}$,
- —O-$L^{2C}$-$NH_2$, —O-$L^{2C}$-$NHR^{2C1}$, —O-$L^{2C}$-$NR^{2C1}{}_2$, —O-$L^{2C}$-$NR^{2C2}R^{2C3}$,
- —C(=O)OH, —C(=O)$OR^{2C1}$,
- —C(=O)$R^{2C1}$,
- —C(=O)$NH_2$, —C(=O)$NHR^{2C1}$, —C(=O)$NR^{2C1}{}_2$, —C(=O)$NR^{2C2}R^{2C3}$,
- —NHC(=O)$R^{2C1}$, —$NR^{2C1}$C(=O)$R^{2C1}$,
- —NHC(=O)$OR^{2C1}$, —$NR^{2C1}$C(=O)$OR^{2C1}$,
- —OC(=O)$NH_2$, —OC(=O)$NHR^{2C1}$, —OC(=O)$NR^{2C1}{}_2$, —OC(=O)$NR^{2C2}R^{2C3}$,
- —NHC(=O)$NH_2$, —NHC(=O)$NHR^{2C1}$,
- —NHC(=O)$NR^{2C1}{}_2$, —NHC(=O)$NR^{2C2}R^{2C3}$,
- —$NR^{2C1}$C(=O)$NH_2$, —$NR^{2C1}$C(=O)$NHR^{2C1}$,
- —$NR^{2C1}$C(=O)$NR^{1C1}{}_2$, —$NR^{2C1}$C(=O)$NR^{2C2}R^{2C3}$,
- —NHS(=O)$_2R^{2C1}$, —$NR^{1C1}$S(=O)$_2R^{2C1}$,
- —S(=O)$_2NH_2$, —S(=O)$_2NHR^{2C1}$, —S(=O)$_2NR^{2C1}{}_2$, —S(=O)$_2NR^{2C2}R^{2C3}$,
- —S(=O)$R^{2C1}$, —S(=O)$_2R^{2C1}$, —OS(=O)$_2R^{2C1}$, or —S(=O)$_2OR^{2C1}$.

In one embodiment, -$Q^{5A}$, if present, is independently:
- —$R^{2A1}$, —$R^{2A2}$, —$R^{2A3}$, —$R^{2A4}$, —$R^{2A5}$, —$R^{2A6}$, —$R^{2A7}$, —$R^{2A8}$,
- -$L^{2A}$-$R^{2A4}$, -$L^{2A}$-$R^{2A5}$, -$L^{2A}$-$R^{2A6}$, -$L^{2A}$-$R^{2A7}$, -$L^{2A}$-$R^{1A8}$,
- —$CF_3$, —$OCF_3$,
- -$L^{2C}$-OH, —O-$L^{2C}$-OH,
- -$L^{2C}$-$OR^{2C1}$, —O-$L^{2C}$-$OR^{2C1}$,
- —O—$R^{2D4}$, —O—$R^{2D6}$, —O—$R^{2D7}$, —O—$R^{2D8}$,
- —O-$L^{2D}$-$R^{2D4}$, —O-$L^{2D}$-$R^{2D6}$, —O-$L^{2D}$-$R^{2D7}$, —O-$L^{2D}$-$R^{2D8}$,
- —$SR^{2C1}$,
- —$NHR^{2C1}$, —$NR^{2C1}{}_2$, —$NR^{2C2}R^{2C3}$,
- -$L^{2C}$-$NH_2$, -$L^{2C}$-$NHR^{2C1}$, -$L^{2C}$-$NR^{2C1}{}_2$, -$L^{2C}$-$NR^{2C2}R^{2C3}$,
- —O-$L^{2C}$-$NH_2$, —O-$L^{2C}$-$NHR^{2C1}$, —O-$L^{2C}$-$NR^{2C1}{}_2$, —O-$L^{2C}$-$NR^{2C2}R^{2C3}$,
- —C(=O)$OR^{2C1}$,
- —C(=O)$R^{2C1}$,
- —C(=O)$NH_2$, —C(=O)$NHR^{2C1}$, —C(=O)$NR^{2C1}{}_2$, —C(=O)$NR^{2C2}R^{2C3}$,
- —NHC(=O)$R^{2C1}$, —$NR^{2C1}$C(=O)$R^{2C1}$, —NHC(=O)NH$_2$, —NHC(=O)NHR$^{2C1}$,
—NHC(=O)NR$^{2C1}$$_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{1C1}$$_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NH$_2$, —S(=O)$_2$NHR$^{2C1}$, —S(=O)$_2$NR$^{2C1}$$_2$,
—S(=O)$_2$NR$^{2C2}$R$^{2C3}$,
—S(=OR$^{2C1}$, or —S(=O)$_2$R$^{2C1}$.

In one embodiment, -Q$^{5A}$, if present, is independently:
—R$^{2A1}$, —R$^{2A2}$, —R$^{2A3}$, —R$^{2A4}$, —R$^{2A5}$, —R$^{2A6}$,
—R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
-L$^{2C}$-OR$^{2C1}$, —O-L$^{2C}$-OR$^{2C1}$,
—O—R$^{2D4}$, —O—R$^{2D6}$, —O—R$^{2D7}$, —O—R$^{2D8}$,
—O-L$^{2D}$-R$^{2D4}$, —O-L$^{2D}$-R$^{2D6}$, —O-L$^{2D}$-R$^{2D7}$,
—O-L$^{2D}$-R$^{2D8}$,
—SR$^{2C1}$,
—NHR$^{2C1}$, —NR$^{2C1}$$_2$, —NR$^{2C2}$R$^{2C3}$,
-L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NHR$^{2C1}$, —O-L$^{2C}$-NR$^{2C1}$$_2$ —O-L$^{2C}$-NR$^{2C2}$R$^{2C3}$,
—C(=O)NHR$^{2C1}$,
—C(=O)NHR$^{2C1}$, —C(=O)NR$^{2C1}$$_2$, —C(=O)NR$^{2C2}$R$^{2C3}$,
—NHC(=O)R$^{2C1}$, —NR$^{2C1}$C(=O)R$^{2C1}$,
—NHC(=O)NHR$^{2C1}$,
—NHC(=O)NR$^{2C1}$$_2$, —NHC(=O)NR$^{2C2}$R$^{2C3}$,
—NR$^{2C1}$C(=O)NHR$^{2C1}$,
—NR$^{2C1}$C(=O)NR$^{1C1}$$_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NHR$^{2C1}$, —S(=O)$_2$NR$^{2C1}$$_2$, —S(=O)$_2$NR$^{2C2}$R$^{2C3}$,
—S(=O)R$^{2C1}$, or —S(=O)$_2$R$^{2C1}$.

In one embodiment, -Q$^{5A}$, if present, is independently:
—R$^{2A1}$, —R$^{2A2}$, —R$^{2A3}$, —R$^{2A4}$, —R$^{2A5}$, —R$^{2A6}$,
—R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
-L$^{2C}$-OR$^{2C1}$, —O-L$^{2C}$-OR$^{2C1}$,
—SR$^{2C1}$,
—NHR$^{2C1}$, —NR$^{2C1}$$_2$, —NR$^{2C2}$R$^{2C3}$,
-L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NHR$^{2C1}$, —O-L$^{2C}$-NR$^{2C1}$$_2$, —O-L$^{2C}$-NR$^{2C2}$R$^{2C3}$,
—C(=O)R$^{2C1}$,
—C(=O)NHR$^{2C1}$, —C(=O)NR$^{2C1}$$_2$, —C(=O)NR$^{2C2}$R$^{2C3}$,
—NHC(=O)R$^{2C1}$, —NR$^{2C1}$C(=O)R$^{2C1}$,
—NHC(=O)NHR$^{2C1}$,
—NHC(=O)NR$^{2C1}$$_2$, —NHC(=O)NR$^{2C2}$R$^{2C3}$,
—NR$^{2C1}$C(=O)NHR$^{2C1}$,
—NR$^{2C1}$C(=O)NR$^{1C1}$$_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NHR$^{2C1}$, —S(=O)$_2$NR$^{2C1}$$_2$, —S(=O)$_2$NR$^{2C2}$R$^{2C3}$,
—S(=O)R$^{2C1}$, or —S(=O)$_2$R$^{2C1}$.

In one embodiment, -Q$^{5A}$, if present, is independently:
—R$^{2A1}$, —R$^{2A2}$, —R$^{2A3}$, —R$^{2A4}$, —R$^{2A5}$, —R$^{2A6}$,
—R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
-L$^{2C}$-OR$^{2C1}$, —O-L$^{2C}$-OR$^{2C1}$,
—SR$^{2C1}$,
—NHR$^{2C1}$, —NR$^{2C1}$$_2$, —NR$^{2C2}$R$^{2C3}$,
-L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NHR$^{2C1}$, —O-L$^{2C}$-NR$^{2C1}$$_2$, —O-L$^{2C}$-NR$^{2C2}$R$^{2C3}$,
—C(=O)NHR$^{2C1}$, —C(=O)NR$^{2C1}$$_2$, —C(=O)NR$^{2C2}$R$^{2C3}$,
—NHC(=O)R$^{2C1}$, or —NR$^{2C1}$C(=O)R$^{2C1}$.

In one embodiment, -Q$^{5A}$, if present, is independently —R$^{2A7}$ or —R$^{2A8}$.

In one embodiment, -Q$^{5A}$, if present, is independently —R$^{2A7}$.

In one embodiment, -Q$^{5A}$, if present, is independently —R$^{2A8}$.

In one embodiment, -Q$^{5A}$, if present, is independently selected from those groups exemplified for -Q$^{5A}$ in the compounds shown below under the heading "Examples of Specific Embodiments".

The Group -Q$^{8A}$

In one embodiment, -Q$^{8A}$, if present, is independently:
—R$^{2A1}$, —R$^{2A2}$, —R$^{2A3}$, —R$^{2A4}$, —R$^{2A5}$, —R$^{2A6}$,
—R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
—F, —Cl, —Br, —I,
—CF$_3$, —OCF$_3$,
—OH, -L$^{2C}$-OH, —O-L$^{2C}$-OH,
-L$^{2C}$-OR$^{2C1}$, —O-L$^{2C}$-OR$^{2C1}$,
—SH, —SR$^{2C1}$,
—NO$_2$,
—NH$_2$, —NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$,
—O-L$^{2C}$-NR$^{2C2}$R$^{2C3}$,
—C(=O)R$^{2C1}$,
—C(=O)NH$_2$, —C(=O)NHR$^{2C1}$, —C(=O)NR$^{2C1}$$_2$,
—C(=O)NR$^{2C2}$R$^{2C3}$,
—NHC(=O)R$^{2C1}$, —NR$^{2C1}$C(=O)R$^{2C1}$,
—NHC(=O)OR$^{2C1}$, —NR$^{2C1}$C(=O)OR$^{2C1}$,
—OC(=O)NH$_2$, —OC(=O)NHR$^{2C1}$, —OC(=O)NR$^{2C1}$$_2$, —OC(=O)NR$^{2C2}$R$^{2C3}$,
—NHC(=O)NH$_2$, —NHC(=O)NHR$^{2C1}$,
—NHC(=O)NR$^{2C1}$$_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{1C1}$$_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NH$_2$, —S(=O)$_2$NHR$^{2C1}$, —S(=O)$_2$NR$^{2C1}$$_2$,
—S(=O)$_2$NR$^{2C2}$R$^{2C3}$,
—S(=O)R$^{2C1}$, —S(=O)$_2$R$^{2C1}$, —OS(=O)$_2$R$^{2C1}$, or
—S(=O)$_2$OR$^{2C1}$.

In one embodiment, -Q$^{8A}$, if present, is independently:
—R$^{2A1}$, —R$^{2A4}$, —R$^{2A6}$, —R$^{2A8}$,
L$^{2A}$-R$^{2A4}$, -L$^{2A}$-R$^{2A6}$, -L$^{2A}$-R$^{1A8}$,
—F, —Cl,
—CF$_3$, —OCF$_3$,
—OH, -L$^{2C}$-OH, —O-L$^{2C}$-OH,
-L$^{2C}$-OR$^{2C1}$, —O-L$^{2C}$-OR$^{2C1}$,
—SR$^{2C1}$,
—NO$_2$,
—NH$_2$, —NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$,
—O-L$^{2C}$-NR$^{2C2}$R$^{2C3}$,
—C(=O)R$^{2C1}$,
—C(=O)NHR$^{2C1}$, —C(=O)NR$^{2C1}$$_2$, —C(=O)NR$^{2C2}$R$^{2C3}$,
—NHC(=O)R$^{2C1}$, —NR$^{2C1}$C(=O)R$^{2C1}$,
—NHC(=O)NHR$^{2C1}$,
—NHC(=O)NR$^{2C1}$$_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{1C1}$$_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$, —S(=O)$_2$NHR$^{2C1}$, —S(=O)$_2$NR$^{2C1}$$_2$, —S(=O)$_2$NR$^{2C2}$R$^{2C3}$,
—S(=O)R$^{2C1}$, or —S(=O)$_2$R$^{2C1}$.

In one embodiment, -Q$^{8A}$, if present, is independently:
—R$^{2A1}$, —R$^{2A4}$,
—F, —Cl,
—NO$_2$,
—CF$_3$, —OCF$_3$,
—OH, -L$^{2C}$-OH, —O-L$^{2C}$-OH,
-L$^{2C}$-OR$^{2C1}$, —O-L$^{2C}$-OR$^{2C1}$,
—SR$^{2C1}$,
—NH$_2$, —NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$, or —O-L$^{2C}$-NR$^{2C2}$R$^{2C3}$.

In one embodiment, -Q$^{8A}$, if present, is independently selected from those groups exemplified for -Q$^{8A}$ in the compounds shown below under the heading "Examples of Specific Embodiments".

The Group -Q$^{5B}$

In one embodiment, -Q$^{5B}$, if present, is independently:
—R$^{2A2}$, —R$^{2A3}$, —R$^{2A4}$, —R$^{2A5}$, —R$^{2A6}$, —R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
—F, —Cl, —Br, —I,
—CF$_3$, —OCF$_3$,
—OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SH, —SR$^{2C1}$,
—CN,
—NO$_2$,
—NH$_2$, —NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$, —O-L$^{2C}$-NR$^{2C2}$R$^{2C3}$,
—C(=O)OH, —C(=O)OR$^{2C1}$,
—C(=O)R$^{2C1}$,
—C(=O)NH$_2$, —C(=O)NHR$^{2C1}$, —C(=O)NR$^{2C1}$$_2$, —C(=O)NR$^{2C2}$R$^{2C3}$,
—NHC(=O)R$^{2C1}$, —NR$^{2C1}$C(=O)R$^{2C1}$,
—NHC(=O)OR$^{2C1}$, —NR$^{2C1}$C(=O)OR$^{2C1}$,
—OC(=O)NH$_2$, —OC(=O)NHR$^{2C1}$, —OC(=O)NR$^{2C1}$$_2$, —OC(=O)NR$^{2C2}$R$^{2C3}$,
—NHC(=O)NH$_2$, —NHC(=O)NHR$^{2C1}$,
—NHC(=O)NR$^{2C1}$$_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{1C1}$$_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NH$_2$, —S(=O)$_2$NHR$^{2C1}$, —S(=O)$_2$NR$^{2C1}$$_2$, —S(=O)$_2$NR$^{2C2}$R$^{2C3}$,
—S(=O)R$^{2C1}$, —S(=O)$_2$R$^{2C1}$, —OS(=O)$_2$R$^{2C1}$, or —S(=O)$_2$OR$^{2C1}$.

In one embodiment, -Q$^{5B}$, if present, is independently:
—R$^{2A2}$, —R$^{2A3}$, —R$^{2A4}$, —R$^{2A5}$, —R$^{2A6}$, —R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
-L$^{2C}$-OH, —O-L$^{2C}$-OH,
—OR$^{2C1}$, -L$^{2C}$-OR$^{2C1}$, —O-L$^{2C}$-OR$^{2C1}$,
—SR$^{2C1}$,
—NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$, —O-L$^{2C}$-NR$^{2C2}$R$^{2C3}$,
—C(=O)R$^{2C1}$,
—C(=O)NH$_2$, —C(=O)NHR$^{2C1}$, —C(=O)NR$^{2C1}$$_2$, —C(=O)NR$^{2C2}$R$^{2C3}$,
—NHC(=O)R$^{2C1}$, —NR$^{2C1}$C(=O)R$^{2C1}$,
—NHC(=O)NHR$^{2C1}$,
—NHC(=O)NR$^{2C1}$$_2$, —NHC(=O)NR$^{2C2}$R$^{2C3}$,
—NR$^{2C1}$C(=O)NHR$^{2C1}$,
—NR$^{2C1}$C(=O)NR$^{1C1}$$_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NHR$^{2C1}$, —S(=O)$_2$NR$^{2C1}$$_2$, —S(=O)$_2$NR$^{2C2}$R$^{2C3}$,
—S(=O)R$^{2C1}$, or —S(=O)$_2$R$^{2C1}$.

In one embodiment, -Q$^{5B}$, if present, is independently:
—R$^{2A2}$, —R$^{2A3}$, —R$^{2A4}$, —R$^{2A5}$, —R$^{2A6}$, —R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
-L$^{2C}$-OH, —O-L$^{2C}$-OH,
—OR$^{2C1}$, -L$^{2C}$-OR$^{2C1}$, —O-L$^{2C}$-OR$^{2C1}$,
—SR$^{2C1}$,
—NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$, —O-L$^{2C}$-NR$^{2C2}$R$^{2C3}$,
—C(=O)NHR$^{2C1}$, —C(=O)NR$^{2C1}$$_2$, —C(=O)NR$^{2C2}$R$^{2C3}$,
—NHC(=O)R$^{2C1}$, or —NR$^{2C1}$C(=O)R$^{2C1}$.

In one embodiment, -Q$^{5B}$, if present, is independently —R$^{2A7}$ or —R$^{2A8}$.

In one embodiment, -Q$^{5B}$, if present, is independently —R$^{2A7}$.

In one embodiment, -Q$^{5B}$, if present, is independently —R$^{2A8}$.

In one embodiment, -Q$^{5B}$, if present, is independently selected from those groups exemplified for -Q$^{5B}$ in the compounds shown below under the heading "Examples of Specific Embodiments".

The Group -Q$^{8B}$

In one embodiment, -Q$^{8B}$, if present, is independently:
—R$^{2A1}$, —R$^{2A2}$, —R$^{2A3}$, —R$^{2A4}$, —R$^{2A5}$, —R$^{2A6}$, —R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
—F, —Cl, —Br, —I,
—CF$_3$, —OCF$_3$, —OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SH, —SR$^{2C1}$,
—ON,
—NO$_2$,
—NH$_2$, —NHR$^{2C1}$, —NR$^{2C1}_2$, —NR$^{2C2}$R$^{2C3}$,
-L$^{2C}$-NH$_2$, -L$^{2C}$-NHR$^{2C1}$, -L$^{2C}$-NR$^{2C1}_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}_2$, —O-L$^{2C}$-NR$^{2C2}$R$^{2C3}$,
—C(=O)OH, —C(=O)OR$^{2C1}$,
—C(=O)R$^{2C1}$,
—C(=O)NH$_2$, —C(=O)NHR$^{2C1}$, —C(=O)NR$^{2C1}_2$, —C(=O)NR$^{2C2}$R$^{2C3}$,
—NHC(=O)R$^{2C1}$, —NR$^{2C1}$C(=O)R$^{2C1}$,
—NHC(=O)OR$^{2C1}$, —NR$^{2C1}$C(=O)OR$^{2C1}$,
—OC(=O)NH$_2$, —OC(=O)NHR$^{2C1}$, —OC(=O)NR$^{2C1}_2$, —OC(=O)NR$^{2C2}$R$^{2C3}$,
—NHC(=O)NH$_2$, —NHC(=O)NHR$^{2C1}$,
—NHC(=O)NR$^{2C1}_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{1C1}_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NH$_2$, —S(=O)$_2$NHR$^{2C1}$, —S(=O)$_2$NR$^{2C1}_2$, —S(=O)$_2$NR$^{2C2}$R$^{2C3}$,
—S(=O)R$^{2C1}$, —S(=O)$_2$R$^{2C1}$, —OS(=O)$_2$R$^{2C1}$, or —S(=O)$_2$OR$^{2C1}$.

In one embodiment, -Q$^{8B}$, if present, is independently:
—R$^{2A1}$, —R$^{2A4}$, —R$^{2A5}$, —R$^{2A6}$, —R$^{2A8}$,
-L$^{2A}$-R$^{2A4}$, -L$^{2A}$-R$^{2A5}$, -L$^{2A}$-R$^{2A6}$, -L$^{2A}$-R$^{1A8}$,
—F, —Cl,
—CF$_3$, —OCF$_3$,
—OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SR$^{2C1}$,
—CN,
—NO$_2$,
—NH$_2$, —NHR$^{2C1}$, —NR$^{2C1}_2$, —NR$^{2C2}$R$^{2C3}$,
-L$^{2C}$-NH$_2$, -L$^{2C}$-NHR$^{2C1}$, -L$^{2C}$-NR$^{2C1}_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}_2$, —O-L$^{2C}$-NR$^{2C2}$R$^{2C3}$,
—C(=O)R$^{2C1}$,
—C(=O)NHR$^{2C1}$, —C(=O)NR$^{2C1}_2$, —C(=O)NR$^{2C2}$R$^{2C3}$,
—NHC(=O)R$^{2C1}$, —NR$^{2C1}$C(=O)R$^{2C1}$,
—NHC(=O)NHR$^{2C1}$,
—NHC(=O)NR$^{2C1}_2$, —NHC(=O)NR$^{2C2}$R$^{2C3}$,
—NR$^{2C1}$C(=O)NHR$^{2C1}$,
—NR$^{2C1}$C(=O)NR$^{1C1}_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NHR$^{2C1}$, —S(=O)$_2$NR$^{2C1}_2$, —S(=O)$_2$NR$^{2C2}$R$^{2C3}$,
—S(=O)R$^{2C1}$, or —S(=O)$_2$R$^{2C1}$.

In one embodiment, -Q$^{8B}$, if present, is independently:
—R$^{2A1}$, —R$^{2A4}$, —R$^{2A8}$,
—F, —Cl,
—CF$_3$, —OCF$_3$,
—OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SR$^{2C1}$,
—CN,
—NH$_2$, —NHR$^{2C1}$, —NR$^{2C1}_2$, —NR$^{2C2}$R$^{2C3}$,
-L$^{2C}$-NH$_2$, -L$^{2C}$-NHR$^{2C1}$, -L$^{2C}$-NR$^{2C1}_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}_2$, or —O-L$^{2C}$-NR$^{2C2}$R$^{2C3}$.

In one embodiment, -Q$^{8B}$, if present, is independently selected from those groups exemplified for -Q$^{8B}$ in the compounds shown below under the heading "Examples of Specific Embodiments".

The Groups -Q$^{6A}$, -Q$^{7A}$, and -Q$^{7B}$

In one embodiment, each of -Q$^{6A}$, -Q$^{7A}$, and -Q$^{7B}$, if present, is independently:
—R$^{2A1}$, —R$^{2A2}$, —R$^{2A3}$, —R$^{2A4}$, —R$^{2A5}$, —R$^{2A6}$, —R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
—F, —Cl, —Br, —I,
—CF$_3$, —OCF$_3$,
—OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SH, —SR$^{2C1}$,
—CN,
—NO$_2$,
—NH$_2$, —NHR$^{2C1}$, —NR$^{2C1}_2$, —NR$^{2C2}$R$^{2C3}$,
-L$^{2C}$-NH$_2$, -L$^{2C}$-NHR$^{2C1}$, -L$^{2C}$-NR$^{2C1}_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}_2$, —O-L$^{2C}$-NR$^{2C2}$R$^{2C3}$,
—C(=O)OH, —C(=O)OR$^{2C1}$,
—C(=O)R$^{2C1}$,
—C(=O)NH$_2$, —C(=O)NHR$^{2C1}$, —C(=O)NR$^{2C1}_2$, —C(=O)NR$^{2C2}$R$^{2C3}$,
—NHC(=O)R$^{2C1}$, —NR$^{2C1}$C(=O)R$^{2C1}$,
—NHC(=O)OR$^{2C1}$, —NR$^{2C1}$C(=O)OR$^{2C1}$,
—OC(=O)NH$_2$, —OC(=O)NHR$^{2C1}$, —OC(=O)NR$^{2C1}_2$, —OC(=O)NR$^{2C2}$R$^{2C3}$,
—NHC(=O)NH$_2$, —NHC(=O)NHR$^{2C1}$,
—NHC(=O)NR$^{2C1}_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{1C1}_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$,
—S(=O)$_2$NH$_2$, —S(=O)$_2$NHR$^{2C1}$, —S(=O)$_2$NR$^{2C1}_2$, —S(=O)$_2$NR$^{2C2}$R$^{2C3}$,
—S(=O)R$^{2C1}$, —S(=O)$_2$R$^{2C1}$, —OS(=O)$_2$R$^{2C1}$, or —S(=O)$_2$OR$^{2C1}$.

In one embodiment, each of -Q$^{6A}$, -Q$^{7A}$, and -Q$^{7B}$, if present, is independently:
—R$^{2A1}$, —R$^{2A2}$, —R$^{2A3}$, —R$^{2A4}$, —R$^{2A5}$, —R$^{2A6}$, —R$^{2A7}$, —R$^{2A8}$,
-L$^{2A}$-R$^{2A4}$, -L$^{2A}$-R$^{2A5}$, -L$^{2A}$-R$^{2A6}$, -L$^{2A}$-R$^{2A7}$, -L$^{2A}$-R$^{1A8}$,
—F, —Cl,
—CF$_3$, —OCF$_3$,
—OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SR$^{2C1}$,
—CN,
—NO$_2$,
—NH$_2$, —NHR$^{2C1}$, NR$^{2C1}_2$, —NR$^{2C2}$R$^{2C3}$,
-L$^{2C}$-NH$_2$, -L$^{2C}$-NHR$^{2C1}$, -L$^{2C}$-NR$^{2C1}_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}_2$, —O-L$^{2C}$-NR$^{2C2}$R$^{2C3}$,
—C(=O)OR$^{2C1}$,
—C(=O)R$^{2C1}$,
—C(=O)NH$_2$, —C(=O)NHR$^{2C1}$, —C(=O)NR$^{2C1}_2$, —C(=O)NR$^{2C2}$R$^{2C3}$,
—NHC(=O)R$^{2C1}$, —NR$^{2C1}$C(=O)R$^{2C1}$,
—NHC(=O)NH$_2$, —NHC(=O)NHR$^{2C1}$,
—NHC(=O)NR$^{2C1}_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{1C1}_2$, —NR$^{2C1}$C(=O)NR$^{2C2}$R$^{2C3}$,
—NHS(=O)$_2$R$^{2C1}$, —NR$^{1C1}$S(=O)$_2$R$^{2C1}$, —S(=O)$_2$NHR$^{2C1}$, —S(=O)$_2$NR$^{2C1}$$_2$, —S(=O)$_2$NR$^{2C2}$R$^{2C3}$,
—S(=O)R$^{2C1}$, or —S(=O)$_2$R$^{2C1}$.

In one embodiment, each of -Q$^{6A}$, -Q$^{7A}$, and -Q$^{7B}$, if present, is independently:
—R$^{2A1}$, —R$^{2A4}$, —R$^{2A6}$, —R$^{2A8}$,
—F, —Cl,
—CF$_3$, —OCF$_3$,
—OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SR$^{2C1}$,
—CN,
—NO$_2$,
—NH$_2$, —NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$, or —O-L$^{2C}$-NR$^{2C2}$R$^{2C3}$.

In one embodiment, -Q$^{6A}$, if present, is independently selected from those groups exemplified for -Q$^{6A}$ in the compounds shown below under the heading "Examples of Specific Embodiments".

In one embodiment, -Q$^{7A}$, if present, is independently selected from those groups exemplified for -Q$^{7A}$ in the compounds shown below under the heading "Examples of Specific Embodiments".

In one embodiment, -Q$^{7B}$, if present, is independently selected from those groups exemplified for -Q$^{7B}$ in the compounds shown below under the heading "Examples of Specific Embodiments".

The Groups Associated with -Q$^{5A}$, -Q$^{5B}$, -Q$^{6A}$, -Q$^{7A}$, -Q$^{7B}$, -Q$^{8A}$, and -Q$^{8B}$ In one embodiment:
each —R$^{2A1}$ is independently saturated aliphatic C$_{1-6}$alkyl;
each —R$^{2A2}$ is independently aliphatic C$_{2-6}$alkenyl;
each —R$^{2A3}$ is independently aliphatic C$_{2-6}$alkynyl;
each —R$^{2A4}$ is independently saturated C$_{3-6}$cycloalkyl;
each —R$^{2A5}$ is independently C$_{3-6}$cycloalkenyl;
each —R$^{2A6}$ is independently non-aromatic C$_{3-8}$heterocyclyl;
each —R$^{2A7}$ is independently C$_{6-10}$carboaryl;
each —R$^{2A8}$ is independently C$_{5-10}$heteroaryl;
each -L$^{2A}$- is independently saturated aliphatic C$_{1-3}$alkylene;

wherein:
each —R$^{2A4}$, —R$^{2A5}$, —R$^{2A6}$, —R$^{2A7}$, and —R$^{2A8}$ is optionally substituted, for example, with one or more substituents —R$^{2B1}$ and/or one or more substituents —R$^{2B2}$, and
each —R$^{2A1}$, —R$^{2A2}$, —R$^{2A3}$, and -L$^{2A}$- is optionally substituted, for example, with one or more substituents —R$^{2B2}$, wherein:
each —R$^{2B1}$ is independently:
—R$^{2D1}$, —R$^{2D2}$, —R$^{2D3}$, —R$^{2D4}$, —R$^{2D5}$, —R$^{2D6}$, —R$^{2D7}$, —R$^{2D8}$,
-L$^{2D}$-R$^{2D4}$, -L$^{2D}$-R$^{2D5}$, -L$^{2D}$-R$^{2D6}$, -L$^{2D}$-R$^{2D7}$, or -L$^{2D}$-R$^{2D8}$;
each —R$^{2B2}$ is independently:
—F, —Cl, —Br, —I,
—CF$_3$, —OCF$_3$,
—OH, -L$^{2C}$-OH, —O-L$^{2C}$-OH,
—OR$^{2C1}$, -L$^{2C}$-OR$^{2C1}$, —O-L$^{2C}$-OR$^{2C1}$,
—SH, —SR$^{2C1}$,
—CN,
—NO$_2$,
—NH$_2$, —NHR$^{2C1}$, —NR$^{2C1}$$_2$, —NR$^{2C2}$R$^{2C3}$,
-L$^{2C}$-NH$_2$, -L$^{2C}$-NHR$^{2C1}$, -L$^{2C}$-NR$^{2C1}$$_2$, -L$^{2C}$-NR$^{2C2}$R$^{2C3}$,
—O-L$^{2C}$-NH$_2$, —O-L$^{2C}$-NHR$^{2C1}$, —O-L$^{2C}$-NR$^{2C1}$$_2$, —O-L$^{2C}$-NR$^{2C2}$R$^{2C3}$,
—C(=O)OH, —C(=O)OR$^{2C1}$,
—C(=O)R$^{2C1}$,
—C(=O)NH$_2$, —C(=O)NHR$^{2C1}$, —C(=O)NR$^{2C1}$$_2$, —C(=O)NR$^{2C2}$R$^{2C3}$,
—NHC(=O)R$^{2C1}$, —NR$^{2C1}$C(=O)R$^{2C1}$,
—NHC(=O)OR$^{2C1}$, —NR$^{2C1}$C(=O)OR$^{2C1}$,
—OC(=O)NH$_2$, —OC(=O)NHR$^{2C1}$, —OC(=O)NR$^{2C1}$$_2$, —OC(=O)NR$^{2C2}$R$^{2C3}$,
—NHC(=O)NH$_2$, —NHC(=O)NHR$^{2C1}$,
—NHC(=O)NR$^{2C1}$$_2$, —NHC(=O)NR$^{2C2}$R$^{2C3}$,
—NR$^{2C1}$C(=O)NH$_2$, —NR$^{2C1}$C(=O)NHR$^{2C1}$,
—NR$^{2C1}$C(=O)NR$^{2C1}$$_2$, —NR$^{2C1}$C(=O)NR$^{2C2}$R$^{2C3}$,
—NHS(=O)$_2$R$^{2C1}$, —NR$^{2C1}$S(=O)$_2$R$^{2C1}$,
—S(=O)$_2$NH$_2$, —S(=O)$_2$NHR$^{2C1}$, —S(=O)$_2$NR$^{2C1}$$_2$, —S(=O)$_2$NR$^{2C2}$R$^{2C3}$,
—S(=O)R$^{2C1}$, —S(=O)$_2$R$^{2C1}$, —OS(=O)$_2$R$^{2C1}$, or —S(=O)$_2$OR$^{2C1}$;

wherein:
each -L$^{2C}$- is independently saturated aliphatic C$_{1-5}$alkylene;
in each group —NR$^{2C2}$R$^{2C3}$, R$^{2C2}$ and R$^{2C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —R$^{2C1}$ is independently:
—R$^{2D1}$, —R$^{2D2}$, —R$^{2D3}$, —R$^{2D4}$, —R$^{2D5}$, —R$^{2D6}$, —R$^{2D7}$, —R$^{2D8}$,
-L$^{2D}$-R$^{2D4}$, -L$^{2D}$-R$^{2D5}$, -L$^{2D}$-R$^{2D6}$, -L$^{2D}$-R$^{2D7}$, or -L$^{2D}$-R$^{2D8}$;
each —R$^{2D1}$ is independently saturated aliphatic C$_{1-6}$alkyl;
each —R$^{2D2}$ is independently aliphatic C$_{2-6}$alkenyl;
each —R$^{2D3}$ is independently aliphatic C$_{2-6}$alkynyl;
each —R$^{2D4}$ is independently saturated C$_{3-6}$cycloalkyl;
each —R$^{2D5}$ is independently C$_{3-6}$cycloalkenyl;
each —R$^{2D6}$ is independently non-aromatic C$_{3-8}$heterocyclyl;
each —R$^{2D7}$ is independently C$_{6-10}$carboaryl;
each —R$^{2D8}$ is independently C$_{5-10}$heteroaryl;
each -L$^{2D}$- is independently saturated aliphatic C$_{1-3}$alkylene;

wherein:
each —R$^{2D4}$, —R$^{2D5}$, —R$^{2D6}$, —R$^{2D7}$, and —R$^{2D8}$ is optionally substituted, for example, with one or more substituents —R$^{2E1}$ and/or one or more substituents —R$^{2E2}$;
each —R$^{2D1}$, —R$^{2D2}$, —R$^{2D3}$, and -L$^{2D}$- is optionally substituted, for example, with one or more substituents —R$^{2E2}$, and wherein:
each —R$^{2E1}$ is independently saturated aliphatic C$_{1-4}$alkyl, phenyl, or benzyl;
each —R$^{2E2}$ is independently:
—F, —Cl, —Br, —I,
—CF$_3$, —OCF$_3$,
—OH, -L$^{2F}$-OH, —O-L$^{2F}$-OH,
—OR$^{2F1}$, -L$^{2F}$-OR$^{2F1}$, —O-L$^{2F}$-OR$^{2F1}$,
—SH, —SR$^{2F1}$,
—CN,
—NO$_2$, —NH$_2$, —NHR$^{2F1}$, —NR$^{2F1}_2$, —NR$^{2F2}$R$^{2F3}$,
-L$^{2F}$-NH$_2$, -L$^{2F}$-NHR$^{2F1}$, -L$^{2F}$-NR$^{2F1}_2$, -L$^{2F}$-NR$^{2F2}$R$^{2F3}$,
—C(=O)OH, —C(=O)OR$^{2F1}$,
—C(=O)NH$_2$, —C(=O)NHR$^{2F1}$, —C(=O)NR$^{2F1}_2$, or —C(=O)NR$^{2F2}$R$^{2F3}$;

wherein:
each —R$^{2F1}$ is independently saturated aliphatic C$_{1-4}$alkyl, phenyl, or benzyl;
each -L$^{2F}$- is independently saturated aliphatic C$_{1-5}$alkylene; and
in each group —NR$^{2F2}$R$^{2F3}$, R$^{2F2}$ and R$^{2F3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each -L$^{2A}$-, if present, is independently —CH$_2$—.

In one embodiment, each —R$^{2A1}$, if present, is independently saturated aliphatic C$_{1-3}$alkyl.

In one embodiment, each —R$^{2A4}$, if present, is independently saturated C$_{5-6}$cycloalkyl.

In one embodiment, each —R$^{2A6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —R$^{2A6}$, if present, is independently pyrrolidinyl, piperidinyl, piperazinyl, morpholinyl, tetrahydrofuranyl, or tetrahydropyranyl, and is optionally substituted.

In one embodiment, each —R$^{2A7}$, if present, is independently phenyl or naphthyl, and is optionally substituted.

In one embodiment, each —R$^{2A7}$, if present, is independently phenyl, and is optionally substituted.

In one embodiment, each —R$^{2A7}$, if present, is independently selected from groups of the following formulae, wherein each —R$^{2X}$ is independently —R$^{2B1}$ or —R$^{2B2}$:

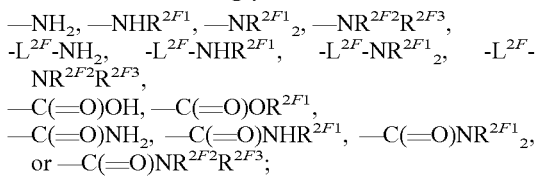

In one embodiment, each —R$^{2A7}$, if present, is independently selected from groups of the following formulae, wherein each —R$^{2X}$ is independently —R$^{2B1}$ or —R$^{2B2}$:

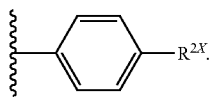

In one embodiment, each —R$^{2A7}$, if present, is independently selected from groups of the following formulae, wherein each —R$^{2X}$ is independently —R$^{2B1}$ or —R$^{2B2}$:

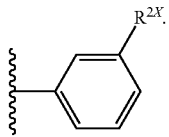

In one embodiment, each —R$^{2A8}$, if present, is independently C$_{5-6}$heteroaryl, and is optionally substituted.

In one embodiment, each —R$^{2A8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —R$^{2A8}$, if present, is independently furanyl, thienyl, pyrazolyl, pyridyl, or pyrimidinyl, and is optionally substituted.

In one embodiment, each —R$^{2A8}$, if present, is independently pyrazolyl, and is optionally substituted.

In one embodiment, each —R$^{2A8}$, if present, is independently pyrazol-4-yl, and is optionally substituted.

In one embodiment, each —R$^{2A8}$, if present, is independently selected from groups of the following formula, wherein each —R$^{2X}$ is independently —R$^{2B1}$ or —R$^{2B2}$:

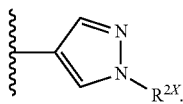

In one embodiment, each —R$^{2A8}$, if present, is independently C$_{9-10}$heteroaryl, and is optionally substituted.

In one embodiment, each —R$^{2A8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzooxadiazolyl, benzopyridyl, benzopyrimidinyl, benzopyridazinyl, 2,3-dihydro-benzofuranyl, benzo[1,3]dioxolyl, 2,3-dihydro-benzo[1,4]dioxinyl, 3,4-dihydro-2H-benzo[b][1,4]dioxepinyl, or 3,4-dihydro-2H-benzo[1,4]oxazinyl, and is optionally substituted.

In one embodiment, each —R$^{2A8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each —R$^{2A8}$, if present, is independently 2,3-dihydro-benzofuranyl, benzo[1,3]dioxolyl, 2,3-dihydro-benzo[1,4]dioxinyl, 3,4-dihydro-2H-benzo[b][1,4]dioxepinyl, or 3,4-dihydro-2H-benzo[1,4]oxazinyl, and is optionally substituted.

In one embodiment, each —R$^{2A8}$, if present, is independently 2,3-dihydro-benzofuran-5-yl, benzo[1,3]dioxol-5-yl, 2,3-dihydro-benzo[1,4]dioxin-6-yl, 3,4-dihydro-2H-benzo[b][1,4]dioxepin-7-yl, or 3,4-dihydro-2H-benzo[1,4]oxazin-7-yl; and is optionally substituted.

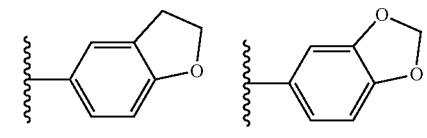

2,3-dihydrobenzofuran-5-yl    benzo[1,3]dioxol-5-yl

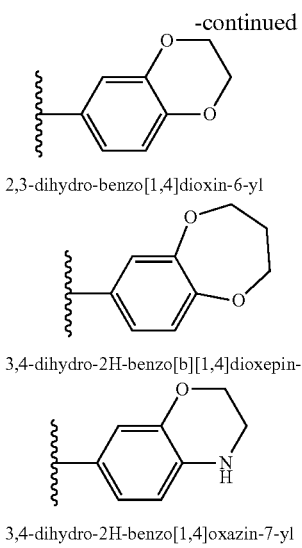

2,3-dihydro-benzo[1,4]dioxin-6-yl 3,4-dihydro-2H-benzo[b][1,4]dioxepin-7-yl 3,4-dihydro-2H-benzo[1,4]oxazin-7-yl In one embodiment, each —$R^{2A8}$, if present, is independently 2,3-dihydro-benzo[1,4]dioxin-6-yl, and is optionally substituted.

In one embodiment, each —$R^{2B1}$ is independently:
—$R^{2D1}$, —$R^{2D2}$, —$R^{2D4}$, —$R^{2D7}$, —$R^{2D8}$,
-$L^{2D}$-$R^{2D4}$, -$L^{2D}$-$R^{2D7}$, or -$L^{2D}$-$R^{2D8}$.

In one embodiment, each —$R^{2B1}$ is independently:
—$R^{2D1}$, —$R^{2D7}$, —$R^{2D8}$, -$L^{2D}$-$R^{2D7}$, or -$L^{2D}$-$R^{2D8}$.

In one embodiment, each —$R^{2B2}$ is independently:
—F, —Cl,
—$CF_3$, —$OCF_3$,
—OH, -$L^{2C}$-OH, —O-$L^{2C}$-OH,
—$OR^{2C1}$, -$L^{2C}$-$OR^{2C1}$, —O-$L^{2C}$-$OR^{2C1}$,
—$SR^{2C1}$,
—CN,
—$NO_2$,
—$NH_2$, —$NHR^{2C1}$, —$NR^{2C1}_2$, —$NR^{2C2}R^{2C3}$,
-$L^{2C}$-$NH_2$, -$L^{2C}$-$NHR^{2C1}$, -$L^{2C}$-$NR^{2C1}_2$, -$L^{2C}$-$NR^{2C2}R^{2C3}$,
—O-$L^{2C}$-$NH_2$, —O-$L^{2C}$-$NHR^{2C1}$, —O-$L^{2C}$-$NR^{2C1}_2$, —O-$L^{2C}$-$NR^{2C2}R^{2C3}$,
—C(=O)OH, —C(=O)$OR^{2C1}$,
—C(=O)$R^{2C1}$,
—C(=O)$NH_2$, —C(=O)$NHR^{2C1}$, —C(=O)$NR^{2C1}_2$, —C(=O)$NR^{2C2}R^{2C3}$,
—NHC(=O)$R^{2C1}$, —$NR^{2C1}$C(=O)$R^{2C1}$,
—NHC(=O)$NH_2$, —NHC(=O)$NHR^{2C1}$,
—NHC(=O)$NR^{2C1}_2$, —NHC(=O)$NR^{2C2}R^{2C3}$,
—$NR^{2C1}$C(=O)$NH_2$, —$NR^{2C1}$C(=O)$NHR^{2C1}$,
—$NR^{2C1}$C(=O)$NR^{2C1}_2$, —$NR^{2C1}$C(=O)$NR^{2C2}R^{2C3}$,
—NHS(=O)$_2R^{2C1}$, —$NR^{2C1}$S(=O)$_2R^{2C1}$,
—S(=O)$_2NH_2$, —S(=O)$_2NHR^{2C1}$, —S(=O)$_2NR^{2C1}_2$,
—S(=O)$_2NR^{2C2}R^{2C3}$,
—S(=O)$R^{2C1}$, or —S(=O)$_2R^{2C1}$.

In one embodiment, each —$R^{2B2}$ is independently:
—F, —Cl,
—$CF_3$, —$OCF_3$,
—OH, -$L^{2C}$-OH, —O-$L^{2C}$-OH,
—$OR^{2C1}$, -$L^{2C}$-$OR^{2C1}$, —O-$L^{2C}$-$OR^{2C1}$,
—$SR^{2C1}$,
—CN,
—$NO_2$,
—$NH_2$, —$NHR^{2C1}$, —$NR^{2C1}_2$, —$NR^{2C2}R^{2C3}$,
-$L^{2C}$-$NH_2$, -$L^{2C}$-$NHR^{2C1}$, -$L^{2C}$-$NR^{2C1}_2$, -$L^{2C}$-$NR^{2C2}R^{2C3}$,
—O-$L^{2C}$-$NH_2$, —O-$L^{2C}$-$NHR^{2C1}$, —O-$L^{2C}$-$NR^{2C1}_2$,
—O-$L^{2C}$-$NR^{2C2}R^{2C3}$,
—C(=O)$R^{2C1}$,
—C(=O)$NH_2$, —C(=O)$NHR^{2C1}$, —C(=O)$NR^{2C1}_2$,
—C(=O)$NR^{2C2}R^{2C3}$,
—NHC(=O)$R^{2C1}$, —$NR^{2C1}$C(=O)$R^{2C1}$,
—NHC(=O)$NH_2$, —NHC(=O)$NHR^{2C1}$,
—NHC(=O)$NR^{2C1}_2$, —NHC(=O)$NR^{2C2}R^{2C3}$,
—$NR^{2C1}$C(=O)$NH_2$, —$NR^{2C1}$C(=O)$NHR^{2C1}$,
—$NR^{2C1}$C(=O)$NR^{2C1}_2$, —$NR^{2C1}$C(=O)$NR^{2C2}R^{2C3}$,
—NHS(=O)$_2R^{2C1}$, —$NR^{2C1}$S(=O)$_2R^{2C1}$,
—S(=O)$_2NH_2$, —S(=O)$_2NHR^{2C1}$, —S(=O)$_2NR^{2C1}_2$,
—S(=O)$_2NR^{2C2}R^{2C3}$,
—S(=O)$R^{2C1}$, or —S(=O)$_2R^{2C1}$.

In one embodiment, each -$L^{2C}$ is saturated aliphatic $C_{1-3}$alkylene.

In one embodiment, each —$NR^{2C2}R^{2C3}$ is independently azetidino, pyrrolidino, imidazolidino, pyrazolidino, piperidino, piperazino, morpholino, azepino, or diazepino, and is optionally substituted, for example, with one or more groups selected from saturated aliphatic $C_{1-3}$alkyl, —F, and —$CF_3$.

In one embodiment, each —$NR^{2C2}R^{2C3}$ is independently pyrrolidino, piperidino, piperazino, or morpholino, and is optionally substituted, for example, with one or more groups selected from saturated aliphatic $C_{1-3}$alkyl, —F, and —$CF_3$.

In one embodiment, each —$R^{2C1}$ is independently:
—$R^{2D1}$, —$R^{2D4}$, —$R^{2D6}$, —$R^{2D7}$, —$R^{2D8}$,
-$L^{2D}$-$R^{2D4}$, -$L^{2D}$-$R^{2D6}$, -$L^{2D}$-$R^{2D7}$, or -$L^{2D}$-$R^{2D8}$.

In one embodiment, each —$R^{2C1}$ is independently:
—$R^{2D1}$, —$R^{2D4}$, —$R^{2D7}$, —$R^{2D8}$,
-$L^{2D}$-$R^{2D4}$, -$L^{2D}$-$R^{2D7}$, or -$L^{2D}$-$R^{2D8}$.

In one embodiment, each —$R^{2C1}$ is independently:
—$R^{2D1}$, —$R^{2D7}$, —$R^{2D8}$, -$L^{2D}$-$R^{2D7}$, or -$L^{2D}$-$R^{2D8}$.

In one embodiment, each —$R^{2C1}$ is independently —$R^{2D1}$, —$R^{2D7}$, or -$L^{2D}$-$R^{2D7}$.

In one embodiment, each —$R^{2C1}$ is independently —$R^{2D7}$, or -$L^{2D}$-$R^{2D7}$.

In one embodiment, each —$R^{2C1}$ is independently —$R^{2D1}$.

In one embodiment, each -$L^{2D}$-, if present, is independently —$CH_2$—.

In one embodiment, each —$R^{2D1}$, if present, is independently saturated aliphatic $C_{1-3}$alkyl.

In one embodiment, each —$R^{2D4}$, if present, is independently saturated $C_{5-6}$cycloalkyl.

In one embodiment, each —$R^{2D6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{2D6}$, if present, is independently pyrrolidinyl, piperidinyl, piperazinyl, morpholinyl, tetrahydrofuranyl, or tetrahydropyranyl, and is optionally substituted.

In one embodiment, each —$R^{2D7}$, if present, is independently phenyl or naphthyl, and is optionally substituted.

In one embodiment, each —$R^{2D7}$, if present, is independently phenyl, and is optionally substituted.

In one embodiment, each —$R^{2D8}$, if present, is independently $C_{5-6}$heteroaryl, and is optionally substituted.

In one embodiment, each —$R^{2D8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{2D8}$, if present, is independently $C_{9-10}$heteroaryl, and is optionally substituted.

In one embodiment, each —$R^{2D8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each —$R^{2E1}$ is independently saturated aliphatic $C_{1-4}$alkyl.

In one embodiment, each —$R^{2E2}$ is independently:
—F, —Cl,
—$CF_3$, —$OCF_3$,
—OH, -$L^{2F}$-OH, —O-$L^{2F}$-OH,
—$OR^{2F1}$, -$L^{2F}$-$OR^{2F1}$, —O-$L^{2F}$-$OR^{2F1}$,
—$SR^{2F1}$,
—CN,
—$NO_2$,
—$NH_2$, —$NHR^{2F1}$, —$NR^{2F1}{}_2$, —$NR^{2F2}R^{2F3}$,
-$L^{2F}$-$NH_2$, -$L^{2F}$-$NHR^{2F1}$, -$L^{2F}$-$NR^{2F1}{}_2$, -$L^{2F}$-$NR^{2F2}R^{2F3}$,
—C(=O)$OR^{2F1}$,
—C(=O)$NH_2$, —C(=O)$NHR^{2F1}$, —C(=O)$NR^{2F1}{}_2$, or —C(=O)$NR^{2F2}R^{2F3}$.

In one embodiment, each —$R^{2E2}$ is independently:
—F, —Cl,
—$CF_3$, —$OCF_3$,
—OH, -$L^{2F}$-OH, —O-$L^{2F}$-OH,
—$OR^{2F1}$, -$L^{2F}$-$OR^{2F1}$, —O-$L^{2F}$-$OR^{2F1}$,
—CN,
—$NH_2$, —$NHR^{2F1}$, —$NR^{2F1}{}_2$, —$NR^{2F2}R^{2F3}$,
-$L^{2F}$-$NH_2$, -$L^{2F}$-$NHR^{2F1}$, -$L^{2F}$-$NR^{2F1}{}_2$, -$L^{2F}$-$NR^{2F2}R^{2F3}$,
—C(=O)$NHR^{2F1}$, —C(=O)$NR^{2F1}{}_2$, or —C(=O)$NR^{2F2}R^{2F3}$.

In one embodiment, each —$R^{2F1}$ is independently saturated aliphatic $C_{1-4}$alkyl.

In one embodiment, each -$L^{2F}$ is saturated aliphatic $C_{1-3}$alkylene.

In one embodiment, each —$NR^{2F2}R^{2F3}$ is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —F, and —$CF_3$.

In one embodiment, each —$NR^{2F2}R^{2F3}$ is independently pyrrolidino, piperidino, piperazino, or morpholino, and is optionally substituted, for example, with one or more groups selected from $C_{1-3}$alkyl, —F, and —$CF_3$.

Some Especially Preferred Compounds

In one especially preferred embodiment, the compound is selected from compounds of the following formulae, and pharmaceutically acceptable salts, hydrates, and solvates thereof:

wherein:
—$R^{5A}$ is independently -$Q^{5A}$;
—$R^{6A}$ is independently —H;
—$R^{7A}$ is independently —H;
—$R^{8A}$ is independently —H;
—$R^{5B}$ is independently -$Q^{5B}$;
—$R^{7B}$ is independently —H;
—$R^{8B}$ is independently —H;
—$R^{WA1}$ is independently —$R^{1A7}$ or —$R^{1A8}$;
—$R^{WB1}$ is independently —$R^{1A7}$ or —$R^{1A8}$;
-$Q^{5A}$ is independently —$R^{2A7}$ or —$R^{2A8}$; and
-$Q^{5B}$ is independently —$R^{2A7}$ or —$R^{2A8}$;
wherein each —$R^{1A7}$, —$R^{1A8}$, —$R^{2A7}$, and —$R^{2A8}$ is as defined herein.

In one embodiment, additionally:
—$R^{WA1}$ is independently —$R^{1A7}$; and
—$R^{WB1}$ is independently —$R^{1A7}$.

In one embodiment, additionally:
—$R^{WA1}$ is independently —$R^{1A7}$;
—$R^{WB1}$ is independently —$R^{1A7}$;
-$Q^{5A}$ is independently —$R^{2A7}$; and
-$Q^{5B}$ is independently —$R^{2A7}$.

Molecular Weight

In one embodiment, the BA compound has a molecular weight of from 174 to 1200.

In one embodiment, the bottom of range is from 180, 200, 225, 250, 275, 300, or 350.

In one embodiment, the top of range is 1100, 1000, 900, 800, 700, or 600.

In one embodiment, the range is 180 to 600.

Combinations

Each and every compatible combination of the embodiments described above is explicitly disclosed herein, as if each and every combination was individually and explicitly recited.

Examples of Specific Embodiments

In one embodiment, the compounds are selected from compounds of the following formulae and pharmaceutically acceptable salts, hydrates, and solvates thereof:

| No. | Code | Structure |
|---|---|---|
| 1 | WW-001 | 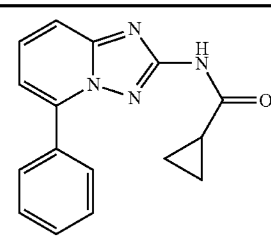 |
| 2 | WW-002 | 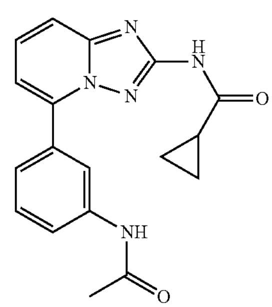 [SMILES: CC(=O)Nc1cccc(-c2cccc3nc(NC(=O)C4CC4)nn23)c1] |

| No. | Code | Structure |
|---|---|---|
| 3 | WW-003 | 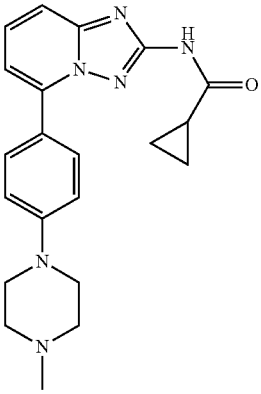 [SMILES: CN1CCN(c2ccc(-c3cccc4nc(NC(=O)C5CC5)nn34)cc2)CC1] |
| 4 | WW-004 | 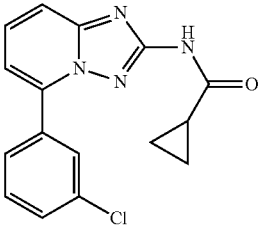 [SMILES: O=C(Nc1nc2cccc(-c3cccc(Cl)c3)n2n1)C1CC1] |
| 5 | WW-005 | 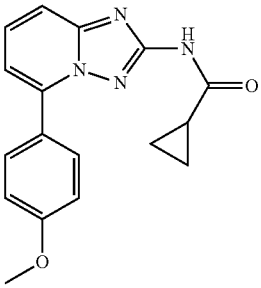 |
| 6 | WW-006 | 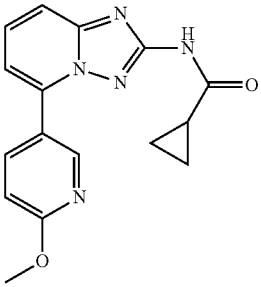 [SMILES: COc1ccc(-c2cccc3nc(NC(=O)C4CC4)nn23)cn1] |
| 7 | WW-007 | 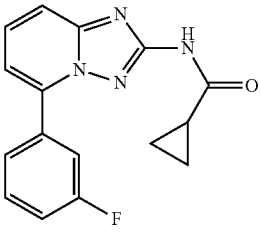 |
| 8 | WW-008 | 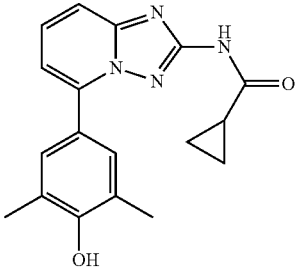 [SMILES: Cc1cc(-c2cccc3nc(NC(=O)C4CC4)nn23)cc(C)c1O] |
| 9 | WW-009 | 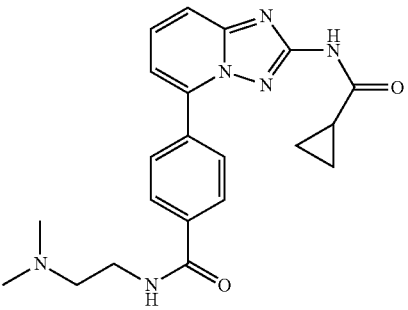 [SMILES: CN(C)CCNC(=O)c1ccc(-c2cccc3nc(NC(=O)C4CC4)nn23)cc1] |
| 10 | WW-010 | 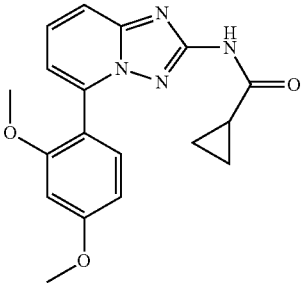 [SMILES: COc1ccc(-c2cccc3nc(NC(=O)C4CC4)nn23)c(OC)c1] |
| 11 | WW-011 | 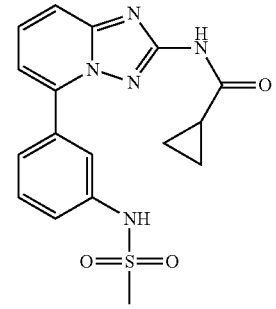 [SMILES: CS(=O)(=O)Nc1cccc(-c2cccc3nc(NC(=O)C4CC4)nn23)c1] |
| 12 | WW-012 | 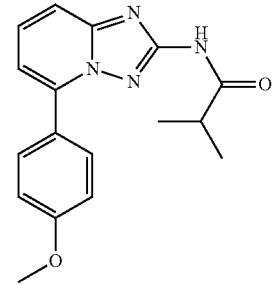 [SMILES: COc1ccc(-c2cccc3nc(NC(=O)C(C)C)nn23)cc1] |

| No. | Code | Structure |
|---|---|---|
| 13 | WW-013 | 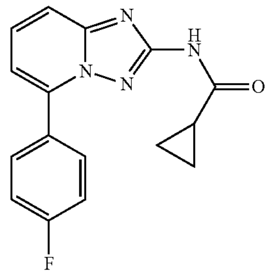 [SMILES: O=C(Nc1nc2cccc(-c3ccc(F)cc3)n2n1)C1CC1] |
| 14 | WW-014 | 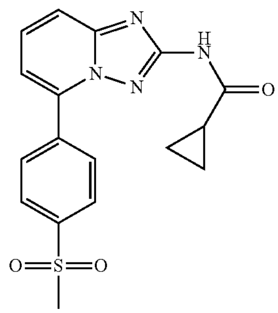 [SMILES: CS(=O)(=O)c1ccc(-c2cccc3nc(NC(=O)C4CC4)nn23)cc1] |
| 15 | WW-015 | 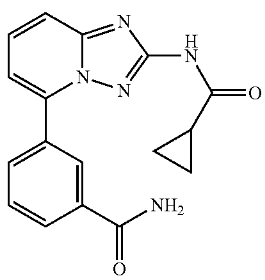 [SMILES: NC(=O)c1cccc(-c2cccc3nc(NC(=O)C4CC4)nn23)c1] |
| 16 | WW-016 | 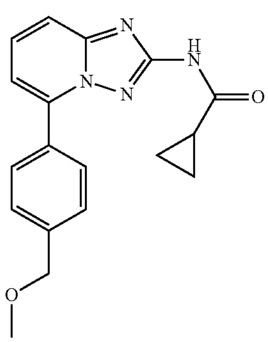 [SMILES: COCc1ccc(-c2cccc3nc(NC(=O)C4CC4)nn23)cc1] |
| 17 | WW-017 | 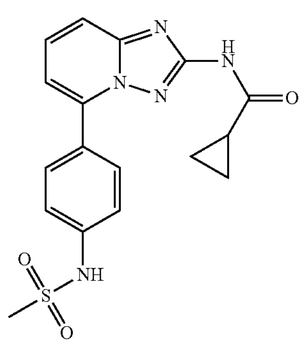 [SMILES: CS(=O)(=O)Nc1ccc(-c2cccc3nc(NC(=O)C4CC4)nn23)cc1] |
| 18 | WW-018 | |
| 19 | WW-019 | |
| 20 | WW-020 | |
| 21 | WW-021 | |
| 22 | WW-022 | |

| No. | Code | Structure |
|---|---|---|
| 23 | WW-023 | 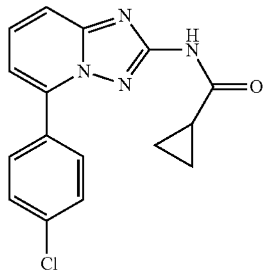 [SMILES: O=C(Nc1nc2cccc(-c3ccc(Cl)cc3)n2n1)C1CC1] |
| 24 | WW-024 | 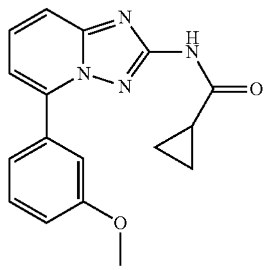 [SMILES: COc1cccc(-c2cccc3nc(NC(=O)C4CC4)nn23)c1] |
| 25 | WW-025 | 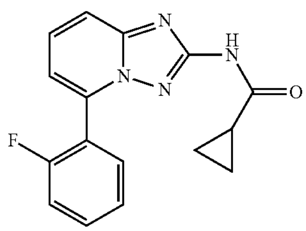 [SMILES: O=C(Nc1nc2cccc(-c3ccccc3F)n2n1)C1CC1] |
| 26 | WW-026 | 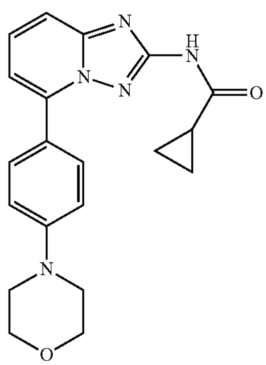 [SMILES: O=C(Nc1nc2cccc(-c3ccc(N4CCOCC4)cc3)n2n1)C1CC1] |
| 27 | WW-027 | 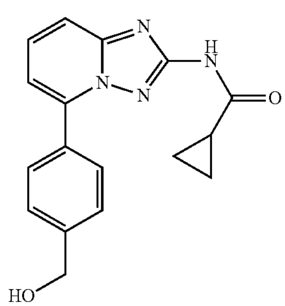 [SMILES: O=C(Nc1nc2cccc(-c3ccc(CO)cc3)n2n1)C1CC1] |
| 28 | WW-028 | |
| 29 | WW-029 | |
| 30 | WW-030 | |
| 31 | WW-031 | |
| 32 | WW-032 | |

| No. | Code | Structure |
|---|---|---|
| 33 | WW-033 | 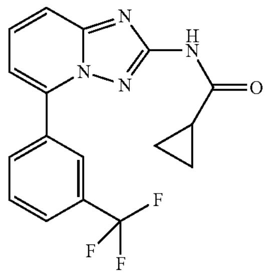 [SMILES: O=C(Nc1nc2cccc(-c3cccc(C(F)(F)F)c3)n2n1)C1CC1] |
| 34 | WW-034 | 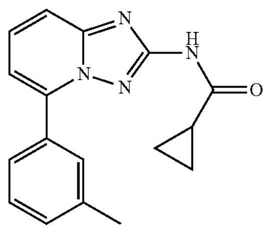 [SMILES: Cc1cccc(-c2cccc3nc(NC(=O)C4CC4)nn23)c1] |
| 35 | WW-035 | 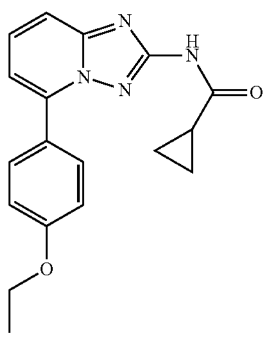 [SMILES: CCOc1ccc(-c2cccc3nc(NC(=O)C4CC4)nn23)cc1] |
| 36 | WW-036 | 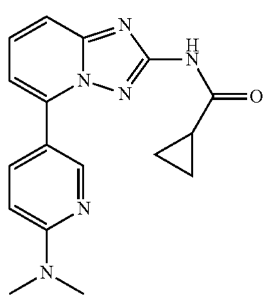 [SMILES: CN(C)c1ccc(-c2cccc3nc(NC(=O)C4CC4)nn23)cn1] |
| 37 | WW-037 | 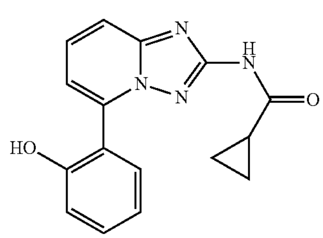 [SMILES: O=C(Nc1nc2cccc(-c3ccccc3O)n2n1)C1CC1] |
| 38 | WW-038 | 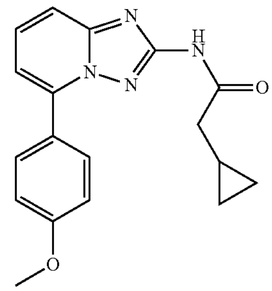 [SMILES: COc1ccc(-c2cccc3nc(NC(=O)CC4CC4)nn23)cc1] |
| 39 | WW-039 | 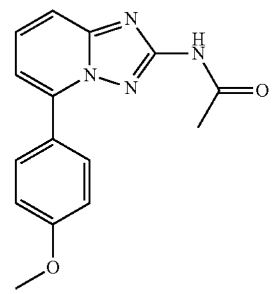 [SMILES: COc1ccc(-c2cccc3nc(NC(C)=O)nn23)cc1] |
| 40 | WW-040 | 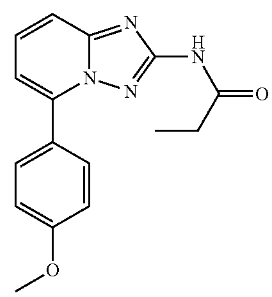 [SMILES: CCC(=O)Nc1nc2cccc(-c3ccc(OC)cc3)n2n1] |
| 41 | WW-041 | 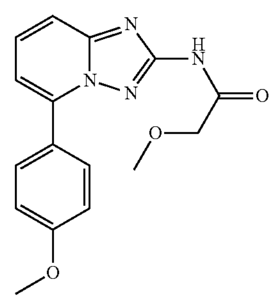 [SMILES: COCC(=O)Nc1nc2cccc(-c3ccc(OC)cc3)n2n1] |
| 42 | WW-042 | 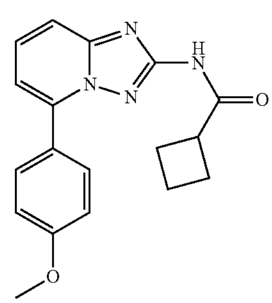 [SMILES: COc1ccc(-c2cccc3nc(NC(=O)C4CCC4)nn23)cc1] |

| No. | Code | Structure |
|---|---|---|
| 43 | WW-043 | 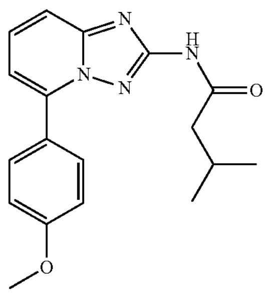 [SMILES: COc1ccc(-c2cccc3nc(NC(=O)CC(C)C)nn23)cc1] |
| 44 | WW-044 | 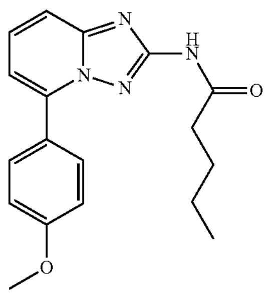 [SMILES: CCCCC(=O)Nc1nc2cccc(-c3ccc(OC)cc3)n2n1] |
| 45 | WW-045 | 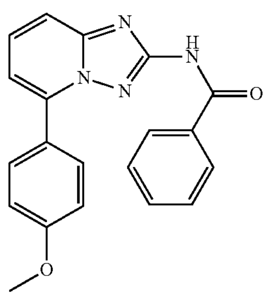 [SMILES: COc1ccc(-c2cccc3nc(NC(=O)c4ccccc4)nn23)cc1] |
| 46 | WW-046 | 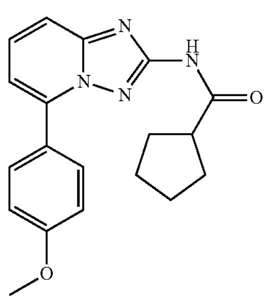 [SMILES: COc1ccc(-c2cccc3nc(NC(=O)C4CCCC4)nn23)cc1] |
| 47 | WW-047 | 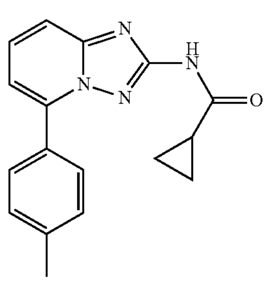 [SMILES: Cc1ccc(-c2cccc3nc(NC(=O)C4CC4)nn23)cc1] |

| No. | Code | Structure |
|---|---|---|
| 48 | WW-048 | |
| 49 | WW-049 | |
| 50 | WW-050 | |
| 51 | WW-051 | |
| 52 | WW-052 | |

| No. | Code | Structure |
|---|---|---|
| 53 | WW-053 | 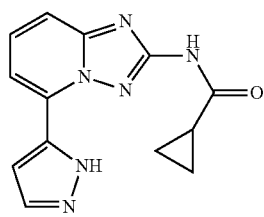 [SMILES: O=C(Nc1nc2cccc(-c3ccn[nH]3)n2n1)C1CC1] |
| 54 | WW-054 | 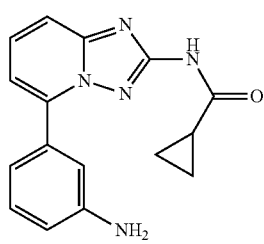 [SMILES: Nc1cccc(-c2cccc3nc(NC(=O)C4CC4)nn23)c1] |
| 55 | WW-055 | 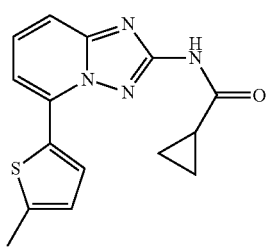 [SMILES: Cc1ccc(-c2cccc3nc(NC(=O)C4CC4)nn23)s1] |
| 56 | WW-056 | 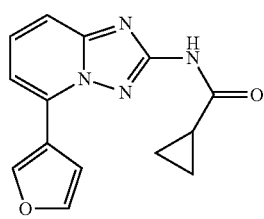 [SMILES: O=C(Nc1nc2cccc(-c3ccoc3)n2n1)C1CC1] |
| 57 | WW-057 | 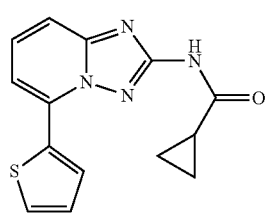 [SMILES: O=C(Nc1nc2cccc(-c3cccs3)n2n1)C1CC1] |
| 58 | WW-058 | 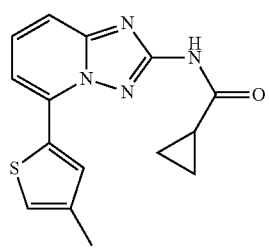 [SMILES: Cc1csc(-c2cccc3nc(NC(=O)C4CC4)nn23)c1] |
| No. | Code | Structure |
|---|---|---|
| 59 | WW-059 | 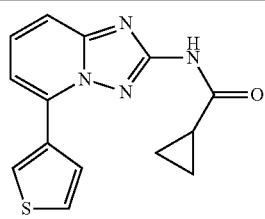 [SMILES: O=C(Nc1nc2cccc(-c3ccsc3)n2n1)C1CC1] |
| 60 | WW-060 | 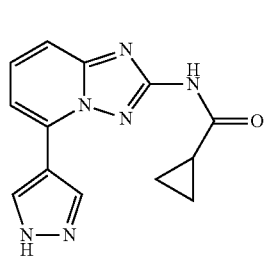 [SMILES: O=C(Nc1nc2cccc(-c3cn[nH]c3)n2n1)C1CC1] |
| 61 | WW-061 | 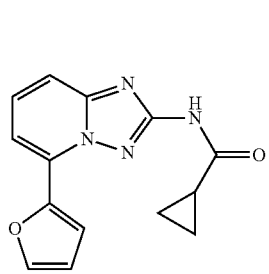 [SMILES: O=C(Nc1nc2cccc(-c3ccco3)n2n1)C1CC1] |
| 62 | WW-062 | 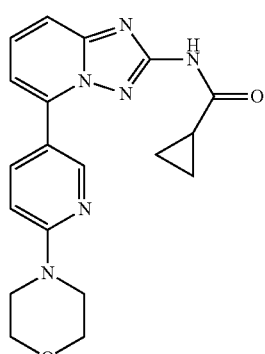 |
| 63 | WW-063 | 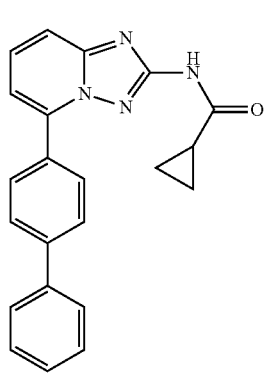 [SMILES: O=C(Nc1nc2cccc(-c3ccc(-c4ccccc4)cc3)n2n1)C1CC1] |

| No. | Code | Structure |
|-----|--------|-----------|
| 64 | WW-064 | 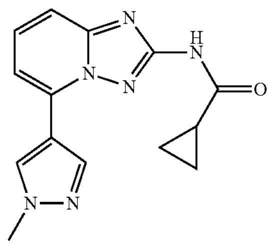 [SMILES: Cn1cc(-c2cccc3nc(NC(=O)C4CC4)nn23)cn1] |
| 65 | WW-065 | 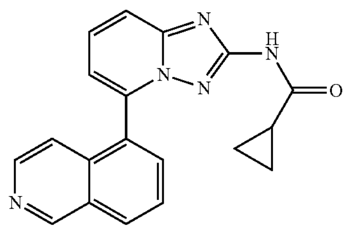 [SMILES: O=C(Nc1nc2cccc(-c3cccc4cnccc34)n2n1)C1CC1] |
| 66 | WW-066 | 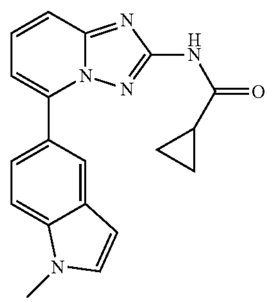 [SMILES: Cn1ccc2cc(-c3cccc4nc(NC(=O)C5CC5)nn34)ccc21] |
| 67 | WW-067 | 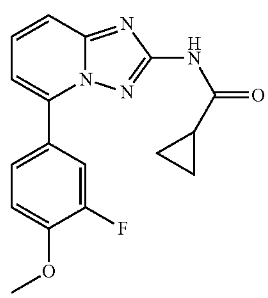 [SMILES: COc1ccc(-c2cccc3nc(NC(=O)C4CC4)nn23)cc1F] |
| 68 | WW-068 | 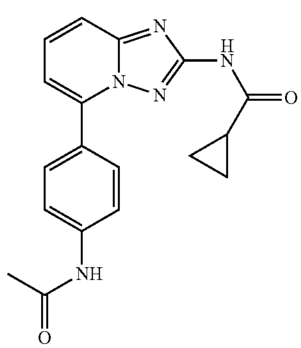 [SMILES: CC(=O)Nc1ccc(-c2cccc3nc(NC(=O)C4CC4)nn23)cc1] |

| No. | Code | Structure |
|-----|--------|-----------|
| 69 | WW-069 | 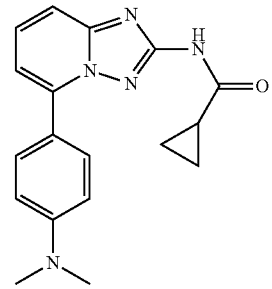 [SMILES: CN(C)c1ccc(-c2cccc3nc(NC(=O)C4CC4)nn23)cc1] |
| 70 | WW-070 | 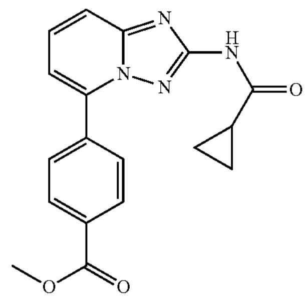 [SMILES: COC(=O)c1ccc(-c2cccc3nc(NC(=O)C4CC4)nn23)cc1] |
| 71 | WW-071 | 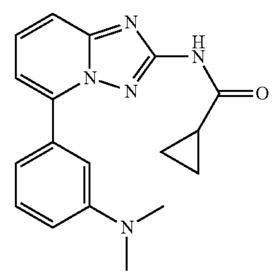 [SMILES: CN(C)c1cccc(-c2cccc3nc(NC(=O)C4CC4)nn23)c1] |
| 72 | WW-072 | 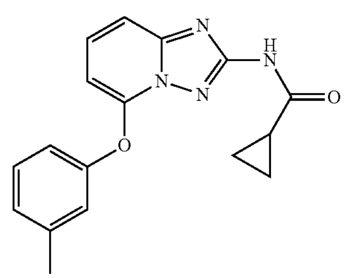 [SMILES: Cc1cccc(Oc2cccc3nc(NC(=O)C4CC4)nn23)c1] |
| 73 | WW-073 | 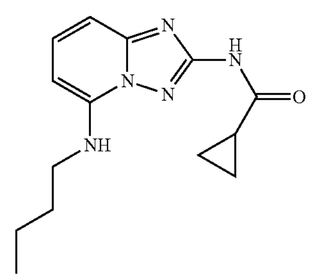 [SMILES: CCCCNc1cccc2nc(NC(=O)C3CC3)nn12] |

| No. | Code | Structure |
|---|---|---|
| 74 | WW-074 | 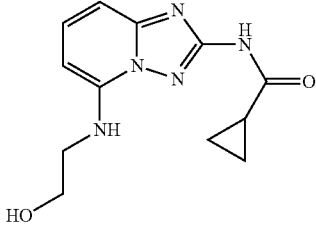 [SMILES: O=C(Nc1nc2cccc(NCCO)n2n1)C1CC1] |
| 75 | WW-075 | 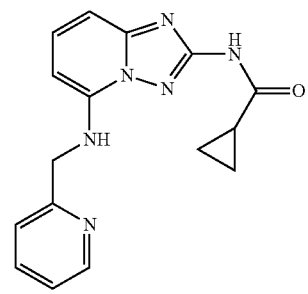 [SMILES: O=C(Nc1nc2cccc(NCc3ccccn3)n2n1)C1CC1] |
| 76 | WW-076 | 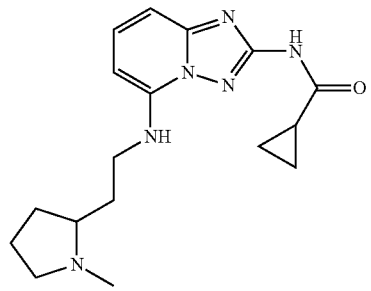 [SMILES: CN1CCCC1CCNc1cccc2nc(NC(=O)C3CC3)nn12] |
| 77 | WW-077 | 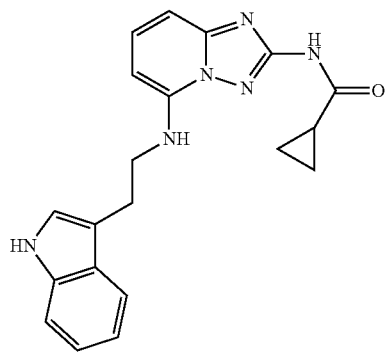 [SMILES: O=C(Nc1nc2cccc(NCCc3c[nH]c4ccccc34)n2n1)C1CC1] |
| 78 | WW-078 | 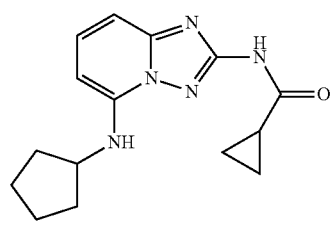 [SMILES: O=C(Nc1nc2cccc(NC3CCCC3)n2n1)C1CC1] |
| No. | Code | Structure |
|---|---|---|
| 79 | WW-079 | 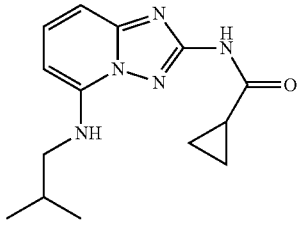 [SMILES: CC(C)CNc1cccc2nc(NC(=O)C3CC3)nn12] |
| 80 | WW-080 | 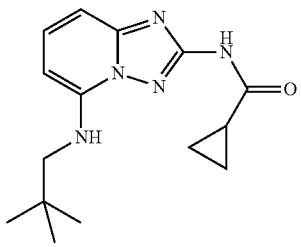 [SMILES: CC(C)(C)CNc1cccc2nc(NC(=O)C3CC3)nn12] |
| 81 | WW-081 | 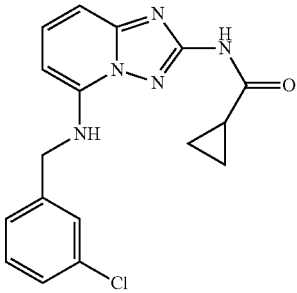 [SMILES: O=C(Nc1nc2cccc(NCc3cccc(Cl)c3)n2n1)C1CC1] |
| 82 | WW-082 | 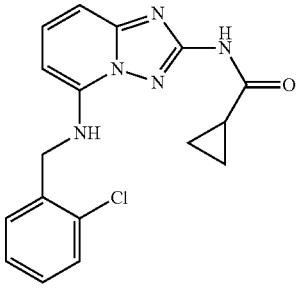 [SMILES: O=C(Nc1nc2cccc(NCc3ccccc3Cl)n2n1)C1CC1] |
| 83 | WW-083 | 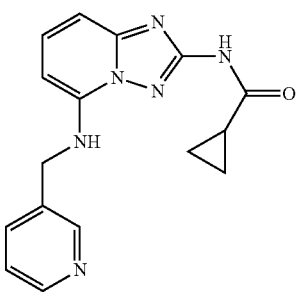 [SMILES: O=C(Nc1nc2cccc(NCc3cccnc3)n2n1)C1CC1] |

| No. | Code | Structure |
|---|---|---|
| 84 | WW-084 | 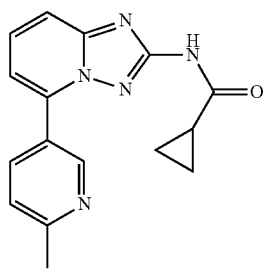 |
| 85 | WW-085 | 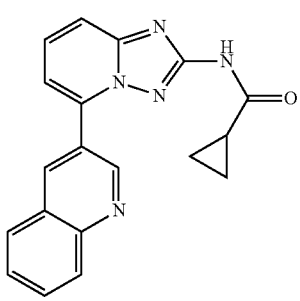 [SMILES: O=C(Nc1nc2cccc(-c3cnc4ccccc4c3)n2n1)C1CC1] |
| 86 | WW-086 | 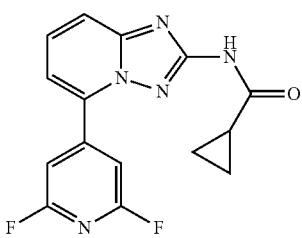 [SMILES: O=C(Nc1nc2cccc(-c3cc(F)nc(F)c3)n2n1)C1CC1] |
| 87 | WW-087 | 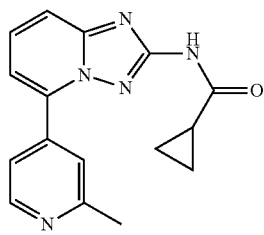 [SMILES: Cc1cc(-c2cccc3nc(NC(=O)C4CC4)nn23)ccn1] |
| 88 | WW-088 | 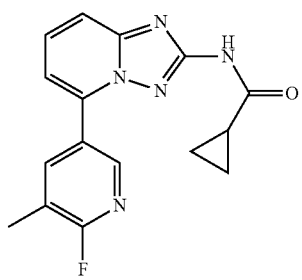 [SMILES: Cc1cc(-c2cccc3nc(NC(=O)C4CC4)nn23)cnc1F] |
| 89 | WW-089 | 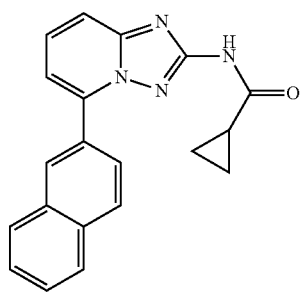 [SMILES: O=C(Nc1nc2cccc(-c3ccc4ccccc4c3)n2n1)C1CC1] |
| 90 | WW-090 | 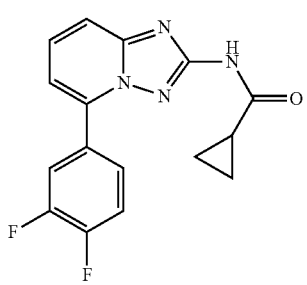 [SMILES: O=C(Nc1nc2cccc(-c3ccc(F)c(F)c3)n2n1)C1CC1] |
| 91 | WW-091 | 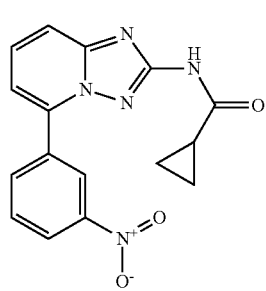 [SMILES: O=C(Nc1nc2cccc(-c3cccc([N+](=O)[O-])c3)n2n1)C1CC1] |
| 92 | WW-092 | 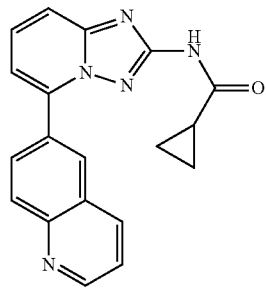 [SMILES: O=C(Nc1nc2cccc(-c3ccc4ncccc4c3)n2n1)C1CC1] |
| 93 | WW-093 | 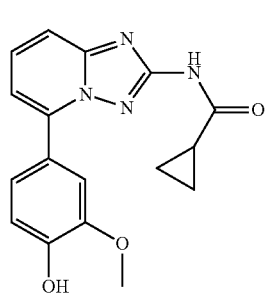 [SMILES: COc1cc(-c2cccc3nc(NC(=O)C4CC4)nn23)ccc1O] |

| No. | Code | Structure |
|---|---|---|
| 94 | WW-094 | 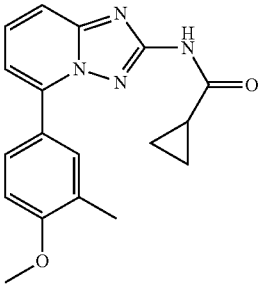 [SMILES: COc1ccc(-c2cccc3nc(NC(=O)C4CC4)nn23)cc1C] |
| 95 | WW-095 | 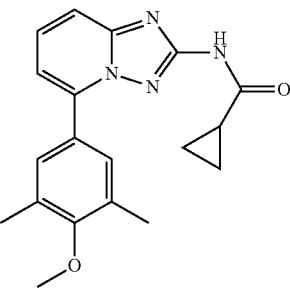 [SMILES: COc1c(C)cc(-c2cccc3nc(NC(=O)C4CC4)nn23)cc1C] |
| 96 | WW-096 | 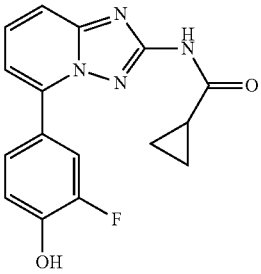 [SMILES: O=C(Nc1nc2cccc(-c3ccc(O)c(F)c3)n2n1)C1CC1] |
| 97 | WW-097 | 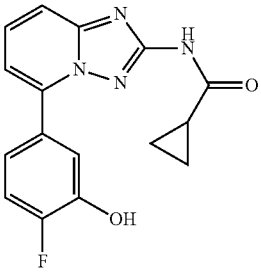 [SMILES: O=C(Nc1nc2cccc(-c3ccc(F)c(O)c3)n2n1)C1CC1] |
| 98 | WW-098 | 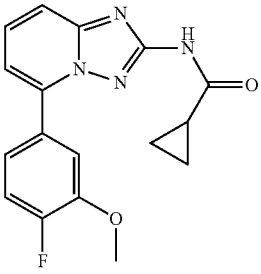 [SMILES: COc1cc(-c2cccc3nc(NC(=O)C4CC4)nn23)ccc1F] |
| No. | Code | Structure |
|---|---|---|
| 99 | WW-099 | 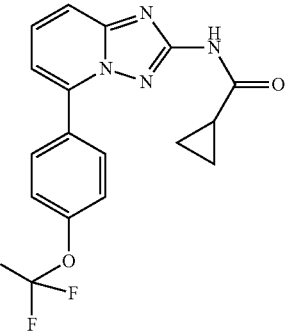 |
| 100 | WW-100 | 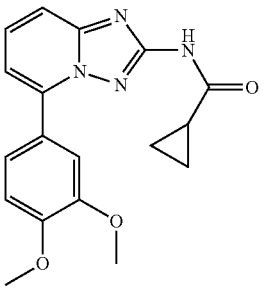 [SMILES: COc1ccc(-c2cccc3nc(NC(=O)C4CC4)nn23)cc1OC] |
| 101 | WW-101 | 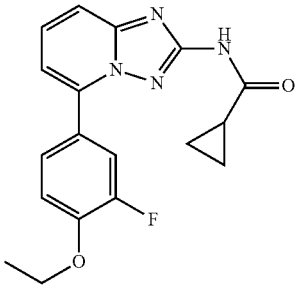 [SMILES: CCOc1ccc(-c2cccc3nc(NC(=O)C4CC4)nn23)cc1F] |
| 102 | WW-102 | 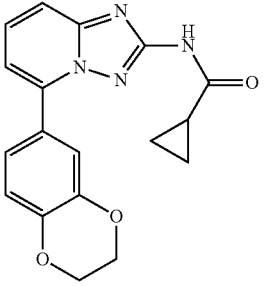 [SMILES: O=C(Nc1nc2cccc(-c3ccc4c(c3)OCCO4)n2n1)C1CC1] |
| 103 | WW-103 | 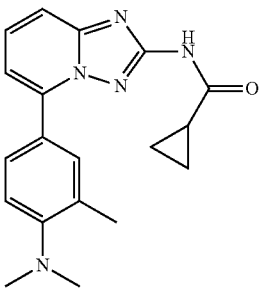 [SMILES: Cc1cc(-c2cccc3nc(NC(=O)C4CC4)nn23)ccc1N(C)C] |

| No. | Code | Structure |
|---|---|---|
| 104 | WW-104 | 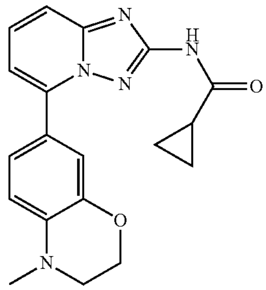 [SMILES: CN1CCOc2cc(-c3cccc4nc(NC(=O)C5CC5)nn34)ccc21] |
| 105 | WW-105 | 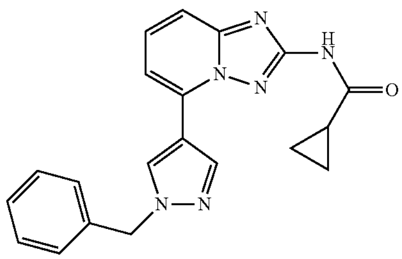 [SMILES: O=C(Nc1nc2cccc(-c3cnn(Cc4ccccc4)c3)n2n1)C1CC1] |
| 106 | WW-106 | 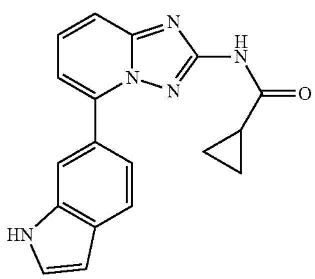 [SMILES: O=C(Nc1nc2cccc(-c3ccc4cc[nH]c4c3)n2n1)C1CC1] |
| 107 | WW-107 | 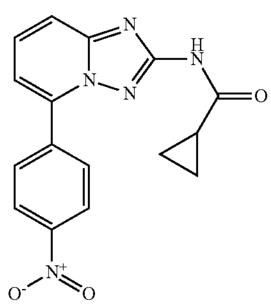 [SMILES: O=C(Nc1nc2cccc(-c3ccc([N+](=O)[O-])cc3)n2n1)C1CC1] |
| 108 | WW-108 | 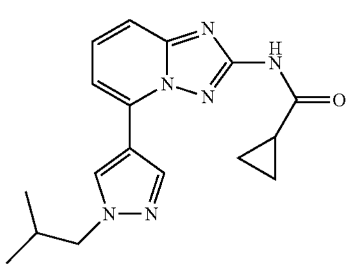 [SMILES: CC(C)Cn1cc(-c2cccc3nc(NC(=O)C4CC4)nn23)cn1] |
| 109 | WW-109 | |
| 110 | WW-110 | |
| 111 | WW-111 | |
| 112 | WW-112 | |
| 113 | WW-113 | |

| No. | Code | Structure |
|---|---|---|
| 114 | WW-114 | 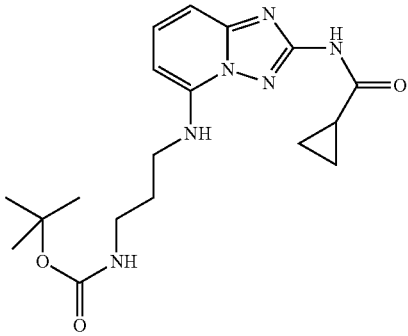 [SMILES: CC(C)(C)OC(=O)NCCCNc1cccc2nc(NC(=O)C3CC3)nn12] |
| 115 | WW-115 | 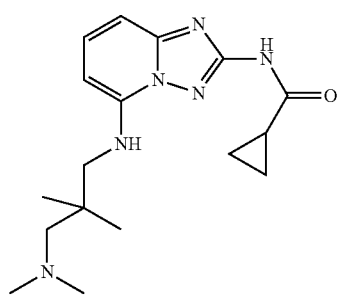 [SMILES: CN(C)CC(C)(C)CNc1cccc2nc(NC(=O)C3CC3)nn12] |
| 116 | WW-116 | 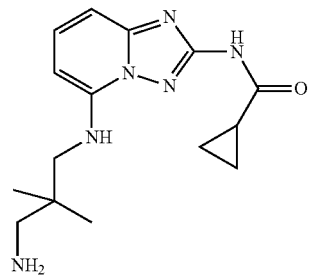 [SMILES: CC(C)(CN)CNc1cccc2nc(NC(=O)C3CC3)nn12] |
| 117 | WW-117 | 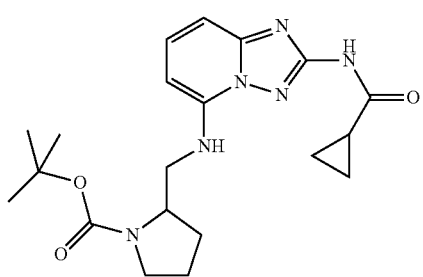 [SMILES: CC(C)(C)OC(=O)N1CCCC1CNc1cccc2nc(NC(=O)C3CC3)nn12] |
| 118 | WW-118 | 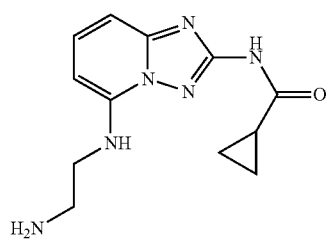 [SMILES: NCCNc1cccc2nc(NC(=O)C3CC3)nn12] |
| No. | Code | Structure |
|---|---|---|
| 119 | WW-119 | 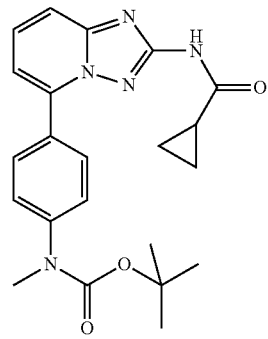 [SMILES: CN(C(=O)OC(C)(C)C)c1ccc(-c2cccc3nc(NC(=O)C4CC4)nn23)cc1] |
| 120 | WW-120 | 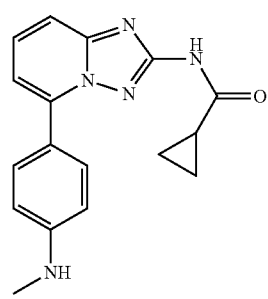 [SMILES: CNc1ccc(-c2cccc3nc(NC(=O)C4CC4)nn23)cc1] |
| 121 | WW-121 | 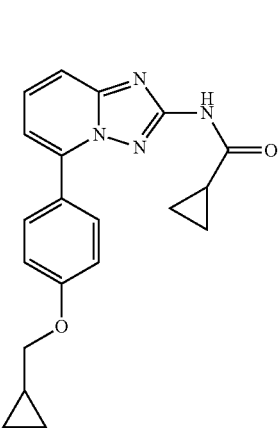 [SMILES: O=C(Nc1nc2cccc(-c3ccc(OCC4CC4)cc3)n2n1)C1CC1] |
| 122 | WW-122 | 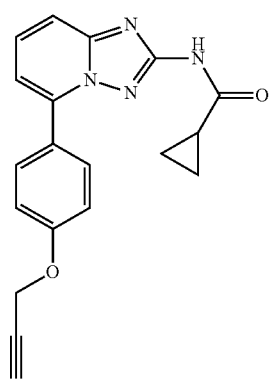 [SMILES: C#CCOc1ccc(-c2cccc3nc(NC(=O)C4CC4)nn23)cc1] |

| No. | Code | Structure |
|---|---|---|
| 123 | WW-123 | |
| 124 | WW-124 | |
| 125 | WW-125 | |
| 126 | WW-126 | |
| 127 | WW-127 | |
| 128 | WW-128 | 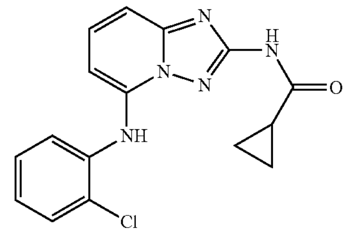 [SMILES: O=C(Nc1nc2cccc(Nc3ccccc3Cl)n2n1)C1CC1] |
| 129 | WW-129 | 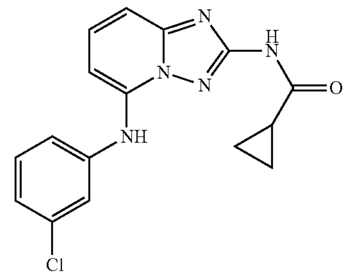 [SMILES: O=C(Nc1nc2cccc(Nc3cccc(Cl)c3)n2n1)C1CC1] |
| 130 | WW-130 | 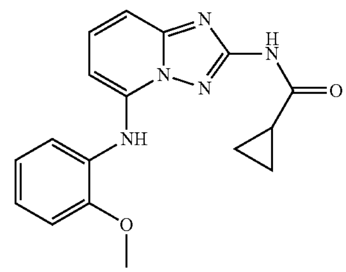 [SMILES: COc1ccccc1Nc1cccc2nc(NC(=O)C3CC3)nn12] |
| 131 | WW-131 | 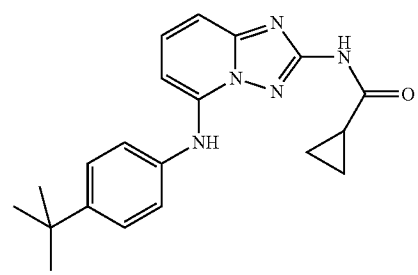 [SMILES: CC(C)(C)c1ccc(Nc2cccc3nc(NC(=O)C4CC4)nn23)cc1] |
| 132 | WW-132 | 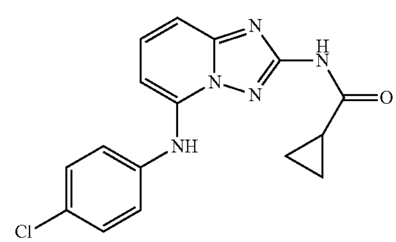 [SMILES: O=C(Nc1nc2cccc(Nc3ccc(Cl)cc3)n2n1)C1CC1] |
| 133 | WW-133 | 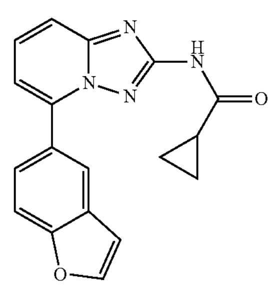 [SMILES: O=C(Nc1nc2cccc(-c3ccc4occc4c3)n2n1)C1CC1] |

| No. | Code | Structure |
|---|---|---|
| 134 | WW-134 | 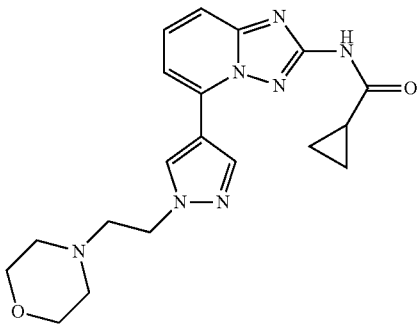 [SMILES: O=C(Nc1nc2cccc(-c3cnn(CCN4CCOCC4)c3)n2n1)C1CC1] |
| 135 | WW-135 | 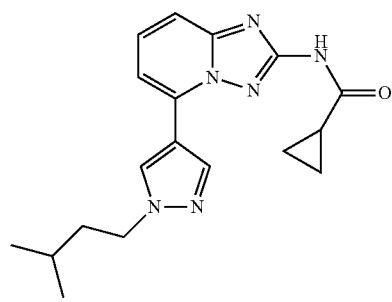 [SMILES: CC(C)CCn1cc(-c2cccc3nc(NC(=O)C4CC4)nn23)cn1] |
| 136 | WW-136 | 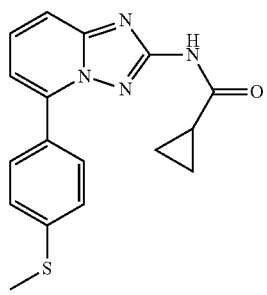 [SMILES: CSc1ccc(-c2cccc3nc(NC(=O)C4CC4)nn23)cc1] |
| 137 | WW-137 | 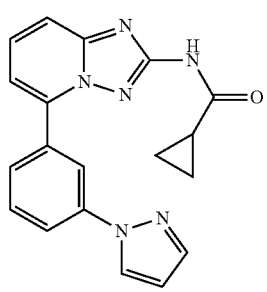 [SMILES: O=C(Nc1nc2cccc(-c3cccc(-n4cccn4)c3)n2n1)C1CC1] |
| 138 | WW-138 | 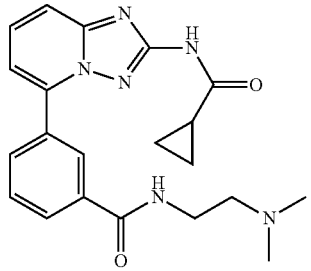 [SMILES: CN(C)CCNC(=O)c1cccc(-c2cccc3nc(NC(=O)C4CC4)nn23)c1] |
| 139 | WW-139 | 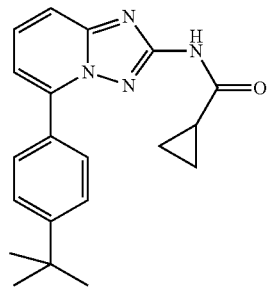 [SMILES: CC(C)(C)c1ccc(-c2cccc3nc(NC(=O)C4CC4)nn23)cc1] |
| 140 | WW-140 | 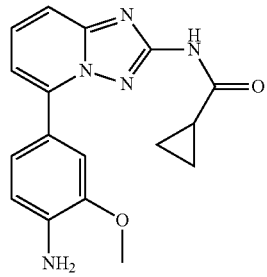 [SMILES: COc1cc(-c2cccc3nc(NC(=O)C4CC4)nn23)ccc1N] |
| 141 | WW-141 | 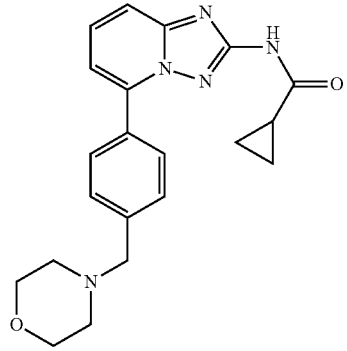 [SMILES: O=C(Nc1nc2cccc(-c3ccc(CN4CCOCC4)cc3)n2n1)C1CC1] |
| 142 | WW-142 | 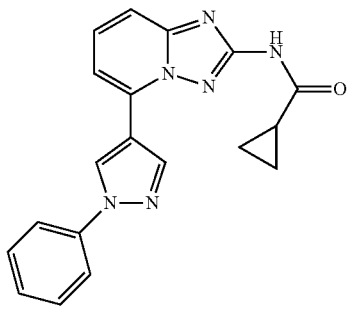 [SMILES: O=C(Nc1nc2cccc(-c3cnn(-c4ccccc4)c3)n2n1)C1CC1] |

-continued

| No. | Code | Structure |
|---|---|---|
| 143 | WW-143 | 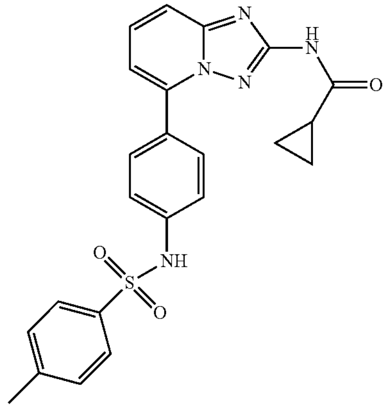 [SMILES: Cc1ccc(S(=O)(=O)Nc2ccc(-c3cccc4nc(NC(=O)C5CC5)nn34)cc2)cc1] |
| 144 | WW-144 | 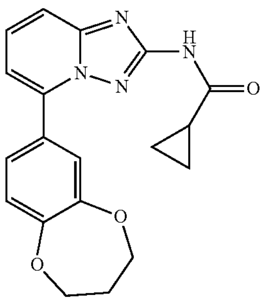 [SMILES: O=C(Nc1nc2cccc(-c3ccc4c(c3)OCCCO4)n2n1)C1CC1] |
| 145 | WW-145 | 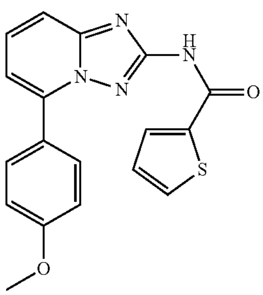 [SMILES: COc1ccc(-c2cccc3nc(NC(=O)c4cccs4)nn23)cc1] |
| 146 | WW-146 | 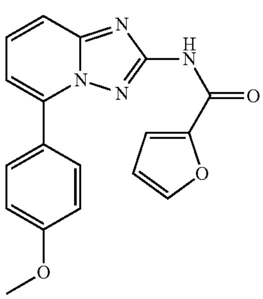 [SMILES: COc1ccc(-c2cccc3nc(NC(=O)c4ccco4)nn23)cc1] |
| 147 | WW-147 | 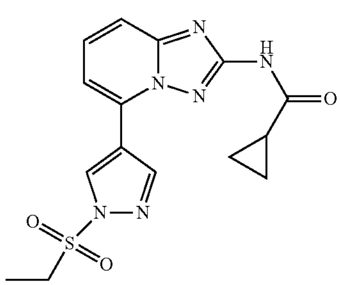 [SMILES: CCS(=O)(=O)n1cc(-c2cccc3nc(NC(=O)C4CC4)nn23)cn1] |

-continued

| No. | Code | Structure |
|---|---|---|
| 148 | WW-148 | 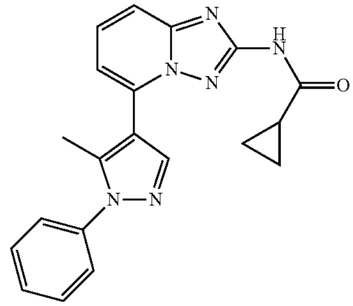 [SMILES: Cc1c(-c2cccc3nc(NC(=O)C4CC4)nn23)cnn1-c1ccccc1] |
| 149 | WW-149 | 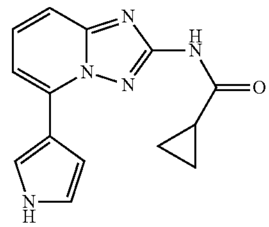 [SMILES: O=C(Nc1nc2cccc(-c3cc[nH]c3)n2n1)C1CC1] |
| 150 | WW-150 | 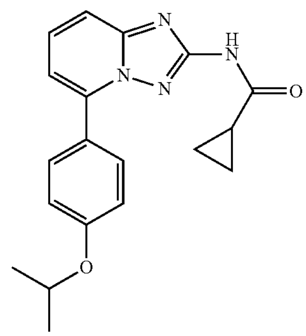 [SMILES: CC(C)Oc1ccc(-c2cccc3nc(NC(=O)C4CC4)nn23)cc1] |
| 151 | WW-151 | 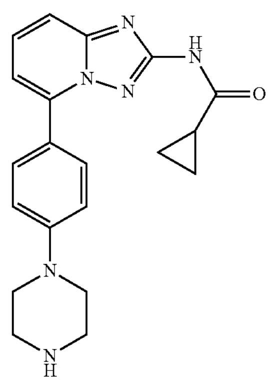 [SMILES: O=C(Nc1nc2cccc(-c3ccc(N4CCNCC4)cc3)n2n1)C1CC1] |
| 152 | WW-152 | 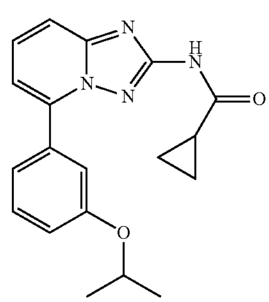 [SMILES: CC(C)Oc1cccc(-c2cccc3nc(NC(=O)C4CC4)nn23)c1] |

-continued
| No. | Code | Structure |
|---|---|---|
| 153 | WW-153 | 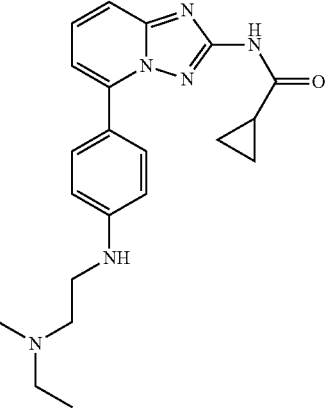 [SMILES: CCN(CC)CCNc1ccc(-c2cccc3nc(NC(=O)C4CC4)nn23)cc1] |
| 154 | WW-154 | 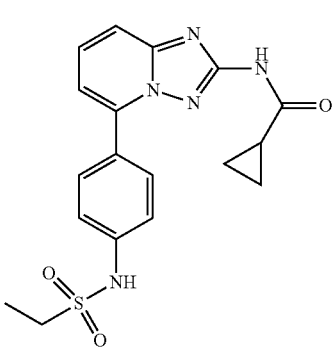 [SMILES: CCS(=O)(=O)Nc1ccc(-c2cccc3nc(NC(=O)C4CC4)nn23)cc1] |
| 155 | WW-155 | 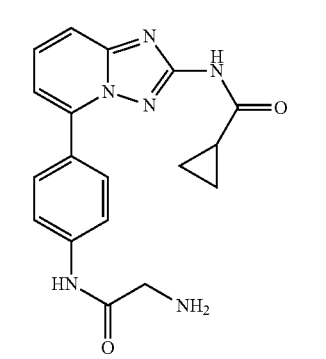 [SMILES: NCC(=O)Nc1ccc(-c2cccc3nc(NC(=O)C4CC4)nn23)cc1] |
| 156 | WW-156 | 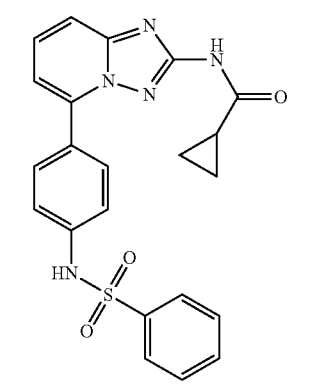 [SMILES: O=C(Nc1nc2cccc(-c3ccc(NS(=O)(=O)c4ccccc4)cc3)n2n1)C1CC1] |
-continued
| No. | Code | Structure |
|---|---|---|
| 157 | WW-157 | 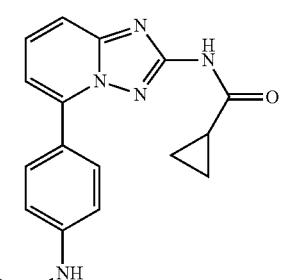 |
| 158 | WW-158 | 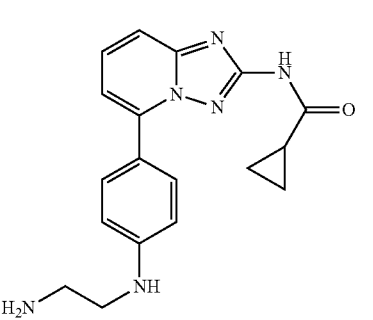 [SMILES: NCCNc1ccc(-c2cccc3nc(NC(=O)C4CC4)nn23)cc1] |
| 159 | WW-159 | 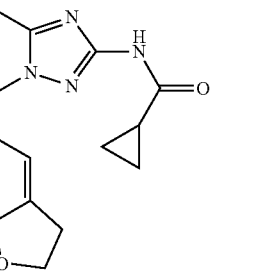 |
| 160 | WW-160 | 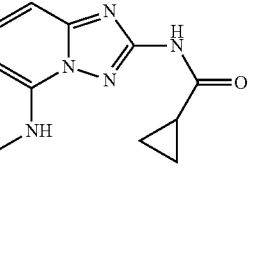 |
| 161 | WW-161 | 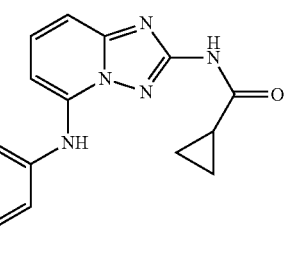 |

| No. | Code | Structure |
|---|---|---|
| 162 | WW-162 | 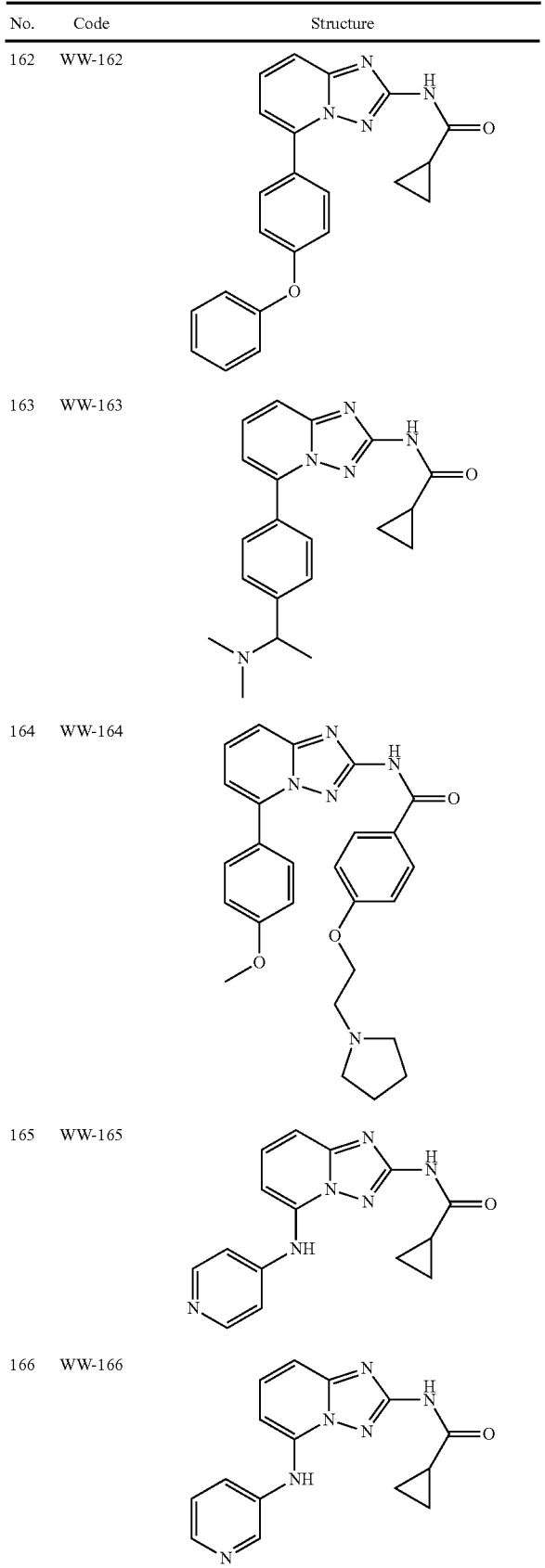 |
| 163 | WW-163 | 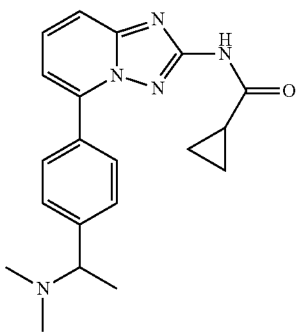 [SMILES: CC(c1ccc(-c2cccc3nc(NC(=O)C4CC4)nn23)cc1)N(C)C] |
| 164 | WW-164 | 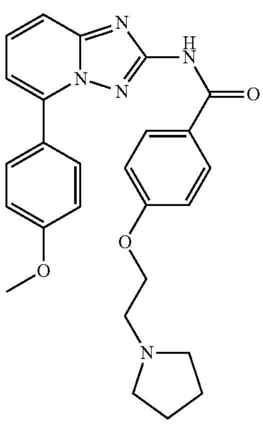 [SMILES: COc1ccc(-c2cccc3nc(NC(=O)c4ccc(OCCN5CCCC5)cc4)nn23)cc1] |
| 165 | WW-165 | 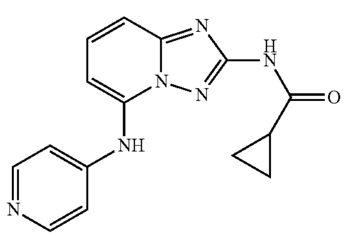 [SMILES: O=C(Nc1nc2cccc(Nc3ccncc3)n2n1)C1CC1] |
| 166 | WW-166 | 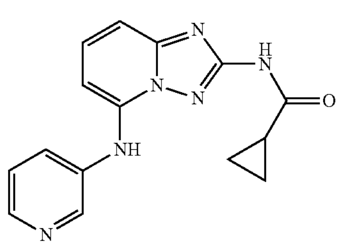 [SMILES: O=C(Nc1nc2cccc(Nc3cccnc3)n2n1)C1CC1] |

| No. | Code | Structure |
|---|---|---|
| 167 | WW-167 | 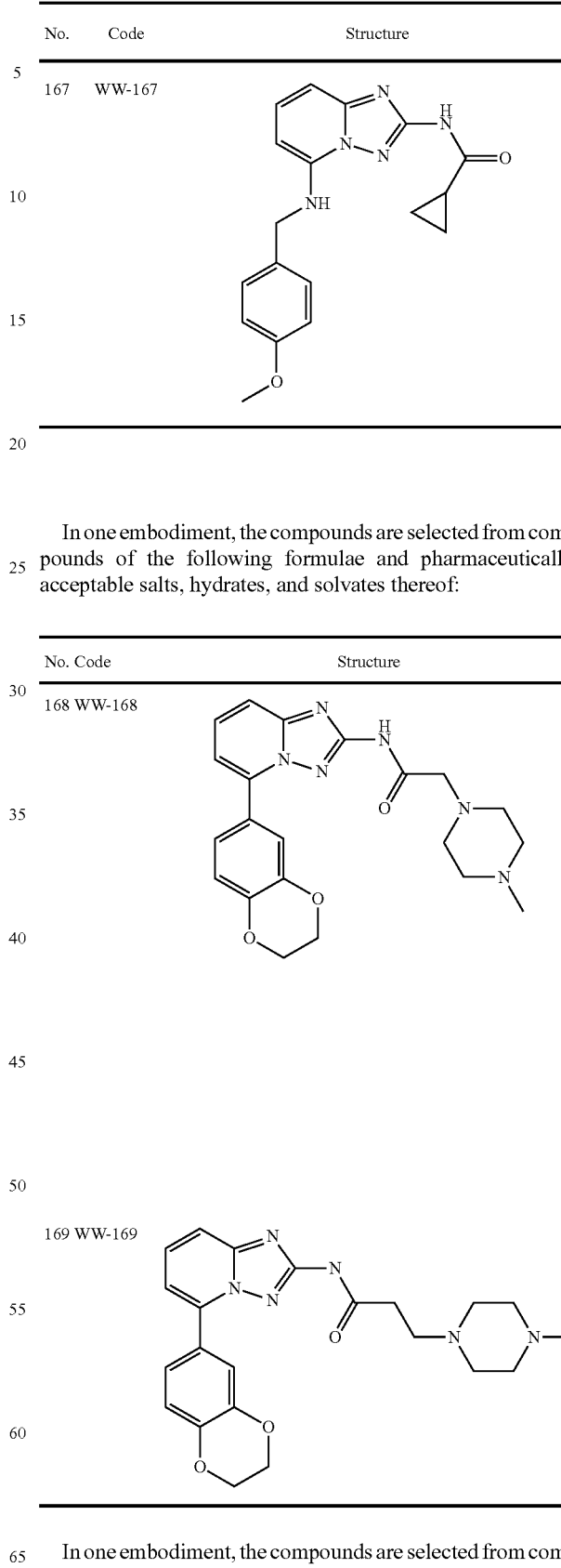 |

In one embodiment, the compounds are selected from compounds of the following formulae and pharmaceutically acceptable salts, hydrates, and solvates thereof:

| No. Code | Structure |
|---|---|
| 168 WW-168 | |
| 169 WW-169 | |

In one embodiment, the compounds are selected from compounds of the following formulae and pharmaceutically acceptable salts, hydrates, and solvates thereof:

| No. | Code | Structure |
|---|---|---|
| 170 | XX-001 | 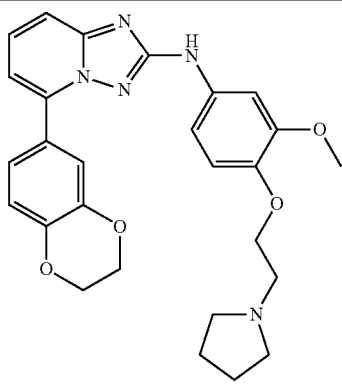 |
| 171 | XX-002 | 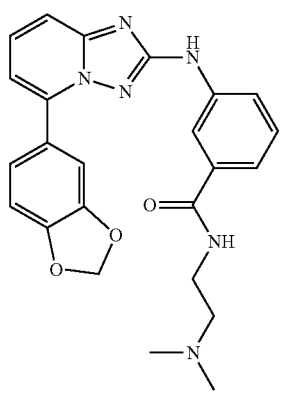 [SMILES: CN(C)CCNC(=O)c1cccc(Nc2nc3cccc(-c4ccc5c(c4)OCO5)n3n2)c1] |
| 172 | XX-003 | 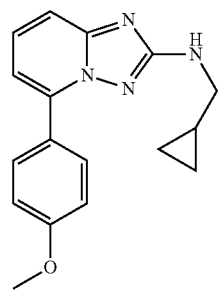 [SMILES: COc1ccc(-c2cccc3nc(NCC4CC4)nn23)cc1] |
| 173 | XX-004 | 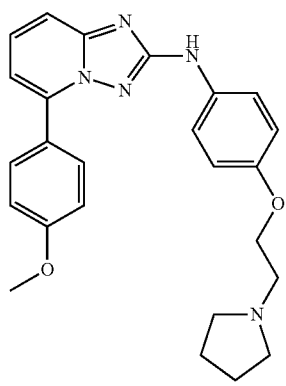 [SMILES: COc1ccc(-c2cccc3nc(Nc4ccc(OCCN5CCCC5)cc4)nn23)cc1] |
-continued
| No. | Code | Structure |
|---|---|---|
| 174 | XX-005 | 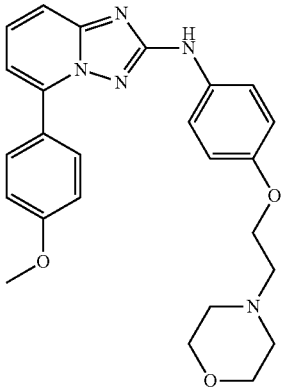 [SMILES: COc1ccc(-c2cccc3nc(Nc4ccc(OCCN5CCOCC5)cc4)nn23)cc1] |
| 175 | XX-006 | 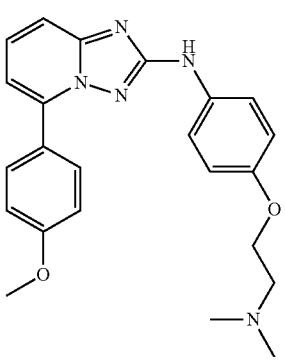 [SMILES: COc1ccc(-c2cccc3nc(Nc4ccc(OCCN(C)C)cc4)nn23)cc1] |
| 176 | XX-007 | 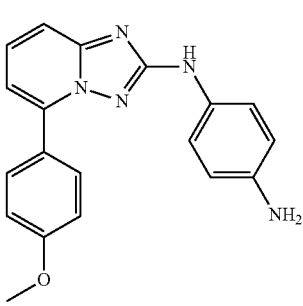 [SMILES: COc1ccc(-c2cccc3nc(Nc4ccc(N)cc4)nn23)cc1] |
| 177 | XX-008 | 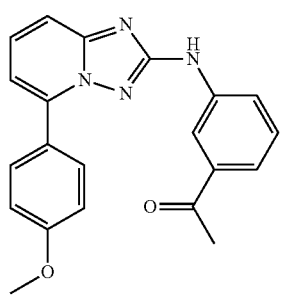 [SMILES: COc1ccc(-c2cccc3nc(Nc4cccc(C(C)=O)c4)nn23)cc1] |

| No. | Code | Structure |
|---|---|---|
| 178 | XX-009 | 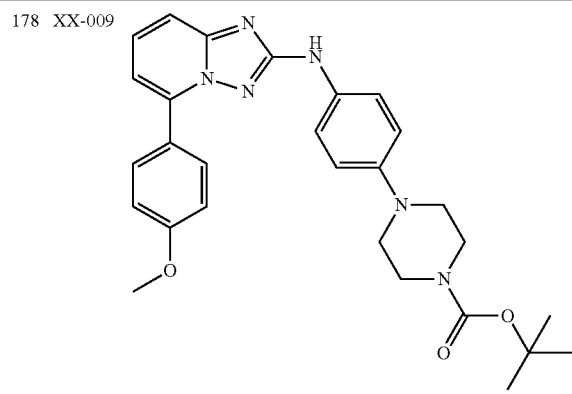 |
| 179 | XX-010 | 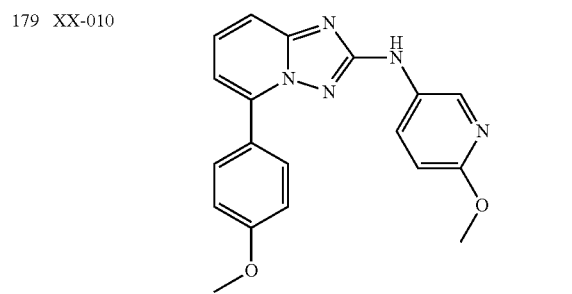 |
| 180 | XX-011 | 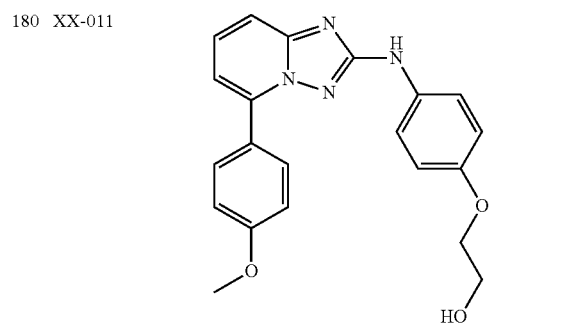 |
| 181 | XX-012 | 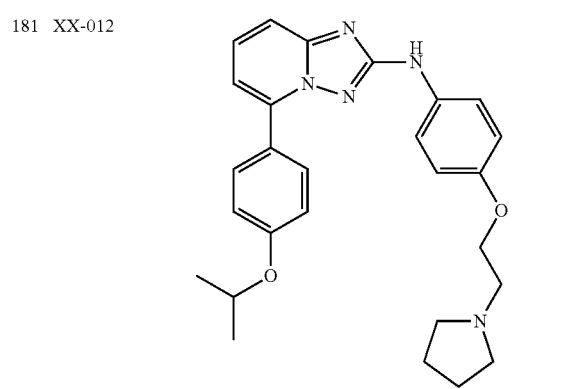 |
| 182 | XX-013 | 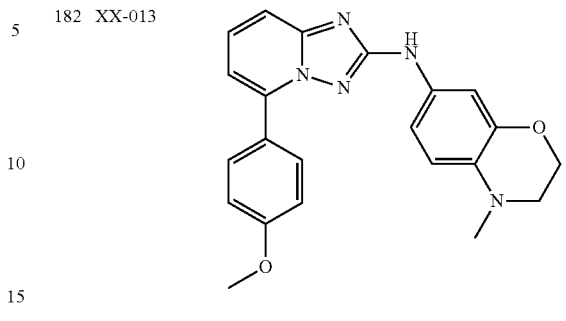 |
| 183 | XX-014 | 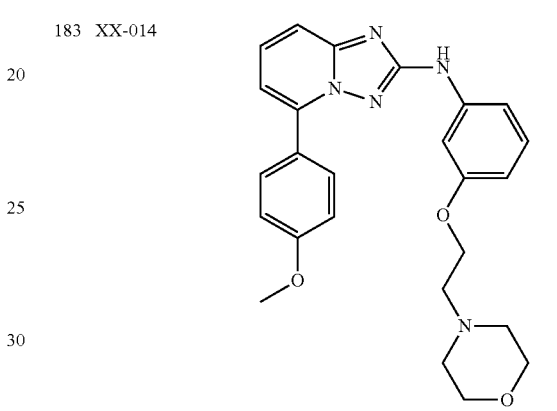 |
| 184 | XX-015 | 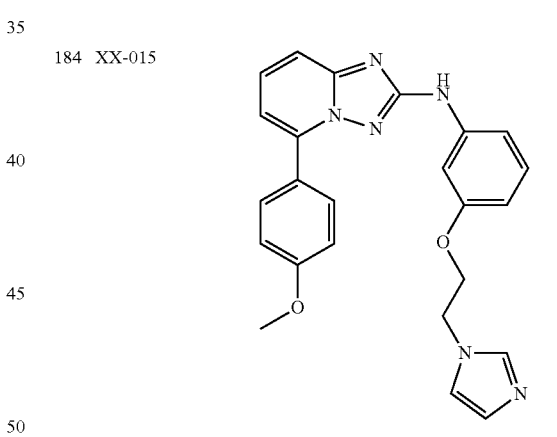 |
| 185 | XX-016 | 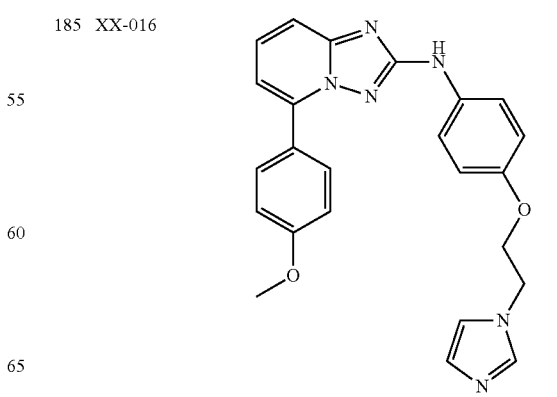 |

| No. | Code | Structure |
|---|---|---|
| 186 | XX-017 | 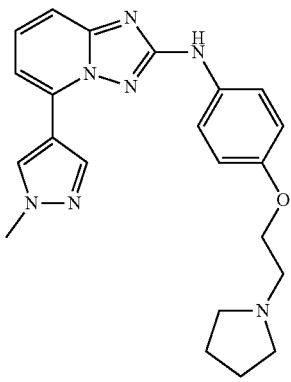 [SMILES: Cn1cc(-c2cccc3nc(Nc4ccc(OCCN5CCCC5)cc4)nn23)cn1] |
| 187 | XX-018 | 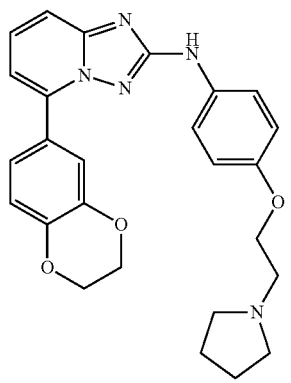 [SMILES: c1cc(-c2ccc3c(c2)OCCO3)n2nc(Nc3ccc(OCCN4CCCC4)cc3)nc2c1] |
| 188 | XX-019 | 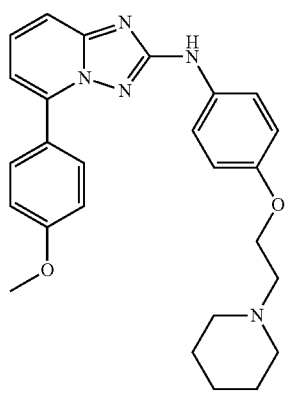 [SMILES: COc1ccc(-c2cccc3nc(Nc4ccc(OCCN5CCCCC5)cc4)nn23)cc1] |
| 189 | XX-020 | 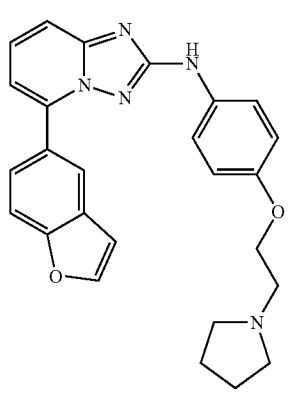 [SMILES: c1cc(-c2ccc3occc3c2)n2nc(Nc3ccc(OCCN4CCCC4)cc3)nc2c1] |
| No. | Code | Structure |
|---|---|---|
| 190 | XX-021 | 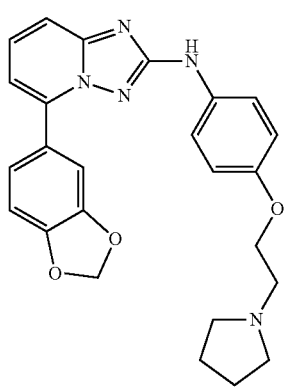 |
| 191 | XX-022 | 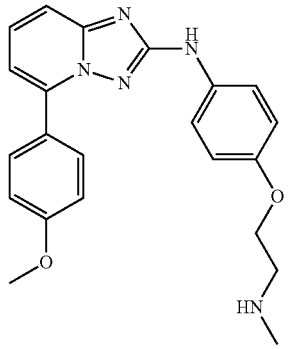 [SMILES: CNCCOc1ccc(Nc2nc3cccc(-c4ccc(OC)cc4)n3n2)cc1] |
| 192 | XX-023 | 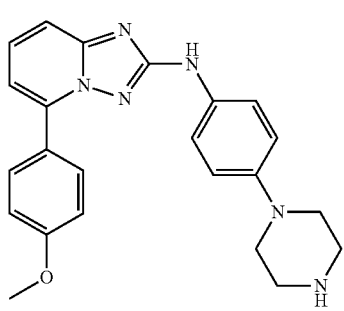 [SMILES: COc1ccc(-c2cccc3nc(Nc4ccc(N5CCNCC5)cc4)nn23)cc1] |
| 193 | XX-024 | 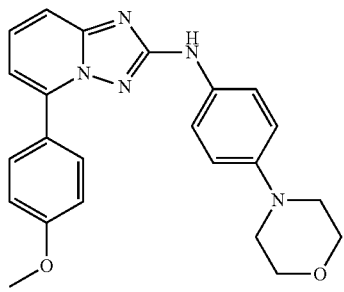 [SMILES: COc1ccc(-c2cccc3nc(Nc4ccc(N5CCOCC5)cc4)nn23)cc1] |

| No. | Code | Structure |
|---|---|---|
| 194 | XX-025 | 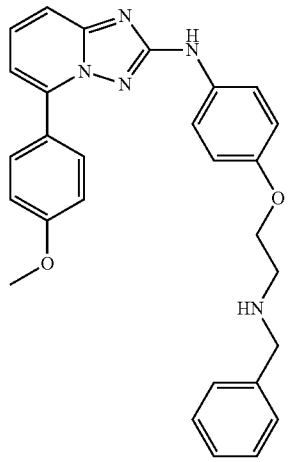 [SMILES: COc1ccc(-c2cccc3nc(Nc4ccc(OCCNCc5ccccc5)cc4)nn23)cc1] |
| 195 | XX-026 | 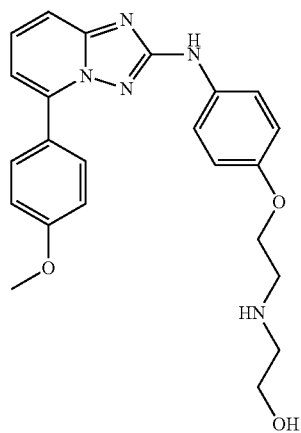 [SMILES: COc1ccc(-c2cccc3nc(Nc4ccc(OCCNCCO)cc4)nn23)cc1] |
| 196 | XX-027 | 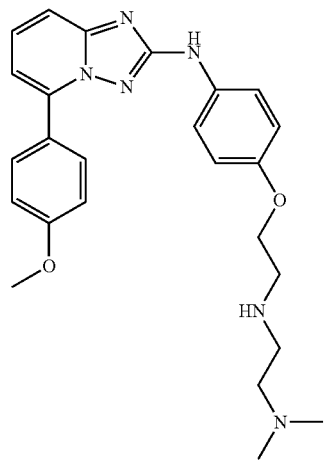 [SMILES: COc1ccc(-c2cccc3nc(Nc4ccc(OCCNCCN(C)C)cc4)nn23)cc1] |
| 197 | XX-028 | 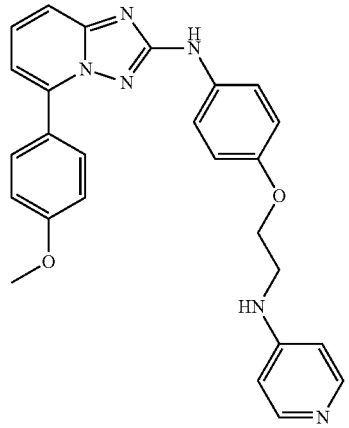 [SMILES: COc1ccc(-c2cccc3nc(Nc4ccc(OCCNc5ccncc5)cc4)nn23)cc1] |
| 198 | XX-029 | 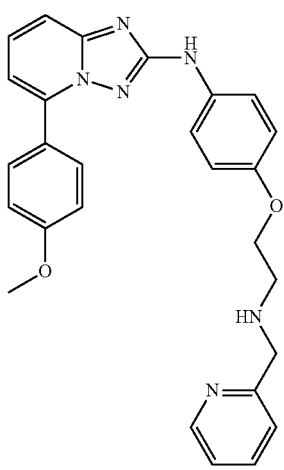 |
| 199 | XX-030 | 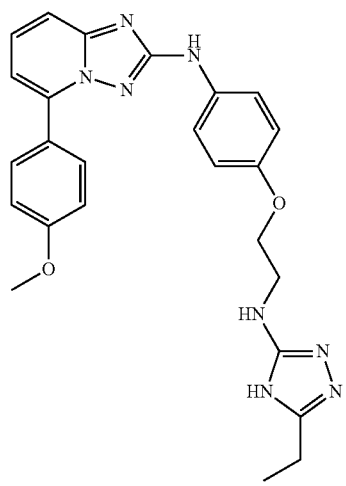 [SMILES: CCc1nnc(NCCOc2ccc(Nc3nc4cccc(-c5ccc(OC)cc5)n4n3)cc2)[nH]1] |

-continued
| No. | Code | Structure |
|-----|------|-----------|
| 200 | XX-031 | 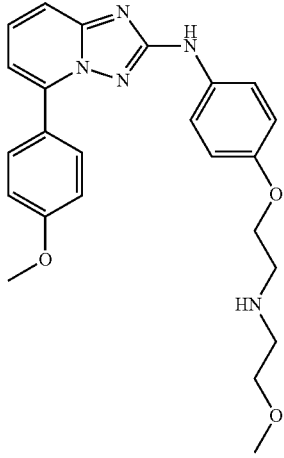 [SMILES: COCCNCCOc1ccc(Nc2nc3cccc(-c4ccc(OC)cc4)n3n2)cc1] |
| 201 | XX-032 | 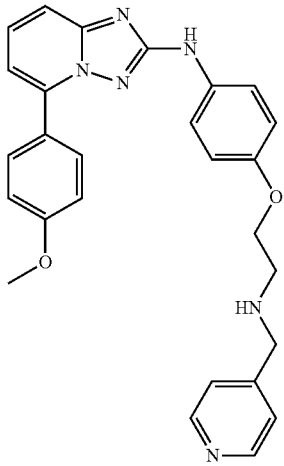 [SMILES: COc1ccc(-c2cccc3nc(Nc4ccc(OCCNCc5ccncc5)cc4)nn23)cc1] |
| 202 | XX-033 | 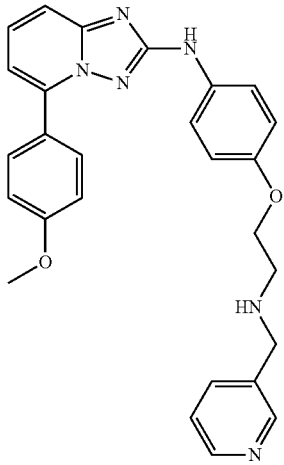 [SMILES: COc1ccc(-c2cccc3nc(Nc4ccc(OCCNCc5cccnc5)cc4)nn23)cc1] |
-continued
| No. | Code | Structure |
|-----|------|-----------|
| 203 | XX-034 | 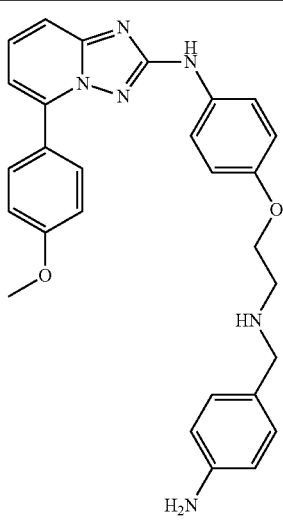 |
| 204 | XX-035 | 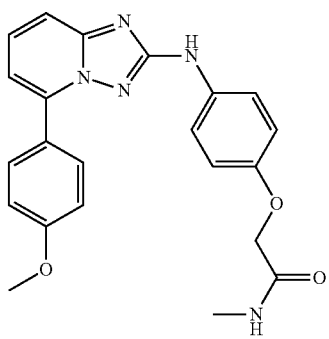 [SMILES: CNC(=O)COc1ccc(Nc2nc3cccc(-c4ccc(OC)cc4)n3n2)cc1] |
| 205 | XX-036 | 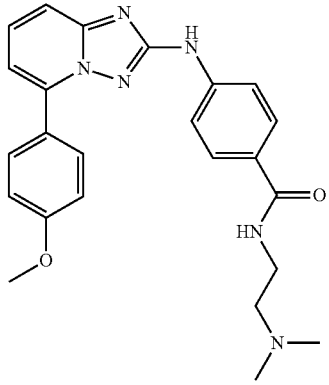 [SMILES: COc1ccc(-c2cccc3nc(Nc4ccc(C(=O)NCCN(C)C)cc4)nn23)cc1] |

-continued
| No. | Code | Structure |
|---|---|---|
| 206 | XX-037 | 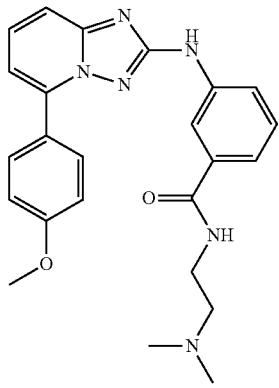 [SMILES: COc1ccc(-c2cccc3nc(Nc4cccc(C(=O)NCCN(C)C)c4)nn23)cc1] |
| 207 | XX-038 | 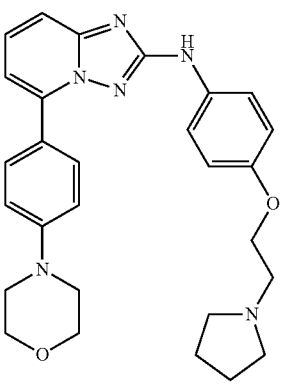 [SMILES: c1cc(-c2ccc(N3CCOCC3)cc2)n2nc(Nc3ccc(OCCN4CCCC4)cc3)nc2c1] |
| 208 | XX-039 | 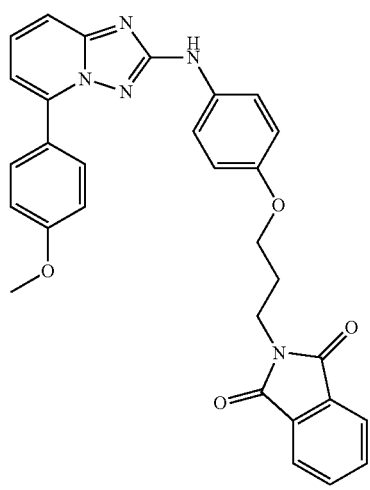 [SMILES: COc1ccc(-c2cccc3nc(Nc4ccc(OCCCN5C(=O)c6ccccc6C5=O)cc4)nn23)cc1] |
-continued
| No. | Code | Structure |
|---|---|---|
| 209 | XX-040 | 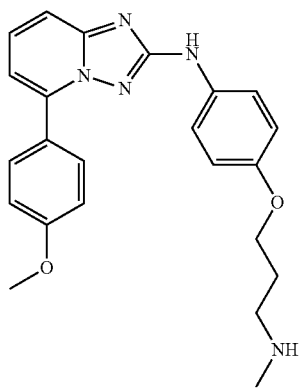 [SMILES: CNCCCOc1ccc(Nc2nc3cccc(-c4ccc(OC)cc4)n3n2)cc1] |
| 210 | XX-041 | 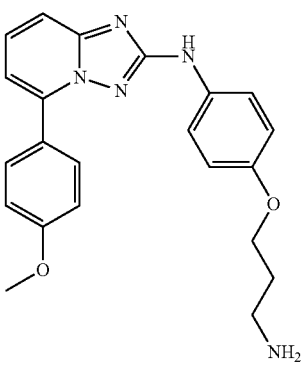 [SMILES: COc1ccc(-c2cccc3nc(Nc4ccc(OCCCN)cc4)nn23)cc1] |
| 211 | XX-042 | 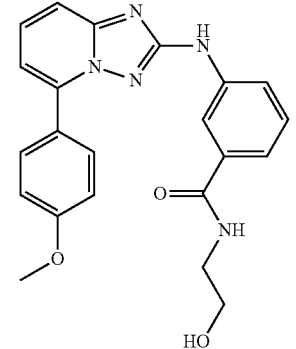 [SMILES: COc1ccc(-c2cccc3nc(Nc4cccc(C(=O)NCCO)c4)nn23)cc1] |
| 212 | XX-043 | 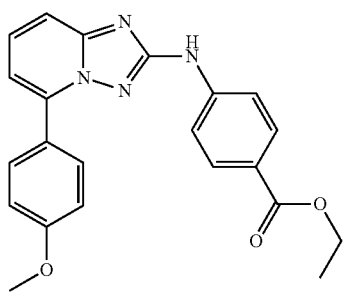 [SMILES: CCOC(=O)c1ccc(Nc2nc3cccc(-c4ccc(OC)cc4)n3n2)cc1] |

-continued
| No. | Code | Structure |
|---|---|---|
| 213 | XX-044 | 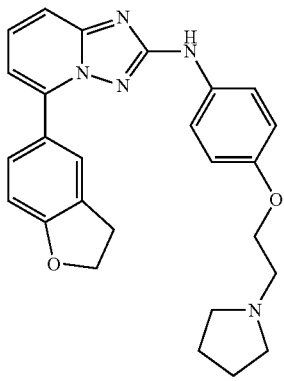 [SMILES: c1cc(-c2ccc3c(c2)CCO3)n2nc(Nc3ccc(OCCN4CCCC4)cc3)nc2c1] |
| 214 | XX-045 | 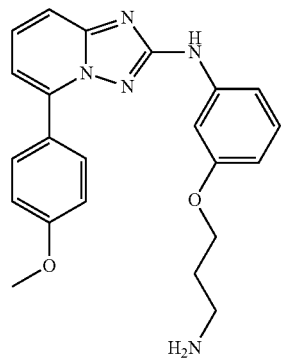 [SMILES: COc1ccc(-c2cccc3nc(Nc4cccc(OCCCN)c4)nn23)cc1] |
| 215 | XX-046 | 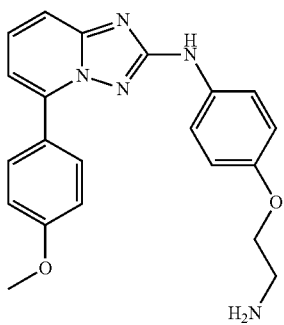 [SMILES: COc1ccc(-c2cccc3nc(Nc4ccc(OCCN)cc4)nn23)cc1] |
| 216 | XX-047 | 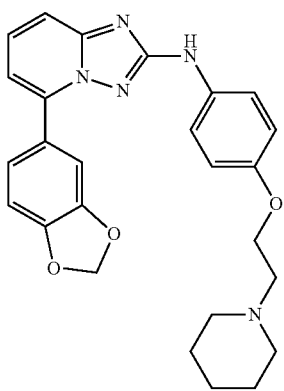 [SMILES: c1cc(-c2ccc3c(c2)OCO3)n2nc(Nc3ccc(OCCN4CCCCC4)cc3)nc2c1] |
-continued
| No. | Code | Structure |
|---|---|---|
| 217 | XX-048 | 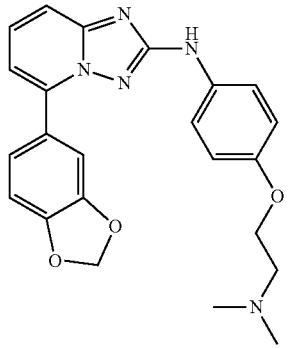 [SMILES: CN(C)CCOc1ccc(Nc2nc3cccc(-c4ccc5c(c4)OCO5)n3n2)cc1] |
| 218 | XX-049 | 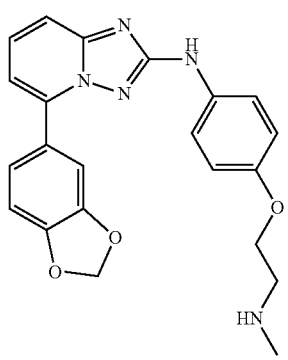 [SMILES: CNCCOc1ccc(Nc2nc3cccc(-c4ccc5c(c4)OCO5)n3n2)cc1] |
| 219 | XX-050 | 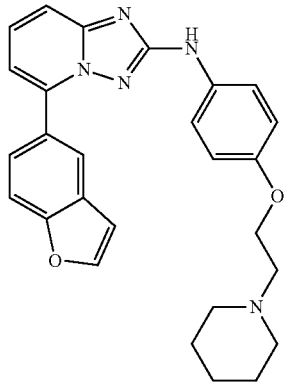 [SMILES: c1cc(-c2ccc3occc3c2)n2nc(Nc3ccc(OCCN4CCCCC4)cc3)nc2c1] |
| 220 | XX-051 | 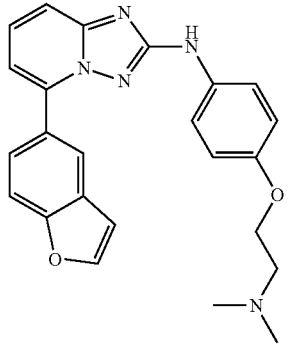 [SMILES: CN(C)CCOc1ccc(Nc2nc3cccc(-c4ccc5occc5c4)n3n2)cc1] |

| No. | Code | Structure |
|---|---|---|
| 221 | XX-052 | 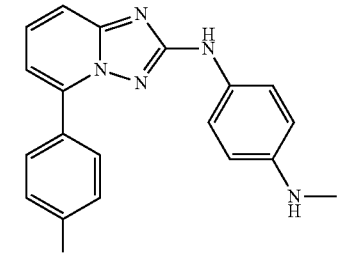 |
| 222 | XX-053 | |
| 223 | XX-054 | |
| 224 | XX-055 | |
| No. | Code | Structure |
|---|---|---|
| 225 | XX-056 | 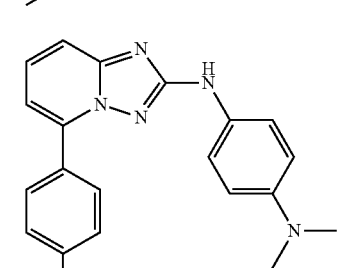 |
| 226 | XX-057 | |
| 227 | XX-058 | |
| 228 | XX-059 | |
| 229 | XX-060 | |

| No. | Code | Structure |
|---|---|---|
| 230 | XX-061 | 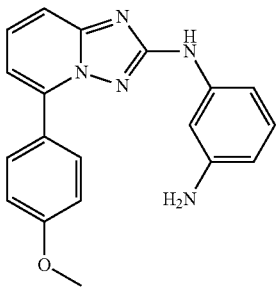 [SMILES: COc1ccc(-c2cccc3nc(Nc4cccc(N)c4)nn23)cc1] |
| 231 | XX-062 | 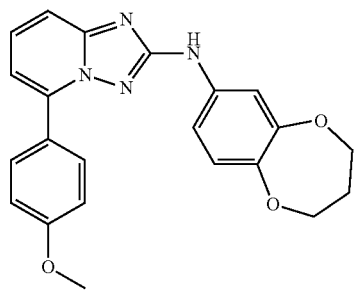 [SMILES: COc1ccc(-c2cccc3nc(Nc4ccc5c(c4)OCCCO5)nn23)cc1] |
| 232 | XX-063 | 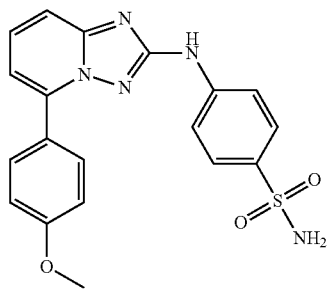 [SMILES: COc1ccc(-c2cccc3nc(Nc4ccc(S(N)(=O)=O)cc4)nn23)cc1] |
| 233 | XX-064 | 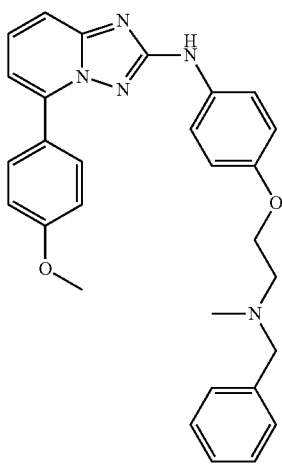 [SMILES: COc1ccc(-c2cccc3nc(Nc4ccc(OCCN(C)Cc5ccccc5)cc4)nn23)cc1] |
| 234 | XX-065 | 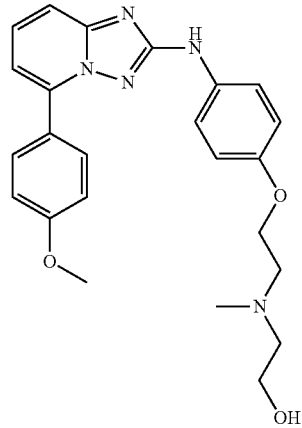 [SMILES: COc1ccc(-c2cccc3nc(Nc4ccc(OCCN(C)CCO)cc4)nn23)cc1] |
| 235 | XX-066 | 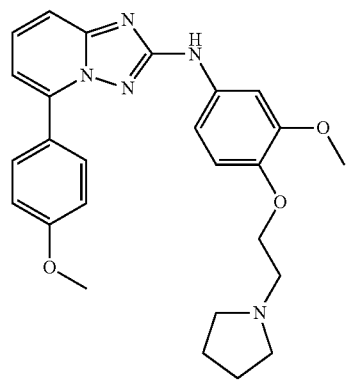 [SMILES: COc1ccc(-c2cccc3nc(Nc4ccc(OCCN5CCCC5)c(OC)c4)nn23)cc1] |
| 236 | XX-067 | 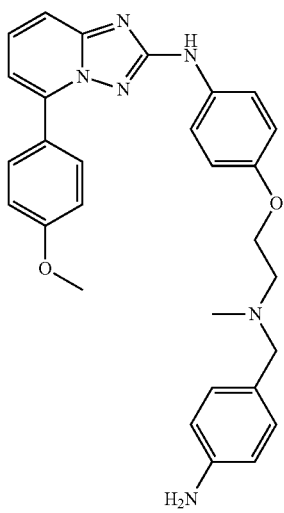 [SMILES: COc1ccc(-c2cccc3nc(Nc4ccc(OCCN(C)Cc5ccc(N)cc5)cc4)nn23)cc1] |

| No. | Code | Structure |
|---|---|---|
| 237 | XX-068 | 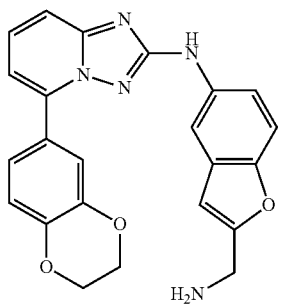 [SMILES: NCc1cc2cc(Nc3nc4cccc(-c5ccc6c(c5)OCCO6)n4n3)ccc2o1] |
| 238 | XX-069 | 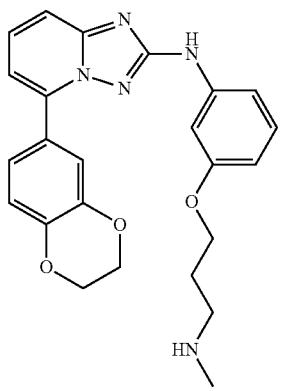 [SMILES: CNCCCOc1cccc(Nc2nc3cccc(-c4ccc5c(c4)OCCO5)n3n2)c1] |
| 239 | XX-070 | 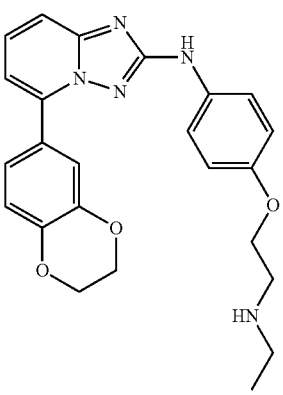 [SMILES: CCNCCOc1ccc(Nc2nc3cccc(-c4ccc5c(c4)OCCO5)n3n2)cc1] |
| 240 | XX-071 | 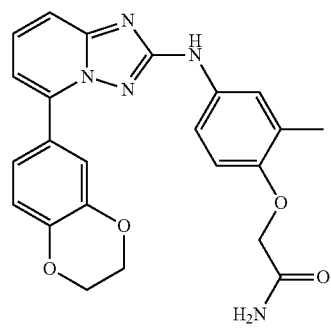 [SMILES: Cc1cc(Nc2nc3cccc(-c4ccc5c(c4)OCCO5)n3n2)ccc1OCC(N)=O] |
| 241 | XX-072 | 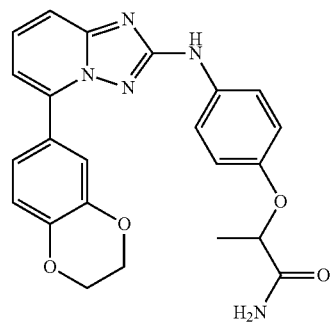 |
| 242 | XX-073 | 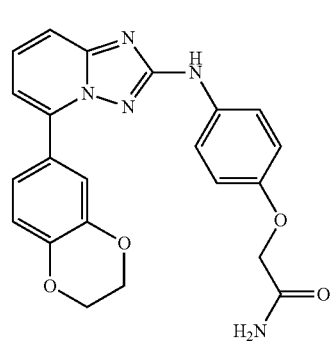 [SMILES: NC(=O)COc1ccc(Nc2nc3cccc(-c4ccc5c(c4)OCCO5)n3n2)cc1] |
| 243 | XX-074 | 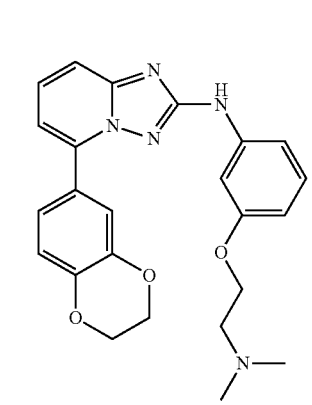 [SMILES: CN(C)CCOc1cccc(Nc2nc3cccc(-c4ccc5c(c4)OCCO5)n3n2)c1] |
| 244 | XX-075 | 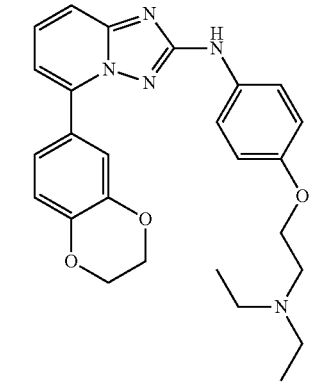 |

| No. | Code | Structure |
|---|---|---|
| 245 | XX-076 | 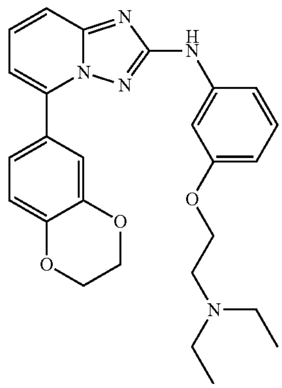 [SMILES: CCN(CC)CCOc1cccc(Nc2nc3cccc(-c4ccc5c(c4)OCCO5)n3n2)c1] |
| 246 | XX-077 | 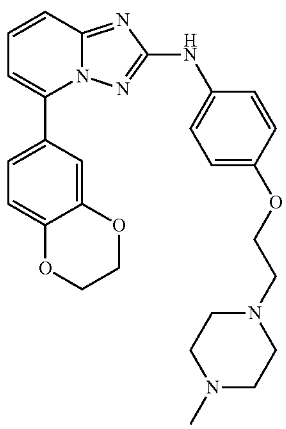 [SMILES: CN1CCN(CCOc2ccc(Nc3nc4cccc(-c5ccc6c(c5)OCCO6)n4n3)cc2)CC1] |
| 247 | XX-078 | 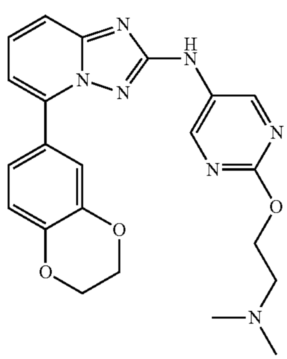 [SMILES: CN(C)CCOc1ncc(Nc2nc3cccc(-c4ccc5c(c4)OCCO5)n3n2)cn1] |
| 248 | XX-079 | 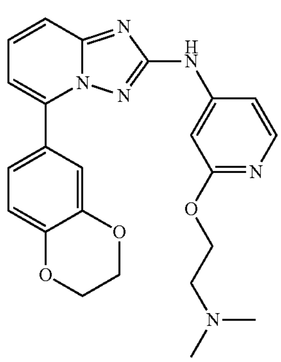 [SMILES: CN(C)CCOc1cc(Nc2nc3cccc(-c4ccc5c(c4)OCCO5)n3n2)ccn1] |
| 249 | XX-080 | |
| 250 | XX-081 | |
| 251 | XX-082 | |
| 252 | XX-083 | |

| No. | Code | Structure |
|---|---|---|
| 253 | XX-084 | 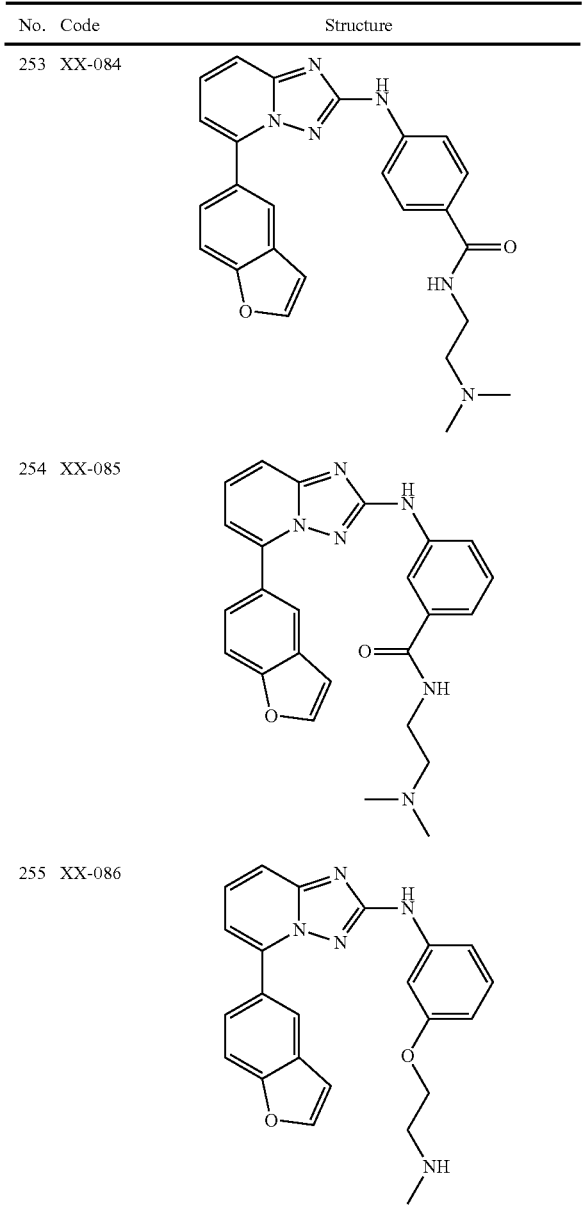 |
| 254 | XX-085 | |
| 255 | XX-086 | |
| No. | Code | Structure |
|---|---|---|
| 256 | XX-087 | 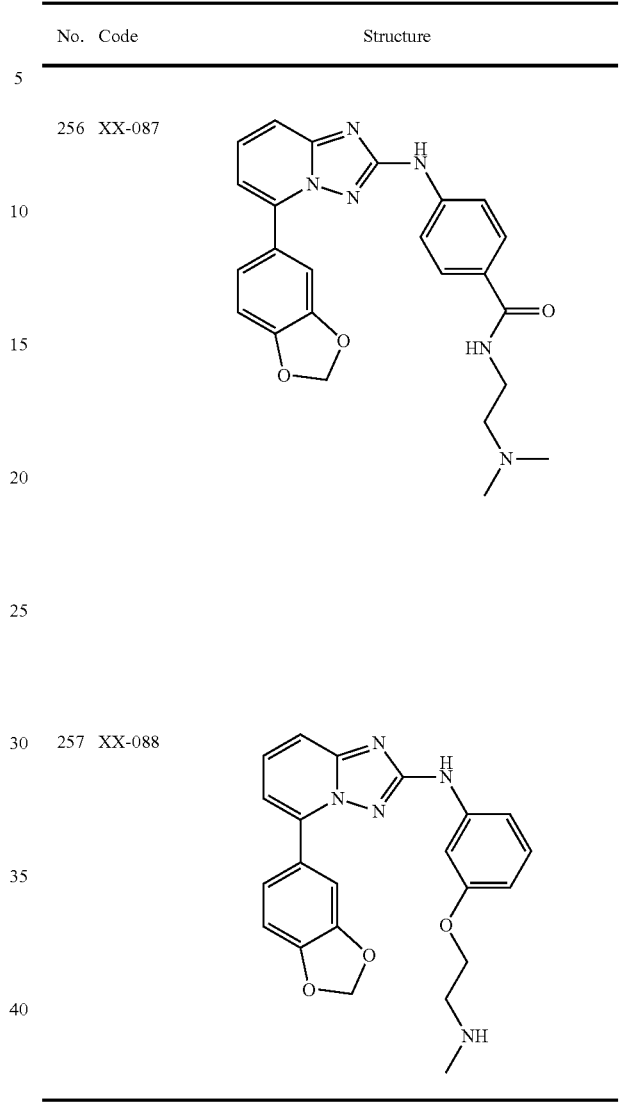 |
| 257 | XX-088 | |
In one embodiment, the compounds are selected from compounds of the following formulae and pharmaceutically acceptable salts, hydrates, and solvates thereof:
| No. | Code | Structure |
|---|---|---|
| 258 | XX-089 | 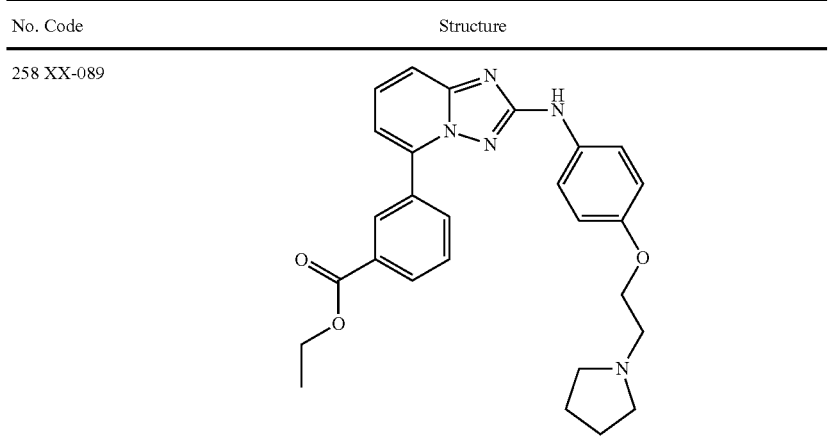 |

| No. Code | Structure |
|---|---|
| 259 XX-090 | 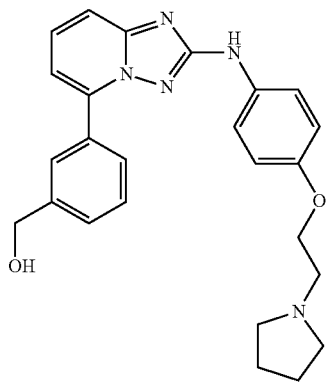 [SMILES: OCc1cccc(-c2cccc3nc(Nc4ccc(OCCN5CCCC5)cc4)nn23)c1] |
| 260 XX-091 | 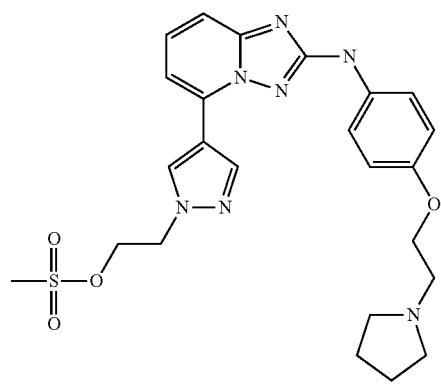 [SMILES: CS(=O)(=O)OCCn1cc(-c2cccc3nc(Nc4ccc(OCCN5CCCC5)cc4)nn23)cn1] |
| 261 XX-092 | 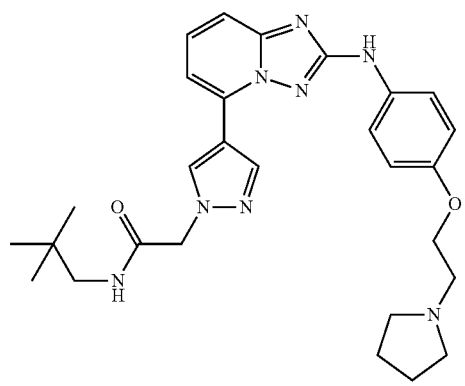 [SMILES: CC(C)(C)CNC(=O)Cn1cc(-c2cccc3nc(Nc4ccc(OCCN5CCCC5)cc4)nn23)cn1] |
| 262 XX-093 | 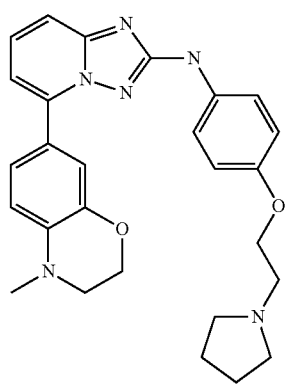 [SMILES: CN1CCOc2cc(-c3cccc4nc(Nc5ccc(OCCN6CCCC6)cc5)nn34)ccc21] |

| No. Code | Structure |
|---|---|
| 263 XX-094 | 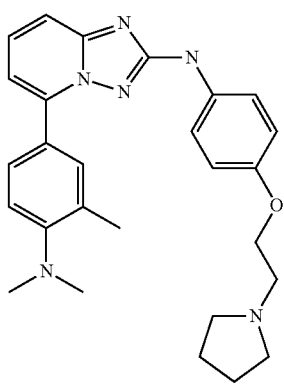 [SMILES: Cc1cc(-c2cccc3nc(Nc4ccc(OCCN5CCCC5)cc4)nn23)ccc1N(C)C] |
| 264 XX-095 | 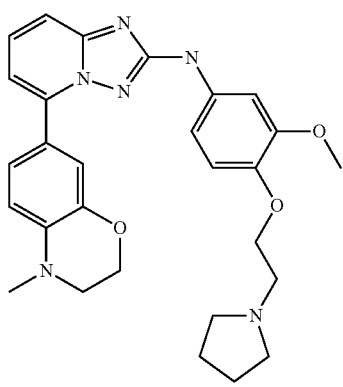 [SMILES: COc1cc(Nc2nc3cccc(-c4ccc5c(c4)OCCN5C)n3n2)ccc1OCCN1CCCC1] |
| 265 XX-096 | 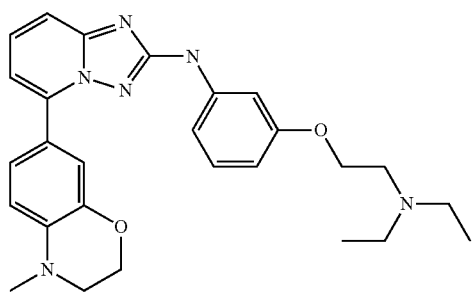 [SMILES: CCN(CC)CCOc1cccc(Nc2nc3cccc(-c4ccc5c(c4)OCCN5C)n3n2)c1] |
| 266 XX-097 | 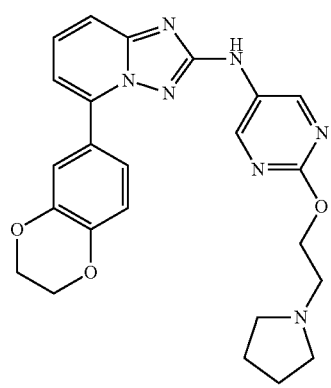 [SMILES: c1cc(-c2ccc3c(c2)OCCO3)n2nc(Nc3cnc(OCCN4CCCC4)nc3)nc2c1] |

-continued
| No. Code | Structure |
|---|---|
| 267 XX-098 | 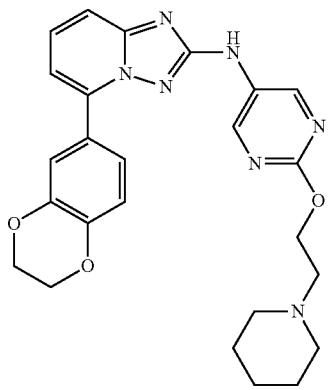 [SMILES: c1cc(-c2ccc3c(c2)OCCO3)n2nc(Nc3cnc(OCCN4CCCCC4)nc3)nc2c1] |
| 268 XX-099 | 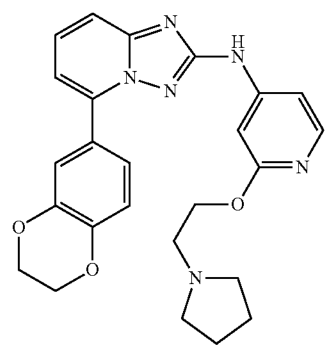 [SMILES: c1cc(-c2ccc3c(c2)OCCO3)n2nc(Nc3ccnc(OCCN4CCCC4)c3)nc2c1] |
| 269 XX-100 | 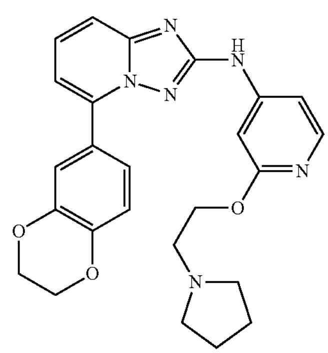 [SMILES: c1cc(-c2ccc3c(c2)OCCO3)n2nc(Nc3ccnc(OCCN4CCCC4)c3)nc2c1] |
| 270 XX-101 | 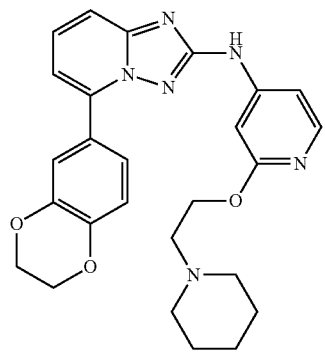 [SMILES: c1cc(-c2ccc3c(c2)OCCO3)n2nc(Nc3ccnc(OCCN4CCCCC4)c3)nc2c1] |

| No. Code | Structure |
|---|---|
| 271 XX-102 | 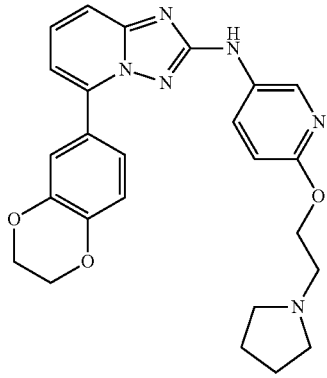 [SMILES: c1cc(-c2ccc3c(c2)OCCO3)n2nc(Nc3ccc(OCCN4CCCC4)nc3)nc2c1] |
| 272 XX-103 | 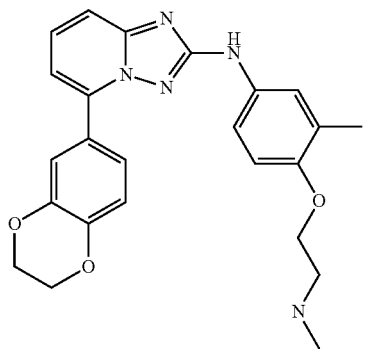 [SMILES: CNCCOc1ccc(Nc2nc3cccc(-c4ccc5c(c4)OCCO5)n3n2)cc1C] |
| 273 XX-104 | 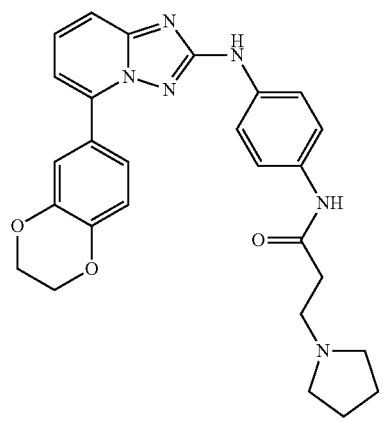 [SMILES: O=C(CCN1CCCC1)Nc1ccc(Nc2nc3cccc(-c4ccc5c(c4)OCCO5)n3n2)cc1] |
| 274 XX-105 | 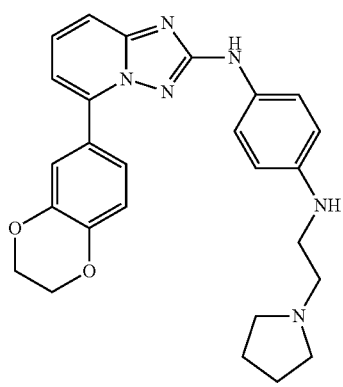 [SMILES: c1cc(-c2ccc3c(c2)OCCO3)n2nc(Nc3ccc(NCCN4CCCC4)cc3)nc2c1] |

| No. Code | Structure |
|---|---|
| 275 XX-106 | 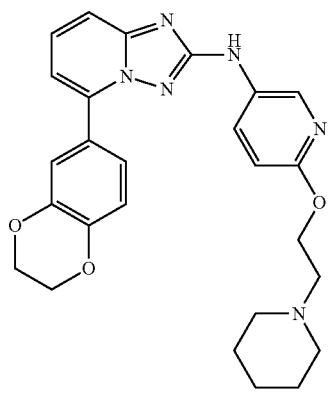 [SMILES: c1cc(-c2ccc3c(c2)OCCO3)n2nc(Nc3ccc(OCCN4CCCCC4)nc3)nc2c1] |
| 276 XX-107 | 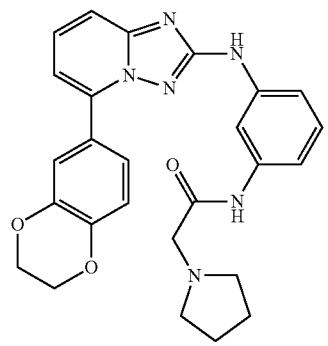 [SMILES: O=C(CN1CCCC1)Nc1cccc(Nc2nc3cccc(-c4ccc5c(c4)OCCO5)n3n2)c1] |
| 277 XX-108 | 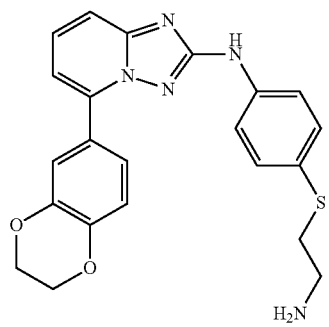 [SMILES: NCCSc1ccc(Nc2nc3cccc(-c4ccc5c(c4)OCCO5)n3n2)cc1] |
| 278 XX-109 | 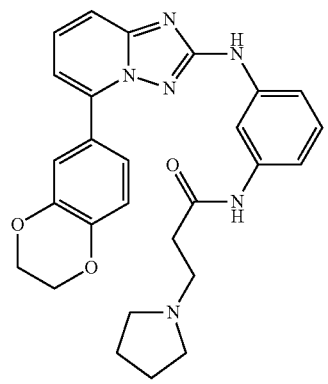 [SMILES: O=C(CCN1CCCC1)Nc1cccc(Nc2nc3cccc(-c4ccc5c(c4)OCCO5)n3n2)c1] |

| No. Code | Structure |
|---|---|
| 279 XX-110 | 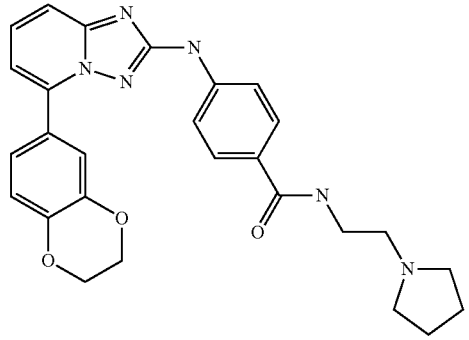 [SMILES: O=C(NCCN1CCCC1)c1ccc(Nc2nc3cccc(-c4ccc5c(c4)OCCO5)n3n2)cc1] |
| 280 XX-111 | 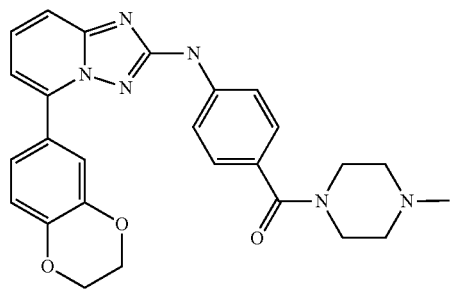 [SMILES: CN1CCN(C(=O)c2ccc(Nc3nc4cccc(-c5ccc6c(c5)OCCO6)n4n3)cc2)CC1] |
| 281 XX-112 | 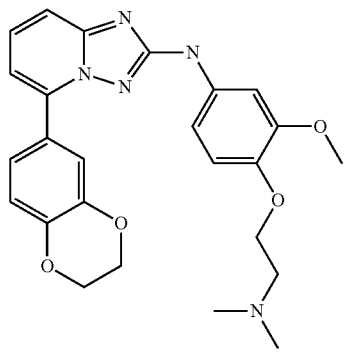 [SMILES: COc1cc(Nc2nc3cccc(-c4ccc5c(c4)OCCO5)n3n2)ccc1OCCN(C)C] |
| 282 XX-113 | 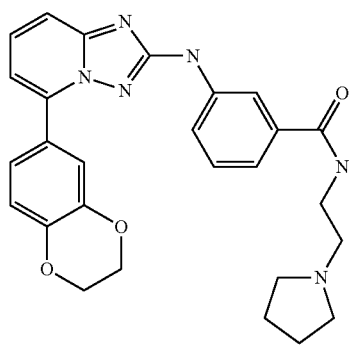 [SMILES: O=C(NCCN1CCCC1)c1cccc(Nc2nc3cccc(-c4ccc5c(c4)OCCO5)n3n2)c1] |

| No. Code | Structure |
|---|---|
| 283 XX-114 | 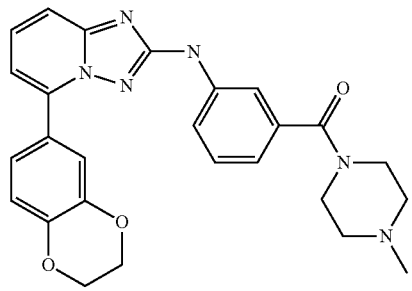 [SMILES: CN1CCN(C(=O)c2cccc(Nc3nc4cccc(-c5ccc6c(c5)OCCO6)n4n3)c2)CC1] |
| 284 XX-115 | 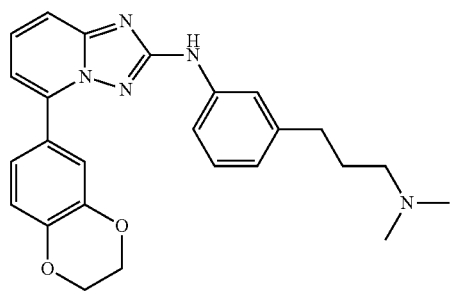 [SMILES: CN(C)CCCc1cccc(Nc2nc3cccc(-c4ccc5c(c4)OCCO5)n3n2)c1] |
| 285 XX-116 | 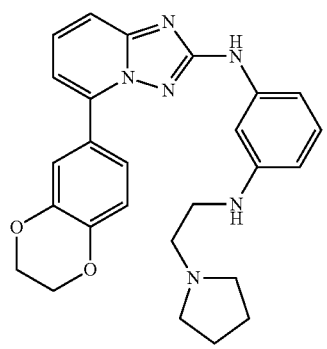 [SMILES: c1cc(NCCN2CCCC2)cc(Nc2nc3cccc(-c4ccc5c(c4)OCCO5)n3n2)c1] |
| 286 XX-117 | 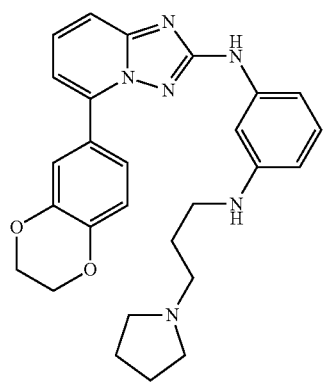 [SMILES: c1cc(NCCCN2CCCC2)cc(Nc2nc3cccc(-c4ccc5c(c4)OCCO5)n3n2)c1] |

-continued
| No. Code | Structure |
|---|---|
| 287 XX-118 | 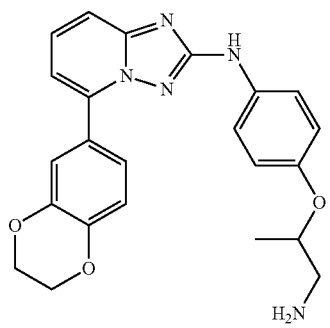 [SMILES: CC(CN)Oc1ccc(Nc2nc3cccc(-c4ccc5c(c4)OCCO5)n3n2)cc1] |
| 288 XX-119 | 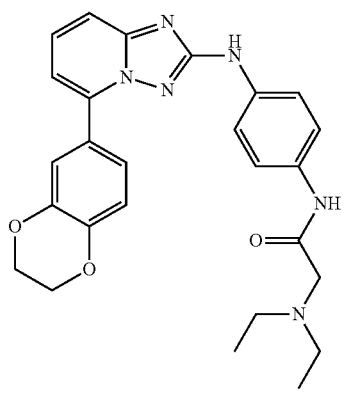 [SMILES: CCN(CC)CC(=O)Nc1ccc(Nc2nc3cccc(-c4ccc5c(c4)OCCO5)n3n2)cc1] |
| 289 XX-120 | 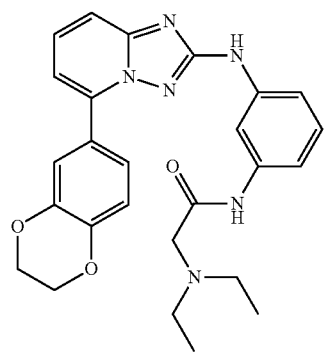 [SMILES: CCN(CC)CC(=O)Nc1cccc(Nc2nc3cccc(-c4ccc5c(c4)OCCO5)n3n2)c1] |
| 290 XX-121 | 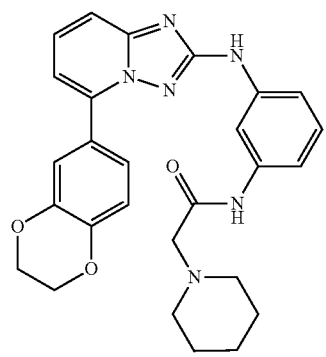 [SMILES: O=C(CN1CCCCC1)Nc1cccc(Nc2nc3cccc(-c4ccc5c(c4)OCCO5)n3n2)c1] |

-continued
| No. Code | Structure |
|---|---|
| 291 XX-122 | 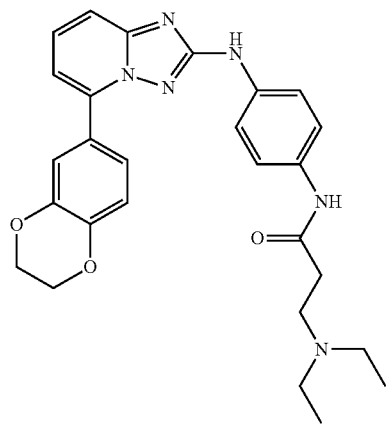 [SMILES: CCN(CC)CCC(=O)Nc1ccc(Nc2nc3cccc(-c4ccc5c(c4)OCCO5)n3n2)cc1] |
| 292 XX-123 | 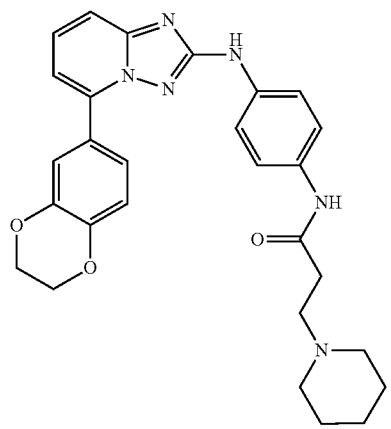 [SMILES: O=C(CCN1CCCCC1)Nc1ccc(Nc2nc3cccc(-c4ccc5c(c4)OCCO5)n3n2)cc1] |
| 293 XX-124 | 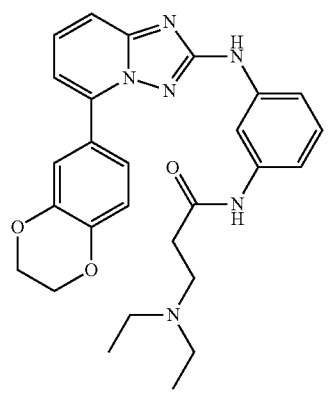 [SMILES: CCN(CC)CCC(=O)Nc1cccc(Nc2nc3cccc(-c4ccc5c(c4)OCCO5)n3n2)c1] |

| No. Code | Structure |
|---|---|
| 294 XX-125 | 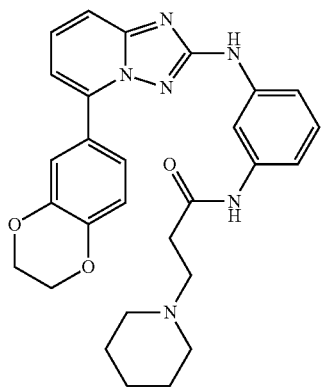 [SMILES: O=C(CCN1CCCCC1)Nc1cccc(Nc2nc3cccc(-c4ccc5c(c4)OCCO5)n3n2)c1] |
| 295 XX-126 | 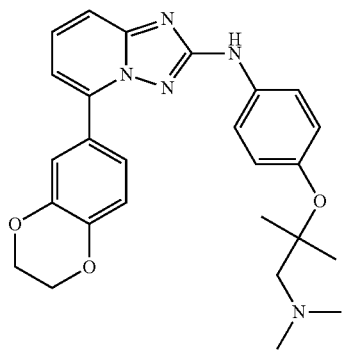 [SMILES: CN(C)CC(C)(C)Oc1ccc(Nc2nc3cccc(-c4ccc5c(c4)OCCO5)n3n2)cc1] |
| 296 XX-127 | 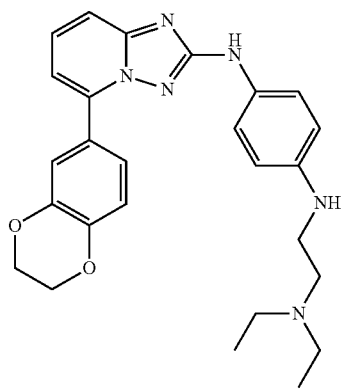 [SMILES: CCN(CC)CCNc1ccc(Nc2nc3cccc(-c4ccc5c(c4)OCCO5)n3n2)cc1] |
| 297 XX-128 | 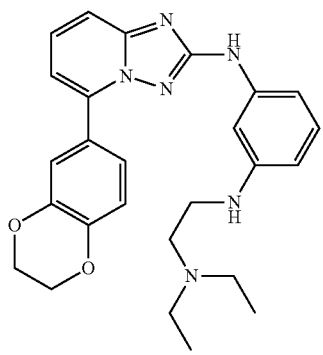 [SMILES: CCN(CC)CCNc1cccc(Nc2nc3cccc(-c4ccc5c(c4)OCCO5)n3n2)c1] |

| No. Code | Structure |
|---|---|
| 298 XX-129 | 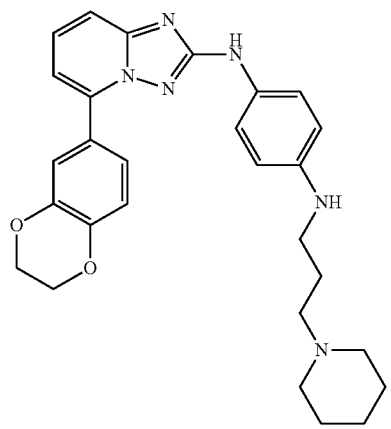 [SMILES: c1cc(-c2ccc3c(c2)OCCO3)n2nc(Nc3ccc(NCCCN4CCCCC4)cc3)nc2c1] |
| 299 XX-130 | 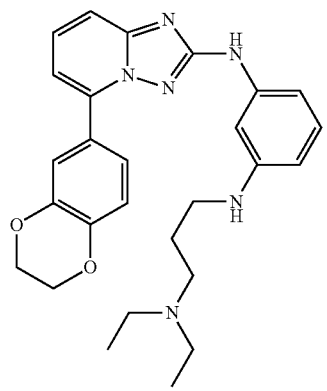 [SMILES: CCN(CC)CCCNc1cccc(Nc2nc3cccc(-c4ccc5c(c4)OCCO5)n3n2)c1] |
| 300 XX-131 | 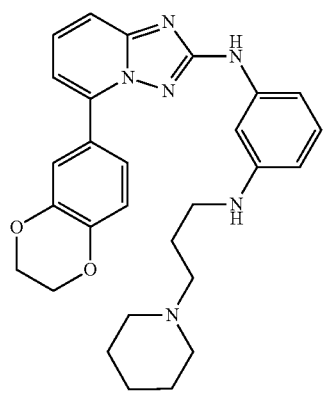 [SMILES: c1cc(NCCCN2CCCCC2)cc(Nc2nc3cccc(-c4ccc5c(c4)OCCO5)n3n2)c1] |
| 301 XX-132 | 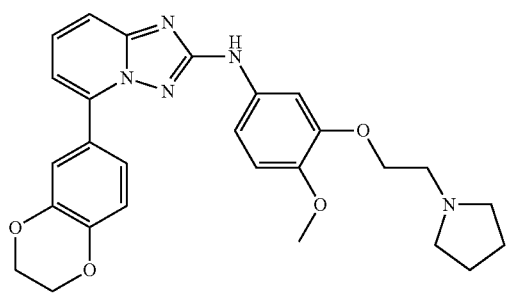 [SMILES: COc1ccc(Nc2nc3cccc(-c4ccc5c(c4)OCCO5)n3n2)cc1OCCN1CCCC1] |

| No. Code | Structure |
|---|---|
| 302 XX-133 | 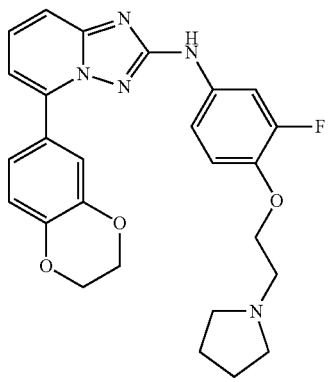 [SMILES: Fc1cc(Nc2nc3cccc(-c4ccc5c(c4)OCCO5)n3n2)ccc1OCCN1CCCC1] |
| 303 XX-134 | 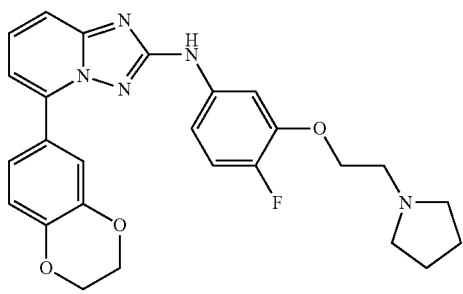 [SMILES: Fc1ccc(Nc2nc3cccc(-c4ccc5c(c4)OCCO5)n3n2)cc1OCCN1CCCC1] |
| XX-135 304 | 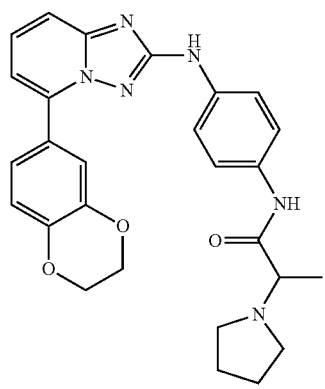 [SMILES: CC(C(=O)Nc1ccc(Nc2nc3cccc(-c4ccc5c(c4)OCCO5)n3n2)cc1)N1CCCC1] |
| 305 XX-136 | 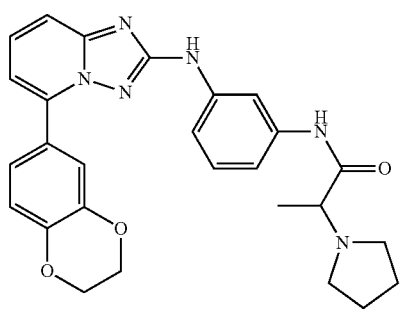 [SMILES: CC(C(=O)Nc1cccc(Nc2nc3cccc(-c4ccc5c(c4)OCCO5)n3n2)c1)N1CCCC1] |

| No. Code | Structure |
|---|---|
| 306 XX-137 | 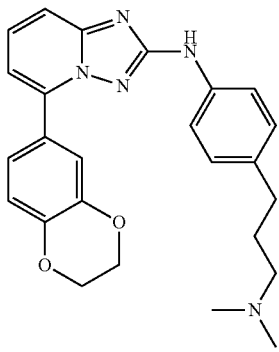 [SMILES: CN(C)CCCc1ccc(Nc2nc3cccc(-c4ccc5c(c4)OCCO5)n3n2)cc1] |
| 307 XX-138 | 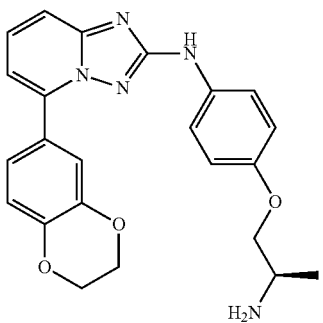 |
| 308 XX-139 | 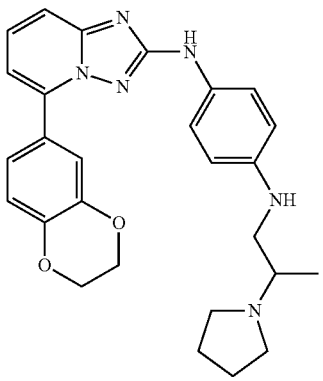 [SMILES: CC(CNc1ccc(Nc2nc3cccc(-c4ccc5c(c4)OCCO5)n3n2)cc1)N1CCCC1] |
| 309 XX-140 | 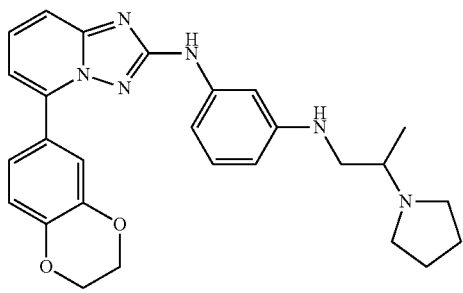 [SMILES: CC(CNc1cccc(Nc2nc3cccc(-c4ccc5c(c4)OCCO5)n3n2)c1)N1CCCC1] |

-continued
| No. Code | Structure |
|---|---|
| 310 XX-141 | 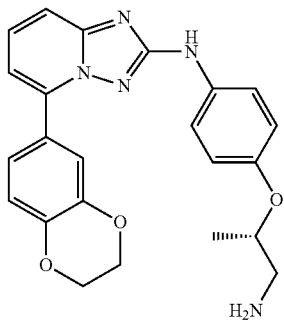 [SMILES: C[C@@H](CN)Oc1ccc(Nc2nc3cccc(-c4ccc5c(c4)OCCO5)n3n2)cc1] |
| 311 XX-142 | 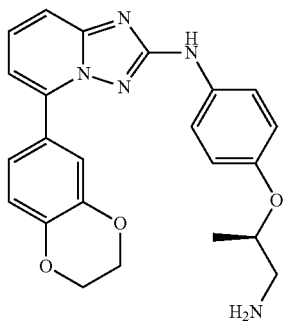 [SMILES: C[C@H](CN)Oc1ccc(Nc2nc3cccc(-c4ccc5c(c4)OCCO5)n3n2)cc1] |
| 312 XX-143 | 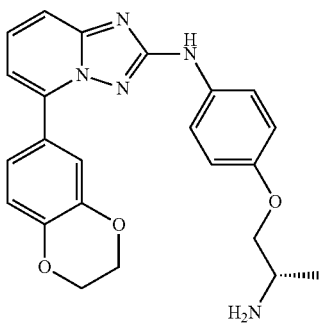 [SMILES: C[C@H](N)COc1ccc(Nc2nc3cccc(-c4ccc5c(c4)OCCO5)n3n2)cc1] |
| 313 XX-144 | 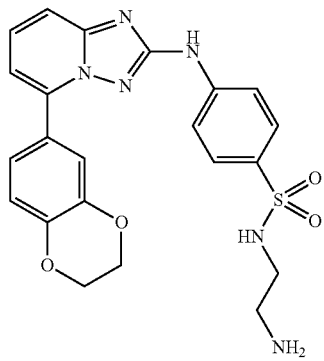 [SMILES: NCCNS(=O)(=O)c1ccc(Nc2nc3cccc(-c4ccc5c(c4)OCCO5)n3n2)cc1] |

| No. Code | Structure |
|---|---|
| 314 XX-145 | 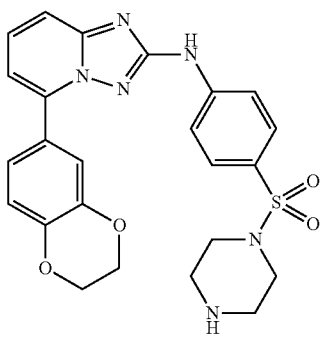 [SMILES: O=S(=O)(c1ccc(Nc2nc3cccc(-c4ccc5c(c4)OCCO5)n3n2)cc1)N1CCNCC1] |
| 315 XX-146 | 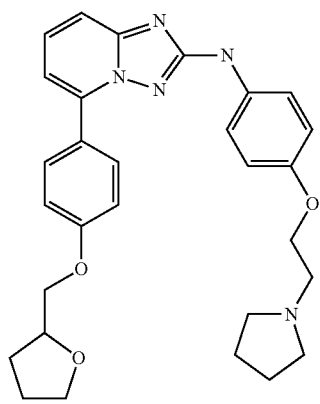 [SMILES: c1cc(-c2ccc(OCC3CCCO3)cc2)n2nc(Nc3ccc(OCCN4CCCC4)cc3)nc2c1] |
| 316 XX-147 | 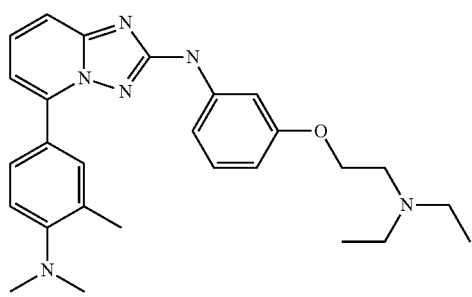 [SMILES: CCN(CC)CCOc1cccc(Nc2nc3cccc(-c4ccc(N(C)C)c(C)c4)n3n2)c1] |
| 317 XX-148 | 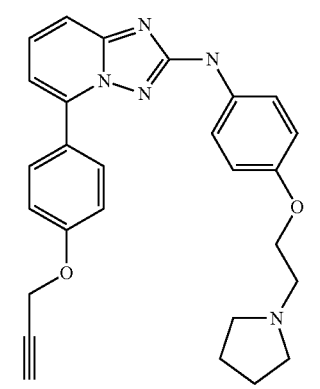 [SMILES: C#CCOc1ccc(-c2cccc3nc(Nc4ccc(OCCN5CCCC5)cc4)nn23)cc1] |

| No. Code | Structure |
|---|---|
| 318 XX-149 | 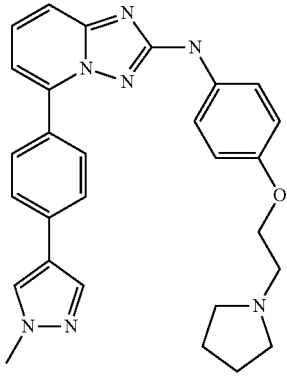 [SMILES: Cn1cc(-c2ccc(-c3cccc4nc(Nc5ccc(OCCN6CCCC6)cc5)nn34)cc2)cn1] |
| 319 XX-150 | 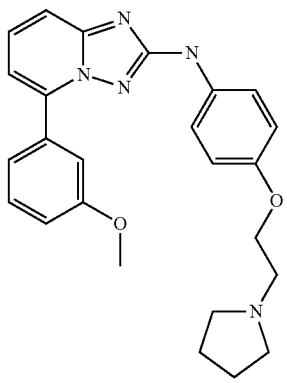 [SMILES: COc1cccc(-c2cccc3nc(Nc4ccc(OCCN5CCCC5)cc4)nn23)c1] |
| 320 XX-151 | 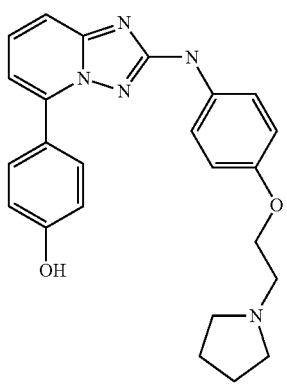 |
| 321 XX-152 | 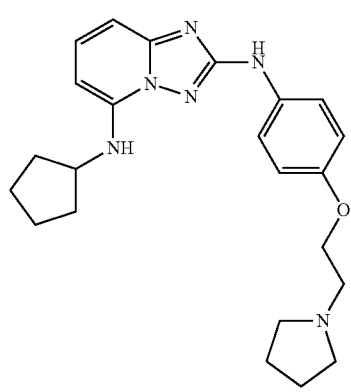 [SMILES: c1cc(NC2CCCC2)n2nc(Nc3ccc(OCCN4CCCC4)cc3)nc2c1] |

| No. Code | Structure |
|---|---|
| 322 XX-153 | 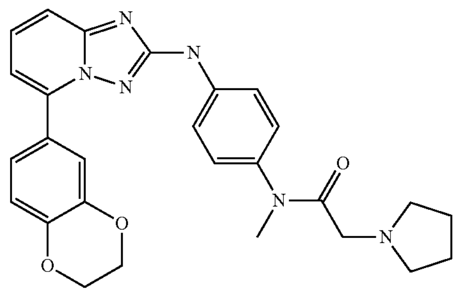 [SMILES: CN(C(=O)CN1CCCC1)c1ccc(Nc2nc3cccc(-c4ccc5c(c4)OCCO5)n3n2)cc1] |
| 323 XX-154 | 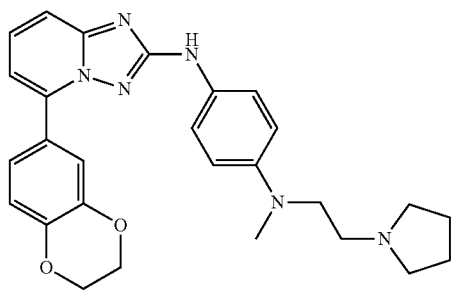 [SMILES: CN(CCN1CCCC1)c1ccc(Nc2nc3cccc(-c4ccc5c(c4)OCCO5)n3n2)cc1] |
| 324 XX-155 | 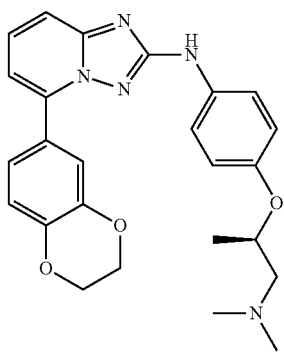 [SMILES: C[C@H](CN(C)C)Oc1ccc(Nc2nc3cccc(-c4ccc5c(c4)OCCO5)n3n2)cc1] |
| 325 XX-156 | 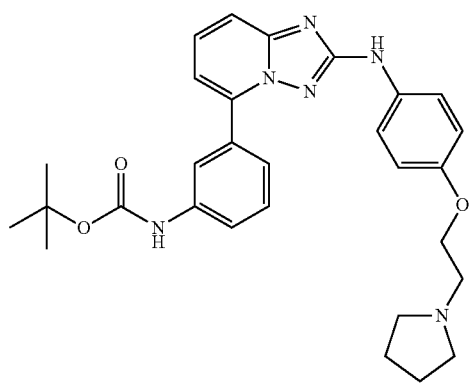 [SMILES: CC(C)(C)OC(=O)Nc1cccc(-c2cccc3nc(Nc4ccc(OCCN5CCCC5)cc4)nn23)c1] |

| No. | Code | Structure |
|---|---|---|
| 326 | XX-157 | 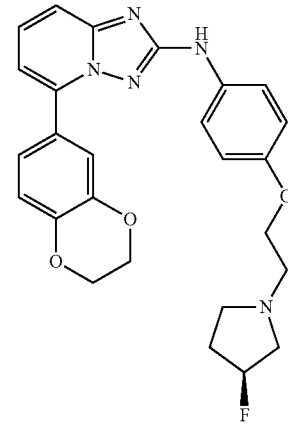 |
| 327 | XX-158 | 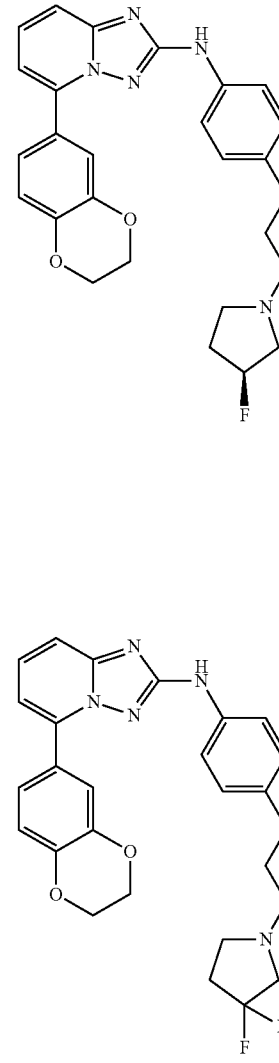 |
| 328 | XX-159 | 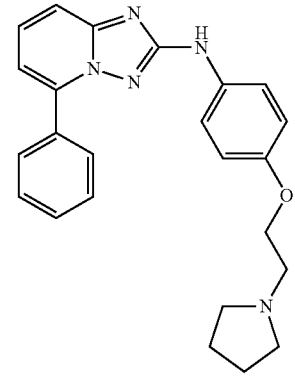 [SMILES: c1ccc(-c2cccc3nc(Nc4ccc(OCCN5CCCC5)cc4)nn23)cc1] |

-continued
| No. Code | Structure |
|---|---|
| 329 XX-160 | 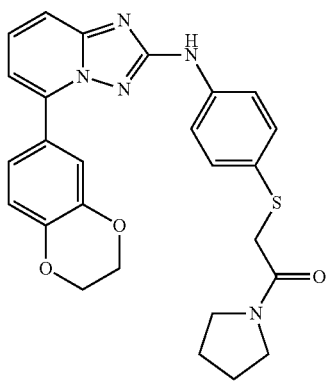 [SMILES: O=C(CSc1ccc(Nc2nc3cccc(-c4ccc5c(c4)OCCO5)n3n2)cc1)N1CCCC1] |
| 330 XX-161 | 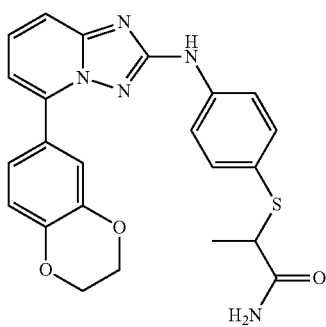 [SMILES: CC(Sc1ccc(Nc2nc3cccc(-c4ccc5c(c4)OCCO5)n3n2)cc1)C(N)=O] |
| 331 XX-162 | 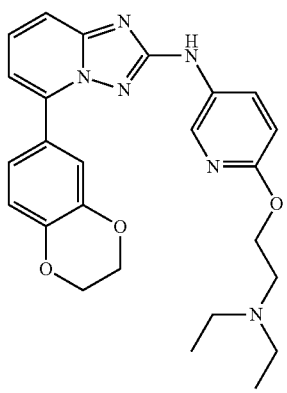 [SMILES: CCN(CC)CCOc1ccc(Nc2nc3cccc(-c4ccc5c(c4)OCCO5)n3n2)cn1] |
| 332 XX-163 | 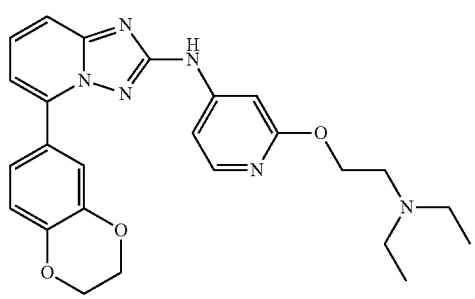 [SMILES: CCN(CC)CCOc1cc(Nc2nc3cccc(-c4ccc5c(c4)OCCO5)n3n2)ccn1] |

| No. Code | Structure |
|---|---|
| 333 XX-164 | 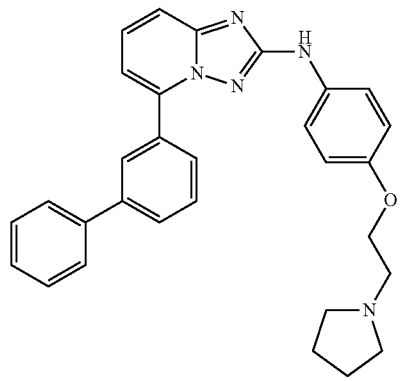 [SMILES: c1ccc(-c2cccc(-c3cccc4nc(Nc5ccc(OCCN6CCCC6)cc5)nn34)c2)cc1] |
| 334 XX-165 | 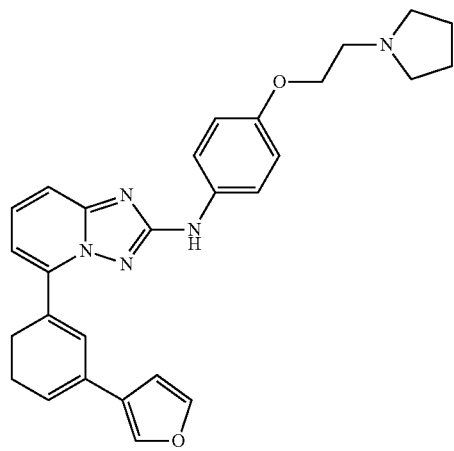 [SMILES: C1=C(c2ccoc2)C=C(c2cccc3nc(Nc4ccc(OCCN5CCCC5)cc4)nn23)CC1] |
| 335 XX-166 | 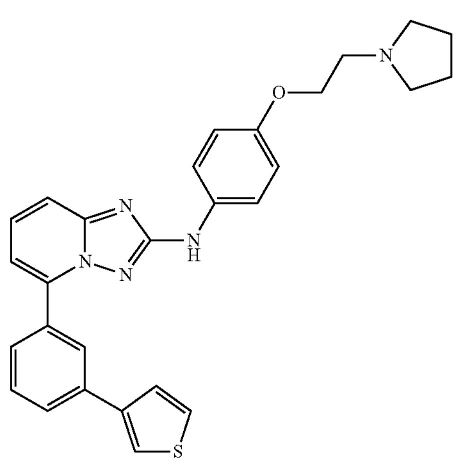 [SMILES: c1cc(-c2ccsc2)cc(-c2cccc3nc(Nc4ccc(OCCN5CCCC5)cc4)nn23)c1] |

| No. Code | Structure |
|---|---|
| 336 XX-167 | 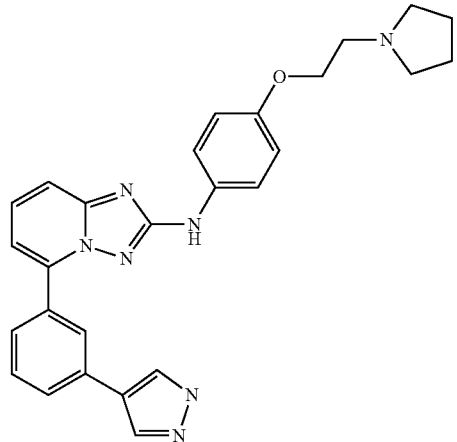 [SMILES: c1cc(-c2cn[nH]c2)cc(-c2cccc3nc(Nc4ccc(OCCN5CCCC5)cc4)nn23)c1] |
| 337 XX-168 | 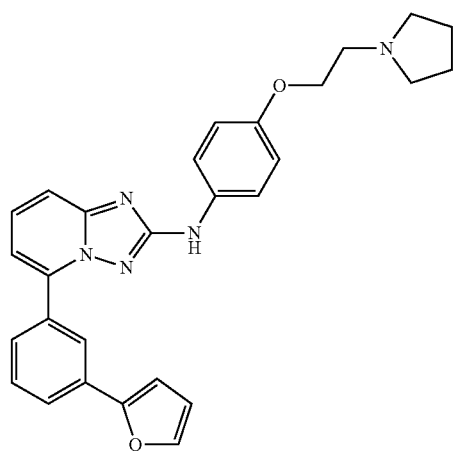 [SMILES: c1cc(-c2ccco2)cc(-c2cccc3nc(Nc4ccc(OCCN5CCCC5)cc4)nn23)c1] |
| 338 XX-169 | 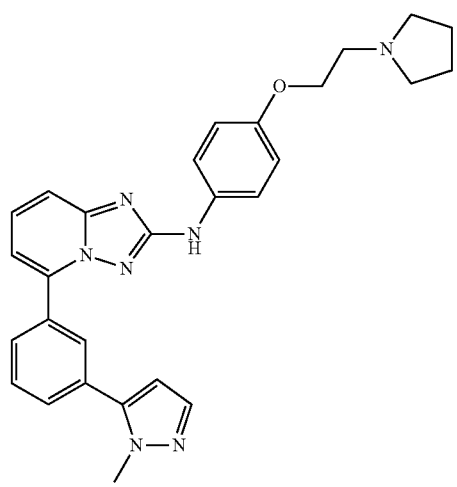 [SMILES: Cn1nccc1-c1cccc(-c2cccc3nc(Nc4ccc(OCCN5CCCC5)cc4)nn23)c1] |

-continued
| No. | Code | Structure |
|---|---|---|
| 339 | XX-170 | 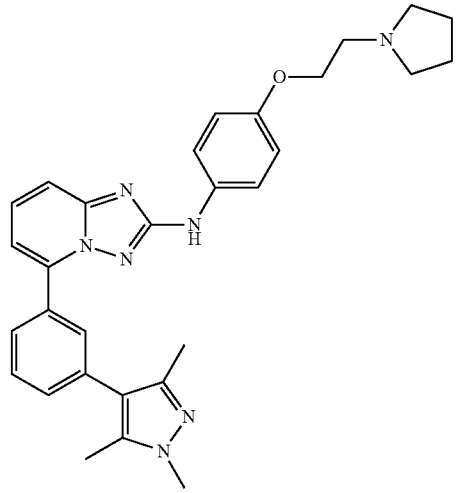 [SMILES: Cc1nn(C)c(C)c1-c1cccc(-c2cccc3nc(Nc4ccc(OCCN5CCCC5)cc4)nn23)c1] |
| 340 | XX-171 | 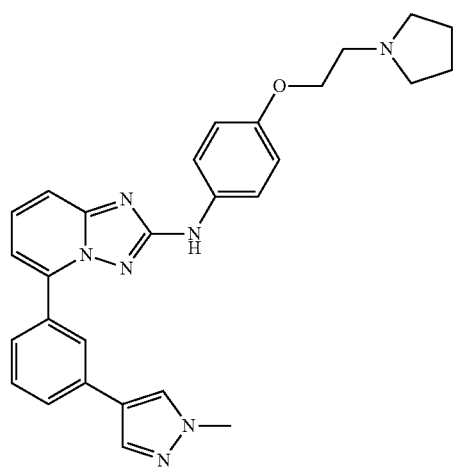 [SMILES: Cn1cc(-c2cccc(-c3cccc4nc(Nc5ccc(OCCN6CCCC6)cc5)nn34)c2)cn1] |
| 341 | XX-172 | 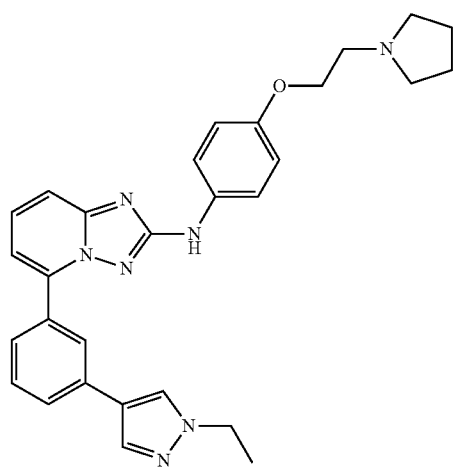 [SMILES: CCn1cc(-c2cccc(-c3cccc4nc(Nc5ccc(OCCN6CCCC6)cc5)nn34)c2)cn1] |

-continued
| No. Code | Structure |
|---|---|
| 342 XX-173 | 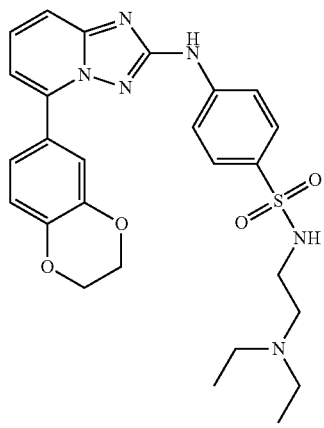 [SMILES: CCN(CC)CCNS(=O)(=O)c1ccc(Nc2nc3cccc(-c4ccc5c(c4)OCCO5)n3n2)cc1] |
| 343 XX-174 | 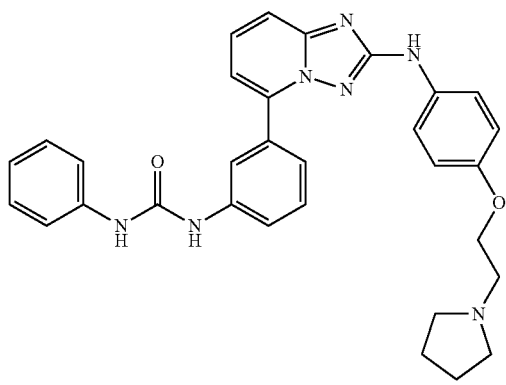 [SMILES: O=C(Nc1ccccc1)Nc1cccc(-c2cccc3nc(Nc4ccc(OCCN5CCCC5)cc4)nn23)c1] |
| 344 XX-175 | 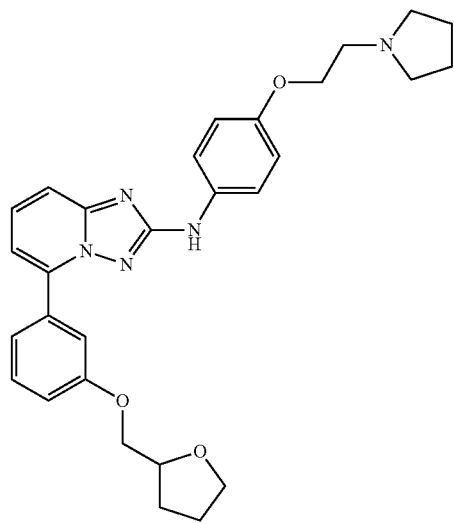 [SMILES: c1cc(OCC2CCCO2)cc(-c2cccc3nc(Nc4ccc(OCCN5CCCC5)cc4)nn23)c1] |

-continued
| No. Code | Structure |
|---|---|
| 345 XX-176 | 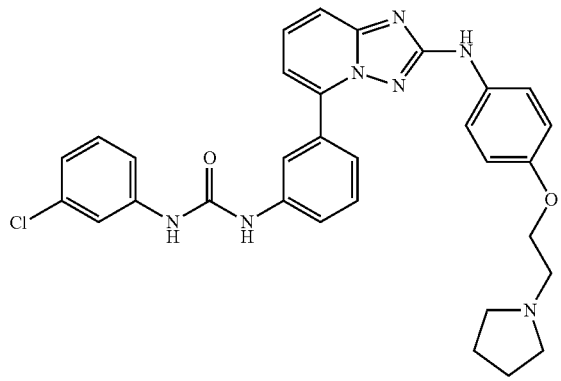 [SMILES: O=C(Nc1cccc(Cl)c1)Nc1cccc(-c2cccc3nc(Nc4ccc(OCCN5CCCC5)cc4)nn23)c1] |
| 346 XX-177 | 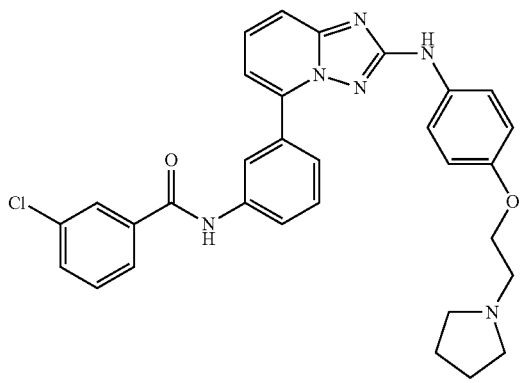 [SMILES: O=C(Nc1cccc(-c2cccc3nc(Nc4ccc(OCCN5CCCC5)cc4)nn23)c1)c1cccc(Cl)c1] |
| 347 XX-178 | 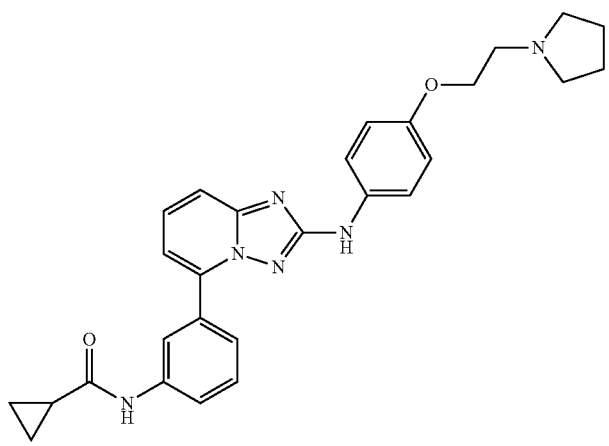 [SMILES: O=C(Nc1cccc(-c2cccc3nc(Nc4ccc(OCCN5CCCC5)cc4)nn23)c1)C1CC1] |

| No. Code | Structure |
|---|---|
| 348 XX-179 | 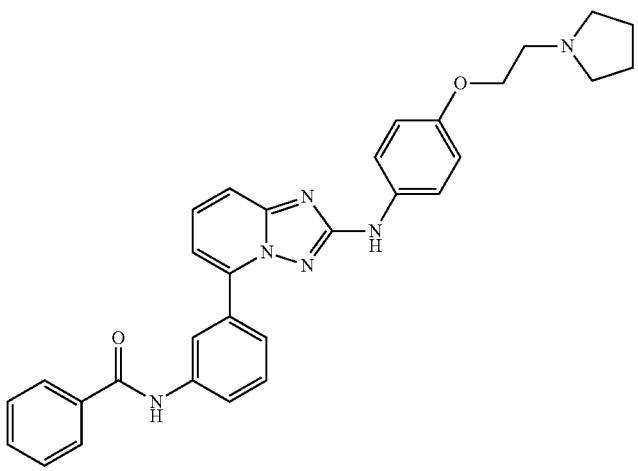 [SMILES: O=C(Nc1cccc(-c2cccc3nc(Nc4ccc(OCCN5CCCC5)cc4)nn23)c1)c1ccccc1] |
| 349 XX-180 | 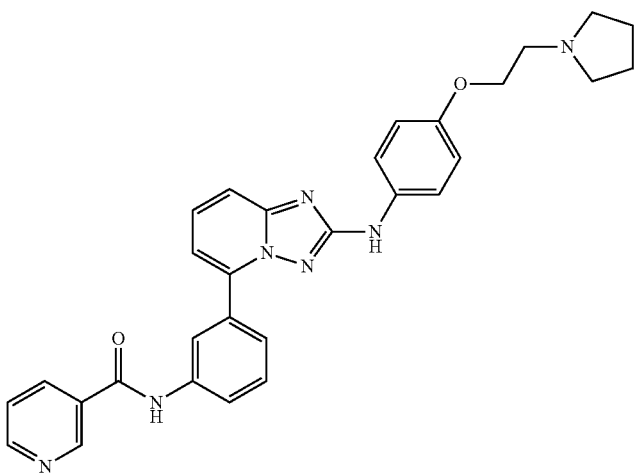 [SMILES: O=C(Nc1cccc(-c2cccc3nc(Nc4ccc(OCCN5CCCC5)cc4)nn23)c1)c1cccnc1] |
| 350 XX-181 | 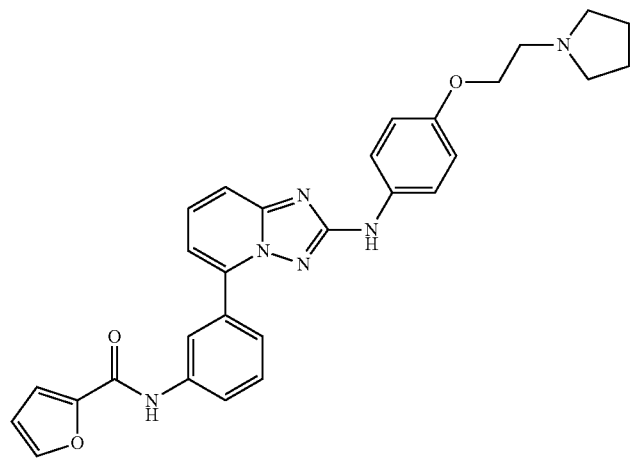 [SMILES: O=C(Nc1cccc(-c2cccc3nc(Nc4ccc(OCCN5CCCC5)cc4)nn23)c1)c1ccco1] |

| No. Code | Structure |
|---|---|
| 351 XX-182 | 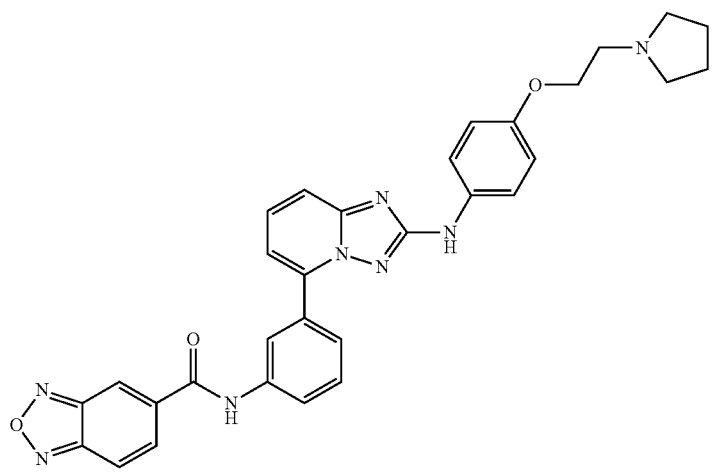 [SMILES: O=C(Nc1cccc(-c2cccc3nc(Nc4ccc(OCCN5CCCC5)cc4)nn23)c1)c1ccc2nonc2c1] |
| 352 XX-183 | 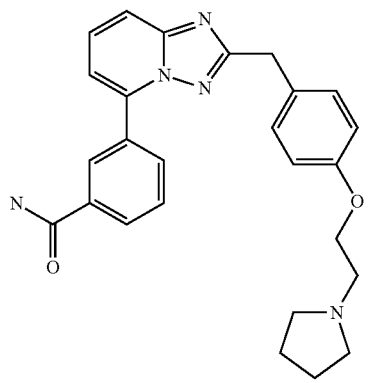 [SMILES: NC(=O)c1cccc(-c2cccc3nc(Cc4ccc(OCCN5CCCC5)cc4)nn23)c1] |
| 353 XX-184 | 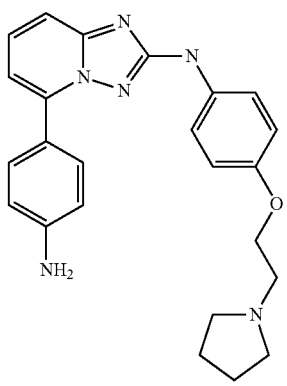 |
| 354 XX-185 | 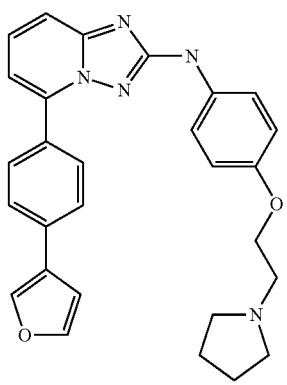 [SMILES: c1cc(-c2ccc(-c3ccoc3)cc2)n2nc(Nc3ccc(OCCN4CCCC4)cc3)nc2c1] |

| No. Code | Structure |
|---|---|
| 355 XX-186 | 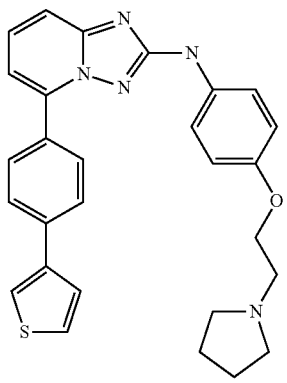 [SMILES: c1cc(-c2ccc(-c3ccsc3)cc2)n2nc(Nc3ccc(OCCN4CCCC4)cc3)nc2c1] |
| 356 XX-187 | 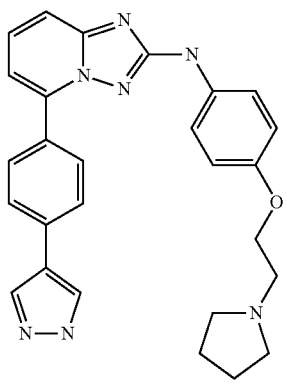 [SMILES: c1cc(-c2ccc(-c3cn[nH]c3)cc2)n2nc(Nc3ccc(OCCN4CCCC4)cc3)nc2c1] |
| 357 XX-188 | 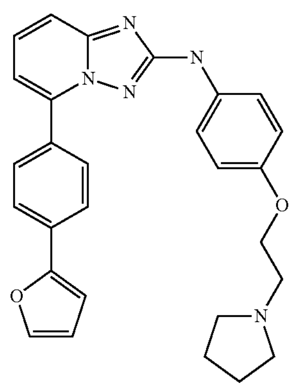 [SMILES: c1coc(-c2ccc(-c3cccc4nc(Nc5ccc(OCCN6CCCC6)cc5)nn34)cc2)c1] |
| 358 XX-189 | 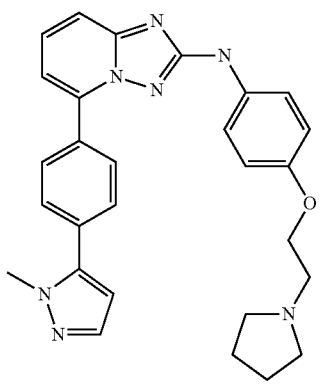 [SMILES: Cn1nccc1-c1ccc(-c2cccc3nc(Nc4ccc(OCCN5CCCC5)cc4)nn23)cc1] |

| No. Code | Structure |
|---|---|
| 359 XX-190 | 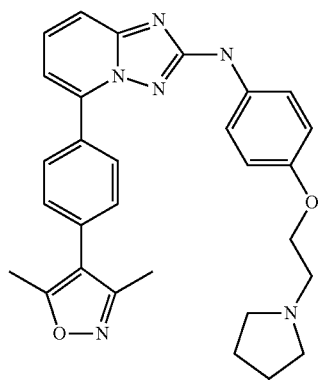 [SMILES: Cc1noc(C)c1-c1ccc(-c2cccc3nc(Nc4ccc(OCCN5CCCC5)cc4)nn23)cc1] |
| 360 XX-191 | 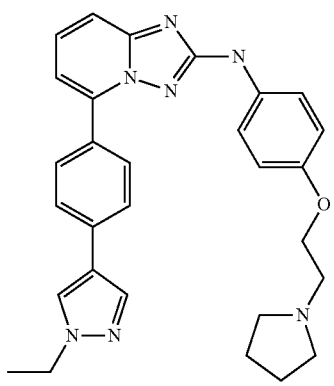 [SMILES: CCn1cc(-c2ccc(-c3cccc4nc(Nc5ccc(OCCN6CCCC6)cc5)nn34)cc2)cn1] |
| 361 XX-192 | 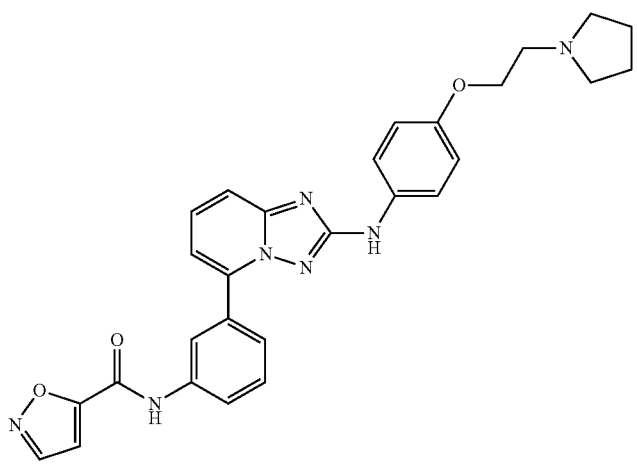 [SMILES: O=C(Nc1cccc(-c2cccc3nc(Nc4ccc(OCCN5CCCC5)cc4)nn23)c1)c1ccno1] |
| 362 XX-193 | 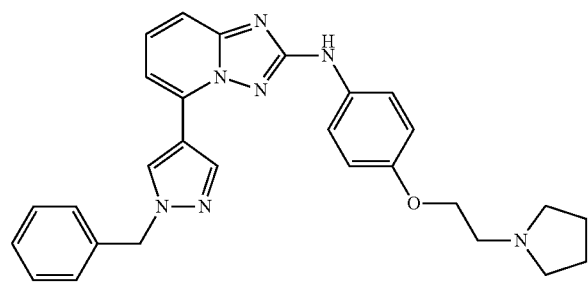 [SMILES: c1ccc(Cn2cc(-c3cccc4nc(Nc5ccc(OCCN6CCCC6)cc5)nn34)cn2)cc1] |

| No. Code | Structure |
|---|---|
| 363 XX-194 | 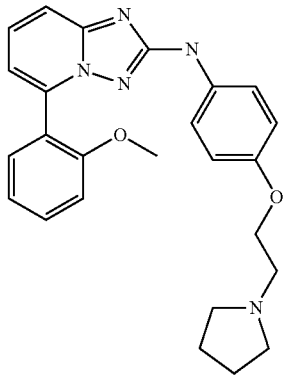 [SMILES: COc1ccccc1-c1cccc2nc(Nc3ccc(OCCN4CCCC4)cc3)nn12] |
| 364 XX-195 | 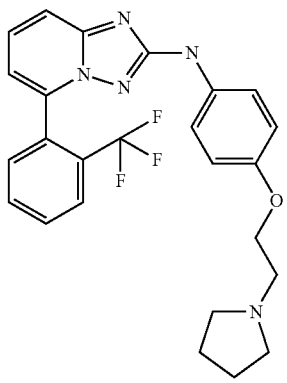 [SMILES: FC(F)(F)c1ccccc1-c1cccc2nc(Nc3ccc(OCCN4CCCC4)cc3)nn12] |
| 365 XX-196 | 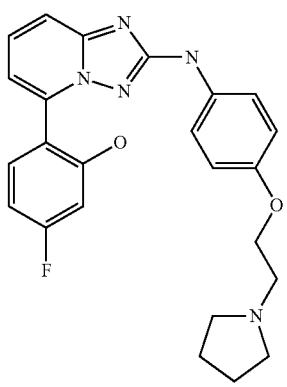 [SMILES: Oc1cc(F)ccc1-c1cccc2nc(Nc3ccc(OCCN4CCCC4)cc3)nn12] |
| 366 XX-197 | 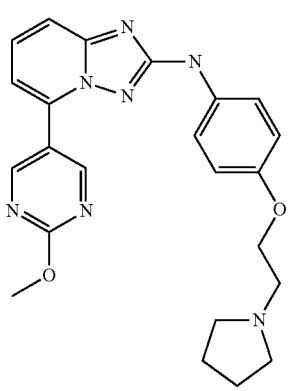 [SMILES: COc1ncc(-c2cccc3nc(Nc4ccc(OCCN5CCCC5)cc4)nn23)cn1] |

-continued
| No. Code | Structure |
|---|---|
| 367 XX-198 | 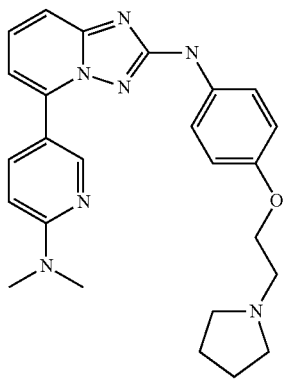 [SMILES: CN(C)c1ccc(-c2cccc3nc(Nc4ccc(OCCN5CCCC5)cc4)nn23)cn1] |
| 368 XX-199 | 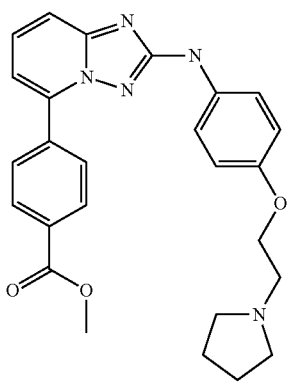 [SMILES: COC(=O)c1ccc(-c2cccc3nc(Nc4ccc(OCCN5CCCC5)cc4)nn23)cc1] |
| 369 XX-200 | 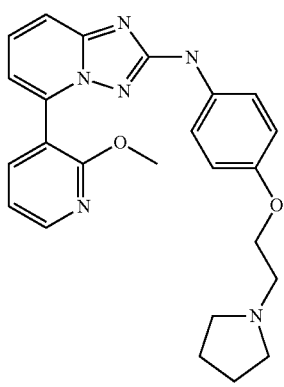 [SMILES: COc1ncccc1-c1cccc2nc(Nc3ccc(OCCN4CCCC4)cc3)nn12] |
| 370 XX-201 | 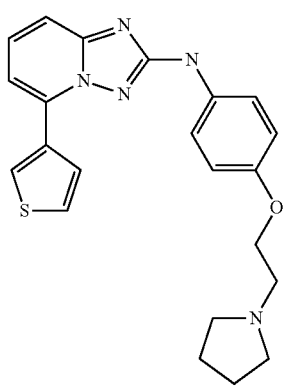 [SMILES: c1cc(-c2ccsc2)n2nc(Nc3ccc(OCCN4CCCC4)cc3)nc2c1] |

| No. Code | Structure |
|---|---|
| 371 XX-202 | 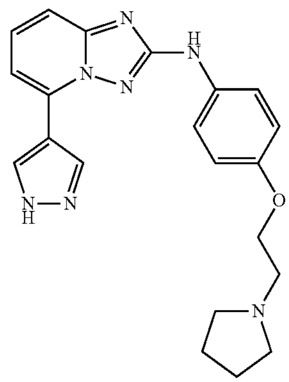 [SMILES: c1cc(-c2cn[nH]c2)n2nc(Nc3ccc(OCCN4CCCC4)cc3)nc2c1] |
| 372 XX-203 | 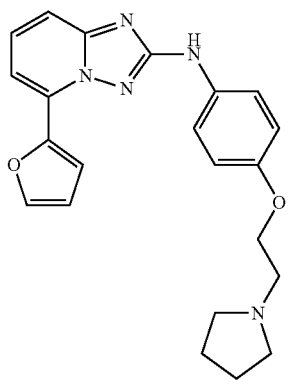 [SMILES: c1coc(-c2cccc3nc(Nc4ccc(OCCN5CCCC5)cc4)nn23)c1] |
| 373 XX-204 | 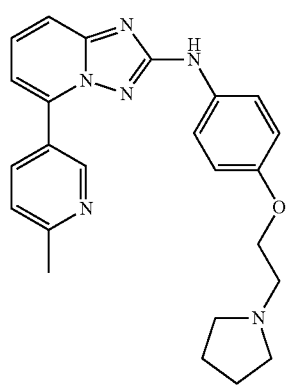 [SMILES: Cc1ccc(-c2cccc3nc(Nc4ccc(OCCN5CCCC5)cc4)nn23)cn1] |
| 374 XX-205 | 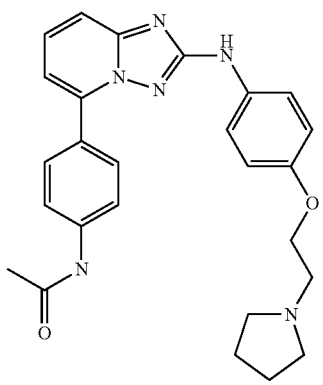 [SMILES: CC(=O)Nc1ccc(-c2cccc3nc(Nc4ccc(OCCN5CCCC5)cc4)nn23)cc1] |

| No. Code | Structure |
|---|---|
| 375 XX-206 | 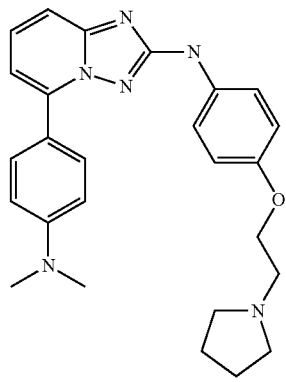 [SMILES: CN(C)c1ccc(-c2cccc3nc(Nc4ccc(OCCN5CCCC5)cc4)nn23)cc1] |
| 376 XX-207 | 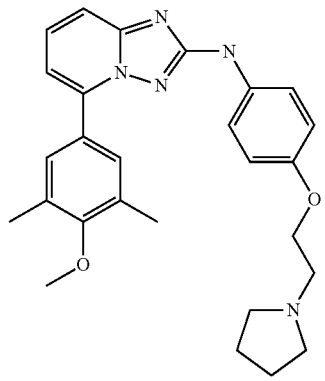 [SMILES: COc1c(C)cc(-c2cccc3nc(Nc4ccc(OCCN5CCCC5)cc4)nn23)cc1C] |
| 377 XX-208 | 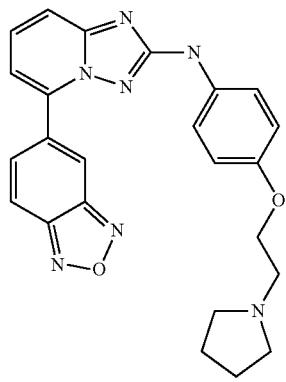 [SMILES: c1cc(-c2ccc3nonc3c2)n2nc(Nc3ccc(OCCN4CCCC4)cc3)nc2c1] |
| 378 XX-209 | 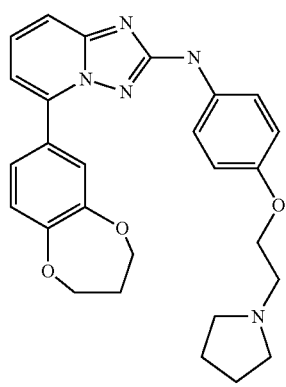 [SMILES: c1cc(-c2ccc3c(c2)OCCCO3)n2nc(Nc3ccc(OCCN4CCCC4)cc3)nc2c1] |

-continued
| No. Code | Structure |
|---|---|
| 379 XX-210 | 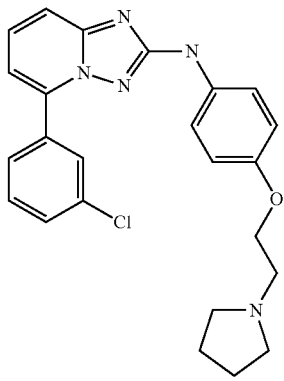 [SMILES: Clc1cccc(-c2cccc3nc(Nc4ccc(OCCN5CCCC5)cc4)nn23)c1] |
| 380 XX-211 | 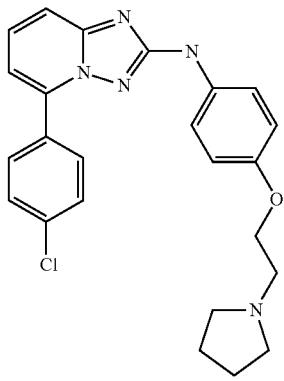 [SMILES: Clc1ccc(-c2cccc3nc(Nc4ccc(OCCN5CCCC5)cc4)nn23)cc1] |
| 381 XX-212 | 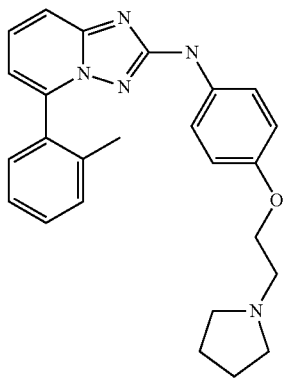 [SMILES: Cc1ccccc1-c1cccc2nc(Nc3ccc(OCCN4CCCC4)cc3)nn12] |
| 382 XX-213 | 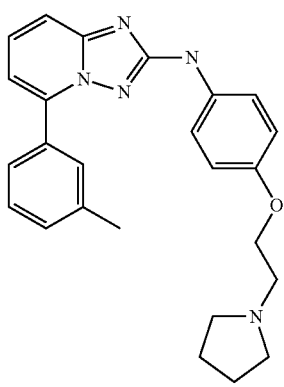 [SMILES: Cc1cccc(-c2cccc3nc(Nc4ccc(OCCN5CCCC5)cc4)nn23)c1] |

| No. Code | Structure |
|---|---|
| 383 XX-214 | 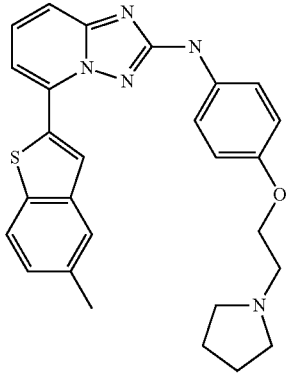 [SMILES: Cc1ccc2sc(-c3cccc4nc(Nc5ccc(OCCN6CCCC6)cc5)nn34)cc2c1] |
| 384 XX-215 | 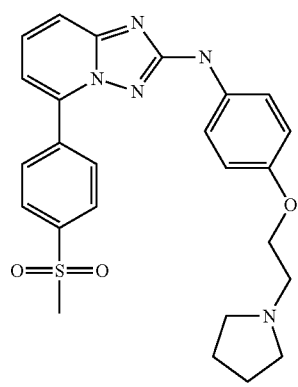 [SMILES: CS(=O)(=O)c1ccc(-c2cccc3nc(Nc4ccc(OCCN5CCCC5)cc4)nn23)cc1] |
| 385 XX-216 | 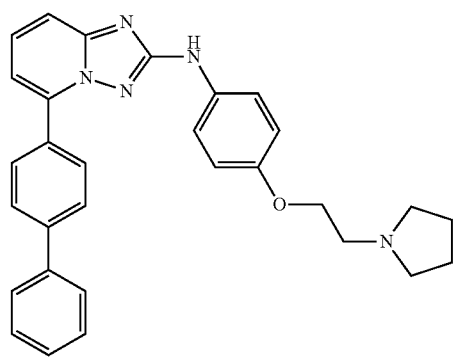 [SMILES: c1ccc(-c2ccc(-c3cccc4nc(Nc5ccc(OCCN6CCCC6)cc5)nn34)cc2)cc1] |
| 386 XX-217 | 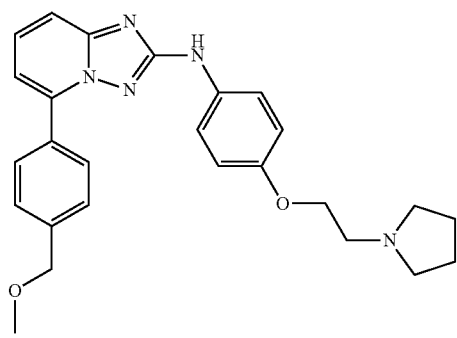 [SMILES: COCc1ccc(-c2cccc3nc(Nc4ccc(OCCN5CCCC5)cc4)nn23)cc1] |

| No. Code | Structure |
|---|---|
| 387 XX-218 | 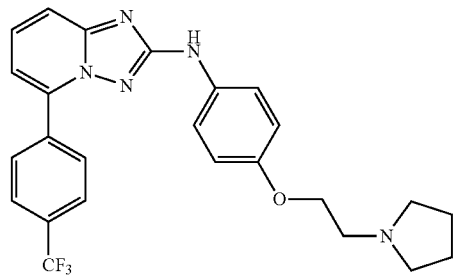 |
| 388 XX-219 | 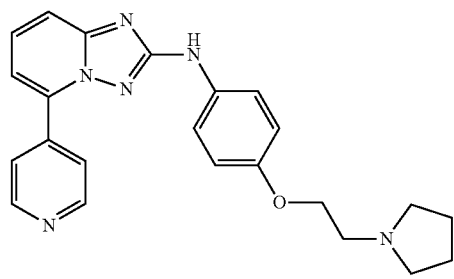 [SMILES: c1cc(-c2ccncc2)n2nc(Nc3ccc(OCCN4CCCC4)cc3)nc2c1] |
| 389 XX-220 | 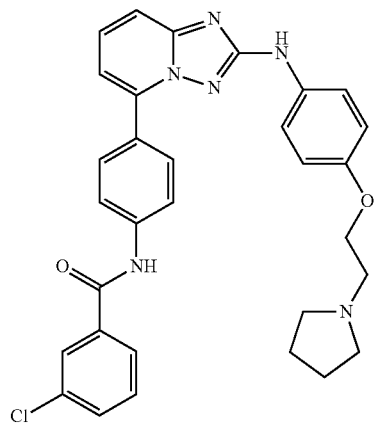 [SMILES: O=C(Nc1ccc(-c2cccc3nc(Nc4ccc(OCCN5CCCC5)cc4)nn23)cc1)c1cccc(Cl)c1] |
| 390 XX-221 | 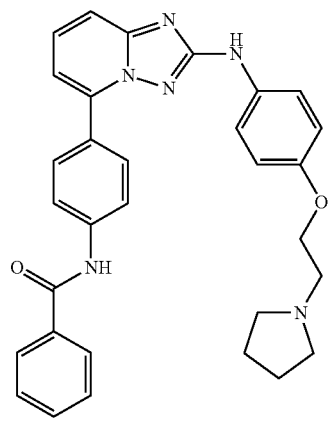 [SMILES: O=C(Nc1ccc(-c2cccc3nc(Nc4ccc(OCCN5CCCC5)cc4)nn23)cc1)c1ccccc1] |

-continued

| No. Code | Structure |
|---|---|
| 391 XX-222 | 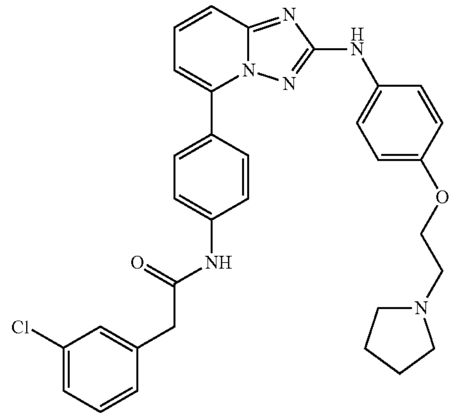 [SMILES: O=C(Cc1cccc(Cl)c1)Nc1ccc(-c2cccc3nc(Nc4ccc(OCCN5CCCC5)cc4)nn23)cc1] |
| 392 XX-223 | 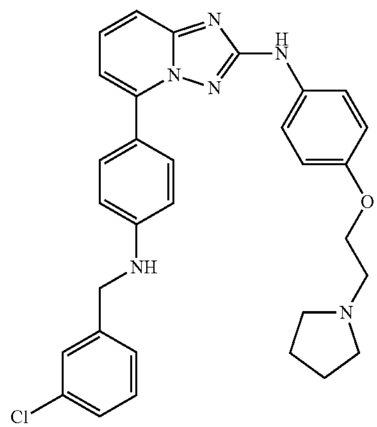 [SMILES: Clc1cccc(CNc2ccc(-c3cccc4nc(Nc5ccc(OCCN6CCCC6)cc5)nn34)cc2)c1] |
| 393 XX-224 | 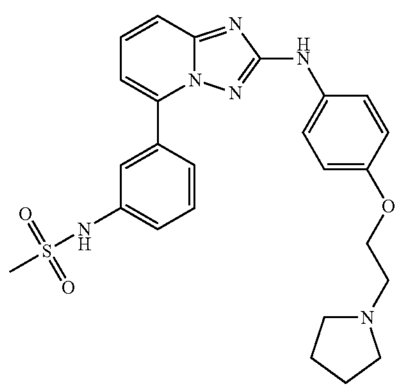 [SMILES: CS(=O)(=O)Nc1cccc(-c2cccc3nc(Nc4ccc(OCCN5CCCC5)cc4)nn23)c1] |
| 394 XX-225 | 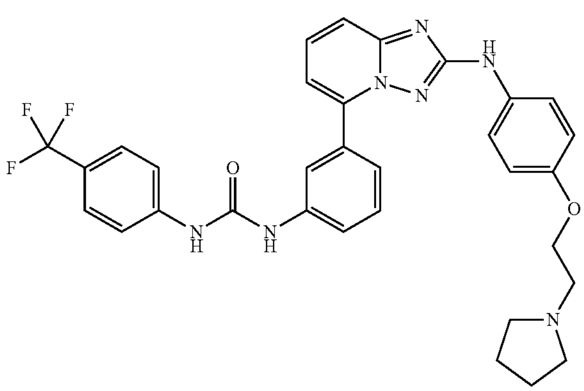 [SMILES: O=C(Nc1ccc(C(F)(F)F)cc1)Nc1cccc(-c2cccc3nc(Nc4ccc(OCCN5CCCC5)cc4)nn23)c1] |

| No. Code | Structure |
|---|---|
| 395 XX-226 | 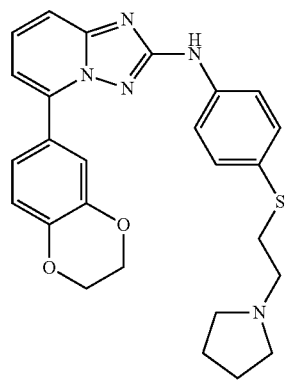 [SMILES: c1cc(-c2ccc3c(c2)OCCO3)n2nc(Nc3ccc(SCCN4CCCC4)cc3)nc2c1] |
| 396 XX-227 | 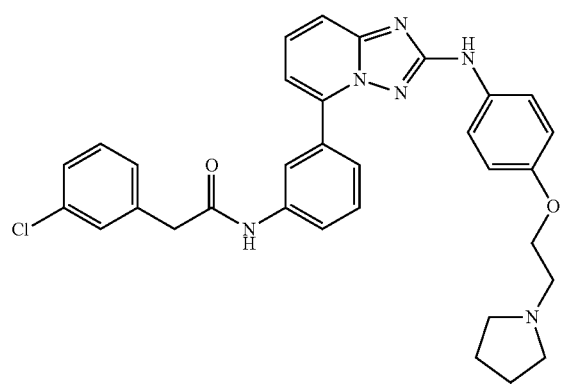 [SMILES: O=C(Cc1cccc(Cl)c1)Nc1cccc(-c2cccc3nc(Nc4ccc(OCCN5CCCC5)cc4)nn23)c1] |
| 397 XX-228 | 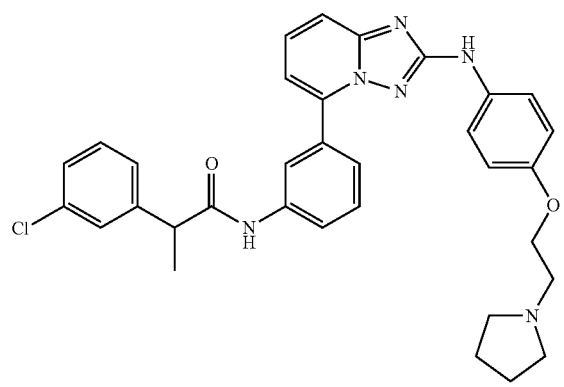 [SMILES: CC(C(=O)Nc1cccc(-c2cccc3nc(Nc4ccc(OCCN5CCCC5)cc4)nn23)c1)c1cccc(Cl)c1] |

-continued
| No. Code | Structure |
|---|---|
| 398 XX-229 | 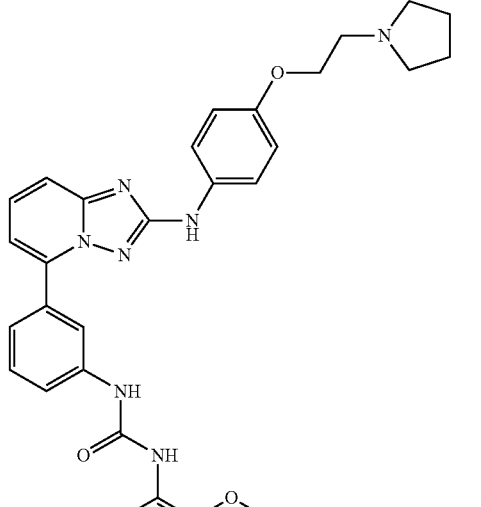 |
| 399 XX-230 | 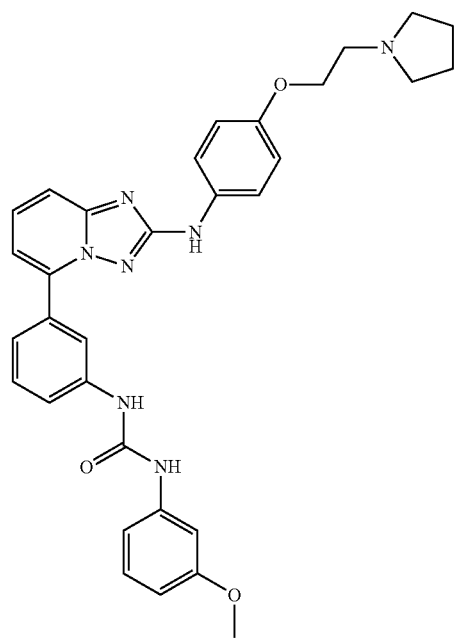 [SMILES: COc1cccc(NC(=O)Nc2cccc(-c3cccc4nc(Nc5ccc(OCCN6CCCC6)cc5)nn34)c2)c1] |

| No. | Code | Structure |
|---|---|---|
| 400 | XX-231 | 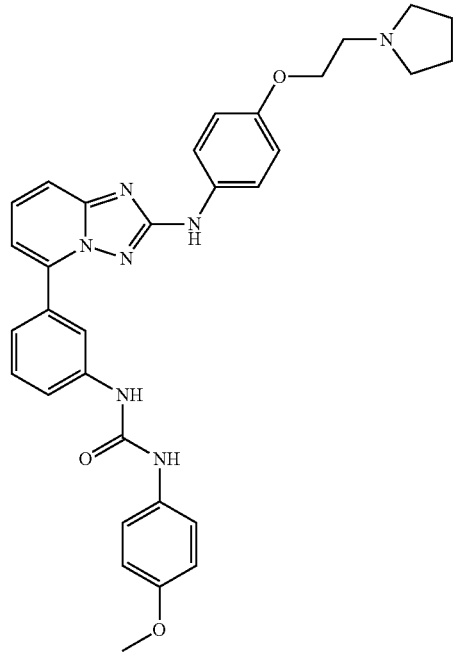 [SMILES: COc1ccc(NC(=O)Nc2cccc(-c3cccc4nc(Nc5ccc(OCCN6CCCC6)cc5)nn34)c2)cc1] |
| 401 | XX-232 | 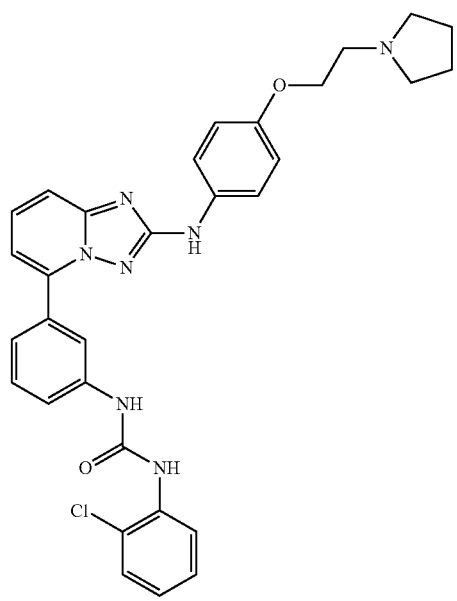 [SMILES: O=C(Nc1cccc(-c2cccc3nc(Nc4ccc(OCCN5CCCC5)cc4)nn23)c1)Nc1ccccc1Cl] |

| No. Code | Structure |
|---|---|
| 402 XX-233 | 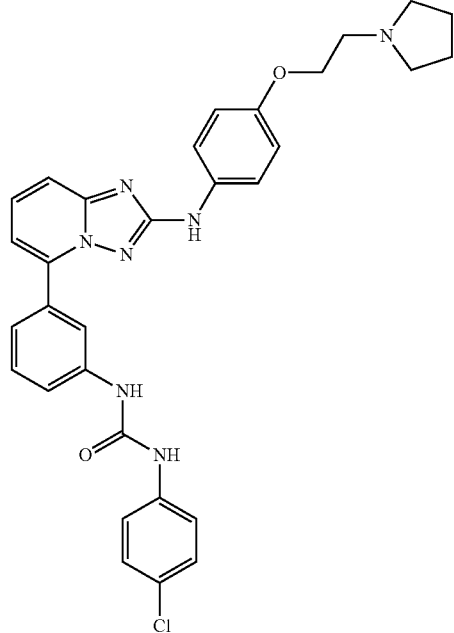 [SMILES: O=C(Nc1ccc(Cl)cc1)Nc1cccc(-c2cccc3nc(Nc4ccc(OCCN5CCCC5)cc4)nn23)c1] |
| 403 XX-234 | 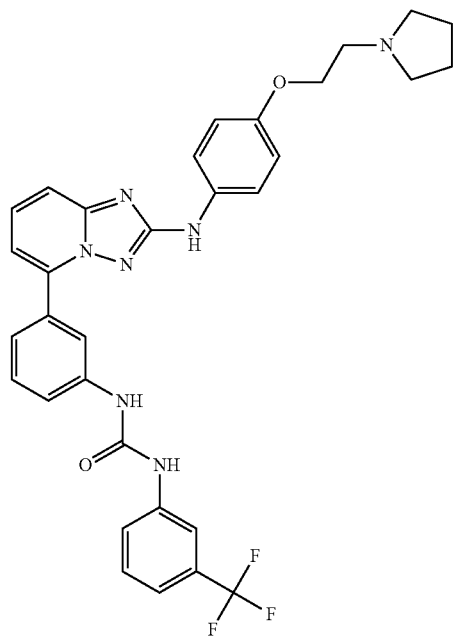 [SMILES: O=C(Nc1cccc(-c2cccc3nc(Nc4ccc(OCCN5CCCC5)cc4)nn23)c1)Nc1cccc(C(F)(F)F)c1] |

-continued
| No. Code | Structure |
|---|---|
| 404 XX-235 | 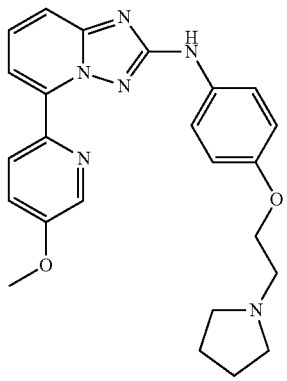 [SMILES: COc1ccc(-c2cccc3nc(Nc4ccc(OCCN5CCCC5)cc4)nn23)nc1] |
| 405 XX-236 | 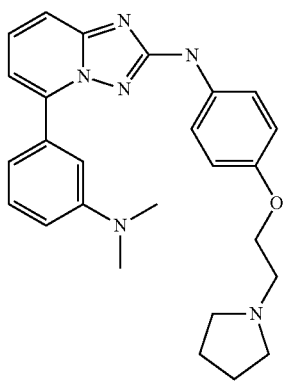 [SMILES: CN(C)c1cccc(-c2cccc3nc(Nc4ccc(OCCN5CCCC5)cc4)nn23)c1] |
| 406 XX-237 | 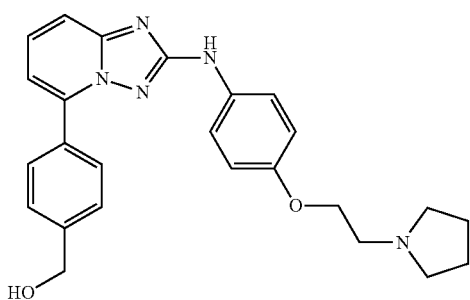 [SMILES: OCc1ccc(-c2cccc3nc(Nc4ccc(OCCN5CCCC5)cc4)nn23)cc1] |
| 407 XX-238 | 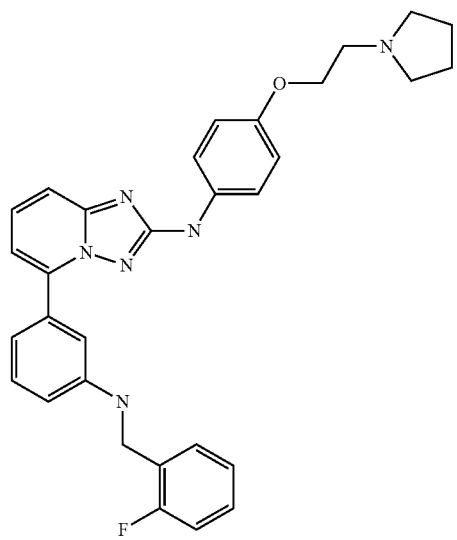 [SMILES: Fc1ccccc1CNc1cccc(-c2cccc3nc(Nc4ccc(OCCN5CCCC5)cc4)nn23)c1] |

| No. Code | Structure |
|---|---|
| 408 XX-239 | 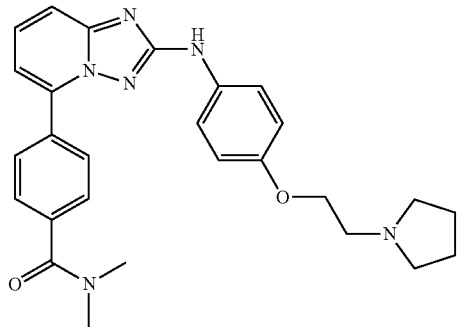 [SMILES: CN(C)C(=O)c1ccc(-c2cccc3nc(Nc4ccc(OCCN5CCCC5)cc4)nn23)cc1] |
| 409 XX-240 | 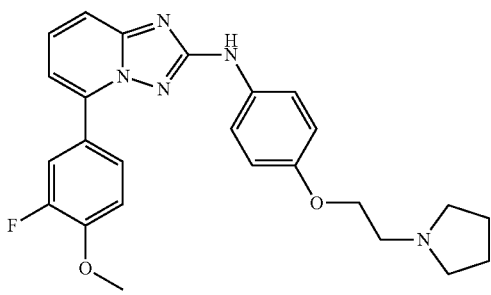 [SMILES: COc1ccc(-c2cccc3nc(Nc4ccc(OCCN5CCCC5)cc4)nn23)cc1F] |
| 410 XX-241 | 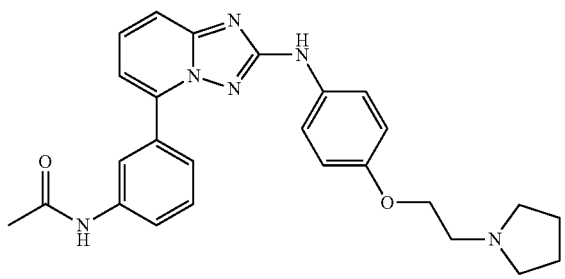 [SMILES: CC(=O)Nc1cccc(-c2cccc3nc(Nc4ccc(OCCN5CCCC5)cc4)nn23)c1] |
| 411 XX-242 | 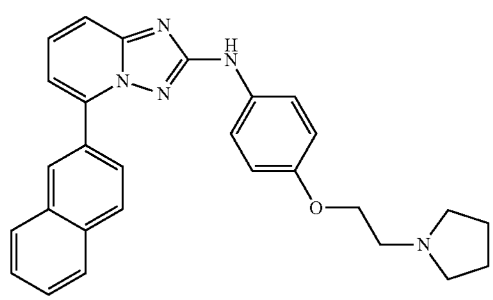 [SMILES: c1ccc2cc(-c3cccc4nc(Nc5ccc(OCCN6CCCC6)cc5)nn34)ccc2c1] |
| 412 XX-243 | 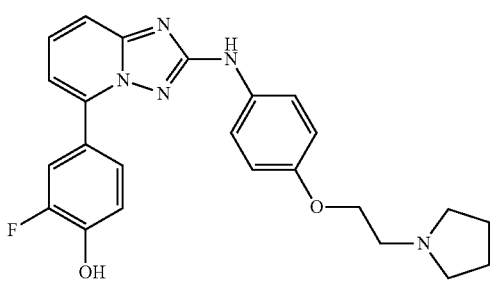 [SMILES: Oc1ccc(-c2cccc3nc(Nc4ccc(OCCN5CCCC5)cc4)nn23)cc1F] |

-continued

| No. Code | Structure |
|---|---|
| 413 XX-244 | 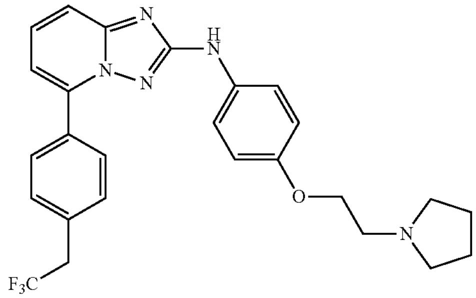 [SMILES: FC(F)(F)Cc1ccc(-c2cccc3nc(Nc4ccc(OCCN5CCCC5)cc4)nn23)cc1] |
| 414 XX-245 | 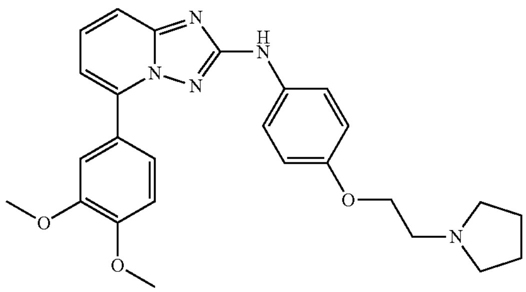 [SMILES: COc1ccc(-c2cccc3nc(Nc4ccc(OCCN5CCCC5)cc4)nn23)cc1OC] |
| 415 XX-246 | 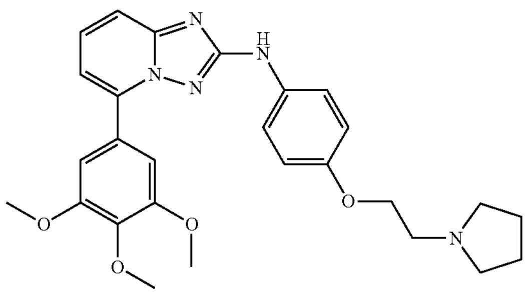 [SMILES: COc1cc(-c2cccc3nc(Nc4ccc(OCCN5CCCC5)cc4)nn23)cc(OC)c1OC] |
| 416 XX-247 | 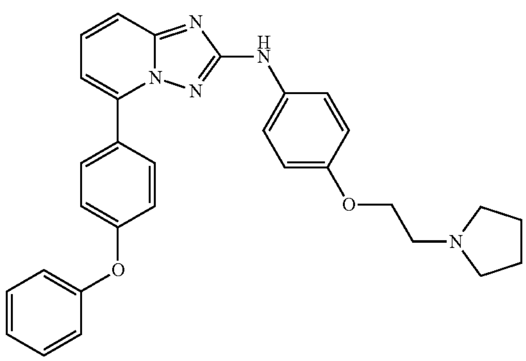 [SMILES: c1ccc(Oc2ccc(-c3cccc4nc(Nc5ccc(OCCN6CCCC6)cc5)nn34)cc2)cc1] |
| 417 XX-248 | 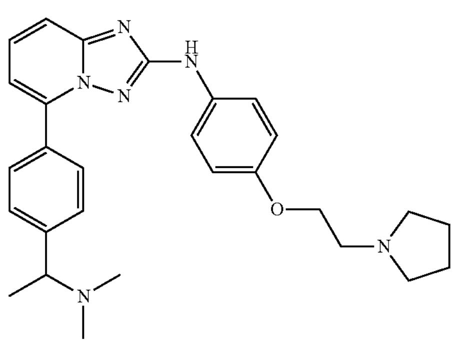 [SMILES: CC(c1ccc(-c2cccc3nc(Nc4ccc(OCCN5CCCC5)cc4)nn23)cc1)N(C)C] |

| No. Code | Structure |
|---|---|
| 418 XX-249 | 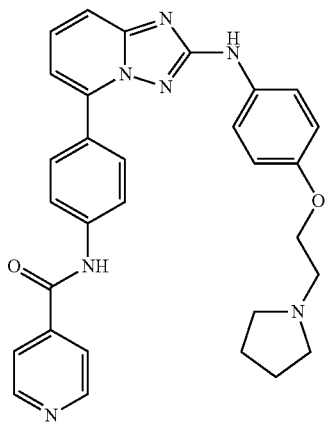 [SMILES: O=C(Nc1ccc(-c2cccc3nc(Nc4ccc(OCCN5CCCC5)cc4)nn23)cc1)c1ccncc1] |
| 419 XX-250 | 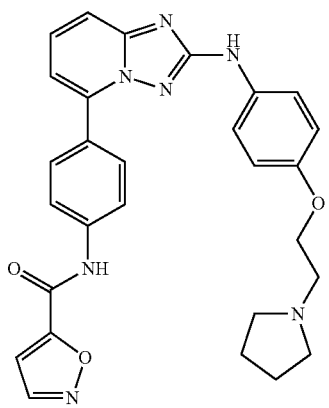 [SMILES: O=C(Nc1ccc(-c2cccc3nc(Nc4ccc(OCCN5CCCC5)cc4)nn23)cc1)c1ccno1] |
| 420 XX-251 | 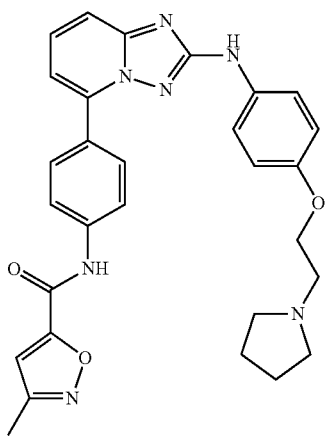 [SMILES: Cc1cc(C(=O)Nc2ccc(-c3cccc4nc(Nc5ccc(OCCN6CCCC6)cc5)nn34)cc2)on1] |

| No. Code | Structure |
|---|---|
| 421 XX-252 | 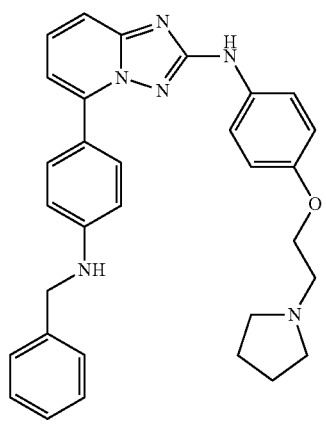 [SMILES: c1ccc(CNc2ccc(-c3cccc4nc(Nc5ccc(OCCN6CCCC6)cc5)nn34)cc2)cc1] |
| 422 XX-253 | 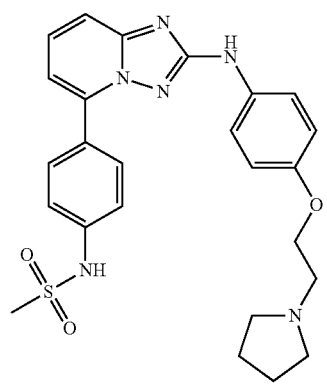 [SMILES: CS(=O)(=O)Nc1ccc(-c2cccc3nc(Nc4ccc(OCCN5CCCC5)cc4)nn23)cc1] |
| 423 XX-254 | 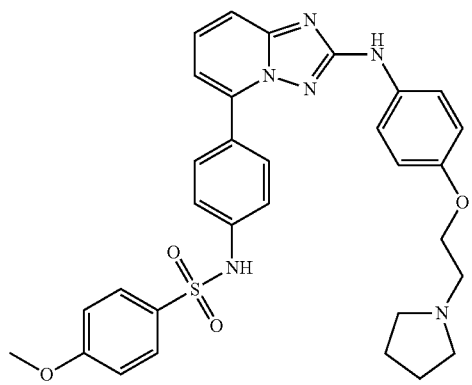 [SMILES: COc1ccc(S(=O)(=O)Nc2ccc(-c3cccc4nc(Nc5ccc(OCCN6CCCC6)cc5)nn34)cc2)cc1] |
| 424 XX-255 | 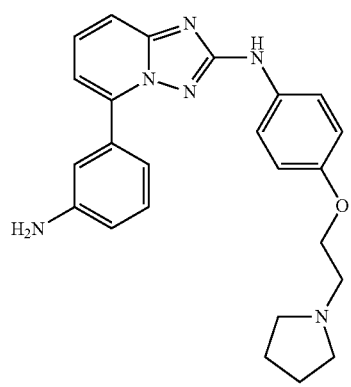 [SMILES: Nc1cccc(-c2cccc3nc(Nc4ccc(OCCN5CCCC5)cc4)nn23)c1] |

| No. Code | Structure |
|---|---|
| 425 XX-256 | 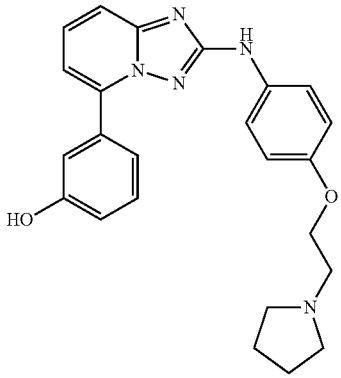 [SMILES: Oc1cccc(-c2cccc3nc(Nc4ccc(OCCN5CCCC5)cc4)nn23)c1] |
| 426 XX-257 | 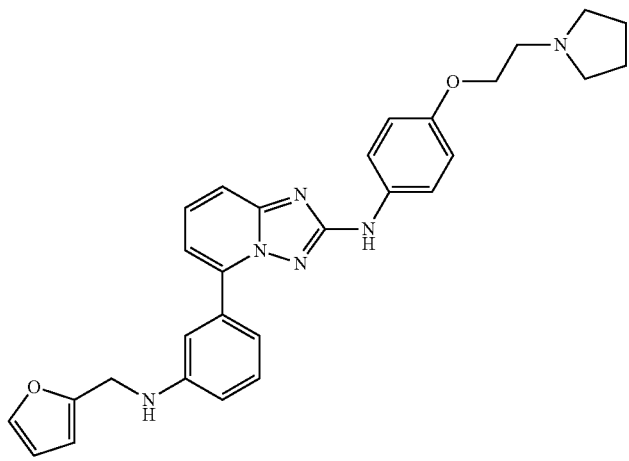 [SMILES: c1cc(NCc2ccco2)cc(-c2cccc3nc(Nc4ccc(OCCN5CCCC5)cc4)nn23)c1] |
| 427 XX-258 | 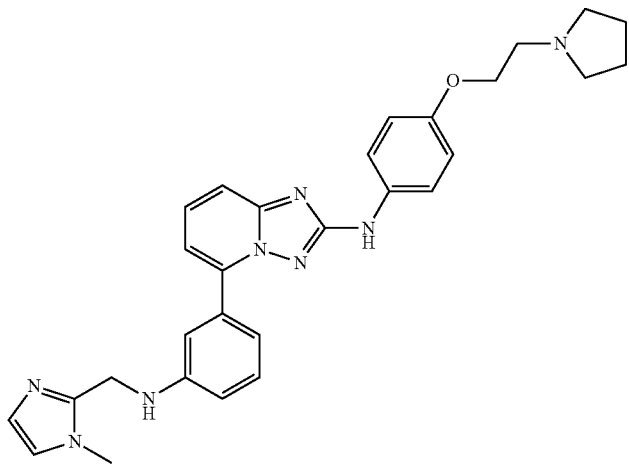 [SMILES: Cn1ccnc1CNc1cccc(-c2cccc3nc(Nc4ccc(OCCN5CCCC5)cc4)nn23)c1] |

-continued
| No. Code | Structure |
|---|---|
| 428 XX-259 | 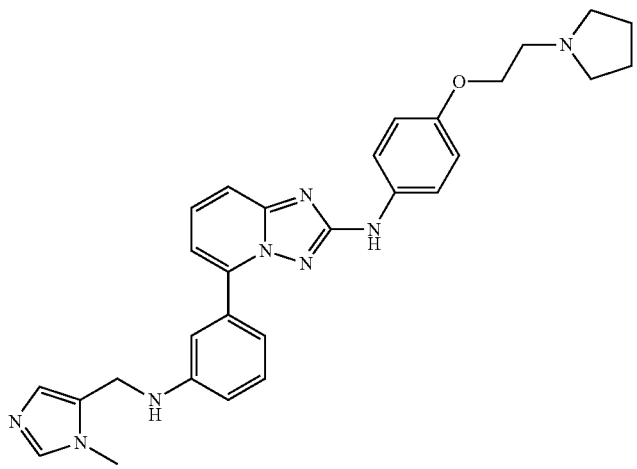 [SMILES: Cn1cncc1CNc1cccc(-c2cccc3nc(Nc4ccc(OCCN5CCCC5)cc4)nn23)c1] |
| 429 XX-260 | 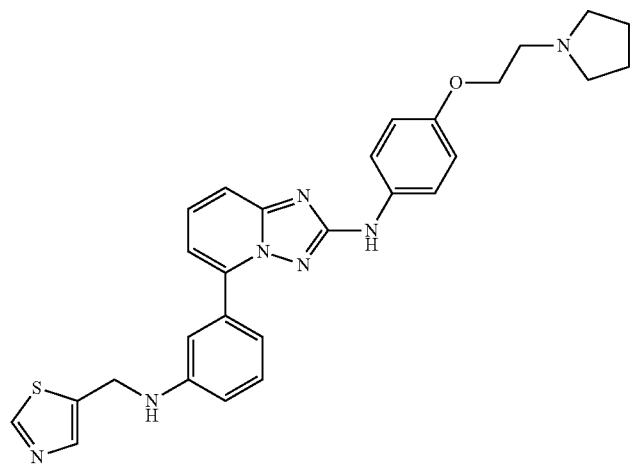 [SMILES: c1cc(NCc2cncs2)cc(-c2cccc3nc(Nc4ccc(OCCN5CCCC5)cc4)nn23)c1] |
| 430 XX-261 | 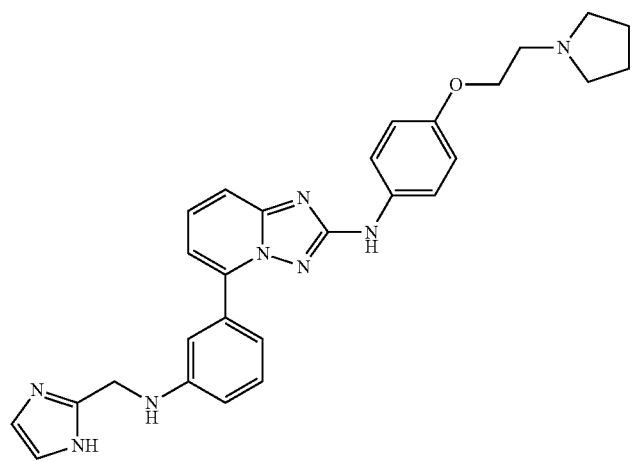 [SMILES: c1cc(NCc2ncc[nH]2)cc(-c2cccc3nc(Nc4ccc(OCCN5CCCC5)cc4)nn23)c1] |

| No. | Code | Structure |
|---|---|---|
| 431 | XX-262 | 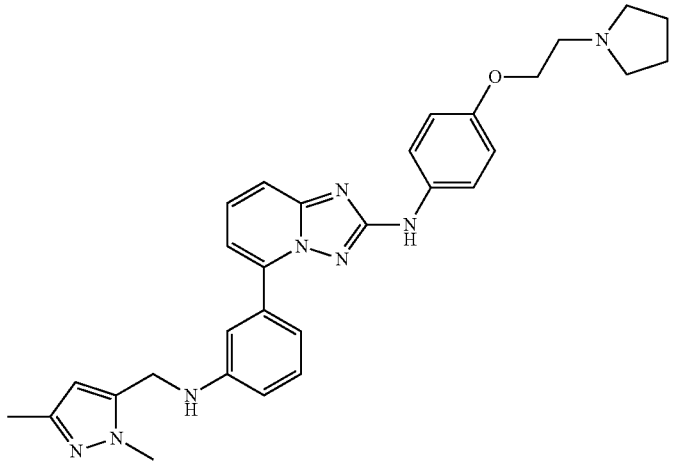 [SMILES: Cc1cc(CNc2cccc(-c3cccc4nc(Nc5ccc(OCCN6CCCC6)cc5)nn34)c2)n(C)n1] |
| 432 | XX-263 | 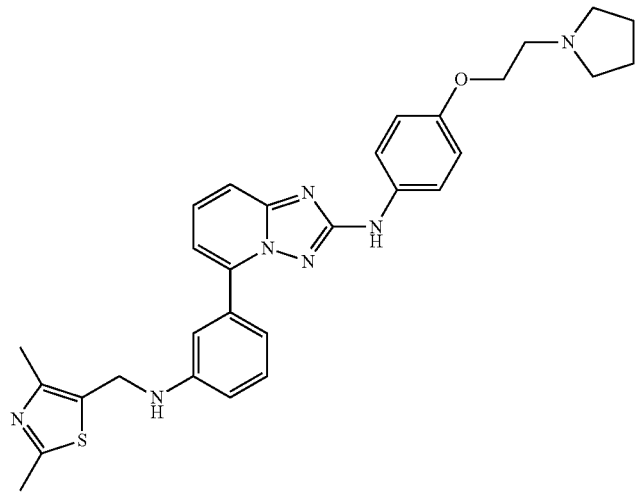 [SMILES: Cc1nc(C)c(CNc2cccc(-c3cccc4nc(Nc5ccc(OCCN6CCCC6)cc5)nn34)c2)s1] |
| 433 | XX-264 | 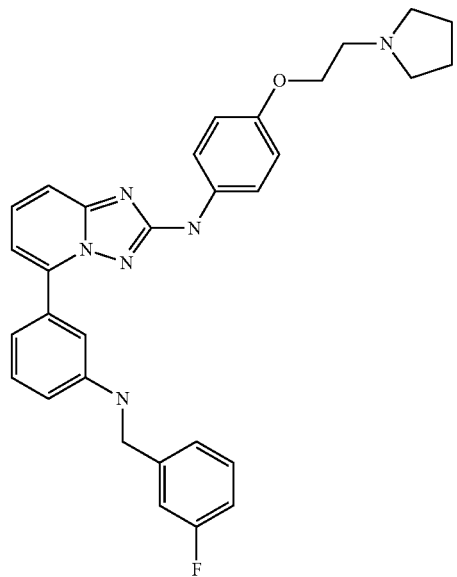 [SMILES: Fc1cccc(CNc2cccc(-c3cccc4nc(Nc5ccc(OCCN6CCCC6)cc5)nn34)c2)c1] |

| No. Code | Structure |
|---|---|
| 434 XX-265 | 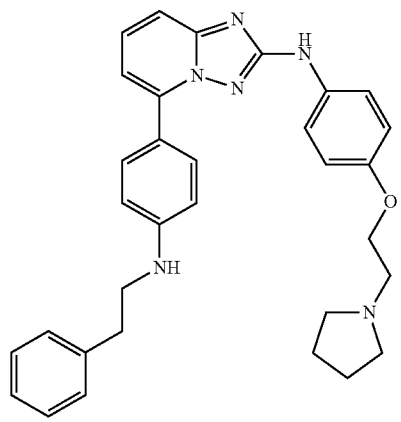 [SMILES: c1ccc(CCNc2ccc(-c3cccc4nc(Nc5ccc(OCCN6CCCC6)cc5)nn34)cc2)cc1] |
| 435 XX-266 | 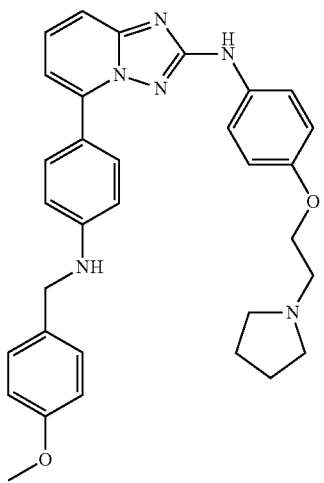 [SMILES: COc1ccc(CNc2ccc(-c3cccc4nc(Nc5ccc(OCCN6CCCC6)cc5)nn34)cc2)cc1] |
| 436 XX-267 | 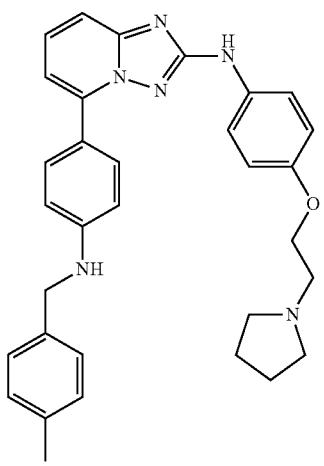 [SMILES: Cc1ccc(CNc2ccc(-c3cccc4nc(Nc5ccc(OCCN6CCCC6)cc5)nn34)cc2)cc1] |

| No. Code | Structure |
|---|---|
| 437 XX-268 | 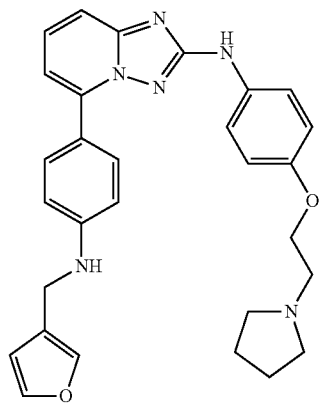 [SMILES: c1cc(-c2ccc(NCc3ccoc3)cc2)n2nc(Nc3ccc(OCCN4CCCC4)cc3)nc2c1] |
| 438 XX-269 | 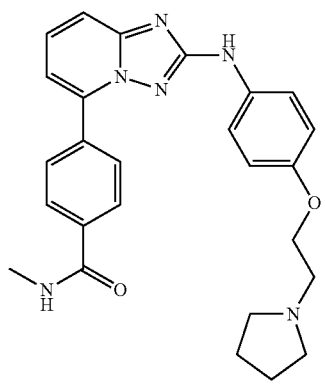 [SMILES: CNC(=O)c1ccc(-c2cccc3nc(Nc4ccc(OCCN5CCCC5)cc4)nn23)cc1] |
| 439 XX-270 | 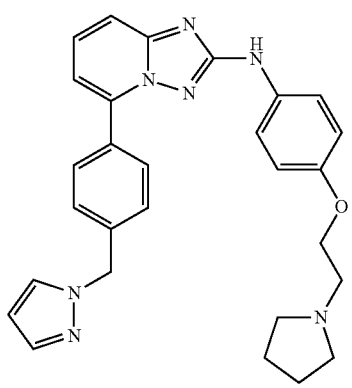 [SMILES: c1cc(-c2ccc(Cn3cccn3)cc2)n2nc(Nc3ccc(OCCN4CCCC4)cc3)nc2c1] |
| 440 XX-271 | 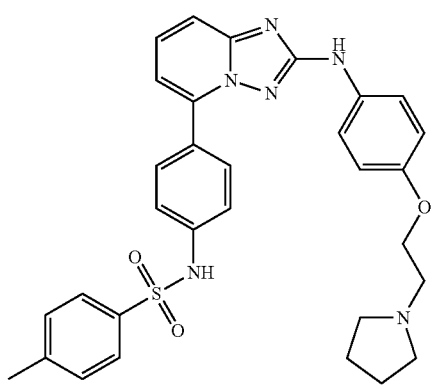 [SMILES: Cc1ccc(S(=O)(=O)Nc2ccc(-c3cccc4nc(Nc5ccc(OCCN6CCCC6)cc5)nn34)cc2)cc1] |

-continued
| No. Code | Structure |
|---|---|
| 441 XX-272 | 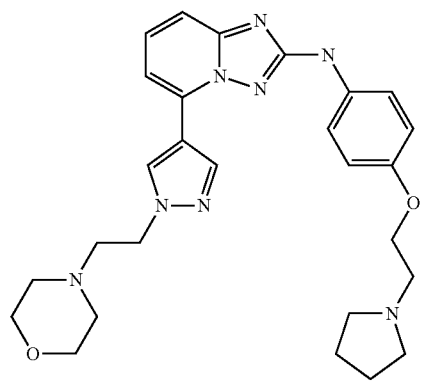 [SMILES: c1cc(-c2cnn(CCN3CCOCC3)c2)n2nc(Nc3ccc(OCCN4CCCC4)cc3)nc2c1] |
| 442 XX-273 | 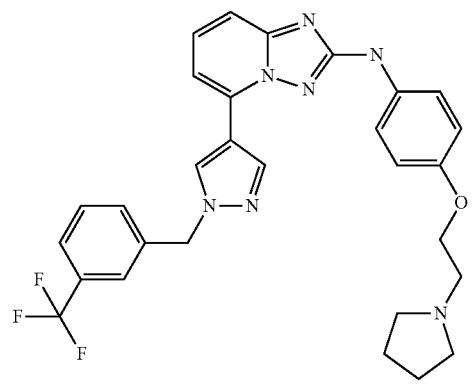 [SMILES: FC(F)(F)c1cccc(Cn2cc(-c3cccc4nc(Nc5ccc(OCCN6CCCC6)cc5)nn34)cn2)c1] |
| 443 XX-274 | 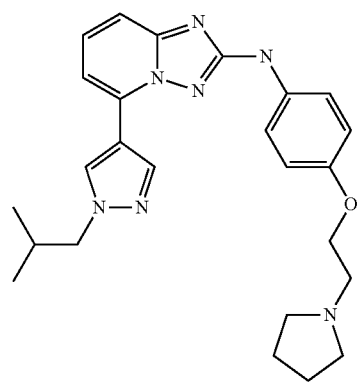 [SMILES: CC(C)Cn1cc(-c2cccc3nc(Nc4ccc(OCCN5CCCC5)cc4)nn23)cn1] |
| 444 XX-275 | 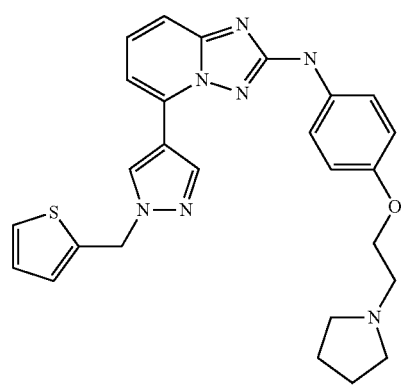 [SMILES: c1csc(Cn2cc(-c3cccc4nc(Nc5ccc(OCCN6CCCC6)cc5)nn34)cn2)c1] |

| No. Code | Structure |
|---|---|
| 445 XX-276 | 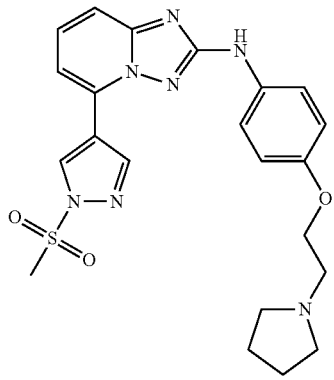 [SMILES: CS(=O)(=O)n1cc(-c2cccc3nc(Nc4ccc(OCCN5CCCC5)cc4)nn23)cn1] |
| 446 XX-277 | 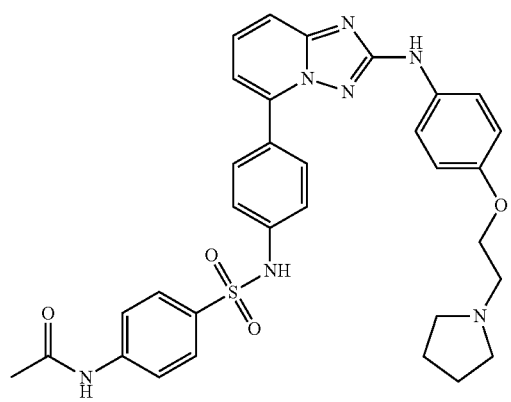 [SMILES: CC(=O)Nc1ccc(S(=O)(=O)Nc2ccc(-c3cccc4nc(Nc5ccc(OCCN6CCCC6)cc5)nn34)cc2)cc1] |
| 447 XX-278 | 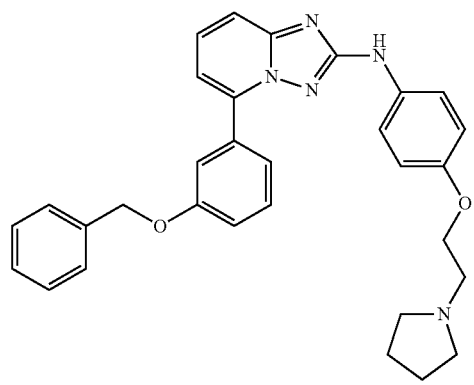 [SMILES: c1ccc(COc2cccc(-c3cccc4nc(Nc5ccc(OCCN6CCCC6)cc5)nn34)c2)cc1] |
| 448 XX-279 | 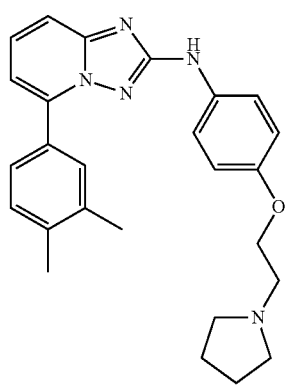 [SMILES: Cc1ccc(-c2cccc3nc(Nc4ccc(OCCN5CCCC5)cc4)nn23)cc1C] |

-continued
| No. Code | Structure |
|---|---|
| 449 XX-280 | 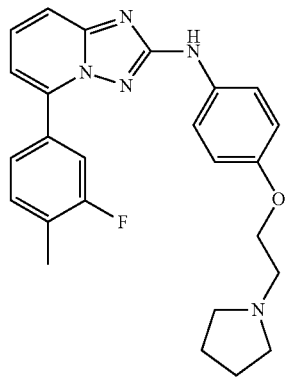 [SMILES: Cc1ccc(-c2cccc3nc(Nc4ccc(OCCN5CCCC5)cc4)nn23)cc1F] |
| 450 XX-281 | 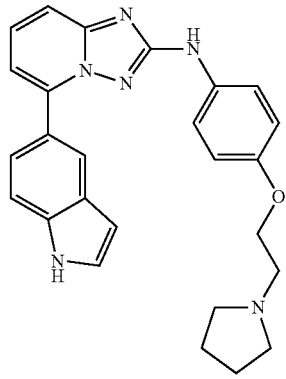 [SMILES: c1cc(-c2ccc3[nH]ccc3c2)n2nc(Nc3ccc(OCCN4CCCC4)cc3)nc2c1] |
| 451 XX-282 | 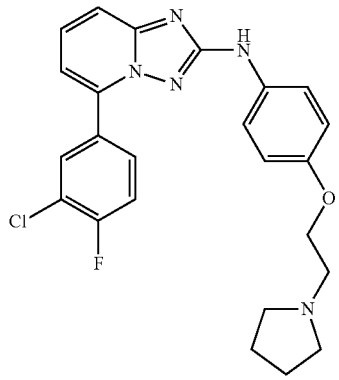 [SMILES: Fc1ccc(-c2cccc3nc(Nc4ccc(OCCN5CCCC5)cc4)nn23)cc1Cl] |
| 452 XX-283 | 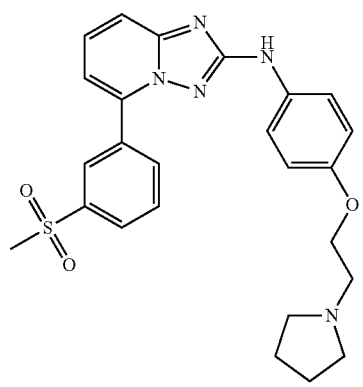 [SMILES: CS(=O)(=O)c1cccc(-c2cccc3nc(Nc4ccc(OCCN5CCCC5)cc4)nn23)c1] |

| No. Code | Structure |
|---|---|
| 453 XX-284 | 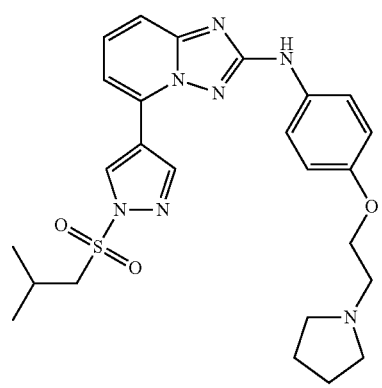 [SMILES: CC(C)CS(=O)(=O)n1cc(-c2cccc3nc(Nc4ccc(OCCN5CCCC5)cc4)nn23)cn1] |
| 454 XX-285 | 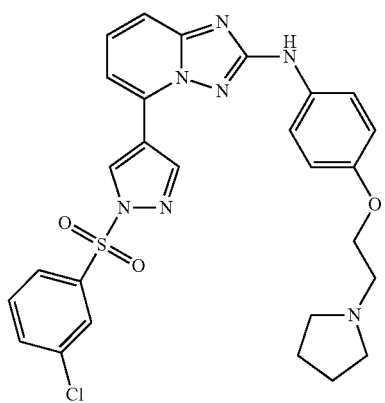 [SMILES: O=S(=O)(c1cccc(Cl)c1)n1cc(-c2cccc3nc(Nc4ccc(OCCN5CCCC5)cc4)nn23)cn1] |
| 455 XX-286 | 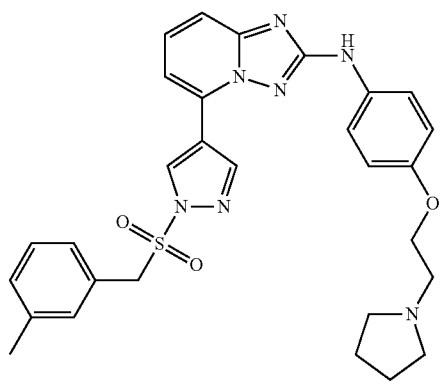 [SMILES: Cc1cccc(CS(=O)(=O)n2cc(-c3cccc4nc(Nc5ccc(OCCN6CCCC6)cc5)nn34)cn2)c1] |
| 456 XX-287 | 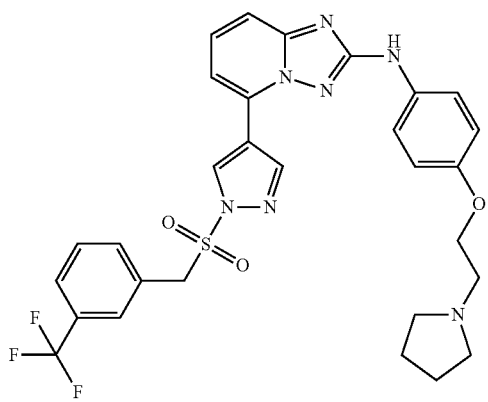 [SMILES: O=S(=O)(Cc1cccc(C(F)(F)F)c1)n1cc(-c2cccc3nc(Nc4ccc(OCCN5CCCC5)cc4)nn23)cn1] |

| No. Code | Structure |
|---|---|
| 457 XX-288 | 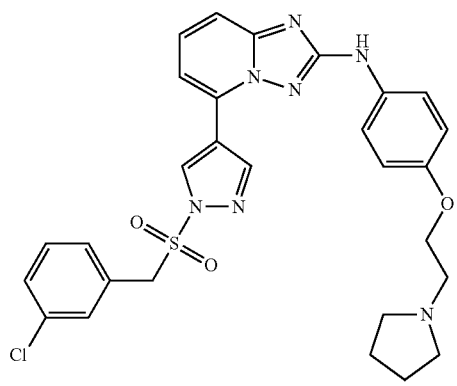 [SMILES: O=S(=O)(Cc1cccc(Cl)c1)n1cc(-c2cccc3nc(Nc4ccc(OCCN5CCCC5)cc4)nn23)cn1] |
| 458 XX-289 | 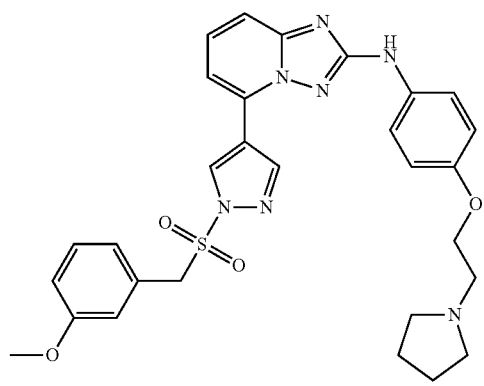 [SMILES: COc1cccc(CS(=O)(=O)n2cc(-c3cccc4nc(Nc5ccc(OCCN6CCCC6)cc5)nn34)cn2)c1] |
| 459 XX-290 | 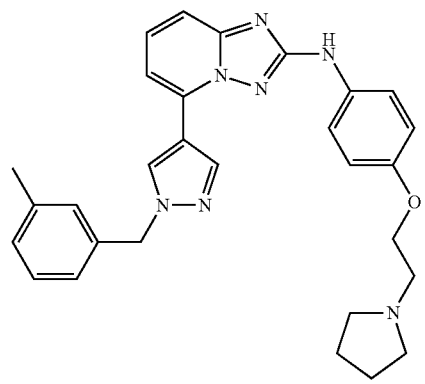 [SMILES: Cc1cccc(Cn2cc(-c3cccc4nc(Nc5ccc(OCCN6CCCC6)cc5)nn34)cn2)c1] |
| 460 XX-291 | 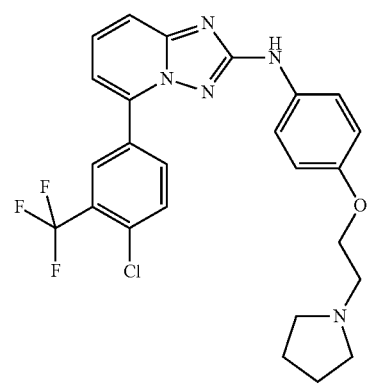 [SMILES: FC(F)(F)c1cc(-c2cccc3nc(Nc4ccc(OCCN5CCCC5)cc4)nn23)ccc1Cl] |

| No. Code | Structure |
|---|---|
| 461 XX-292 | 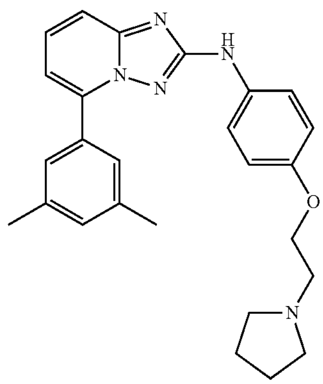 [SMILES: Cc1cc(C)cc(-c2cccc3nc(Nc4ccc(OCCN5CCCC5)cc4)nn23)c1] |
| 462 XX-293 | 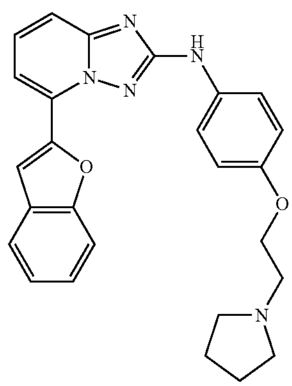 [SMILES: c1ccc2oc(-c3cccc4nc(Nc5ccc(OCCN6CCCC6)cc5)nn34)cc2c1] |
| 463 XX-294 | 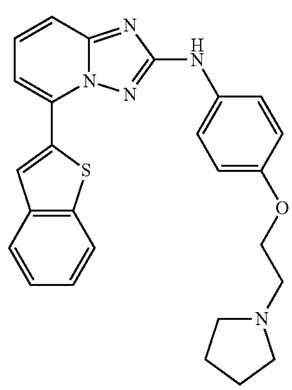 [SMILES: c1ccc2sc(-c3cccc4nc(Nc5ccc(OCCN6CCCC6)cc5)nn34)cc2c1] |
| 464 XX-295 | 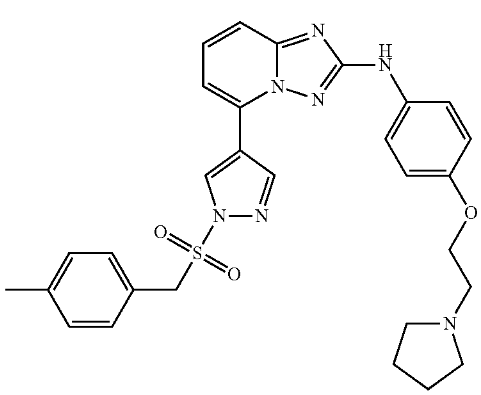 [SMILES: Cc1ccc(CS(=O)(=O)n2cc(-c3cccc4nc(Nc5ccc(OCCN6CCCC6)cc5)nn34)cn2)cc1] |

| No. Code | Structure |
|---|---|
| 465 XX-296 | 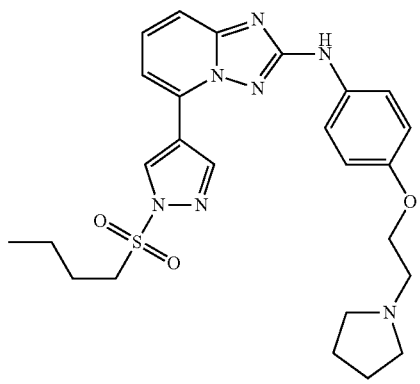 [SMILES: CCCCS(=O)(=O)n1cc(-c2cccc3nc(Nc4ccc(OCCN5CCCC5)cc4)nn23)cn1] |
| 466 XX-297 | 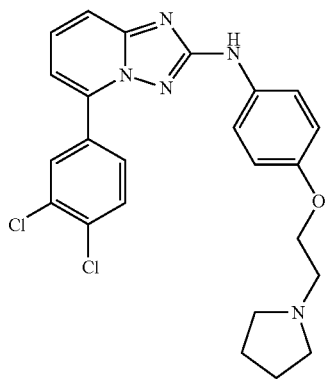 [SMILES: Clc1ccc(-c2cccc3nc(Nc4ccc(OCCN5CCCC5)cc4)nn23)cc1Cl] |
| 467 XX-298 | 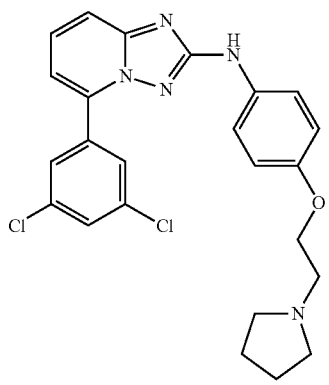 [SMILES: Clc1cc(Cl)cc(-c2cccc3nc(Nc4ccc(OCCN5CCCC5)cc4)nn23)c1] |
| 468 XX-299 | 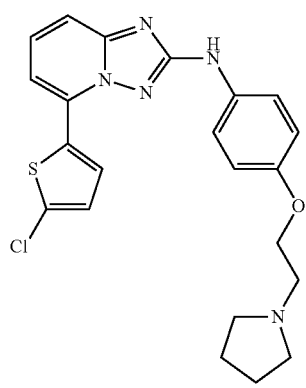 [SMILES: Clc1ccc(-c2cccc3nc(Nc4ccc(OCCN5CCCC5)cc4)nn23)s1] |

-continued
| No. Code | Structure |
|---|---|
| 469 XX-300 | 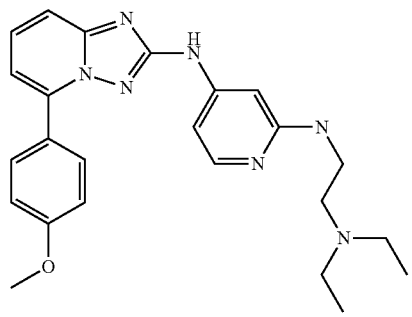 [SMILES: CCN(CC)CCNc1cc(Nc2nc3cccc(-c4ccc(OC)cc4)n3n2)ccn1] |
| 470 XX-301 | 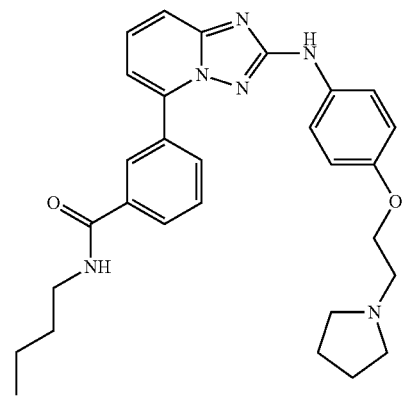 [SMILES: CCCCNC(=O)c1cccc(-c2cccc3nc(Nc4ccc(OCCN5CCCC5)cc4)nn23)c1] |
| 471 XX-302 | 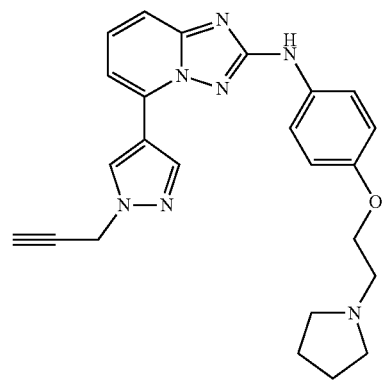 [SMILES: C#CCn1cc(-c2cccc3nc(Nc4ccc(OCCN5CCCC5)cc4)nn23)cn1] |
| 472 XX-303 | 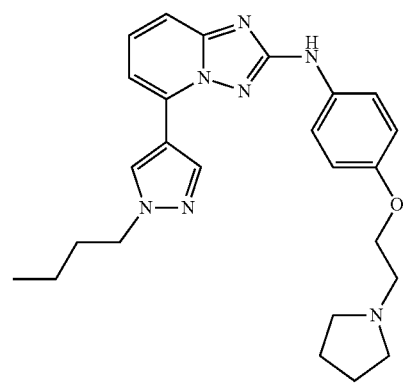 [SMILES: CCCCn1cc(-c2cccc3nc(Nc4ccc(OCCN5CCCC5)cc4)nn23)cn1] |

| No. | Code | Structure |
|---|---|---|
| 473 | XX-304 | 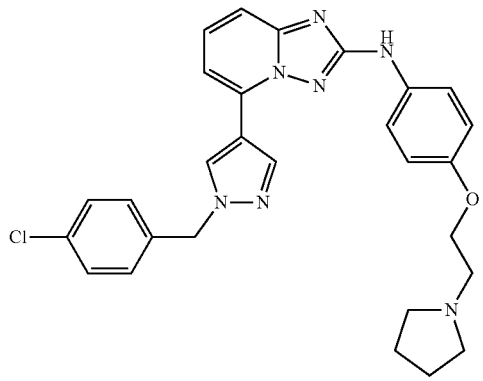 [SMILES: Clc1ccc(Cn2cc(-c3cccc4nc(Nc5ccc(OCCN6CCCC6)cc5)nn34)cn2)cc1] |
| 474 | XX-305 | 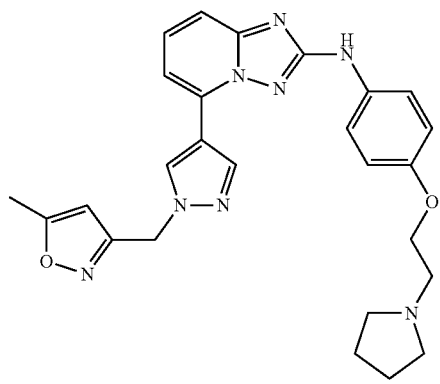 [SMILES: Cc1cc(Cn2cc(-c3cccc4nc(Nc5ccc(OCCN6CCCC6)cc5)nn34)cn2)no1] |
| 475 | XX-306 | 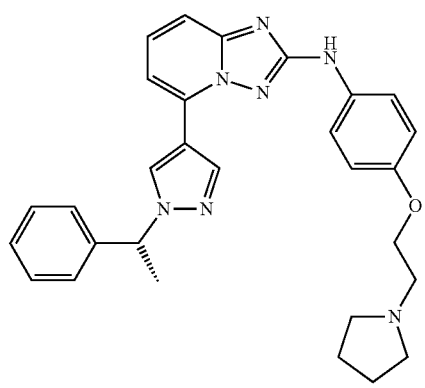 |
| 476 | XX-307 | 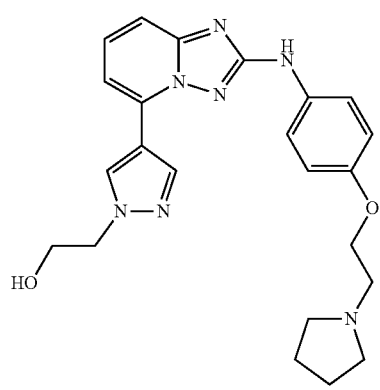 [SMILES: OCCn1cc(-c2cccc3nc(Nc4ccc(OCCN5CCCC5)cc4)nn23)cn1] |

| No. Code | Structure |
|---|---|
| 477 XX-308 | 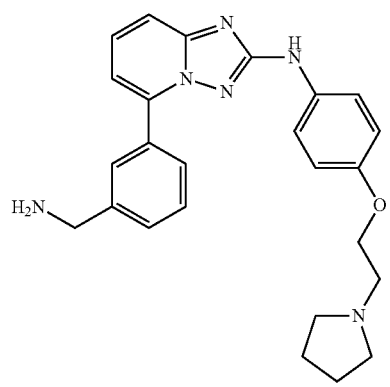 [SMILES: NCc1cccc(-c2cccc3nc(Nc4ccc(OCCN5CCCC5)cc4)nn23)c1] |
| 478 XX-309 | 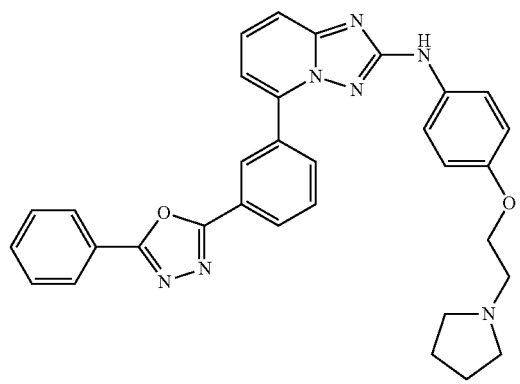 [SMILES: c1ccc(-c2nnc(-c3cccc(-c4cccc5nc(Nc6ccc(OCCN7CCCC7)cc6)nn45)c3)o2)cc1] |
| 479 XX-310 | 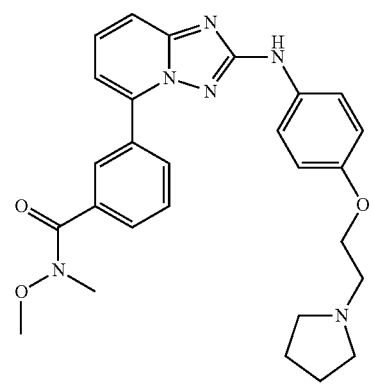 [SMILES: CON(C)C(=O)c1cccc(-c2cccc3nc(Nc4ccc(OCCN5CCCC5)cc4)nn23)c1] |
| 480 XX-311 | 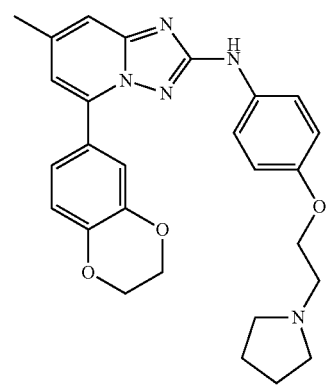 [SMILES: Cc1cc(-c2ccc3c(c2)OCCO3)n2nc(Nc3ccc(OCCN4CCCC4)cc3)nc2c1] |

-continued
| No. Code | Structure |
|---|---|
| 481 XX-312 | 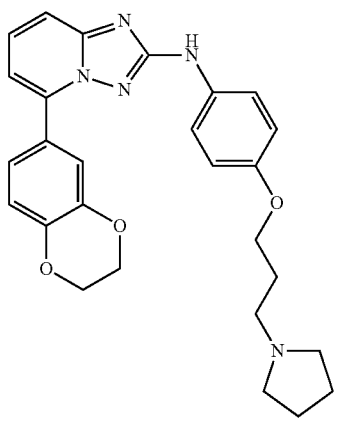 [SMILES: c1cc(-c2ccc3c(c2)OCCO3)n2nc(Nc3ccc(OCCCN4CCCC4)cc3)nc2c1] |
| 482 XX-313 | 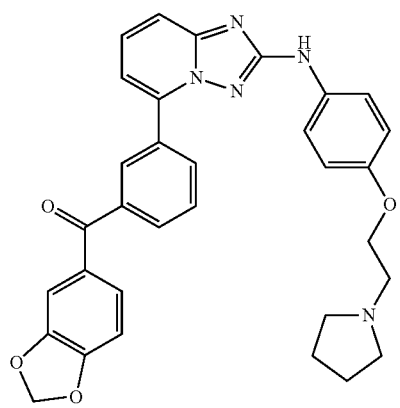 [SMILES: O=C(c1cccc(-c2cccc3nc(Nc4ccc(OCCN5CCCC5)cc4)nn23)c1)c1ccc2c(c1)OCO2] |
| 483 XX-314 | 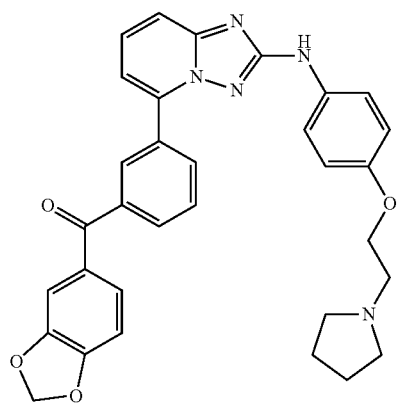 [SMILES: O=C(c1cccc(-c2cccc3nc(Nc4ccc(OCCN5CCCC5)cc4)nn23)c1)c1ccc2c(c1)OCO2] |
| 484 XX-315 | 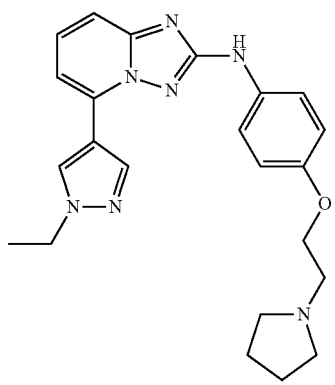 [SMILES: CCn1cc(-c2cccc3nc(Nc4ccc(OCCN5CCCC5)cc4)nn23)cn1] |

| No. Code | Structure |
|---|---|
| 485 XX-316 | 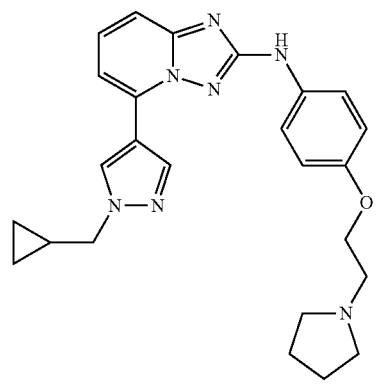 [SMILES: c1cc(-c2cnn(CC3CC3)c2)n2nc(Nc3ccc(OCCN4CCCC4)cc3)nc2c1] |
| 486 XX-317 | 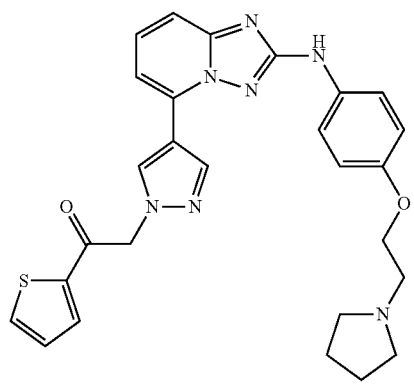 [SMILES: O=C(Cn1cc(-c2cccc3nc(Nc4ccc(OCCN5CCCC5)cc4)nn23)cn1)c1cccs1] |
| 487 XX-318 | 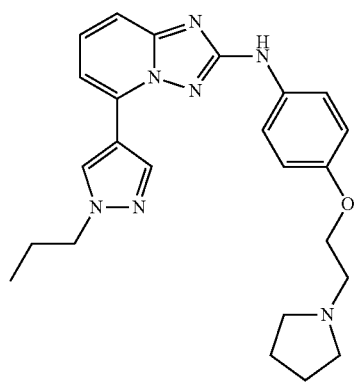 [SMILES: CCCn1cc(-c2cccc3nc(Nc4ccc(OCCN5CCCC5)cc4)nn23)cn1] |
| 488 XX-319 | 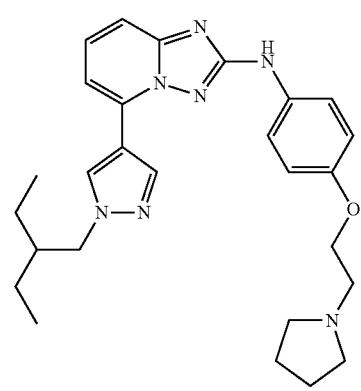 [SMILES: CCC(CC)Cn1cc(-c2cccc3nc(Nc4ccc(OCCN5CCCC5)cc4)nn23)cn1] |

| No. Code | Structure |
|---|---|
| 489 XX-320 | 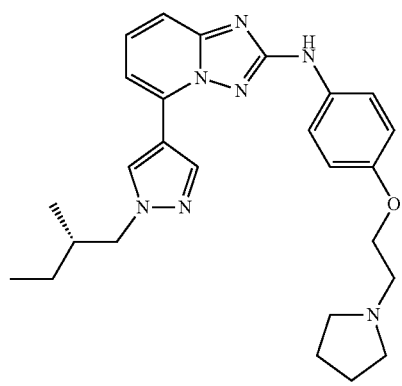 [SMILES: CC[C@H](C)Cn1cc(-c2cccc3nc(Nc4ccc(OCCN5CCCC5)cc4)nn23)cn1] |
| 490 XX-321 | 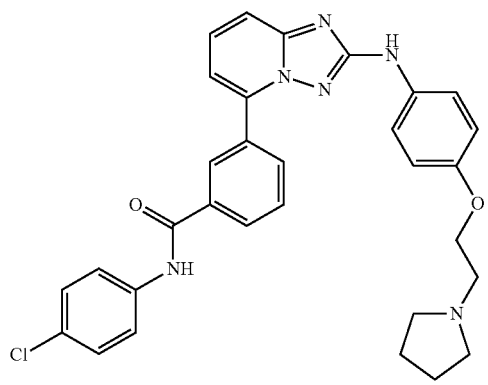 [SMILES: O=C(Nc1ccc(Cl)cc1)c1cccc(-c2cccc3nc(Nc4ccc(OCCN5CCCC5)cc4)nn23)c1] |
| 491 XX-322 | 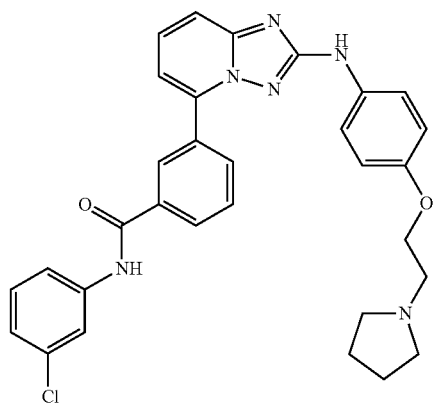 [SMILES: O=C(Nc1cccc(Cl)c1)c1cccc(-c2cccc3nc(Nc4ccc(OCCN5CCCC5)cc4)nn23)c1] |
| 492 XX-323 | 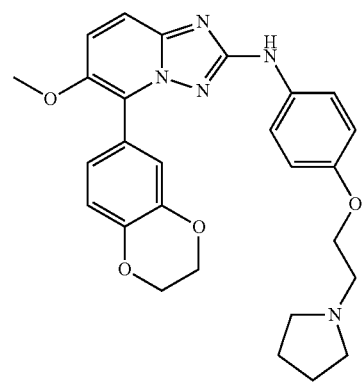 [SMILES: COc1ccc2nc(Nc3ccc(OCCN4CCCC4)cc3)nn2c1-c1ccc2c(c1)OCCO2] |

| No. Code | Structure |
|---|---|
| 493 XX-324 | 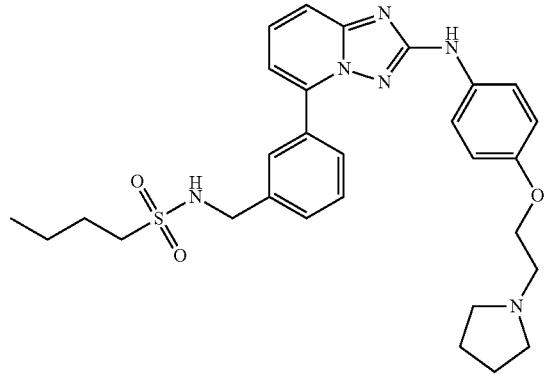 [SMILES: CCCCS(=O)(=O)NCc1cccc(-c2cccc3nc(Nc4ccc(OCCN5CCCC5)cc4)nn23)c1] |
| 494 XX-325 | 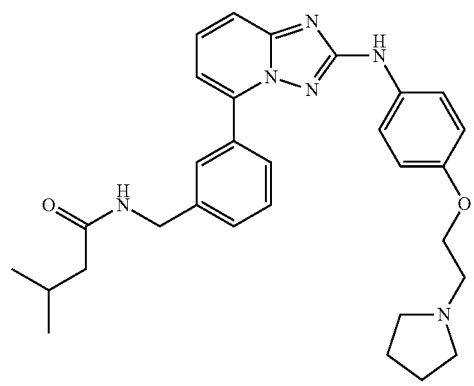 [SMILES: CC(C)CC(=O)NCc1cccc(-c2cccc3nc(Nc4ccc(OCCN5CCCC5)cc4)nn23)c1] |
| 495 XX-326 | 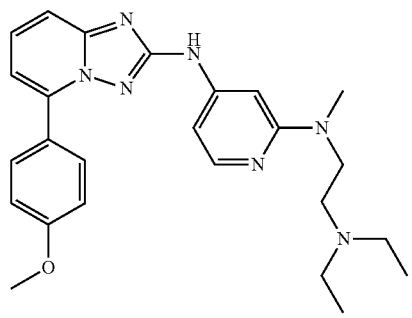 [SMILES: CCN(CC)CCN(C)c1cc(Nc2nc3cccc(-c4ccc(OC)cc4)n3n2)ccn1] |
| 496 XX-327 | 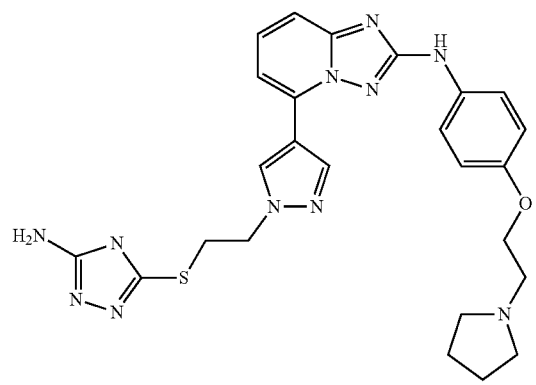 [SMILES: Nc1nnc(SCCn2cc(-c3cccc4nc(Nc5ccc(OCCN6CCCC6)cc5)nn34)cn2)[nH]1] |

-continued

| No. Code | Structure |
|---|---|
| 497 XX-328 | 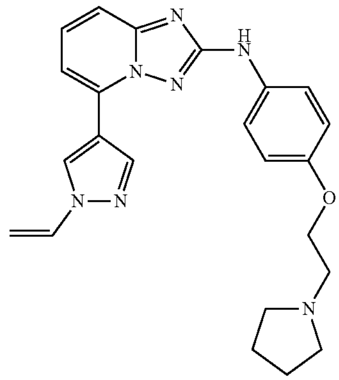 [SMILES: C=Cn1cc(-c2cccc3nc(Nc4ccc(OCCN5CCCC5)cc4)nn23)cn1] |
| 498 XX-329 | 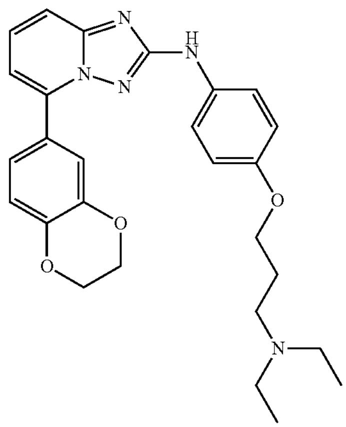 [SMILES: CCN(CC)CCCOc1ccc(Nc2nc3cccc(-c4ccc5c(c4)OCCO5)n3n2)cc1] |
| 499 XX-330 | 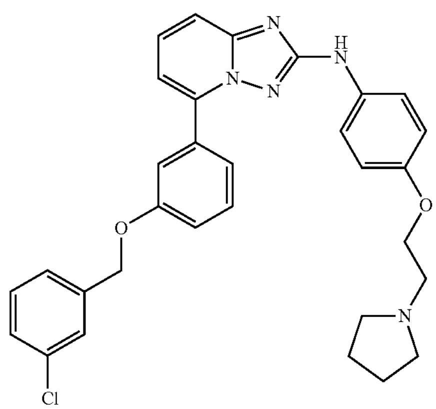 [SMILES: Clc1cccc(COc2cccc(-c3cccc4nc(Nc5ccc(OCCN6CCCC6)cc5)nn34)c2)c1] |
| 500 XX-331 | 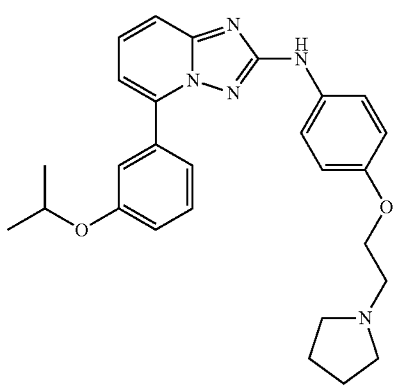 [SMILES: CC(C)Oc1cccc(-c2cccc3nc(Nc4ccc(OCCN5CCCC5)cc4)nn23)c1] |

-continued
| No. Code | Structure |
|---|---|
| 501 XX-332 | 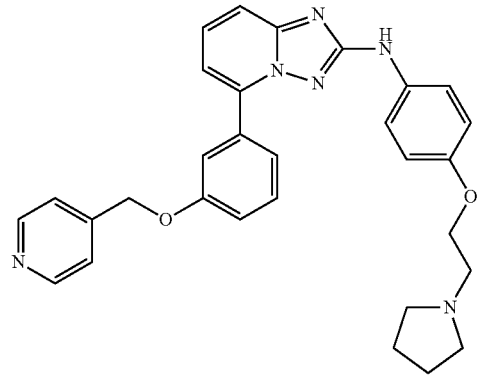 [SMILES: c1cc(OCc2ccncc2)cc(-c2cccc3nc(Nc4ccc(OCCN5CCCC5)cc4)nn23)c1] |
| 502 XX-333 | 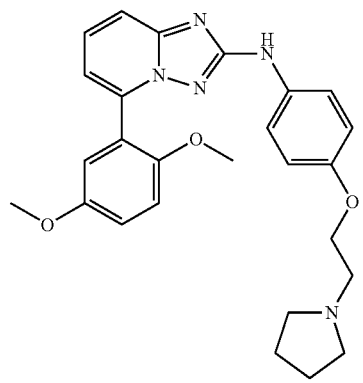 [SMILES: COc1ccc(OC)c(-c2cccc3nc(Nc4ccc(OCCN5CCCC5)cc4)nn23)c1] |
| 503 XX-334 | 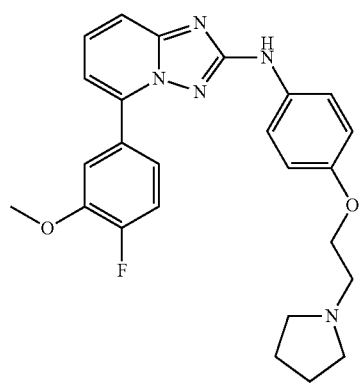 [SMILES: COc1cc(-c2cccc3nc(Nc4ccc(OCCN5CCCC5)cc4)nn23)ccc1F] |
| 504 XX-335 | 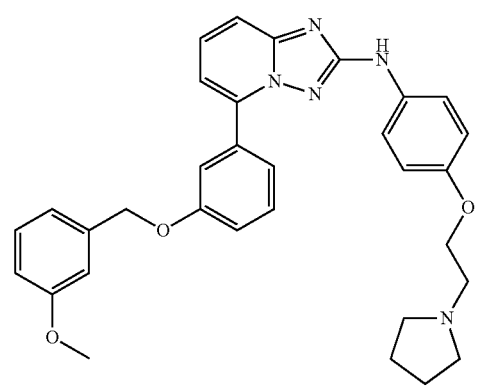 [SMILES: COc1cccc(COc2cccc(-c3cccc4nc(Nc5ccc(OCCN6CCCC6)cc5)nn34)c2)c1] |

| No. Code | Structure |
|---|---|
| 505 XX-336 | 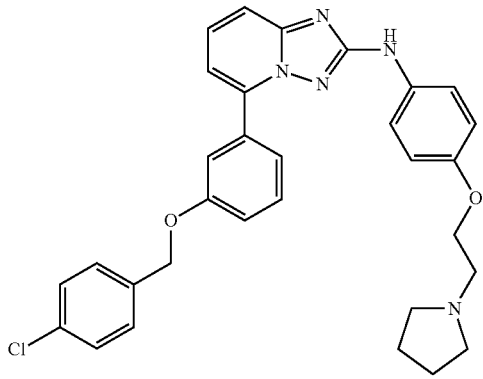 [SMILES: Clc1ccc(COc2cccc(-c3cccc4nc(Nc5ccc(OCCN6CCCC6)cc5)nn34)c2)cc1] |
| 506 XX-337 | 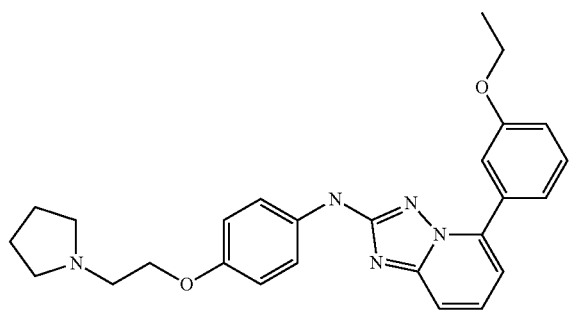 [SMILES: CCOc1cccc(-c2cccc3nc(Nc4ccc(OCCN5CCCC5)cc4)nn23)c1] |
| 507 XX-338 | 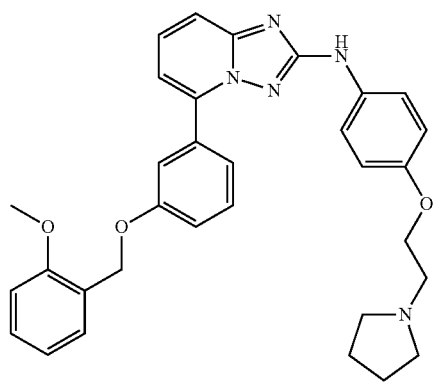 [SMILES: COc1ccccc1COc1cccc(-c2cccc3nc(Nc4ccc(OCCN5CCCC5)cc4)nn23)c1] |
| 508 XX-339 | 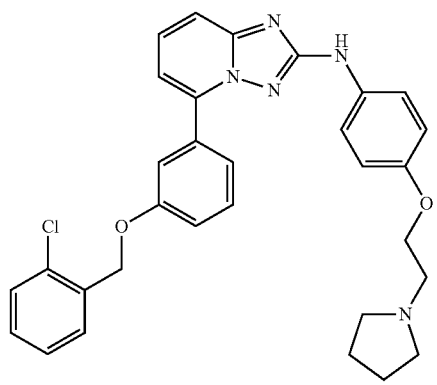 [SMILES: Clc1ccccc1COc1cccc(-c2cccc3nc(Nc4ccc(OCCN5CCCC5)cc4)nn23)c1] |

| No. Code | Structure |
|---|---|
| 509 XX-340 | 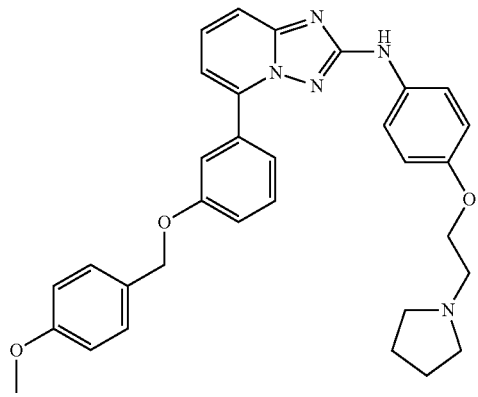 [SMILES: COc1ccc(COc2cccc(-c3cccc4nc(Nc5ccc(OCCN6CCCC6)cc5)nn34)c2)cc1] |
| 510 XX-341 | 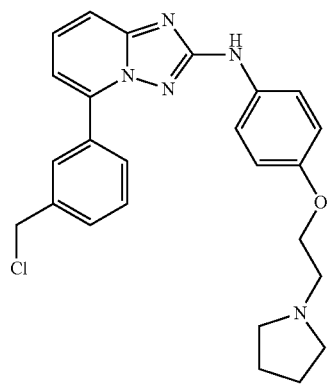 [SMILES: ClCc1cccc(-c2cccc3nc(Nc4ccc(OCCN5CCCC5)cc4)nn23)c1] |
| 511 XX-342 | 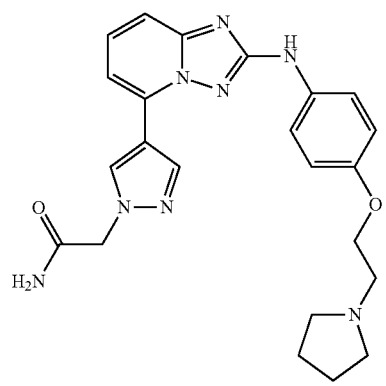 [SMILES: NC(=O)Cn1cc(-c2cccc3nc(Nc4ccc(OCCN5CCCC5)cc4)nn23)cn1] |
| 512 XX-343 | 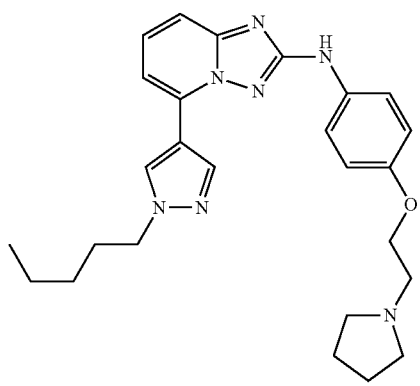 [SMILES: CCCCCn1cc(-c2cccc3nc(Nc4ccc(OCCN5CCCC5)cc4)nn23)cn1] |

-continued
| No. Code | Structure |
|---|---|
| 513 XX-344 | 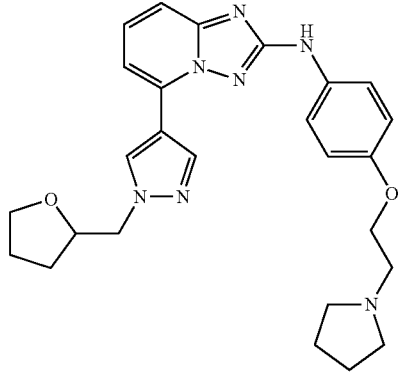 [SMILES: c1cc(-c2cnn(CC3CCCO3)c2)n2nc(Nc3ccc(OCCN4CCCC4)cc3)nc2c1] |
| 514 XX-345 | 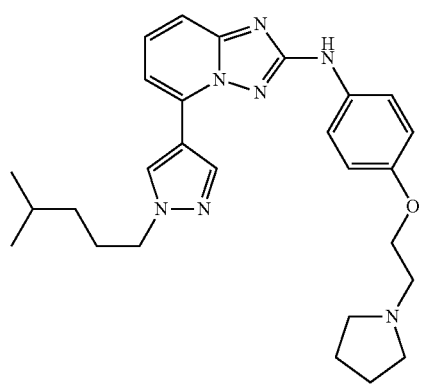 [SMILES: CC(C)CCCn1cc(-c2cccc3nc(Nc4ccc(OCCN5CCCC5)cc4)nn23)cn1] |
| 515 XX-346 | 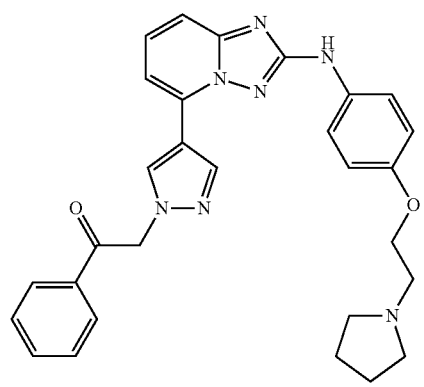 [SMILES: O=C(Cn1cc(-c2cccc3nc(Nc4ccc(OCCN5CCCC5)cc4)nn23)cn1)c1ccccc1] |
| 516 XX-347 | 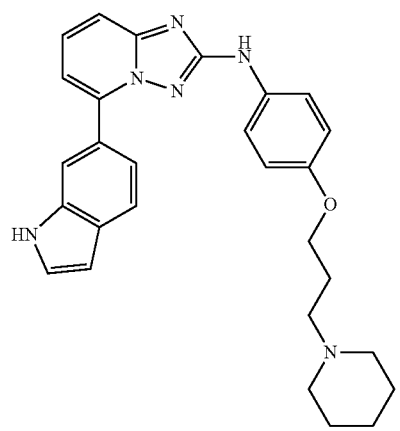 [SMILES: c1cc(-c2ccc3cc[nH]c3c2)n2nc(Nc3ccc(OCCCN4CCCCC4)cc3)nc2c1] |

| No. Code | Structure |
|---|---|
| 517 XX-348 | 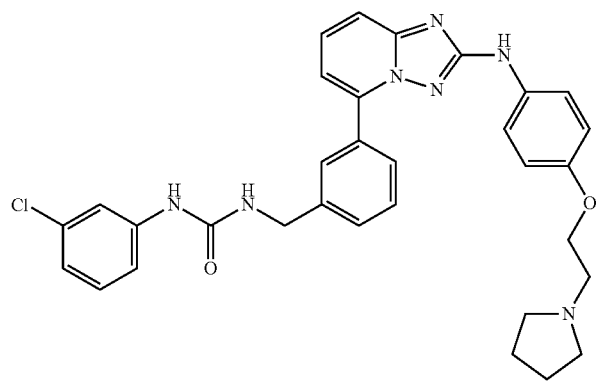 [SMILES: O=C(NCc1cccc(-c2cccc3nc(Nc4ccc(OCCN5CCCC5)cc4)nn23)c1)Nc1cccc(Cl)c1] |
| 518 XX-349 | 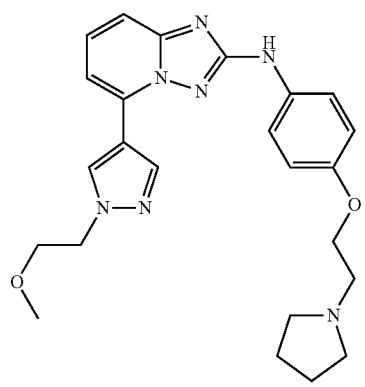 [SMILES: COCCn1cc(-c2cccc3nc(Nc4ccc(OCCN5CCCC5)cc4)nn23)cn1] |
| 519 XX-350 | 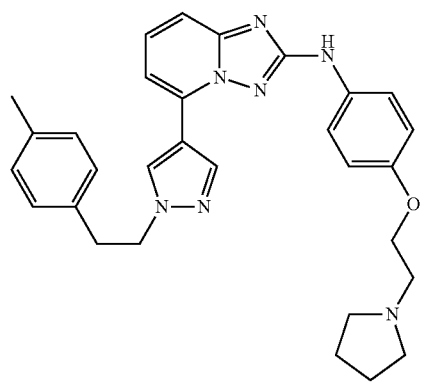 [SMILES: Cc1ccc(CCn2cc(-c3cccc4nc(Nc5ccc(OCCN6CCCC6)cc5)nn34)cn2)cc1] |
| 520 XX-351 | 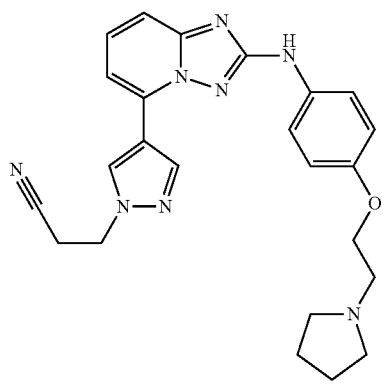 [SMILES: N#CCCn1cc(-c2cccc3nc(Nc4ccc(OCCN5CCCC5)cc4)nn23)cn1] |

| No. Code | Structure |
|---|---|
| 521 XX-352 | 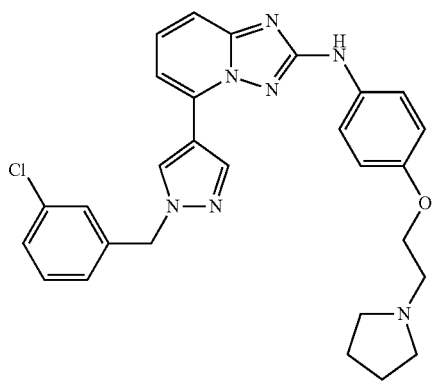 [SMILES: Clc1cccc(Cn2cc(-c3cccc4nc(Nc5ccc(OCCN6CCCC6)cc5)nn34)cn2)c1] |
| 522 XX-353 | 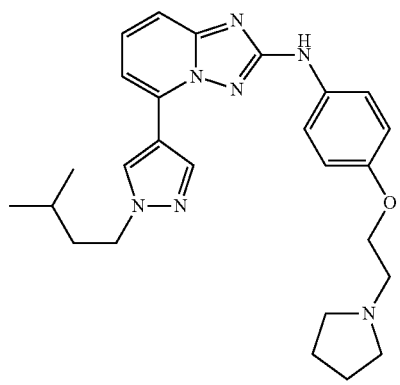 [SMILES: CC(C)CCn1cc(-c2cccc3nc(Nc4ccc(OCCN5CCCC5)cc4)nn23)cn1] |
| 523 XX-354 | 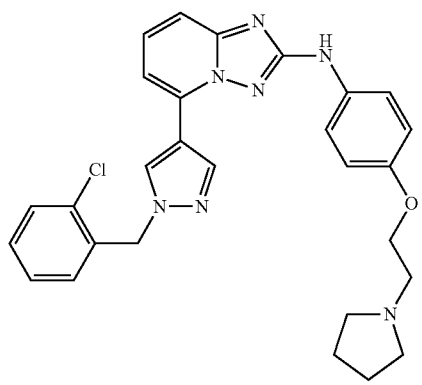 [SMILES: Clc1ccccc1Cn1cc(-c2cccc3nc(Nc4ccc(OCCN5CCCC5)cc4)nn23)cn1] |
| 524 XX-355 | 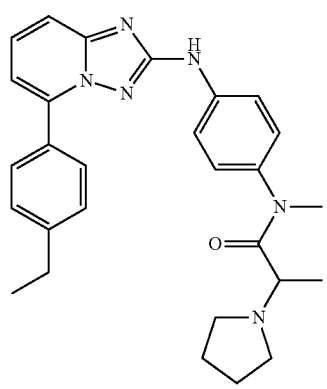 [SMILES: CCc1ccc(-c2cccc3nc(Nc4ccc(N(C)C(=O)C(C)N5CCCC5)cc4)nn23)cc1] |

-continued
| No. Code | Structure |
|---|---|
| 525 XX-356 | 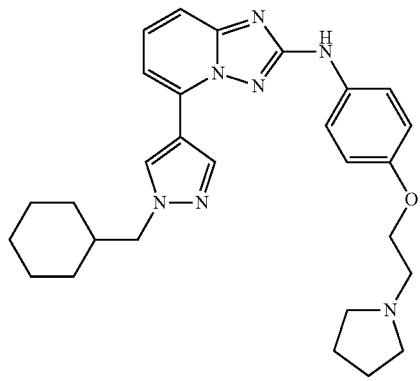 [SMILES: c1cc(-c2cnn(CC3CCCCC3)c2)n2nc(Nc3ccc(OCCN4CCCC4)cc3)nc2c1] |
| 526 XX-357 | 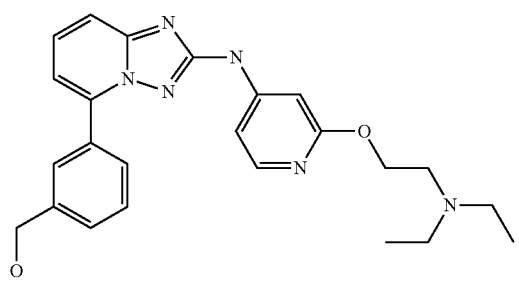 [SMILES: CCN(CC)CCOc1cc(Nc2nc3cccc(-c4cccc(CO)c4)n3n2)ccn1] |
| 527 XX-358 | 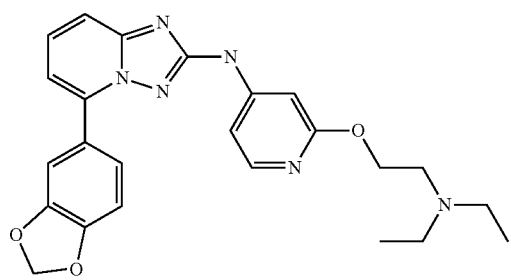 [SMILES: CCN(CC)CCOc1cc(Nc2nc3cccc(-c4ccc5c(c4)OCO5)n3n2)ccn1] |
| 528 XX-359 | 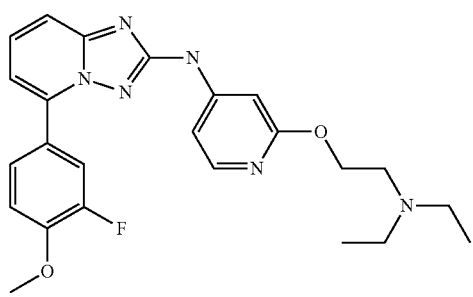 [SMILES: CCN(CC)CCOc1cc(Nc2nc3cccc(-c4ccc(OC)c(F)c4)n3n2)ccn1] |
| 529 XX-360 | 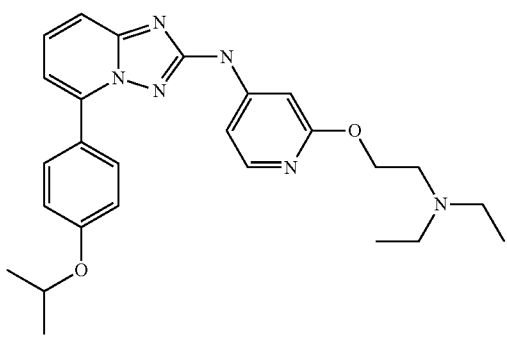 [SMILES: CCN(CC)CCOc1cc(Nc2nc3cccc(-c4ccc(OC(C)C)cc4)n3n2)ccn1] |

-continued
| No. Code | Structure |
|---|---|
| 530 XX-361 | 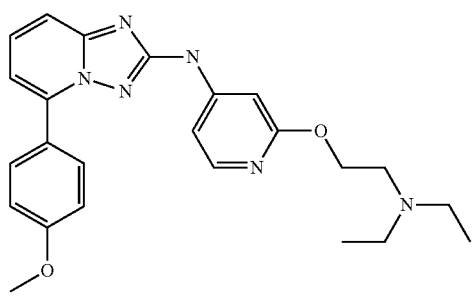 [SMILES: CCN(CC)CCOc1cc(Nc2nc3cccc(-c4ccc(OC)cc4)n3n2)ccn1] |
| 531 XX-362 | 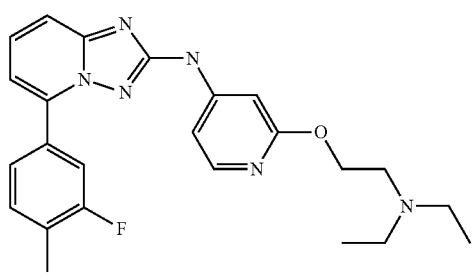 [SMILES: CCN(CC)CCOc1cc(Nc2nc3cccc(-c4ccc(C)c(F)c4)n3n2)ccn1] |
| 532 XX-363 | 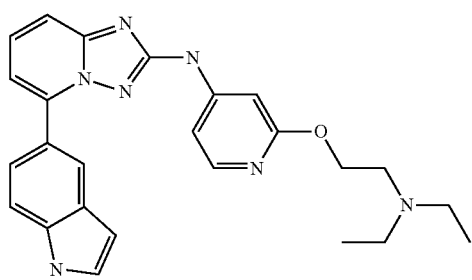 [SMILES: CCN(CC)CCOc1cc(Nc2nc3cccc(-c4ccc5[nH]ccc5c4)n3n2)ccn1] |
| 533 XX-364 | 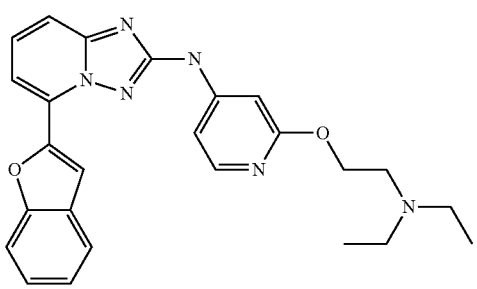 [SMILES: CCN(CC)CCOc1cc(Nc2nc3cccc(-c4cc5ccccc5o4)n3n2)ccn1] |
| 534 XX-365 | 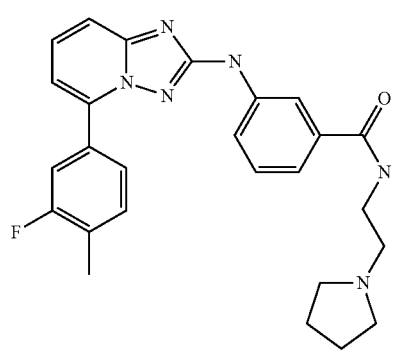 [SMILES: Cc1ccc(-c2cccc3nc(Nc4cccc(C(=O)NCCN5CCCC5)c4)nn23)cc1F] |

-continued
| No. Code | Structure |
|---|---|
| 535 XX-366 | 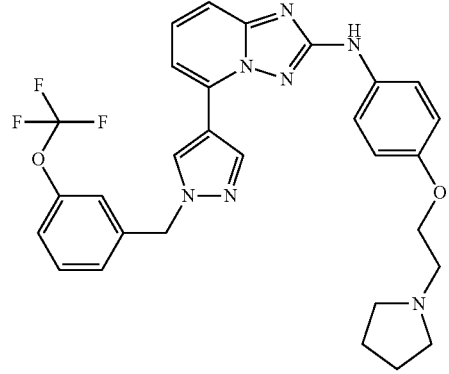 [SMILES: FC(F)(F)Oc1cccc(Cn2cc(-c3cccc4nc(Nc5ccc(OCCN6CCCC6)cc5)nn34)cn2)c1] |
| 536 XX-367 | 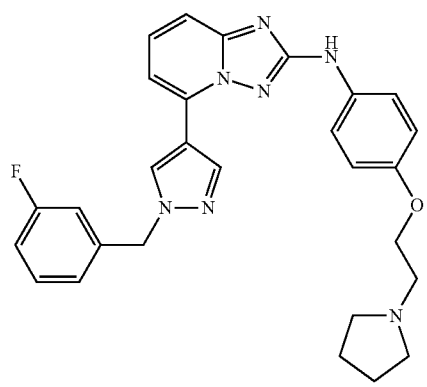 [SMILES: Fc1cccc(Cn2cc(-c3cccc4nc(Nc5ccc(OCCN6CCCC6)cc5)nn34)cn2)c1] |
| 537 XX-368 | 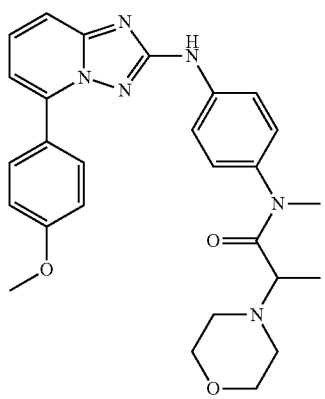 [SMILES: COc1ccc(-c2cccc3nc(Nc4ccc(N(C)C(=O)C(C)N5CCOCC5)cc4)nn23)cc1] |
| 538 XX-369 | 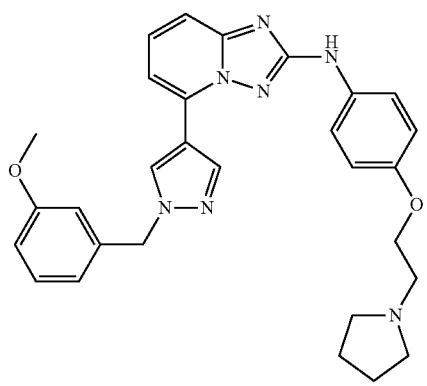 |

| No. Code | Structure |
|---|---|
| 539 XX-370 | 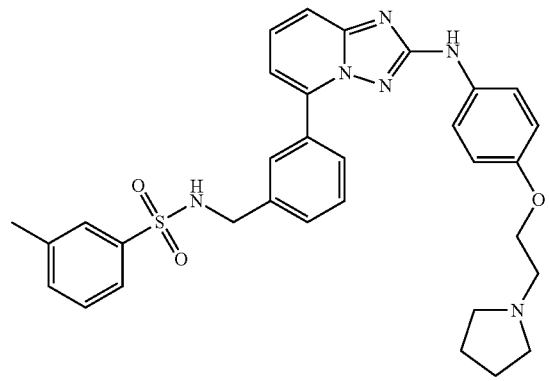 [SMILES: Cc1cccc(S(=O)(=O)NCc2cccc(-c3cccc4nc(Nc5ccc(OCCN6CCCC6)cc5)nn34)c2)c1] |
| 540 XX-371 | 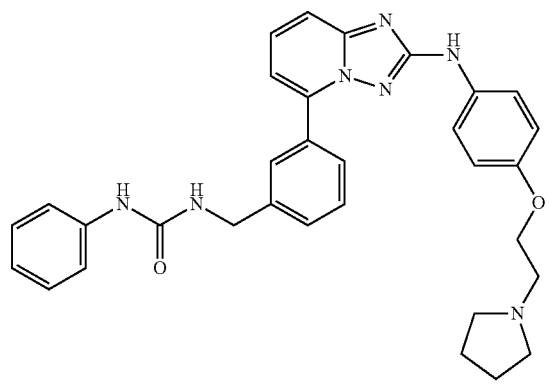 [SMILES: O=C(NCc1cccc(-c2cccc3nc(Nc4ccc(OCCN5CCCC5)cc4)nn23)c1)Nc1ccccc1] |
| 541 XX-372 | 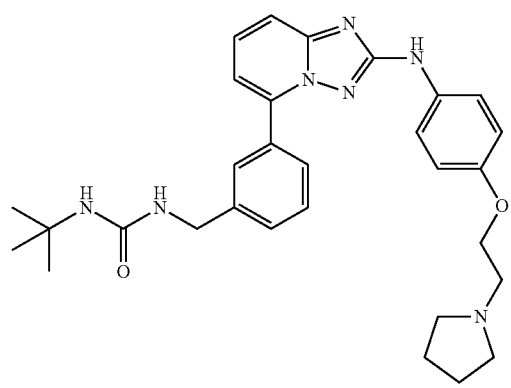 [SMILES: CC(C)(C)NC(=O)NCc1cccc(-c2cccc3nc(Nc4ccc(OCCN5CCCC5)cc4)nn23)c1] |
| 542 XX-373 | 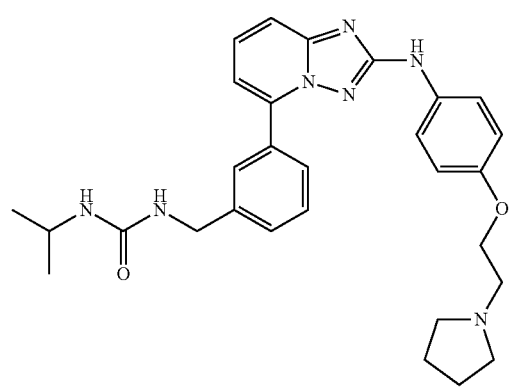 [SMILES: CC(C)NC(=O)NCc1cccc(-c2cccc3nc(Nc4ccc(OCCN5CCCC5)cc4)nn23)c1] |

| No. Code | Structure |
|---|---|
| 543 XX-374 | 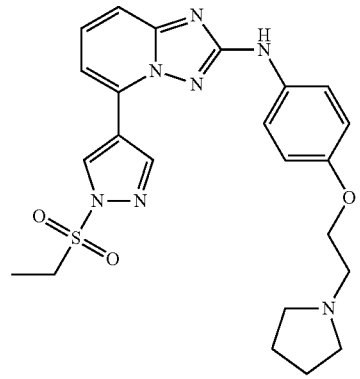 [SMILES: CCS(=O)(=O)n1cc(-c2cccc3nc(Nc4ccc(OCCN5CCCC5)cc4)nn23)cn1] |
| 544 XX-375 | 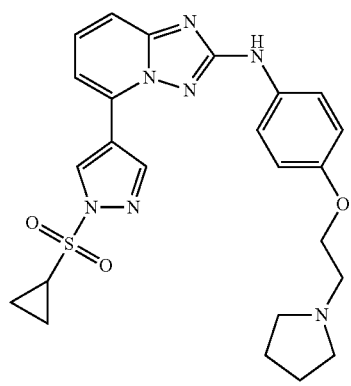 [SMILES: O=S(=O)(C1CC1)n1cc(-c2cccc3nc(Nc4ccc(OCCN5CCCC5)cc4)nn23)cn1] |
| 545 XX-376 | 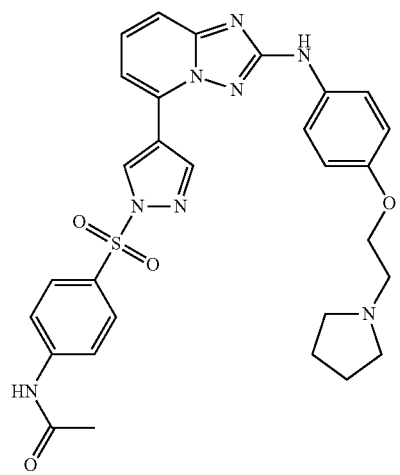 [SMILES: CC(=O)Nc1ccc(S(=O)(=O)n2cc(-c3cccc4nc(Nc5ccc(OCCN6CCCC6)cc5)nn34)cn2)cc1] |

| No. Code | Structure |
|---|---|
| 546 XX-377 | 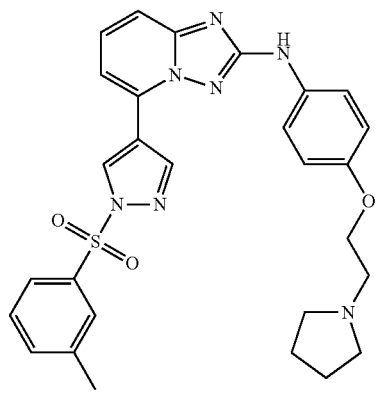 [SMILES: Cc1cccc(S(=O)(=O)n2cc(-c3cccc4nc(Nc5ccc(OCCN6CCCC6)cc5)nn34)cn2)c1] |
| 547 XX-378 | 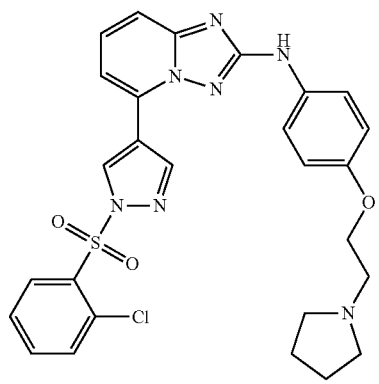 [SMILES: O=S(=O)(c1ccccc1Cl)n1cc(-c2cccc3nc(Nc4ccc(OCCN5CCCC5)cc4)nn23)cn1] |
| 548 XX-379 | 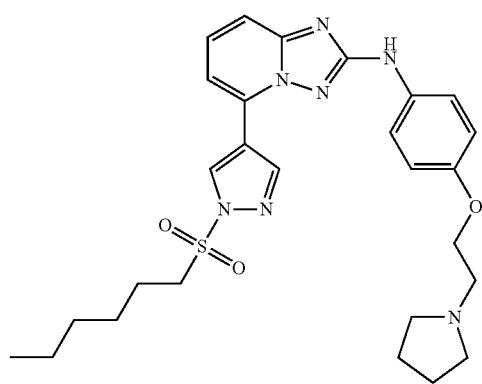 [SMILES: CCCCCCS(=O)(=O)n1cc(-c2cccc3nc(Nc4ccc(OCCN5CCCC5)cc4)nn23)cn1] |
| 549 XX-380 | 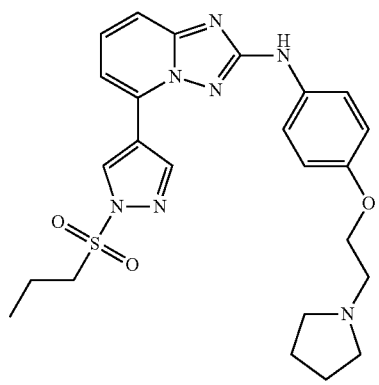 [SMILES: CCCS(=O)(=O)n1cc(-c2cccc3nc(Nc4ccc(OCCN5CCCC5)cc4)nn23)cn1] |

-continued
| No. Code | Structure |
|---|---|
| 550 XX-381 | 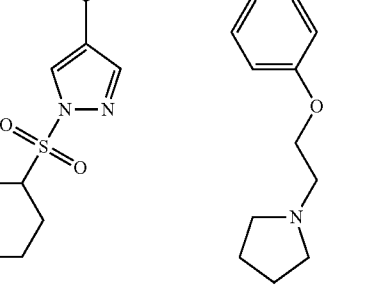 |
| 551 XX-382 | 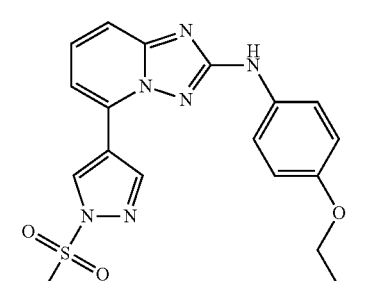 |
| 552 XX-383 | 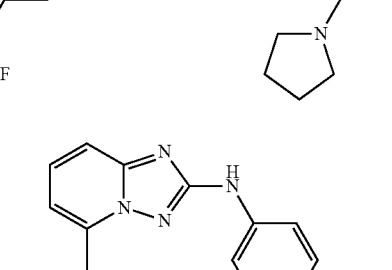 |
| 553 XX-384 | 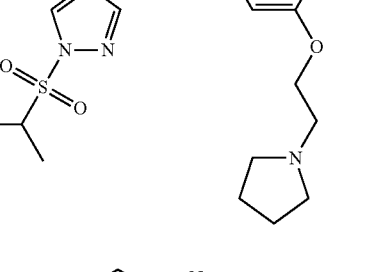 |

| No. Code | Structure |
|---|---|
| 554 XX-385 | 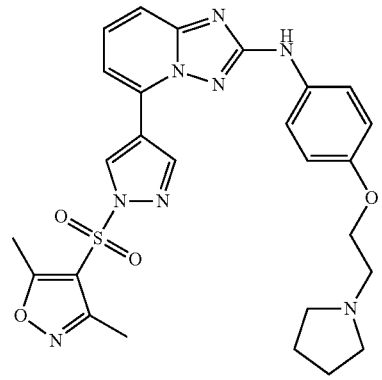 [SMILES: Cc1noc(C)c1S(=O)(=O)n1cc(-c2cccc3nc(Nc4ccc(OCCN5CCCC5)cc4)nn23)cn1] |
| 555 XX-386 | 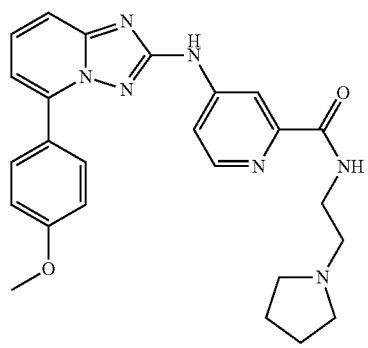 [SMILES: COc1ccc(-c2cccc3nc(Nc4ccnc(C(=O)NCCN5CCCC5)c4)nn23)cc1] |
| 556 XX-387 | 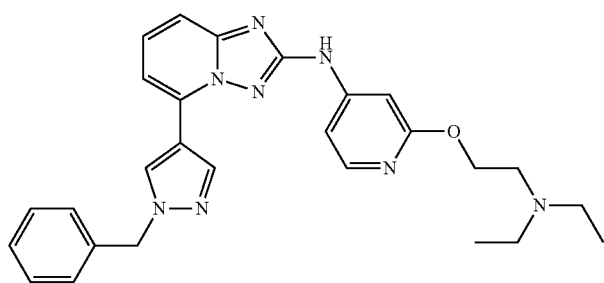 [SMILES: CCN(CC)CCOc1cc(Nc2nc3cccc(-c4cnn(Cc5ccccc5)c4)n3n2)ccn1] |
| 557 XX-388 | 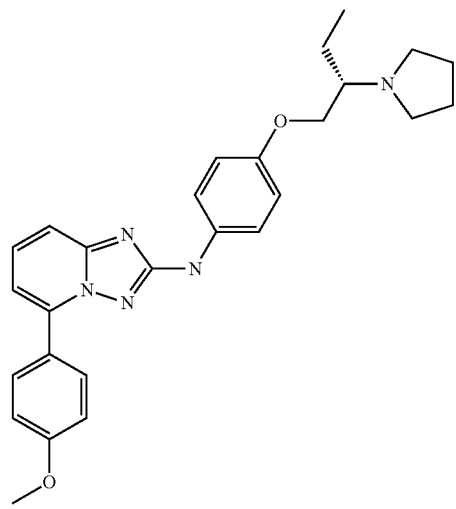 [SMILES: CC[C@@H](COc1ccc(Nc2nc3cccc(-c4ccc(OC)cc4)n3n2)cc1)N1CCCC1] |

| No. Code | Structure |
|---|---|
| 558 XX-389 | 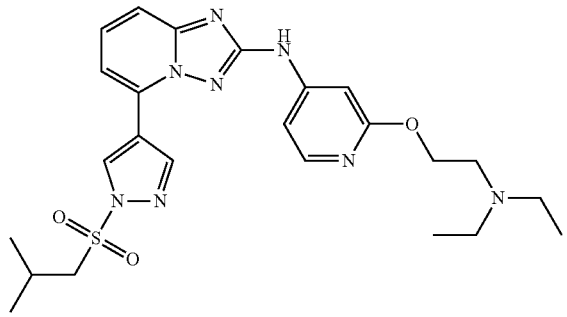 [SMILES: CCN(CC)CCOc1cc(Nc2nc3cccc(-c4cnn(S(=O)(=O)CC(C)C)c4)n3n2)ccn1] |
| 559 XX-390 | 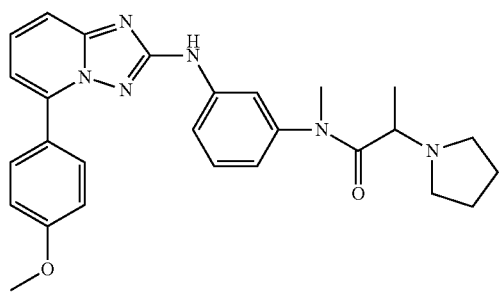 [SMILES: COc1ccc(-c2cccc3nc(Nc4cccc(N(C)C(=O)C(C)N5CCCC5)c4)nn23)cc1] |
| 560 XX-391 | 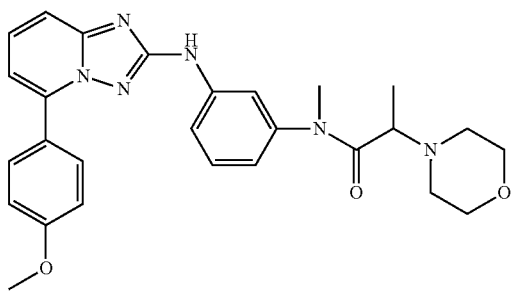 [SMILES: COc1ccc(-c2cccc3nc(Nc4cccc(N(C)C(=O)C(C)N5CCOCC5)c4)nn23)cc1] |
| 561 XX-392 | 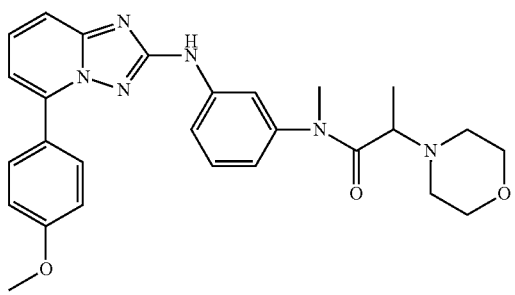 [SMILES: COc1ccc(-c2cccc3nc(Nc4cccc(N(C)C(=O)C(C)N5CCOCC5)c4)nn23)cc1] |
| 562 XX-393 | 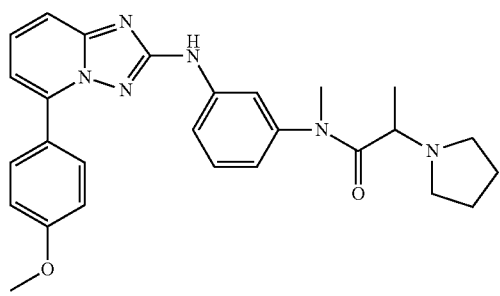 [SMILES: COc1ccc(-c2cccc3nc(Nc4cccc(N(C)C(=O)C(C)N5CCCC5)c4)nn23)cc1] |

| No. Code | Structure |
|---|---|
| 563 XX-394 | 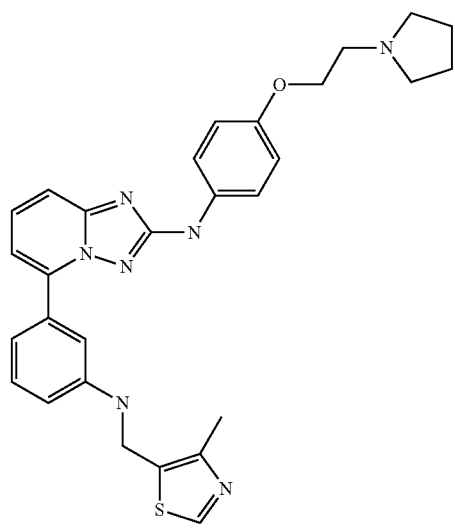 [SMILES: Cc1ncsc1CNc1cccc(-c2cccc3nc(Nc4ccc(OCCN5CCCC5)cc4)nn23)c1] |
| 564 XX-395 | 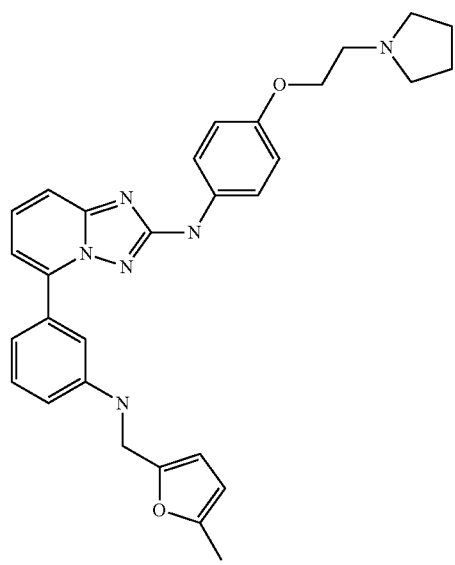 [SMILES: Cc1ccc(CNc2cccc(-c3cccc4nc(Nc5ccc(OCCN6CCCC6)cc5)nn34)c2)o1] |
| 565 XX-396 | 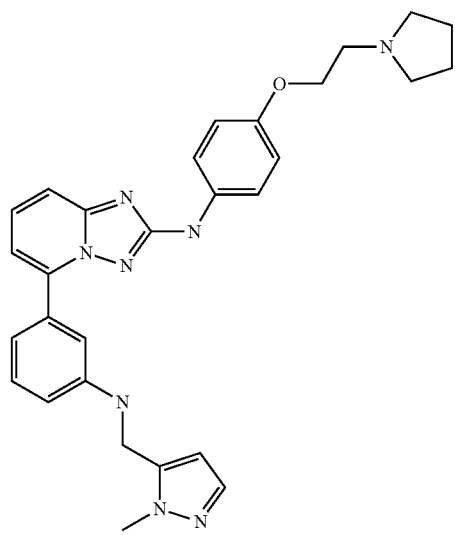 [SMILES: Cn1nccc1CNc1cccc(-c2cccc3nc(Nc4ccc(OCCN5CCCC5)cc4)nn23)c1] |

| No. Code | Structure |
|---|---|
| 566 XX-397 | 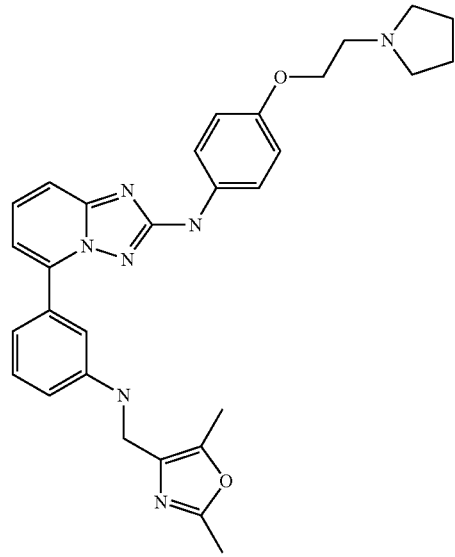 [SMILES: Cc1nc(CNc2cccc(-c3cccc4nc(Nc5ccc(OCCN6CCCC6)cc5)nn34)c2)c(C)o1] |
| 567 XX-398 | 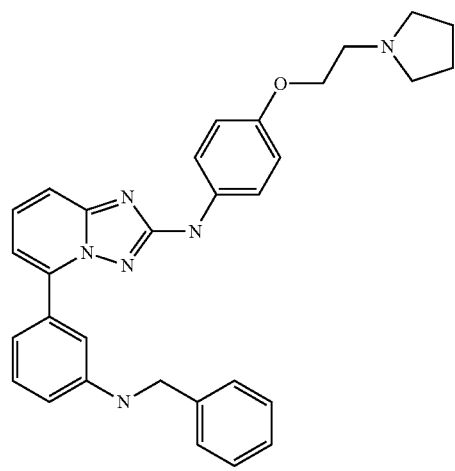 [SMILES: c1ccc(CNc2cccc(-c3cccc4nc(Nc5ccc(OCCN6CCCC6)cc5)nn34)c2)cc1] |
| 568 XX-399 | 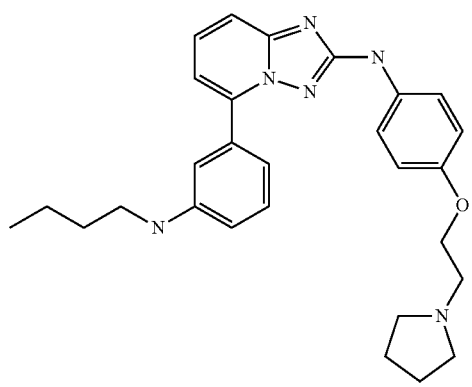 [SMILES: CCCCNc1cccc(-c2cccc3nc(Nc4ccc(OCCN5CCCC5)cc4)nn23)c1] |

| No. Code | Structure |
|---|---|
| 569 XX-400 | 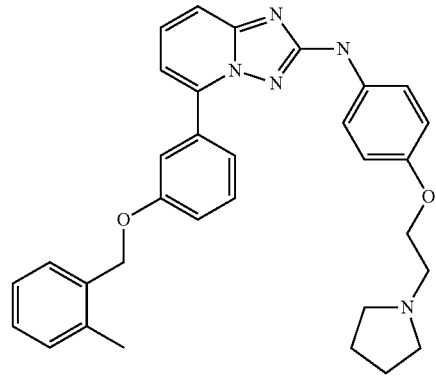 [SMILES: Cc1ccccc1COc1cccc(-c2cccc3nc(Nc4ccc(OCCN5CCCC5)cc4)nn23)c1] |
| 570 XX-401 | 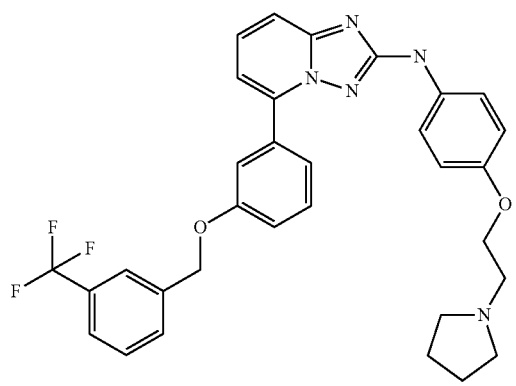 [SMILES: FC(F)(F)c1cccc(COc2cccc(-c3cccc4nc(Nc5ccc(OCCN6CCCC6)cc5)nn34)c2)c1] |
| 571 XX-402 | 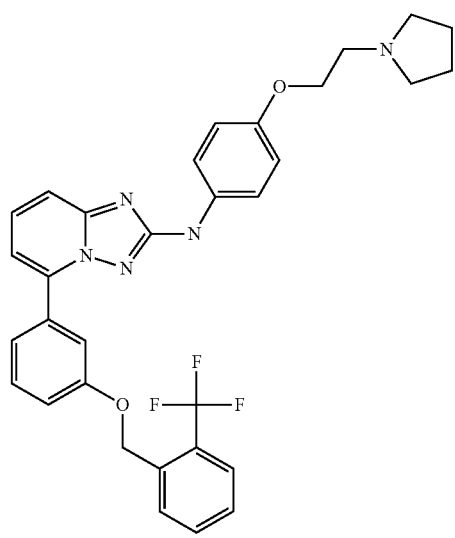 [SMILES: FC(F)(F)c1ccccc1COc1cccc(-c2cccc3nc(Nc4ccc(OCCN5CCCC5)cc4)nn23)c1] |

-continued
| No. Code | Structure |
|---|---|
| 572 XX-403 | 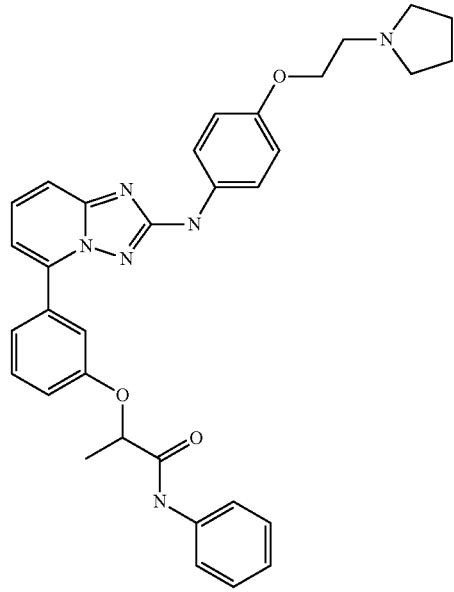 [SMILES: CC(Oc1cccc(-c2cccc3nc(Nc4ccc(OCCN5CCCC5)cc4)nn23)c1)C(=O)Nc1ccccc1] |
| 573 XX-404 | 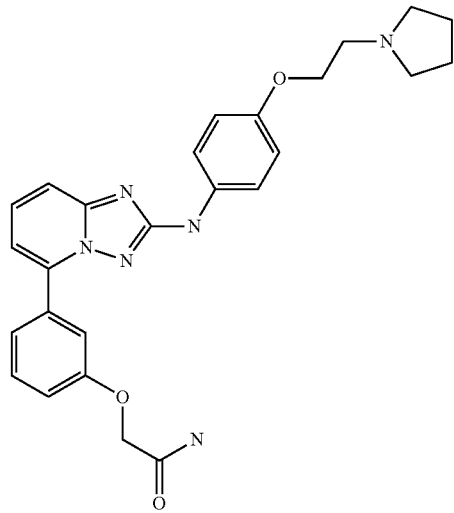 [SMILES: NC(=O)COc1cccc(-c2cccc3nc(Nc4ccc(OCCN5CCCC5)cc4)nn23)c1] |
| 574 XX-405 | 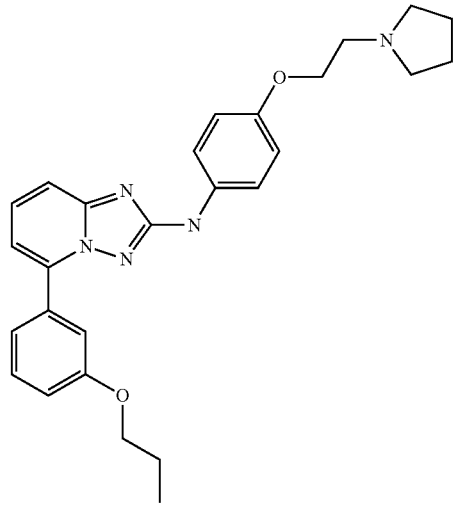 [SMILES: CCCOc1cccc(-c2cccc3nc(Nc4ccc(OCCN5CCCC5)cc4)nn23)c1] |

-continued
| No. Code | Structure |
|---|---|
| 575 XX-406 | 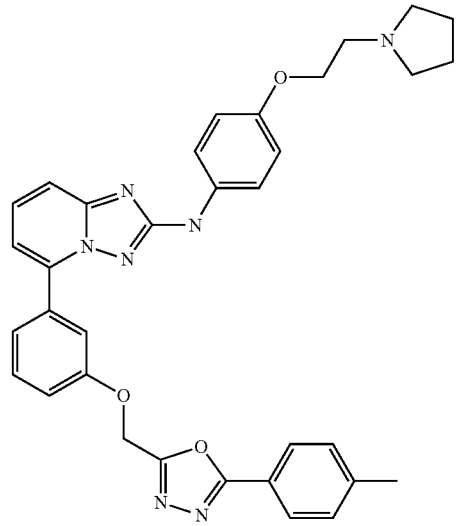 [SMILES: Cc1ccc(-c2nnc(COc3cccc(-c4cccc5nc(Nc6ccc(OCCN7CCCC7)cc6)nn45)c3)o2)cc1] |
| 576 XX-407 | 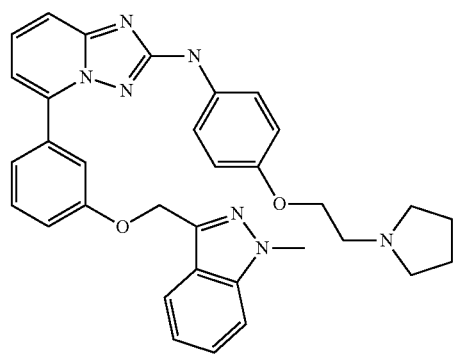 [SMILES: Cn1nc(COc2cccc(-c3cccc4nc(Nc5ccc(OCCN6CCCC6)cc5)nn34)c2)c2ccccc21] |
| 577 XX-408 | 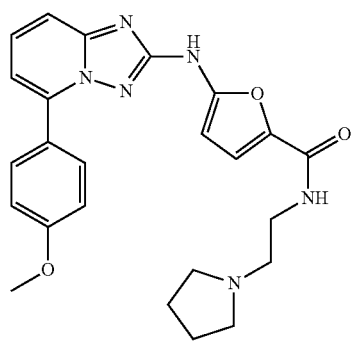 [SMILES: COc1ccc(-c2cccc3nc(Nc4ccc(C(=O)NCCN5CCCC5)o4)nn23)cc1] |
| 578 XX-409 | 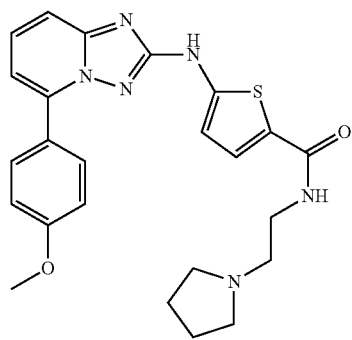 [SMILES: COc1ccc(-c2cccc3nc(Nc4ccc(C(=O)NCCN5CCCC5)s4)nn23)cc1] |

-continued
| No. Code | Structure |
|---|---|
| 579 XX-410 | 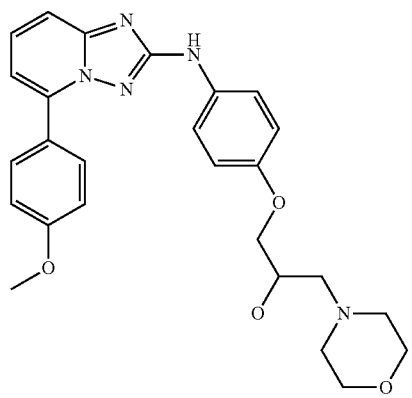 [SMILES: COc1ccc(-c2cccc3nc(Nc4ccc(OCC(O)CN5CCOCC5)cc4)nn23)cc1] |
| 580 XX-411 | 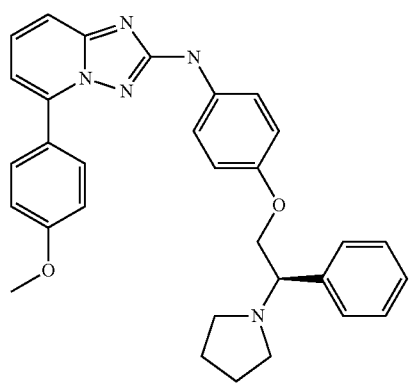 [SMILES: COc1ccc(-c2cccc3nc(Nc4ccc(OC[C@@H](c5ccccc5)N5CCCC5)cc4)nn23)cc1] |
| 581 XX-412 | 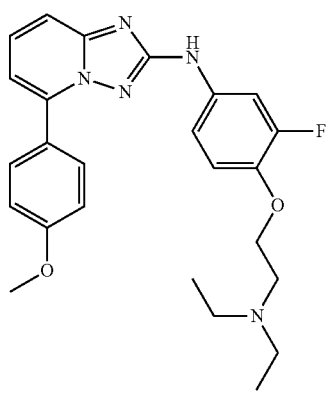 [SMILES: CCN(CC)CCOc1ccc(Nc2nc3cccc(-c4ccc(OC)cc4)n3n2)cc1F] |
| 582 XX-413 | 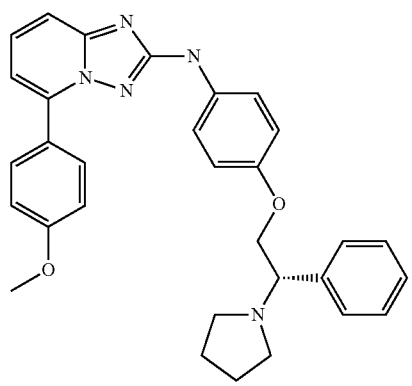 [SMILES: COc1ccc(-c2cccc3nc(Nc4ccc(OC[C@H](c5ccccc5)N5CCCC5)cc4)nn23)cc1] |

| No. Code | Structure |
|---|---|
| 583 XX-414 | 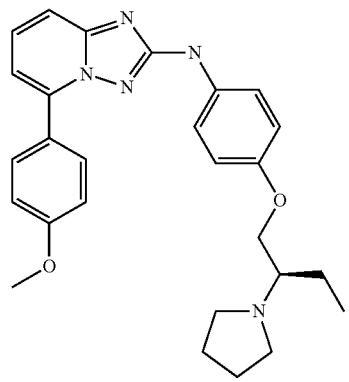 [SMILES: CC[C@H](COc1ccc(Nc2nc3cccc(-c4ccc(OC)cc4)n3n2)cc1)N1CCCC1] |
| 584 XX-415 | 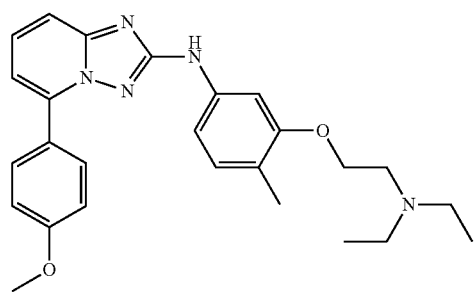 [SMILES: CCN(CC)CCOc1cc(Nc2nc3cccc(-c4ccc(OC)cc4)n3n2)ccc1C] |
| 585 XX-416 | 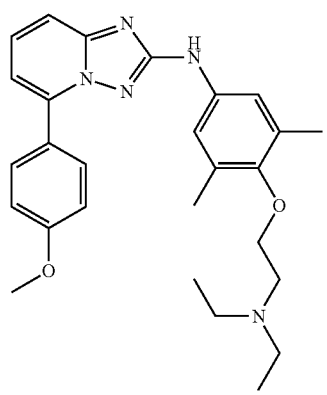 [SMILES: CCN(CC)CCOc1c(C)cc(Nc2nc3cccc(-c4ccc(OC)cc4)n3n2)cc1C] |
| 586 XX-417 | 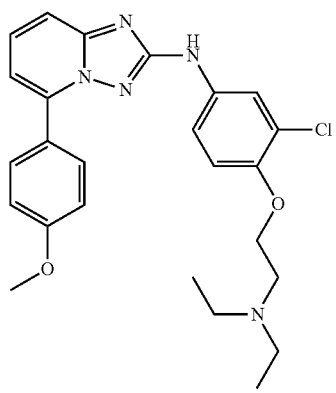 [SMILES: CCN(CC)CCOc1ccc(Nc2nc3cccc(-c4ccc(OC)cc4)n3n2)cc1Cl] |

| No. Code | Structure |
|---|---|
| 587 XX-418 | 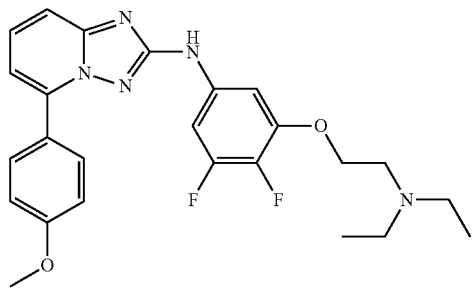 [SMILES: CCN(CC)CCOc1cc(Nc2nc3cccc(-c4ccc(OC)cc4)n3n2)cc(F)c1F] |
| 588 XX-419 | 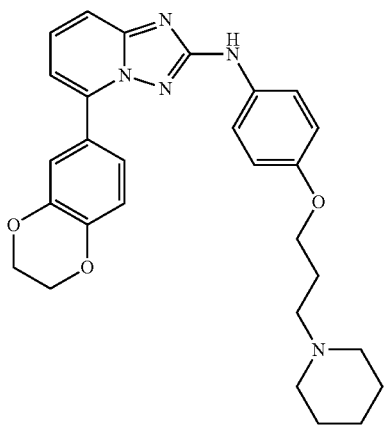 [SMILES: c1cc(-c2ccc3c(c2)OCCO3)n2nc(Nc3ccc(OCCCN4CCCCC4)cc3)nc2c1] |
| 589 XX-420 | 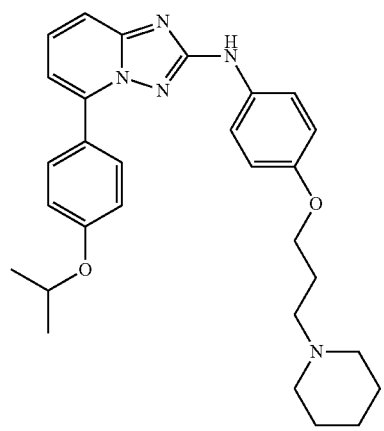 [SMILES: CC(C)Oc1ccc(-c2cccc3nc(Nc4ccc(OCCCN5CCCCC5)cc4)nn23)cc1] |
| 590 XX-421 | 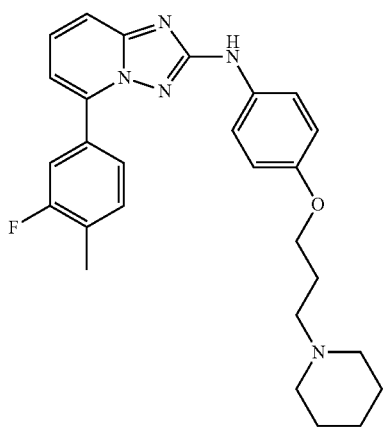 [SMILES: Cc1ccc(-c2cccc3nc(Nc4ccc(OCCCN5CCCCC5)cc4)nn23)cc1F] |

-continued
| No. Code | Structure |
|---|---|
| 591 XX-422 | 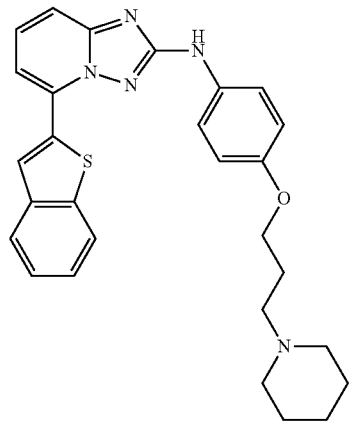 [SMILES: c1ccc2sc(-c3cccc4nc(Nc5ccc(OCCCN6CCCCC6)cc5)nn34)cc2c1] |
| 592 XX-423 | 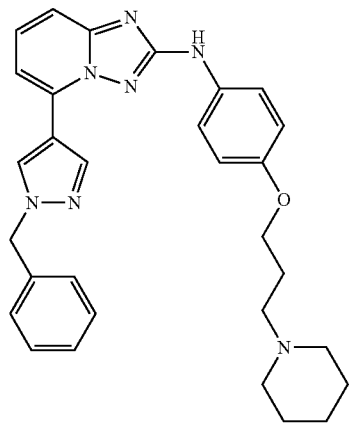 [SMILES: c1ccc(Cn2cc(-c3cccc4nc(Nc5ccc(OCCCN6CCCCC6)cc5)nn34)cn2)cc1] |
| 593 XX-424 | 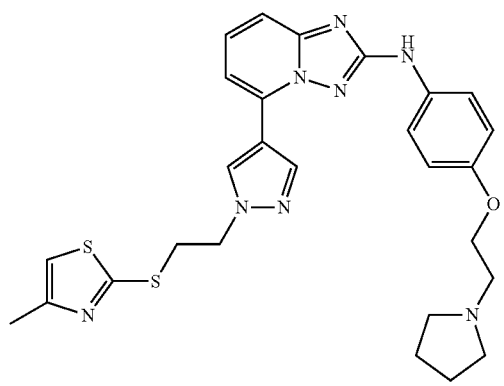 [SMILES: Cc1csc(SCCn2cc(-c3cccc4nc(Nc5ccc(OCCN6CCCC6)cc5)nn34)cn2)n1] |

| No. Code | Structure |
|---|---|
| 594 XX-425 | 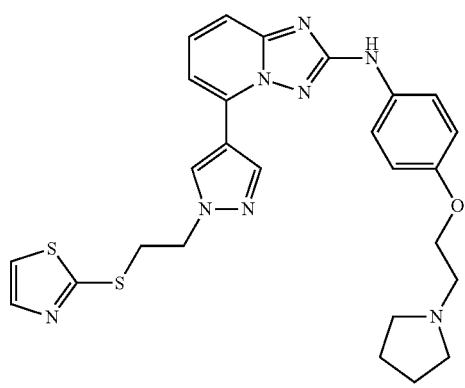 [SMILES: c1cc(-c2cnn(CCSc3nccs3)c2)n2nc(Nc3ccc(OCCN4CCCC4)cc3)nc2c1] |
| 595 XX-426 | 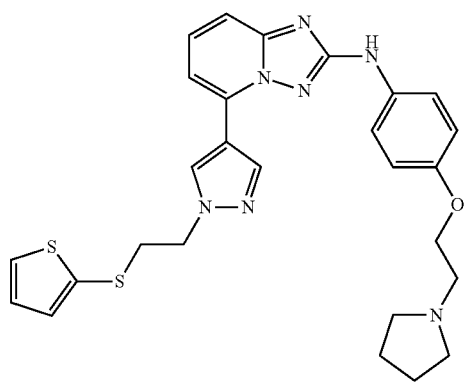 [SMILES: c1csc(SCCn2cc(-c3cccc4nc(Nc5ccc(OCCN6CCCC6)cc5)nn34)cn2)c1] |
| 596 XX-427 | 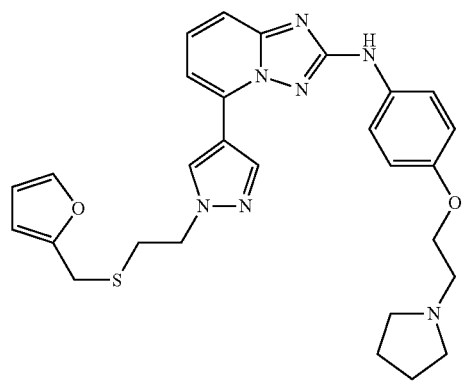 [SMILES: c1coc(CSCCn2cc(-c3cccc4nc(Nc5ccc(OCCN6CCCC6)cc5)nn34)cn2)c1] |
| 597 XX-428 | 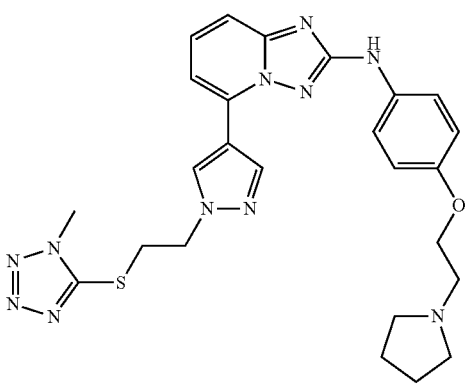 [SMILES: Cn1nnnc1SCCn1cc(-c2cccc3nc(Nc4ccc(OCCN5CCCC5)cc4)nn23)cn1] |

| No. Code | Structure |
|---|---|
| 598 XX-429 | 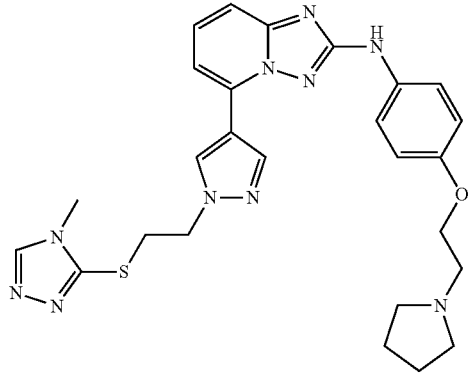 [SMILES: Cn1cnnc1SCCn1cc(-c2cccc3nc(Nc4ccc(OCCN5CCCC5)cc4)nn23)cn1] |
| 599 XX-430 | 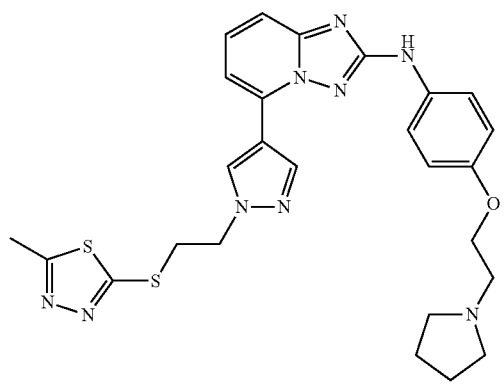 [SMILES: Cc1nnc(SCCn2cc(-c3cccc4nc(Nc5ccc(OCCN6CCCC6)cc5)nn34)cn2)s1] |
| 600 XX-431 | 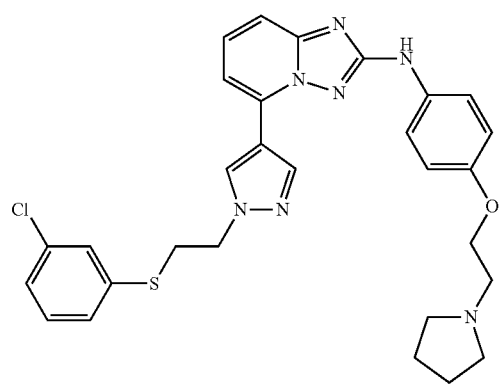 [SMILES: Clc1cccc(SCCn2cc(-c3cccc4nc(Nc5ccc(OCCN6CCCC6)cc5)nn34)cn2)c1] |
| 601 XX-432 | 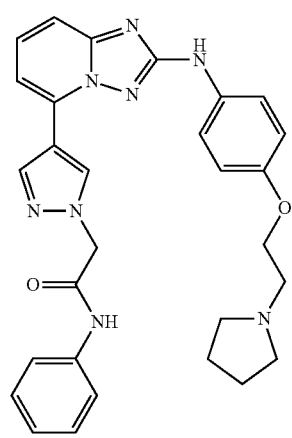 [SMILES: O=C(Cn1cc(-c2cccc3nc(Nc4ccc(OCCN5CCCC5)cc4)nn23)cn1)Nc1ccccc1] |

| No. Code | Structure |
|---|---|
| 602 XX-433 | 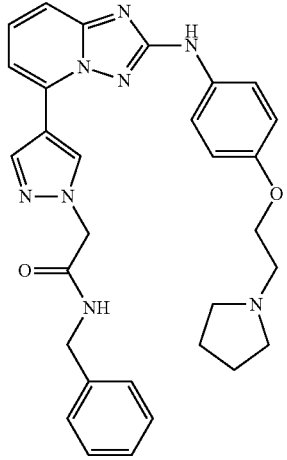 [SMILES: O=C(Cn1cc(-c2cccc3nc(Nc4ccc(OCCN5CCCC5)cc4)nn23)cn1)NCc1ccccc1] |
| 603 XX-434 | 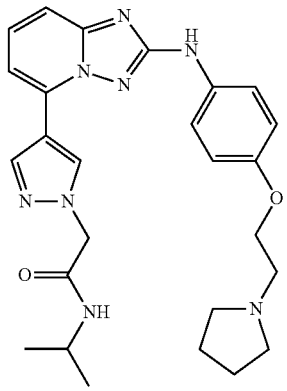 [SMILES: CC(C)NC(=O)Cn1cc(-c2cccc3nc(Nc4ccc(OCCN5CCCC5)cc4)nn23)cn1] |
| 604 XX-435 | 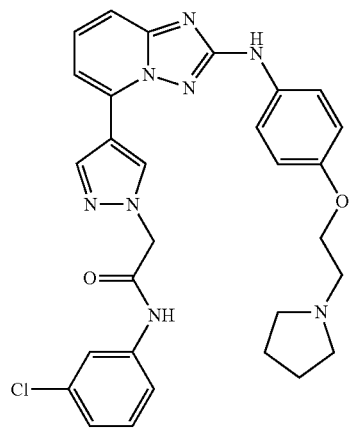 [SMILES: O=C(Cn1cc(-c2cccc3nc(Nc4ccc(OCCN5CCCC5)cc4)nn23)cn1)Nc1cccc(Cl)c1] |

| No. Code | Structure |
|---|---|
| 605 XX-436 | 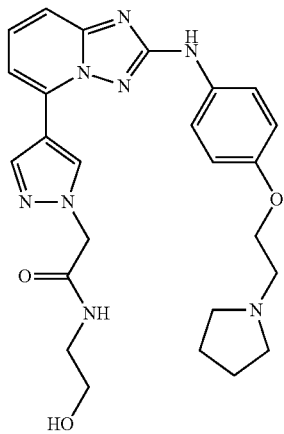 [SMILES: O=C(Cn1cc(-c2cccc3nc(Nc4ccc(OCCN5CCCC5)cc4)nn23)cn1)NCCO] |
| 606 XX-437 | 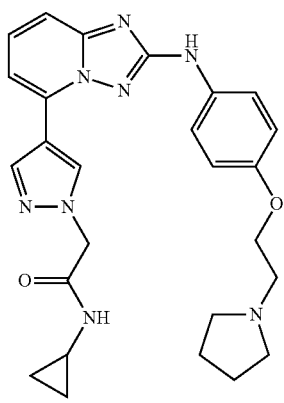 [SMILES: O=C(Cn1cc(-c2cccc3nc(Nc4ccc(OCCN5CCCC5)cc4)nn23)cn1)NC1CC1] |
| 607 XX-438 | 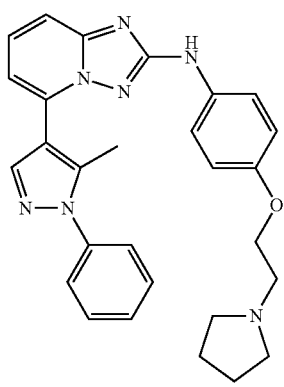 [SMILES: Cc1c(-c2cccc3nc(Nc4ccc(OCCN5CCCC5)cc4)nn23)cnn1-c1ccccc1] |
| 608 XX-439 | 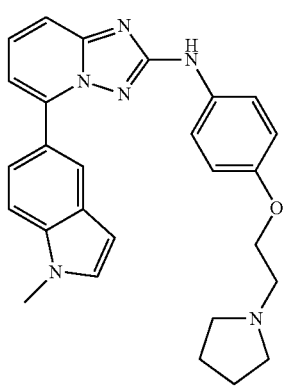 [SMILES: Cn1ccc2cc(-c3cccc4nc(Nc5ccc(OCCN6CCCC6)cc5)nn34)ccc21] |

| No. | Code | Structure |
|---|---|---|
| 609 | XX-440 | 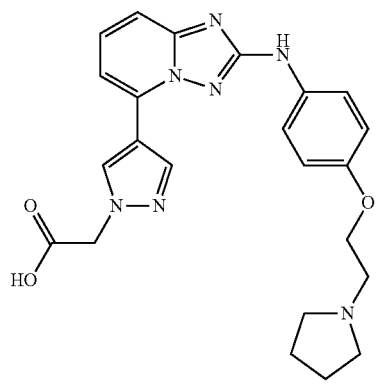 [SMILES: O=C(O)Cn1cc(-c2cccc3nc(Nc4ccc(OCCN5CCCC5)cc4)nn23)cn1] |
| 610 | XX-441 | 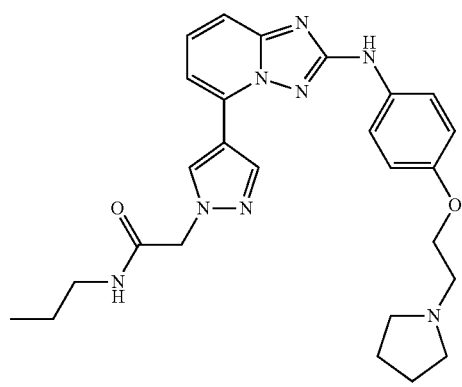 [SMILES: CCCNC(=O)Cn1cc(-c2cccc3nc(Nc4ccc(OCCN5CCCC5)cc4)nn23)cn1] |
| 611 | XX-442 | 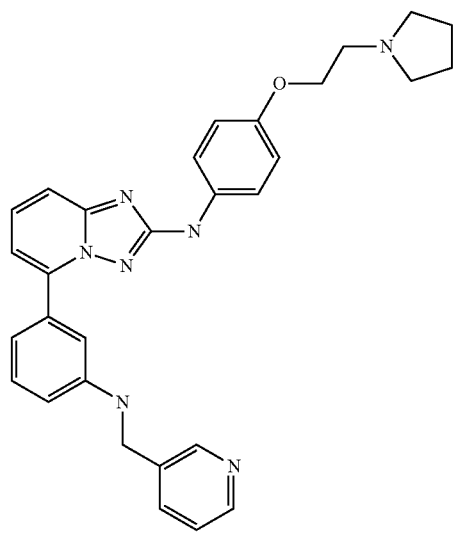 [SMILES: c1cncc(CNc2cccc(-c3cccc4nc(Nc5ccc(OCCN6CCCC6)cc5)nn34)c2)c1] |

| No. Code | Structure |
|---|---|
| 612 XX-443 | 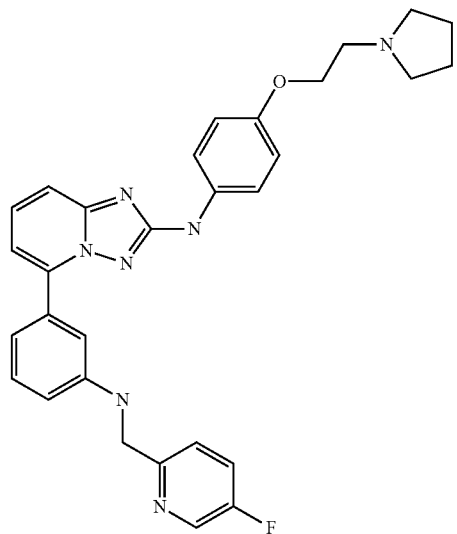 [SMILES: Fc1ccc(CNc2cccc(-c3cccc4nc(Nc5ccc(OCCN6CCCC6)cc5)nn34)c2)nc1] |
| 613 XX-444 | 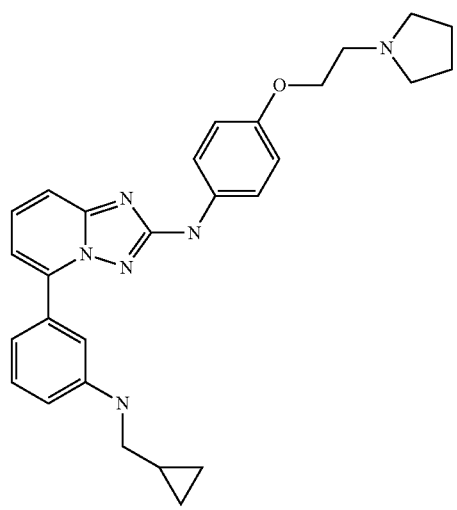 [SMILES: c1cc(NCC2CC2)cc(-c2cccc3nc(Nc4ccc(OCCN5CCCC5)cc4)nn23)c1] |
| 614 XX-445 | 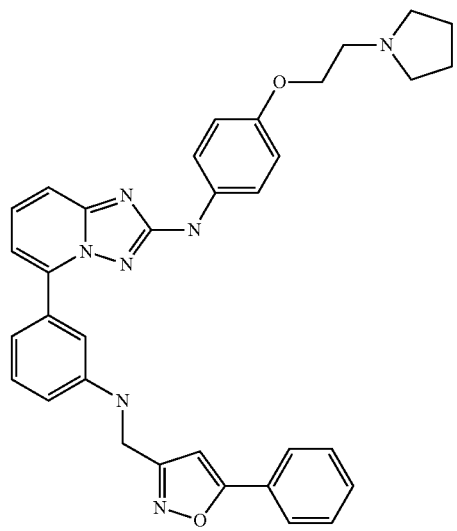 [SMILES: c1ccc(-c2cc(CNc3cccc(-c4cccc5nc(Nc6ccc(OCCN7CCCC7)cc6)nn45)c3)no2)cc1] |

| No. | Code | Structure |
|---|---|---|
| 615 | XX-446 | 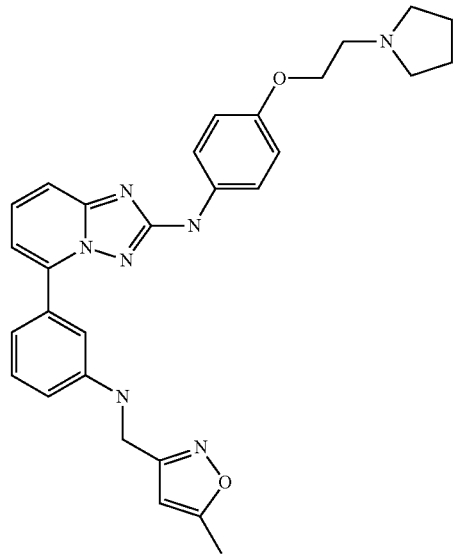 [SMILES: Cc1cc(CNc2cccc(-c3cccc4nc(Nc5ccc(OCCN6CCCC6)cc5)nn34)c2)no1] |
| 616 | XX-447 | 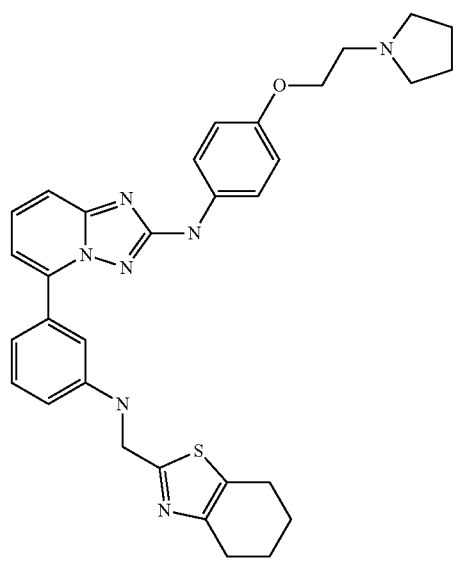 [SMILES: c1cc(NCc2nc3c(s2)CCCC3)cc(-c2cccc3nc(Nc4ccc(OCCN5CCCC5)cc4)nn23)c1] |

| No. Code | Structure |
|---|---|
| 617 XX-448 | 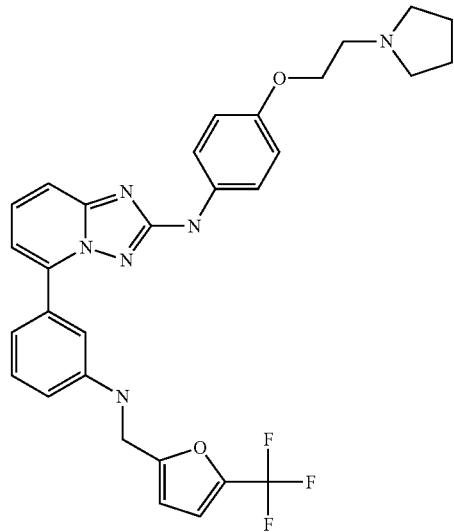 [SMILES: FC(F)(F)c1ccc(CNc2cccc(-c3cccc4nc(Nc5ccc(OCCN6CCCC6)cc5)nn34)c2)o1] |
| 618 XX-449 | 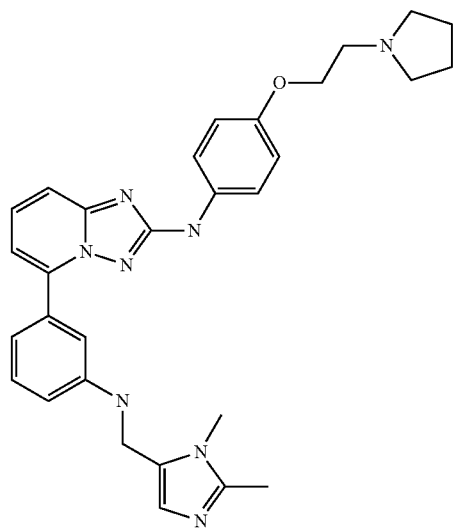 [SMILES: Cc1ncc(CNc2cccc(-c3cccc4nc(Nc5ccc(OCCN6CCCC6)cc5)nn34)c2)n1C] |

| No. | Code | Structure |
|---|---|---|
| 619 | XX-450 | 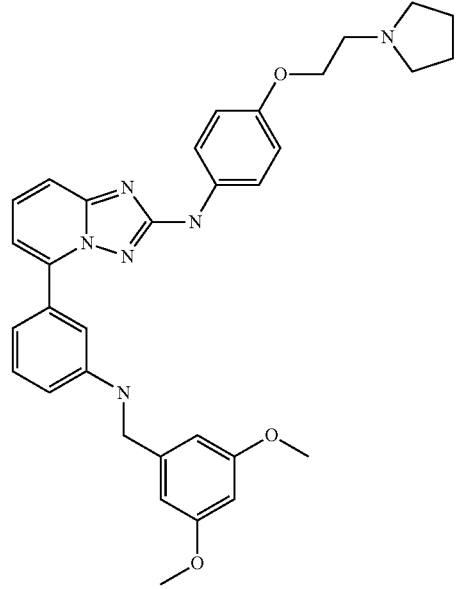 [SMILES: COc1cc(CNc2cccc(-c3cccc4nc(Nc5ccc(OCCN6CCCC6)cc5)nn34)c2)cc(OC)c1] |
| 620 | XX-451 | 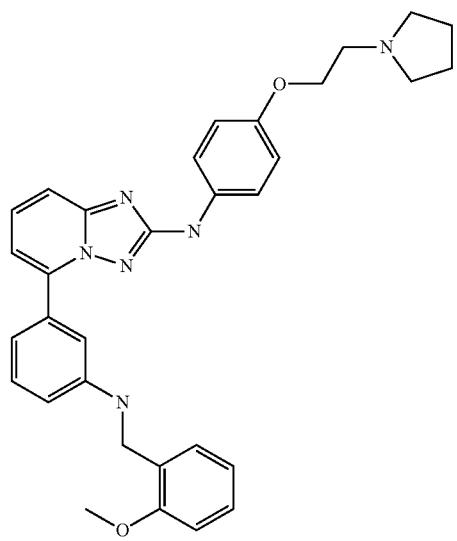 [SMILES: COc1ccccc1CNc1cccc(-c2cccc3nc(Nc4ccc(OCCN5CCCC5)cc4)nn23)c1] |

| No. Code | Structure |
|---|---|
| 621 XX-452 | 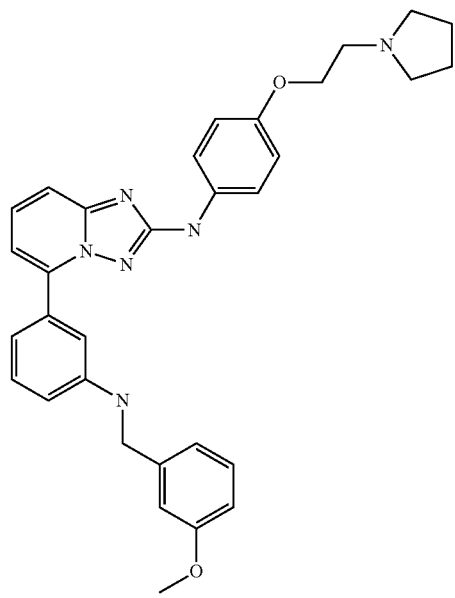 [SMILES: COc1cccc(CNc2cccc(-c3cccc4nc(Nc5ccc(OCCN6CCCC6)cc5)nn34)c2)c1] |
| 622 XX-453 | 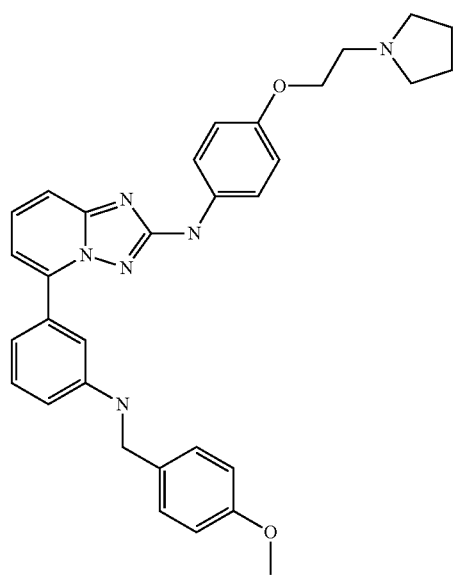 [SMILES: COc1ccc(CNc2cccc(-c3cccc4nc(Nc5ccc(OCCN6CCCC6)cc5)nn34)c2)cc1] |

| No. | Code | Structure |
|---|---|---|
| 623 | XX-454 | 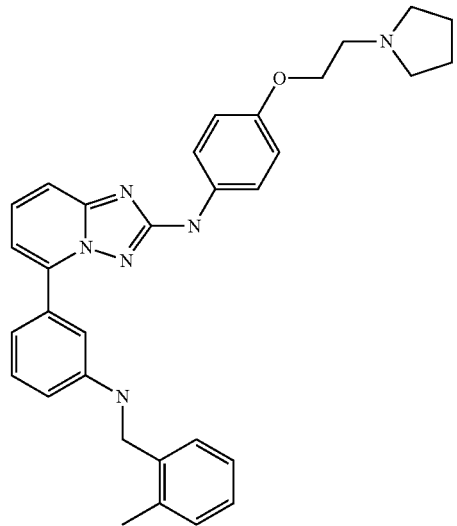 [SMILES: Cc1ccccc1CNc1cccc(-c2cccc3nc(Nc4ccc(OCCN5CCCC5)cc4)nn23)c1] |
| 624 | XX-455 | 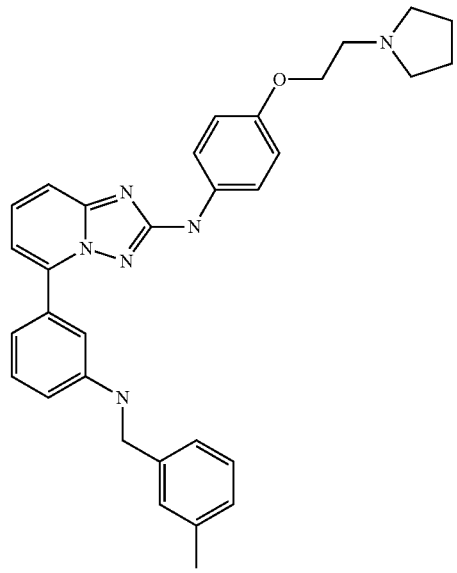 [SMILES: Cc1cccc(CNc2cccc(-c3cccc4nc(Nc5ccc(OCCN6CCCC6)cc5)nn34)c2)c1] |

| No. | Code | Structure |
|---|---|---|
| 625 | XX-456 | 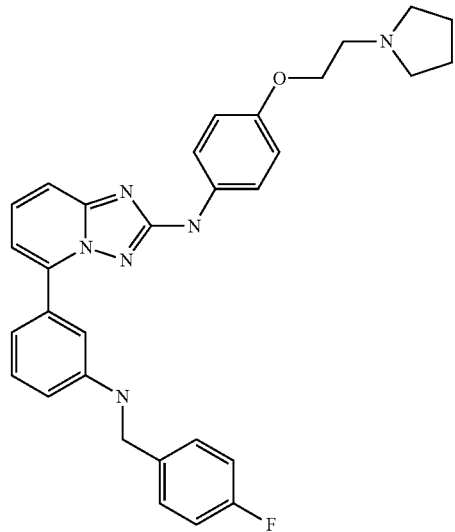 [SMILES: Fc1ccc(CNc2cccc(-c3cccc4nc(Nc5ccc(OCCN6CCCC6)cc5)nn34)c2)cc1] |
| 626 | XX-457 | 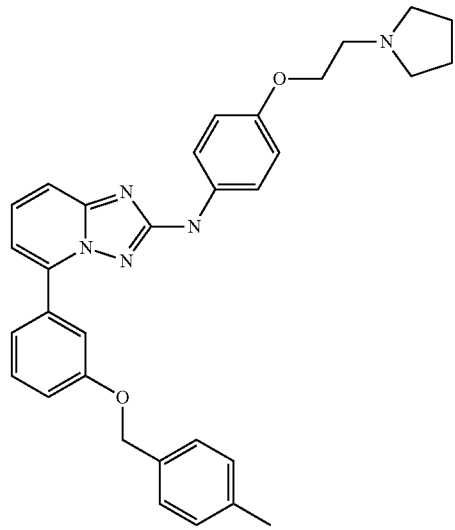 [SMILES: Cc1ccc(COc2cccc(-c3cccc4nc(Nc5ccc(OCCN6CCCC6)cc5)nn34)c2)cc1] |

| No. Code | Structure |
|---|---|
| 627 XX-458 | 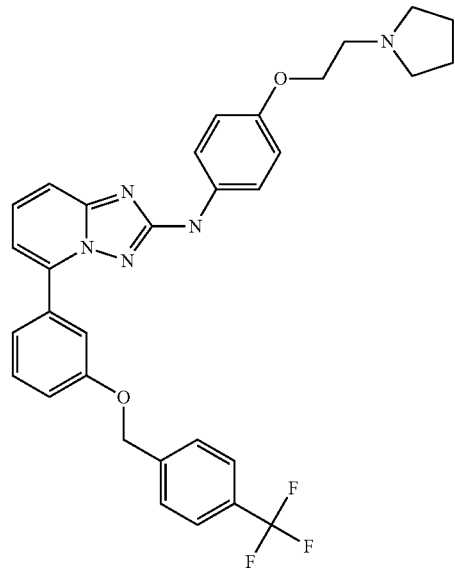 [SMILES: FC(F)(F)c1ccc(COc2cccc(-c3cccc4nc(Nc5ccc(OCCN6CCCC6)cc5)nn34)c2)cc1] |
| 628 XX-459 | 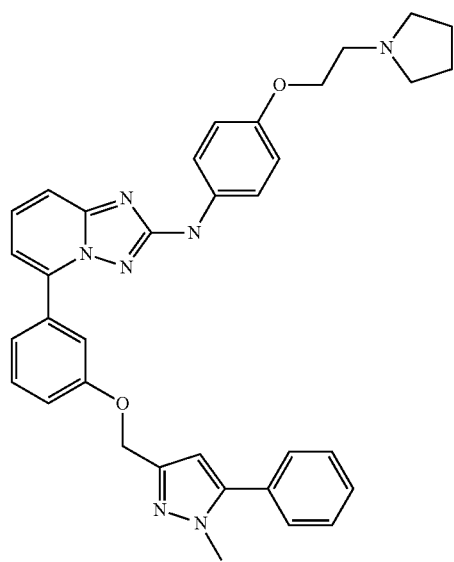 [SMILES: Cn1nc(COc2cccc(-c3cccc4nc(Nc5ccc(OCCN6CCCC6)cc5)nn34)c2)cc1-c1ccccc1] |

| No. Code | Structure |
|---|---|
| 629 XX-460 | 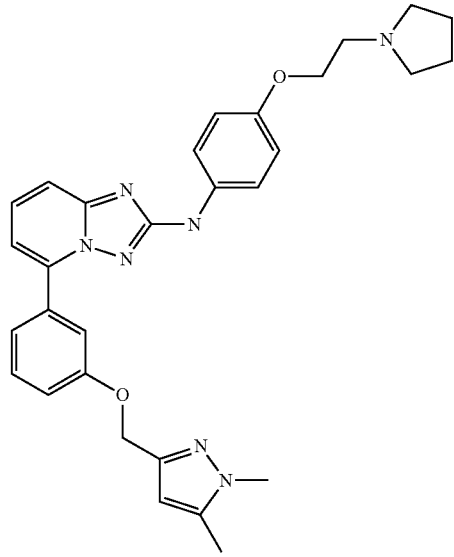 [SMILES: Cc1cc(COc2cccc(-c3cccc4nc(Nc5ccc(OCCN6CCCC6)cc5)nn34)c2)nn1C] |
| 630 XX-461 | 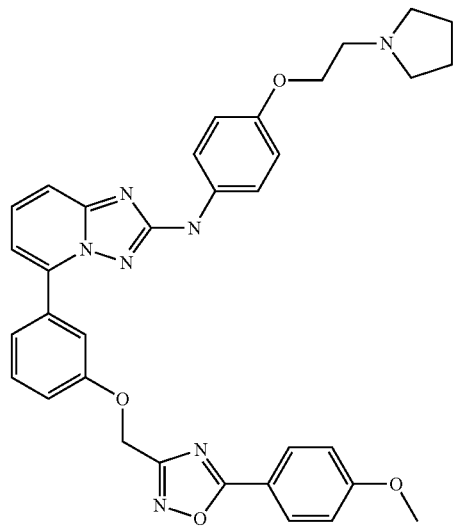 [SMILES: COc1ccc(-c2nc(COc3cccc(-c4cccc5nc(Nc6ccc(OCCN7CCCC7)cc6)nn45)c3)no2)cc1] |
| 631 XX-462 | 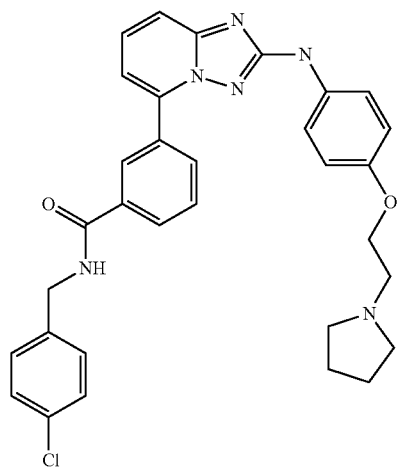 [SMILES: O=C(NCc1ccc(Cl)cc1)c1cccc(-c2cccc3nc(Nc4ccc(OCCN5CCCC5)cc4)nn23)c1] |

| No. Code | Structure |
|---|---|
| 632 XX-463 | 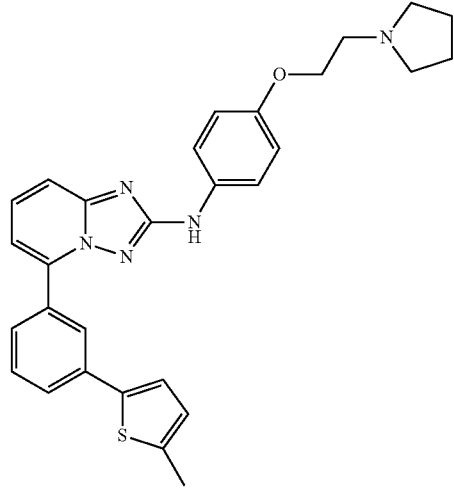 [SMILES: Cc1ccc(-c2cccc(-c3cccc4nc(Nc5ccc(OCCN6CCCC6)cc5)nn34)c2)s1] |
| 633 XX-464 | 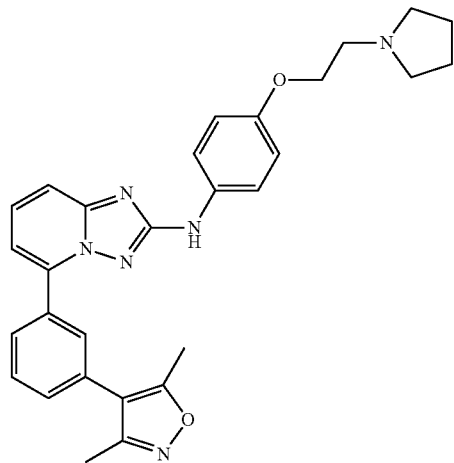 [SMILES: Cc1noc(C)c1-c1cccc(-c2cccc3nc(Nc4ccc(OCCN5CCCC5)cc4)nn23)c1] |
| 634 XX-465 | 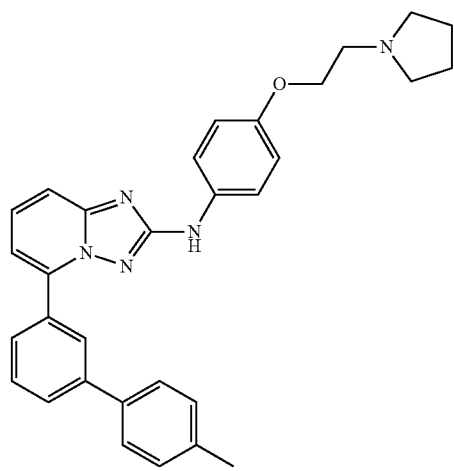 [SMILES: Cc1ccc(-c2cccc(-c3cccc4nc(Nc5ccc(OCCN6CCCC6)cc5)nn34)c2)cc1] |

-continued
| No. Code | Structure |
|---|---|
| 635 XX-466 | 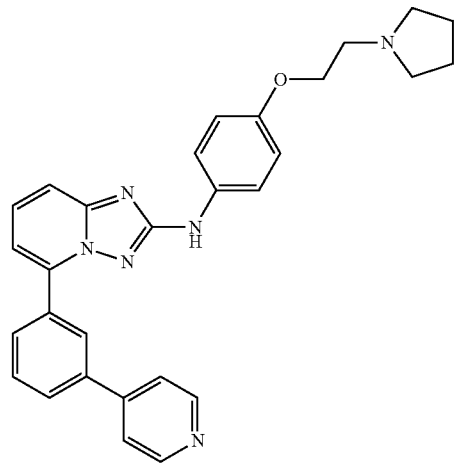 [SMILES: c1cc(-c2ccncc2)cc(-c2cccc3nc(Nc4ccc(OCCN5CCCC5)cc4)nn23)c1] |
| 636 XX-467 | 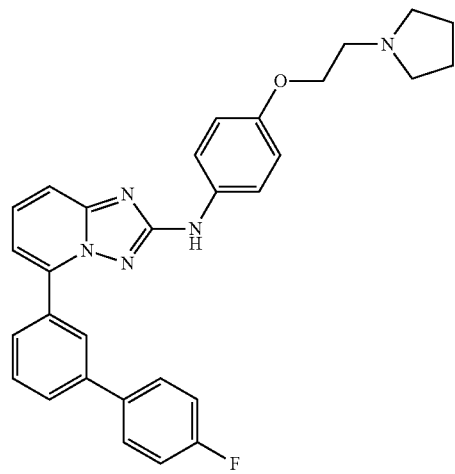 [SMILES: Fc1ccc(-c2cccc(-c3cccc4nc(Nc5ccc(OCCN6CCCC6)cc5)nn34)c2)cc1] |
| 637 XX-468 | 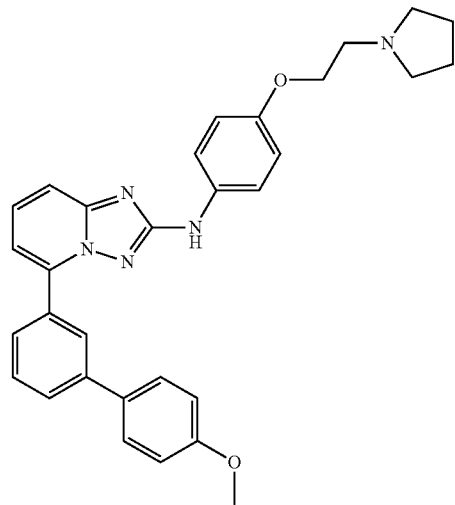 [SMILES: COc1ccc(-c2cccc(-c3cccc4nc(Nc5ccc(OCCN6CCCC6)cc5)nn34)c2)cc1] |

| No. | Code | Structure |
|---|---|---|
| 638 | XX-469 | 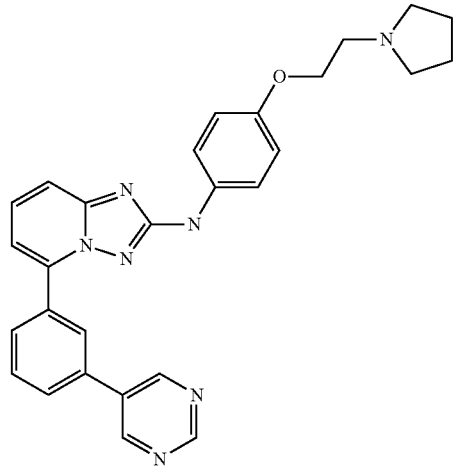 [SMILES: c1cc(-c2cncnc2)cc(-c2cccc3nc(Nc4ccc(OCCN5CCCC5)cc4)nn23)c1] |

In one embodiment, the compounds are selected from compounds of the following formulae and pharmaceutically acceptable salts, hydrates, and solvates thereof:

| No. | Code | Structure |
|---|---|---|
| 639 | YY-001 | 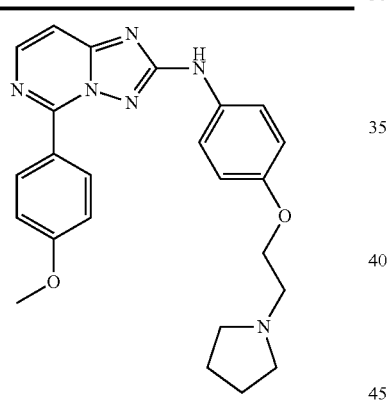 |
| 640 | YY-002 | 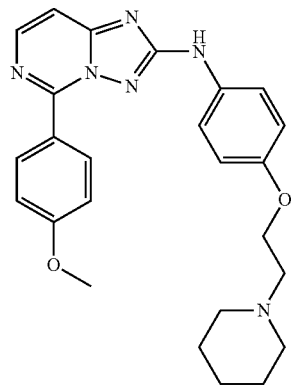 [SMILES: COc1ccc(-c2nccc3nc(Nc4ccc(OCCN5CCCCC5)cc4)nn23)cc1] |
| 641 | YY-003 | 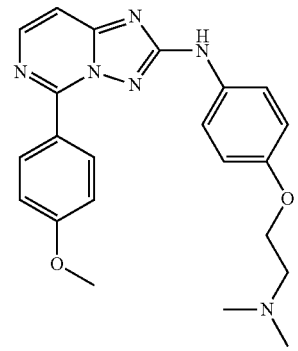 [SMILES: COc1ccc(-c2nccc3nc(Nc4ccc(OCCN(C)C)cc4)nn23)cc1] |
| 642 | YY-004 | 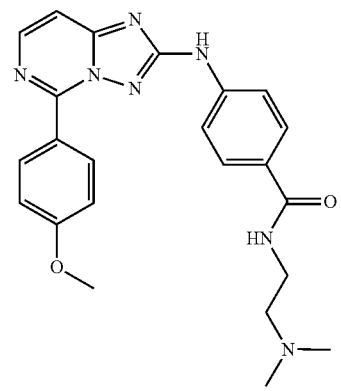 [SMILES: COc1ccc(-c2nccc3nc(Nc4ccc(C(=O)NCCN(C)C)cc4)nn23)cc1] |

In one embodiment, the compounds are selected from compounds of the following formulae and pharmaceutically acceptable salts, hydrates, and solvates thereof:

| No. | Code | Structure |
|---|---|---|
| 643 | YY-005 | 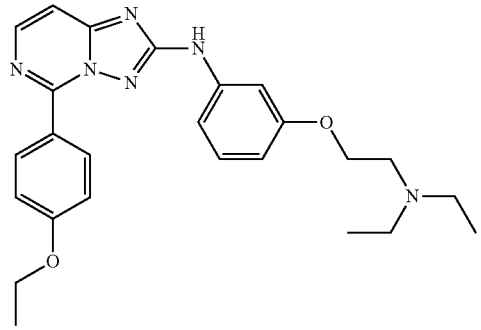 [SMILES: CCOc1ccc(-c2nccc3nc(Nc4cccc(OCCN(CC)CC)c4)nn23)cc1] |
| 644 | YY-006 | 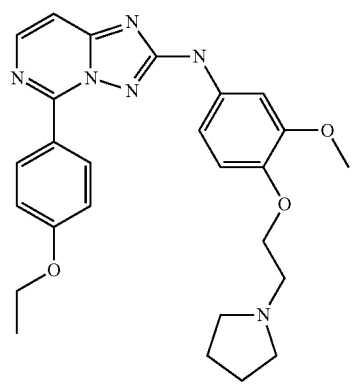 [SMILES: CCOc1ccc(-c2nccc3nc(Nc4ccc(OCCN5CCCC5)c(OC)c4)nn23)cc1] |
| 645 | YY-007 | 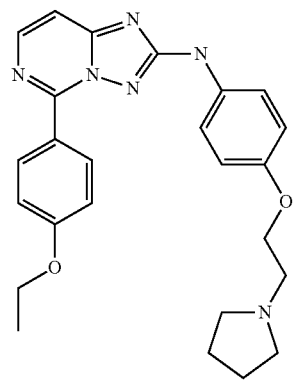 [SMILES: CCOc1ccc(-c2nccc3nc(Nc4ccc(OCCN5CCCC5)cc4)nn23)cc1] |
| 646 | YY-008 | 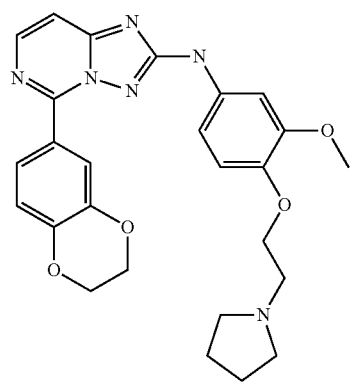 [SMILES: COc1cc(Nc2nc3ccnc(-c4ccc5c(c4)OCCO5)n3n2)ccc1OCCN1CCCC1] |

-continued
| No. | Code | Structure |
|---|---|---|
| 647 | YY-009 | 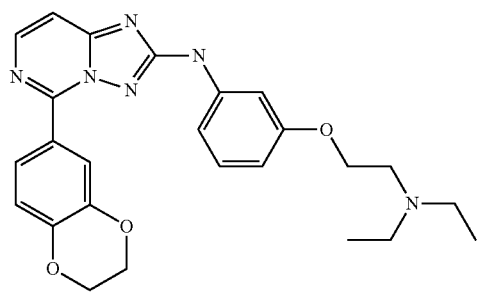 [SMILES: CCN(CC)CCOc1cccc(Nc2nc3ccnc(-c4ccc5c(c4)OCCO5)n3n2)c1] |
| 648 | YY-010 | 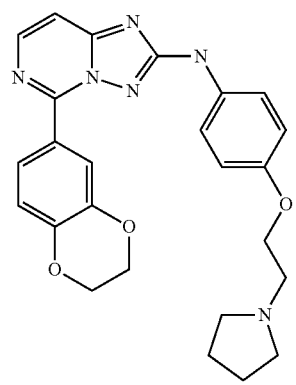 [SMILES: c1cc2nc(Nc3ccc(OCCN4CCCC4)cc3)nn2c(-c2ccc3c(c2)OCCO3)n1] |
| 649 | YY-011 | 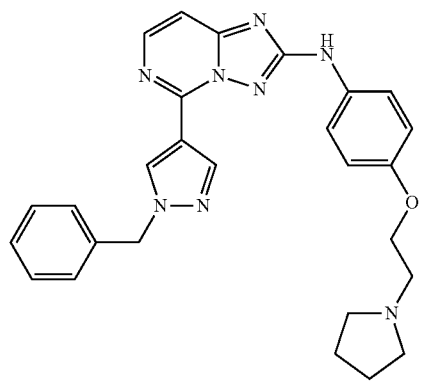 [SMILES: c1ccc(Cn2cc(-c3nccc4nc(Nc5ccc(OCCN6CCCC6)cc5)nn34)cn2)cc1] |
| 650 | YY-012 | 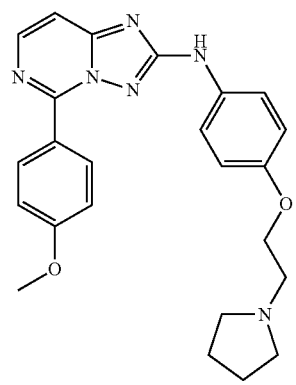 [SMILES: COc1ccc(-c2nccc3nc(Nc4ccc(OCCN5CCCC5)cc4)nn23)cc1] |

-continued
| No. | Code | Structure |
|---|---|---|
| 651 | YY-013 | 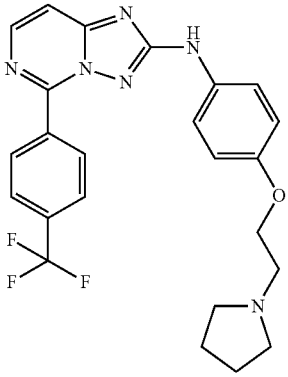 [SMILES: FC(F)(F)c1ccc(-c2nccc3nc(Nc4ccc(OCCN5CCCC5)cc4)nn23)cc1] |
| 652 | YY-014 | 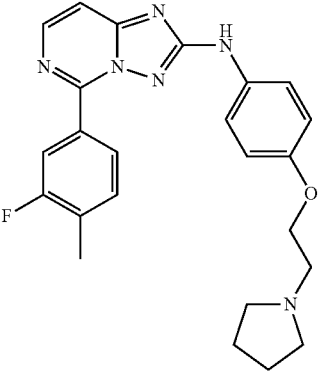 [SMILES: Cc1ccc(-c2nccc3nc(Nc4ccc(OCCN5CCCC5)cc4)nn23)cc1F] |
| 653 | YY-015 | 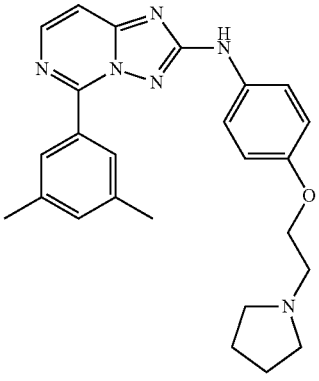 [SMILES: Cc1cc(C)cc(-c2nccc3nc(Nc4ccc(OCCN5CCCC5)cc4)nn23)c1] |
| 654 | YY-016 | 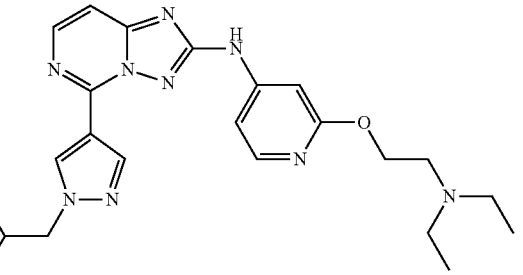 |
In one embodiment, the compounds are selected from compounds of the following formulae and pharmaceutically acceptable salts, hydrates, and solvates thereof:

| No. | Code | Structure |
|---|---|---|
| 655 | ZZ-001 | 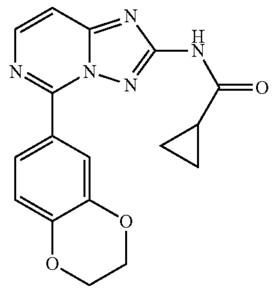 [SMILES: O=C(Nc1nc2ccnc(-c3ccc4c(c3)OCCO4)n2n1)C1CC1] |
| 656 | ZZ-002 | 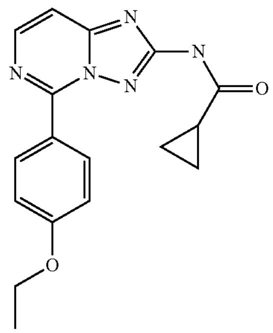 [SMILES: CCOc1ccc(-c2nccc3nc(NC(=O)C4CC4)nn23)cc1] |
| 657 | ZZ-003 | 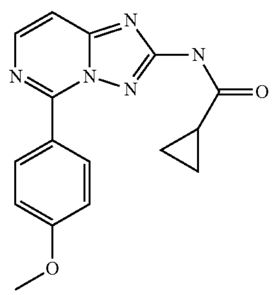 [SMILES: COc1ccc(-c2nccc3nc(NC(=O)C4CC4)nn23)cc1] |

Substantially Purified Forms

One aspect of the present invention pertains to TAZ compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

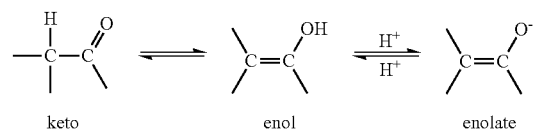

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci., Vol.* 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding hydrate or solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)$CH_3$, —OAc).

For example, an aldehyde or ketone group may be protected as an acetal (R—CH(OR)$_2$) or ketal ($R_2C(OR)_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—$CH_3$); a benzyloxy amide (—NHCO—$OCH_2C_6H_5$, —NH-Cbz); as a t-butoxy amide (—NHCO—OC($CH_3$)$_3$, —NH-Boc); a 2-biphenyl-2-propoxy amide (—NHCO—OC($CH_3$)$_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—$CH_2$NHC(=O)$CH_3$).

Chemical Synthesis

Several methods for the chemical synthesis of TAZ compounds of the present invention are described herein. These and/or other well known methods may be modified and/or adapted in known ways in order to facilitate the synthesis of additional compounds within the scope of the present invention.

Compositions

One aspect of the present invention pertains to a composition (e.g., a pharmaceutical composition) comprising a TAZ compound, as described herein, and a pharmaceutically acceptable carrier, diluent, or excipient.

Another aspect of the present invention pertains to a method of preparing a composition (e.g., a pharmaceutical composition) comprising admixing a TAZ compound, as described herein, and a pharmaceutically acceptable carrier, diluent, or excipient.

Uses

The compounds described herein are useful, for example, in the treatment of diseases and conditions that are ameliorated by the inhibition of AXL receptor tyrosine kinase, such as, for example, proliferative conditions, cancer, etc.

Use in Methods of Inhibiting AXL Receptor Tyrosine Kinase

One aspect of the present invention pertains to a method of inhibiting AXL receptor tyrosine kinase function, in vitro or in vivo, comprising contacting a AXL receptor tyrosine kinase with an effective amount of a TAZ compound, as described herein.

One aspect of the present invention pertains to a method of inhibiting AXL receptor tyrosine kinase function in a cell, in vitro or in vivo, comprising contacting the cell with an effective amount of a TAZ compound, as described herein.

Suitable assays for determining AXL receptor tyrosine kinase function inhibition are described herein and/or are known in the art.

Use in Methods of Inhibiting Cell Proliferation, Etc.

The TAZ compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a TAZ compound, as described herein.

In one embodiment, the method is a method of regulating (e.g., inhibiting) cell proliferation (e.g., proliferation of a cell), in vitro or in vivo, comprising contacting a cell with an effective amount of a TAZ compound, as described herein.

In one embodiment, the method is performed in vitro.

In one embodiment, the method is performed in vivo.

In one embodiment, the TAZ compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a TAZ compound, as described herein, for use in a method of treatment of the human or animal body by therapy.

Use in the Manufacture of Medicaments

Another aspect of the present invention pertains to use of a TAZ compound, as described herein, in the manufacture of a medicament for use in treatment.

In one embodiment, the medicament comprises the TAZ compound.

Methods of Treatment

Another aspect of the present invention pertains to a method of treatment comprising administering to a patient in need of treatment a therapeutically effective amount of a TAZ compound, as described herein, preferably in the form of a pharmaceutical composition.

Conditions Treated—Conditions Mediated by AXL Receptor Tyrosine Kinase

In one embodiment (e.g., of use in methods of therapy, of use in the manufacture of medicaments, of methods of treatment), the treatment is treatment of a disease or condition that is mediated by AXL receptor tyrosine kinase.

Conditions Treated—Conditions Ameliorated by the Inhibition of AXL Receptor Tyrosine Kinase Function In one embodiment (e.g., of use in methods of therapy, of use in the manufacture of medicaments, of methods of treatment), the treatment is treatment of: a disease or condition that is ameliorated by the inhibition of AXL receptor tyrosine kinase function.

Conditions Treated—Proliferative Conditions and Cancer

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as, neoplastic or hyperplastic growth.

In one embodiment, the treatment is treatment of: a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:

a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);

a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;

a hematopoietic tumor of myeloid lineage, for example acute and chronic myelogenous leukemias, myelodysplastic syndrome, or promyelocytic leukemia;

a tumour of mesenchymal origin, for example fibrosarcoma or habdomyosarcoma;

a tumor of the central or peripheral nervous system, for example astrocytoma, neuroblastoma, glioma or schwannoma;

melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of liquid tumour cancer.

In one embodiment, the treatment is treatment of hematological cancer.

In one embodiment, the treatment is treatment of: colon cancer, gastric cancer, breast cancer, lung cancer, acute myeloid leukemia, thyroid cancer, ocular cancer, prostate cancer, ocular melanoma cancer, ovarian cancer, renal cancer, skin cancer, or squamous cell carcinoma.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The TAZ compounds described herein may also be used as cell culture additives to inhibit AXL receptor tyrosine kinase function, e.g., to inhibit cell proliferation, etc.

The TAZ compounds described herein may also be used as part of an in vitro assay, for example, in order to determine whether a candidate host is likely to benefit from treatment with the compound in question.

The TAZ compounds described herein may also be used as a standard, for example, in an assay, in order to identify other compounds, other AXL receptor tyrosine kinase function inhibitors, other anti-proliferative agents, other anti-cancer agents, etc.

Kits

One aspect of the invention pertains to a kit comprising (a) a TAZ compound as described herein, or a composition comprising a TAZ compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The TAZ compound or pharmaceutical composition comprising the TAZ compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the TAZ compound to be administered alone, it is preferable to present it as a pharmaceutical formulation (e.g., composition, preparation, medicament) comprising at least one TAZ compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one TAZ compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the TAZ compounds, and compositions comprising the TAZ compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular TAZ compound, the route of administration, the time of administration, the rate of excretion of the TAZ compound, the duration of the treatment, other drugs, compounds, and/or materials used in combination, the severity of the condition, and the species, sex, age, weight, condition, general health, and prior medical history of the patient. The amount of TAZ compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the TAZ compound is in the range of about 10 μg to about 250 mg (more typically about 100 μg to about 25 mg) per kilogram body weight of the subject per day. Where the compound is a salt, hydrate, or solvate, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

For convenience, the following common abbreviations are used herein:
LCMS for Liquid Chromatography-Mass Spectrometry.
HPLC for High Pressure Liquid Chromatography.
NMR for Nuclear Magnetic Resonance.
DMSO for Dimethylsulfoxide.
RT for Retention Time.
MI for Molecular Ion.
Boc for tert-Butoxycarbonyl.
DIPEA for N,N,-Di-isopropyethylamine, Hunig's base.
MeOH for Methyl alcohol, Methanol.
EtOH for Ethyl alcohol, Ethanol.
$Pd(dba)_2$ for Bis(dibenzylideneacetone)palladium(0).
DMA for N,N-Dimethylacetamide.
MW for Microwave.
$Et_3N$ for Triethylamine.
DCM for Dichloromethane, Methylene chloride.
NaOtBu for sodium tert-butoxide.
KOtBu for potassium tert-butoxide.
TFA for Trifluoroacetic acid.
THF for Tetrahydrofuran.
$EtSO_2Cl$ for Ethanesulfonyl chloride.
MsCl for Methanesulfonyl chloride.
HBTU for 2-(1H-Benzotriazole-1-yl)-1,1,3,3-tetramethylaminium hexafluorophosphate.
MP-TsOH for microporous p-toluenesulfonic acid.
DMF for N,N-Dimethylformamide.
BuLi for Butyl lithium.
Xantphos for 4,5-Bis(diphenylphosphino)-9,9-dimethylxanthene.
h for hours.
min for minutes.

Synthesis Examples

General Methods: Flash Chromatography
Flash chromatography was performed using BDH silica gel 60.
General Methods: NMR
Proton NMR spectra were recorded using a Bruker AMX-300 NMR machine at 300 MHz. Shifts were reported in ppm values relative to an internal standard of tetramethylsilane (TMS) or residual protic solvent. The following abbreviations were used to describe the splitting patterns: s (singlet), d (doublet), t (triplet), q (quartet), m (multiplet), dd (double-doublet), dt (double-triplet), br (broad).
General Methods: LCMS Methods
Samples analysed by High Performance Liquid Chromatography-Mass Spectrometry employed the following conditions.
Method 1
Method 1 employed Gilson 306 pumps, Gilson 811C mixer, Gilson 806 manometric module, and Gilson UV/VIS 152 detector at 254 nm wavelength. The mass spectrometer was a Finnigan AQA and a Waters SunFire, 5 μm pore size, C18 column of dimensions 50×4.60 mm was used. The injection volume was 10 μL.

The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.
Method: 2
Method: 2 employed Waters 515 pumps, a Waters 2525 mixer and a Waters 2996 diode array detector. The detection was performed between 210 nm and 650 nm. The mass spectrometer was a Waters micromass ZQ and a Waters SunFire, 5 μm pore size, C18 column of dimensions 50×4.60 mm was used. The injection volume was 10 μL.

The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.
Method: 3
Method: 3 employed a LAA209 Waters ZQ MUX LCMS system, Waters 1525 pumps and a Waters 2996 diode array detector with CTC PAL auto-sampler. The detection was performed between 210 nm and 400 nm. The mass spectrometer was a Waters micromass ZQ and a Phenomenex Luna C18 column (3 μm pore size) of dimensions 50×4.60 mm was used. The injection volume was 10 μL.

The mobile phase consisted of a mixture of water and acetonitrile containing 0.1% formic acid. The eluent flow rate was 2 mL/min, using 80% water: 20% acetonitrile, changed linearly to 20% water: 80% acetonitrile over 2.5 minutes and then maintained at this mixture for 1.5 minutes.
Method Basic
The pumps used was a Waters 2545 with valves directing to the different columns, the UV detector was a Waters 2996. The detection was done between 210 nm and 650 nm. The mass spectrometer used was a Waters 3100 which detected masses between 100 and 700 g/mol. The column used was a XBridge, 5 micron pore size, C18, 50×4.60 mm. The injection volume was 10 μL of a solution (around 1 mg/mL). The flow rate was 1.5 mL/min and the mobile phases of water pH 10 0.03% ammonium hydroxide) (3 ml/10 l) and acetonitrile 0.03% ammonium hydroxide (3 ml/10 l). The elution was started at 95% water: 5% acetonitrile ramping up to 5% water: 95% acetonitrile over 5.50 minutes. The eluent level was returned to the starting conditions of 95% water: 5% acetonitrile over 6 seconds. These conditions were held for 1.4 minutes to allow equilibration of the column before the next sample was injected. The run lasted 7 minutes in total.
General Methods: Preparatory HPLC
Samples purified by Mass Spectrometry directed High Performance Liquid Chromatography employed the following conditions.

Waters 515 pumps, a Waters 2525 mixer and a Waters 2996 diode array detector. The detection was performed between 210 nm and 650 nm. The mass spectrometer was a Waters micromass ZQ and a SunFire, 5 μm pore size, C18 column of dimensions 50×19 mm was used. The injection volume was up to 500 μL of solution at a maximum concentration of 50 mg/mL. The mobile phase consisted of a mixture of water and acetonitrile containing 0.1% formic acid. The eluent flow rate was 25 mL/min using 95% water, 5% acetonitrile, changing linearly over 5.3 minutes to 95% acetonitrile, 5% water, and maintaining for 0.5 minutes.

Or, compound ds could be purified following a basic method:

The pump used was a Waters 2545 with valves directing to the different columns, the UV detector was a Waters 2996. The detection was done between 210 nm and 650 nm. The mass spectrometer used was a Waters 3100 which detected masses between 100 and 700 g/mol. A XBridge, 5 micron pore size, C18 column of dimensions 19×50 mm was used. The injection volume was chosen by the user and can be up to 500 μL of the solution (max 50 mg/mL). The flow rate was 25 mL/min and the mobile phases of water pH 10 0.03% ammonium hydroxide (3 ml/10 l) and acetonitrile 0.03% ammonium hydroxide (3 ml/10 l). The elution was started at 95% water: 5% acetonitrile ramping up to 5% water: 95% acetonitrile over 5.30 minutes. The eluent level was returned to the starting conditions of 95% water: 5% acetonitrile over 0.6 minutes. These conditions were held for 1.4 minutes to allow equilibration of the column before the next sample was injected. The run lasted 7 minutes in total.

General Synthesis Procedure A

Compounds were synthesised starting from 2-amino-6-bromopyridine following the scheme illustrated below. In general, 2-amino-6-bromopyridine and ethoxycarbonyl isothiocyanate are stirred in dichloromethane at ambient temperature. After concentration under reduced pressure and washing with an appropriate solvent, the solid was collected via filtration. The thiourea derivative which was subjected to a cyclisation procedure, employing hydroxylamine in a protic solvent, to yield intermediate 2-amino-5-bromo-[1,2,4]triazolo[1,5-a]pyridine. The bromo derivative was involved in a Suzuki type reaction utilising a palladium catalyst or other suitable catalyst such as tetrakis(triphenylphosphine)palladium and a suitable boronic acid or boronic ester. The amide derivatives may be synthesised starting from acid chlorides or other suitable activated esters or carboxylic acids and a peptide coupling agent such as HBTU.

Scheme 1

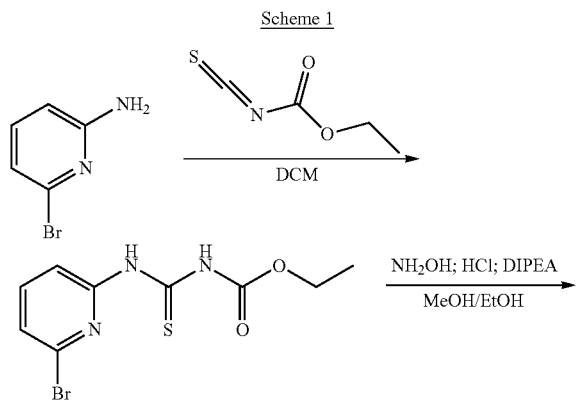

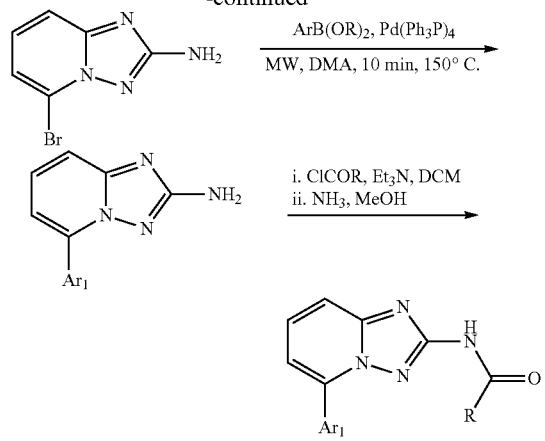

Synthesis 1

1-(6-Bromo-pyridin-2-yl)-3-carboethoxy-thiourea

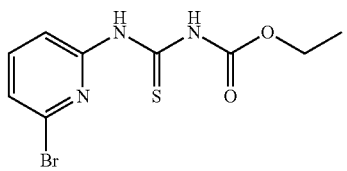 [SMILES: CCOC(=O)NC(=S)Nc1cccc(Br)n1]

To a solution of 2-amino-6-bromopyridine (25 g, 144.5 mmol) in dichloromethane (25 mL) cooled to 5° C. was added ethoxycarbonyl isothiocyanate (17.1 mL, 144.5 mmol) dropwise over 15 min. The reaction mixture was then allowed to warm to room temperature at which it was stirred for 16 h. Evaporation in vacuo gave a yellow solid, which was collected by filtration and thoroughly washed with cyclohexane. No further purification was required. Yield: 41.5 g, 94%; LCMS method: 1, RT: 5.66 min, MI: 304-306 [M+1].

Synthesis 2

5-Bromo-[1,2,4]triazolo[1,5-a]pyridin-2-ylamine

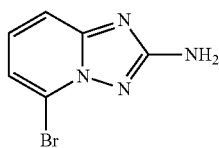 [SMILES: Nc1nc2cccc(Br)n2n1]

To a suspension of hydroxylamine hydrochloride (22.84 g, 329 mmol) in ethanol/methanol (100 mL/100 mL) was added N,N-diisopropylethylamine (34.4 mL, 197 mmol) and the mixture was stirred at room temperature for 1 h. 1-(6-Bromo-pyridin-2-yl)-3-carboethoxy-thiourea (20 g, 65.75 mmol) was then added and the mixture slowly heated to reflux. After 3 h at reflux the mixture was allowed to cool and filtered to collect the precipitated solid. Further product was collected by evaporation in vacuo of the filtrate, addition of water and filtration. The combined solids were washed successively with water, ethanol/methanol and diethyl ether then dried in vacuo to afford the expected compound as a white solid. No further purification was required. Yield: 12.3 g, 88%; LCMS method: 1, RT: 1.34 min, MI: 213-215 [M+1].

Synthesis 3

5-(4-Methoxy-phenyl)-[1,2,4]triazolo[1,5-a]pyridin-2-ylamine

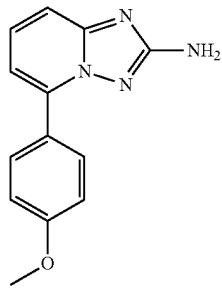 [SMILES: COc1ccc(-c2cccc3nc(N)nn23)cc1]

5-Bromo-[1,2,4]triazolo[1,5-a]pyridin-2-ylamine (2 g, 9.4 mmol), 4-methoxybenzeneboronic acid (1.71 g, 11.26 mmol), potassium phosphate (3.98 g, 18.77 mmol) and tetrakis(triphenylphosphine)palladium (0.54 g, 0.47 mmol) were added to a microwave tube containing a stirrer bar. Dimethylacetamide (12 mL) and water (4 mL) were then added and the reaction was heated to 150° C. for 10 min. The reaction was filtered through silica and washed through with methanol and concentrated under reduced pressure. The crude was suspended in diethyl ether and the solid collected and was used without further purification. Yield: 1.70 g, 71%; LCMS method: 1, RT: 3.43 min, MI: 241 [M+1]. NMR 1H (DMSO): 3.82 (s, 3H), 6.16 (brs, 2H), 6.96 (d, 1H), 7.06 (d, 2H), 7.29 (d, 1H), 7.46 (t, 1H), 7.92 (d, 2H).

Synthesis 4

N-[5-(4-Methoxy-phenyl)-[1,2,4]triazolo[1,5-a]pyridin-2-yl]-isobutyramide (WW-012)

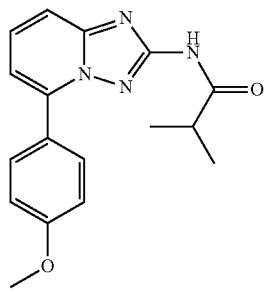 [SMILES: COc1ccc(-c2cccc3nc(NC(=O)C(C)C)nn23)cc1]

To a solution of the 5-(4-methoxy-phenyl)-[1,2,4]triazolo[1,5-a]pyridin-2-ylamine (0.07 g, 0.291 mmol) in dry acetonitrile (2 mL) was added triethylamine (0.12 mL, 0.874 mmol) followed by isopropanecarbonyl chloride (0.046 mL, 0.437 mmol). The reaction mixture was then allowed to warm to ambient temperature overnight. Further triethylamine (1.5 eq) and acid chloride (1.2 eq) were added to ensure complete reaction. The solvent was then removed and 3 mL of methanol-ammonia 7M was added to the crude and the mixture was stirred 6h. The solution was concentrated under reduced pressure and the crude was purified by preparatory HPLC. LCMS method: 2, RT: 4.33 min, MI: 311 [M+1]. NMR 1H (DMSO): 1.05 (d, 6H), 2.65-2.75 (m, 1H), 3.86 (s, 3H), 7.06 (d, 2H), 7.19 (d, 1H), 7.57-7.69 (m, 2H), 7.95 (d, 2H), 10.68 (brs, 1H).

The following compounds were synthesised using the same general method.

| Code No. | Characterisation |
| --- | --- |
| WW-039 | RT: 3.3 min, MI: 283, Method: 2 |
| WW-040 | RT: 3.40 min, MI: 297, Method: 2 |
| WW-041 | RT: 3.3 min, MI: 313, Method: 2 |
| WW-042 | RT: 3.83 min, MI: 323, Method: 2 |
| WW-043 | RT: 4.01 min, MI: 325, Method: 2 |
| WW-044 | RT: 3.95 min, MI: 325, Method: 2 |
| WW-045 | RT: 3.98 min, MI: 345, Method: 2 |
| WW-038 | RT: 3.73 min; MI: 323, Method: 2 |
| WW-145 | RT: 3.94 min, MI: 351, Method: 2 |
| WW-146 | RT: 3.64 min, MI: 335, Method: 2 |
| WW-125 | RT: 4.51 min; MI: 345; Method 1 |
| WW-046 | RT: 4.80 min, MI: 337; Method 1 |
| WW-164 | RT: 2.02 min, MI: 458, Method: 2 |
| WW-012 | RT: 4.33 min, MI: 311; Method 1 |

General Procedure Synthesis B

Compounds were synthesised starting from 5-bromo-[1,2,4]triazolo[1,5-a]pyridin-2-ylamine (described above) following the scheme illustrated below. In general, amide derivatives may be synthesised starting from acid chlorides or other suitable activated esters or carboxylic acids and a peptide coupling agent such as HBTU. The bromo derivative was involved in a Suzuki reaction utilising a palladium catalyst such as tetrakis(triphenylphosphine)palladium or other suitable catalyst and a suitable boronic acid or boronic ester.

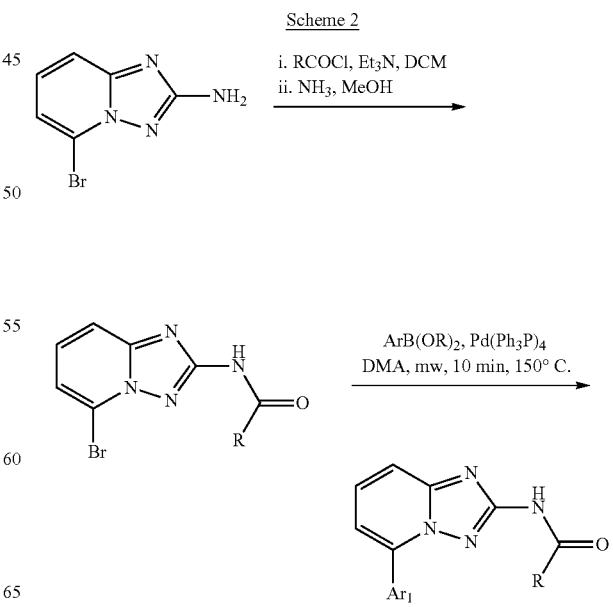

Scheme 2

Synthesis 5

(5-bromo-[1,2,4]triazolo[1,5-a]pyridin-2-yl)-amide

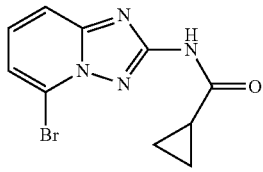 [SMILES: O=C(Nc1nc2cccc(Br)n2n1)C1CC1]

To a solution of the 5-bromo-[1,2,4]triazolo[1,5-a]pyridin-2-ylamine (3 g, 14.08 mmol) in dry acetonitrile (20 mL) was added triethylamine (4.9 mL, 35.2 mmol) followed by cyclopropanecarbonyl chloride (1.5 mL, 15.5 mmol). The reaction mixture was then allowed to warm to ambient temperature and was stirred overnight. The solvent was removed under reduced pressure then water was added to the crude and extracted with ethyl acetate. The organic was dried over magnesium sulfate and concentrated under reduced pressure. To the crude, 20 mL of methanol-ammonia 7M was added and the solution was stirred for 6 h. The solution was concentrated under reduced pressure and the crude was washed with diethyl ether. Yield: 2.81 g, 71%, LCMS method: 1, RT: 4.61 min, MI: 280-282 [M+1].

Synthesis 6

Cyclopropanecarboxylic acid [5-(1-propyl-1H-pyrazol-4-yl)-[1,2,4]triazolo[1,5-a]pyridin-2-yl]-amide (WW-124)

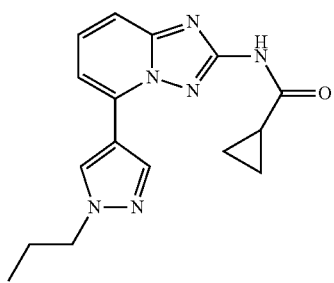 [SMILES: CCCn1cc(-c2cccc3nc(NC(=O)C4CC4)nn23)cn1]

Cyclopropanecarboxylic acid (5-bromo-[1,2,4]triazolo[1,5-a]pyridin-2-yl)-amide (0.05 g, 0.178 mmol), 1-propyl-1H-pyrazole-4-boronic acid, pinacol ester (0.054 g, 0.231 mmol) and dimethylacetamide (1 mL) were added to a microwave tube containing a stirrer bar, potassium phosphate solution (0.5M in water, 0.7 mL, 0.356 mmol) and tetrakis(triphenylphosphine)palladium (0.02 g, 0.018 mmol). The reaction was heated to 150° C. for 10 min under microwave heating. The crude was purified straight away by preparatory chromatography after filtration. LCMS method: 2, RT: 3.75 min; MI: 311 [M+1]; NMR 1H (DMSO): 0.80-0.88 (m, 7H), 1.78-1.90 (m, 2H), 2.05 (brs, 1H), 4.16 (t, 2H), 7.52 (dd, 1H), 7.55 (d, 1H), 7.66 (t, 1H), 8.51 (s, 1H), 8.86 (s, 1H), 11.11 (brs, 1H).

The following compounds were synthesised using the same general method.

| Code No. | Characterisation |
|---|---|
| WW-007 | RT: 2.34 min; MI: 297; Method: 3 |
| WW-034 | RT: 3.75 min; MI: 293; Method 1 |
| WW-036 | RT: 1.98 min; MI: 323; Method 1 |
| WW-052 | RT: 2.96 min, MI: 298, Method: 2 |
| WW-053 | RT: 2.68 min, MI: 269, Method: 2 |
| WW-054 | RT: 2.32 min, MI: 294, Method: 2 |
| WW-055 | RT: 3.9 min, MI: 299, Method: 2 |
| WW-056 | RT: 3.38 min, MI: 269, Method: 2 |
| WW-057 | RT: 3.55 min, MI: 285, Method: 2 |
| WW-058 | RT: 3.87 min, MI: 299, Method: 2 |
| WW-059 | RT: 3.53 min, MI: 285, Method: 2 |
| WW-060 | RT: 2.52 min, MI: 269, Method: 2 |
| WW-061 | RT: 3.45 min, MI: 269, Method: 2 |
| WW-062 | RT: 2.53 min, MI: 365, Method: 2 |
| WW-063 | RT: 4.51 min, MI: 355, Method: 2 |
| WW-064 | RT: 2.71 min, MI: 283, Method: 2 |
| WW-065 | RT: 2.07 min, MI: 330, Method: 2 |
| WW-066 | RT: 3.75 min, MI: 332, Method: 2 |
| WW-067 | RT: 3.65 min, MI: 327, Method: 2 |
| WW-068 | RT: 2.83 min, MI: 336, Method: 2 |
| WW-069 | RT: 3.6 min, MI: 322, Method: 2 |
| WW-070 | RT: 4.21 min; MI: 337; Method 1 |
| WW-084 | RT: 1.98 min, MI: 294, Method: 2 |
| WW-085 | RT: 2.95 min, MI: 330, Method: 2 |
| WW-086 | RT: 3.48 min, MI: 316, Method: 2 |
| WW-087 | RT: 1.83 min, MI: 294, Method: 2 |
| WW-088 | RT: 3.21 min, MI: 312, Method: 2 |
| WW-089 | RT: 4.08 min, MI: 329, Method: 2 |
| WW-090 | RT: 4.3 min, MI: 315, Method: 2 |
| WW-091 | RT: 3.52 min, MI: 324, Method: 2 |
| WW-092 | RT: 4.54 min, MI: 330, Method: 2 |
| WW-093 | RT: 2.91 min, MI: 325, Method: 2 |
| WW-094 | RT: 4.49 min, MI: 323, Method: 2 |
| WW-095 | RT: 4.57 min, MI: 337, Method: 2 |
| WW-096 | RT: 3 min, MI: 313, Method: 2 |
| WW-097 | RT: 3.15 min, MI: 313, Method: 2 |
| WW-051 | RT: 3.49 min; MI: 323; Method 1 |
| WW-098 | RT: 3.66 min, MI: 327, Method: 2 |
| WW-099 | RT: 4.2 min, MI: 363, Method: 2 |
| WW-100 | RT: 3.23 min, MI: 339, Method: 2 |
| WW-101 | RT: 3.98 min, MI: 341, Method: 2 |
| WW-102 | RT: 3.5 min, MI: 337, Method: 2 |
| WW-103 | RT: 2.82 min, MI: 336, Method: 2 |
| WW-104 | RT: 3.63 min, MI: 350, Method 1 |
| WW-133 | RT: 3.66 min, MI: 319, Method: 2 |
| WW-134 | RT: 1.91 min, MI: 382, Method: 2 |
| WW-135 | RT: 3.81 min, MI: 339, Method: 2 |
| WW-136 | RT: 2.79 min, MI: 324, Method: 2 |
| WW-137 | RT: 3.49 min, MI: 345, Method: 2 |
| WW-138 | RT: 1.98 min, MI: 393, Method: 2 |
| WW-139 | RT: 4.64 min, MI: 335, Method: 2 |
| WW-140 | RT: 2.78 min, MI: 324, Method: 2 |
| WW-141 | RT: 1.91 min, MI: 378, Method: 2 |
| WW-142 | RT: 3.43 min, MI: 345, Method: 2 |
| WW-143 | RT: 3.82 min, MI: 448, Method: 2 |
| WW-144 | RT: 3.58 min, MI: 351, Method: 2 |
| WW-124 | RT: 3.75 min; MI: 311; Method 1 |
| WW-110 | RT: 4.03 min; MI: 394; Method: 2 |
| WW-105 | RT: 3.58 min; MI: 359; Method: 2 |
| WW-106 | RT: 3.50 min; MI: 318; Method: 2 |
| WW-107 | RT: 3.53 min; MI: 324; Method: 2 |
| WW-119 | RT: 4.19 min; MI: 408; Method: 2 |
| WW-148 | RT: 4.16 min; MI: 359; Method 1 |
| WW-149 | RT: 2.85 min; MI: 268; Method: 2 |
| WW-150 | RT: 4.08 min; MI: 337; Method: 2 |
| WW-152 | RT: 4.10 min; MI: 337; Method: 2 |
| WW-163 | RT: 2.25 min; MI: 350; Method 1 |
| WW-159 | RT: 4.13 min; MI: 321; Method 1 |
| WW-162 | RT: 5.21 min; MI: 371; Method 1 |
| WW-013 | RT: 3.55 min; MI: 297, Method: 2. |
| WW-014 | RT: 2.87 min, MI: 357, Method: 2 |
| WW-015 | RT: 2.57 min, MI: 322, Method: 2 |
| WW-016 | RT: 3.38 min, MI: 323, Method: 2 |
| WW-018 | RT: 3.32 min, MI: 318, Method: 2 |
| WW-019 | RT: 2.48 min, MI: 322, Method: 2 |
| WW-020 | RT: 3.00 min, MI: 295, Method: 2 |
| WW-021 | RT: 3.58 min, MI: 314, Method: 2 |
| WW-022 | RT: 2.87 min, MI: 295, Method: 2 |

339 -continued

| Code No. | Characterisation |
|---|---|
| WW-023 | RT: 3.90 min, MI: 314, Method: 2 |
| WW-024 | RT: 3.57 min, MI: 309, Method: 2 |
| WW-025 | RT: 3.40 min, MI: 296, Method: 2 |
| WW-032 | RT: 2.73 min, MI: 311, Method: 2 |
| WW-026 | RT: 3.41 min, MI: 364, Method: 2 |
| WW-027 | RT: 2.73 min, MI: 309, Method: 2 |
| WW-028 | RT: 2.77 min, MI: 309, Method: 2 |
| WW-029 | RT: 2.75 min, MI: 350, Method: 2 |
| WW-030 | RT: 2.96 min, MI: 298, Method: 2 |
| WW-049 | RT: 4.25 min, MI: 323; Method 1 |
| WW-005 | RT: 2.27 min; MI: 309; Method: 3 |
| WW-035 | RT: 4.50 min; MI: 323; Method: 1 |
| WW-047 | RT: 4.43 min; MI: 293; Method 1 |
| WW-017 | RT: 2.96 min, MI: 372, Method: 2 |
| WW-109 | RT: 3.42 min; MI: 345; Method: 2 |
| WW-108 | RT: 3.44 min; MI: 325; Method: 2 |
| WW-001 | RT: 2.26 min, MI: 279, Method: 3 |
| WW-071 | RT: 3.53 min, MI: 322, Method 1 |
| WW-006 | RT: 1.97 min; MI: 310; Method: 3 |
| WW-004 | RT: 2.54 min; MI: 313; Method: 3 |
| WW-008 | RT: 2.12 min; MI: 323; Method: 3 |
| WW-011 | RT: 3.87 min; MI: 347; Method: 3 |
| WW-031 | RT: 4.08 min, MI: 347, Method: 2 |
| WW-003 | RT: 1.95 min; MI: 377; Method: 3 |
| WW-050 | RT: 2.03 min, MI: 308, Method: 2 |
| WW-033 | RT: 3.87 min; MI: 347; Method 1 |
| WW-010 | RT: 2.26 min; MI: 339; Method: 3 |
| WW-037 | RT: 3.21 min; MI: 295; Method 1 |
| WW-002 | RT: 1.69 min; MI: 336; Method: 3 |
| WW-009 | RT: 1.55 min; MI: 393; Method: 3 |

General Synthesis Procedure C

Compounds were synthesised starting from cyclopropanecarboxylic acid (5-bromo-[1,2,4]triazolo[1,5-a]pyridin-2-yl)-amide (described above) following the scheme illustrated below. In general, the 5-amino derivatives may be obtained via a nucleophilic substitution of an appropriately substituted amine on the bromo derivative via microwave heating or conventional heating Scheme 3

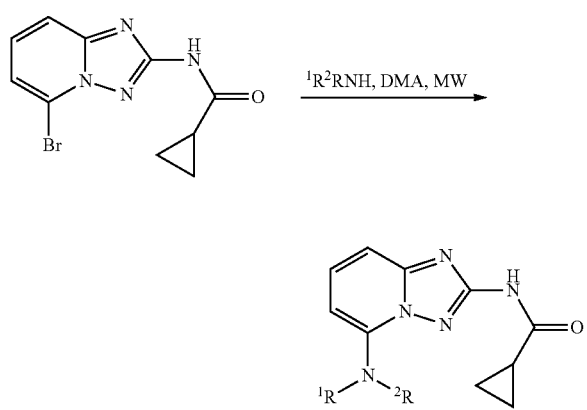

Synthesis 7

Cyclopropanecarboxylic acid {5-[(pyridin-2-ylmethyl)-amino]-[1,2,4]triazolo[1,5-a]pyridin-2-yl}-amide (WW-075)

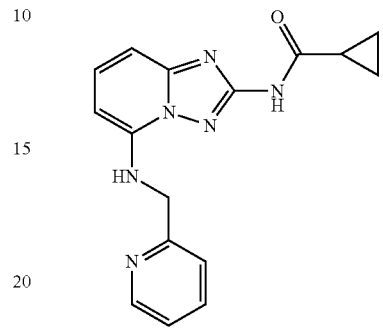

To a solution of cyclopropanecarboxylic acid (5-bromo-[1,2,4]triazolo[1,5-a]pyridin-2-yl)-amide (0.05 g, 0.178 mmol) in dimethylacetamide (1 mL) in a microwave vial, 2-aminomethylpyridine (0.096 g, 0.89 mmol) was added and the solution was heated in the microwave at 150° C. for 15 min. The crude was purified straight away by preparatory chromatography after filtration. LCMS method: 2, RT: 2.07 min, MI: 309 [M+1]. NMR (1H, DMSO, 300 MHz): 10.91 (s, 1H), 8.57 (d, 1H), 7.77 (t, 1H), 7.30-7.49 (m, 4H), 6.85 (d, 1H), 6.08 (d, 1H), 4.67 (d, 2H), 2.07 (brs, 1H), 0.83 (d, 4H)

The following compounds were synthesised using the same general method.

| Code No. | Characterisation |
|---|---|
| WW-073 | RT: 3.40 min, MI: 274, Method: 2 |
| WW-167 | RT: 3.48 min, MI: 338, Method: 2 |
| WW-074 | RT: 2.12 min, MI: 262, Method: 2 |
| WW-075 | RT: 2.07 min, MI: 309, Method: 2 |
| WW-076 | RT: 1.78 min, MI: 329, Method: 2 |
| WW-077 | RT: 3.58 min, MI: 361, Method: 2 |
| WW-078 | RT: 3.48 min, MI: 286, Method: 2 |
| WW-079 | RT: 3.35 min, MI: 274, Method: 2 |
| WW-080 | RT: 3.62 min, MI: 288, Method: 2 |
| WW-081 | RT: 3.87 min, MI: 342, Method: 2 |
| WW-082 | RT: 4.50 min, MI: 342, Method: 2 |
| WW-083 | RT: 1.82 min, MI: 309, Method: 2 |
| WW-048 | RT: 4.17 min, MI: 308, Method 1 |
| WW-112 | RT: 3.46 min, MI: 338, Method: 2 |
| WW-113 | RT: 3.72 min, MI: 322, Method: 2 |
| WW-114 | RT: 3.21 min, MI: 375, Method: 2 |
| WW-115 | RT: 1.87 min, MI: 331, Method: 2 |
| WW-116 | RT: 1.86 min, MI: 303, Method: 2 |
| WW-117 | RT: 3.68 min, MI: 401, Method: 2 |
| WW-118 | RT: 1.60 min, MI: 261, Method: 2 |

General Synthesis Procedure D

Compounds were synthesised starting from cyclopropanecarboxylic acid (5-bromo-[1,2,4]triazolo[1,5-a]pyridin-2-yl)-amide (described above) following the scheme illustrated below. In general, the aniline derivatives may be obtained via a palladium catalysed reaction assisted by microwave or conventional heating and an appropriately substituted aniline.

Scheme 4

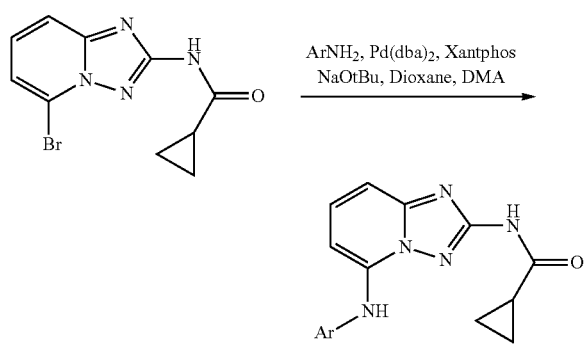

Synthesis 8

Cyclopropanecarboxylic acid [5-(4-methoxy-phenylamino)-[1,2,4]triazolo[1,5-a]pyridin-2-yl]-amide (WW-127)

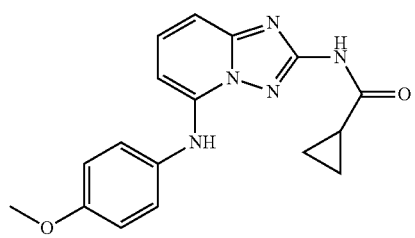 [SMILES: COc1ccc(Nc2cccc3nc(NC(=O)C4CC4)nn23)cc1]

A microwave tube was charged with cyclopropanecarboxylic acid (5-bromo-[1,2,4]triazolo[1,5-a]pyridin-2-yl)-amide (0.05 g, 0.178 mmol), p-anisidine (0.044 g, 0.356 mmol), bis(dibenzylideneacetone)palladium (0.008 g, 0.009 mmol), xantphos (0.010 g, 0.018 mmol) and sodium tert-butoxide (0.038 g, 0.392 mmol) in dioxane (1 mL). A couple of drops of dimethylacetamide were added to assist with microwave absorption. The mixture was heated at 140° C. for 30 min. The mixture was filtered and concentrated in vacuo. The crude product was purified by preparatory HPLC. LCMS method: 2, RT: 3.49 min, MI: 324 [M+1]. NMR (1H, DMSO, 300 MHz): 10.88 (brs, 1H), 8.73 (s, 1H), 7.43 (4, 1H), 7.33 (d, 2H), 6.99 (d, 2H), 6.95 (d, 1H), 6.24 (d, 1H), 3.11 (s, 3H), 2.08 (brs, 1H), 0.83 (d, 4H)

The following compounds were synthesised using the same general method.

| Code No. | Characterisation |
|---|---|
| WW-127 | RT: 3.49 min, MI: 324, Method: 2 |
| WW-128 | RT: 3.75 min, MI: 328, Method: 2 |
| WW-129 | RT: 4.07 min, MI: 328, Method: 2 |
| WW-130 | RT: 3.54 min, MI: 324, Method: 2 |
| WW-131 | RT: 4.71 min, MI: 350, Method: 2 |
| WW-132 | RT: 4.05 min, MI: 328, Method: 2 |
| WW-160 | RT: 3.67 min, MI: 324, Method: 2 |
| WW-161 | RT: 3.34 min, MI: 384, Method: 2 |
| WW-165 | RT: 1.76 min, MI: 295, Method: 2 |
| WW-166 | RT: 2.07 min, MI: 295, Method: 2 |

General Synthesis Procedure E

Compounds were synthesised starting from cyclopropanecarboxylic acid (5-bromo-[1,2,4]triazolo[1,5-a]pyridin-2-yl)-amide (described above) following the scheme illustrated below. In general, the oxo derivatives may be obtained via a nucleophilic substitution reaction utilising an appropriately substituted phenol and potassium carbonate or other suitable base.

Scheme 5

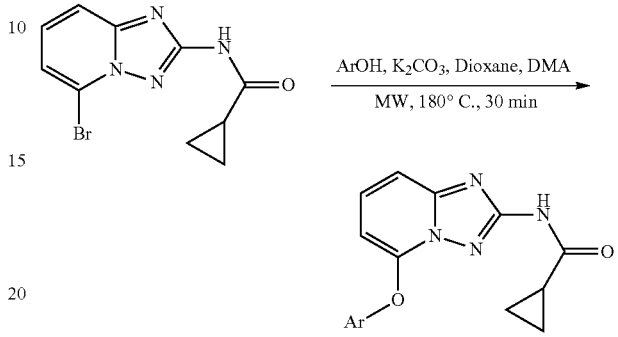

Synthesis 9

Cyclopropanecarboxylic acid (5-m-tolyloxy-[1,2,4]triazolo[1,5-a]pyridin-2-yl)-amide (WW-072)

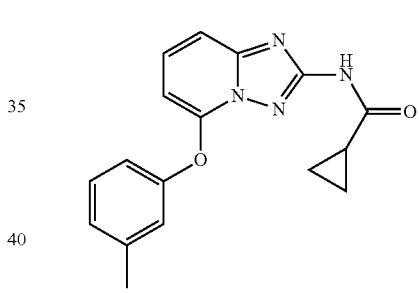

5-Bromo-[1,2,4]triazolo[1,5-a]pyridin-2-ylamine (0.05 g, 0.178 mmol) and m-cresol (0.096 g, 0.889 mmol) were dissolved in dioxane (1 mL). Potassium carbonate (0.123 g, 0.889 mmol) and a couple of drop of dimethylacetamide were added and the mixture was heated to 180° C. for 30 mins in the microwave. The crude product was filtered and purified by preparatory HPLC. LCMS method: 2, RT: 3.63 min, MI: 309.

The following compounds were synthesised using the same general method.

| Code No. | Characterisation |
|---|---|
| WW-072 | RT: 3.63 min, MI: 309, Method: 2 |

General Synthesis Procedure F

Compounds were synthesised starting from cyclopropanecarboxylic acid (5-bromo-[1,2,4]triazolo[1,5-a]pyridin-2-yl)-amide (described above) following the scheme illustrated below. In general, the thio derivatives may be obtained via a nucleophilic substitution reaction utilising an appropriately substituted thio-phenol and sodium hydride or other suitable base.

Scheme 6

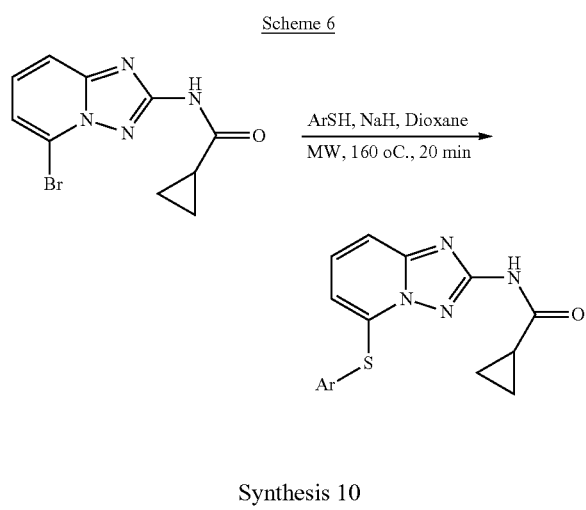

Synthesis 10

Cyclopropanecarboxylic acid (5-phenylsulfanyl-[1,2,4]triazolo[1,5-a]pyridin-2-yl)-amide (WW-111)

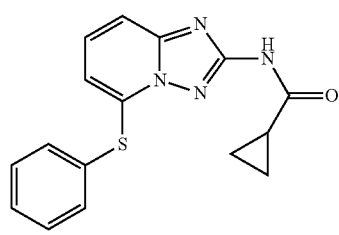 [SMILES: O=C(Nc1nc2cccc(Sc3ccccc3)n2n1)C1CC1]

A microwave tube was charged with sodium hydride (0.036 g, 0.889 mmol) in anhydrous well-degassed dioxane (1 mL). Thiophenol (0.091 mL, 0.889 mmol) was added dropwise and the mixture allowed to stir for 5 min. Cyclopropanecarboxylic acid (5-bromo-[1,2,4]triazolo[1,5-a]pyridin-2-yl)-amide (0.05 g, 0.178 mmol) was added and the mixture was heated to 160° C. for 20 min in a microwave. The crude product was purified by preparatory HPLC. LCMS method: 2, RT: 4.32 min, MI: 311 [M+1]. NMR (1H, DMSO, 300 MHz): 11.17 (s, 1H), 7.70 (m, 2H), 7.57 (m, 3H), 7.49 (d, 2H), 6.28 (t, 1H), 2.03 (brs, 1H), 0.83 (d, 4H)

The following compounds were synthesised using the same general method.

| Code No. | Characterisation |
| --- | --- |
| WW-111 | RT: 4.32 min, MI: 311, Method: 2 |
| WW-126 | RT: 3.82 min, MI: 341, Method: 2 |

General Synthesis Procedure G

Compounds were synthesised starting from the phthalimido cyclopropanecarboxylic acid (5-bromo-[1,2,4]triazolo[1,5-a]pyridin-2-yl)-amide derivatives (described above) following the scheme illustrated below. In general, the phthalimido group may be removed by hydrazinolysis in a refluxing solvent such as ethanol.

Scheme 7

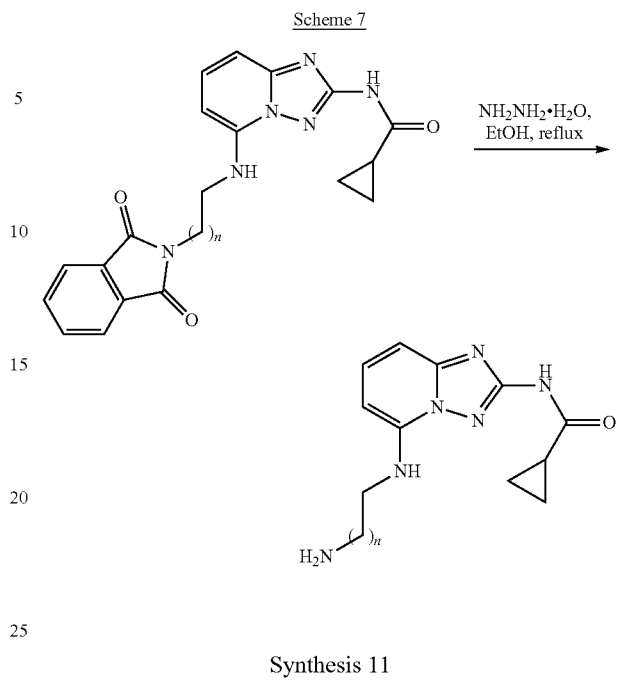

Synthesis 11

Cyclopropanecarboxylic acid {5-[4-(2-amino-ethylamino)-phenyl]-[1,2,4]triazolo[1,5-a]pyridin-2-yl}-amide (WW-158)

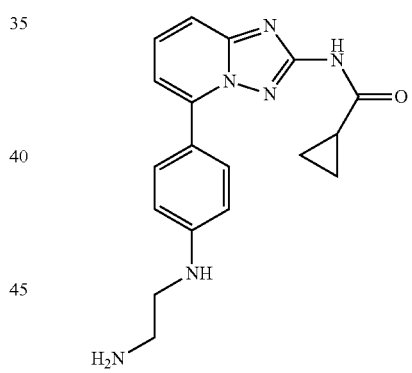

Under an atmosphere of nitrogen cyclopropanecarboxylic acid (5-{4-[2-(1,3-dioxo-1,3-dihydro-isoindol-2-yl)-ethylamino]-phenyl}-[1,2,4]triazolo[1,5-a]pyridin-2-yl)-amide (0.08 g, 0.17 mmol) and hydrazine monohydrate (0.082 mL, 1.7 mmol) were dissolved in ethanol (10 mL). The mixture was refluxed overnight. The mixture was cooled and the solid filtered off and washed with ethanol. The filtrate was passed over an SCX cartridge, and washed with ethyl acetate. The product was cleaved from the cartridge using 2M ammonia/methanol. The eluent was concentrated in vacuo, and the crude product was purified by preparatory HPLC. LCMS Method: 2: RT: 1.95 min, MI: 337 [M+1], NMR (DMSO, 300 MHz): 7.87 (d, 2H), 7.63 (m, 1H), 7.51 (d, 1H), 7.17 (d, 1H), 6.72 (d, 2H), 3.45 (t, 2H), 2.97 (t, 2H), 2.25 (brs, 1H) 0.81 (m, 4H).

The following compounds were synthesised using the same general method.

| Code No. | Characterisation |
|---|---|
| WW-157 | RT: 1.94 min, MI: 351, Method: 2 |
| WW-158 | RT: 1.95 min, MI: 337, Method: 2 |

General Synthesis Procedure H

Compound was synthesised starting from {4-[2-(cyclopropanecarbonyl-amino)-[1,2,4]triazolo[1,5-a]pyridin-5-yl]-phenyl}-methyl-carbamic acid tert-butyl ester (WW-119, described above) following the scheme illustrated below. In general, the Boc group may be cleaved utilising trifluoroacetic acid or other suitable conditions known to someone skilled in the art.

Scheme 8

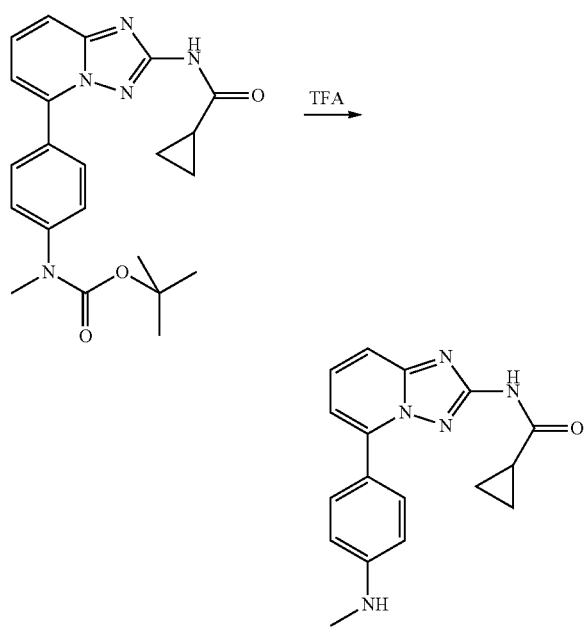

Synthesis 12

Cyclopropanecarboxylic acid [5-(4-methylamino-phenyl)-[1,2,4]triazolo[1,5-a]pyridin-2-yl]-amide (WW-120)

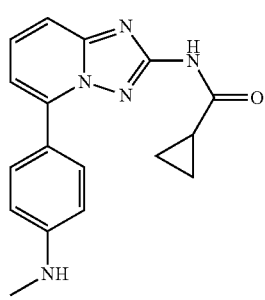 [SMILES: CNc1ccc(-c2cccc3nc(NC(=O)C4CC4)nn23)cc1]

To {4-[2-(cyclopropanecarbonyl-amino)-[1,2,4]triazolo[1,5-a]pyridin-5-yl]-phenyl}-carbamic acid tert-butyl ester (WW-119) (0.05 g, 0.123 mmol), trifluoroacetic acid (1 mL) was added and the solution was stirred for 2 h. The solvent was removed under reduced pressure and the crude product was purified by preparatory HPLC. LCMS method: 1, RT: 3.62 min; MI: 308 [M+1]. NMR 1H (DMSO) 0.80-0.83 (m, 4H), 1.93 (brs, 1H), 2.73 (s, 3H), 6.63 (d, 2H), 7.16 (d, 1H), 7.42 (d, 1H), 7.57 (t, 1H), 8.01 (d, 2H).

The following compound was synthesised using the same general method.

| Code No. | Characterisation |
|---|---|
| WW-120 | RT: 3.62 min; MI: 308; Method 1 |

General Synthesis Procedure I

Compound was synthesised starting from cyclopropanecarboxylic acid [5-(1H-pyrazol-4-yl)-[1,2,4]triazolo[1,5-a]pyridin-2-yl]-amide (WW-060, described above) following the scheme illustrated below. In general, sulfonamides may be obtained using an appropriately substituted sulfonyl chloride, a suitable base such as triethylamine and the pyrazolo derivative.

Scheme 9

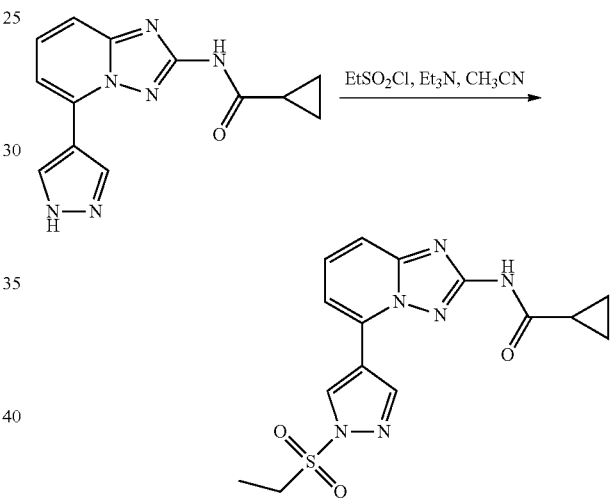

Synthesis 13

Cyclopropanecarboxylic acid [5-(1-ethanesulfonyl-1H-pyrazol-4-yl)-[1,2,4]triazolo[1,5-a]pyridin-2-yl]-amide (WW-147)

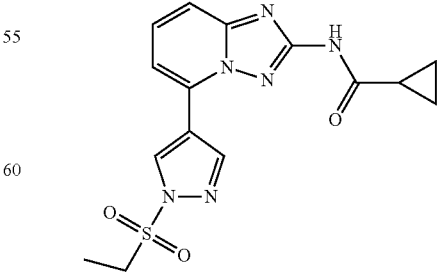

To a solution of cyclopropanecarboxylic acid [5-(1H-pyrazol-4-yl)-[1,2,4]triazolo[1,5-a]pyridin-2-yl]-amide (WW- 060) (0.05 g, 0.186 mmol) in acetonitrile (2 mL), ethanesulfonyl chloride (0.022 ml, 0.224 mmol) and triethylamine (0.052 mL, 0.373 mmol) were added successively and the mixture was stirred overnight. After concentration under reduced pressure water was added and extracted with ethyl acetate, dried over magnesium sulfate and concentrated under reduced pressure. The crude product was purified by preparatory HPLC. LCMS method: 1, RT: 3.87 min; MI: 361 [M+1]; NMR 1H (DMSO): 0.81-0.95 (m, 4H), 1.15 (t, 3H), 1.94 (brs, 1H), 3.82 (q, 2H), 7.66 (d, 1H), 7.73 (t, 1H), 7.81 (dd, 1H), 8.99 (s, 1H), 9.46 (s, 1H).

The following compound was synthesised using the same general method.

| Code No. | Characterisation |
|---|---|
| WW-147 | RT: 3.87 min; MI: 361; Method 1 |

General Synthesis Procedure J

Compounds were synthesised starting from cyclopropanecarboxylic acid [5-(4-amino-phenyl)-[1,2,4]triazolo[1,5-a]pyridin-2-yl]-amide (described above) following the scheme illustrated below. In general, sulfonamides may be obtained using an appropriately substituted sulfonyl chloride, a suitable base such as pyridine and the amine derivative.

Scheme 10

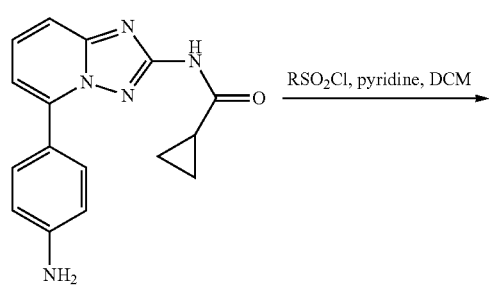

Synthesis 14

Cyclopropanecarboxylic acid [5-(4-ethanesulfonylamino-phenyl)-[1,2,4]triazolo[1,5-a]pyridin-2-yl]-amide (WW-154)

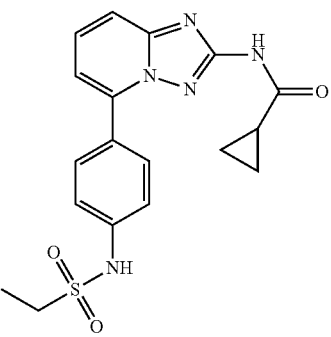 [SMILES: CCS(=O)(=O)Nc1ccc(-c2cccc3nc(NC(=O)C4CC4)nn23)cc1]

Cyclopropanecarboxylic acid [5-(4-amino-phenyl)-[1,2,4]triazolo[1,5-a]pyridin-2-yl]-amide (0.05, 0.17 mmol) was suspended in dichloromethane (2 mL). Pyridine (0.027 mL, 0.34 mmol) and ethanesulfonyl chloride (0.019 mL, 0.204 mmol) were added and the mixture was stirred for 4 hours. A further equivalent of pyridine and ethanesulfonyl chloride were added and the mixture was stirred overnight. The volatiles were removed in vacuo and the crude product was purified by preparatory HPLC. LCMS method: 2, RT: 3.11 min, MI: 386 [M+1]. NMR (1H, DMSO, 300 MHz): 0.82 (d, 4H), 1.24 (t, 3H), 2.01 (brs, 1H), 3.20 (q, 2H), 7.27 (dd, 1H), 7.36 (d, 2H), 7.68 (m, 2H), 8.02 (d, 2H), 9.98 (brs, 1H), 11.15 (s, 1H).

The following compounds were synthesised using the same general method.

| Code No. | Characterisation |
|---|---|
| WW-154 | RT: 3.11 min; MI: 386: Method 1 |
| WW-156 | RT: 3.62 min, MI: 434, Method 1 |

General Synthesis Procedure K

Compounds were synthesised starting from 2-(1,3-dioxo-1,3-dihydro-isoindol-2-yl)-N-[5-(4-methoxy-phenyl)-[1,2,4]triazolo[1,5-a]pyridin-2-yl]-acetamide (WW-022, described above) following the scheme illustrated below. In general, the ethers were obtained via a nucleophilic substitution reaction using a halogeno-alkyl and the phenol precursor and an appropriate base such as potassium carbonate.

Scheme 11

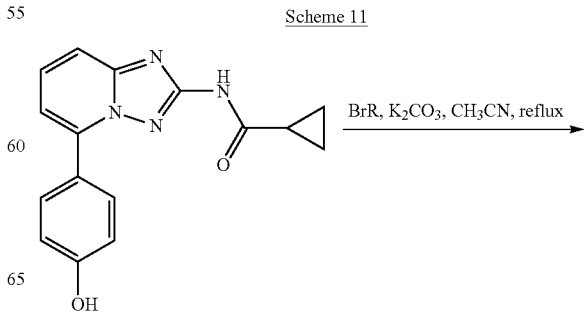

-continued

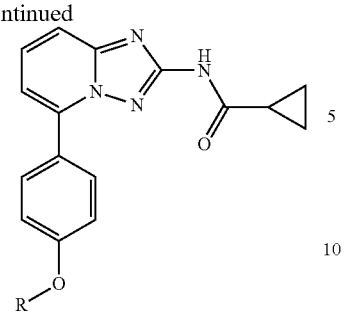

Synthesis 15

Cyclopropanecarboxylic acid {5-[4-(3-methoxy-benzyloxy)-phenyl]-[1,2,4]triazolo[1,5-a]pyridin-2-yl}-amide (WW-123)

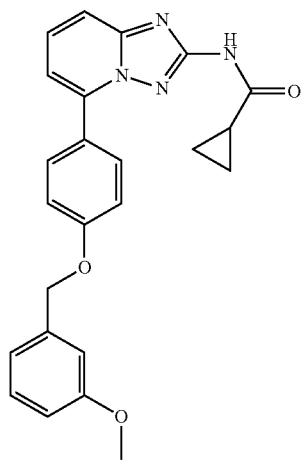 [SMILES: COc1cccc(COc2ccc(-c3cccc4nc(NC(=O)C5CC5)nn34)cc2)c1]

To a solution of cyclopropanecarboxylic acid [5-(4-hydroxy-phenyl)-[1,2,4]triazolo[1,5-a]pyridin-2-yl]-amide (WW-022) (0.05 g, 0.17 mmol) in acetonitrile (3 mL), potassium carbonate (0.047 g, 0.34 mmol) was added and the mixture was refluxed for 30 min. 3-Methoxybenzylbromide (0.047 mL, 0.34 mmol) was then added and the solution was refluxed overnight. The mixture was filtered and purified by preparatory HPLC. LCMS method: 1, RT: 5.16 min; MI: 415 [M+1]. NMR 1H (DMSO): 0.79-0.83 (m, 4H), 2.06 (brs, 1H), 3.76 (s, 3H), 5.08 (s, 2H), 6.88 (dd, 1H), 77.03-7.08 (m, 2H), 7.16 (d, 2H), 7.24 (dd, 1H), 7.31 (t, 1H), 7.60-7.67 (m, 2H), 8.00 (dd, 2H).

The following compounds were synthesised using the same general method.

| Code No. | Characterisation |
| --- | --- |
| WW-121 | RT: 4.84 min; MI: 349; Method 1 |
| WW-122 | RT: 4.36 min; MI: 333; Method 1 |
| WW-123 | RT: 5.16 min; MI: 415; Method 1 |

General Synthesis Procedure L

Compound was synthesised starting from 4-{4-[2-(cyclopropanecarbonyl-amino)-[1,2,4]triazolo[1,5-a]pyridin-5-yl]-phenyl}-piperazine-1-carboxylic acid tert-butyl ester (described above) following the scheme illustrated below. In general, the Boc group may be cleaved utilising trifluoroacetic acid or other suitable conditions know to those skilled in the art.

Scheme 12

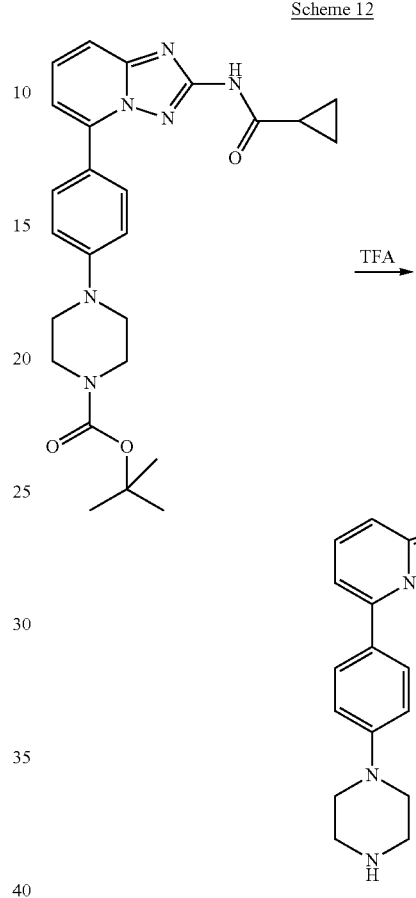

Synthesis 16

Cyclopropanecarboxylic acid [5-(4-piperazin-1-yl-phenyl)-[1,2,4]triazolo[1,5-a]pyridin-2-yl]-amide (WW-151)

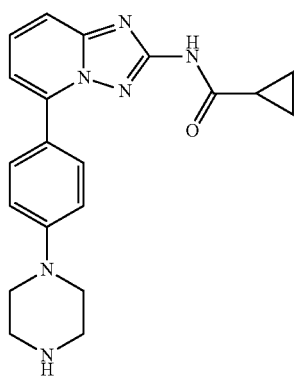 [SMILES: O=C(Nc1nc2cccc(-c3ccc(N4CCNCC4)cc3)n2n1)C1CC1]

A solution of 4-{4-[2-(cyclopropanecarbonyl-amino)-[1,2,4]triazolo[1,5-a]pyridin-5-yl]-phenyl}-piperazine-1-carboxylic acid tert-butyl ester (0.042 g, 0.091 mmol) in trifluoroacetic acid (2 mL) was stirred for 2 h. Saturated sodium hydrogen carbonate was then added and the mixture was extracted with ethyl acetate and dried over magnesium sulfate. After filtration and concentration under reduced pressure the crude product was purified by preparatory HPLC. LCMS method: 2, RT: 1.97 min; MI: 363 [M+1]. NMR 1H (DMSO) 0.79-0.82 (m, 4H), 1.05 (s, 1H), 2.01 (brs, 1H), 3.10-3.16 (m, 4H), 3.38-3.43 (m, 4H), 7.10 (d, 2H), 7.24 (dd, 1H), 7.58 (dd, 1H), 7.65 (t, 1H), 7.99 (d, 2H).

The following compound was synthesised using the same general method.

| Code No. | Characterisation |
| --- | --- |
| WW-151 | RT: 1.97 min; MI: 363; Method: 2 |

General Synthesis Procedure M

Compound was synthesised starting from cyclopropanecarboxylic acid [5-(4-amino-phenyl)-[1,2,4]triazolo[1,5-a]pyridin-2-yl]-amide (described above) following the scheme illustrated below. In general, alkylated amines may be generated via the nucleophilic substitution on a halo derivative by the amino functionality under microwave or other conditions using a base such as N,N-diisopropylethylamine in a suitable solvent.

Scheme 13

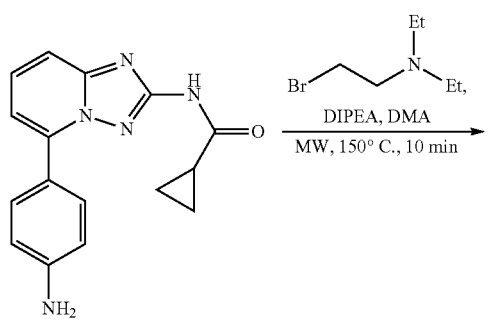

Synthesis 17

Cyclopropanecarboxylic acid {5-[4-(2-diethylamino-ethylamino)-phenyl]-[1,2,4]triazolo[1,5-a]pyridin-2-yl}-amide (WW-153)

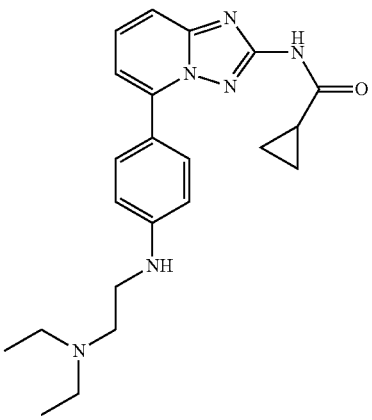 [SMILES: CCN(CC)CCNc1ccc(-c2cccc3nc(NC(=O)C4CC4)nn23)cc1]

Cyclopropanecarboxylic acid [5-(4-amino-phenyl)-[1,2,4]triazolo[1,5-a]pyridin-2-yl]-amide (0.05 g, 0.17 mmol), 2-bromo-N,N-diethylethylamine hydrobromide (0.133 g, 0.511 mmol) and diisopropylethylamine (0.089 mL, 0.511 mmol) were added to a microwave tube and the mixture was heated for 10 min at 150° C. The mixture was filtered and purified by preparatory LCMS. LCMS Method: 2: RT: 2.07 min; MI: 393 [M+1]. NMR (DMSO, 300 MHz): 0.81 (d, 4H), 1.10 (t, 6H), 2.04 (brs, 1H), 2.89 (m, 6H), 3.33 (t, 2H), 6.75 (d, 2H), 7.20 (dd, 1H), 7.53 (m, 1H), 7.64 (m, 1H), 7.92 (d, 2H), 8.18 (s, 1H), 11.00 (s, 1H)

The following compound was synthesised using the same general method.

| Code No. | Characterisation |
| --- | --- |
| WW-153 | RT: 2.07 min, MI: 393.35, Method: 2 |

General Synthesis Procedure N

Compound was synthesised starting from cyclopropanecarboxylic acid [5-(4-amino-phenyl)-[1,2,4]triazolo[1,5-a]pyridin-2-yl]-amide (described above) following the scheme illustrated below. In general, the amide products may be obtained using amide coupling agents such as HBTU or other reagents that generate an activated ester. The cleavage of the Boc group may be obtained utilising a solid supported reagent such as MP-TsOH or TFA or by any other method known to anyone skilled in the art.

Scheme 14

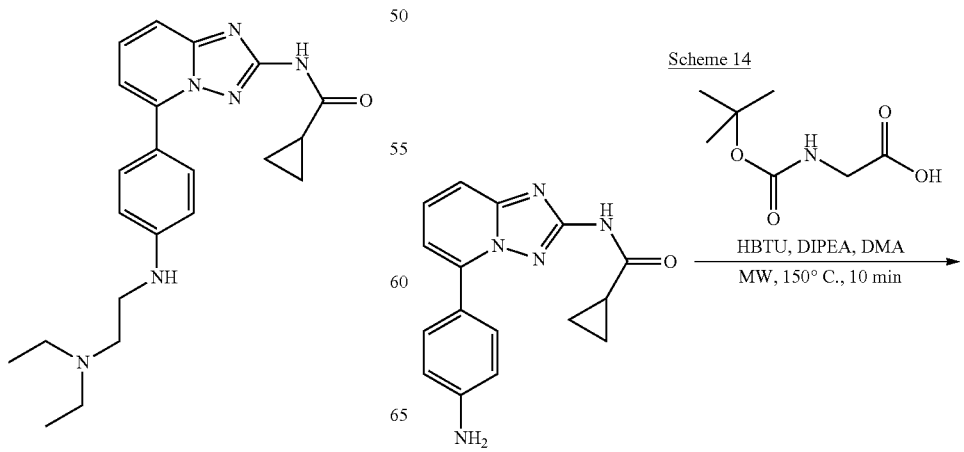

-continued

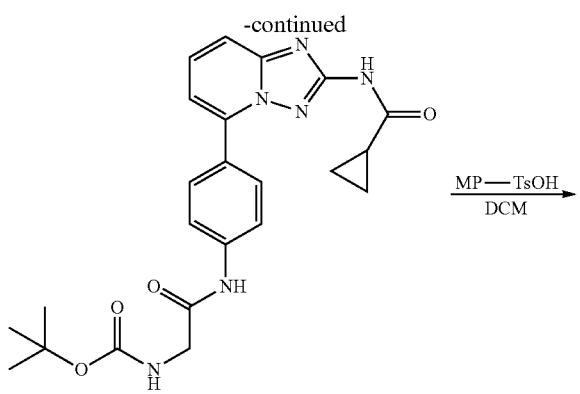

Synthesis 18

({4-[2-(Cyclopropanecarbonyl-amino)-[1,2,4]triazolo[1,5-a]pyridin-5-yl]-phenylcarbamoyl}-methyl)-carbamic acid tert-butyl ester

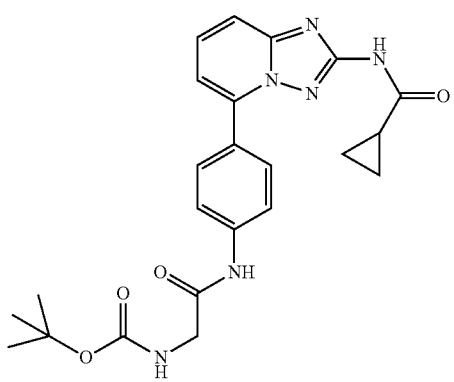 [SMILES: CC(C)(C)OC(=O)NCC(=O)Nc1ccc(-c2cccc3nc(NC(=O)C4CC4)nn23)cc1]

Cyclopropanecarboxylic acid [5-(4-amino-phenyl)-[1,2,4]triazolo[1,5-a]pyridin-2-yl]-amide (0.05 g, 0.17 mmol) was dissolved in dimethylacetamide (1 mL), diisopropylethylamine (0.036 mL, 0.204 mmol) and N-(tert-butoxycarbonyl)glycine (0.036 g, 0.204 mmol) were added followed by 2-(1H-benzotriazole-1-yl)-1,1,3,3-tetramethylaminium hexafluorophosphate (0.078 g, 0.204 mmol) and the mixture was heated to 150° C. for 10 min in a microwave. The reaction mixture was transferred to a vial and purified by prep LCMS. LCMS method: 1, RT: 4.08 min, MI: 451 [M+1].

Synthesis 19

Cyclopropanecarboxylic acid {5-[4-(2-amino-acetylamino)-phenyl]-[1,2,4]triazolo[1,5-a]pyridin-2-yl}-amide (WW-155)

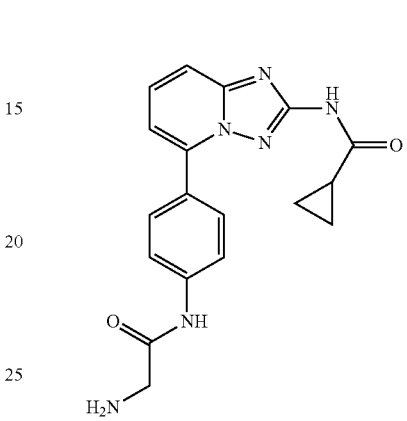

({4-[2-(Cyclopropanecarbonyl-amino)-[1,2,4]triazolo[1,5-a]pyridin-5-yl]-phenylcarbamoyl}-methyl)-carbamic acid tert-butyl ester (0.08 g, 0.17 mmol) was dissolved in dichloromethane (3 ml), microporous p-toluenesulfonic acid (0.16 g, 0.51 mmol) was added and the mixture was shaken overnight. The resin was washed several times with methanol, and then the product was cleaved from the resin using a 2M ammonia/methanol solution. This solution was concentrated in vacuo to give clean product. LCMS method: 2, RT: 1.86 min, MI: 351 [M+1]. NMR (1H, DMSO, 300 MHz): 11.04 (brs, 1H), 8.02 (d, 2H), 7.82 (d, 2H), 7.66 (m, 2H), 7.28 (dd, 1H), 3.34 (brs, 2H), 2.03 (brs, 1H), 0.82 (d, 4H).

The following compound was synthesised using the same general method.

| Code No. | Characterisation |
|---|---|
| WW-155 | RT: 1.86 min; MI: 351, Method: 2 |

General Synthesis Procedure O

Compounds were synthesised starting from 5-aryl-[1,2,4]triazolo[1,5-a]pyridin-2-ylamine (described above) following the scheme illustrated below. In general, the chloro derivative may be obtained by the addition of a chloro acetyl chloride followed by the nucleophilic attack of an amine.

Scheme 15

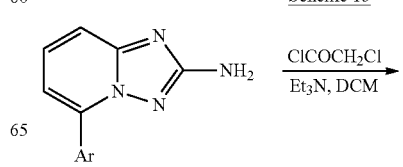

-continued

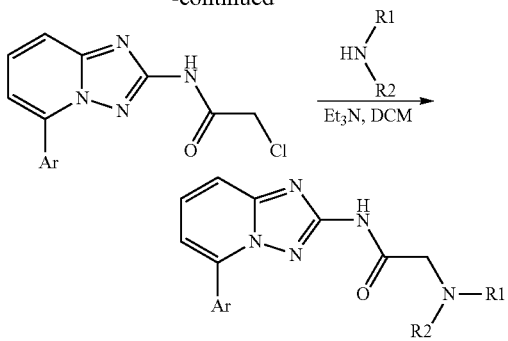

Synthesis 20

2-Chloro-N-[5-(2,3-dihydro-benzo[1,4]dioxin-6-yl)-[1,2,4]triazolo[1,5-a]pyridin-2-yl]-acetamide

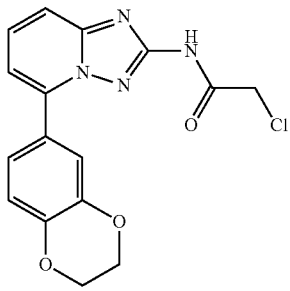 [SMILES: O=C(CCl)Nc1nc2cccc(-c3ccc4c(c3)OCCO4)n2n1]

To a solution of 5-(2,3-dihydro-benzo[1,4]dioxin-6-yl)-[1,2,4]triazolo[1,5-a]pyridin-2-ylamine (0.4 g, 1.5 mmol) in dichloromethane (20 mL), triethylamine (0.62 mL, 4.47 mmol) and chloroacetyl chloride (0.142 mL, 1.8 mmol) were added successively. The mixture was then stirred overnight. Water was added and the mixture was extracted with dichloromethane, dried over magnesium sulphate and concentrated under reduced pressure. The crude was used without further purification. Yield: 0.52 g, 100%; LCMS Method: 2: 3.57 min, 345-347 [M+1].

Synthesis 21

N-[5-(2,3-Dihydro-benzo[1,4]dioxin-6-yl)-[1,2,4]triazolo[1,5-a]pyridin-2-yl]-2-(4-methyl-piperazin-1-yl)-acetamide (WW-168)

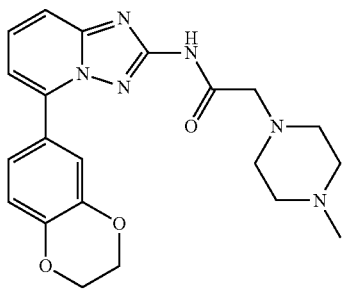 [SMILES: CN1CCN(CC(=O)Nc2nc3cccc(-c4ccc5c(c4)OCCO5)n3n2)CC1]

To a solution of 2-chloro-N-[5-(2,3-dihydro-benzo[1,4]dioxin-6-yl)-[1,2,4]triazolo[1,5-a]pyridin-2-yl]-acetamide (0.1 g, 0.29 mmol) in dichloromethane (2 mL), triethylamine (0.061 mL, 0.43 mmol) and N-methylpiperazine (0.036 mL, 0.32 mmol) were added successively and the mixture was stirred overnight. The solvent was removed under reduced pressure and the crude then purified by prep LCMS. LCMS Method: 2, RT=2.19 min, MI=409 [M+1], NMR 1H (DMSO): 2.29 (s, 3H), 2.48-2.50 (m, 4H), 2.53-2.58 (m, 4H), 3.25 (brs, 2H), 4.33 (brs, 4H), 7.03 (d, 1H), 7.25 (dd, 1H), 7.47 (dd, 1H), 7.62-7.71 (m, 3H).

The following compound was synthesised using the same general method.

| Code No. | LCMS |
| --- | --- |
| WW-168 | RT: 2.19 min, MI: 409, Method: 2 |

General Synthesis Procedure P

Compounds were synthesised starting from 5-aryl-[1,2,4]triazolo[1,5-a]pyridin-2-ylamine (described above) following the scheme illustrated below. In general, the Michael acceptor may be synthesised starting from the acid chloride or an activated ester. Addition of an amine at room temperature led to formation of the corresponding Michael adduct.

Scheme 16

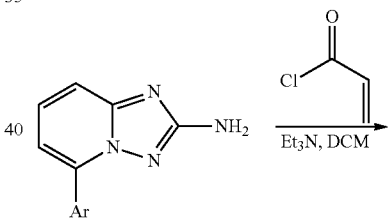

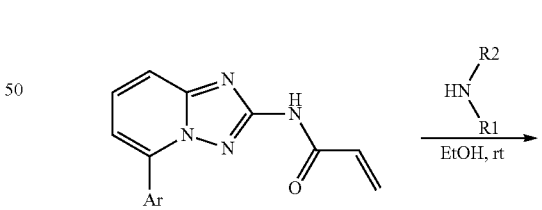

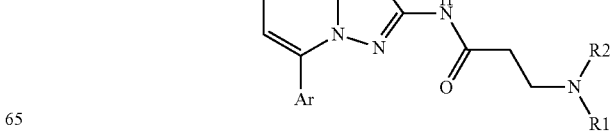

Synthesis 22

N-[5-(2,3-Dihydro-benzo[1,4]dioxin-6-yl)-[1,2,4]triazolo[1,5-a]pyridin-2-yl]-acrylamide

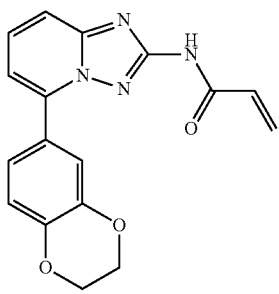 [SMILES: C=CC(=O)Nc1nc2cccc(-c3ccc4c(c3)OCCO4)n2n1]

To a solution of 5-(2,3-dihydro-benzo[1,4]dioxin-6-yl)-[1,2,4]triazolo[1,5-a]pyridin-2-ylamine (0.3 g, 1.12 mmol) in dichloromethane (10 mL), triethylamine (0.19 mL, 1.34 mmol) and acryloyl chloride (0.11 mL, 1.23 mmol) were added successively and the mixture was stirred overnight. The reaction was hydrolysed, and the organic phase washed with water, dried over magnesium sulfate and concentrated under reduced pressure. A minimum amount of dichloromethane was added to the crude, diethylether was added and the resulting solid collected by filtration. LCMS Method: 2: RT: 4.23 min, 323 [M+1].

Synthesis 23

N-[5-(2,3-Dihydro-benzo[1,4]dioxin-6-yl)-[1,2,4]triazolo[1,5-a]pyridin-2-yl]-3-imidazol-1-yl-propionamide (WW-169)

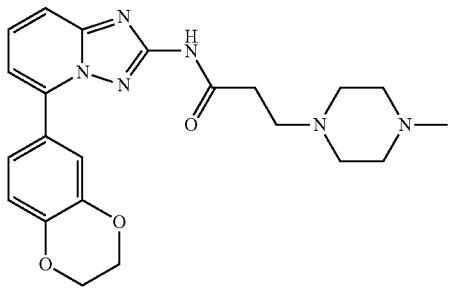 [SMILES: CN1CCN(CCC(=O)Nc2nc3cccc(-c4ccc5c(c4)OCCO5)n3n2)CC1]

To a solution of N-[5-(2,3-dihydro-benzo[1,4]dioxin-6-yl)-[1,2,4]triazolo[1,5-a]pyridin-2-yl]-acrylamide (0.05 g, 0.155 mmol) in ethanol (2 mL) was added N-methylpiperazine (0.13 g, 1.86 mmol) and the solution was stirred overnight. The reaction mixture was purified by prep LCMS. LCMS Method: 2, RT: 2.09 min, MI: 423 [M+1].

| Code No. | LCMS |
|---|---|
| WW-169 | RT: 2.09 min; MI: 423; Method: 2 |

General Synthesis Procedure Q

Compounds were synthesised starting from 5-aryl-[1,2,4]triazolo[1,5-a]pyridin-2-ylamine (described above) following the scheme illustrated below. In general, the amino derivatives may be obtained via a standard cross-coupling reaction utilising a catalyst such as bis(dibenzylideneacetone)palladium and an appropriate bromo derivative under standards conditions.

Scheme 17

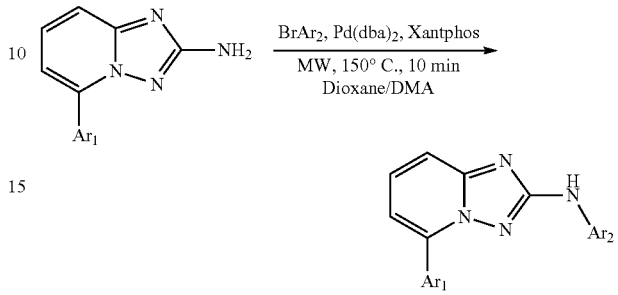

Synthesis 24

[3-(2-Imidazol-1-yl-ethoxy)-phenyl]-[5-(4-methoxyphenyl)-[1,2,4]triazolo[1,5-a]pyridin-2-yl]-amine (XX-015)

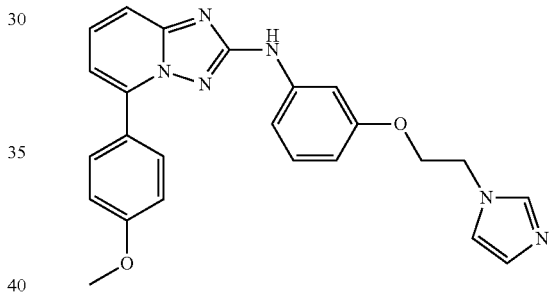

In a microwave vial, 5-(4-methoxy-phenyl)-[1,2,4]triazolo[1,5-a]pyridin-2-ylamine (0.05 g, 0.208 mmol), 1-[2-(3-bromo-phenoxy)-ethyl]-1H-imidazole (0.073 g, 0.27 mmol), bis(dibenzylideneacetone)palladium (0.01 g, 0.01 mmol), xantphos (0.012 g, 0.02 mmol) and sodium tertbutoxide (0.04 g, 0.416 mmol) were added successively. 1,4-Dioxane (1.2 mL) and dimethylacetamide (4 drops) were added and the vial was sealed and heated in the microwave (150° C., 10 min). The mixture was filtered and purified by preparatory LCMS. LCMS method: 2, RT: 3.36 min; MI: 427 [M+1]. NMR 1H (DMSO): 3.85 (s, 3H), 4.18 (t, 2H), 4.36 (t, 2H), 6.42 (dd, 1H), 6.94 (s, 1H), 7.11-7.15 (m, 5H), 7.26 (s, 1H), 7.46-7.64 (m, 3H), 7.78 (s, 1H), 8.02 (d, 2H), 9.65 (s, 1H).

Compounds were synthesised starting from bromoaryl esters following the scheme illustrated below.

Scheme 18

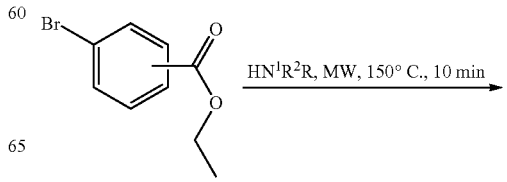

-continued

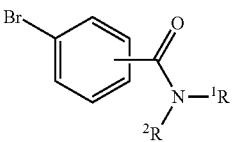

Synthesis 25

4-Bromo-N-(2-dimethylamino-ethyl)-benzamide

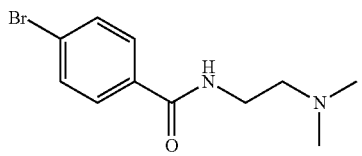

A microwave vial containing 4-bromo-benzoic acid ethyl ester (1 g, 4.36 mmol) and N,N-dimethylethylenediamine (2.37 g, 21.38 mmol) was heated under microwave radiation (150° C., 10 min). The volatiles were removed under rotary evaporation and the crude was used in the next step without further purification. Yield: 1.18 g, 100%. LCMS method: 2, RT: 1.93 min; MI: 271-273 [M+1].

Compounds were synthesised starting from bromophenols following the scheme illustrated below.

Scheme 19

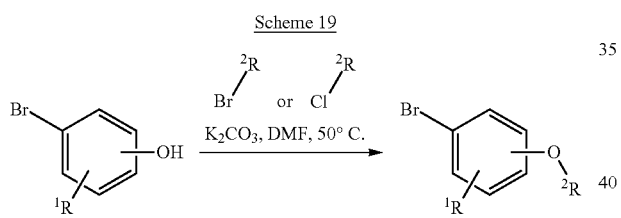

Synthesis 26

2-[2-(4-Bromo-phenoxy)-ethyl]-isoindole-1,3-dione

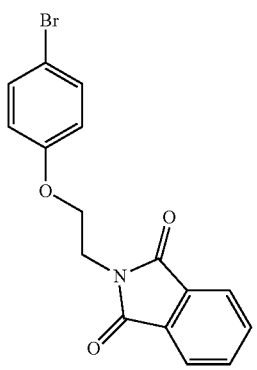 [SMILES: O=C1c2ccccc2C(=O)N1CCOc1ccc(Br)cc1]

4-Bromophenol, N-(2-bromoethyl)phthalimide and potassium carbonate were suspended in dimethylformamide and heated to 50° C. overnight under nitrogen. The dimethylformamide was removed under reduced pressure. The resulting residue was partitioned between ethyl acetate and water. The aqueous phase was extracted twice with ethyl acetate. The organics were combined, washed several times with brine, dried over magnesium sulfate, filtered and concentrated in vacuo. Yield: 2 g, 98%; LCMS: RT method: 2, RT: 5.33 min, MI: 382-384 [M+1].

Compounds were synthesised starting from bromobenzaldehydes following the scheme illustrated below.

Scheme 20

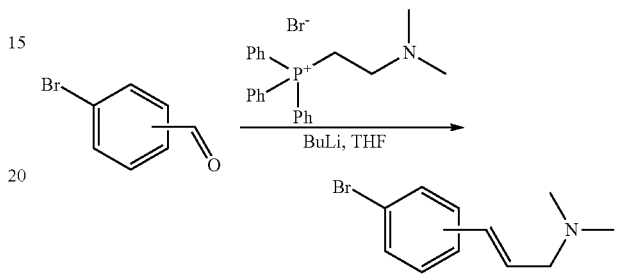

Synthesis 27

[(E)-3-(4-Bromo-phenyl)-allyl]-dimethyl-amine

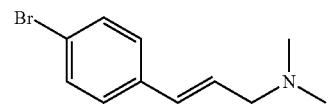

To a stirred solution of (2-dimethylaminoethyl)triphenylphosphonium bromide (1.12 g, 2.7 mmol) in tetrahydrofuran (10 ml) was added 2.5 M n-BuLi in hexanes (1.08 ml, 2.7 mmol) under nitrogen at 0° C. After 30 minutes 4-bromobenzaldehyde (0.5 g, 2.7 mmol) was added slowly and the reaction mixture was stirred at 60° C. overnight. The reaction mixture was acidified with 2M hydrochloric acid and extracted with toluene. The aqueous layer was then made alkaline with 2N sodium hydroxide and extracted twice with ethyl acetate. The organics were combined, dried over anhydrous magnesium sulfate, filtered and concentrated in vacuo to give the product as yellow oil. Yield 0.41 g, 63%. LCMS method: 2, RT: 2.62 min; MI: 240-242 [M+1].

Compounds were synthesised from bromo chloro heterocycles following the scheme shown below. In general the bromo heteroaryl compounds may be obtained by nucleophilic substitution of an activated aryl halogen by an alcohol in the presence of sodium hydride or other suitable base.

Scheme 21

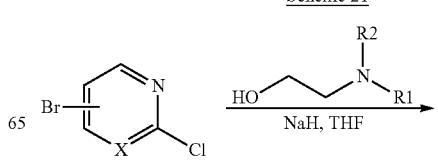

-continued

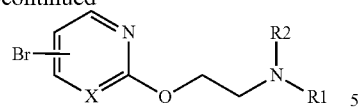

with X = CH, N

Synthesis 28

[2-(5-Bromo-pyrimidin-2-yloxy)-ethyl]-dimethyl-amine

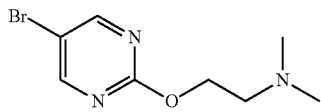

2-Dimethylaminoethanol (0.113 mL, 1.113 mmol) was suspended in anhydrous tetrahydrofuran (10 mL). Sodium hydride (60% in mineral oil, 0.134 g, 3.334 mmol) was added and the mixture was stirred for 5 minutes. 5-Bromo-2-chloropyrimidine (0.2 g, 1.03 mmol) was added and the mixture was stirred for 2 hours. The reaction mixture was diluted with 10% aqueous ammonium chloride and extracted with ethyl acetate. The extract was washed with water and brine, dried over anhydrous magnesium sulfate, filtered and concentrated in vacuo. LCMS method: 1, RT: 0.63 min, MI: 246-248 [M+1].

Compounds were synthesised starting from bromoanilines following the scheme illustrated below Scheme 22

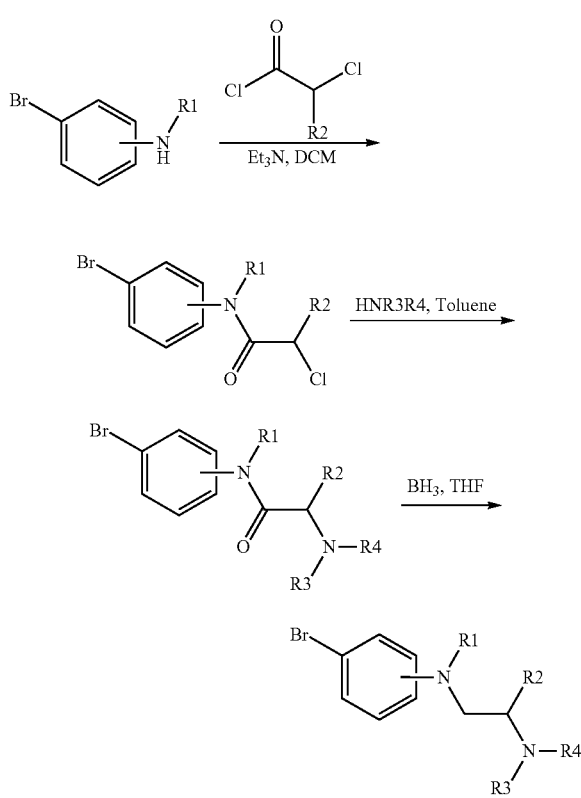

Synthesis 29

N-(4-Bromo-phenyl)-2-chloro-acetamide

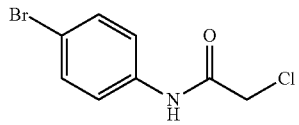 [SMILES: O=C(CCl)Nc1ccc(Br)cc1]

A solution of bromoaniline (2 g, 11.63 mmol) and triethylamine (4.84 ml, 34.89 mmol) in dichloromethane (50 ml) at 0° C. was added chloroacetyl chloride dropwise (1.11 ml, 13.96 mol). The mixture was stirred at 0° C. for 15 min then warmed to room temperature and stirred for 1 hour. Saturated aqueous ammonium chloride was added and the mixture was extracted twice with dichloromethane. The organics were combined, washed with brine, dried over anhydrous magnesium sulfate, filtered and concentrated in vacuo. Yield 2.20 g, 76%. LCMS method: 2, RT: 4.85 min; MI: 289-291 [M+1].

Synthesis 30

N-(4-Bromo-phenyl)-2-pyrrolidin-1-yl-acetamide

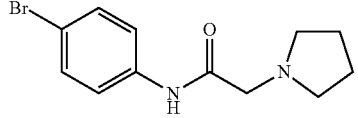 [SMILES: O=C(CN1CCCC1)Nc1ccc(Br)cc1]

N-(4-Bromo-phenyl)-2-chloro-acetamide (0.3 g, 1.21 mmol) was dissolved in anhydrous toluene (10 ml). Pyrrolidine (0.3 ml, 3.63 mmol) was added dropwise to the mixture, which was then heated to reflux and stirred overnight. The toluene was removed under reduced pressure and the residue was dissolved in ethyl acetate. Saturated ammonium chloride was added and the aqueous layer was extracted twice with ethyl acetate. The organics were combined, washed with brine, dried over anhydrous magnesium sulfate and concentrated in vacuo. Yield 0.22 g, 65%. LCMS method: 2, RT: 2.62 min; MI: 283-285 [M+1].

Synthesis 31

(4-Bromo-phenyl)-(2-pyrrolidin-1-yl-ethyl)-amine

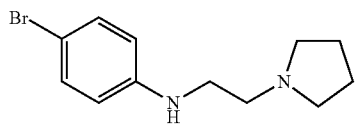 [SMILES: Brc1ccc(NCCN2CCCC2)cc1]

A 1M solution of BH$_3$ in tetrahydrofuran (7.7 ml, 7.7 mmol) was added dropwise to N-(4-bromo-phenyl)-2-pyrrolidin-1-yl-acetamide (0.22 g, 0.77 mmol) and the solution was stirred overnight at reflux then subsequently hydrolysed by slow addition of excess of methanol and refluxing for a further 2 hours. The solvent was removed under reduced pressure and aqueous ammonium chloride was added. The aqueous was extracted twice with ethyl acetate and the organics were combined, dried over anhydrous magnesium sulfate and concentrated in vacuo to give the desired product. Yield 0.18 g, 86%. LCMS method: 2, RT: 4.62 min; MI: 267-269 [M+1].

Compounds were synthesised starting from bromoanilines following the scheme illustrated below.

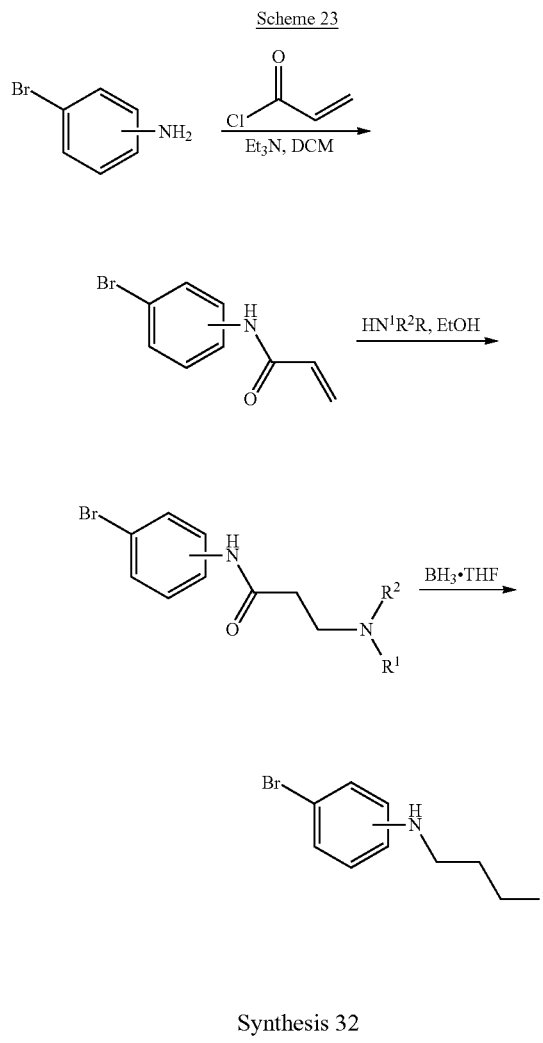

Scheme 23

Synthesis 32

N-(4-Bromo-phenyl)-acrylamide

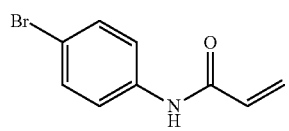

A mixture of 4-bromoaniline (2.0 g, 11.63 mmol) and triethylamine (1.9 ml, 13.96 mmol) in dichloromethane (50 ml) was cooled to 0° C. and acroloyl chloride (1.04 ml, 12.76 mmol) was added dropwise over 5 min. The resulting mixture was stirred for 2 hours at 0° C. The mixture was diluted with dichloromethane, washed with brine and dried over magnesium sulfate, filtered and concentrated in vacuo to give the desired product. Yield 0.97 g, 37%. LCMS method: 2, RT: 2.91 min; MI: 227-229 [M+1].

Synthesis 33

N-(4-Bromo-phenyl)-3-pyrrolidin-1-yl-propionamide

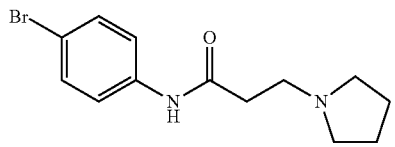 [SMILES: O=C(CCN1CCCC1)Nc1ccc(Br)cc1]

N-(4-Bromo-phenyl)-acrylamide (0.3 g, 1.33 mmol) was dissolved in ethanol. Pyrrolidine (0.12 ml, 1.46 mmol) was added and the mixture was heated to reflux overnight. The solvent was removed under reduced pressure and the residue was dissolved in ethyl acetate. Aqueous ammonium chloride was added and the aqueous layer was extracted twice with ethyl acetate. The organics were combined, dried over anhydrous magnesium sulfate, filtered and concentrated in vacuo to yield the desired product. Yield 0.24 g, 60%. LCMS method: 2, RT: 2.67 min; MI: 297-299 [M+1].

Synthesis 34

(3-Bromo-phenyl)-(3-pyrrolidin-1-yl-propyl)-amine

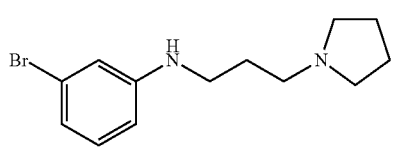 [SMILES: Brc1cccc(NCCCN2CCCC2)c1]

A 1M solution of $BH_3$ in tetrahydrofuran (10 ml, 10 mmol) was added dropwise to N-(3-bromo-phenyl)-3-pyrrolidin-1-yl-propionamide (0.3 g, 1 mmol) and the solution was stirred overnight at reflux then subsequently hydrolysed by slow addition of excess of methanol and refluxing for a further 2 hours. The solvent was removed under reduced pressure and aqueous ammonium chloride was added. The aqueous phase was extracted twice with ethyl acetate and the organics were combined, dried over anhydrous magnesium sulfate and concentrated in vacuo. The resulting residue was dissolved in methanol and loaded onto an SCX cartridge, which was washed with methanol and the product subsequently eluted with 2M ammonia in methanol. Removal of all solvents under rotary evaporation gave the desired product. Yield 0.23 g, 82%. LCMS method: 2, RT: 2.71 min; MI: 283-285 [M+1].

Compounds were synthesised from 2-(4-bromo-phenoxy)-amides as shown in the scheme below. In general, the amide was reduced using borane-tetrahydrofuran complex or by using any other suitable reducing agent.

Scheme 24

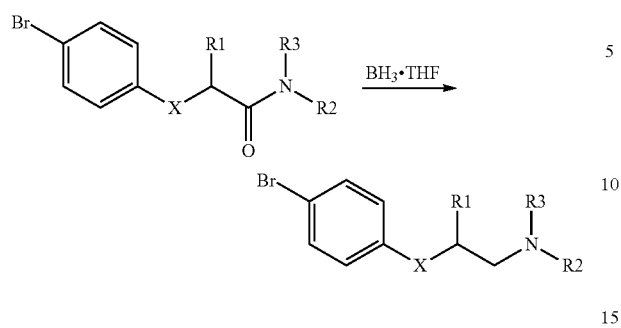

Synthesis 35

2-(4-Bromo-phenoxy)-propylamine

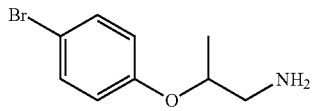

A 1M solution of borane in tetrahydrofuran (8.2 ml, 8.2 mmol) was added dropwise to 2-(4-bromo-phenoxy)-propionamide (0.2 g, 0.82 mmol) and the solution was stirred overnight at reflux then subsequently hydrolysed by slow addition of excess of methanol and refluxing for a further 2 hours. The solvent was removed under reduced pressure and aqueous ammonium chloride was added. The aqueous phase was extracted twice with ethyl acetate and the organics were combined, dried over anhydrous magnesium sulfate and concentrated in vacuo to give the desired product. Yield 0.13 g, 68%. LCMS method: 2, RT: 2.74 min; MI: 271-273 [M+1].

Compounds were synthesised from bromoanilines and carboxylic acids as shown in the scheme below. In general, HBTU or any other suitable coupling agent may be used to form the amide. A borane-tetrahydrofuran complex or any other suitable reducing agent may be used for the subsequent reduction.

Scheme 25

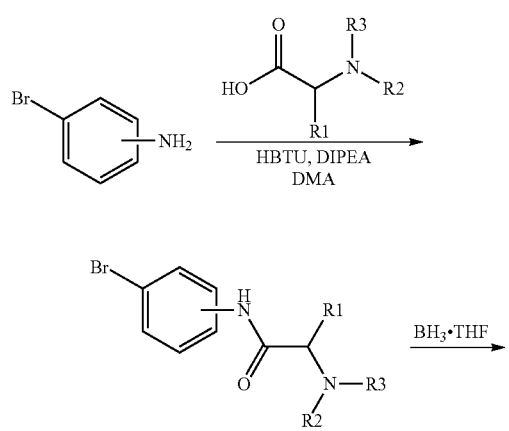

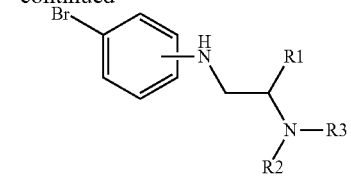

Synthesis 36

N-(4-Bromo-phenyl)-2-pyrrolidin-1-yl-propionamide

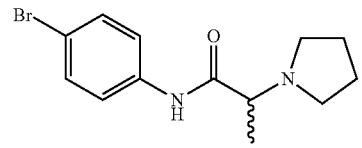 [SMILES: CC(C(=O)Nc1ccc(Br)cc1)N1CCCC1]

4-Bromo aniline (0.25 g, 1.45 mmol), 2-pyrrolidin-1-yl-propanoic acid (0.25 g, 1.74 mmol) and diisopropylethylamine (0.3 ml, 1.74 mmol) were dissolved in dimethylacetamide (5 ml). HBTU (0.66 g, 1.74 mmol) was subsequently added and the mixture was stirred overnight. The reaction mixture was added to water and extracted twice with ethyl acetate. The combined organics were washed several times with brine, dried over anhydrous magnesium sulfate, filtered and concentrated in vacuo to give the desired product. Yield: 0.43 g, 100%. LCMS method: 2, RT: 2.73 min; MI: 297-299 [M+1].

Synthesis 37

(4-Bromo-phenyl)-(2-pyrrolidin-1-yl-propyl)-amine

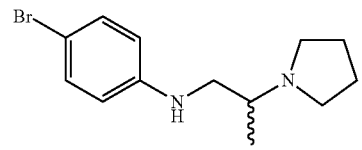 [SMILES: CC(CNc1ccc(Br)cc1)N1CCCC1]

A 1M solution of BH$_3$ in tetrahydrofuran (10 ml, 10 mmol) was added dropwise to N-(4-bromo-phenyl)-2-pyrrolidin-1-yl-propionamide (0.44 g, 1.48 mmol) and the solution was stirred overnight at reflux then subsequently hydrolysed by slow addition of excess of methanol and refluxing for a further 2 hours. The reaction mixture was loaded onto an SCX cartridge, which was washed with methanol and the product subsequently eluted with 2M ammonia in methanol. Removal of all solvents under rotary evaporation gave the desired product. Yield: 0.04 g, 10%. LCMS method: 2, RT: 3.07 min; MI: 283-285 [M+1].

Compounds were synthesised from boc-protected amino acids as shown in the scheme below. A borane-tetrahydrofuran complex or any other suitable reducing agent may be used for the selective reduction of the acid. DBAD or any other Mitsunobu reagent and triphenylphosphine can be used to form the ether

Scheme 26

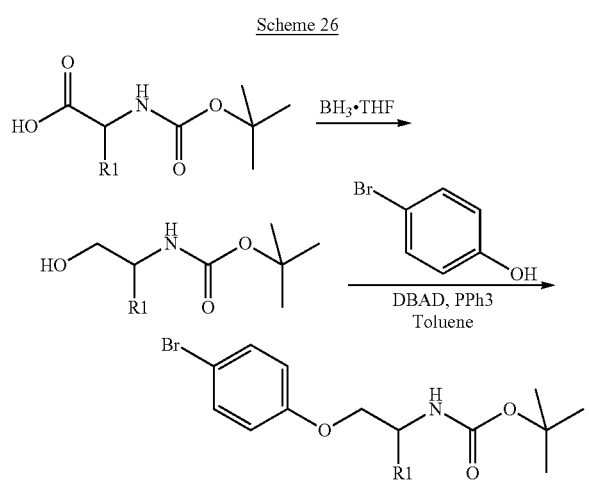

Synthesis 38

((R)-2-Hydroxy-1-methyl-ethyl)-carbamic acid tert-butyl ester

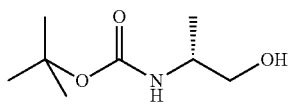

A solution of Boc-D-Ala-OH (1.0 g, 5.28 mmol) in tetrahydrofuran (10 ml) was added dropwise to a stirred solution of BH$_3$, 1M in tetrahydrofuran (10 ml) at 0° C. The mixture was stirred for a further hour at 0° C., then quenched with 10% acetic acid in methanol. After solvent evaporation, the crude product was dissolved in ethyl acetate and washed with 1M HCl, water and then 1M sodium hydrogencarbonate. The organic layer was dried over anhydrous magnesium sulfate, filtered and concentrated in vacuo to give the desired product. Yield 0.39 g, 42%.: NMR 1H (300 MHz, CDCl$_3$): 0.97 (d, 3H), 1.36 (s, 9H), 3.14 (m, 1H), 3.29 (m, 1H), 3.40 (m, 1H), 4.57 (m, 1H)

Synthesis 39

[(R)-2-(4-Bromo-phenoxy)-1-methyl-ethyl]-carbamic acid tert-butyl ester

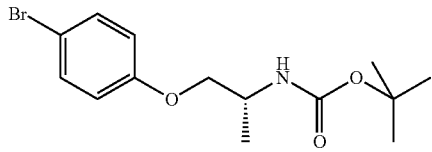 [SMILES: C[C@H](COc1ccc(Br)cc1)NC(=O)OC(C)(C)C]

4-Bromophenol (0.2 g, 1.14 mmol), ((R)-2-hydroxy-1-methyl-ethyl)-carbamic acid tert-butyl ester (0.2 g, 1.14 mmol) and triphenylphosphine (0.45 g, 1.71 mmol) were dissolved in anhydrous toluene (10 ml) under an atmosphere of nitrogen. A solution of di-tert-butyl azodicarboxylate (0.39 g, 1.71 mmol) in toluene (5 ml) was added slowly ensuring that the temperature did not exceed 35° C. The reaction mixture was heated to 80° C. and stirred overnight. The solvent was removed in vacuo and the residue was dissolved in ethyl acetate and subsequently washed with 1M HCl, water, brine then dried over magnesium sulfate, filtered and concentrated in vacuo. Purification by Flash Chromatography using 10% ethyl acetate/cyclohexane as the elutant gave the final product. Yield 80 mg, 21%. LCMS method: 2, RT: 6.17 min; MI: 330-332 [M+1].

Compounds were synthesised from lactamides as shown in the scheme below. A borane-tetrahydrofuran complex or any other suitable reducing agent may be used for the reduction to the amine. Di-tert-butyl dicarbonate can be used to protect the amine, and DBAD or any other Mitsunobu reagent and triphenylphosphine can be used to form the ether.

Scheme 27

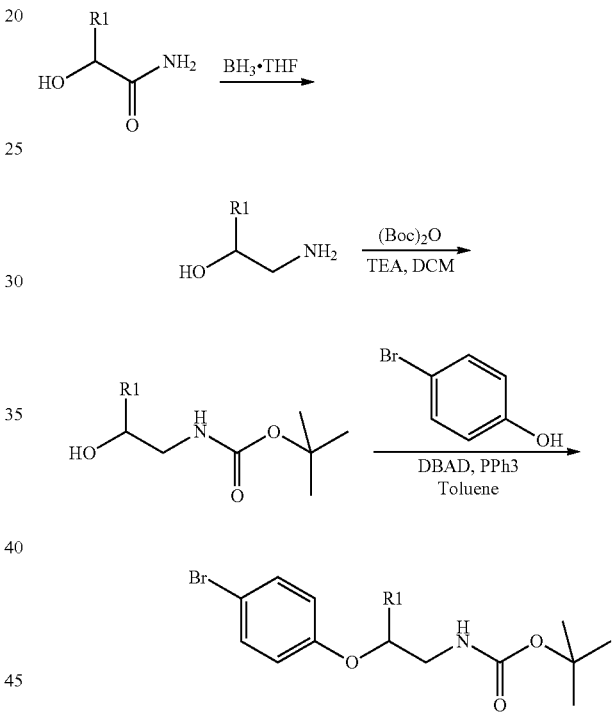

Synthesis 40

(R)-1-Amino-propan-2-ol

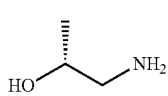

A 1M solution of borane in tetrahydrofuran (10 ml, 10 mmol) was added dropwise to (R)-lactamide (0.5 g, 5.6 mmol) and the solution was stirred overnight at reflux then subsequently hydrolysed by slow addition of excess of methanol and refluxing for a further 2 hours. The reaction mixture was loaded onto an SCX cartridge, which was washed with methanol and the product subsequently eluted with 2M ammonia in methanol. Removal of all solvents under rotary evaporation gave the desired product. Yield: 0.20 g, 48%. NMR 1H (300 MHz, CDCl₃): 1.05 (d, 3H), 3.64 (m, 1H) (CH₂ under water peak).

Synthesis 41

((R)-2-Hydroxy-propyl)-carbamic acid tert-butyl ester

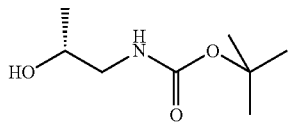

To a stirred solution of (R)-1-amino-propan-2-ol (0.2 g, 2.66 mmol) and triethylamine (385 µL, 2.78 mmol) in dichloromethane (5 ml) at 0° C. was added di-tert-butyl dicarbonate (0.6 g, 2.78 mmol) and the reaction mixture was stirred for 1 hr at 0° C. under N₂. Saturated aqueous sodium hydrogencarbonate was added and extracted twice with dichloromethane. The organics were combined, washed with brine, dried over anhydrous magnesium sulfate, filtered and concentrated in vacuo to give the desired product. Yield 0.33 g, 70%. NMR 1H (300 MHz, CDCl₃): 1.16 (d, 3H), 1.44 (s, 9H), 2.99 (m, 1H), 3.26 (m, 1H), 3.88 (m, 1H), 4.96 (brs, 1H)

Synthesis 42

[(S)-2-(4-Bromo-phenoxy)-propyl]-carbamic acid tert-butyl ester

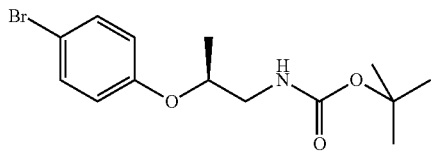 [SMILES: C[C@@H](CNC(=O)OC(C)(C)C)Oc1ccc(Br)cc1]

4-Bromophenol (0.33 g, 1.88 mmol), ((R)-2-hydroxy-propyl)-carbamic acid tert-butyl ester (0.33 g, 1.88 mmol) and triphenylphosphine (0.74 g, 2.82 mmol) were dissolved in anhydrous toluene. A solution of di-tert-butyl azodicarboxylate (0.65 g, 2.82 mmol) in toluene (5 ml) was added slowly ensuring that the temperature did not exceed 35° C. The reaction mixture was heated to 80° C. and stirred overnight. The solvent was removed in vacuo and the residue was dissolved in ethyl acetate and subsequently washed with 1M HCl, water, then brine and dried over magnesium sulfate, filtered and concentrated in vacuo to give the desired product. Yield: 0.62 g, 100. LCMS method: 2, RT: 6.18 min; MI: 330-332 [M+1].

Compounds were synthesised from 4-bromophenol as shown in the scheme below. In general DBAD or any other Mitsunobu reagent and polystyrene supported triphenylphosphine can be used to form the ether Scheme 28

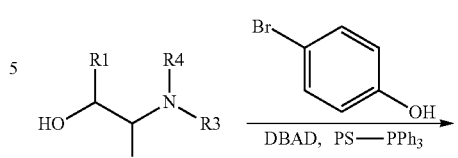

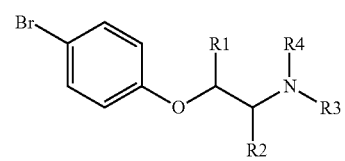

Synthesis 43

[(R)-2-(4-Bromo-phenoxy)-propyl]-dimethyl-amine

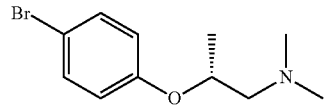

4-Bromophenol (0.2 g, 1.16 mmol) and (S)-(+)-1-dimethylamino-2-propanol (0.14 ml, 1.16 mmol) were dissolved in dichloromethane (10 ml). PS-Triphenylphospine (1.74 g, 1.74 mmol) was added, followed by di-tert-butyl azodicarboxylate (0.4 g, 1.74 mmol). The mixture was stirred overnight at room temperature, then filtered and the filtrate washed with sodium hydrogenocarbonate then brine. The organic phase was dried over anhydrous magnesium sulfate, filtered and concentrated in vacuo to give the desired product. Yield: 0.3 g, 100%. LCMS method: 2, RT: 2.62 min; MI: 258-260 [M+1].

Scheme 29

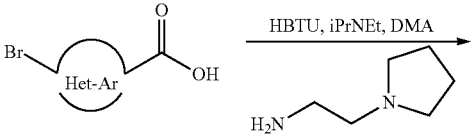

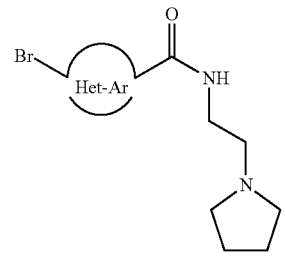

Synthesis 44

4-Bromo-pyridine-2-carboxylic acid (2-pyrrolidin-1-yl-ethyl)-amide

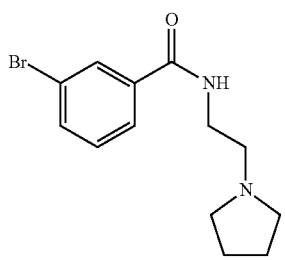 [SMILES: O=C(NCCN1CCCC1)c1cccc(Br)c1]

To a solution of 4-bromo-pyridine-2-carboxylic acid (0.2 g, 0.99 mmol) in dimethylacetamide (5 mL), N,N-diisopropylethylamine (0.26 mL, 1.485 mmol), 1-(2-aminoethyl)pyrrolidine (0.17 g, 1.485 mmol) and HBTU (0.565 g, 1.485 mmol) were added successively. The mixture was stirred overnight and then hydrolysed. Ethyl acetate was added and the two layers then separated. The aqueous layer was extracted with ethyl acetate and the organics combined, washed with water (×2) then brine and dried over anhydrous magnesium sulfate. The crude was used without further purification. Yield: 0.24 g, 80%. LCMS Method: 2:1.92 min, 298-300 [M+1].

Compounds were synthesised from an amino-alcohol as shown in the scheme below. In general, the cyclic amine was obtained using dibromobutane under standard conditions. A Mitsunobu reaction was then performed to generate the amino-ether derivative.

Scheme 30

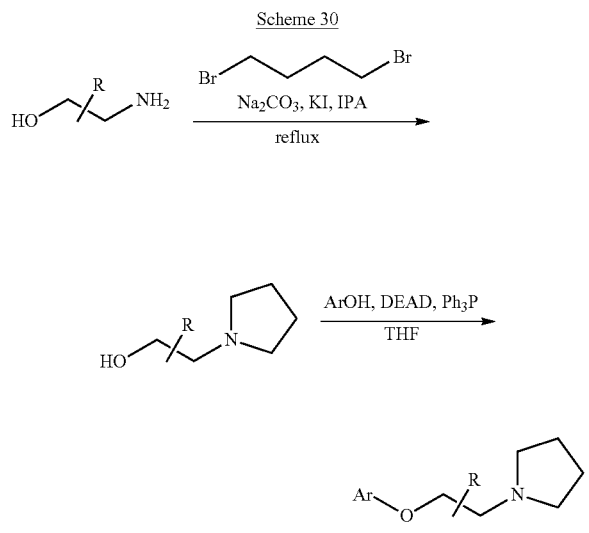

Synthesis 45

(R)-2-Phenyl-2-pyrrolidin-1-yl-ethanol

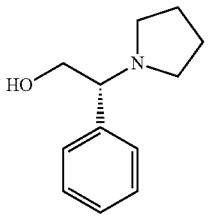 [SMILES: OC[C@@H](c1ccccc1)N1CCCC1]

To a solution of (R)-2-amino-2-phenyl-ethanol (0.5 g, 3.64 mmol) in 2-propanol (40 mL) were added sodium carbonate (1 g, 9.48 mmol), 1,4-dibromobutane (0.57 mL, 4.74 mmol) and potassium iodide (catalytic) in succession, and the mixture was refluxed overnight. After filtration, the solvent was removed under reduced pressure and the crude was used without further purification (0.53 g, 76%). LCMS method: 2, RT: 2.27 min; MI: 191-193 [M+1].

Synthesis 46

1-[(R)-2-(4-Bromo-phenoxy)-1-phenyl-ethyl]-pyrrolidine

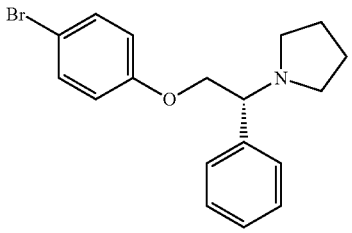 [SMILES: Brc1ccc(OC[C@@H](c2ccccc2)N2CCCC2)cc1]

To a solution of 4-bromophenol (0.226 g, 1.31 mmol) in tetrahydrofuran, were added triphenylphosphine (0.342 g, 1.31 mmol), (R)-2-phenyl-2-pyrrolidin-1-yl-ethanol (0.3 g, 1.57 mmol) and diethyl azodicarboxylate (0.205 mL, 1.31 mmol) successively. The solution was stirred overnight at room temperature and the solvent removed under reduced pressure. The crude was passed through an SCX column, which was washed with methanol and then the compound released using a solution of ammonia in methanol (2M) and concentrated under reduced pressure. The resulting oil was used without further purification. Yield: 0.43 g, 80%. LCMS method: 2, RT: 3.36 min; MI: 346-348 [M+1].

Compounds were synthesised from 4-bromo-2-chloropyridine as shown in the scheme below. In general, the 2-aminopyridine was obtained by nucleophilic addition of the amine function on the bromo-chloro derivative under microwave conditions.

Scheme 31

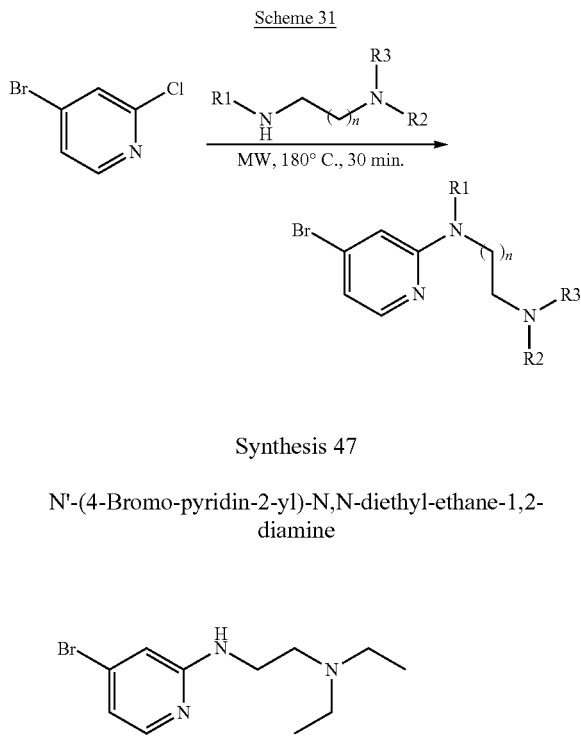

Synthesis 47

N'-(4-Bromo-pyridin-2-yl)-N,N-diethyl-ethane-1,2-diamine

In a microwave vial, 4-Bromo-2-chloro-pyridine (0.3 g, 1.56 mmol) and N,N-diethylethylenediamine (0.9 g, 7.8 mmol) were heated under microwave irradiations (180° C., 30 min). Water and Ethyl acetate were then added and the layers separated. The aqueous layer was extracted with ethyl acetate and the organics combined, washed twice with brine, dried over magnesium sulphate and concentrated under reduced pressure. The crude was used without further purification. Yield: 0.31 g, 71%. LCMS method: 2, RT: 0.47 min; MI: 272-274 [M+1].

The following compounds were synthesised using the same general method.

| Code No. | Characterisation |
|---|---|
| XX-024 | RT: 4.38 min; MI: 401; Method 1 |
| XX-022 | RT: 3.26 min; MI: 390; Method 1 |
| XX-021 | RT: 3.33 min; MI: 444; Method 1 |
| XX-020 | RT: 3.44 min; MI: 440; Method 1 |
| XX-019 | RT: 3.38 min; MI: 444; Method: 2 |
| XX-018 | RT: 3.32 min; MI: 458; Method: 2 |
| XX-017 | RT: 3.01 min; MI: 404; Method: 2 |
| XX-016 | RT: 3.32 min; MI: 427; Method 1 |
| XX-015 | RT: 3.36 min; MI: 427; Method 1 |
| XX-013 | RT: 5.13 min; MI: 388; Method: 2 |
| XX-012 | RT: 3.56 min; MI: 458; Method: 2 |
| XX-011 | RT: 3.77 min; MI: 377; Method: 2 |
| XX-010 | RT: 4.22 min; MI: 348; Method: 2 |
| XX-009 | RT: 4.95 min; MI: 501; Method 1 |
| XX-007 | RT: 2.47 min; MI: 332; Method: 2 |
| XX-008 | RT: 4.56 min; MI: 359; Method: 2 |
| XX-006 | RT: 2.54 min; MI: 404; Method: 2 |
| XX-005 | RT: 2.57 min; MI: 446; Method: 2 |
| XX-004 | RT: 2.57 min; MI: 430; Method: 2 |
| XX-014 | RT: 3.28 min; MI: 446; Method: 2 |
| XX-036 | RT: 2.48 min; MI: 431; Method: 2 |
| XX-054 | RT: 2.64 min; MI: 472, Method: 2 |
| XX-051 | RT: 2.60 min; MI: 414, Method: 2 |
| XX-062 | RT: 4.65 min; MI: 389, Method: 2 |
| XX-057 | RT: 2.61 min, MI: 360, Method: 2 |
| XX-056 | RT: 2.53 min, MI: 346, Method: 2 |
| XX-055 | RT: 2.54 min, MI: 432, Method: 2 |
| XX-053 | RT: 2.54 min, MI: 416, Method: 2 |
| XX-052 | RT: 2.65 min, MI: 456, Method: 2 |
| XX-050 | RT: 2.72 min, MI: 454, Method: 2 |
| XX-049 | RT: 2.52 min, MI: 404, Method: 2 |
| XX-048 | RT: 2.53 min, MI: 418, Method: 2 |
| XX-047 | RT: 2.62 min, MI: 458, Method: 2 |
| XX-044 | RT: 2.61 min, MI: 442, Method: 2 |
| XX-063 | RT: 3.82 min, MI: 396, Method: 2 |
| XX-043 | RT: 5.11 min; MI: 389; Method: 2 |
| XX-040 | RT: 3.34 min; MI: 404; Method 1 |
| XX-038 | RT: 3.32 min; MI: 485; Method 1 |
| XX-035 | RT: 4.46 min; MI: 404; Method 1 |
| XX-042 | RT: 4.14 min; MI: 404; Method: 2 |
| XX-037 | RT: 2.50 min; MI: 431; Method: 2 |
| XX-039 | RT: 4.87 min; MI: 520; Method: 2 |
| XX-001 | RT: 3.38 min; MI: 488; Method 1 |
| XX-066 | RT: 3.38 min; MI: 460; Method 1 |
| XX-068 | RT: 2.52 min, MI: 414, Method: 2 |
| XX-069 | RT: 2.60 min, MI: 432, Method: 2 |
| XX-070 | RT: 2.53 min, MI: 432, Method: 2 |
| XX-071 | RT: 3.72 min, MI: 432, Method: 2 |
| XX-072 | RT: 3.68 min, MI: 432, Method: 2 |
| XX-073 | RT: 3.58 min, MI: 418, Method: 2 |
| XX-074 | RT: 2.57 min, MI: 432, Method: 2 |
| XX-075 | RT: 2.65 min, MI: 460, Method: 2 |
| XX-076 | RT: 2.66 min, MI: 460, Method: 2 |
| XX-077 | RT: 2.58 min, MI: 487, Method: 2 |
| XX-078 | RT: 2.42 min, MI: 434, Method: 2 |
| XX-079 | RT: 2.32 min, MI: 433, Method: 2 |
| XX-080 | RT: 2.52 min, MI: 459, Method: 2 |
| XX-081 | RT: 2.53 min, MI: 418, Method: 2 |
| XX-082 | RT: 2.66 min, MI: 427, Method: 2 |
| XX-083 | RT: 2.67 min, MI: 428, Method: 2 |
| XX-084 | RT: 2.60 min, MI: 441, Method: 2 |
| XX-085 | RT: 2.60 min, MI: 441, Method: 2 |
| XX-086 | RT: 2.59 min, MI: 400, Method: 2 |
| XX-087 | RT: 2.50 min, MI: 445, Method: 2 |
| XX-088 | RT: 2.50 min, MI: 404, Method: 2 |
| XX-002 | RT: 2.51 min, MI: 445, Method: 2 |

The following compounds were also synthesised using the same general method.

| Code No. | LCMS |
|---|---|
| XX-097 | RT: 2.44 min, MI: 460, Method: 2 |
| XX-094 | RT: 2.24 min, MI: 457, Method: 2 |
| XX-098 | RT: 2.47 min, MI: 474, Method: 2 |
| XX-099 | RT: 2.32 min, MI: 459, Method: 2 |
| XX-438 | RT: 2.57 min, MI: 480.33, Method: 2 |
| XX-439 | RT: 2.66 min, MI: 453.33, Method: 2 |
| XX-272 | RT: 1.91 min, MI: 503, Method: 2 |
| XX-100 | RT: 2.62 min, MI: 458, Method: 2 |
| XX-101 | RT: 2.38 min, MI: 473, Method: 2 |
| XX-102 | RT: 2.51 min, MI: 459, Method: 2 |
| XX-103 | RT: 2.59 min, MI: 432, Method: 2 |
| XX-104 | RT: 2.57 min, MI: 485, Method: 2 |
| XX-386 | RT: 2.45 min, MI: 458, Method: 2 |
| XX-105 | RT: 2.57 min, MI: 457, Method: 2 |
| XX-274 | RT: 2.57 min, MI: 446, Method: 2 |
| XX-300 | RT: 2.03 min, MI: 432 [M + 1]. |
| XX-326 | RT: 2.54 min, MI: 446, Method: 2 |
| XX-413 | RT: 2.87 min, MI: 506, Method: 2 |
| XX-411 | RT: 2.86 min, MI: 506, Method: 2 |
| XX-410 | RT: 2.52 min, MI: 476, Method: 2 |
| XX-412 | RT: 2.66 min, MI: 450, Metyhod2 |
| XX-416 | RT: 2.75 min, MI: 460, Method: 2 |
| XX-417 | RT: 2.76 min, MI: 466, Method: 2 |
| XX-418 | RT: 2.83 min, MI: 468, Method: 2 |
| XX-415 | RT: 2.75 min, MI: 446, Method: 2 |
| XX-414 | RT: 2.71 min, MI: 458, Method: 2 |
| XX-409 | RT: 2.49 min, MI: 463, Method: 2 |
| XX-106 | RT: 2.51 min, MI: 473, Method: 2 |

375
-continued

| Code No. | LCMS |
|---|---|
| XX-107 | RT: 2.58 min, MI: 471, Method: 2 |
| XX-108 | RT: 2.62 min, MI: 420, Method: 2 |
| XX-109 | RT: 2.61 min, MI: 485, Method: 2 |
| XX-116 | RT: 2.64 min, MI: 457, Method: 2 |
| XX-117 | RT: 2.62 min, MI: 471, Method: 2 |
| XX-118 | RT: 2.58 min, MI: 418, Method: 2 |
| XX-275 | RT: 2.59 min, MI: 486, Method: 2 |
| XX-119 | RT: 2.58 min, MI: 473, Method: 2 |
| XX-120 | RT: 2.63 min, MI: 473, Method: 2 |
| XX-408 | RT: 2.49 min, MI: 447, Method: 2 |
| XX-121 | RT: 2.65 min, MI: 485, Method: 2 |
| XX-122 | RT: 2.58 min, MI: 487, Method: 2 |
| XX-387 | RT: 2.51 min, MI: 483 [M + 1], Method: 2 |
| XX-123 | RT: 2.61 min, MI: 499, Method: 2 |
| XX-124 | RT: 2.66 min, MI: 487, Method: 2 |
| XX-388 | RT: 2.80 min, MI: 458, Method: 2 |
| XX-125 | RT: 2.67 min, MI: 499, Method: 2 |
| XX-126 | RT: 2.68 min, MI: 460, Method: 2 |
| XX-127 | RT: 2.59 min, MI: 459, Method: 2 |
| XX-128 | RT: 2.66 min, MI: 459, Method: 2 |
| XX-129 | RT: 2.41 min, MI: 485, Method: 2 |
| XX-130 | RT: 2.63 min, MI: 473, Method: 2 |
| XX-131 | RT: 2.65 min, MI: 485, Method: 2 |
| XX-132 | RT: 2.63 min, MI: 488, Method: 2 |
| XX-133 | RT: 2.68 min, MI: 476, Method: 2 |
| XX-134 | RT: 2.71 min, MI: 476, Method: 2 |
| XX-135 | RT: 2.57 min, MI: 485, Method: 2 |
| XX-136 | RT: 2.62 min, MI: 485, Method: 2 |
| XX-139 | RT: 2.63 min, MI: 471, Method: 2 |
| XX-140 | RT: 2.71 min, MI: 471, Method: 2 |
| XX-144 | RT: 2.55 min, MI: 467, Method: 2 |
| XX-145 | RT: 2.66 min, MI: 493, Method: 2 |
| XX-153 | RT: 2.58 min, MI: 485, Method: 2 |
| XX-154 | RT: 2.63 min, MI: 471, Method: 2 |
| XX-155 | RT: 2.64 min, MI: 446, Method: 2 |
| XX-160 | RT: 4.24 min, MI: 488, Method: 2 |
| XX-161 | RT: 3.90 min, MI: 448, Method: 2 |
| XX-162 | RT: 2.57 min, MI: 461, Method: 2 |
| XX-163 | RT: 2.39 min, MI: 461, Method: 2 |
| XX-173 | RT: 2.66 min, MI: 523, Method: 2 |
| XX-226 | RT: 2.75 min, MI: 474, Method: 2 |
| XX-355 | RT: 2.71 min, MI: 471, Method: 2 |
| XX-368 | RT: 2.62 min, MI: 487, Method: 2 |
| XX-390 | RT: 2.66 min, MI: 471, Method: 2 |
| XX-391 | RT: 2.66 min, MI: 487, Method: 2 |
| XX-393 | RT: 2.69 min, MI: 457, Method: 2 |
| XX-392 | RT: 4.50 min, MI: 473, Method: basic |
| XX-093 | RT: 2.66 min; MI: 471; Method: 2 |
| XX-095 | RT: 2.63 min; MI: 501; Method: 2 |
| XX-096 | RT: 2.71 min; MI: 473; Method: 2 |
| XX-110 | RT: 2.57 min, MI: 485; Method: 2 |
| XX-111 | RT: 2.43 min, MI: 471; Method: 2 |
| XX-112 | RT: 2.54 min, MI: 462; Method: 2 |
| XX-113 | RT: 2.55 min, MI: 485; Method: 2 |
| XX-114 | RT: 2.45 min, MI: 471; Method: 2 |
| XX-147 | RT: 2.45 min, MI: 459; Method: 2 |
| XX-150 | RT: 2.61 min, MI: 430; Method: 2 |
| XX-159 | RT: 2.57 min, MI: 400; Method: 2 |

General Synthesis Procedure R

Compounds were synthesised starting from 2-{4-[5-(4-aryl)-[1,2,4]triazolo[1,5-a]pyridin-2-ylamino]-phenoxy}-ethanol, for example, 2-{4-[5-(4-methoxy-phenyl)-[1,2,4]triazolo[1,5-a]pyridin-2-ylamino]-phenoxy}-ethanol (XX-011, described above), following the scheme illustrated below. In general, after conversion of the terminal alcohol into a leaving group such as a mesylate, displacement by an amine may be performed under microwave conditions or thermal conditions.

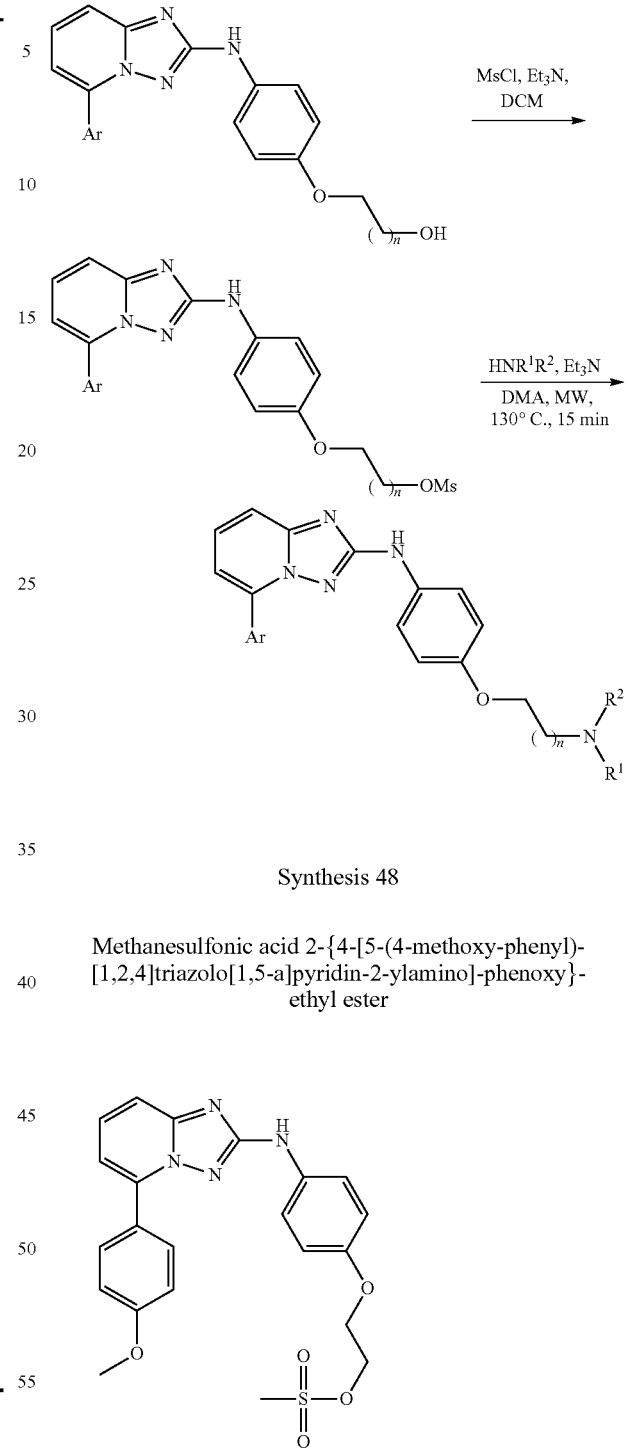

Scheme 32

Synthesis 48

Methanesulfonic acid 2-{4-[5-(4-methoxy-phenyl)-[1,2,4]triazolo[1,5-a]pyridin-2-ylamino]-phenoxy}-ethyl ester

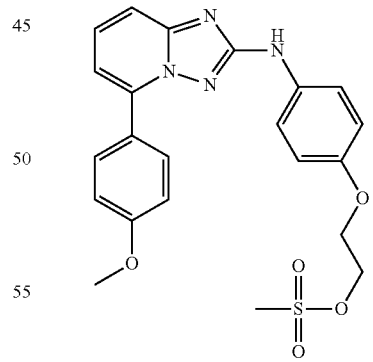

2-{4-[5-(4-Methoxy-phenyl)-[1,2,4]triazolo[1,5-a]pyridin-2-ylamino]-phenoxy}-ethanol (XX-011) (0.48 g, 1.26 mmol) was dissolved in dichloromethane (20 mL). Triethyl amine (0.805 mL, 5.8 mmol) was added and the mixture cooled to 0° C., then methanesulfonyl chloride (0.39 mL, 5.05 mmol) was added dropwise and the reaction was allowed to warm to room temperature. The reaction mixture was washed with 5% sodium hydrogencarbonate, dried over magnesium sulfate and concentrated in vacuo and used without further purification. LCMS method: 1, RT: 5.11 min, MI: 455 [M+1].

Synthesis 49

{4-[2-(Benzyl-methyl-amino)-ethoxy]phenyl}-[5-(4-methoxy-phenyl)-[1,2,4]triazolo[1,5-a]pyridin-2-yl]-amine (XX-025)

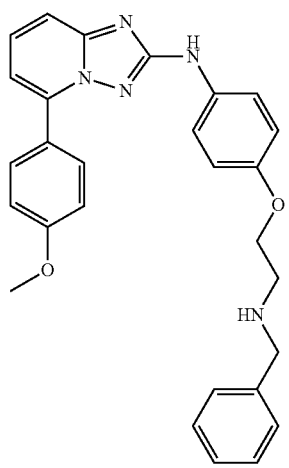 [SMILES: COc1ccc(-c2cccc3nc(Nc4ccc(OCCNCc5ccccc5)cc4)nn23)cc1]

Methanesulfonic acid 2-{4-[5-(4-methoxy-phenyl)-[1,2,4]triazolo[1,5-a]pyridin-2-ylamino]-phenoxy}-ethyl ester (0.05 g, 0.11 mmol) was dissolved in dimethylacetamide (1 mL). N-Benzylmethylamine (0.071 mL, 0.55 mmol) and triethylamine (0.076 mL, 0.55 mmol) were added and the reaction was heated to 130° C. for 15 minutes in the microwave. The reaction mixture was transferred to a vial and purified by preparatory HPLC. LCMS method: 2, RT: 2.86 min, MI: 466 [M+1].

The following compounds were synthesised using the same general method.

| Code No. | Characterisation |
| --- | --- |
| XX-025 | RT: 2.86 min, MI: 466, Method: 2 |
| XX-026 | RT: 2.53 min, MI: 420, Method: 2 |
| XX-027 | RT: 2.37 min, MI: 447, Method: 2 |
| XX-028 | RT: 2.68 min, MI: 453, Method: 2 |
| XX-029 | RT: 2.70 min, MI: 467, Method: 2 |
| XX-030 | RT: 2.72 min, MI: 471, Method: 2 |
| XX-031 | RT: 2.61 min, MI: 434, Method: 2 |
| XX-032 | RT: 2.54 min, MI: 467, Method: 2 |
| XX-033 | RT: 2.52 min, MI: 467, Method: 2 |
| XX-034 | RT: 2.57 min, MI: 481, Method: 2 |
| XX-067 | RT: 2.57 min, MI: 495, Method: 2 |
| XX-065 | RT: 2.50 min, MI: 434, Method: 2 |
| XX-064 | RT: 2.77 min, MI: 480, Method: 2 |

The following compounds were also synthesised using the same general method.

| Code No. | LCMS |
| --- | --- |
| XX-157 | RT: 2.62 min, MI: 476, Method: 2 |
| XX-158 | RT: 2.95 min, MI: 494, Method: 2 |
| XX-312 | RT: 2.65 min, MI: 472, Method: 2 |
| XX-329 | RT: 2.66 min, MI: 474, Method: 2 |

General Synthesis Procedure S

Compound was synthesised starting from {4-[5-(4-methoxy-phenyl)-[1,2,4]triazolo[1,5-a]pyridin-2-ylamino]-phenyl-carbamic acid tert-butyl ester (described above) following the scheme illustrated below. In general, the Boc group may be cleaved utilising trifluoroacetic acid or other suitable conditions known to one skilled in the art.

Scheme 33

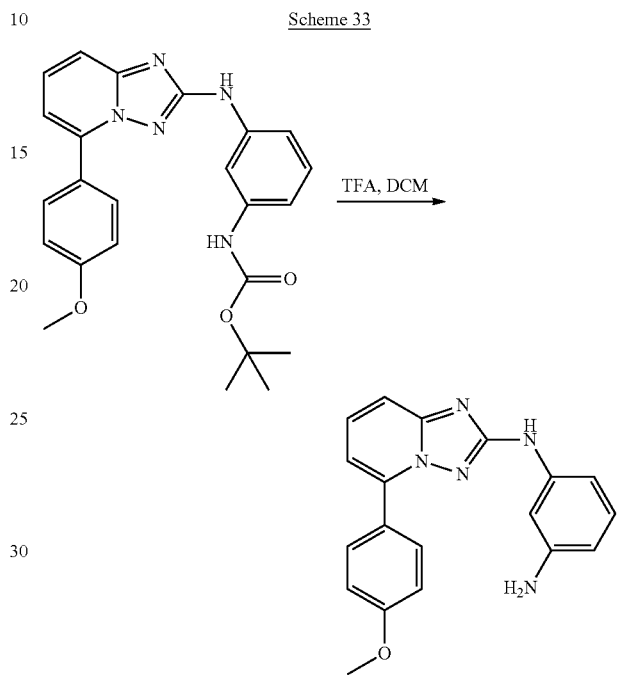

Synthesis 50

N-[5-(4-Methoxy-phenyl)-[1,2,4]triazolo[1,5-a]pyridin-2-yl]-benzene-1,3-diamine (XX-061)

{4-[5-(4-Methoxy-phenyl)-[1,2,4]triazolo[1,5-a]pyridin-2-ylamino]-phenyl-carbamic acid tert-butyl ester (0.08 g, 0.186 mmol) was dissolved in dichloromethane (3 ml) and trifluoroacetic acid (1 ml) was added. The mixture was stirred for 3 hours at room temperature then neutralised with saturated aqueous sodium hydrogencarbonate and extracted twice with ethyl acetate. The organics were combined, dried over anhydrous magnesium sulfate and concentrated in vacuo. The residue was dissolved in dimethylacetamide and purified by prep LCMS. LCMS method: 2, RT: 2.91 min, MI: 332.

The following compound was synthesised using the same general method.

| Code No. | Characterisation |
|---|---|
| XX-061 | RT: 2.91 min, MI: 332, Method: 2 |

General Synthesis Procedure T

Compounds were synthesised starting from the Boc protected 5-aryl(4-piperazin-1-yl-phenyl)-[1,2,4]triazolo[1,5-a]pyridin-2-yl-amine (described above) following the scheme illustrated below. In general, the Boc group may be cleaved utilising trifluoroacetic acid or other suitable conditions known to one skilled in the art.

Scheme 34

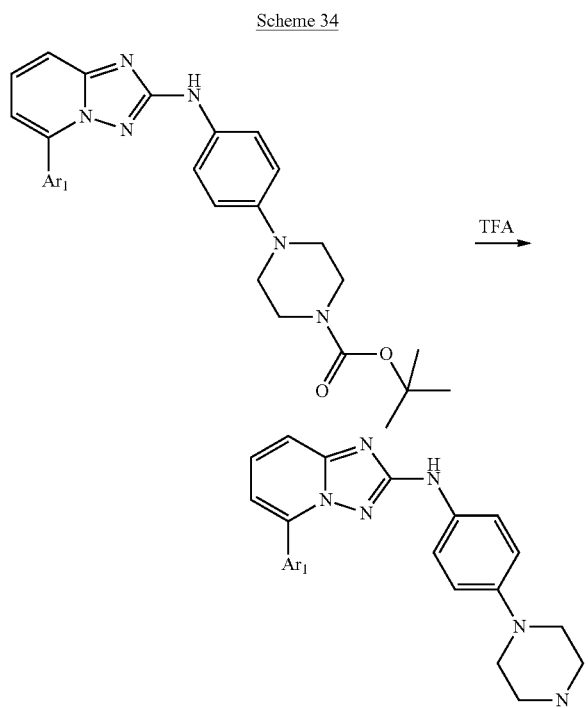

Synthesis 51

[5-(4-Methoxy-phenyl)-[1,2,4]triazolo[1,5-a]pyridin-2-yl]-(4-piperazin-1-yl-phenyl)-amine (XX-023)

A solution of 5-(4-methoxy-phenyl)-[1,2,4]triazolo[1,5-a]pyridin-2-ylamine (XX-009) (0.05 g, 0.208 mmol) in trifluoroacetic acid (1 mL) was stirred for 2 hours. Saturated sodium hydrogencarbonate was added to neutrality and the mixture was extracted with ethyl acetate. The crude product was purified by preparatory HPLC. LCMS Method: 2, RT: 3.18 min; MI: 401 [M+1]. NMR 1H (DMSO): 2.47-2.52 (m, 4H), 3.08-3.15 (m, 4H), 3.86 (s, 3H), 6.93 (d, 2H), 7.09-7.15 (m, 3H), 7.47 (dd, 1H), 7.55-7.61 (m, 3H), 8.02 (d, 2H), 9.37 (s, 1H)

The following compounds were synthesised using the same general method.

| Code No. | Characterisation |
|---|---|
| XX-023 | RT: 3.18 min; MI: 401; Method: 2 |
| XX-058 | RT: 2.59 min, MI: 411, Method: 2 |
| XX-060 | RT: 2.51 min, MI: 429, Method: 2 |
| XX-059 | RT: 2.51 min, MI: 413, Method: 2 |

General Synthesis Procedure U

Compounds were synthesised starting from the phthalimido-[5-(4-methoxy-phenyl)-[1,2,4]triazolo[1,5-a]pyridin-2-yl]-phenyl-amines (described above) following the scheme illustrated below. In general, the phthalimido group may be removed by hydrazinolysis in a refluxing solvent such as ethanol.

Scheme 35

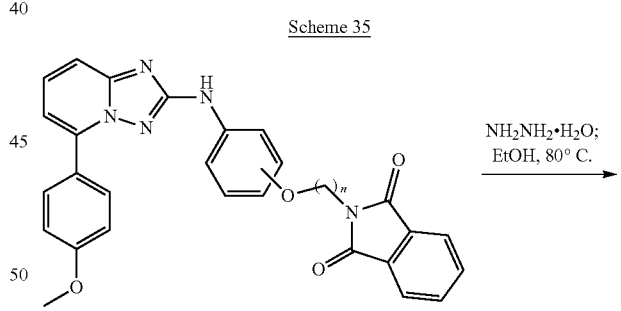

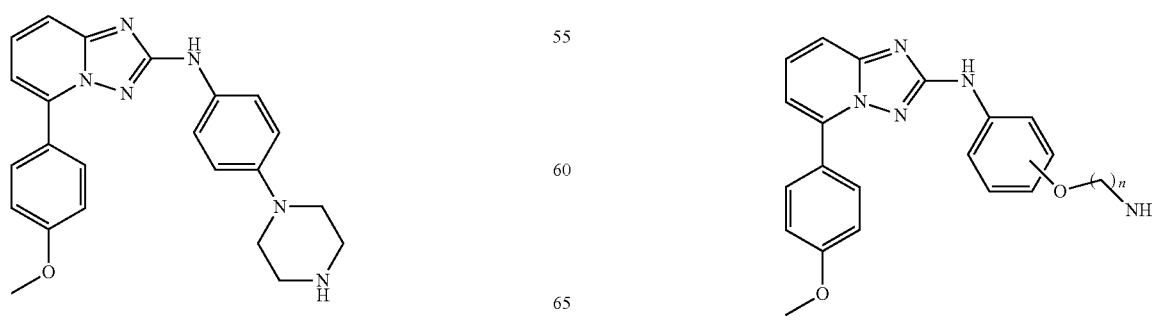

Synthesis 52

[4-(3-Amino-propoxy)-phenyl]-[5-(4-methoxy-phenyl)-[1,2,4]triazolo[1,5-a]pyridin-2-yl]-amine (XX-041)

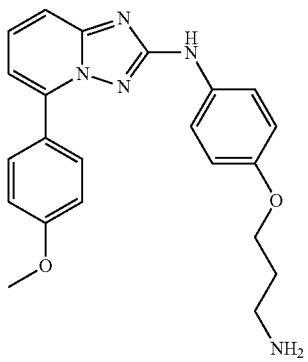 [SMILES: COc1ccc(-c2cccc3nc(Nc4ccc(OCCCN)cc4)nn23)cc1]

To a solution of 2-(3-{4-[5-(4-methoxy-phenyl)-[1,2,4]triazolo[1,5-a]pyridin-2-ylamino]-phenoxy}-propyl)-isoindole-1,3-dione (XX-039) (0.1 g, 0.192 mmol) in ethanol (2 mL), hydrazine hydrate (0.05 mL, 0.192 mmol) was added and the solution was refluxed overnight. After removal of the volatiles under reduced pressure, the crude product was purified by preparatory HPLC. LCMS Method: 2: RT: 2.62 min, MI: 390 [M+1].

The following compounds were synthesised using the same general method.

| Code No. | Characterisation |
|---|---|
| XX-046 | RT: 2.52 min, MI: 376, Method: 2 |
| XX-045 | RT: 2.62 min, MI: 390, Method: 2 |
| XX-041 | RT: 2.53 min; MI: 390; Method 1 |

General Synthesis Procedure V

Compounds were synthesised starting from the [5-(2,3-dihydro-benzo[1,4]dioxin-6-yl)-[1,2,4]triazolo[1,5-a]pyridin-2-yl]-[(3-dimethylamino-propenyl)-phenyl]-amines (described above) following the scheme illustrated below. In general, the alkene may be reduced using palladium catalysed hydrolysis in a solvent such as ethanol.

Scheme 36

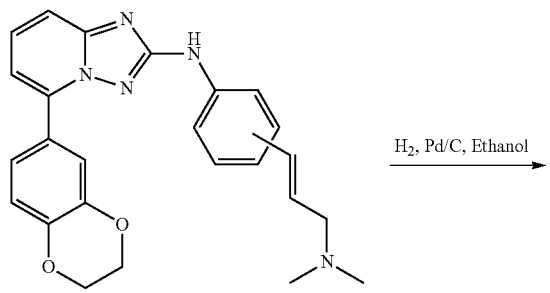

H₂, Pd/C, Ethanol

-continued

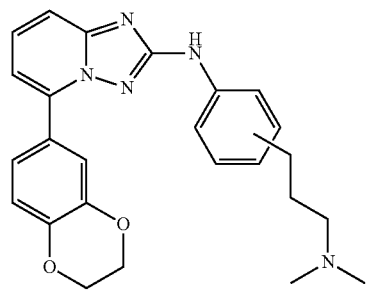

Synthesis 53

[5-(2,3-Dihydro-benzo[1,4]dioxin-6-yl)-[1,2,4]triazolo[1,5-a]pyridin-2-yl]-[3-(3-dimethylamino-propyl)-phenyl]-amine (XX-115)

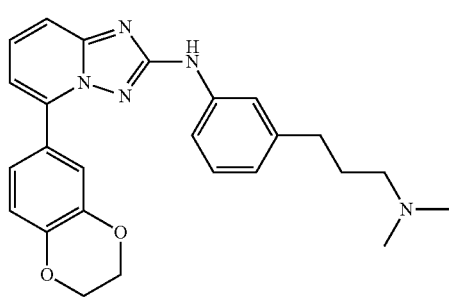 [SMILES: CN(C)CCCc1cccc(Nc2nc3cccc(-c4ccc5c(c4)OCCO5)n3n2)c1]

[5-(2,3-Dihydro-benzo[1,4]dioxan-6-yl)-[1,2,4]triazolo[1,5-a]pyridin-2-yl]-[3-((E)-3-dimethylamino-propenyl)-phenyl]-amine (80 mg, 0.186 mmol) was dissolved in degassed ethanol (10 ml) and 5% palladium on carbon (50 mg) was added. The flask was evacuated then back-filled with nitrogen, which was repeated 3 times and the flask evacuated one final time. A balloon of hydrogen was attached to the flask and the solution was stirred overnight. The reaction was filtered through celite, washed with ethyl acetate and concentrated in vacuo then purified by prep LCMS. LCMS Method: 2, RT: 2.64 min; MI: 430 [M+1].

The following compounds were synthesised using the same general method.

| Code No. | LCMS |
|---|---|
| XX-115 | RT: 2.64 min, MI: 430, Method: 2 |
| XX-137 | RT: 2.72 min, MI: 430, Method: 2 |

General Synthesis Procedure W

Compounds were synthesised starting from boc-protected (2-{4-[5-(2,3-dihydro-benzo[1,4]dioxin-6-yl)-[1,2,4]triazolo[1,5-a]pyridin-2-ylamino]phenoxy}-alkyl)-carbamic acid tert-butyl esters (described above) following the scheme illustrated below. In general, the Boc group may be cleaved utilising MP-TsOH or trifluoroacetic acid or other suitable conditions known to one skilled in the art.

Scheme 37

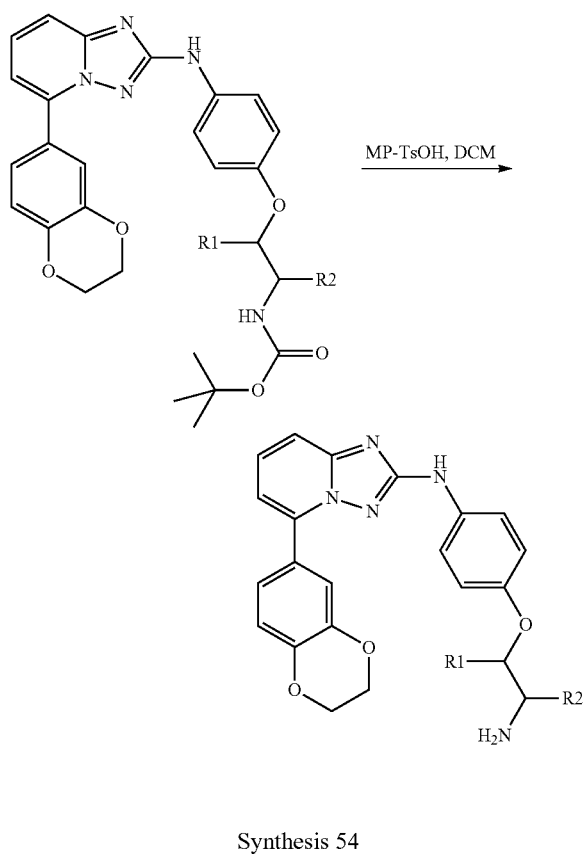

Synthesis 54

[4-((S)-2-Amino-propoxy)-phenyl]-[5-(2,3-dihydro-benzo[1,4]dioxin-6-yl)-[1,2,4]triazolo[1,5-a]pyridin-2-yl]-amine (XX-143)

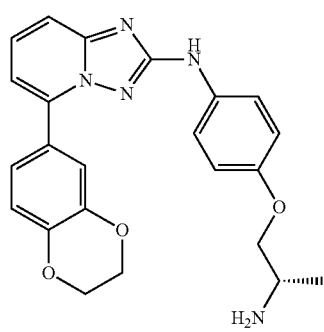 [SMILES: C[C@H](N)COc1ccc(Nc2nc3cccc(-c4ccc5c(c4)OCCO5)n3n2)cc1]

((S)-2-{4-[5-(2,3-Dihydro-benzo[1,4]dioxin-6-yl)-[1,2,4]triazolo[1,5-a]pyridin-2-ylamino]-phenoxy}-propyl)-carbamic acid tert-butyl ester (100 mg, 0.196 mmol) was dissolved in dichloromethane (4 ml) and MP-TsOH (1 g, 3.23 mmol) added. The mixture was shaken overnight at room temperature. The resin was collected by filtration and washed with methanol. The product was then cleaved from the resin with 2M ammonia in methanol. The eluant was concentrated in vacuo and the product was purified by prep LCMS.

The following compounds were synthesised using the same general method.

| Code No. | LCMS |
|---|---|
| XX-138 | RT: 2.6 min, MI: 418, Method: 2 |
| XX-141 | RT: 2.6 min, MI: 418, Method: 2 |
| XX-142 | RT: 2.51 min, MI: 418, Method: 2 |
| XX-143 | RT: 2.59 min, MI: 418, Method: 2 |

General Synthesis Procedure X

Compounds were synthesised starting from 5-bromo-[1,2,4]triazolo[1,5-a]pyridin-2-ylamine following the scheme illustrated below. In general, stirring the starting material with sodium thiomethoxide in dimethylformamide at 60° C. formed the methylsulfanyl derivative. This was then followed by a Buchwald reaction to introduce the first aryl group and subsequently a copper-mediated Suzuki type reaction to introduce the second aryl group.

Scheme 38

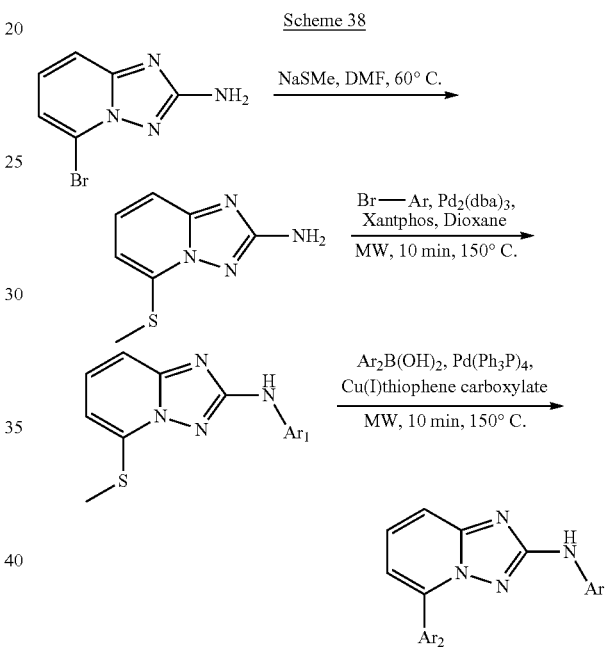

Synthesis 55

5-Methylsulfanyl-[1,2,4]triazolo[1,5-a]pyridin-2-ylamine

To a stirred solution of 5-bromo-[1,2,4]triazolo[1,5-a]pyridin-2-ylamine (20 g, 93.9 mmol) in dimethylformamide (60 mL) was added sodium thiomethoxide (8.60 g, 122 mmol) portionwise, and the reaction mixture was stirred at 60° C. for 2 hours. The mixture was allowed to cool, water added (350 mL) and the product collected by filtration to afford the expected compound as a white solid. No further purification was required. Yield: 15.7 g, 93%; LCMS method: 3, RT: 1.38 min, MI: 181 [M+1].

Synthesis 56

(5-Methylsulfanyl-[1,2,4]triazolo[1,5-a]pyridin-2-yl)-[4-(2-pyrrolidin-1-yl-ethoxy)-phenyl]-amine

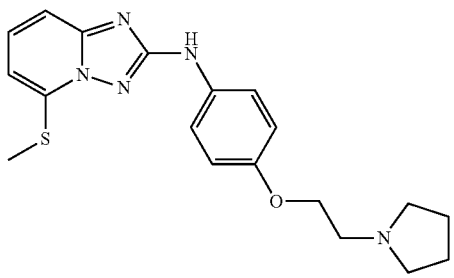 [SMILES: CSc1cccc2nc(Nc3ccc(OCCN4CCCC4)cc3)nn12]

A microwave vial containing 5-methylsulfanyl-[1,2,4]triazolo[1,5-a]pyridin-2-ylamine (13.5 g, 74.9 mmol), 1-(2-(4-bromophenoxy)ethyl)pyrrolidine (20.2 mL, 97.3 mmol), tris(dibenzylideneacetone)dipalladium (3.42 g, 3.74 mmol), xantphos (4.33 g, 7.49 mmol), sodium tert-butoxide (14.7 g, 150 mmol) and 1,4-dioxane (90 mL) was heated under microwave radiation (150° C., 10 min). N,N-Dimethylacetamide (1 mL) was added to assist with microwave absorption. The volatiles were removed under rotary evaporation and the product then purified by graduated flash column chromatography (2-10% methanol: dichloromethane) to provide a pale brown solid. Yield: 19.3 g, 70%; LCMS method: 2, RT: 2.28 min, MI: 370 [M+1]. $^1$H NMR (CDCl$_3$, 300 MHz): 7.53 (d, 2H), 7.40 (d 1H), 7.26 (d, 1H), 7.10 (s, 1H), 6.93 (d 2H), 6.64 (d, 1H), 4.11 (t, 2H), 2.90 (t, 2H), 2.64 (s, 7H), 1.81 (s, 4H).

Synthesis 57

[5-(4-Methanesulfonyl-phenyl)-[1,2,4]triazolo[1,5-a]pyridin-2-yl]-[4-(2-pyrrolidin-1-yl-ethoxy)-phenyl]-amine (XX-215)

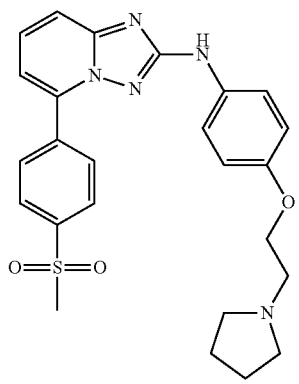

(5-Methylsulfanyl-[1,2,4]triazolo[1,5-a]pyridin-2-yl)-[4-(2-pyrrolidin-1-yl-ethoxy)-phenyl]-amine (50 mg, 0.135 mmol), 4-methanesulfonyloxybenzeneboronic acid (60 mg, 0.300 mmol), copper(1)thiophene carboxylate (575 mg, 0.300 mmol), tetrakis(triphenylphosphine)palladium (16 mg, 0.014 mmol) and tetrahydrofuran (1.2 mL) were added to a microwave tube containing a stirrer bar. The mixture was heated under microwave irradiation to 150° C. for 10 min. The reaction mixture was loaded onto an SCX cartridge, which was washed with methanol and the product subsequently eluted with 2M ammonia in methanol. Having removed all solvents under rotary evaporation, the product was purified by preparatory HPLC. LCMS method: 3, RT: 2.39 min, MI: 478 [M+1]. $^1$H NMR (CDCl$_3$, 300 MHz): 8.54 (s, 1H), 8.25 (d, 2H), 8.13 (d, 2H), 7.55 (d, 2H), 7.47 (d, 2H), 7.03 (t, 1H), 6.92 (t, 3H), 4.24 (t, 2H), 3.19 (t, 2H), 3.16 (s, 3H), 3.02 (s, 4H), 1.89 (s, 4H).

The following compounds were synthesised using the same general method.

| Code No. | Characterisation |
| --- | --- |
| XX-216 | RT: 3.06 min, MI: 476, Method: 3 |
| XX-419 | RT: 2.67 min, MI: 486, Method: 2 |
| XX-420 | RT: 2.92 min, MI: 486.32, Method: 2 |
| XX-421 | RT: 2.84 min, MI: 460.33, Method: 2 |
| XX-422 | RT: 3.14 min, MI: 484.3, Method: 2 |
| XX-423 | RT: 2.68 min, MI: 508.37, Method: 2 |
| XX-213 | RT: 2.63 min, MI: 414, Method: 2 |
| XX-201 | RT: 2.56 min, MI: 406, Method: 2 |
| XX-215 | RT: 2.39 min, MI: 478, Method: 3 |
| XX-200 | RT: 2.37 min, MI: 431, Method: 2 |
| XX-217 | RT: 2.57 min, MI: 444, Method: 3 |
| XX-212 | RT: 2.73 min, MI: 414, Method: 2 |
| XX-218 | RT: 2.81 min, MI: 468, Method: 3 |
| XX-361 | RT: 2.41 min, MI: 433, Method: 2 |
| XX-219 | RT: 2.03 min, MI: 401, Method: 3 |
| XX-237 | RT: 2.32 min, MI: 430, Method: 3 |
| XX-090 | RT: 2.33 min, MI: 430, Method: 3 |
| XX-239 | RT: 2.36 min, MI: 471, Method: 3 |
| XX-236 | RT: 2.48 min, MI: 443, Method: 2 |
| XX-240 | RT: 2.66 min, MI: 448, Method: 3 |
| XX-241 | RT: 2.36 min, MI: 457, Method: 3 |
| XX-362 | RT: 2.63 min, MI: 435, Method: 2 |
| XX-347 | RT: 2.72 min, MI: 467.35, Method: 2 |
| XX-242 | RT: 2.87 min, MI: 450, Method: 3 |
| XX-357 | RT: 2.43 min, MI: 433, Method: 2 |
| XX-243 | RT: 2.46 min, MI: 434, Method: 3 |
| XX-244 | RT: 2.90 min, MI: 484, Method: 3 |
| XX-207 | RT: 2.78 min, MI: 458, Method: 2 |
| XX-363 | RT: 2.34 min, MI: 442, Method: 2 |
| XX-358 | RT: 2.38 min, MI: 447, Method: 2 |
| XX-210 | RT: 2.61 min, MI: 434, Method: 2 |
| XX-245 | RT: 2.52 min, MI: 460, Method: 3 |
| XX-208 | RT: 2.62 min, MI: 442, Method: 2 |
| XX-246 | RT: 2.55 min, MI: 490, Method: 3 |
| XX-247 | RT: 3.04 min, MI: 492, Method: 3 |
| XX-209 | RT: 2.66 min, MI: 472, Method: 2 |
| XX-248 | RT: 2.01 min, MI: 471, Method: 3 |
| XX-211 | RT: 2.45 min, MI: 434, Method: 2 |
| XX-206 | RT: 2.67 min, MI: 443, Method: 2 |
| XX-156 | RT: 2.82 min, MI: 515, Method: 2 |
| XX-199 | RT: 2.64 min, MI: 458, Method: 2 |
| XX-269 | RT: 2.30 min, MI: 457, Method: 2 |
| XX-205 | RT: 2.37 min, MI: 457, Method: 2 |
| XX-270 | RT: 2.63 min, MI: 480, Method: 2 |
| XX-278 | RT: 3.02 min, MI: 506, Method: 2 |
| XX-279 | RT: 2.79 min, MI: 428, Method: 2 |
| XX-359 | RT: 2.42 min, MI: 451, Method: 2 |
| XX-280 | RT: 2.78 min, MI: 432, Method: 2 |
| XX-204 | RT: 2.09 min, MI: 415, Method: 2 |
| XX-281 | RT: 2.51 min, MI: 439, Method: 2 |
| XX-282 | RT: 2.80 min, MI: 451, Method: 2 |
| XX-283 | RT: 2.37 min, MI: 478, Method: 2 |
| XX-360 | RT: 2.66 min, MI: 461, Method: 2 |
| XX-291 | RT: 2.89 min, MI: 502, Method: 2 |
| XX-194 | RT: 2.54 min, MI: 430, Method: 2 |
| XX-292 | RT: 2.82 min, MI: 428, Method: 2 |
| XX-293 | RT: 2.88 min, MI: 440, Method: 2 |
| XX-364 | RT: 2.77 min, MI: 443, Method: 2 |
| XX-195 | RT: 2.81 min, MI: 468, Method: 2 |
| XX-294 | RT: 2.88 min, MI: 456, Method: 2 |

387
-continued

| Code No. | Characterisation |
|---|---|
| XX-297 | RT: 2.86 min, MI: 468, Method: 2 |
| XX-298 | RT: 2.87 min, MI: 468, Method: 2 |
| XX-299 | RT: 2.69 min, MI: 440, Method: 2 |
| XX-365 | RT: 2.73 min, MI: 458, Method: 2 |
| XX-214 | RT: 3.02 min, MI: 470, Method: 2 |
| XX-235 | RT: 2.43 min, MI: 431, Method: 2 |
| XX-202 | RT: 2.29 min, MI: 390, Method: 2 |
| XX-089 | RT: 2.73 min, MI: 472, Method: 2 |
| XX-331 | RT: 5.05 min, MI: 458, Method: basic |
| XX-333 | RT: 2.62 min, MI: 460, Method: 2 |
| XX-334 | RT: 2.73 min, MI: 448, Method: 2 |
| XX-196 | RT: 2.49 min, MI: 434, Method: 2 |
| XX-335 | RT: 3.04 min, MI: 536, Method: 2 |
| XX-336 | RT: 3.10 min, MI: 540, Method: 2 |
| XX-337 | RT: 2.79 min, MI: 444, Method: 2 |
| XX-338 | RT: 3.08 min, MI: 536, Method: 2 |
| XX-339 | RT: 3.16 min, MI: 540, Method: 2 |
| XX-340 | RT: 3.07 min, MI: 536 Method: 2 |
| XX-183 | RT: 2.18 min, MI: 443, Method: 2 |
| XX-197 | RT: 2.32 min, MI: 432, Method: 2 |
| XX-198 | RT: 2.07 min, MI: 444, Method: 2 |
| XX-203 | RT: 2.55 min, MI: 390, Method: 2 |

General Synthesis Procedure Y

Compounds were synthesised starting from {5-[3-(4-methoxy-benzyloxy)-phenyl]-[1,2,4]triazolo[1,5-a]pyridin-2-yl}-[4-(2-pyrrolidin-1-yl-ethoxy)-phenyl]-amine or {5-[4-(4-methoxy-benzyloxy)-phenyl]-[1,2,4]triazolo[1,5-a]pyridin-2-yl}-[4-(2-pyrrolidin-1-yl-ethoxy)-phenyl]-amine (described above) following the scheme illustrated below. The para-methoxybenzyl group can be removed using trifluoroacetic acid or any other conditions known to one skilled in the art.

Scheme 39

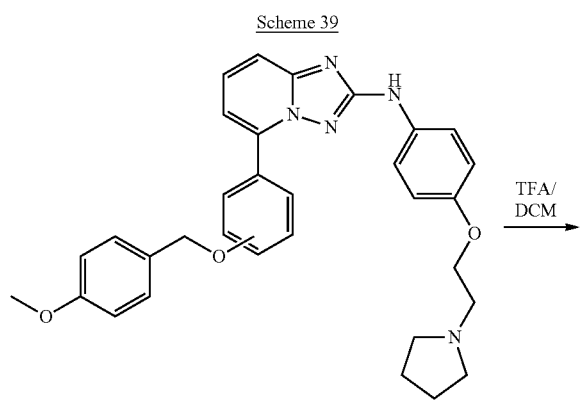

388
Synthesis 58

3-{2-[4-(2-Pyrrolidin-1-yl-ethoxy)-phenylamino]-[1,2,4]triazolo[1,5-a]pyridin-5-yl}-phenol (XX-256)

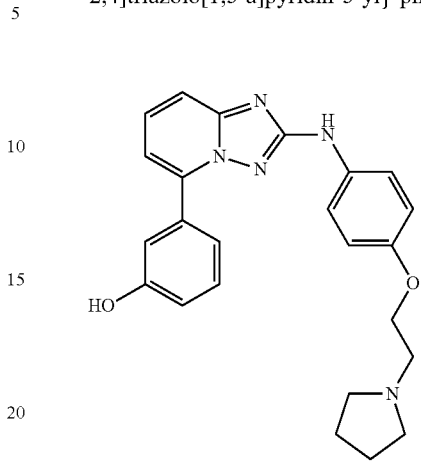

{5-[3-(4-Methoxy-phenoxy)-phenyl]-[1,2,4]triazolo[1,5-a]pyridin-2-yl}-[4-(2-pyrrolidin-1-yl-ethoxy)-phenyl]-amine (2.90 g, 5.41 mmol) was dissolved in dichloromethane (10 ml). Trifluoroacetic acid (10 ml) was added and the reaction mixture stirred for 2 hours. Neutralisation was performed by adding saturated aqueous sodium hydrogencarbonate. The aqueous was extracted twice with dichloromethane, then the combined organics were washed with brine, dried over anhydrous magnesium sulfate, filtered and concentrated in vacuo to give the desired compound. Yield 2.01 g, 89%. 50 mg was purified by preparatory HPLC.

The following compounds were synthesised using the same general method.

| Code No. | Characterisation |
|---|---|
| XX-256 | RT: 2.39 min, MI: 416, Method: 2 |
| XX-151 | RT: 2.40 min, MI: 416, Method: 2 |

General Synthetic Procedure Z

Compounds were synthesised starting from {2-[4-(2-pyrrolidin-1-yl-ethoxy)-phenylamino]-[1,2,4]triazolo[1,5-a]pyridin-5-yl}-phenols (described above) following the scheme below.

Scheme 40

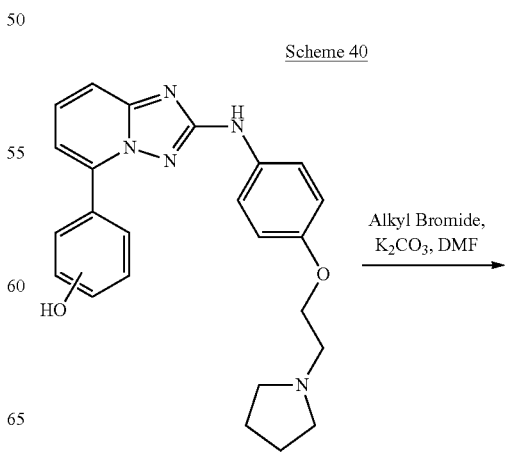

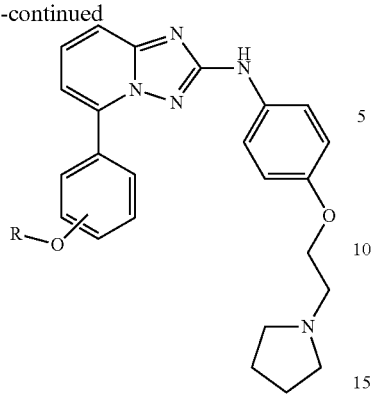

Synthesis 59

[4-(2-Pyrrolidin-1-yl-ethoxy)-phenyl]-{5-[3-(tetrahydro-furan-2-ylmethoxy)-phenyl]-[1,2,4]triazolo[1,5-a]pyridin-2-yl}-amine (XX-175)

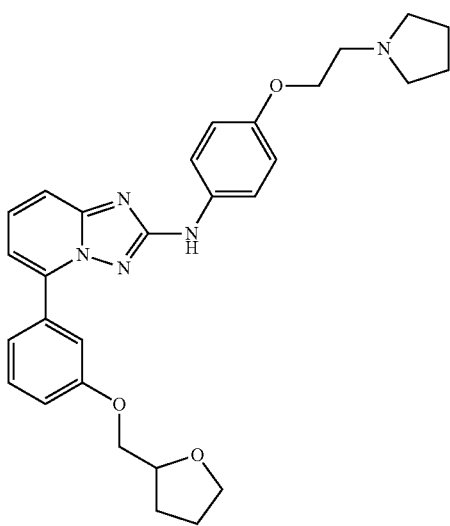 [SMILES: c1cc(OCC2CCCO2)cc(-c2cccc3nc(Nc4ccc(OCCN5CCCC5)cc4)nn23)c1]

Tetrahydrofurfuryl bromide (20 mg, 0.18 mmol) was added to a stirred solution of 3-{2-[4-(2-pyrrolidin-1-yl-ethoxy)-phenylamino]-[1,2,4]triazolo[1,5-a]pyridin-5-yl}-phenol (50 mg, 0.12 mmol) and potassium carbonate (25 mg, 0.18 mmol) in dimethylformamide (1.5 ml). The mixture was heated overnight at 80° C. then cooled and transferred to a vial for purification by preparatory HPLC. RT: 2.70 min, MI: 500.22, Method: 2.

The following compounds were synthesised using the same general method.

| Code No. | Characterisation |
| --- | --- |
| XX-175 | RT: 2.70 min, MI: 500, Method: 2 |
| XX-330 | RT: 2.82 min, MI: 540, Method: basic |
| XX-332 | RT: 3.86 min, MI: 508, Method: basic |
| XX-146 | RT: 2.76 min, MI: 500; Method: 2 |
| XX-148 | RT: 2.78 min, MI: 454, Method: 2 |
| XX-341 | RT: 2.56 min, MI: 448, Method: 2 |
| XX-400 | RT: 3.1 min, MI: 520, Method: 2 |
| XX-401 | RT: 3.21 min, MI: 574, Method: 2 |
| XX-402 | RT: 3.16 min, MI: 574, Method: 2 |
| XX-403 | RT: 2.85 min, MI: 563, Method: 2 |
| XX-404 | RT: 3.31 min, MI: 472, Method: 2 |
| XX-405 | RT: 5.26 min, MI: 458, Method: 2 |
| XX-406 | RT: 3.67 min, MI: 556, Method: 2 |
| XX-407 | RT: 3.23 min, MI: 560, Method: 2 |
| XX-457 | MI: 520.40, RT: 5.71 min, Method: basic |
| XX-458 | MI: 574.36, RT: 5.80 min, Method: basic |
| XX-459 | MI: 577.44, RT: 2.77 min, Method: 2 |
| XX-460 | MI: 524.40, RT: 2.63 min, Method: 2 |
| XX-461 | MI: 604.44, RT: 3.15 min, Method: 2 |

General Synthetic Procedure AA

Compounds were synthesised starting from {2-[4-(2-pyrrolidin-1-yl-ethoxy)-phenylamino]-[1,2,4]triazolo[1,5-a]pyridin-5-yl}-phenols (described above) following the scheme illustrated below. Triflate formation may be accomplished using N-phenyl-bis(trifluoromethanesulfonimide) or any other method known to one skilled in the art. The subsequent bi-aryl can be formed using Suzuki chemistry utilising tetrakis(triphenylphosphine)palladium or another suitable catalyst.

Scheme 41

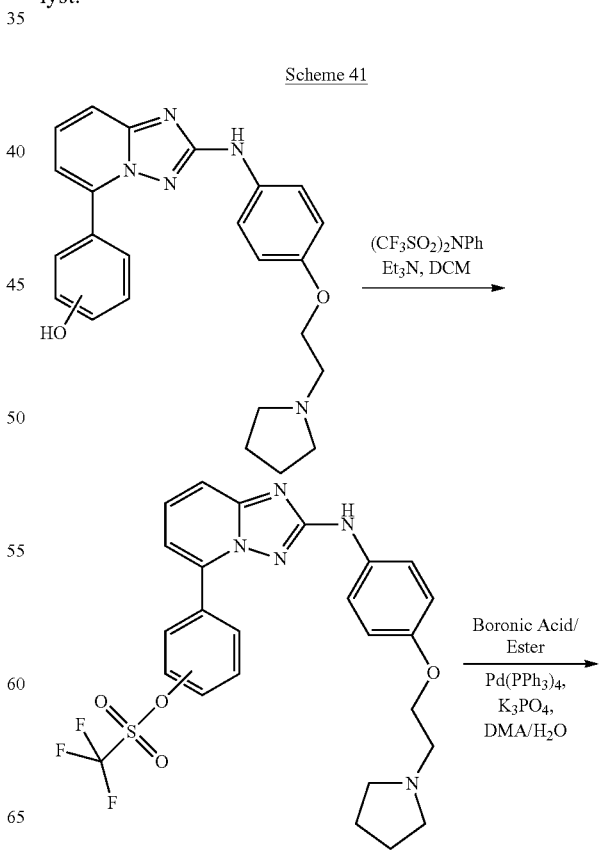

-continued

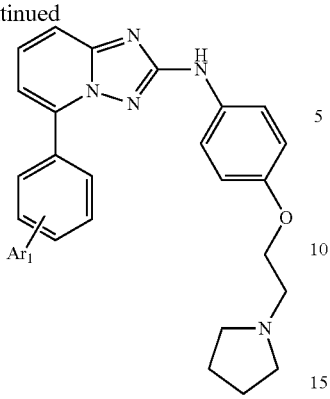

Synthesis 60

Trifluoro-methanesulfonic acid 3-{2-[4-(2-pyrrolidin-1-yl-ethoxy)-phenylamino]-[1,2,4]triazolo[1,5-a]pyridin-5-yl}-phenyl ester

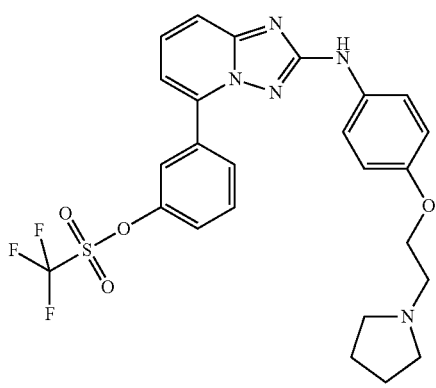 [SMILES: O=S(=O)(Oc1cccc(-c2cccc3nc(Nc4ccc(OCCN5CCCC5)cc4)nn23)c1)C(F)(F)F]

N-Phenyl-bis(trifluoromethanesulfonimide) (0.51 g, 1.44 mmol) was added to a stirred solution of 3-{2-[4-(2-pyrrolidin-1-yl-ethoxy)-phenylamino]-[1,2,4]triazolo[1,5-a]pyridin-5-yl}-phenol 0.4 g, 0.96 mmol) and triethylamine (0.27 ml, 1.92 mmol) in dichloromethane (20 ml). The mixture was stirred for 2 hours at room temperature. Water was added and the product extracted into dichloromethane (×2). The organics were combined, washed with brine, dried over anhydrous magnesium sulfate, filtered and concentrated in vacuo to give the desired product. Yield 0.53 g, 100%. LCMS RT: 5.08 min, MI: 548, Method: 2.

Synthesis 61

(5-Biphenyl-3-yl-[1,2,4]triazolo[1,5-a]pyridin-2-yl)-[4-(2-pyrrolidin-1-yl-ethoxy)-phenyl]-amine (XX-164)

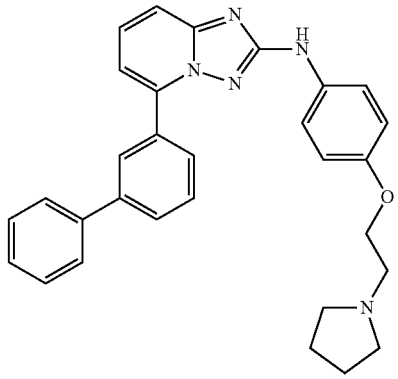 [SMILES: c1ccc(-c2cccc(-c3cccc4nc(Nc5ccc(OCCN6CCCC6)cc5)nn34)c2)cc1]

A microwave vial was charged with trifluoro-methanesulfonic acid 3-{2-[4-(2-pyrrolidin-1-yl-ethoxy)-phenylamino]-[1,2,4]triazolo[1,5-a]pyridin-5-yl}-phenyl ester (50 mg, 0.09 mmol), benzeneboronic acid (15 mg, 0.12 mmol), tetrakis(triphenylphosphine)palladium (10 mg, 0.009 mmol), potassium phosphate (0.5M in water, 0.36 ml, 0.18 mmol) and N,N'-dimethylacetamide (1 ml). The reaction was heated to 150° C. for 10 minutes under microwave irradiation. The mixture was then filtered through a plug of silica, washed with methanol and concentrated in vacuo. The product was purified by preparatory LCMS to yield the desired product. RT: 2.96 min, MI: 476.22, Method: 2

The following compounds were synthesised using the same general method.

| Code No. | Characterisation |
|---|---|
| XX-164 | RT: 2.96 min, MI: 476, Method: 2 |
| XX-188 | RT: 2.9 min, MI: 466, Method: 2 |
| XX-165 | RT: 2.82 min, MI: 466, Method: 2 |
| XX-185 | RT: 2.96 min, MI: 466, Method: 2 |
| XX-166 | RT: 2.91 min, MI: 482, Method: 2 |
| XX-167 | RT: 2.52 min, MI: 466, Method: 2 |
| XX-186 | RT: 2.96 min, MI: 482, Method: 2 |
| XX-187 | RT: 2.49 min, MI: 466, Method: 2 |
| XX-168 | RT: 2.86 min, MI: 466, Method: 2 |
| XX-191 | RT: 2.67 min, MI: 495, Method: 2 |
| XX-149 | RT: 2.62 min, MI: 480, Method: 2 |
| XX-189 | RT: 2.59 min, MI: 480, Method: 2 |
| XX-169 | RT: 2.58 min, MI: 480, Method: 2 |
| XX-190 | RT: 2.75 min, MI: 495, Method: 2 |
| XX-170 | RT: 2.62 min, MI: 508, Method: 2 |
| XX-171 | RT: 2.58 min, MI: 480, Method: 2 |
| XX-172 | RT: 2.66 min, MI: 494, Method: 2 |
| XX-463 | MI: 496.30, RT: 3.00 min, Method: 2 |
| XX-464 | MI: 495.32, RT: 2.66 min, Method: 2 |
| XX-465 | MI: 490.37, RT: 3.04 min, Method: 2 |
| XX-466 | MI: 478.30, RT: 2.22 min, Method: 2 |
| XX-467 | MI: 494.34, RT: 2.96 min, Method: 2 |
| XX-468 | MI: 506.35, RT: 2.93 min, Method: 2 |
| XX-469 | MI: 478.30, RT: 2.45 min, Method: 2 |

General Synthesis Procedure BB

Compounds were synthesised starting from (3-{2-[4-(2-pyrrolidin-1-yl-ethoxy)-phenylamino]-[1,2,4]triazolo[1,5-a]pyridin-5-yl}-phenyl)-carbamic acid tert-butyl ester (described above) following the scheme illustrated below. The Boc group can be removed using trifluoroacetic acid or any other conditions known to one skilled in the art.

Scheme 42

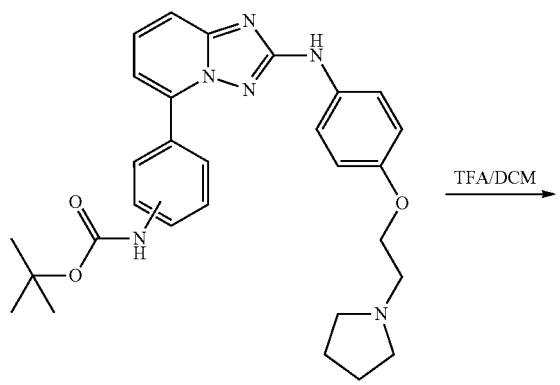

Synthesis 62

[5-(3-Amino-phenyl)-[1,2,4]triazolo[1,5-a]pyridin-2-yl]-[4-(2-pyrrolidin-1-yl-ethoxy)-phenyl]-amine (XX-255)

(3-{2-[4-(2-Pyrrolidin-1-yl-ethoxy)-phenylamino]-[1,2,4]triazolo[1,5-a]pyridin-5-yl}-phenyl)-carbamic acid tert-butyl ester (1.39 g, 2.71 mmol) was dissolved in dichloromethane (10 ml). Trifluoroacetic acid (10 ml) was added and the reaction mixture stirred for 2 hours. Neutralisation was performed by adding saturated aqueous sodium hydrogencarbonate. The aqueous phase was extracted twice with dichloromethane, and the combined organics washed with brine, dried over anhydrous magnesium sulgate, filtered and concentrated in vacuo to give the desired compound. Yield 830 mg, 74%. 50 mg was purified by preparatory LCMS.

The following compounds were synthesised using the same general method.

| Code No. | Characterisation |
| --- | --- |
| XX-255 | RT: 2.17 min, MI: 415, Method: 2 |
| XX-184 | RT: 2.32 min, MI: 415, Method: 2 |

General Synthetic Procedure BB

Compounds were synthesised starting from {2-[4-(2-pyrrolidin-1-yl-ethoxy)-phenylamino]-[1,2,4]triazolo[1,5-a]pyridin-5-yl}-amines following the scheme illustrated below. Reaction of the aniline with an acyl chloride can be performed in the presence of triethylamine to generate the corresponding amide.

Scheme 43

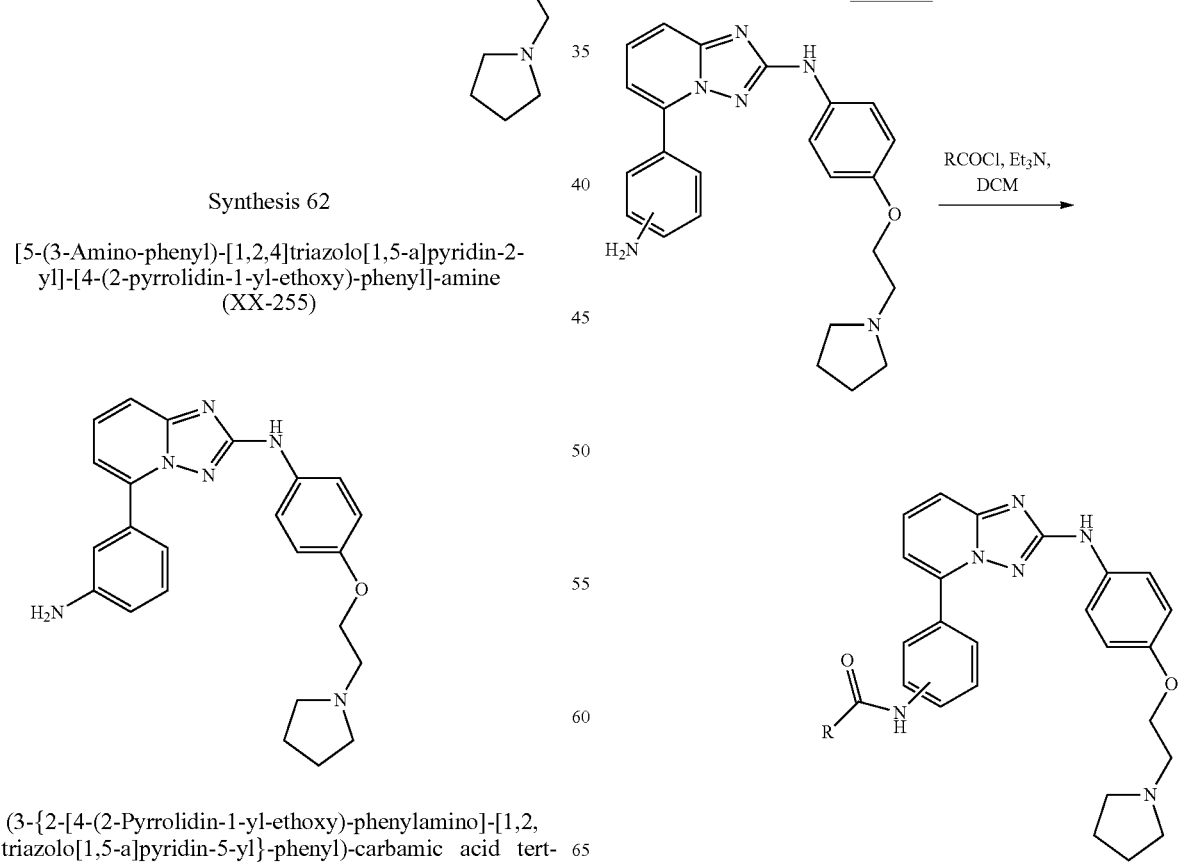

Synthesis 63

N-(4-{2-[4-(2-Pyrrolidin-1-yl-ethoxy)-phenylamino]-[1,2,4]triazolo[1,5-a]pyridin-5-yl}-phenyl)-benzamide (XX-221)

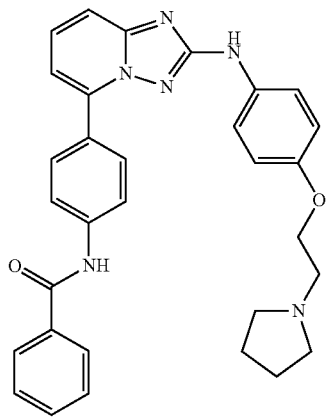 [SMILES: O=C(Nc1ccc(-c2cccc3nc(Nc4ccc(OCCN5CCCC5)cc4)nn23)cc1)c1ccccc1]

To a stirred suspension of [5-(4-amino-phenyl)-[1,2,4]triazolo[1,5-a]pyridin-2-yl]-[4-(2-pyrrolidin-1-yl-ethoxy)-phenyl]-amine (0.05 g, 0.121 mmol) and triethylamine (19 μl, 0.133 mmol) in dichloromethane (1 ml) was added benzoyl chloride (17 μl, 0.133 mmol). The mixture was stirred for 18 hours at room temperature, then filtered through a plug of silica, washed with methanol and the filtrates combined and concentrated in vacuo. The product was purified by preparatory LCMS to provide the desired product. RT: 2.77 min, MI: 519, Method: 2; $^1$H NMR (DMSO, 300 MHz): 8.62 (s, 1H), 8.07 (2H, d), 7.97 (2H, d), 7.92 (d, 2H) 7.54-7.41 (m, 5H), 7.01 (1H, d), 6.85 (d, 2H), 4.31 (t, 2H), 3.37 (t, 2H), 3.26 (s, 4H), 3.12 (s, 1H), 2.99 (s, 1H), 2.02 (s, 4H).

The following compounds were synthesised using the same general method.

| Code No. | Characterisation |
|---|---|
| XX-221 | RT: 2.77 min, MI: 519, Method: 2 |
| XX-220 | RT: 2.91 min, MI: 553; 555, Method: 2 |
| XX-222 | RT: 2.98 min, MI: 566; Method: 2 |
| XX-249 | RT: 2.40 min, MI: 520; Method: 2 |
| XX-250 | RT: 2.54 min, MI: 510; Method: 2 |
| XX-251 | RT: 2.69 min, MI: 524; Method: 2 |
| XX-177 | RT: 2.82 min, MI: 553, Method: 2 |
| XX-178 | RT: 2.55 min, MI: 483, Method: 2 |
| XX-179 | RT: 2.71 min, MI: 519, Method: 2 |
| XX-180 | RT: 2.43 min, MI: 520, Method: 2 |
| XX-181 | RT: 2.57 min, MI: 509, Method: 2 |
| XX-182 | RT: 2.83 min, MI: 561, Method: 2 |
| XX-192 | RT: 2.54 min, MI: 510, Method: 2 |

General Synthetic Procedure CC

Compounds were synthesised starting from [5-(aminophenyl)-[1,2,4]triazolo[1,5-a]pyridin-2-yl]-[4-(2-pyrrolidin-1-yl-ethoxy)-phenyl]-amines (described above) following the scheme below. Amides can be formed using any amide coupling reagents such as HBTU in the presence of base known to one skilled in the art.

Scheme 44

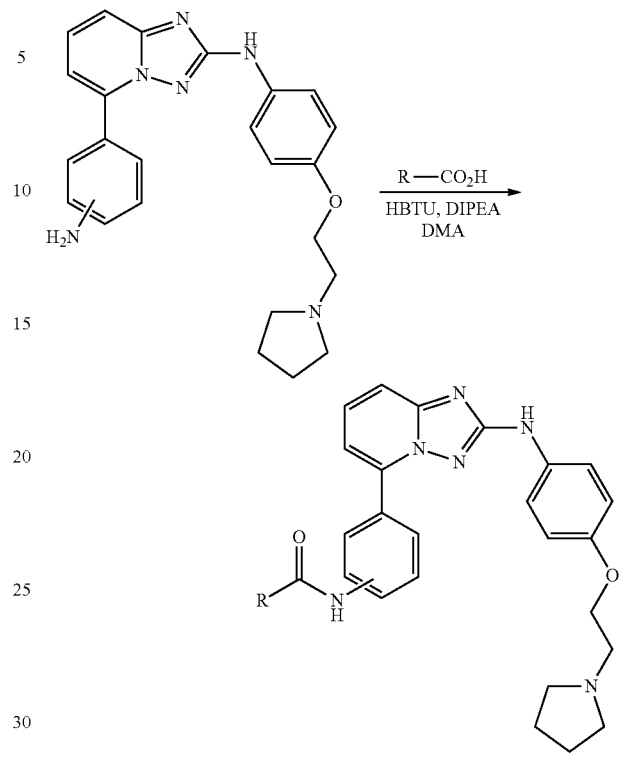

Synthesis 64

2-(3-Chloro-phenyl)-N-(3-{2-[4-(2-pyrrolidin-1-yl-ethoxy)-phenylamino]-[1,2,4]triazolo[1,5-a]pyridin-5-yl}-phenyl)-acetamide (XX-227)

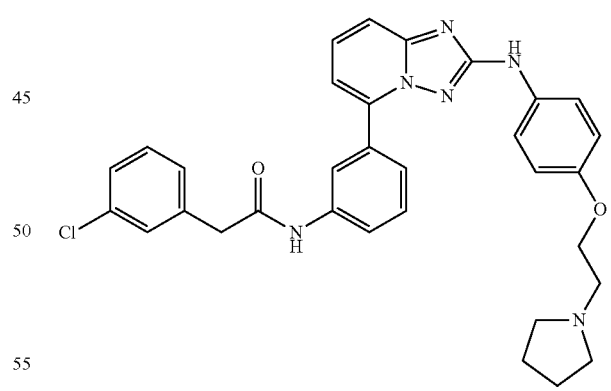

[5-(3-Amino-phenyl)-[1,2,4]triazolo[1,5-a]pyridin-2-yl]-[4-(2-pyrrolidin-1-yl-ethoxy)-phenyl]-amine (50 mg, 0.121 mmol), 3-chlorophenylacetic acid (25 mg, 0.145 mmol) and di-isopropylethylamine (25 μL, 0.145 mmol) were dissolved in dimethylacetamide (1 ml). HBTU (55 mg, 0.145 mmol) was subsequently added and the mixture was stirred overnight. The product was purified by preparatory HPLC. RT: 2.9 min, MI: 567, Method: 2.

Compounds were made starting from 2-(4-chloro-phenyl)-propionic acid methyl ester as shown in the scheme below. In general, methylation can be performed using methyl iodide and any strong non-nucelophilic base such as lithium hexamethyldisilizane. The carboxylic acid can be formed by either acid or base catalysed hydrolysis of the ester.

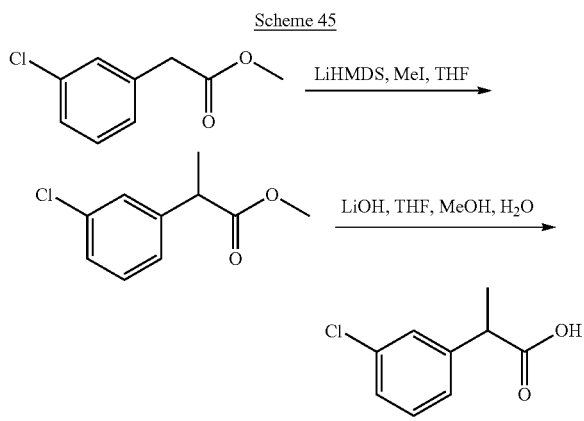

Scheme 45

Synthesis 65

2-(4-Chloro-phenyl)-propionic acid methyl ester

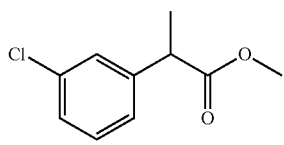

Methyl 3-chlorophenylacetate (0.5 g, 2.71 mmol) in anhydrous tetrahydrofuran (10 ml) was added dropwise to a −78° C. solution of 1M lithium hexamethyldisilizane in tetrahydrofuran (3.25 ml, 3.25 mmol). After 30 min, iodomethane (0.2 ml, 3.25 mmol) was added and the mixture was stirred for 30 min, warmed to room temperature, and stirred for 4 hr. The volatiles were removed in vacuo. Water was added and the product extracted into ethyl acetate (×2). The organics were combined, washed with aqueous sodium thiosulphate then brine, dried, filtered and concentrated in vacuo to give the desired product. Yield 0.47 g, 87%. LCMS RT: 4.78 min, MI: 199-201, Method: 2.

Synthesis 66

2-(4-Chloro-phenyl)-propionic acid

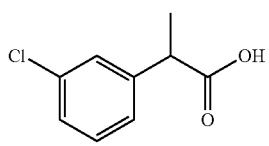

Lithium hydroxide (0.17 g, 7.10 mmol) was added to a stirred solution of 2-(4-chloro-phenyl)-propionic acid methyl ester (0.47 g, 2.366 mmol) in tetrahydrofuran, water and methanol (4:1:1, 12 ml). The mixture was stirred overnight and the volatiles evaporated in vacuo. The mixture was basified by addition of aqueous sodium hydrogencarbonate and washed with ethyl acetate. The aqueous was then acidified with 2M HCl and the product extracted into ethyl acetate. The organic phase was washed with brine, dried over anhydrous magnesium sulfate, filtered and concentrated in vacuo to give the desired product. Yield 0.4 g, 91%. NMR 1H (300 MHz, DMSO): 1.36 (d, 3H), 3.72 (q, 1H), 7.23-7.38 (m, 4ArH), 12.48 (bs, 1H).

The following compounds were synthesised using the same general method.

| Code No. | Characterisation |
|---|---|
| XX-227 | RT: 2.9 min, MI: 567, Method: 2 |
| XX-228 | RT: 3.02 min, MI: 581, Method: 2 |

General Synthetic Procedure DD

Compounds were synthesised starting from {2-[4-(2-pyrrolidin-1-yl-ethoxy)-phenylamino]-[1,2,4]triazolo[1,5-a]pyridin-5-yl}-amines following the scheme illustrated below. Reaction of the aniline with an aldehyde can be performed in the presence of MP-CNBH$_3$ and acetic acid to generate the desired amine.

Scheme 46

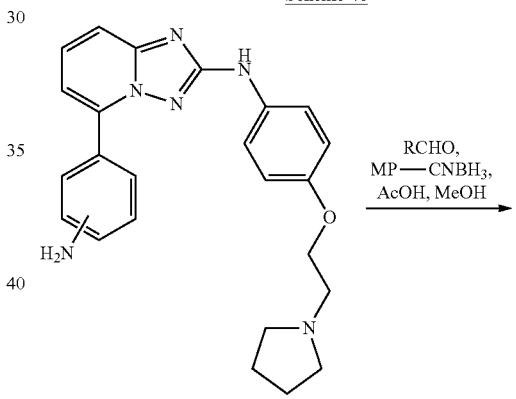

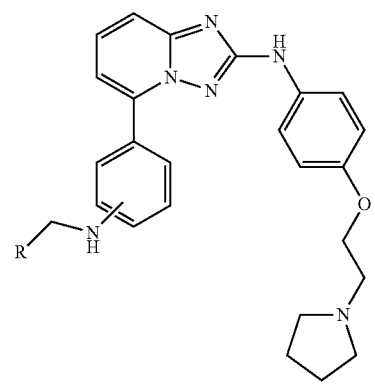

Synthesis 67

{5-[4-(3-Chloro-benzylamino)-phenyl]-[1,2,4]triazolo[1,5-a]pyridin-2-yl}-[4-(2-pyrrolidin-1-yl-ethoxy)-phenyl]-amine (XX-223)

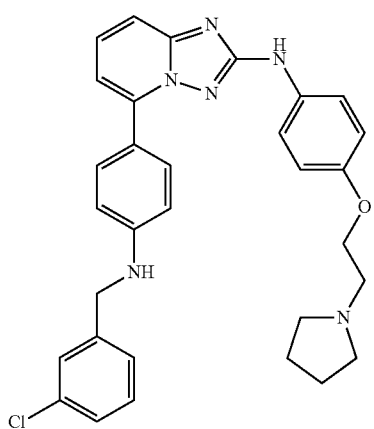 [SMILES: Clc1cccc(CNc2ccc(-c3cccc4nc(Nc5ccc(OCCN6CCCC6)cc5)nn34)cc2)c1]

To a stirred suspension of [5-(4-amino-phenyl)-[1,2,4]triazolo[1,5-a]pyridin-2-yl]-[4-(2-pyrrolidin-1-yl-ethoxy)-phenyl]-amine (0.05 g, 0.121 mmol) and MP-CNBH$_3$ (180 mg, 0.360 mmol) in methanol (1 ml) was added acetic acid (6 μl, 0.121 mmol) followed by 3-chlorobenzaldehyde (15 μl, 0.133 mmol). The mixture was stirred for 18 hours at room temperature, then filtered and concentrated in vacuo. The product was purified by preparatory HPLC to yield the desired product. RT: 3.09 min, MI: 539, Method: 2; $^1$H NMR (DMSO, 300 MHz): 8.47 (s, 1H), 7.90 (2H, d), 7.50-7.27 (m, 8H), 6.92 (d, 1H), 6.84 (d, 2H), 6.74 (d, 2H), 4.42 (s, 2H), 4.30 (t, 2H), 3.37 (t, 2H), 3.26 (s, 4H), 2.03 (s, 4H).

The following compounds were synthesised using the same general method.

| Code No. | Characterisation |
|---|---|
| XX-223 | RT: 3.09 min, MI: 539, Method: 2 |
| XX-252 | RT: 2.9 min, MI: 505, Method: 2 |
| XX-265 | RT: 3.07 min, MI: 519, Method: 2 |
| XX-266 | RT: 2.87 min, MI: 535, Method: 2 |
| XX-267 | RT: 3.05 min, MI: 519, Method: 2 |
| XX-268 | RT: 2.8 min, MI: 495, Method: 2 |
| XX-257 | RT: 2.79 min, MI: 495, Method: 2 |
| XX-258 | RT: 2.11 min, MI: 509, Method: 2 |
| XX-259 | RT: 2.17 min, MI: 509, Method: 2 |
| XX-260 | RT: 2.58 min, MI: 512, Method: 2 |
| XX-261 | RT: 2.29 min, MI: 495, Method: 2 |
| XX-262 | RT: 2.59 min, MI: 523, Method: 2 |
| XX-263 | RT: 2.59 min, MI: 540, Method: 2 |
| XX-394 | RT: 4.25 min, MI: 526 Method: 2 |
| XX-395 | RT: 4.97 min, MI: 509, Method: 2 |
| XX-396 | RT: 2.61 min, MI: 509.36, Method: 2 |
| XX-397 | RT: 2.64 min, MI: 524.35, Method: 2 |
| XX-398 | RT: 2.92 min, MI: 505.35, Method: 2 |
| XX-399 | RT: 2.77 min, MI: 471.33, Method: 2 |
| XX-442 | MI: 506.35, RT: 2.13 min, Method: 2 |
| XX-443 | MI: 524.32, RT: 2.61 min, Method: 2 |
| XX-444 | MI: 469.30, RT: 2.52 min, Method: 2 |
| XX-445 | MI: 572.35, RT: 2.91 min, Method: 2 |
| XX-446 | MI: 510.32, RT: 2.60 min, Method: 2 |
| XX-447 | MI: 566.34, RT: 2.79 min, Method: 2 |
| XX-448 | MI: 563.34, RT: 2.96 min, Method: 2 |
| XX-449 | MI: 523.37, RT: 2.03 min, Method: 2 |
| XX-450 | MI: 565.37, RT: 2.85 min, Method: 2 |
| XX-451 | MI: 535.37, RT: 2.83 min, Method: 2 |
| XX-452 | MI: 535.37, RT: 2.85 min, Method: 2 |
| XX-453 | MI: 535.37, RT: 2.82 min, Method: 2 |
| XX-454 | MI: 519.37, RT: 2.96 min, Method: 2 |
| XX-455 | MI: 519.37, RT: 2.95 min, Method: 2 |
| XX-456 | MI: 523.36, RT: 2.89 min, Method: 2 |
| XX-238 | MI: 523.35, RT: 2.88 min, Method: 2 |
| XX-264 | MI: 523.36, RT: 2.91 min, Method: 2 |

General Synthetic Procedure EE

Compounds were synthesised starting from {2-[4-(2-prrolidin-1-yl-ethoxy)-phenylamino]-[1,2,4]triazolo[1,5-a]pyridin-5-yl}-amines following the scheme illustrated below. Reaction of the aniline with a sulfonyl chloride can be performed in the presence of triethylamine to produce the corresponding sulfonamide.

Scheme 47

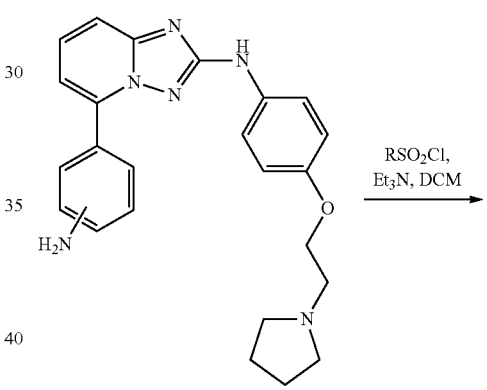

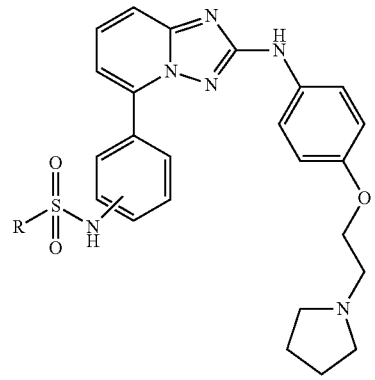

Synthesis 68

4-Methoxy-N-(4-{2-[4-(2-pyrrolidin-1-yl-ethoxy)-phenylamino]-[1,2,4]triazolo[1,5-a]pyridin-5-yl}-phenyl)-benzenesulfonamide (XX-254)

Scheme 48

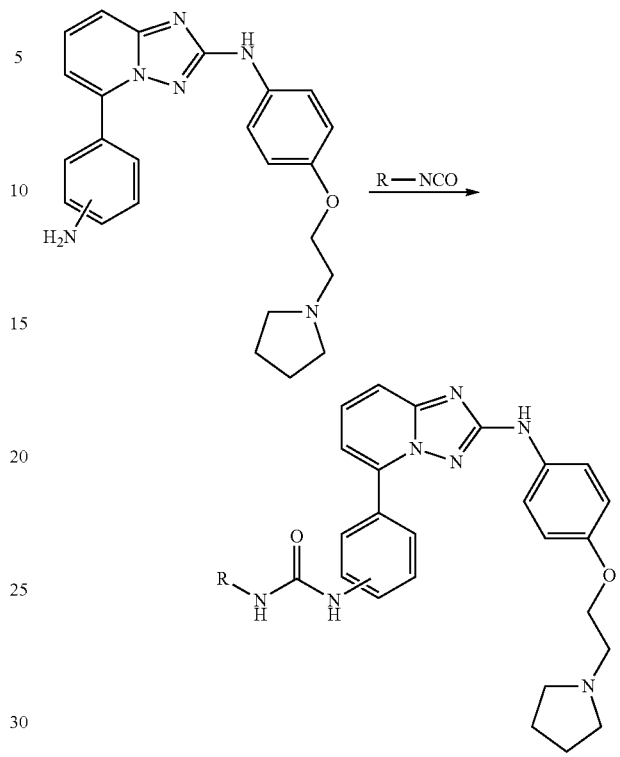

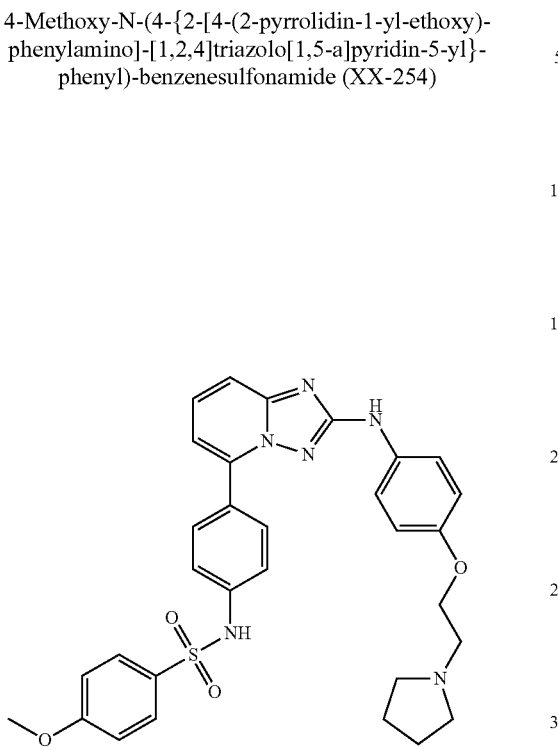

To a stirred solution of [5-(4-amino-phenyl)-[1,2,4]triazolo[1,5-a]pyridin-2-yl]-[4-(2-pyrrolidin-1-yl-ethoxy)-phenyl]-amine (0.05 g, 0.121 mmol) in dichloromethane, triethylamine (22 μl, 0.154 mmol) followed by 3-methoxybenzylsulfonyl chloride (15 μl, 0.133 mmol). The mixture was stirred for 18 hours at room temperature, then filtered and concentrated in vacuo. The product was purified by preparatory HPLC to give the desired product. RT: 2.77 min, MI: 585, Method: 2; $^1$H NMR (DMSO, 300 MHz): 9.38 (s, 1H), 8.16 (s, 1H), 7.92 (d, 2H), 7.81 (d, 2H), 7.55-7.51 (m, 4H), 7.27 (d, 2H), 7.09 (d, 2H), 6.88 (d, 2H), 4.06 (t, 2H), 3.80 (s, 3H), 2.94 (t, 2H), 2.70 (s, 4H), 1.75 (s, 4H).

The following compounds were synthesised using the same general method.

| Code No. | Characterisation |
|---|---|
| XX-253 | RT: 2.42 min, MI: 493; Method: 2 |
| XX-254 | RT: 2.77 min, MI: 585; Method: 2 |
| XX-271 | RT: 2.84 min, MI: 569; Method: 2 |
| XX-277 | RT: 2.64 min, MI: 612; Method: 2 |
| XX-224 | RT: 2.33 min, MI: 493, Method: 2 |

General Synthetic Procedure FF

Compounds were synthesised starting from [5-(amino-phenyl)-[1,2,4]triazolo[1,5-a]pyridin-2-yl]-[4-(2-pyrrolidin-1-yl-ethoxy)-phenyl]-amines (described above) following the scheme below. Ureas can be formed by reaction of the aniline with an isocyanate in an appropriate solvent.

Synthesis 69

1-Phenyl-3-(3-{2-[4-(2-pyrrolidin-1-yl-ethoxy)-phenylamino]-[1,2,4]triazolo[1,5-a]pyridin-5-yl}-phenyl)-urea (XX-174)

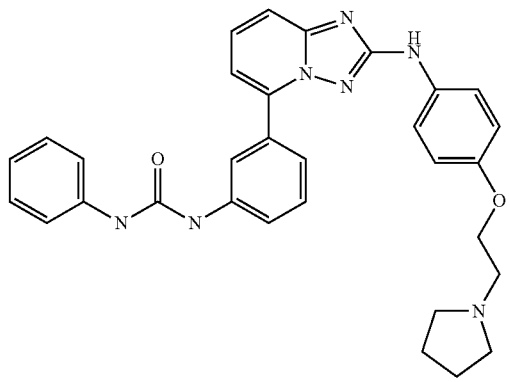 [SMILES: O=C(Nc1ccccc1)Nc1cccc(-c2cccc3nc(Nc4ccc(OCCN5CCCC5)cc4)nn23)c1]

[5-(3-Amino-phenyl)-[1,2,4]triazolo[1,5-a]pyridin-2-yl]-[4-(2-pyrrolidin-1-yl-ethoxy)-phenyl]-amine (50 mg, 0.121 mmol) was dissolved in chloroform (3 ml). Phenylisocyanate (0.12 ml, 0.131 mmol) was added and the mixture stirred overnight. The solvent was removed under reduced pressure and the product was purified by preparatory HPLC to give the desired product. RT: 2.78 min, MI: 534, Method: 2. 1H NMR (DMSO, 300 MHz): 1.76 (m, 4H), 2.80 (m, 4H), 2.99 (t, 2H), 3.99 (t, 2H), 6.86 (d, 2H), 6.94 (t, 1H), 7.13 (d, 1H), 7.26 (t, 2H), 7.34-7.66 (m, 9H), 8.32 (s, 1H), 9.43 (bs, 1H), 9.68 (bs, 1H), 9.81 (s, br, 1H).

The following compounds were synthesised using the same general method.

| Code No. | Characterisation |
| --- | --- |
| XX-174 | RT: 2.78 min, MI: 534, Method: 2 |
| XX-176 | RT: 3.04 min, MI: 568, Method: 2 |
| XX-225 | RT: 3.14 min, MI: 602, Method: 2 |
| XX-229 | RT: 2.83 min, MI: 564, Method: 2 |
| XX-230 | RT: 2.82 min, MI: 564, Method: 2 |
| XX-231 | RT: 2.78 min, MI: 564, Method: 2 |
| XX-232 | RT: 2.91 min, MI: 568, Method: 2 |
| XX-233 | RT: 3.11 min, MI: 568, Method: 2 |
| XX-234 | RT: 3.14 min, MI: 602, Method: 2 |

General Synthetic Procedure FF

Compounds were synthesised starting from (3-{2-[4-(2-pyrrolidin-1-yl-ethoxy)-phenylamino]-[1,2,4]triazolo[1,5-a]pyridin-5-yl}-benzyl)-carbamic acid tert-butyl ester (described above) following the scheme illustrated below. The Boc group can be removed using trifluoroacetic acid or any other conditions known to one skilled in the art.

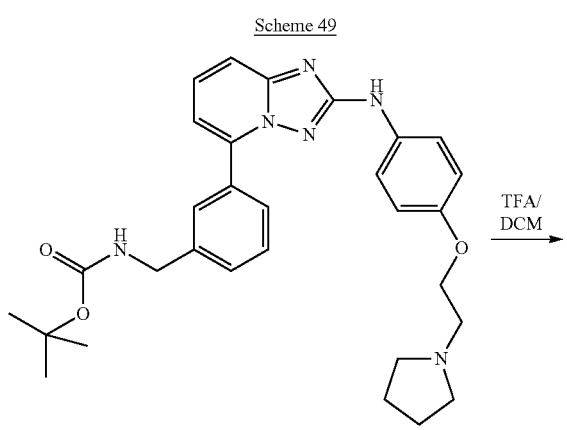

Scheme 49

Synthesis 70

[5-(3-Aminomethyl-phenyl)-[1,2,4]triazolo[1,5-a]pyridin-2-yl]-[4-(2-pyrrolidin-1-yl-ethoxy)-phenyl]-amine (XX-308)

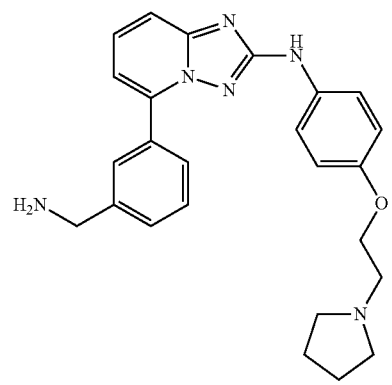 [SMILES: NCc1cccc(-c2cccc3nc(Nc4ccc(OCCN5CCCC5)cc4)nn23)c1]

(3-{2-[4-(2-Pyrrolidin-1-yl-ethoxy)-phenylamino]-[1,2,4]triazolo[1,5-a]pyridin-5-yl}-benzyl)-carbamic acid tert-butyl ester (1.78 g, 3.37 mmol) was dissolved in dichloromethane (20 ml). Trifluoroacetic acid (20 ml) was added and the reaction was stirred for 2 hours. Neutralisation was performed by adding saturated aqueous sodium hydrogencarbonate. The aqueous phase was extracted twice with dichloromethane, and the combined organics washed with brine, dried over anhydrous magnesium sulfate, filtered and concentrated in vacuo to give the desired compound. Yield: 460 mg, 32%. 50 mg was purified by preparatory HPLC.

The following compound was synthesised using this method.

| Code No. | Characterisation |
| --- | --- |
| XX-308 | RT: 1.93 min, MI: 429, Method: 2 |

General Synthetic Procedure GG

Compounds were synthesised starting from [5-(3-aminomethyl-phenyl)-[1,2,4]triazolo[1,5-a]pyridin-2-yl]-[4-(2-pyrrolidin-1-yl-ethoxy)-phenyl]-amine following the scheme illustrated below. Reaction of the amine with an acyl chloride can be performed in the presence of triethylamine to generate the corresponding amide.

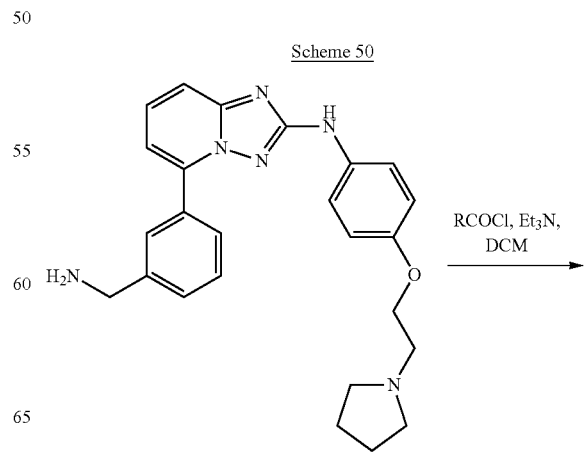

Scheme 50

-continued

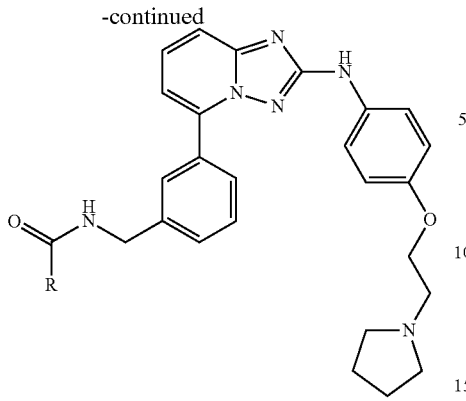

Synthesis 71

3-Methyl-N-(3-{2-[4-(2-pyrrolidin-1-yl-ethoxy)-phenylamino]-[1,2,4]triazolo[1,5-a]pyridin-5-yl}-benzyl)-butyramide (XX-325)

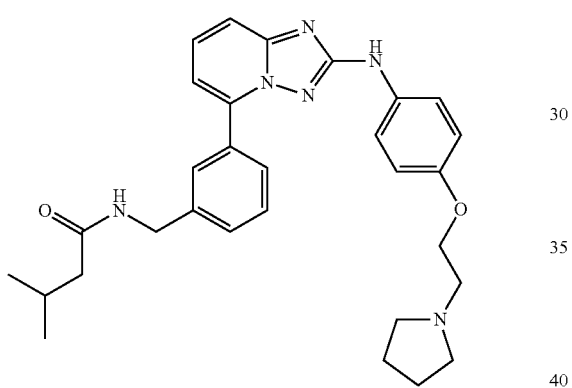

To a stirred suspension of [5-(4-amino-phenyl)-[1,2,4]triazolo[1,5-a]pyridin-2-yl]-[4-(2-pyrrolidin-1-yl-ethoxy)-phenyl]-amine (0.03 g, 0.07 mmol) and triethylamine (11 µl, 0.077 mmol) in dichloromethane (1 ml) was added isovaleryl chloride (10 µl, 0.077 mmol). The mixture was stirred for 18 hours at room temperature, then filtered through a plug of silica, washed with methanol and concentrated in vacuo. The crude was purified by preparatory HPLC to give the desired product. LCMS RT: 2.54 min, MI: 513, Method: 2; $^1$H NMR (DMSO, 300 MHz): 9.37 (s, 1H), 8.38 (t, 1H), 8.18 (s, 1H), 7.89 (s, 1H), 7.56 (m, 4H), 7.40 (d, 1H), 7.08 (d, 1H), 6.85 (d, 2H), 4.36 (d, 2H), 3.98 (t, 2H), 2.79 (t, 2H), 2.55 (s, 4H), 1.98 (s, 2H), 1.66 (s, 5H), 0.82 (s, 6H).

The following compounds were synthesised using the same general method.

| Code No. | Characterisation |
|---|---|
| XX-325 | RT: 2.54 min, MI: 513, Method: 2 |

General Synthetic Procedure HH

Compounds were synthesised starting from [5-(3-aminomethyl-phenyl)-[1,2,4]triazolo[1,5-a]pyridin-2-yl]-[4-(2-pyrrolidin-1-yl-ethoxy)-phenyl]-amine (described above) following the scheme below. Ureas can be formed by reaction of the aniline with an isocyanate in an appropriate solvent.

Scheme 51

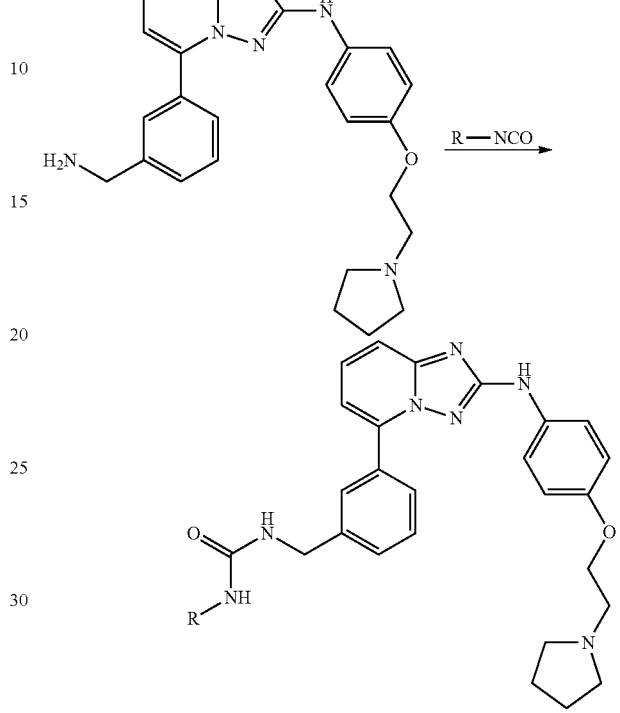

Synthesis 72

1-(3-Chloro-phenyl)-3-(3-{2-[4-(2-pyrrolidin-1-yl-ethoxy)-phenylamino]-[1,2,4]triazolo[1,5-a]pyridin-5-yl}-benzyl)-urea (XX-348)

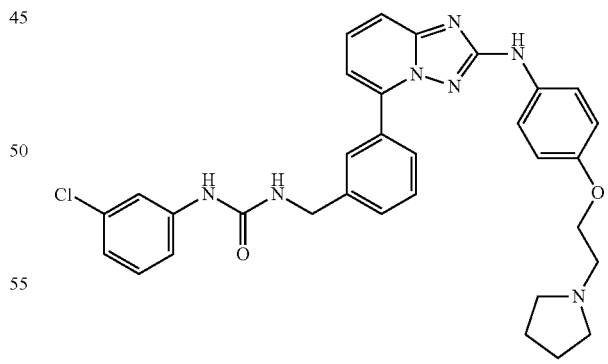

[5-(3-Aminomethyl-phenyl)-[1,2,4]triazolo[1,5-a]pyridin-2-yl]-[4-(2-pyrrolidin-1-yl-ethoxy)-phenyl]-amine (40 mg, 0.093 mmol) was dissolved in dichloromethane (1 ml). 3-Chlorophenyl isocyanate (13 µl, 0.103 mmol) was added and the mixture stirred overnight. The solvent was removed under reduced pressure and the product was purified by preparatory HPLC to give the desired product. LCMS RT: 2.86 min, MI: 582, Method: 2. $^1$H NMR (DMSO, 300 MHz): 9.38

(s, 1H), 8.99 (s, 1H), 8.16 (s, 1H), 7.96 (s, 1H), 7.86 (d, 1H), 7.66-7.49 (m, 5H), 7.17 (d, 2H), 7.11 (d, 1H), 7.01 (t, 1H), 6.84 (d, 2H), 4.39 (d, 2H), 3.98 (t, 2H), 2.81 (t, 2H), 2.53 (s, 4H), 1.67 (s, 4H).

The following compounds were synthesised using the same general method.

| Code No. | Characterisation |
| --- | --- |
| XX-348 | RT: 2.86 min, MI: 582, Method: 2 |
| XX-373 | RT: 2.50 min, MI: 514, Method: 2 |
| XX-372 | RT: 2.63 min, MI: 528, Method: 2 |
| XX-371 | RT: 2.70 min, MI: 548, Method: 2 |

General Synthetic Procedure II

Compounds were synthesised starting from [5-(3-aminomethyl-phenyl)-[1,2,4]triazolo[1,5-a]pyridin-2-yl]-[4-(2-pyrrolidin-1-yl-ethoxy)-phenyl]-amine following the scheme illustrated below. Reaction of the amine with a sulfonyl chloride can be performed in the presence of triethylamine to produce the corresponding sulfonamide.

Scheme 52

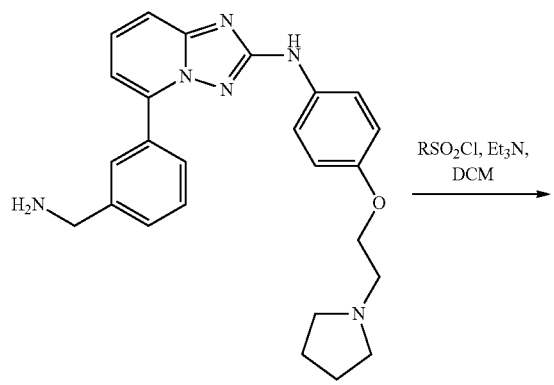

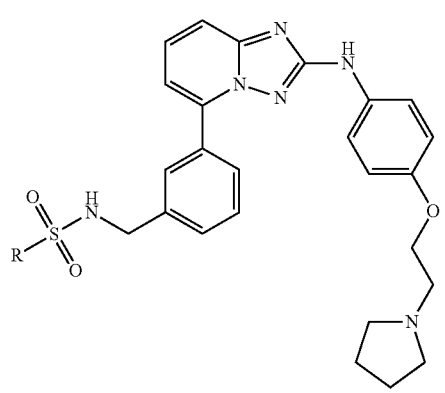

Synthesis 73

Butane-1-sulfonic acid 3-{2-[4-(2-pyrrolidin-1-yl-ethoxy)-phenylamino]-[1,2,4]triazolo[1,5-a]pyridin-5-yl}-benzylamide (XX-324)

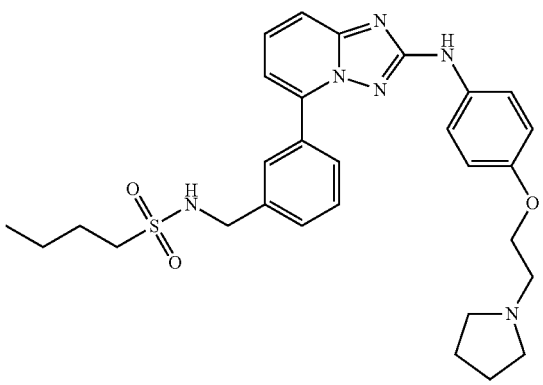 [SMILES: CCCCS(=O)(=O)NCc1cccc(-c2cccc3nc(Nc4ccc(OCCN5CCCC5)cc4)nn23)c1]

To a stirred solution of [5-(3-aminomethyl-phenyl)-[1,2,4]triazolo[1,5-a]pyridin-2-yl]-[4-(2-pyrrolidin-1-yl-ethoxy)-phenyl]-amine (0.03 g, 0.070 mmol) in dichloromethane (1 ml) was added triethylamine (13 μl, 0.091 mmol) followed by butanesulfonyl chloride (11 μl, 0.084 mmol). The mixture was stirred for 18 hours at room temperature, then filtered and concentrated in vacuo. The product was purified by preparatory HPLC to provide the desired product. LCMS RT: 2.66 min, MI: 549, Method: 2; $^1$H NMR (DMSO, 300 MHz): 9.43 (s, 1H), 8.18 (s, 1H), 8.03 (d, 1H), 7.65 (m, 6H), 7.16 (d, 1H), 6.90 (d, 2H), 4.27 (d, 2H), 4.05 (t, 2H), 2.93 (t, 2H), 2.70 (s, 4H), 2.45 (dd, 2H), 1.74 (s, 4H), 1.59 (m, 2H), 1.28 (m, 2H), 0.82 (m, 3H).

The following compounds were synthesised using the same general method.

| Code No. | Characterisation |
| --- | --- |
| XX-324 | RT: 2.66 min, MI: 549; Method: 2 |
| XX-370 | RT: 2.82 min, MI: 583; Method: 2 |

General Synthetic Procedure JJ

Compounds were synthesised starting from {2-[4-(2-pyrrolidin-1-yl-ethoxy)-phenylamino]-[1,2,4]triazolo[1,5-a]pyridin-5-yl}-benzoic acid ethyl esters (described above) as shown in the scheme below. In general, the carboxylic acid can be formed by either acid or base catalysed ester hydrolysis. Oxadiazole synthesis can be accomplished by refluxing with a suitable hydrazide in phosphorus oxychloride or by any other means known to one skilled in the art.

Scheme 53

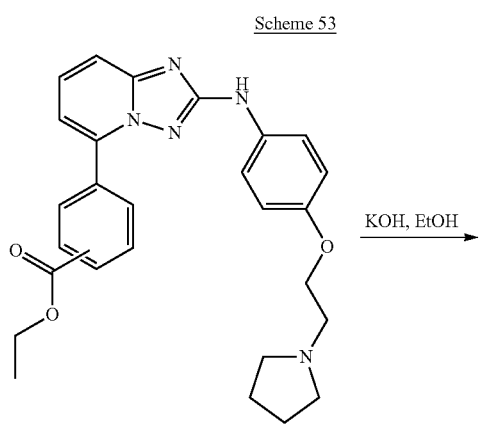

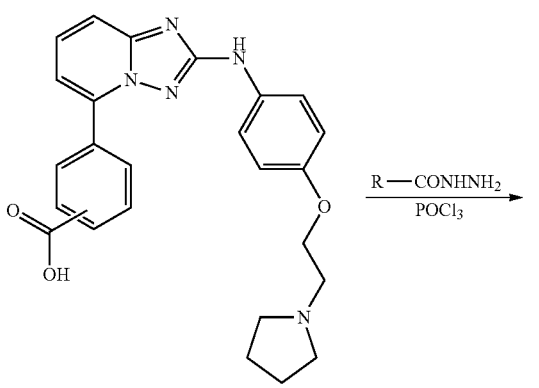

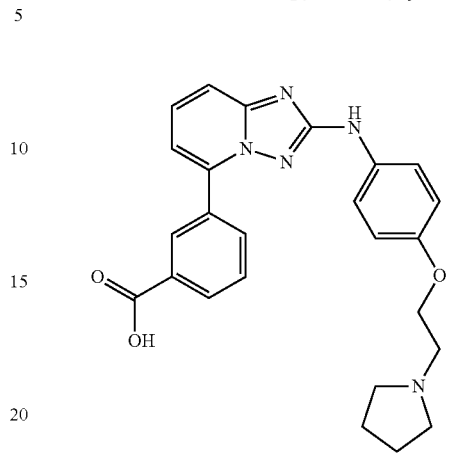

Synthesis 74

3-{2-[4-(2-Pyrrolidin-1-yl-ethoxy)-phenylamino]-[1,2,4]triazolo[1,5-a]pyridin-5-yl}-benzoic acid 3-{2-[4-(2-Pyrrolidin-1-yl-ethoxy)-phenylamino]-[1,2,4]triazolo[1,5-a]pyridin-5-yl}-benzoic acid ethyl ester (1.28 g, 2.71 mmol) was dissolved in ethanol (20 ml) and potassium hydroxide (0.45 g, 8.12 mmol) was added. The reaction was heated to reflux for 3 hrs. Upon cooling the solvent was removed in vacuo and aqueous sodium hydrogencarbonate added to the residue. The basic aqueous layer was washed with dichloromethane, then neutralised with 2M HCl and the resulting precipitate collected by filtration, washed with water and toluene, then dried under vacuum to give the desired product. Yield: 0.64 g, 53%. LCMS RT: 2.45 min, MI: 444, Method: 2.

Synthesis 75

{5-[3-(5-Phenyl-[1,3,4]oxadiazol-2-yl)-phenyl]-[1,2,4]triazolo[1,5-a]pyridin-2-yl}-[4-(2-pyrrolidin-1-yl-ethoxy)-phenyl]-amine (XX-309)

Phosphorus oxychloride (5 ml) was added dropwise to 3-{2-[4-(2-pyrrolidin-1-yl-ethoxy)-phenylamino]-[1,2,4]triazolo[1,5-a]pyridin-5-yl}-benzoic acid (50 mg, 0.113 mmol) and benzhydrazide (15 mg, 0.113 mmol). The solution was heated to reflux overnight. Once cooled the reaction mixture was added gradually to ice/water. The solution was basified with saturated aqueous sodium hydrogencarbonate and subsequently extracted twice with dichloromethane. The organics were combined, washed several times with brine, dried over anhydrous magnesium sulfate, filtered and concentrated in vacuo. The product was purified by preparatory HPLC. LCMS RT: 2.80 min, MI: 544, Method: 2.

The following compounds were synthesised using the same general method.

| Code No. | Characterisation |
|---|---|
| XX-309 | RT: 2.80 min, MI: 544, Method: 2 |

General Synthetic Procedure KK

Compounds were synthesised starting from 3-{2-[4-(2-pyrrolidin-1-yl-ethoxy)-phenylamino]-[1,2,4]triazolo[1,5-a]pyridin-5-yl}-benzoic acid ethyl ester (described above) as shown in the scheme below.

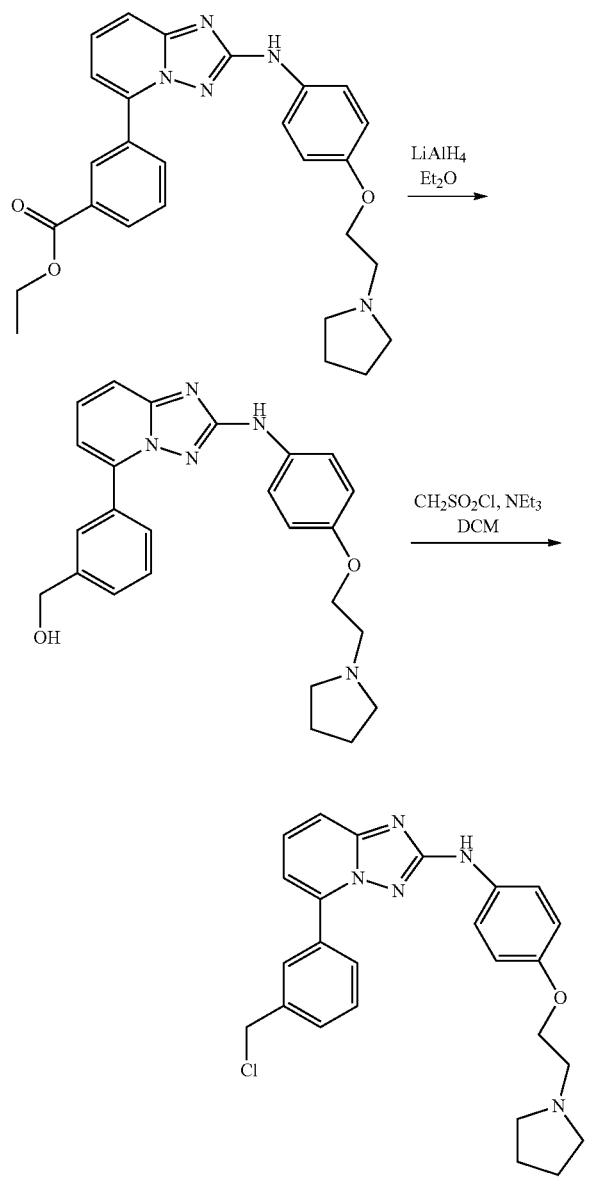

Scheme 54

Synthesis 76

(3-{2-[4-(2-Pyrrolidin-1-yl-ethoxy)-phenylamino]-[1,2,4]triazolo[1,5-a]pyridin-5-yl}-phenyl)-methanol (XX-090)

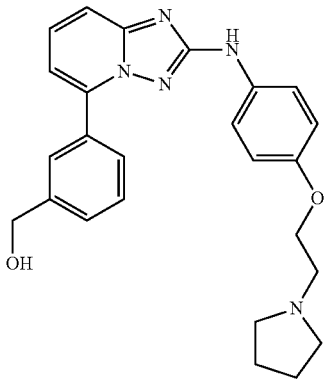 [SMILES: OCc1cccc(-c2cccc3nc(Nc4ccc(OCCN5CCCC5)cc4)nn23)c1]

To a slurry of lithium aluminium hydride (82.6 mg, 2.12 mmol) in diethylether (10 mL) was added 3-{2-[4-(2-pyrrolidin-1-yl-ethoxy)-phenylamino]-[1,2,4]triazolo[1,5-a]pyridin-5-yl}-benzoic acid ethyl ester (0.50 g, 1.06 mmol) portionwise. The mixture was stirred at room temperature for 6 hrs. Water was added to quench the hydride and the aqueous layer was removed. The organic layer was concentrated in vacuo, and the crude product loaded onto an SCX column, which was washed with methanol and the product eluted with 2M ammonia in methanol, then concentrated in vacuo. Yield: 0.35 g, 76%. A small amount was purified by preparatory HPLC. RT: 2.32, MI: 430, Method: 2.

Synthesis 77

[5-(3-Chloromethyl-phenyl)-[1,2,4]triazolo[1,5-a]pyridin-2-yl]-[4-(2-pyrrolidin-1-yl-ethoxy)-phenyl]-amine (XX-341)

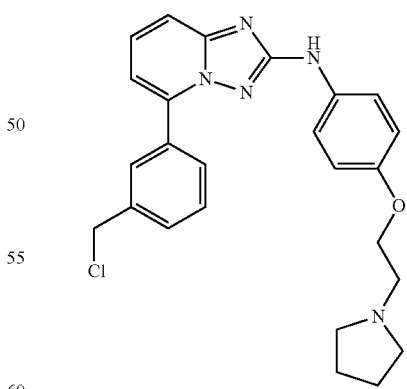

(3-{2-[4-(2-Pyrrolidin-1-yl-ethoxy)-phenylamino]-[1,2,4]triazolo[1,5-a]pyridin-5-yl}-phenyl)-methanol (0.35 g, 0.815 mmol) was dissolved in dichloromethane (20 mL). Triethylamine (508 uμL, 3.670 mmol) was added and the mixture cooled to 0° C., then methanesulfonyl chloride (252 μL, 3.260 mmol) was added dropwise and the reaction was allowed to warm to room temperature and stirred overnight. A small sample of the desired product was purified by preparatory HPLC. RT: 2.56 min, MI: 448 and 450.18, Method: 2.

The following compounds were synthesised using the same general method.

| Code No. | Characterisation |
|----------|------------------|
| XX-341   | RT: 2.56 min, MI: 448, 450, Method: 2 |

General Synthetic Procedure LL

Compounds were synthesised starting from {2-[4-(2-pyrrolidin-1-yl-ethoxy)-phenylamino]-[1,2,4]triazolo[1,5-a]pyridin-5-yl}-benzoic acids (described above) as shown in the scheme below. In general the biaryl ketones can be obtained by reaction of a Weinreb amide with a Grignard reagent.

Scheme 55

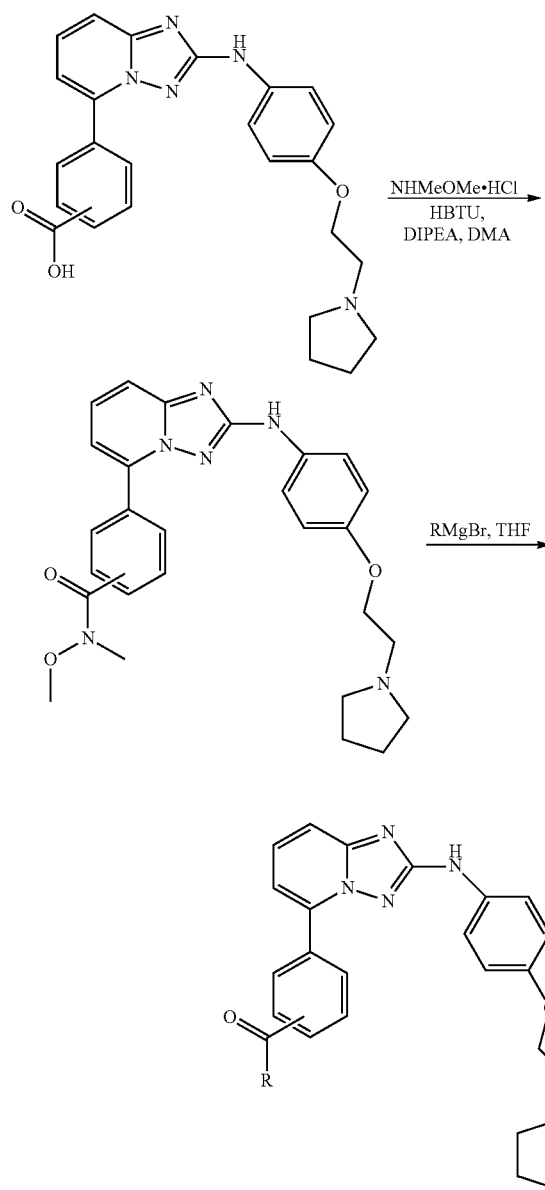

Synthesis 78

N-Methoxy-N-methyl-3-{2-[4-(2-pyrrolidin-1-yl-ethoxy)-phenylamino]-[1,2,4]triazolo[1,5-a]pyridin-5-yl}-benzamide

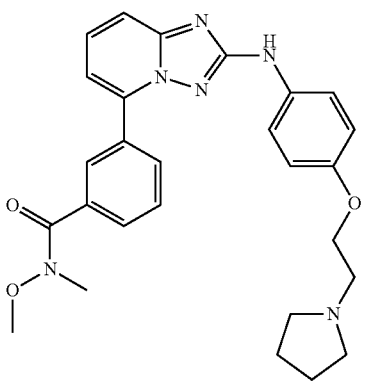 [SMILES: CON(C)C(=O)c1cccc(-c2cccc3nc(Nc4ccc(OCCN5CCCC5)cc4)nn23)c1]

3-{2-[4-(2-Pyrrolidin-1-yl-ethoxy)-phenylamino]-[1,2,4]triazolo[1,5-a]pyridin-5-yl}-benzoic acid (0.2 g, 0.451 mmol) was dissolved in dimethylacetamide (5 ml). N—O-Dimethylhydroxylamine hydrochloride (53 mg, 0.541 mmol) and di-isopropylethylamine (0.19 ml, 1.08 mmol) were added followed by HBTU (0.21 g, 0.541 mmol). The mixture was stirred overnight at room temperature. The reaction mixture was diluted with dichloromethane and saturated aqueous sodium hydrogencarbonate was added. The product was extracted into dichloromethane (×2), and the combined organics washed several times with brine, dried over anhydrous magnesium sulfate, filtered and concentrated in vacuo to give the desired product. Yield 0.2 g, 91%. LCMS RT: 2.41 min, MI: 487 Method: 2.

Synthesis 79

Benzo[1,3]dioxol-5-yl-(3-{2-[4-(2-pyrrolidin-1-yl-ethoxy)-phenylamino]-[1,2,4]triazolo[1,5-a]pyridin-5-yl}-phenyl)-methanone (XX-310)

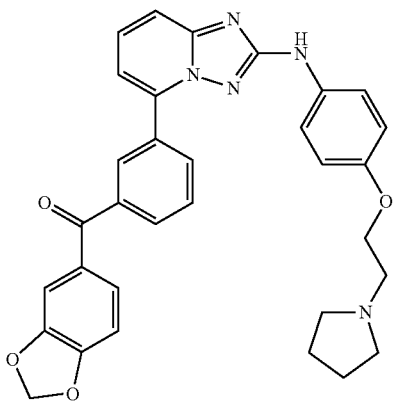 [SMILES: O=C(c1cccc(-c2cccc3nc(Nc4ccc(OCCN5CCCC5)cc4)nn23)c1)c1ccc2c(c1)OCO2]

A solution of 3-amino-6-phenyl-pyrazine-2-carboxylic acid methoxy-methyl-amide (50 mg, 0.10 mmol) in tetrahydrofuran (5 ml) was cooled to 0° C. and 3,4-(methylenedioxy)phenyl-magnesium bromide (1M in tetrahydrofuran/toluene)

(1.0 ml, 1.0 mmol) was added dropwise under an atmosphere of nitrogen. The mixture was allowed to slowly warm to room temperature and stirred for an hour. The product was initially purified over an SCX cartridge then by preparatory HPLC. LCMS RT: 2.77 min, MI: 548, Method: 2

The following compounds were synthesised using the same general method.

| Code No. | Characterisation |
| --- | --- |
| XX-310 | RT: 2.77 min, MI: 548, Method: 2 |
| XX-313 | RT: 2.96 min, MI: 538, Method: 2 |
| XX-314 | RT: 2.96 min, MI: 538, Method: 2 |

General Synthetic Procedure MM

Compounds were synthesised starting from 3-{2-[4-(2-pyrrolidin-1-yl-ethoxy)-phenylamino]-[1,2,4]triazolo[1,5-a]pyridin-5-yl}-benzoic acid (described above) as shown in the scheme below. Amide synthesis can be accomplished using HBTU or coupling reagents or by any other means known to one skilled in the art.

Scheme 56

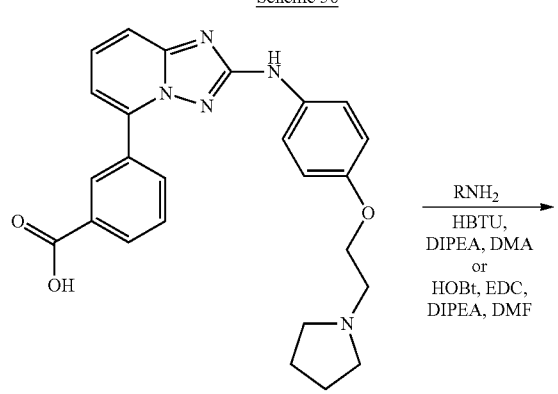

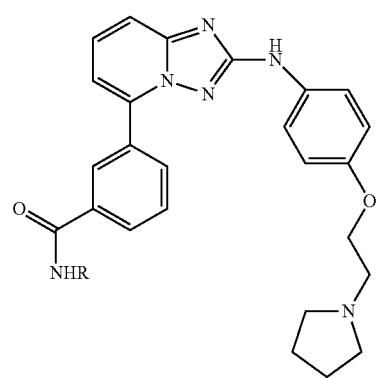

Synthesis 80

N-(4-Chloro-benzyl)-3-{2-[4-(2-pyrrolidin-1-yl-ethoxy)-phenylamino]-[1,2,4]triazolo[1,5-a]pyridin-5-yl}-benzamide (XX-462)

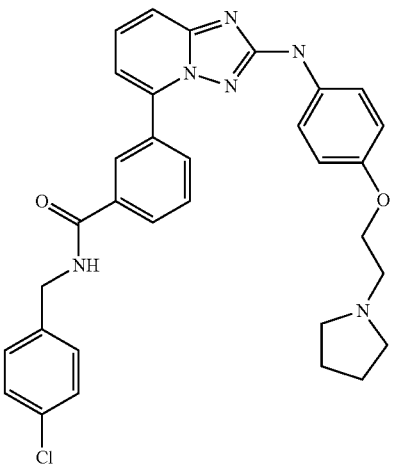 [SMILES: O=C(NCc1ccc(Cl)cc1)c1cccc(-c2cccc3nc(Nc4ccc(OCCN5CCCC5)cc4)nn23)c1]

To a stirred solution of 3-{2-[4-(2-pyrrolidin-1-yl-ethoxy)-phenylamino]-[1,2,4]triazolo[1,5-a]pyridin-5-yl}-benzoic acid (50 mg, 0.113 mmol), 4-chlorobenzylamine (27.5 µL, 0.226 mmol), EDC (44 mg, 0.226 mmol) and di-isopropyl-ethylamine (98.5 µL, 0.564 mmol) was added HOBt (31 mg, 0.226 mmol). The mixture was stirred overnight at room temperature, and the desired product purified by preparatory HPLC. RT: 4.63 min, MI: 567.31, Method: basic. $^1$H NMR (DMSO, 300 MHz): 9.43 (s, 1H), 9.22 (t, 1H), 8.58 (s, 1H), 8.19 (t, 1H), 8.03 (d, 1H), 7.63 (m, 6H), 7.36 (s, 3H), 7.24 (dd, 1H), 6.84 (d, 2H), 4.50 (d, 2H), 3.99 (t, 2H), 2.81 (t, 2H), 2.50 (d, 2H), 2.36 (s, 2H), 1.69 (m, 4H).

The following compounds were synthesised using the same general method.

| Code No. | Characterisation |
| --- | --- |
| X-301 | RT: 2.59 min, MI: 499, Method: 2 |
| XX-321 | RT: 2.87 min, MI: 553, Method: 2 |
| XX-322 | RT: 2.87 min, MI: 553, Method: 2 |
| XX-462 | MI: 567.31, RT: 4.63 min, Method: basic |

General Synthesis Procedure NN

Compounds were synthesised starting from 5-bromo-[1,2,4]triazolo[1,5-a]pyridin-2-ylamine following the scheme illustrated below. In general, this compound was reacted with 1-benzylpyrazole-4-boronic acid pinacol ester under standard Suzuki conditions using tetrakis(triphenylphosphine) palladium as a catalyst. A Buchwald reaction was then used to install an aryl group, Ar$_1$, and deprotection of the benzyl group carried out under hydrogenation conditions to provide the free pyrazole.

Scheme 57

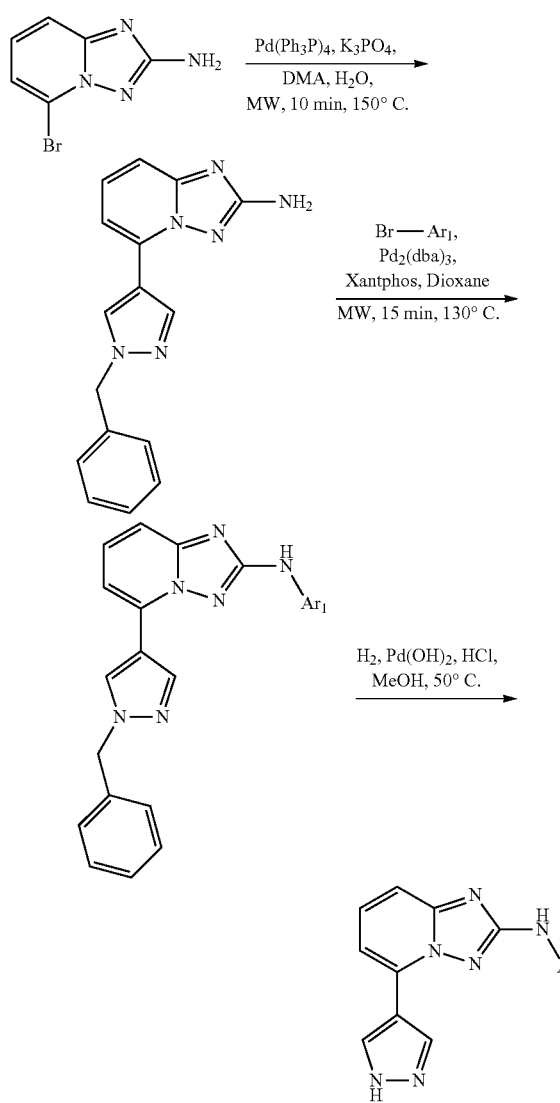

Synthesis 81

5-(1-Benzyl-1H-pyrazol-4-yl)-[1,2,4]triazolo[1,5-a]pyridin-2-ylamine

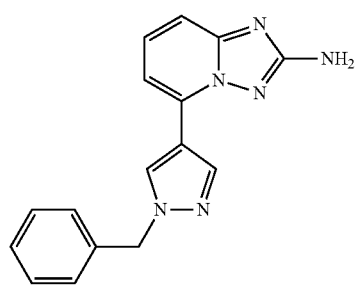 [SMILES: Nc1nc2cccc(-c3cnn(Cc4ccccc4)c3)n2n1]

A vial was charged with 5-bromo-[1,2,4]triazolo[1,5-a]pyridin-2-ylamine (2.00 g, 9.39 mmol), 1-benzylpyrazole-4-boronic acid, pinacol ester (3.20 g, 11.3 mmol), potassium phosphate (4.00 g, 18.8 mmol) and tetrakis(triphenylphosphine)palladium (1.10 g, 0.94 mmol). Dimethylacetamide (24 ml) and water (8 ml) were added and the reaction mixture was heated under microwave irradiation to 150° C. for 10 min. The mixture was partitioned between ethyl acetate and water, and the aqueous phase extracted with ethyl acetate. The combined organic phases were washed several times with water, once with brine, dried over magnesium sulfate and concentrated in vacuo. Trituration in the minimum amount of dichloromethane and diethyl ether afforded an orange solid which required no further purification. Yield: 1.82 g, 67%; LCMS method: 2, RT: 2.37 min, MI: 291 [M+1].

Synthesis 82

[5-(1-Benzyl-1H-pyrazol-4-yl)-[1,2,4]triazolo[1,5-a]pyridin-2-yl]-[4-(2-pyrrolidin-1-yl-ethoxy)-phenyl]-amine (XX-193)

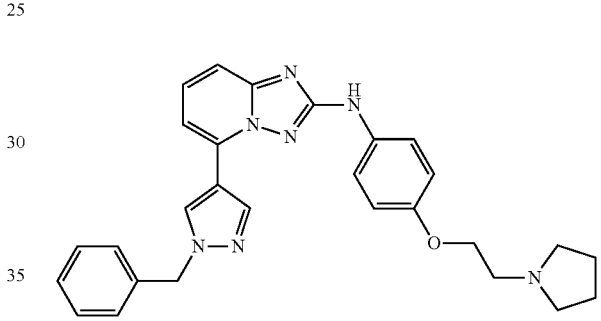

A microwave vial containing 5-(1-benzyl-1H-pyrazol-4-yl)-[1,2,4]triazolo[1,5-a]pyridin-2-ylamine (6.42 g, 22.1 mmol), 1-(2-(4-bromophenoxy)ethyl)pyrrolidine (5.1 mL, 24.3 mmol), tris(dibenzylideneacetone)dipalladium (0.633 g, 1.11 mmol), xantphos (1.28 g, 2.22 mmol), sodium tert-butoxide (4.34 g, 44.2 mmol) and 1,4-dioxane (50 mL) was heated under microwave irradiation (130° C., 15 min). Dimethylacetamide (2.5 mL) was added to assist with microwave absorption. The volatiles were removed under rotary evaporation, and the residue partitioned between ethyl acetate and water. The aqueous phase was extracted with ethyl acetate and the combined organics washed with water followed by brine. The organic phase was dried over magnesium sulfate, concentrated in vacuo and after trituration with the minimum amount of dichloromethane in diethylether afforded a pale yellow solid. Yield: 8.12 g, 77%; LCMS method: 2, RT: 2.52 min, MI: 480 [M+1].

The following compounds were synthesised using the same general method.

| Code No. | Characterisation |
| --- | --- |
| XX-193 | RT: 2.52 min, MI: 480; Method: 2 |

Synthesis 83

[5-(1H-Pyrazol-4-yl)-[1,2,4]triazolo[1,5-a]pyridin-2-yl]-[4-(2-pyrrolidin-1-yl-ethoxy)-phenyl]-amine (XX-202)

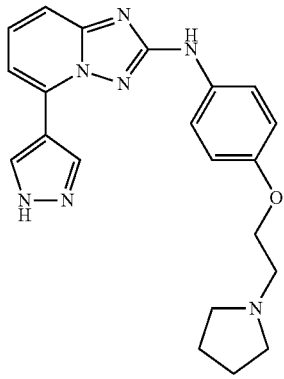 [SMILES: c1cc(-c2cn[nH]c2)n2nc(Nc3ccc(OCCN4CCCC4)cc3)nc2c1]

[5-(1-Benzyl-1H-pyrazol-4-yl)-[1,2,4]triazolo[1,5-a]pyridin-2-yl]-[4-(2-pyrrolidin-1-yl-ethoxy)-phenyl]-amine (1.66 g, 3.46 mmol) and palladium hydroxide (1.6 g) were suspended in methanol (50 mL) and conc. HCl (1 mL) added. The suspension was then stirred under an atmosphere of hydrogen at 50° C. for 18 hours after which the catalyst was removed by filtration and the filtrate concentrated in vacuo. Sodium carbonate (50% sat.) was added, and the precipitate, a pale brown solid, collected by filtration. Yield: 1.22 g, 90%; LCMS method: 2, RT: 2.13 min, MI: 390 [M+1]. $^1$H NMR (DMSO): 1.75-1.85 (m, 4H), 2.92-2.98 (m, 4H), 3.16 (t, 2H), 4.15 (t, 2H), 6.95 (d, 2H), 7.38 (d, 1H), 7.46 (d, 1H), 7.55 (d, 1H), 7.65 (d, 2H), 8.24 (s, 1H), 8.69 (s, 1H), 9.43 (s, 1H).

The following compounds were synthesised using the same general method.

| Code No. | Characterisation |
|---|---|
| XX-202 | RT: 2.13 min, MI: 390; Method: 2 |

General Synthetic Procedure OO

Compounds were synthesised starting from [5-(1H-pyrazol-4-yl)-[1,2,4]triazolo[1,5-a]pyridin-2-yl]-[4-(2-pyrrolidin-1-yl-ethoxy)-phenyl]-amine following the scheme illustrated below. Reaction of the pyrazole with a sulfonyl chloride can be performed in the presence of triethylamine to produce the corresponding sulfonamide.

Scheme 58

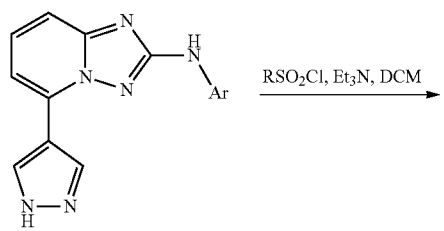

RSO$_2$Cl, Et$_3$N, DCM

-continued

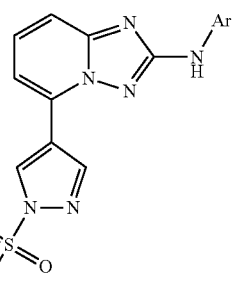

Synthesis 84

[5-(1-Methanesulfonyl-1H-pyrazol-4-yl)-[1,2,4]triazolo[1,5-a]pyridin-2-yl]-[4-(2-pyrrolidin-1-yl-ethoxy)-phenyl]-amine (XX-276)

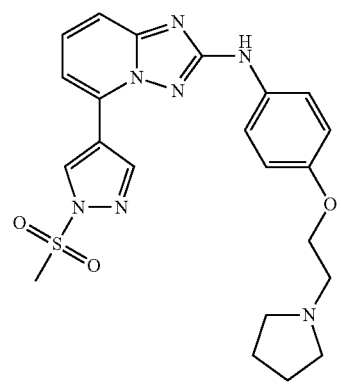 [SMILES: CS(=O)(=O)n1cc(-c2cccc3nc(Nc4ccc(OCCN5CCCC5)cc4)nn23)cn1]

To a stirred solution of [5-(1H-pyrazol-4-yl)-[1,2,4]triazolo[1,5-a]pyridin-2-yl]-[4-(2-pyrrolidin-1-yl-ethoxy)-phenyl]-amine (0.05 g, 0.128 mmol) in dichloromethane (1 ml) was added triethylamine (23 µl, 0.166 mmol) followed by methanesulfonyl chloride (12 µl, 0.154 mmol). The mixture was stirred for 18 hours at room temperature, then filtered and concentrated in vacuo. The product was purified by preparatory HPLC to yield the desired product. RT: 2.41 min, MI: 468, Method: 2; $^1$H NMR (DMSO, 300 MHz): 9.56 (s, 1H), 9.47 (s, 1H), 8.94 (s, 1H), 8.18 (s, 2H), 7.69-7.54 (m, 3H), 6.93 (d, 2H), 4.06 (t, 2H), 3.72 (s, 3H), 2.92 (t, 2H), 2.67 (s, 4H), 1.74 (s, 4H).

The following compounds were synthesised using the same general method.

| Code No. | Characterisation |
|---|---|
| XX-276 | RT: 2.14 min, MI: 468; Method: 2 |
| XX-284 | RT: 2.57 min, MI: 510; Method: 2 |
| XX-285 | RT: 2.82 min, MI: 564; Method: 2 |
| XX-286 | RT: 2.71 min, MI: 558; Method: 2 |
| XX-287 | RT: 2.74 min, MI: 612; Method: 2 |
| XX-288 | RT: 2.70 min, MI: 578; Method: 2 |
| XX-389 | RT: 2.45 min, MI: 513, Method: 2 |
| XX-289 | RT: 2.72 min, MI: 560; Method: 2 |
| XX-295 | RT: 2.67 min, MI: 558; Method: 2 |
| XX-296 | RT: 2.66 min, MI: 510; Method: 2 |
| XX-374 | RT: 4.08 min, MI: 482; Method: basic |
| XX-375 | RT: 2.54 min, MI: 494; Method: 2 |
| XX-376 | RT: 2.57 min, MI: 587; Method: 2 |

-continued

| Code No. | Characterisation |
|---|---|
| XX-377 | RT: 2.82 min, MI: 514; Method: 2 |
| XX-378 | RT: 2.79 min, MI: 564; Method: 2 |
| XX-379 | RT: 2.96 min, MI: 538; Method: 2 |
| XX-380 | RT: 2.60 min, MI: 496; Method: 2 |
| XX-381 | RT: 2.81 min, MI: 536; Method: 2 |
| XX-382 | RT: 2.72 min, MI: 550; Method: 2 |
| XX-383 | RT: 2.64 min, MI: 510; Method: 2 |
| XX-384 | RT: 2.84 min, MI: 524; Method: 2 |
| XX-385 | RT: 2.74 min, MI: 549; Method: 2 |

General Synthetic Procedure PP

Compounds were synthesised starting from [5-(1H-pyrazol-4-yl)-[1,2,4]triazolo[1,5-a]pyridin-2-yl]-[4-(2-pyrrolidin-1-yl-ethoxy)-phenyl]-amine following the scheme illustrated below. Reaction of the pyrazole with a halo-alkyl can be performed in the presence of potassium carbonate to produce the corresponding alkylated amine.

Scheme 59

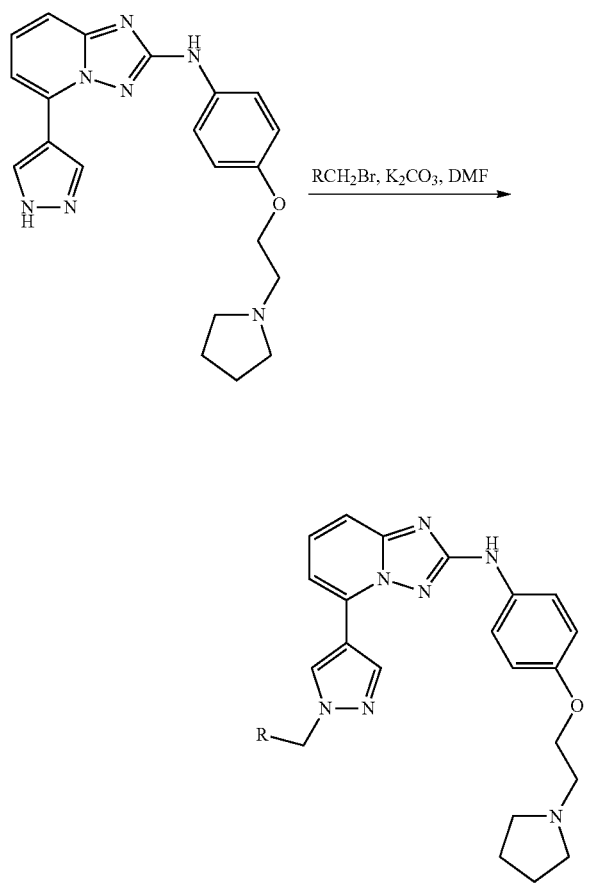

Synthesis 85

[5-(1-Butyl-1H-pyrazol-4-yl)-[1,2,4]triazolo[1,5-a]pyridin-2-yl]-[4-(2-pyrrolidin-1-yl-ethoxy)-phenyl]-amine (XX-303)

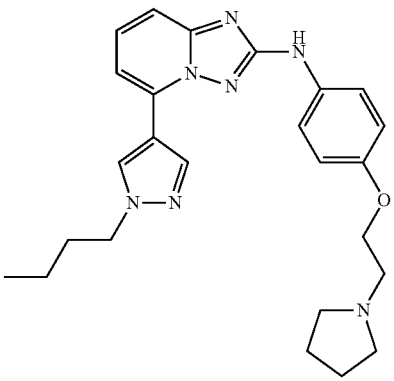 [SMILES: CCCCn1cc(-c2cccc3nc(Nc4ccc(OCCN5CCCC5)cc4)nn23)cn1]

To a stirred solution of [5-(1H-pyrazol-4-yl)-[1,2,4]triazolo[1,5-a]pyridin-2-yl]-[4-(2-pyrrolidin-1-yl-ethoxy)-phenyl]-amine (0.05 g, 0.128 mmol) in dimethylacetamide (1 ml) was added potassium carbonate (265 mg, 0.192 mmol) followed by 1-bromobutane (13 µl, 0.115 mmol). The mixture was stirred for 18 hours at room temperature, then filtered and concentrated in vacuo. The product was purified by preparatory HPLC to yield the desired product. LCMS: RT: 2.56 min, MI: 446, Method: 2; $^1$H NMR (DMSO, 300 MHz): 9.42 (s, 1H), 8.84 (s, 1H), 8.47 (s, 1H), 8.25 (s, 1H), 7.64 (d, 2H), 7.57 (d, 1H), 7.40 (dd, 2H), 6.95 (d, 2H), 4.26 (t, 2H), 4.09 (t, 2H), 2.96 (t, 2H), 2.72 (s, 4H), 1.88 (t, 2H), 1.83 (s, 4H), 1.30 (dd, 2H), 0.92 (t, 3H).

The following compounds were synthesised using the same general method.

| Code No. | Characterisation |
|---|---|
| XX-303 | RT: 2.56 min, MI: 446; Method: 2 |
| XX-290 | RT: 2.72 min MI: 494;, Method: 2 |
| XX-302 | RT: 2.36 min, MI: 428; Method: 2 |
| XX-304 | RT: 2.75 min, MI: 514; Method: 2 |
| XX-305 | RT: 2.41 min, MI: 485; Method: 2 |
| XX-306 | RT: 2.67 min, MI: 494; Method: 2 |
| XX-307 | RT: 2.10 min, MI: 434; Method: 2 |
| XX-315 | RT: 3.75 min, MI: 418; Method: basic |
| XX-316 | RT: 4.05 min, MI: 445; Method: basic |
| XX-317 | RT: 2.42 min, MI: 514; Method: 2 |
| XX-318 | RT: 2.42 min, MI: 432; Method: 2 |
| XX-319 | RT: 2.77 min, MI: 474; Method: 2 |
| XX-320 | RT: 2.65 min, MI: 460, Method: 2 |
| XX-328 | RT: 2.41 min, MI: 416.; Method: 2 |
| XX-273 | RT: 2.82 min, MI: 548, Method: 2 |
| XX-342 | RT: 2.14 min, MI: 447; Method: 2 |
| XX-343 | RT: 2.74 min, MI: 460; Method: 2 |
| XX-344 | RT: 2.42 min, MI: 474; Method: 2 |
| XX-345 | RT: 2.84 min, MI: 474; Method: 2 |
| XX-346 | RT: 2.56 min, MI: 508; Method: 2 |
| XX-349 | RT: 2.35 min, MI: 448; Method: 2 |
| XX-350 | RT: 2.81 min, MI: 508; Method: 2 |
| XX-351 | RT: 2.33 min, MI: 443; Method: 2 |
| XX-352 | RT: 2.78 min, MI: 514; Method: 2 |
| XX-353 | RT: 2.72 min, MI: 460; Method: 2 |
| XX-354 | RT: 2.74 min, MI: 515; Method: 2 |
| XX-356 | RT: 2.83 min, MI: 486; Method: 2 |
| XX-366 | RT: 2.62 min, MI: 564; Method: 2 |

-continued

| Code No. | Characterisation |
|---|---|
| XX-367 | RT: 2.62 min, MI: 498; Method: 2 |
| XX-369 | RT: 2.56 min, MI: 510; Method: 2 |

General Synthetic Procedure QQ

Compounds were synthesised starting from [5-(1H-pyrazol-4-yl)-[1,2,4]triazolo[1,5-a]pyridin-2-yl]-[4-(2-pyrrolidin-1-yl-ethoxy)-phenyl]-amine following the scheme illustrated below. Reaction of the pyrazole with 2-chloroethanol in the presence of potassium carbonate provided an alcohol, which was reacted with methane sulfonyl chloride to generate the corresponding methane sulfonate. Reaction with a mercaptam in the presence of potassium carbonate afforded the desired thiol.

Scheme 60

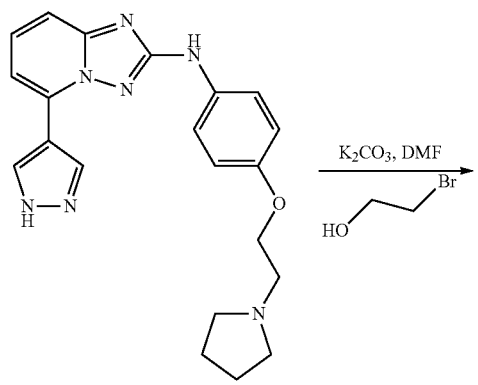

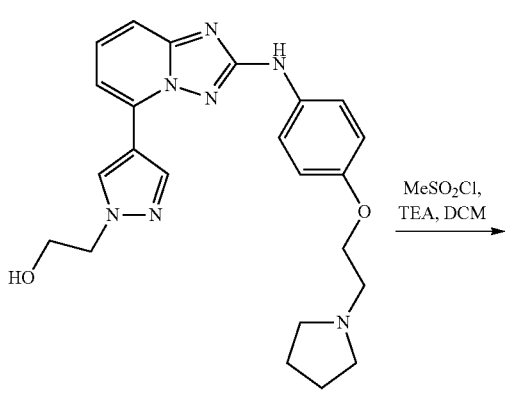

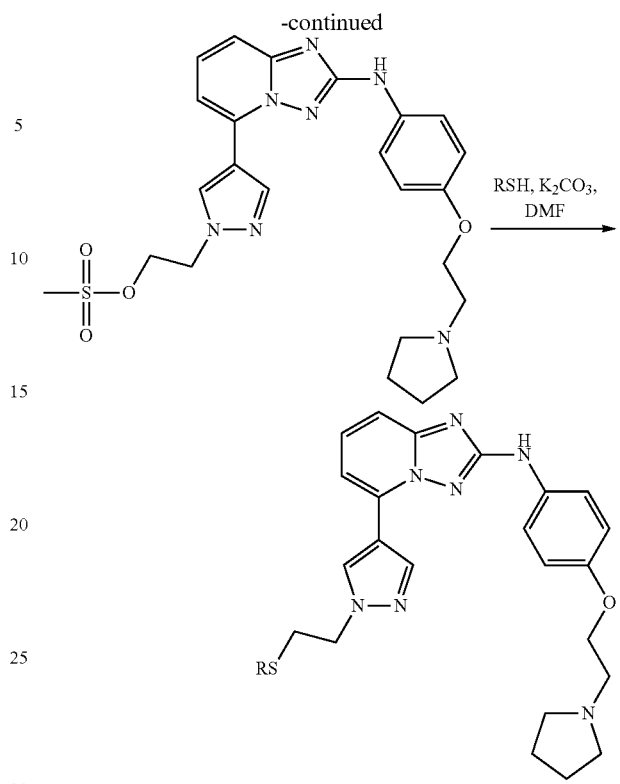

Synthesis 86

2-(4-{2-[4-(2-Pyrrolidin-1-yl-ethoxy)-phenylamino]-[1,2,4]triazolo[1,5-a]pyridin-5-yl}-pyrazol-1-yl)-ethanol (XX-307)

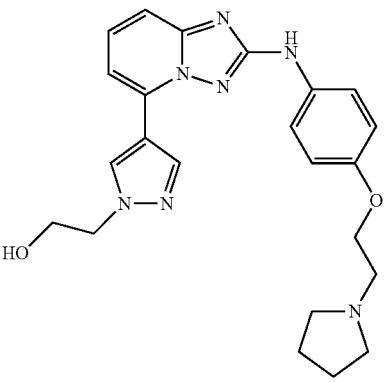 [SMILES: OCCn1cc(-c2cccc3nc(Nc4ccc(OCCN5CCCC5)cc4)nn23)cn1]

To a stirred solution of [5-(1H-pyrazol-4-yl)-[1,2,4]triazolo[1,5-a]pyridin-2-yl]-[4-(2-pyrrolidin-1-yl-ethoxy)-phenyl]-amine (0.40 g, 1.03 mmol) in dimethylformamide (10 ml) was added potassium carbonate (2 g) followed by 1-chloroethanol (140 μl, 2.06 mmol). The mixture was stirred for 18 hours at room temperature, then filtered and concentrated in vacuo to provide a yellow solid. No further purification was required. Yield: 0.45 g, 89%; LCMS method: 2, RT: 2.10 min, MI: 434 [M+1].

Synthesis 87

Methanesulfonic acid 2-(4-{2-[4-(2-pyrrolidin-1-yl-ethoxy)-phenylamino]-[1,2,4]triazolo[1,5-a]pyridin-5-yl}-pyrazol-1-yl)-ethyl ester (XX-091)

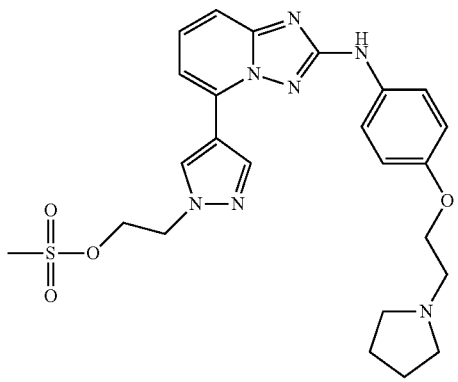 [SMILES: CS(=O)(=O)OCCn1cc(-c2cccc3nc(Nc4ccc(OCCN5CCCC5)cc4)nn23)cn1]

To a stirred solution of 2-(4-{2-[4-(2-pyrrolidin-1-yl-ethoxy)-phenylamino]-[1,2,4]triazolo[1,5-a]pyridin-5-yl}-pyrazol-1-yl)-ethanol (0.55 g, 1.28 mmol) in dichloromethane (5 ml) was added triethylamine (450 µl, 3.20 mmol) followed by methanesulfonyl chloride (200 µl, 2.56 mmol). The mixture was stirred for 18 hours at room temperature, and partitioned between ethyl acetate and ammonium chloride. The aqueous phase was extracted multiple times with ethyl acetate, and the combined organic phases dried over magnesium sulfate, filtered and concentrated in vacuo to provide a white fluffy solid. No further purification was required. Yield: 0.34 g, 52%; LCMS method: 2, RT: 2.25 min, MI: 512 [M+1].

Synthesis 88

(5-{1-[2-(5-Amino-4H-[1,2,4]triazol-3-ylsulfanyl)-ethyl]-1H-pyrazol-4-yl}-[1,2,4]triazolo[1,5-a]pyridin-2-yl)-[4-(2-pyrrolidin-1-yl-ethoxy)-phenyl]-amine (XX-327)

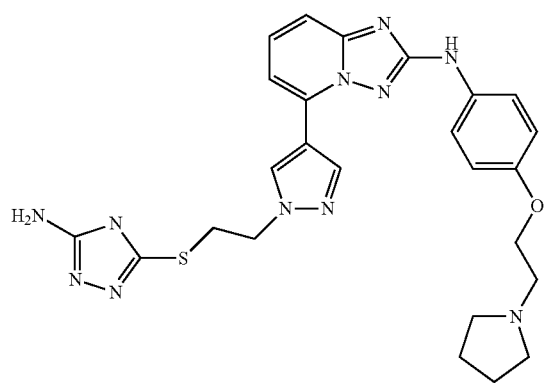 [SMILES: Nc1nnc(SCCn2cc(-c3cccc4nc(Nc5ccc(OCCN6CCCC6)cc5)nn34)cn2)[nH]1]

To a stirred solution of methanesulfonic acid 2-(4-{2-[4-(2-pyrrolidin-1-yl-ethoxy)-phenylamino]-[1,2,4]triazolo[1,5-a]pyridin-5-yl}-pyrazol-1-yl)-ethyl ester (0.40 g, 0.78 mmol) in dimethylformamide (1 ml) was added potassium carbonate (150 mg) followed by 3-amino-5-mercapto-1,2,4-triazole (19 mg, 0.156 mmol). The mixture was stirred for 18 hours at room temperature, then filtered and concentrated in vacuo. The title compound was purified by preparatory HPLC to yield the desired product. LCMS method: 2, RT: 2.15 min, MI: 532 [M+1]; $^1$H NMR (300 MHz, DMSO) 9.35 (s, 1H), 8.81 (s, 1H), 8.45 (s, 1H), 8.22 (s, 2H), 7.58 (d, 2H), 7.55 (d, 1H), 7.40 (dd, 2H), 6.85 (d, 2H), 6.13 (s, 1H), 4.51 (t, 2H), 3.98 (t, 2H), 3.48 (t, 2H), 2.75 (t, 2H), 2.49 (s, 4H), 1.65 (s, 4H).

The following compounds were synthesised using the same general method.

| Code No. | Characterisation |
| --- | --- |
| XX-091 | RT: 2.25 min, MI: 512; Method: 2 |
| XX-327 | RT: 2.15 min, MI: 532; Method: 2 |
| XX-424 | RT: 4.36 min, MI: 547, Method basic |
| XX-426 | RT: 2.59 min, MI: 532; Method: 2 |
| XX-427 | RT: 4.58 min, MI: 531, Method basic |
| XX-428 | RT: 2.28 min, MI: 532; Method: 2 |
| XX-430 | RT: 2.34 min, MI: 549, Method: 2 |
| XX-431 | RT: 5.05 min, MI: 562, Method basic |
| XX-429 | RT: 2.24 min, MI: 531, Method: 2 |
| XX-425 | RT: 2.46 min, MI: 533, Method: 2 |

General Synthetic Procedure RR

Compounds were synthesised starting from [5-(1H-pyrazol-4-yl)-[1,2,4]triazolo[1,5-a]pyridin-2-yl]-[4-(2-pyrrolidin-1-yl-ethoxy)-phenyl]-amine following the scheme illustrated below. Reaction of the pyrazole with methyl bromoacetate in the presence of ceasium carbonate provided an ester, which was hydrolysed with sodium hydroxide to generate the corresponding carboxylic acid. Reaction with an amine under standard coupling conditions afforded the desired amide.

Scheme 61

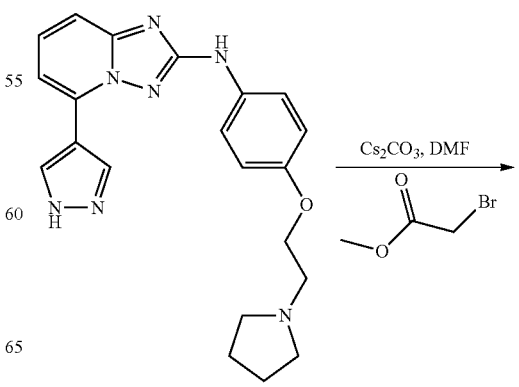

427

-continued

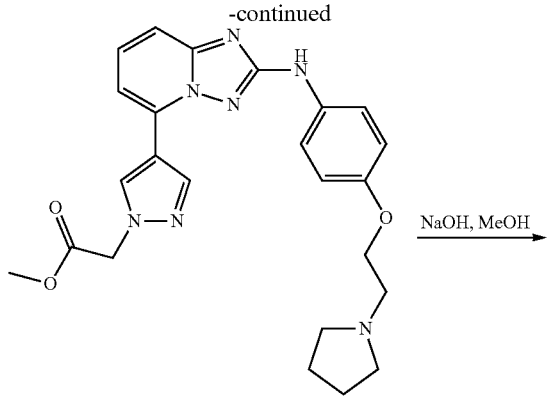

NaOH, MeOH

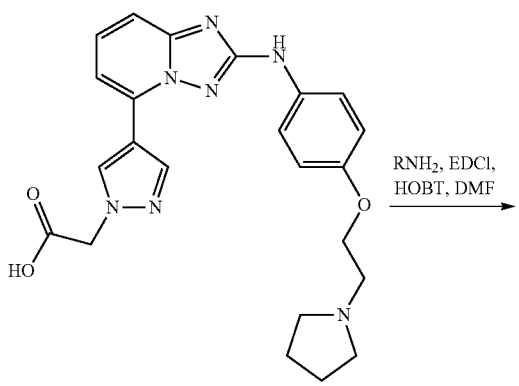

RNH₂, EDCl,
HOBT, DMF

428

Synthesis 89

(4-{2-[4-(2-Pyrrolidin-1-yl-ethoxy)-phenylamino]-
[1,2,4]triazolo[1,5-a]pyridin-5-yl}-pyrazol-1-yl)-
acetic acid methyl ester

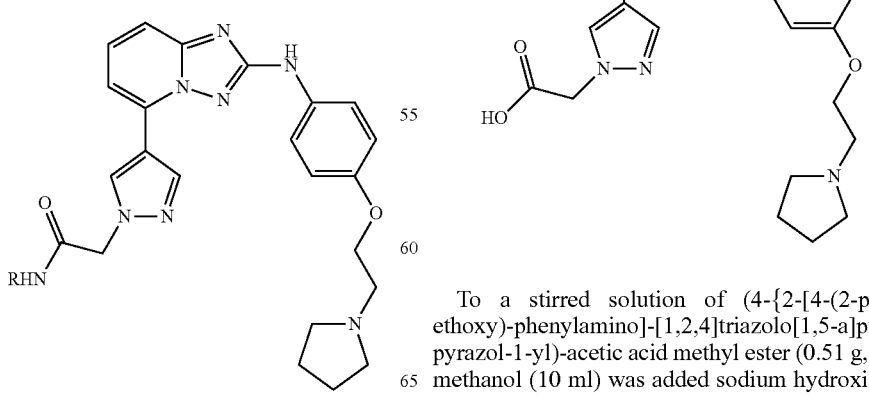

To a stirred solution of [5-(1H-pyrazol-4-yl)-[1,2,4]triazolo[1,5-a]pyridin-2-yl]-[4-(2-pyrrolidin-1-yl-ethoxy)-phenyl]-amine (0.70 g, 1.80 mmol) in dimethylformamide (14 ml) was added ceasium carbonate (2 g) followed by methyl bromoacetate (255 μl, 2.70 mmol). The mixture was stirred for 18 hours at room temperature, and partitioned between ethyl acetate and water. The aqueous phase was extracted with three portions of ethyl acetate, and the combined organic phases dried over magnesium sulfate and concentrated in vacuo to provide a yellow solid. No further purification was required. Yield: 0.51 g, 61%; LCMS method: basic, RT: 3.77 min, MI: 462 [M+1].

Synthesis 90

(4-{2-[4-(2-Pyrrolidin-1-yl-ethoxy)-phenylamino]-
[1,2,4]triazolo[1,5-a]pyridin-5-yl}-pyrazol-1-yl)-
acetic acid (XX-440)

To a stirred solution of (4-{2-[4-(2-pyrrolidin-1-yl-ethoxy)-phenylamino]-[1,2,4]triazolo[1,5-a]pyridin-5-yl}-pyrazol-1-yl)-acetic acid methyl ester (0.51 g, 1.11 mmol) in methanol (10 ml) was added sodium hydroxide (2N, 1 mL) and the mixture stirred for 3 hours at room temperature. All solvents were removed in vacuo to afford the title compound as a pale yellow solid. No further purification was required. Yield: 0.40 g, 80%; LCMS method: 2, RT: 2.36 min, MI: 448 [M+1].

Synthesis 91

N-(2,2-Dimethyl-propyl)-2-(4-{2-[4-(2-pyrrolidin-1-yl-ethoxy)-phenylamino]-[1,2,4]triazolo[1,5-a]pyridin-5-yl}-pyrazol-1-yl)-acetamide (XX-092)

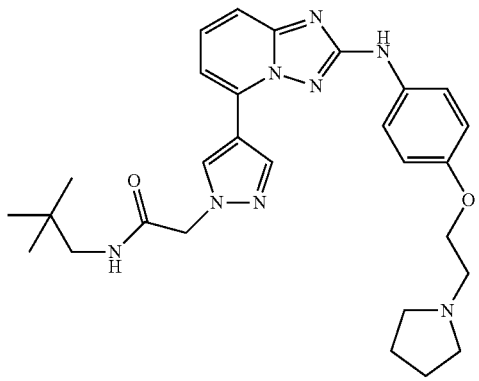 [SMILES: CC(C)(C)CNC(=O)Cn1cc(-c2cccc3nc(Nc4ccc(OCCN5CCCC5)cc4)nn23)cn1]

To a stirred solution of (4-{2-[4-(2-pyrrolidin-1-yl-ethoxy)-phenylamino]-[1,2,4]triazolo[1,5-a]pyridin-5-yl}-pyrazol-1-yl)-acetic acid (0.60 g, 0.128 mmol) in dimethylformamide (1 ml) was added EDCI (50 mg, 0.256 mmol), diisopropylethylamine (112 µl, 0.640 mmol), HOBT (35 mg, 0.256 mmol) and finally neopentylamine (30 µl, 0.256 mmol). The mixture was stirred for 18 hours at room temperature, then filtered and concentrated in vacuo. The title compound was purified by preparatory HPLC to yield the desired product. LCMS method: 2, RT: 2.51 min, MI: 517 [M+1]; $^1$H NMR (300 MHz, DMSO) 9.40 (s, 1H), 8.85 (s, 1H), 8.42 (s, 1H), 8.16 (s, 2H), 7.61 (d, 2H), 7.54 (d, 1H), 7.40 (dd, 2H), 6.92 (d, 2H), 4.98 (s, 2H), 4.02 (t, 2H), 2.93 (d, 2H), 2.87 (t, 2H), 2.63 (s, 4H), 1.69 (s, 4H), 0.83 (m, 9H).

The following compounds were synthesised using the same general method.

| Code No. | Characterisation |
| --- | --- |
| XX-092 | RT: 2.51 min, MI: 517; Method: 2 |
| XX-440 | RT: 2.19 min, MI: 448, Method: 2 |
| XX-435 | RT: 2.62 min, MI: 557, Method: 2 |
| XX-437 | RT: 2.16 min, MI: 487, Method: 2 |
| XX-434 | RT: 2.22 min, MI: 489, Method: 2 |
| XX-436 | RT: 2.06 min, MI: 491, Method: 2 |
| XX-433 | RT: 2.4 min, MI: 537, Method: 2 |
| XX-432 | RT: 2.46 min, MI: 523, Method: 2 |
| XX-441 | RT: 2.26 min, MI: 489, Method: 2 |

General Synthetic Procedure SS

Compounds were synthesised starting from 5-bromo-[1,2,4]triazolo[1,5-a]pyridin-2-ylamine following the scheme illustrated below. In general, addition of an amine to the bromo derivative led to the di-amino compound. The final derivatives may be obtained via a standard cross-coupling reaction utilising a catalyst such as bis(dibenzylideneacetone)palladium and an appropriate bromo derivative under standard conditions.

Scheme 62

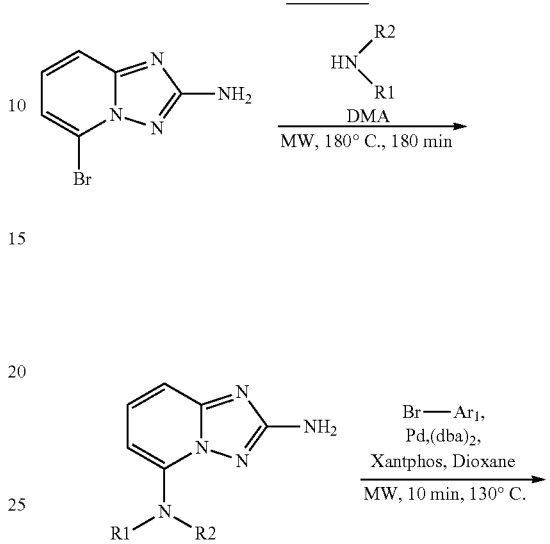

Synthesis 92

N*5*-Cyclopentyl-[1,2,4]triazolo[1,5-a]pyridine-2,5-diamine

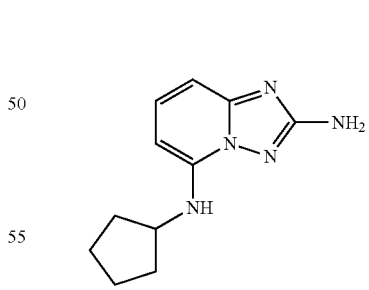

To a solution of 5-bromo-[1,2,4]triazolo[1,5-a]pyridin-2-ylamine (0.5 g, 2.35 mmol) in dimethylacetamide (2 mL), cyclopentylamine (2.3 mL, 23.5 mmol) was added and the solution was heated under microwave irradiation (180° C., 180 min). The resulting mixture was diluted with water and extracted into ethyl acetate. The organics were washed with water then brine, and dried over magnesium sulfate. The solid (0.5 g) was used without further purification. LCMS1: 2.84 min, 218 [M+1].

Synthesis 93

N*5*-Cyclopentyl-N*2*-[4-(2-pyrrolidin-1-yl-ethoxy)-phenyl]-[1,2,4]triazolo[1,5-a]pyridine-2,5-diamine (XX-152)

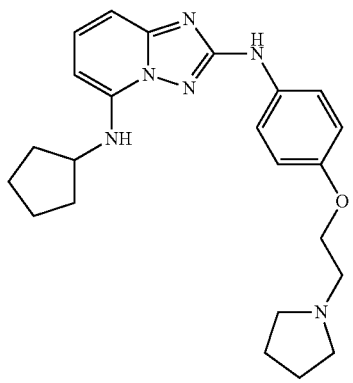 [SMILES: c1cc(NC2CCCC2)n2nc(Nc3ccc(OCCN4CCCC4)cc3)nc2c1]

In a microwave vial, N*5*-cyclopentyl-[1,2,4]triazolo[1,5-a]pyridine-2,5-diamine (0.07 g, 0.322 mmol), 1-(2-(4-bromophenoxy)ethyl)pyrrolidine (0.13 g, 0.483 mmol), bis(dibenzylideneacetone)palladium (0.01 g, 0.016 mmol), xantphos (0.019 g, 0.032 mmol) and sodium tert-butoxide (0.063 g, 0.644 mmol) were added successively. 1,4-Dioxane (1.2 mL) and dimethylacetamide (4 drops) were added and the vial was sealed and heated under microwave irradiation (150° C., 10 min). The mixture was filtered and purified by preparatory HPLC. LCMS Method: 2: RT: 2.51 min, MI: 407 [M+1]. NMR 1H (DMSO): 1.55-1.75 (m, 10H), 2.03-2.08 (m, 2H), 2.55-2.65 (m, 4H), 2.84 (t, 2H), 3.93-4.00 (m, 1H), 4.01 (t, 2H), 6.10 (d, 1H), 6.15 (d, 1H), 6.69 (d, 1H), 6.87 (d, 2H), 7.37 (t, 1H), 7.63 (d, 2H), 9.17 (s, 1H).

Compounds were synthesised starting from bromoaryl esters following the scheme illustrated below.

| Code No. | Characterisation |
|---|---|
| XX-152 | RT: 2.51 min, MI: 407, Method: 2 |

General Synthetic Procedure TT

Compounds were synthesised from 2-(chloromethyl)-2-methyloxirane as shown in the scheme below.

Scheme 63

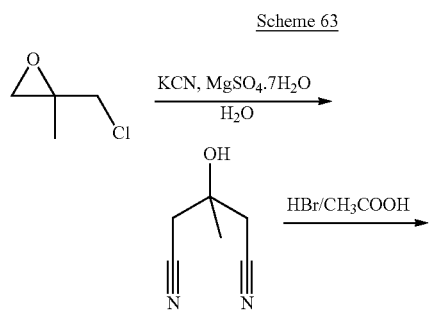

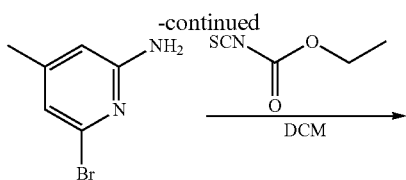

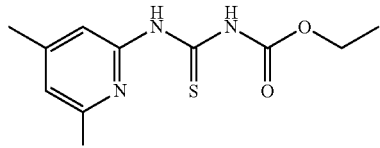

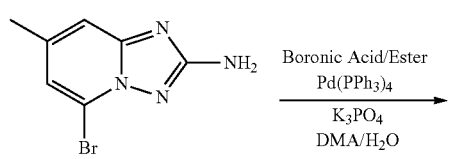

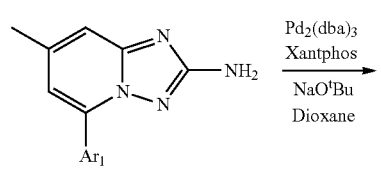

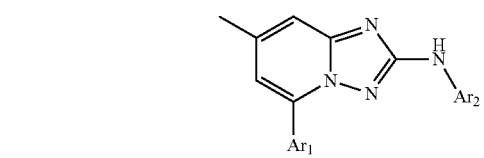

Synthesis 94

3-Hydroxy-3-methyl-pentanedinitrile

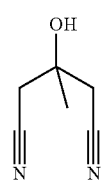

A three-necked flask was fitted with dropping funnel and a thermometer. The flask was placed in an ice bath and filled with nitrogen. Magnesium sulfate heptahydrate (16.84 g, 68.26 mmol) was dissolved in water (80 ml) and added to the flask. The solution was cooled to 10° C. and potassium cyanide (4.88 g, 75.08 mmol) was added. 2-(Chloromethyl)-2-methyloxirane (4.00 g, 37.54 mmol) was added portion-wise and the mixture was stirred at room temperature overnight. Dichloromethane was added to the reaction mixture and the product extracted twice. The combined organics were washed with brine, dried over anhydrous magnesium sulfate, filtered and concentrated in vacuo to give the desired product. Yield 3.57 g, 77%, ¹H NMR (CDCl₃, 300 MHz): 1.57 (s, 3H), 2.69 (dd, 4H).

Synthesis 95

6-Bromo-4-methyl-pyridin-2-ylamine

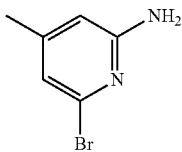

Hydrogen bromide solution (33 wt. % in acetic acid) (17.8 ml, 98.92 mmol) was added dropwise to 3-hydroxy-3-methyl-pentanedinitrile (3.07 g, 24.73 mmol) with stirring. The reaction was stirred overnight at room temperature. Saturated aqueous sodium hydrogencarbonate was added until neutralised. The resulting white precipitate was collected by filtration, washed with water and dried under vacuum to give the desired product. Yield 2.55 g, 55%. LCMS MI: 186.89+188.91, RT: 3.16 min, Method: 2.

Synthesis 96

1-(6-Bromo-4-methyl-pyridin-2-yl)-3-carboethoxy-thiourea

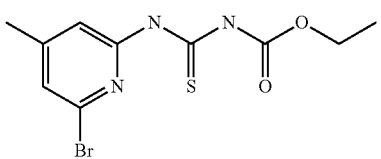 [SMILES: CCOC(=O)NC(=S)Nc1cc(C)cc(Br)n1]

To a solution of 6-bromo-4-methyl-pyridin-2-ylamine (0.5 g, 2.67 mmol) in dichloromethane (20 ml) cooled to 5° C. was added ethoxycarbonyl isothiocyanate (0.32 ml, 2.67 mmol) dropwise over 15 min. The reaction mixture was then allowed to warm to room temperature at which it was stirred for 16 h. Evaporation in vacuo gave a solid that was collected by filtration and thoroughly washed with cyclohexane to give the desired product. Yield 0.59 g, 69%. LCMS MI: 317.92+319.94, RT: 5.05 min, Method: 2

Synthesis 97

5-Bromo-7-methyl-[1,2,4]triazolo[1,5-a]pyridin-2-ylamine

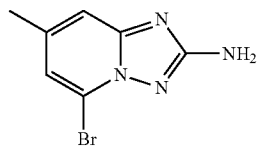

To a suspension of hydroxylamine hydrochloride (0.65 g, 9.27 mmol) in ethanol/methanol (1:1, 20 ml) was added diisopropylethylamine (0.97 ml, 5.56 mmol) and the mixture was stirred at room temp. (20° C.) for 1 h. 1-(6-Bromo-4-methyl-pyridin-2-yl)-3-carboethoxy-thiourea (0.59 g, 1.84 mmol) was added and the mixture slowly heated to reflux. Having refluxed overnight the mixture was allowed to cool and filtered to collect the precipitated solid. Further product was collected by evaporation in vacuo of the filtrate, addition of water and filtration. The combined solids were washed successively with water, ethanol/methanol and diethylether, then dried in vacuo to give the desired product. Yield 0.19 g, 45%. LCMS MI: 226.91+228.89, RT: 2.52 min, Method: 2

Synthesis 98

5-(2,3-Dihydro-benzo[1,4]dioxin-6-yl)-7-methyl-[1,2,4]triazolo[1,5-a]pyridin-2-ylamine 5-Bromo-7-methyl-[1,2,4]triazolo[1,5-a]pyridin-2-ylamine (0.19 g, 0.84 mmol), 1,4-benzodioxane-6-boronic acid (0.18 g, 1.00 mmol), palladium(tetrakis)triphenylphosphine (97 mg, 0.084 mmol), potassium phosphate (0.36 g, 1.67 mmol), dimethylacetamide (3 ml) and water (1 ml) were added to a microwave vial containing a stirrer bar. The reaction was heated to 150° C. for 10 min. Water was added to the reaction mixture and the product extracted into ethyl acetate (×2). The organics were combined, washed several times with brine, dried over anhydrous magnesium sulfate, filtered and concentrated in vacuo. The residue was triturated with diethyl ether and collected by filtration to give the desired product. LCMS RT: 2.82 min, MI: 283.17, Method: 2

Synthesis 99

[5-(2,3-Dihydro-benzo[1,4]dioxin-6-yl)-7-methyl-[1,2,4]triazolo[1,5-a]pyridin-2-yl]-[4-(2-pyrrolidin-1-yl-ethoxy)-phenyl]-amine (XX-311)

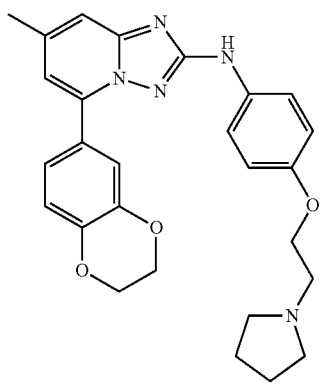 [SMILES: Cc1cc(-c2ccc3c(c2)OCCO3)n2nc(Nc3ccc(OCCN4CCCC4)cc3)nc2c1]

A microwave tube was charged with 5-(2,3-dihydro-benzo[1,4]dioxin-6-yl)-7-methyl-[1,2,4]triazolo[1,5-a]pyridin-2-ylamine (50 mg, 0.177 mmol), 1-[2-(4-bromophenoxy)ethyl]pyrrolidine (0.05 ml, 0.23 mmol), tris(dibenzylideneacetone)dipalladium (8 mg. 0.009 mmol), Xantphos (10 mg, 0.018 mmol), sodium tert butoxide (35 mg, 0.354 mmol) and dioxane (1 ml). Dimethylacetamide (2 drops) was added to assist with microwave absorption. The mixture was heated at 130° C. for 15 min. Upon cooling the reaction mixture was filtered through a plug of silica and washed with methanol. The volatiles were removed in vacuo and the product was purified by preparatory HPLC. LCMS RT: 2.67 min, MI: 472, Method: 2. $^1$H NMR (DMSO, 300 MHz): 1.79 (m, 4H), 2.42 (s, 3H), 2.85 (m, 4H), 3.08 (t, 2H), 4.09 (t, 2H), 4.33 (brs, 4H), 6.89 (d, 2H), 7.00 (d, 1H), 7.04 (d, 2H), 7.29 (s, 1H), 7.60 (m, 3H), 7.65 (d, 2H), 9.36 (s, 1H).

The following compounds were synthesised using the same general method.

| Code No. | Characterisation |
|---|---|
| XX-311 | RT: 2.67 min, MI: 472, Method: 2 |

General Synthetic Procedure UU

Compounds were synthesised from 2-bromo-3-methoxypyridine as shown in the scheme below.

Scheme 63

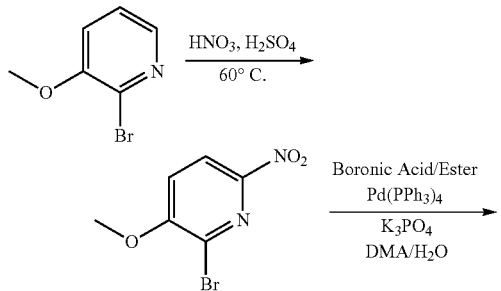

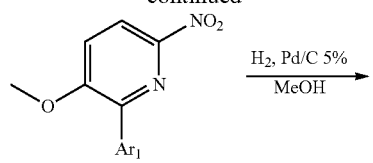

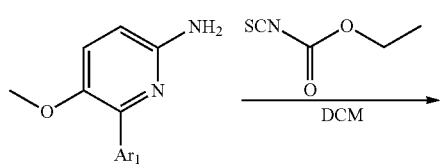

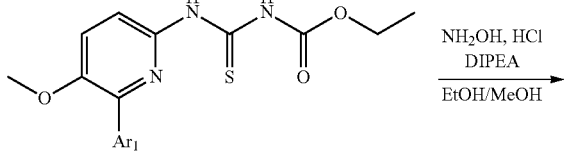

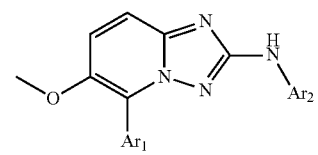

Synthesis 100

2-Bromo-3-methoxy-6-nitro-pyridine

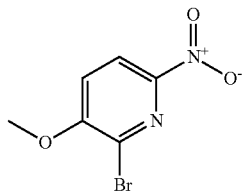

2-Bromo-3-methoxy-pyridine (1 g, 5.32 mmol) was dissolved in concentrated sulphuric acid (2 mL) and a mixture of concentrated sulphuric acid/fuming nitric acid (2mL/4 mL) was added dropwise. The mixture was heated at 60° C. for 1 h and then poured into ice and basified with ammonium hydroxide. Extraction with chloroform gave the nitro derivative which was used without further purification (1.05 g, 85%). LCMS Method: 2: RT: 3.77 min, MI: 234 [M+1].

Synthesis 101

2-(2,3-Dihydro-benzo[1,4]dioxin-6-yl)-3-methoxy-6-nitro-pyridine

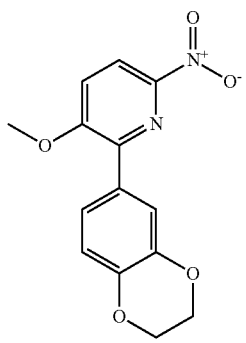 [SMILES: COc1ccc([N+](=O)[O-])nc1-c1ccc2c(c1)OCCO2]

2-Bromo-3-methoxy-6-nitro-pyridine (0.5 g, 2.14 mmol), 1,4-benzodioxane-6-boronic acid (0.5 g, 2.79 mmol) and a mixture of dimethylacetamide/water (10 mL/3 mL) were added to a microwave tube containing potassium phosphate (0.91 g, 4.29 mmol) and palladium tetrakistriphenylphosphine (0.4 g, 0.2 mmol) and the reaction was heated to 150° C. for 10 min. The solution was added in a separating funnel and water and ethyl acetate were added. The organic layer was separated and the aqueous was extracted again with ethyl acetate. The combined organics were washed with water (*2) then brine, dried over magnesium sulphate and concentrated in vacuo. The crude was used without further purification (0.48 g, 77%). LCMS Method: 2: RT: 4.41 min, MI: 289 [M+1].

Synthesis 102

6-(2,3-Dihydro-benzo[1,4]dioxin-6-yl)-5-methoxy-pyridin-2-ylamine

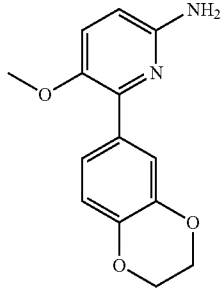 [SMILES: COc1ccc(N)nc1-c1ccc2c(c1)OCCO2]

To a solution of N-[4-(6-nitro-pyridin-3-yloxy)-phenyl]-acetamide in methanol (0.48 g, 1.66 mmol) was added 5% Pd/C (0.4 g) and the mixture treated with hydrogen gas at atmospheric pressure. After 19h, the catalyst was removed by filtration through celite and the solution concentrated under reduced pressure and the resulting crude used without further purification (0.41 g, 95%). LCMS Method: 2: RT: 2.57 min, MI: 259 [M+1].

Synthesis 103

1-[6-(2,3-Dihydro-benzo[1,4]dioxin-6-yl)-4-methoxy-pyridin-2-yl]-3-carboethoxy-thiourea

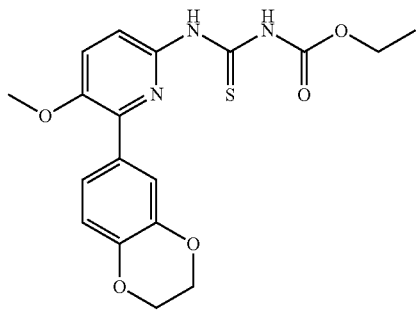 [SMILES: CCOC(=O)NC(=S)Nc1ccc(OC)c(-c2ccc3c(c2)OCCO3)n1]

To a solution of 6-(2,3-dihydro-benzo[1,4]dioxin-6-yl)-5-methoxy-pyridin-2-ylamine (0.35 g, 1.35 mmol) in dichloromethane (5 mL) cooled at 5° C. was added ethoxycarbonyl isothiocyanate (0.16 mL, 1.35 mmol) dropwise over 15 min. The reaction mixture was then allowed to warm to room temperature at which it was stirred overnight. Evaporation in vacuo gave a yellow solid which was collected by filtration and thoroughly washed with diethylether. The solid was used without further purification (0.53 g, 100%). LCMS Method: 2: RT: 4.84 min, MI: 390 [M+1].

Synthesis 104

5-(2,3-Dihydro-benzo[1,4]dioxin-6-yl)-6-methoxy-[1,2,4]triazolo[1,5-a]pyridin-2-ylamine

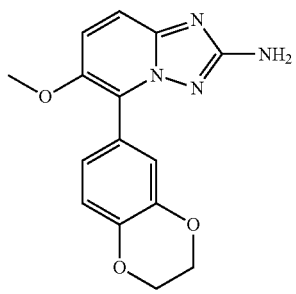 [SMILES: COc1ccc2nc(N)nn2c1-c1ccc2c(c1)OCCO2]

To a mixture ethanol/methanol (5 mL/5 mL), hydroxylamine hydrochloride (0.47 g, 6.8 mmol) and diisopropylethylamine (0.71 mL, 4.08 mmol) were added successively. The mixture was stirred for 1 hour and 1-[6-(2,3-dihydro-benzo[1,4]dioxin-6-yl)-4-methoxy-pyridin-2-yl]-3-carboethoxy-thiourea was added portionwise. The mixture was refluxed for 3 hours and then allowed to cool to room temperature. The solvent was removed under reduced pressure, and the resulting solid collected by filtration and washed with water followed by methanol. The solid was used without further purification (0.33 g, 80%). LCMS Method: 2: RT: 2.57 min, MI: 299 [M+1].

Synthesis 105

[5-(2,3-Dihydro-benzo[1,4]dioxin-6-yl)-6-methoxy-[1,2,4]triazolo[1,5-a]pyridin-2-yl]-[4-(2-pyrrolidin-1-yl-ethoxy)-phenyl]-amine (XX-323)

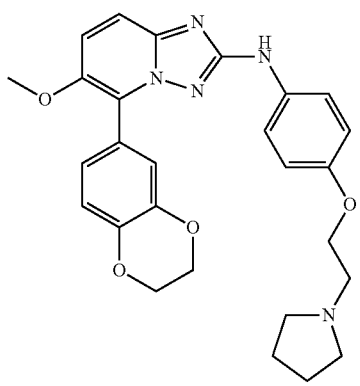 [SMILES: COc1ccc2nc(Nc3ccc(OCCN4CCCC4)cc3)nn2c1-c1ccc2c(c1)OCCO2]

In a microwave vial, 5-(2,3-dihydro-benzo[1,4]dioxin-6-yl)-6-methoxy-[1,2,4]triazolo[1,5-a]pyridin-2-ylamine (0.05 g, 0.17 mmol), 1-[2-(4-bromophenoxy)ethyl]-pyrrolidine (0.068 g, 0.251 mmol), bis(dibenzylideneacetone)palladium (0.005 g, 0.008 mmol), Xantphos (0.01 g, 0.017 mmol) and sodium tert-butoxide (0.033 g, 0.335 mmol) were added successively. Dioxane (1.2 mL) and dimethylacetamide (2 drops) were added and the vial was sealed and heated in the microwave (150° C., 10 min). The crude was purified using an SCX cartridge, by washing with methanol and releasing the compound with 2M ammonia in methanol. After concentration under reduced pressure, the crude was purified by preparatory LCMS. LCMS Method: 2: RT: 2.52 min, MI: 488 [M+1].

The following compounds were synthesised using the same general method.

| Code No. | Characterisation |
|---|---|
| XX-323 | RT: 2.52 min, MI: 488, Method: 2 |

General Synthesis Procedure VV

Compounds were synthesised starting from the 2-chloropyrimidin-4-ylamine following the scheme illustrated below. In general, the chloro derivative was involved in a Suzuki reaction utilising a palladium catalyst such as tetrakis(triphenylphosphine)palladium or other suitable catalyst and a suitable boronic acid or boronic ester. The 2-amino-pyrimidine and ethoxycarbonyl isothiocyanate are stirred in dichloromethane at ambient temperature. After concentration under reduced pressure and washing with an appropriate solvent, the solid was collected via filtration. The thiourea derivative was subjected to a cyclisation procedure, employing hydroxylamine in a protic solvent, to yield intermediate 2-amino-5-bromo-[1,2,4]triazolo[1,5-a]pyridine. The arylamino derivatives may be obtained via a standard cross-coupling reaction utilising a catalyst such as bis(dibenzylideneacetone)palladium and an appropriate bromo derivative under standards conditions.

Scheme 64

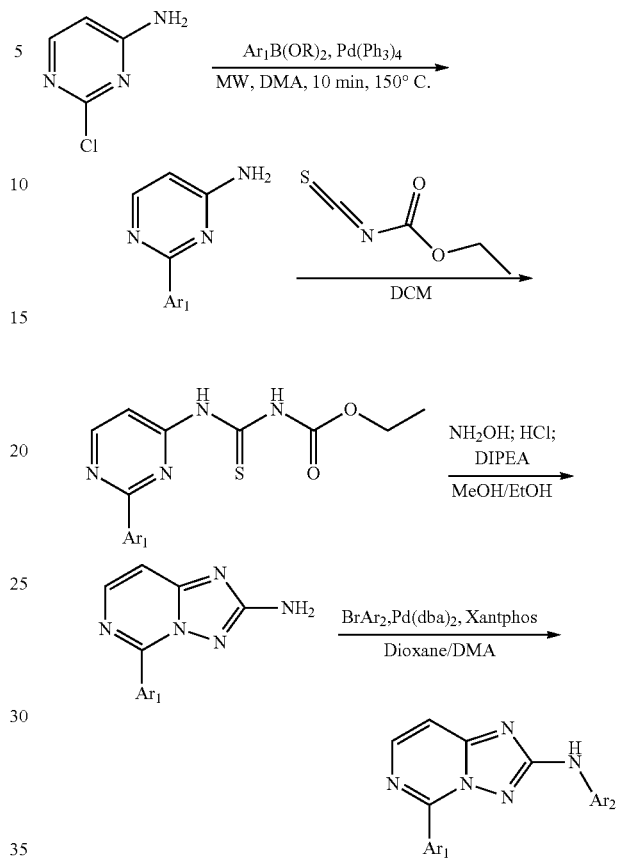

Synthesis 106

2-(2,3-Dihydro-benzo[1,4]dioxin-6-yl)-pyrimidin-4-ylamine

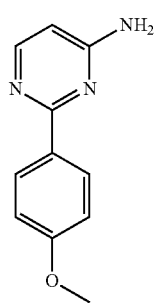

2-Chloro-pyrimidin-4-ylamine (1 g, 7.7 mmol), 4-methoxybenzeneboronic acid (1.41 g, 9.26 mmol) and dimethylacetamide (12 mL) were added to a microwave tube containing a stirrer bar, potassium phosphate (3.28 g, 15.44 mmol) was dissolved in water (4 mL) and added to the vial. The tetrakis(triphenylphosphine)palladium (0.44 g, 0.386 mmol) was added and the reaction was heated to 150° C. for 10 min. The reaction was filtered through silica and washed through with methanol and concentrated. Yield: 1.10 g, 71%; LCMS method: 1, RT: 3.43 min, MI: 241 [M+1].

Synthesis 107

2-(2,3-Dihydro-benzo[1,4]dioxin-6-yl)-pyrimidin-4-carboethoxy-thiourea

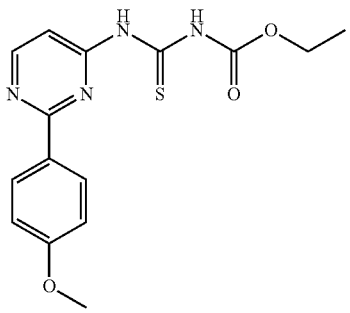 [SMILES: CCOC(=O)NC(=S)Nc1ccnc(-c2ccc(OC)cc2)n1]

To a solution of 2-(2,3-dihydro-benzo[1,4]dioxin-6-yl)-pyrimidin-4-ylamine (1.55 g, 7.7 mmol) in dichloromethane (5 mL) cooled to 5° C. was added ethoxycarbonyl isothiocyanate (0.92 mL, 7.7 mmol) dropwise over 15 min. The reaction mixture was then allowed to warm to room temp. (20° C.) at which it was stirred for 16 h. Evaporation in vacuo gave a yellow solid, which was collected by filtration, thoroughly washed with cyclohexane. No further purification was required. Yield: 2.45 g, 96%; LCMS method: 2, RT: 4.90 min; MI: 333 [M+1]:

Synthesis 108

5-(4-Methoxy-phenyl)-[1,2,4]triazolo[1,5-c]pyrimidin-2-ylamine

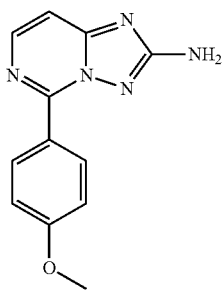

To a suspension of hydroxylamine hydrochloride (1.1 g, 15.94 mmol) in ethanol/methanol (7 mL/7 mL) was added N,N-diisopropylethylamine (1.67 mL, 9.57 mmol) and the mixture was stirred at room temperature for 1 h. 2-(2,3-Dihydro-benzo[1,4]dioxin-6-yl)-pyrimidin-4-carboethoxy-thiourea (1.06 g, 3.19 mmol) was then added and the mixture slowly heated to reflux. After 3 h at reflux the mixture was allowed to cool and filtered to collect the precipitated solid. Further product was collected by evaporation in vacuo of the filtrate, addition of water and filtration. The combined solids were washed successively with water, ethanol/methanol and diethyl ether then dried in vacuo to afford the expected compound as a white solid. No further purification was required. Yield: 0.68 g, 88%; LCMS method: 1, 1.34 min, MI; 242 [M+1].

Synthesis 109

[5-(4-Methoxy-phenyl)-[1,2,4]triazolo[1,5-c]pyrimidin-2-yl]-[4-(2-pyrrolidin-1-yl-ethoxy)-phenyl]-amine (YY-001)

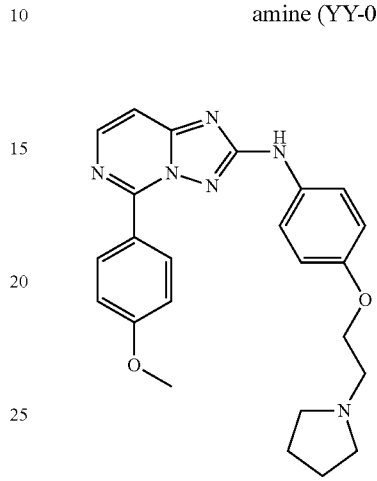

In a microwave vial, 5-(4-methoxy-phenyl)-[1,2,4]triazolo[1,5-c]pyrimidin-2-ylamine (0.05 g, 0.207 mmol), 1-[2-(3-bromo-phenoxy)-ethyl]-1H-imidazole (0.073 g, 0.27 mmol), bis(dibenzylideneacetone)palladium (0.01 g, 0.01 mmol), xantphos (0.012 g, 0.02 mmol) and sodium tert butoxide (0.04 g, 0.416 mmol) were added successively. 1,4-Dioxane (1.2 mL) and dimethylacetamide (4 drops) were added and the vial was sealed and heated in the microwave (150° C., 10 min). The mixture was filtered and purified by preparatory LCMS. LCMS method: 1, RT: 3.27 min; MI: 431 [M+1].

The following compounds were synthesised using the same general method.

| Code No. | Characterisation |
| --- | --- |
| YY-001 | RT: 3.27 min; MI: 431; Method 1 |
| YY-003 | RT: 3.16 min; MI: 405: Method 1 |
| YY-004 | RT: 3.11 min; MI: 432; Method 1 |
| YY-002 | RT: 3.33 min; MI: 445; Method 1 |

The following compounds were also synthesised using the same general method.

| Code No. | Characterisation |
| --- | --- |
| YY-005 | RT: 2.71 min; MI: 447; Method: 2 |
| YY-006 | RT: 2.65 min; MI: 475; Method: 2 |
| YY-007 | RT: 2.65 min; MI: 445; Method: 2 |
| YY-008 | RT: 2.52 min; MI: 489; Method: 2 |
| YY-009 | RT: 2.58 min; MI: 461; Method: 2 |
| YY-010 | RT: 2.52 min; MI: 459; Method: 2 |

General Synthesis Procedure WW

Compounds were synthesised starting from 2-chloro-pyrimidin-4-ylamine following the scheme illustrated below. In general, the amino derivative was converted to the corresponding amide using acid chlorides or other activated esters.

Scheme 65

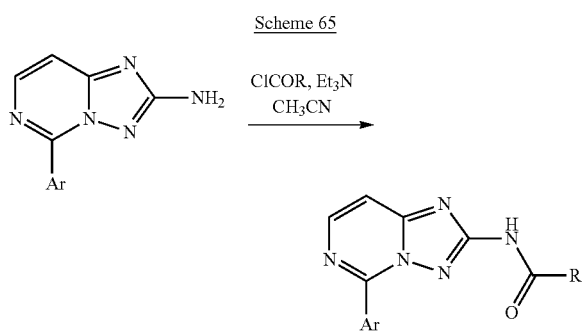

Synthesis 110

Cyclopropanecarboxylic acid [5-(2,3-dihydro-benzo[1,4]dioxin-6-yl)-[1,2,4]triazolo[1,5-c]pyrimidin-2-yl]-amide (ZZ-001)

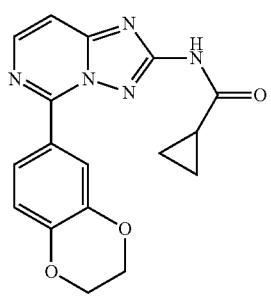 [SMILES: O=C(Nc1nc2ccnc(-c3ccc4c(c3)OCCO4)n2n1)C1CC1]

To a solution of 5-(2,3-dihydro-benzo[1,4]dioxin-6-yl)-[1,2,4]triazolo[1,5-c]pyrimidin-2-ylamine (0.04 g, 0.148 mmol) in dry acetonitrile (2 mL) was added triethylamine (0.052 mL, 0.371 mmol) followed by cyclopropanecarbonyl chloride (0.034 mL, 0.371 mmol). The reaction mixture was then allowed to warm to ambient temperature, and the solvent removed under reduced pressure. The crude product was purified by preparatory HPLC. $^1$H NMR (300 MHz, DMSO): 1.84-1.88 (m, 4H), 2.00-2.08 (m, 1H), 4.31-4.36 (m, 4H), 7.06 (d, 1H), 7.64 (d, 1H), 8.21 (dd, 1H), 8.35 (d, 1H), 8.39 (d, 1H), 11.37 (s, 1H). LCMS Method: 2: RT: 3.51 min, MI: 338 [M+1].

The following compounds were synthesised using the same general method.

| Code No. | Characterisation |
|---|---|
| ZZ-001 | RT: 3.51 min, MI: 338, Method: 2 |
| ZZ-002 | RT: 3.87 min, MI: 324, Method: 2 |
| ZZ-003 | RT: 4.54 min, MI: 310; Method: 2 |

General Synthesis Procedure XX

Compounds were synthesised starting from 2-chloro-pyrimidin-4-ylamine following the scheme illustrated below. In general, the chloro derivative was converted to the methanesulfinyl derivative using sodium thiomethoxide. Reaction of this compound with ethylcarbonyl isothiocyanate provided the corresponding thiourea, which was cyclised to the [1,2,4]triazolo[1,5-a]pyridine intermediate using hydroxylamine. This compound was involved in a Suzuki reaction utilising a palladium catalyst such as tetrakis(triphenylphosphine)palladium or other suitable catalyst and a suitable boronic acid. Finally, the aryl-amino derivatives may be obtained via a standard cross-coupling reaction utilising a catalyst such as bis(dibenzylideneacetone)palladium and an appropriate bromo derivative under standard conditions.

Scheme 66

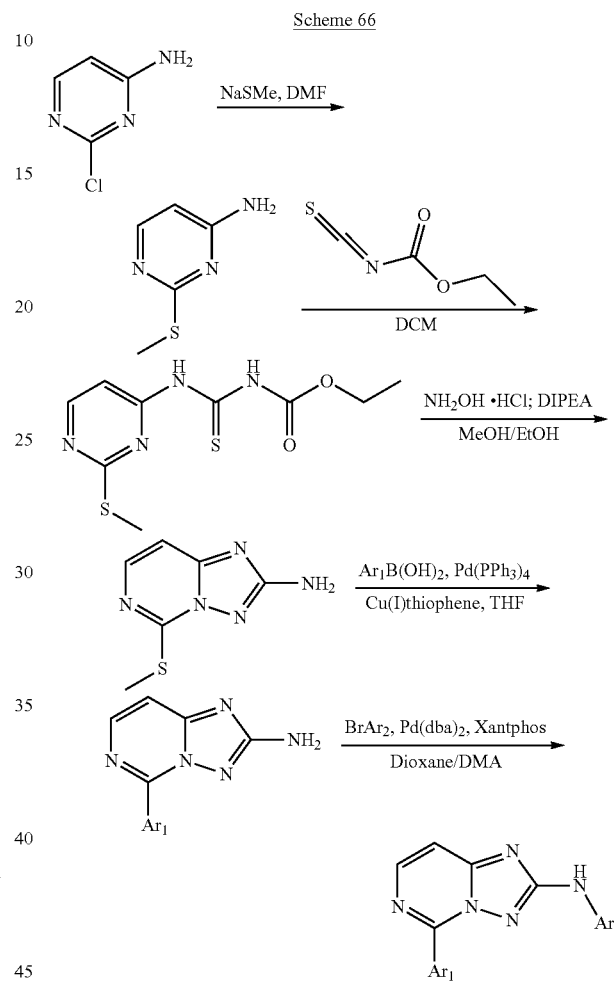

Synthesis 111

2-Methanesulfanyl-pyrimidin-4-yl-3-carboethoxy-thiourea

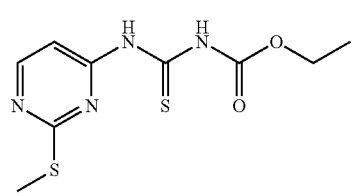 [SMILES: CCOC(=O)NC(=S)Nc1ccnc(SC)n1]

To a stirred solution of 2-chloro-pyrimidin-4-ylamine (5 g, 38.6 mmol) in dimethylformamide (20 mL) was added sodium thiomethoxide (3.52 g, 50.2 mmol) and the reaction mixture heated at 60° C. for 1 hour. Having cooled to room temperature, water (100 mL) was added and the product extracted into dichloromethane twice. The combined organic phases were washed with water several times, washed once with brine, dried over magnesium sulfate and concentrated in vacuo to provide a colourless oil. This oil was dissolved in dichloromethane (40 mL) and cooled to 0° C. Ethylcarbonyl isothiocyanate (9.2 mL, 77.2 mmol) was added dropwise and the reaction mixture stirred at room temperature overnight. All solvents were removed in vacuo, and the product, a yellow solid, collected by filtration and washed with cyclohexane. No further purification was required. Yield: 7.01 g, 67%; LCMS method: 2, RT: 4.46 min, MI: 273 [M+1]. $^1$H NMR (DMSO); 12.15 (s, 1H), 12.10 (s, 1H), 8.59 (d, 1H), 8.19 (d, 1H), 4.23 (q, 2H), 2.54 (s, 3H), 1.26 (t, 3H).

Synthesis 112

5-Methylsulfanyl-[1,2,4]triazolo[1,5-c]pyrimidin-2-ylamine

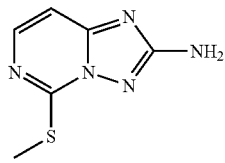

To a stirred suspension of hydroxylamine hydrochloride (4.1 g, 59.0 mmol) in ethanol/methanol (15 mL/15 mL) was added diisopropylethylamine (6.2 mL, 35.4 mmol) and the mixture was stirred at room temperature for 1 h. 2-Methanesulfanyl-pyrimidin-4-yl-3-carboethoxy-thiourea (3.21 g, 11.8 mmol) was then added and the mixture slowly heated to reflux. After 3 hours at reflux the mixture was allowed to cool and filtered to collect the precipitated solid. Further product was collected by evaporation in vacuo of the filtrate, addition of water and filtration. The combined solids were washed successively with water, ethanol/methanol and diethyl ether, then dried in vacuo to afford the expected compound as a white solid. No further purification was required. Yield: 1.76 g, 82%; LCMS method: 2, RT: 2.36 min, MI; 182 [M+1]. $^1$H NMR (DMSO); 8.04 (d, 1H), 7.16 (d, 1H), 6.54 (s, 2H), 2.63 (s, 3H).

Synthesis 113

5-(1-Benzyl-1H-pyrazol-4-yl)-[1,2,4]triazolo[1,5-c]pyrimidin-2-ylamine

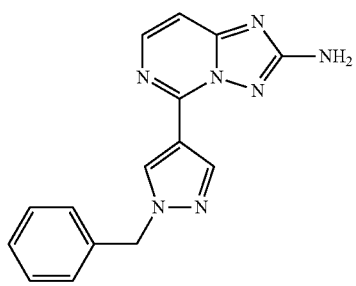 [SMILES: Nc1nc2ccnc(-c3cnn(Cc4ccccc4)c3)n2n1]

A microwave vial containing 5-methylsulfanyl-[1,2,4]triazolo[1,5-c]pyrimidin-2-ylamine (0.05 g, 0.276 mmol), 1-benzyl-1H-pyrazole-4-boronic acid (123 mg, 0.607 mmol), copper(1)thiophene carboxylate (116 mg, 0.607 mmol) and tetrakis(triphenylphosphine)palladium (33 mg, 0.028 mmol) in THF (1.2 mL) was heated under microwave irradiation (130° C., 15 min). The reaction mixture was filtered through celite and the cake washed with dichloromethane. The filtrate was washed with water followed by brine, dried over magnesium sulfate and concentrated under vacuum. Trituration with diethyl ether provided a yellow solid that did not require further purification. Yield: 0.05 g, 63%; LCMS method: 2, RT: 3.18 min, MI: 292 [M+1].

Synthesis 114

[5-(1-Benzyl-1H-pyrazol-4-yl)-[1,2,4]triazolo[1,5-c]pyrimidin-2-yl]-[4-(2-pyrrolidin-1-yl-ethoxy)-phenyl]-amine (YY-011)

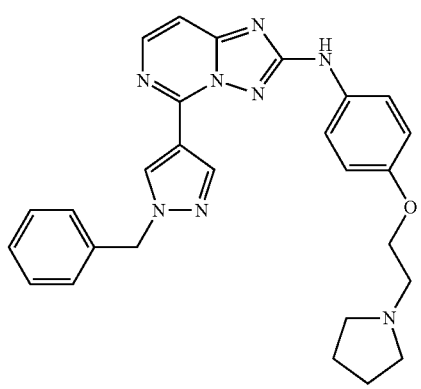 [SMILES: c1ccc(Cn2cc(-c3nccc4nc(Nc5ccc(OCCN6CCCC6)cc5)nn34)cn2)cc1]

In a microwave vial, 5-(1-benzyl-1H-pyrazol-4-yl)-[1,2,4]triazolo[1,5-c]pyrimidin-2-ylamine (0.05 g, 0.165 mmol), 1-(2-(4-bromophenoxy)ethyl)pyrrolidine (0.045 g, 0.215 mmol), bis(dibenzylideneacetone)palladium (0.005 g, 0.008 mmol), xantphos (0.01 g, 0.017 mmol) and sodium tert butoxide (0.032 g, 0.330 mmol) were added successively. 1,4-Dioxane (1.2 mL) and dimethylacetamide (4 drops) were added and the vial was sealed and heated in the microwave (130° C., 15 min). The mixture was filtered and purified by preparatory HPLC. LCMS method: 2, RT: 2.54 min; MI: 481 [M+1]. $^1$H NMR (DMSO) 9.70 (s, 1H), 8.92 (s, 1H), 8.49 (s, 1H), 8.20 (d, 2H), 7.54 (d, 2H), 7.32 (m, 3H), 6.92 (d, 2H), 5.50 (s, 2H), 4.09 (t, 2H), 2.78 (t, 2H), 2.52 (s, 4H), 1.64 (s, 4H).

The following compounds were synthesised using the same general method.

| Code No. | Characterisation |
| --- | --- |
| 7YY-011 | RT: 2.54 min, MI: 481, Method: 2 |
| YY-012 | RT: 2.57 min, MI: 430, Method: 2 |
| YY-013 | RT: 5.06 min, MI: 469, Method: basic |
| YY-014 | RT: 2.65 min, MI: 433, Method: 2 |
| YY-015 | RT: 5.15 min, MI: 428, Method basic |
| YY-016 | RT: 2.46 min, MI: 484, Method: 2 |

General Synthesis Procedure YY

Compounds were synthesised starting from 5-aryl-[1,2,4]triazolo[1,5-a]pyridin-2-yl]-amides, such as cyclopropanecarboxylic acid [5-(4-methoxy-phenyl)-[1,2,4]triazolo[1,5-a]pyridin-2-yl]-amide (WW-005, described above), following the scheme illustrated below. In general, the alkylino derivatives may be obtained via the reduction of its corresponding amide utilising a reducing agent such as Borane THF complex.

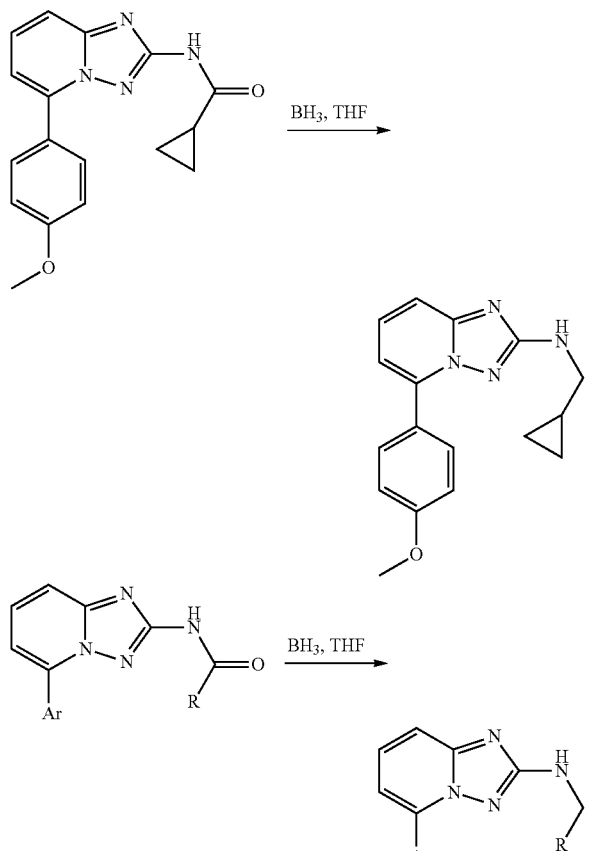

Scheme 67

Synthesis 115

Cyclopropylmethyl-[5-(4-methoxy-phenyl)-[1,2,4]triazolo[1,5-a]pyridin-2-yl]-amine (XX-003)

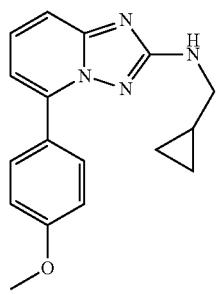 [SMILES: COc1ccc(-c2cccc3nc(NCC4CC4)nn23)cc1]

To cyclopropanecarboxylic acid [5-(4-methoxy-phenyl)-[1,2,4]triazolo[1,5-a]pyridin-2-yl]-amide (WW-005) ((0.07 g, 0.227 mmol), BH$_3$ (1M in tetrahydrofuran, 1.2 mL, 1.2 mmol) was added dropwise and the mixture was stirred overnight. The reaction was quenched with methanol and the solvents were removed under reduced pressure. The crude product was purified by preparatory HPLC. LCMS method: 1, 4.45 min, MI: 295 [M+1]. 1H NMR (DMSO): 0.18-0.22 (m, 2H), 0.35-0.41 (m, 2H), 1.04-1.08 (m, 1H), 2.87 (t, 2H), 3.86 (s, 3H), 6.64 (t, 1H), 6.97 (d, 1H), 7.06 (d, 2H), 7.32 (d, 1H), 7.46 (t, 1H), 7.96 (d, 2H).

The following compound was synthesised using the same general method.

| Code No. | Characterisation |
|---|---|
| XX-003 | RT: 4.45 min, MI: 295, Method 1 |

Biological Methods
AXL (Human Catalytic Domain) Enzyme Activity Assay
Reagents
Kinase Assay Reaction Buffer: This consisted of 20 mM HEPES pH 7.0, 10 mM MgCl$_2$, 1 mM DTT, 0.25 M EGTA, 0.01% Triton X100 (v/v), and 0.01% BSA (w/v). All buffer components were purchased from Sigma-Aldrich at reagent grade or higher.
Kinase: Recombinant AXL isoform 1 (aa473-894 corresponding to Genbank Accession Number NP 068713) at 2 mg/mL (20.8 µM) was purchased from Upstate Ltd. (Product code 14-512, lot #28164U). The enzyme was stored at −80° C. and a working stock was prepared to a concentration of 30 nM by diluting 20.8 µM stock 1:693 in cold (4° C.) 1×Reaction Buffer. Final enzyme concentration in the assay was 15 nM.
Substrate: Fluorescein labelled CSK-tide 5FAM-KKKKEE-IYFFFG-NH$_2$ was obtained from Molecular Devices (Product code R7270) and used at a working concentration of 200 nM by diluting the 100 µM stock 1:500 in 1×Reaction Buffer in a mix with the enzyme. A negative control (lacking enzyme) was prepared at the same concentrations. Final substrate concentration in the assay was 100 nM.
ATP: Supplied by Sigma (product code A-7699). A 100 mM ATP stock was prepared in 20 mM NaOH and used at a working concentration of 375 µM by diluting the 100 mM stock 1:266.6 in Reaction Buffer. Final ATP concentration in the assay was 150 µM; this concentration represents the $K_{M,ATP}$ for this enzyme calculated in this assay.
IMAP Reagents: IMAP screening express kit was obtained from Molecular Devices (product code R8127). The binding reagent was gently re-suspended before diluting by 1:1000 in buffer (Binding Buffer is supplied as a 5× stock and so was diluted with water prior to use—this assay used 40% buffer A and 60% buffer B) and then vortexed before addition to wells. The binding reagent was used at a final dilution of 1:1333.
Method
1 µL samples of test compounds in 10% DMSO/water were added to "test" wells by dry-spotting using a Matrix Platemate Plus. 5 µL Kinase/Substrate in Reaction Buffer were added to columns 1-22 of a Corning black low binding 384 well #6754 (90 µL volume) microplate to give 12 nM and 100 nM reaction concentration respectively. 5 µL substrate in Reaction Buffer was added to columns 23 and 24 to give 100 nM reaction concentration. 4 µL ATP in Reaction Buffer was added to all wells to give 150 µM reaction concentration. The reaction mixture was then incubated at room temperature for 60 minutes. The incubation period was followed by the addition of 20 µL IMAP Binding Reagent in Binding Buffer to all wells. The IMAP reaction detection was further incubated at room temperature overnight. The FP on a Tecan Ultra Plate reader was recorded as a single read at Ex485 Em535.

Percentage inhibition was calculated based on activity of the test sample minus the average values in the blank wells relative to the average values measured in control wells minus the average values in the blank wells.

IC$_{50}$ values were calculated from 10 point dose sigmoid 'dose-response' curves using Xlfit software (IDBS Inc, USA). Data were fitted to a 4 parameter logistic model/sigmoidal dose response defined by the following equation:

$$\text{Fit} = A + \left(\frac{(B-A)}{\left(1+\left(\frac{C}{X}\right)^D\right)}\right)$$

where:
A=fit minimum (locked to 0);
B=fit maximum (locked to 100);
C=fit midpoint (pre-fit to 1); and
D=slope at linear portion of curve, hillslope (pre-fit to 0.1).

The value for C represents the IC$_{50}$ of the test compound.

AXL Inhibition Cell Based ELISA Assay

This cell based ELISA assay is a simple cell-based method used to monitor activation of proteins by phosphorylation. The Active Motif, Fast Activated Cell-based ELISA (FACE) kit (Active Motif Cat No: 48120) was used in this case to monitor the inhibition, by test compounds, of Axl activation via the downstream phosphorylation of Akt (serine 473). In this system, cells are cultured in 96 well plates and treated with test compounds and Axl is activated by the introduction of Gas6 (Axl ligand). The inhibition of Axl can be directly assessed via the reduction of pS$^{473}$Akt levels.

Reagents

Active Motif FACE Kit reagents (Active Motif Cat. No: 48120(AKT)).
10% hydrogen peroxide (Sigma H1009).
10% Sodium azide (Sigma 7128).
37% Formaldehyde (Sigma F8775).
Axl/Fc conjugate (R&D Systems 154-AL).
Recombinant mouse Gas6 (R&D Systems 986-GS-025).

Method

All cell incubations were carried out in humidified incubators set at 5% CO$_2$ and 37° C. All removal of media from the 96 well plates was carried out by tapping plates on towel, as this reduced the loss of cells at each step. MDA-MB-231 cells were grown in E4 media+10% FCS in T150 vented flasks (Corning) to 85% confluence. Cells were harvested and re-suspended at 2×10$^5$ cells/mL and 100 µL of cells was aliquoted into each well of a 96 well tissue culture treated plate (Corning). The plate was incubated for 24 hours to allow cells to attach.

The media was replaced with 100 µL E4, 0.5% serum supplemented with 400 ng/mL Axl/Fc. Cells were then incubated overnight. Cells were then pre-treated for 30 minutes with test compound by replacing media with 50 µL test compound in E4, 0.5% serum. 50 µL Gas6 [200 ngml$^{-1}$ final concentration] in E4, 0.5% serum was added to wells and incubated for 15 minutes. The media was removed and the cells were fixed by the addition of 100 µL of freshly prepared fixing buffer (3.7% (v/v) formaldehyde in PBS) to each well. The plates were then incubated at room temperature for 20 minutes. The plates were then washed (3×5 minutes) with 200 µL wash buffer (0.1% TritonX-100 in PBS).

Immunostaining (carried out as outlined in FACE kit protocol). The wash buffer was removed and replaced with 100 µL quench buffer (1% H$_2$O$_2$ and 0.1% Azide in wash buffer). The plates were then incubated for 20 minutes at room temperature. The plates were then washed (2×5 minutes) with 200 µL wash buffer. The media was removed and replaced with 100 µL antibody blocking buffer (as supplied in the kit) and the plates were then incubated for 1 hour at room temperature. The blocking buffer was removed and the plates washed (2×5 minutes) with 200 µL wash buffer. 40 µL of diluted primary phospho-Akt (kit) in quench buffer (to kit dilution specifications) was added to each well, and the plates were incubated overnight at 4° C. with shaking, while ensuring that the plates were tightly sealed. The primary antibody was removed and plates were washed (3×5 minutes) with 200 µL wash buffer. The last wash was removed and 100 µL diluted secondary antibody (as supplied with the kit) was added. Plates were covered and incubated at room temperature for 1 hour. During this time, the developing solution was left at room temperature in the dark. The secondary antibody was removed and the plates were washed (3×5 minutes) with 200 µL wash buffer and then (2×5 minutes) with 200 µL PBS. 100 µL developing solution was added to each well and monitored for colour change to medium to dark blue (2 to 20 minutes). 100 µL of stop solution was then added and absorbance was read at 450 nm within 5 minutes of addition.

Crystal Violet cell staining. After reading absorbance at 450 nm, the plates were washed twice with 200 µL wash buffer and twice with 200 µL PBS. The plates were then air dried for 5 minutes. 100 µL of crystal violet stain was added to each well and the plates were incubated for 30 minutes at room temperature. The plates were washed (3×5 minutes) with 100 µL PBS. 100 µL 1% SDS solution was added to each well and the plates were incubated for 1 hour at room temperature. Absorbance was read at 595 nm. Readings from OD$_{450}$ were corrected for cell number by dividing the OD$_{450}$ by OD$_{595}$ for the same well.

Data Analysis

Percentage inhibition was calculated based on the activity of test sample minus the average values in the blank wells (no cells) relative to the average values measured in control wells minus the average values in the blank wells.

EC50 values were calculated from a 10-point dose sigmoidal 'dose response' curve using Xlfit software (IDBS Inc., USA). Data were fitted to a parameter logistic model/sigmoidal dose response:

$$\text{Fit} = A + \left(\frac{(B-A)}{\left(1+\left(\frac{C}{X}\right)^D\right)}\right)$$

where:
A=fit minimum (locked to 0);
B=fit maximum (locked to 100);
C=fit midpoint (pre-fit to 1);
D=slope at linear portion of curve, hillslope (pre-fit to 0.1)

The value for C represents the IC$_{50}$ of the test compound.

Biological Data

Biological data were obtained using the AXL (human catalytic domain) Enzyme Activity Assay described above for the following compounds: WW-001 through WW-166, XX-001 through XX-89, and YY-001 through YY-004.

For the AXL (human catalytic domain) Enzyme Activity Assay, the following compounds have an IC50 of less than 1 µM: WW-001, WW-005, WW-018, WW-022, WW-026, WW-035, WW-047, WW-049, WW-054, WW-059, WW-063, WW-064, WW-066, WW-069, WW-089, WW-092, WW-094, WW-096, WW-097, WW-102, WW-103, WW-104, WW-106, WW-133, WW-159, XX-001, XX-002, XX-004, XX-005, XX-006, XX-007, XX-011, XX-012, XX-013, XX-014, XX-015, XX-016, XX-017, XX-018, XX-019, XX-020, XX-021, XX-022, XX-023, XX-025, XX-026, XX-027, XX-028, XX-029, XX-030, XX-031, XX-032, XX-033, XX-034, XX-036, XX-037, XX-038, XX-040, XX-041, XX-044, XX-045, XX-046, XX-047, XX-048, XX-049, XX-050, XX-051, XX-052, XX-053, XX-054, XX-055, XX-058, XX-059, XX-060, XX-064, XX-065, XX-066, XX-067, XX-068, XX-069, XX-070, XX-072, XX-073, XX-074, XX-075, XX-076, XX-077, XX-078, XX-079, XX-080, XX-081, XX-082, XX-083, XX-084, XX-085, XX-086, XX-087, XX-088, YY-001, YY-002, YY-003, YY-004.

For the AXL (human catalytic domain) Enzyme Activity Assay, the following compounds have an IC50 of 1 µM or more, and less than 10 µM: WW-002, WW-003, WW-004, WW-006, WW-007, WW-008, WW-009, WW-010, WW-011, WW-013, WW-014, WW-015, WW-016, WW-017, WW-019, WW-020, WW-023, WW-024, WW-025, WW-027, WW-028, WW-029, WW-030, WW-031, WW-033, WW-034, WW-036, WW-037, WW-038, WW-039, WW-040, WW-041, WW-042, WW-043, WW-046, WW-050, WW-052, WW-053, WW-055, WW-056, WW-057, WW-058, WW-060, WW-061, WW-062, WW-067, WW-068, WW-070, WW-071, WW-073, WW-075, WW-076, WW-077, WW-078, WW-079, WW-080, WW-081, WW-082, WW-084, WW-085, WW-087, WW-088, WW-090, WW-091, WW-093, WW-095, WW-098, WW-099, WW-100, WW-101, WW-105, WW-107, WW-108, WW-109, WW-110, WW-113, WW-119, WW-120, WW-121, WW-122, WW-123, WW-124, WW-125, WW-127, WW-128, WW-129, WW-135, WW-136, WW-137, WW-139, WW-144, WW-147, WW-148, WW-149, WW-150, WW-151, WW-152, WW-153, WW-155, WW-156, WW-157, WW-158, WW-160, WW-161, WW-162, WW-167, XX-003, XX-010, XX-024, XX-035, XX-056, XX-057, XX-061, XX-062, XX-063, XX-071.

For the AXL (human catalytic domain) Enzyme Activity Assay, all of the compounds have an IC50 of less than 30 µM.

One compound, compound WW-103, has an IC50 value of 0.664 µM.

One compound, compound XX-025, has an IC50 value of 0.114 µM.

One compound, compound YY-003, has an IC50 value of 0.105 µM.

One compound, compound ZZ-001, has an IC50 value of 0.364 µM.

Biological data were also obtained using the AXL (human catalytic domain) Enzyme Activity Assay described above for the following compounds: WW-001 through WW-169, XX-001 through XX-469, YY-001 through YY-016, and ZZ-001 through ZZ-003.

For the AXL (human catalytic domain) Enzyme Activity Assay, the following compounds have an IC50 of less than or equal to 0.1 µM: XX-001, XX-005, XX-007, XX-019, XX-020, XX-021, XX-023, XX-024, XX-032, XX-035, XX-037, XX-038, XX-046, XX-050, XX-051, XX-053, XX-054, XX-055, XX-058, XX-060, XX-065, XX-066, XX-067, XX-068, XX-069, XX-070, XX-074, XX-075, XX-076, XX-077, XX-079, XX-080, XX-081, XX-082, XX-083, XX-084, XX-085, XX-086, XX-090, XX-101, XX-108, XX-110, XX-113, XX-118, XX-127, XX-130, XX-131, XX-132, XX-133, XX-136, XX-139, XX-153, XX-154, XX-162, XX-163, XX-167, XX-211, XX-280, XX-290, XX-304, XX-312, XX-316, XX-318, XX-319, XX-320, XX-326, XX-353, XX-359, XX-360, XX-361, XX-363, XX-374, XX-375, XX-378, XX-380, XX-381, XX-382, XX-383, XX-383, XX-388, XX-390, XX-394, XX-396, XX-414, XX-416, YY-002, YY-004, YY-014.

For the AXL (human catalytic domain) Enzyme Activity Assay, the following compounds have an IC50 of more than 0.1 µM, and less than or equal to 1.0 µM: WW-001, WW-005, WW-018, WW-022, WW-026, WW-035, WW-047, WW-049, WW-054, WW-059, WW-063, WW-064, WW-066, WW-069, WW-089, WW-092, WW-094, WW-096, WW-097, WW-102, WW-103, WW-104, WW-106, WW-133, WW-159, XX-002, XX-003, XX-006, XX-008, XX-012, XX-013, XX-014, XX-015, XX-016, XX-017, XX-018, XX-022, XX-026, XX-027, XX-028, XX-029, XX-030, XX-031, XX-033, XX-034, XX-039, XX-041, XX-042, XX-045, XX-047, XX-048, XX-049, XX-052, XX-059, XX-064, XX-072, XX-073, XX-078, XX-087, XX-088, XX-091, XX-093, XX-094, XX-095, XX-096, XX-097, XX-099, XX-100, XX-102, XX-103, XX-104, XX-105, XX-106, XX-107, XX-109, XX-111, XX-112, XX-114, XX-115, XX-116, XX-117, XX-119, XX-120, XX-121, XX-122, XX-123, XX-124, XX-125, XX-126, XX-128, XX-129, XX-134, XX-135, XX-137, XX-138, XX-140, XX-141, XX-142, XX-143, XX-144, XX-145, XX-146, XX-147, XX-148, XX-149, XX-151, XX-155, XX-157, XX-159, XX-161, XX-164, XX-165, XX-166, XX-168, XX-169, XX-170, XX-171, XX-172, XX-173, XX-174, XX-175, XX-176, XX-177, XX-178, XX-179, XX-180, XX-181, XX-182, XX-184, XX-185, XX-186, XX-187, XX-188, XX-189, XX-190, XX-191, XX-192, XX-193, XX-198, XX-199, XX-201, XX-202, XX-203, XX-205, XX-206, XX-207, XX-208, XX-209, XX-210, XX-213, XX-214, XX-215, XX-216, XX-217, XX-218, XX-224, XX-226, XX-231, XX-235, XX-236, XX-237, XX-238, XX-240, XX-241, XX-242, XX-243, XX-244, XX-247, XX-248, XX-249, XX-250, XX-251, XX-252, XX-253, XX-254, XX-255, XX-256, XX-257, XX-259, XX-261, XX-263, XX-264, XX-266, XX-267, XX-268, XX-270, XX-271, XX-273, XX-275, XX-276, XX-278, XX-279, XX-282, XX-283, XX-284, XX-285, XX-286, XX-287, XX-288, XX-289, XX-291, XX-292, XX-293, XX-294, XX-295, XX-297, XX-298, XX-299, XX-300, XX-302, XX-305, XX-306, XX-307, XX-310, XX-311, XX-313, XX-314, XX-315, XX-317, XX-325, XX-328, XX-329, XX-332, XX-334, XX-335, XX-337, XX-340, XX-341, XX-343, XX-344, XX-345, XX-346, XX-347, XX-349, XX-350, XX-351, XX-352, XX-354, XX-355, XX-356, XX-357, XX-358, XX-364, XX-365, XX-366, XX-367, XX-368, XX-369, XX-370, XX-371, XX-372, XX-373, XX-376, XX-377, XX-379, XX-384, XX-385, XX-387, XX-389, XX-391, XX-392, XX-393, XX-395, XX-397, XX-398, XX-399, XX-403, XX-407, XX-408, XX-409, XX-410, XX-411, XX-413, XX-415, XX-417, XX-418, XX-419, XX-420, XX-421, XX-422, XX-423, XX-424, XX-425, XX-426, XX-427, XX-429, XX-430, XX-431, XX-432, XX-433, XX-435, XX-436, XX-438, XX-439, XX-441, XX-442, XX-443, XX-444, XX-445, XX-446, XX-447, XX-448, XX-449, XX-450, XX-451, XX-452, XX-453, XX-454, XX-456, XX-460, XX-464, XX-466, XX-469, YY-001, YY-003, YY-006, YY-007, YY-008, YY-009, YY-010, YY-011, YY-012, YY-013, YY-015, ZZ-001, ZZ-002.

For the AXL (human catalytic domain) Enzyme Activity Assay, the following compounds have an IC50 of more than 1.0 µM, and less than or equal to 10 µM: WW-002, WW-003, WW-004, WW-006, WW-007, WW-008, WW-009, WW-010, WW-011, WW-013, WW-014, WW-015, WW-016, WW-017, WW-019, WW-020, WW-023, WW-024, WW-025, WW-027, WW-028, WW-029, WW-030, WW-031, WW-033, WW-034, WW-036, WW-037, WW-038, WW-039, WW-040, WW-041, WW-042, WW-043, WW-046, WW-050, WW-052, WW-053, WW-055, WW-056, WW-057, WW-058, WW-060, WW-061, WW-062, WW-067, WW-068, WW-070, WW-071, WW-073, WW-075, WW-076, WW-077, WW-078, WW-079, WW-080, WW-081, WW-082, WW-084, WW-085, WW-087, WW-088, WW-090, WW-091, WW-093, WW-095, WW-098, WW-099, WW-100, WW-101, WW-105, WW-107, WW-108, WW-109, WW-110, WW-113, WW-119, WW-120, WW-121, WW-122, WW-123, WW-124, WW-125, WW-127, WW-128, WW-129, WW-135, WW-136, WW-137, WW-139, WW-144, WW-147, WW-148, WW-149, WW-150, WW-151, WW-152, WW-153, WW-155, WW-156, WW-157, WW-158, WW-160, WW-161, WW-162, WW-167, WW-169, XX-004, XX-011, XX-025, XX-036, XX-056, XX-057, XX-061, XX-062, XX-063, XX-071, XX-089, XX-092, XX-098, XX-150, XX-152, XX-156, XX-158, XX-160, XX-183, XX-194, XX-195, XX-196, XX-197, XX-200, XX-204, XX-212, XX-219, XX-220, XX-221, XX-222, XX-223, XX-225, XX-227, XX-228, XX-229, XX-230, XX-232, XX-233, XX-239, XX-245, XX-246, XX-258, XX-260, XX-262, XX-265, XX-269, XX-272, XX-274, XX-277, XX-281, XX-296, XX-301, XX-308, XX-309, XX-321, XX-322, XX-323, XX-324, XX-327, XX-330, XX-331, XX-333, XX-336, XX-338, XX-339, XX-342, XX-348, XX-386, XX-400, XX-401, XX-402, XX-404, XX-405, XX-406, XX-412, XX-428, XX-434, XX-437, XX-440, XX-455, XX-457, XX-459, XX-461, XX-462, XX-463, XX-465, XX-467, XX-468, YY-005, YY-016, ZZ-003.

For the AXL (human catalytic domain) Enzyme Activity Assay, all of the compounds have an IC50 of less than 30 µM.

Biological data were also obtained using the AXL Inhibition Cell Based ELISA Assay described above for the following compounds: WW-104, XX-001, XX-012, XX-020, XX-021, XX-036, XX-037, XX-045, XX-053, XX-054, XX-058, XX-060, XX-065, XX-066, XX-068, XX-069, XX-070, XX-074, XX-076, XX-083, YY-001, YY-002.

For the AXL Inhibition Cell Based ELISA Assay, all of these compounds have an IC50 of less than 10 µM.

One compound, compound WW-104, has an IC50 value of 8.491 µM.

One compound, compound XX-070, has an IC50 value of 1.027 µM.

One compound, compound YY-001, has an IC50 value of 3.003 µM.

Biological data were also obtained using the AXL Inhibition Cell Based ELISA Assay described above for the following compounds: WW-104, WW-114, XX-001, XX-005, XX-007, XX-013, XX-013, XX-019, XX-020, XX-021, XX-022, XX-023, XX-024, XX-032, XX-035, XX-037, XX-038, XX-046, XX-050, XX-051, XX-053, XX-054, XX-055, XX-058, XX-060, XX-065, XX-066, XX-067, XX-068, XX-069, XX-070, XX-074, XX-076, XX-079, XX-081, XX-082, XX-083, XX-084, XX-085, XX-086, XX-090, XX-094, XX-095, XX-100, XX-101, XX-108, XX-110, XX-113, XX-115, XX-116, XX-117, XX-118, XX-119, XX-120, XX-121, XX-122, XX-123, XX-124, XX-125, XX-126, XX-127, XX-131, XX-132, XX-133, XX-135, XX-136, XX-139, XX-143, XX-153, XX-154, XX-155, XX-162, XX-163, XX-167, XX-170, XX-173, XX-186, XX-188, XX-193, XX-201, XX-209, XX-211, XX-226, XX-237, XX-240, XX-255, XX-258, XX-259, XX-260, XX-261, XX-262, XX-274, XX-275, XX-279, XX-280, XX-281, XX-284, XX-293, XX-294, XX-296, XX-303, XX-323, XX-353, XX-359, XX-360, XX-361, YY-001, YY-002, YY-004, YY-010, YY-011.

For the AXL Inhibition Cell Based ELISA Assay, all of these compounds have an IC50 of less than 10 µM.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

References

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Alessi, D. R., et al., 1996, "Mechanism of activation of protein kinase B by insulin and IGF-1", *EMBO J.*, Vol. 15, pp. 6541-6551.

Bellosta, P., et al., 1995, "The receptor tyrosine kinase ARK mediates cell aggregation by homophilic binding", *Mol. Cell Biol.*, Vol. 15, No. 2, pp. 614-625.

Bellosta, P., et al., 1997, "Signaling through the ARK tyrosine kinase receptor protects from apoptosis in the absence of growth stimulation", *Oncogene*, Vol. 15, No. 20, pp. 2387-2397.

Braunger, J., et al., 1997, "Intracellular signaling of the Ufo/Axl receptor tyrosine kinase is mediated mainly by a multisubstrate docking-site", *Oncogene*, Vol. 14, No. 22, pp. 2619-2631.

Fridell, Y. W., et al., 1998, "GAS6 induces Axl-mediated chemotaxis of vascular smooth muscle cells", *J. Biol. Chem.*, Vol. 273, No. 12, pp. 7123-7126.

Graham, D. K., et al., 1994, "Cloning and mRNA expression analysis of a novel human protooncogene, c-mer", *Cell Growth Differ.*, Vol. 5, No. 6, pp. 647-657.

Green, J., 2006, "Overexpression of the Axl tyrosine kinase receptor in cutaneous SCC-derived cell lines and tumours", *Br. J. Cancer*, Vol. 94, No. 10, pp. 1446-1451.

Hafizi, S., et al., 2002, "Interaction of Axl receptor tyrosine kinase with C1-TEN, a novel C1 domain-containing protein with homology to tensin", *Biochem. Biophys. Res. Commun.*, Vol. 299, No. 5, pp. 793-800.

Hafizi, S., et al., 2006a, "Signalling and functional diversity within the Axl subfamily of receptor tyrosine kinases", *Cytokine Growth Factor Rev.*, Vol. 17, No. 4, pp. 295-304.

Hafizi, S., et al., 2006b, "Gas6 and protein S. Vitamin K-dependent ligands for the Axl receptor tyrosine kinase subfamily", *FEBS J.*, Vol. 273, No. 23, pp. 5231-5244.

Hanada, M., 2004, "Structure, regulation and function of PKB/AKT—a major therapeutic target", *Biochim. Biophys. Acta*, Vol. 1697, pp. 3-16.

Holland, S. J., et al., 2005, "Multiple roles for the receptor tyrosine kinase axl in tumor formation", *Cancer Res.*, Vol. 65, No. 20, pp. 9294-9303.

Manfioletti, G., 1993, "The protein encoded by a growth arrest-specific gene (gas6) is a new member of the vitamin K-dependent proteins related to protein S, a negative coregulator in the blood coagulation cascade", *Mol. Cell Biol.*, Vol. 13, pp. 4976-4985.

Mark, M. R., et al., 1994, "rse, a novel receptor-type tyrosine kinase with homology to Axl/Ufo, is expressed at high levels in the brain", *J. Biol. Chem.*, Vol. 269, No. 14, pp. 10720-10728.

Meric, F., et al., 2002, "Expression profile of tyrosine kinases in breast cancer", *Clin. Cancer Res.*, Vol. 8, No. 2, pp. 361-367.

O'Bryan, J. P. et al., 1991, "axl, a transforming gene isolated from primary human myeloid leukemia cells, encodes a novel receptor tyrosine kinase", *Mol. Cell Biol.*, Vol. 11, pp. 5016-5031.

Rescigno, J., et al., 1991, "A putative receptor tyrosine kinase with unique structural topology", *Oncogene*, Vol. 6, No. 10, pp. 1909-1913.

Sainaghi, P. P., et al., 2005, "Gas6 induces proliferation in prostate carcinoma cell lines expressing the Axl receptor", *J. Cell Physiol.*, Vol. 204, No. 1, pp. 36-44.

Sawabu, T., et al., 2007, "Growth arrest-specific gene 6 and Axl signaling enhances gastric cancer cell survival via Akt pathway", *Mol. Carcinog.*, Vol. 46, No. 2. pp. 155-164.

Shankar, S. L., et al., 2006, "Gas6/Axl signaling activates the phosphatidylinositol 3-kinase/Akt1 survival pathway to protect oligodendrocytes from tumor necrosis factor alpha-induced apoptosis", *J. Neurosci.*, Vol. 26, No. 21, pp. 5638-5648.

Shieh, Y. S., et al., 2005, "Expression of axl in lung adenocarcinoma and correlation with tumor progression", *Neoplasia*, Vol. 7, No. 12, p. 1058-1064.

Sun, W. S., et al., 2003, "Clinical implications of coexpression of growth arrest-specific gene 6 and receptor tyrosine kinases Axl and Sky in human uterine leiomyoma", *Mol. Hum. Reprod.*, Vol. 9, No. 11, pp. 701-707.

Vajkoczy, P., et al., 2006, "Dominant-negative inhibition of the Axl receptor tyrosine kinase suppresses brain tumor cell growth and invasion and prolongs survival", *Proc. Nat. Acad. Sci. USA*, Vol. 103, No. 15, pp. 5799-5804.

Abd Elmonem, M. E., et al., 1991, "Synthesis of 8,11-dihydro-10-methyl-8,11-diphenylpyrazolo[4',3':5,6]pyrano[3,2-e][1,2,4]triazolo[1,5-c]pyrimidine and some derivatives", *Collection of Czechoslovak Chemical Communications*, Vol. 56, No. 9, pp. 1977-1982.

Abdel-Monem, W. R., et al., 2004, "Synthesis and biological evaluation of some new fused heterobicyclic derivatives containing 1,2,4-triazolo/1,2,4-triazinopyridinone moieties", *Egypt. Chemical Papers*, Vol. 58, No. 4, pp. 276-285.

Adenot, M., et al., 1997, "Interest of cluster significance analysis in structure-affinity relationships for non-xanthine heterocyclic antagonists of adenosine", *Eur. J. Med. Chem.*, Vol. 32, No. 6, pp. 493-504.

Ahmed, E., et al., 2006, "Heterocyclization of Orthoaminoester and Orthoamino-nitrile-thieno[2,3-c]pyridine: The Facile Synthesis of Fused Pyridothienopyrimidines", *Phosphorus, Sulfur and Silicon and the Related Elements*, 2006, Vol. 181, No. 3, pp. 497-510.

Aranyi, P., et al., 2005, "Preparation of pyrrolidinecarbonitrile compounds and analogs for DPP-IV enzyme inhibition", international patent application publication number WO 2005/021536.

Bakhite, E. A.-G., 2000, "Benzoquinolines II. Synthesis of some new benzo[h]pyrimido[4',5':4,5]thieno[2,3-b]quinoline derivatives and related fused hexacyclic systems", *Phosphorus, Sulfur and Silicon and the Related Elements*, Vol. 159, pp. 171-194.

Baqsyouni, W. M., et al., 1997, "Pyrrolo[2,3-d]pyrimidines. Part 3. Synthesis of some novel 4-substituted pyrrolo[2,3-d]pyrimidines and their related triazolo derivatives", *J. Chem. Research, Synopses*, No. 12, pp. 452-453.

Baraldi, P. G., et al., 2004, "Synthesis of new pyrazolo[4,3-e]-1,2,4-triazolo[1,5-c]pyrimidines and related heterocycles", *Tetrahedron*, Vol. 60, No. 23, pp. 5093-5104.

Bru-Magniez, N., et al., 1993, "Preparation of triazolopyrimidines as angiotensin II antagonists", European patent publication number EP 521768.

Bru-Magniez, N., et al., 1994, "Triazolopyrimidine derivatives which are angiotensin II receptor antagonists", U.S. Pat. No. 5,358,950.

Butler, D., et al., 2006, "Preparation of triazolopyridine derivatives as antibacterial agents", international patent application publication number WO 2006/038116.

Chuiguk, V. A., et al., 1982, "Mesoionic heterocycles based on 2-amino-1,2,4-triazolo[1.5-a]pyridine", *Ukrainskii Khimicheskii Zhurnal* (Russian Edition), Vol. 48, No. 6, pp. 647-649.

El-Sayed, A. M., et al., 1998, "Synthesis of some new heterocycles derived from (arylmethylene)malononitriles", *Synthetic Communications*, Vol. 28, No. 18, pp. 3331-3343.

Fratev, F., et al., 2005, "CoMFA study of non-peptide angiotensin II receptor (AT1) antagonist", *Oxidation Communications*, Vol. 28, No. 1, pp. 230-236.

Fujimoto, Y., et al., 1965, "Pyrimidine and purine bases. II. Synthesis of adenine from malonic ester. 2", *Yakuaaku Zasshi*, Vol. 85, No. 4, pp. 367-370.

Hafidh, A., et al., 1996, "Reaction of hydrazine and its derivatives on γ-ketonitriles. Synthesis of diamino and triazolodihydropyridines", *Journal de la Societe Chimique de Tunisie*, Vol. 3, No. 11, pp. 771-780.

Hafidh, A., et al., 2002, "Synthesis of novel heterocyclic polynuclear compounds: pyranopyrimidines and pyranopyrimidotriazoles", *Journal de la Societe Alqerienne de Chimie*, Vol. 12, No. 1, pp. 89-97.

Haniu, T., et al., 1998, "Silver halide photographic photosensitive material with improved pressure resistance", Japanese patent publication number JP 10-148903.

Hassan, K. M., et al., 1989, "Synthesis of tricyclic compounds with pyridinethione rings", *Assiut, Egypt. Phosphorus, Sulfur and Silicon and the Related Elements*, Vol. 45, No. 3-4, pp. 261-267.

Hozien, Z. A., et al., 1997, "Synthesis of some biologically active agents derived from thieno[2,3-d]pyrimidine derivatives", *Pharmazie*, Vol. 52, No. 10, pp. 753-758.

Huber Trottmann, G., et al., 2001, "Preparation of 5-amino-substituted triazolopyridines for treating diseases related to the adenosine A2A receptor", international patent application publication number WO 2001/017999.

Hussein, A. H. M., 1999, "Pyridines as building blocks in heterocyclic synthesis. An expeditious synthesis of triazolopyridines, tetrazolopyridines, pyridotriazines, thienopyridines and isoquinolines", *Assiut, Egypt. Afinidad*, Vol. 56, No 484, pp. 377-382.

Issac, Y. A., 2003, "Synthesis of annulated and substituted pyrido[2,3-d]pyrimidines as antimicrobial agents", *Pigment & Resin Technology*, Vol. 32, No. 6, pp. 371-381.

Issac, Y. A., et al., 2003, "A convenient synthesis of new penta-aza-cyclo-pentanaphthalene and penta-aza-phenanthrene derivatives", *Zeitschrift fuer Naturforschung, B: Chemical Sciences*, Vol. 58, No. 12, pp. 1227-1233.

Issac, Y. A., et al., 2003, "Some reactions with 2-(2-carboxyethenyl)-4-hydrazinoquinazoline: synthesis of annelated and substituted quinazolines", *Egyptian Journal of Chemistry*, Vol. 45, No. 5, pp. 947-961.

Jacob, R. M., et al., 1961, "piperazine derivative", French patent publication number FR 19600804.

Johnson, T. C., et al., 1999, "Preparation of N-([1,2,4]triazoloazinyl)benzenesulfonamide and pyridinesulfonamide compounds as herbicides", U.S. Pat. No. 5,858,924

Kaneko, Y., et al., 1992, "Silver halide photographic material", Japanese patent publication number JP 04-204441.

Kurup, A., 2001, "Comparative QSAR: Angiotensin II Antagonists", Chemical Reviews, Vol 101, No. 9, pp. 2727-2750.

Medwid, J. B., et al., 1990, "Preparation of triazolo[1,5-c] pyrimidines as potential antiasthma agents", J. Med. Chem., Vol. 33, No. 4, pp. 1230-1241.

Miller et al., 1962, "Mono-Acyl Derivatives of s-Triazolo[2,3-c]Pyrimidines", U.S. Pat. No. 3,046,276 granted 24 Jul. 1962.

Miller et al., 1962, "Mono-Acyl Derivatives of s-Triazolo[2,3-c]Pyrimidines", U.S. Pat. No. 3,053,844 granted 11 Sep. 1962.

Miller, G. W., et al., 1961, "Heterocyclic compounds", United Kingdom patent publication number GB 873223.

Miller, G. W., et al., 1962, "s-Triazolo[2,3-c]pyrimidine derivatives", United Kingdom patent publication number GB 897870.

Miller, G. W., et al., 1963, "s-Triazolopyrimidines. I. Synthesis as potential therapeutic agents", J. Chem. Soc., pp. 5642-5659.

Miller, G. W., et al., 1965, "s-Triazolopyrimidines. II. Synthesis of potential therapeutic agents", J. Chem. Soc., pp. 3357-3368.

Mitsuya, M., et al., 2004, "Preparation of pyridinecarboxamide derivatives having glucokinase activating effect for the treatment of diabetes", international patent application publication number WO 2004/081001.

Molina, P., et al., 1983, "Fused mesoionic heterocycles: synthesis of 1,3,4-triazolo(3,2-a)pyridine derivatives", Tetrahedron Lett., Vol. 24, No. 33, pp. 3523-3526.

Molina, P., et al., 1984, "Fused mesoionic heterocycles: synthesis of 1,3,4-triazolo[3,2-a]pyridine derivatives", J. Chem. Soc., Perkin Trans. 1: Organic and Bio-Organic Chemistry, Vol. 8, pp. 1891-1897.

Molina, P., et al., 1986, "Heterocyclization reactions with carbodiimides: synthesis of fused 1,2,4-triazoles", Heterocycles, Vol. 24, No. 12, pp. 3363-3368.

Molina, P., et al., 1986, "Heterocyclization reactions with carbodiimides: synthesis of fused 1,2,4-triazoles", Heterocycles, Vol. 24, No. 12, pp. 3363-3368.

Nettekoven et al., 2003, "8-Methoxy-(1,2,4)Triazolo(1,5-A) Pyridine Derivatives and Their Use as Adenosine Receptor Ligands", international patent application publication number WO 03/010167 A1, published 6 Feb. 2003.

Nettekoven et al., 2004, "Adenosine Receptor Ligands", U.S. Pat. No. 6,693,116 granted 17 Feb. 2004.

Nettekoven, M., et al., 2003, "Preparation of 5-methoxy-8-aryl-[1,2,4]triazolo[1,5-a]pyridines as adenosine receptor antagonists", international patent application publication number WO 2003/031445.

Nettekoven, M., et al., 2003, "Preparation of aromatic and heteroaromatic substituted 1,2,4-triazolopyridine derivatives as selective A2a adenosine receptor antagonists", U.S. Pat. No. 6,514,989.

Nettekoven, M., et al., 2003, "Synthetic access to 2-amido-5-aryl-8-methoxy-triazolopyridine and 2-amido-5-morpholino-8-methoxy-triazolopyridine derivatives as potential inhibitors of the adenosine receptor subtypes", Synthesis, No. 11, pp. 1649-1652.

Nicolai, E., et al., 1994, "Synthesis and SAR Studies of Novel Triazolopyrimidine Derivatives as Potent, Orally Active Angiotensin II Receptor Antagonists", J. Med. Chem., Vol. 37, No. 15, pp. 2371-2386.

Paul et al., 1985, "5-Substituted(1,2,4)triazolo(1,5-c)pyrimidine-2-amines", European patent application publication number EP 0 132 851 published 13 Feb. 1985.

Paul, R., et al., 1985, "5-Substituted-[1,2,4]triazolo[1,5-c] pyrimidin-2-amines", German patent publication number DE 3427823.

Rangnekar, D. W., et al., 1987, "Synthesis of 7H-benzo[de]-s-triazolo[5,1-a]isoquinolin-7-one derivatives and study of their fluorescent properties", Dyes and Pigments, Vol. 8, No. 4, pp. 291-299.

Ried, W., et al., 1968, "Reactions with aminoguanidine. I. s-Triazolo[1,5-c]quinazoline derivatives", Chem. Ber., Vol. 101, No. 6, pp. 2106-2116.

Said, M., et al., 2004, "Synthesis and biological evaluation of new thiazolopyrimidines", Egypt. Archives of Pharmacal Research, Vol. 27, No. 5, pp. 471-477.

Tachdjian, C., et al., 2006, "Molecules comprising linked organic moieties as flavor modifiers for comestible compositions", international patent application publication number WO 2006/084184.

Takahashi, M. et al., 2003, "Fused triazole compounds useful for colorants, their microparticle dispersions and ink jet inks containing them and printing method using them", Japanese patent publication number JP 2003-213152.

Westman, J., et al., 2005, "Preparation of triazoloquinazoline compounds binding to purine receptor for the treatment of CNS disorders, inflammation", international patent application publication number WO 2005/018532.

Wilson et al., 2008, "Triazole Derivatives as Kinase Inhibitors," European patent application publication number EP 1 894 931 A1, published 5 Mar. 2008.

Wilson et al., 2008, "Triazole Derivatives as Kinase Inhibitors", international patent application publication number WO 2008/025821, published 6 Mar. 2008.

Xie, L., et al., 2005, "Preparation of imidazo-pyrimidines and triazolo-pyrimidines as benzodiazepine receptor ligands for the treatment of central nervous system diseases", international patent application publication number WO 2005/012306.

Xu, Y., et al., 2006, "Preparation of pyrazolylmethyl heteroaryl derivatives as modulators of GABAA receptors for treating CNS disorders", international patent application publication number WO 2006/052546.

Yamazaki, C., et al., 1994, "Cyclization of isothiosemicarbazones. Part 10. A novel route to 2-amino[1,2,4]triazolo[1,5-a]pyridine derivatives", J. Chem. Soc., Perkin Trans. 1: Organic and Bio-Organic Chemistry, Vol. 7, pp. 825-828.

The invention claimed is:

1. A compound selected from compounds of the following formula, or a pharmaceutically acceptable salt thereof:

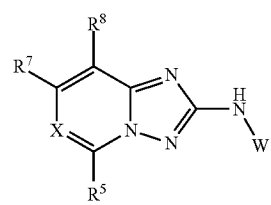

wherein:
—X= is —CR$^6$;

and wherein:
- —$R^5$ is independently —$R^{5A}$;
- —$R^6$ is independently —$R^{6A}$;
- —$R^7$ is independently —$R^{7A}$;
- —$R^8$ is independently —$R^{8A}$; and
- —W is independently —$W^A$;

wherein:
- —$R^{5A}$ is independently -$Q^{5A}$;
- —$R^{6A}$ is —H;
- —$R^{7A}$ is —H;
- —$R^{8A}$ is —H; and
- —$W^A$ is independently —$R^{WA1}$;

wherein:
—$R^{WA1}$ is independently:
- —$R^{1A1}$, —$R^{1A2}$, —$R^{1A3}$, —$R^{1A4}$, —$R^{1A5}$, —$R^{1A6}$, —$R^{1A7}$, —$R^{1A8}$,
- -$L^{1A}$-$R^{1A4}$, -$L^{1A}$-$R^{1A5}$, -$L^{1A}$-$R^{1A6}$, -$L^{1A}$-$R^{1A7}$, or -$L^{1A}$-$R^{1A8}$;

wherein:
- each —$R^{1A1}$ is independently saturated aliphatic $C_{1-6}$alkyl;
- each —$R^{1A2}$ is independently aliphatic $C_{2-6}$alkenyl;
- each —$R^{1A3}$ is independently aliphatic $C_{2-6}$alkynyl;
- each —$R^{1A4}$ is independently saturated $C_{3-6}$cycloalkyl;
- each —$R^{1A5}$ is independently $C_{3-6}$cycloalkenyl;
- each —$R^{1A6}$ is independently non-aromatic $C_{3-8}$heterocyclyl;
- each —$R^{1A7}$ is independently $C_{6-10}$carboaryl;
- each —$R^{1A8}$ is independently $C_{5-10}$heteroaryl;
- each -$L^{1A}$- is independently saturated aliphatic $C_{1-3}$alkylene;

wherein:
- each —$R^{1A4}$, —$R^{1A5}$, —$R^{1A6}$, —$R^{1A7}$, and —$R^{1A8}$ is optionally substituted with one or more substituents —$R^{1B1}$ and/or one or more substituents —$R^{1B2}$, and
- each —$R^{1A1}$, —$R^{1A2}$, —$R^{1A3}$, and -$L^{1A}$- is optionally substituted with one or more substituents —$R^{1B2}$, wherein:
each —$R^{1B1}$ is independently:
- —$R^{1D1}$, —$R^{1D2}$, —$R^{1D3}$, —$R^{1D4}$, —$R^{1D5}$, —$R^{1D6}$, —$R^{1D7}$, —$R^{1D8}$,
- -$L^{1D}$-$R^{1D4}$, -$L^{1D}$-$R^{1D5}$, -$L^{1D}$-$R^{1D6}$, -$L^{1D}$-$R^{1D7}$, -$L^{1D}$-$R^{1D8}$, each —$R^{1B2}$ is independently:
- —F, —Cl, —Br, —I,
- —$CF_3$, —$OCF_3$,
- —OH, -$L^{1C}$-OH, —O-$L^{1C}$-OH,
- —$OR^{1C1}$, -$L^{1C}$-$OR^{1C1}$, —O-$L^{1C}$-$OR^{1C1}$,
- —SH, —$SR^{1C1}$,
- —CN,
- —$NO_2$,
- —$NH_2$, —$NHR^{1C1}$, —$NR^{1C1}_2$, —$NR^{1C2}R^{1C3}$,
- -$L^{1C}$-$NH_2$, -$L^{1C}$-$NHR^{1C1}$, -$L^{1C}$-$NR^{1C2}R^{1C3}$,
- —O-$L^{1C}$-$NH_2$, —O-$L^{1C}$-$NHR^{1C1}$, —O-$L^{1C}$-$NR^{1C2}R^{1C3}$,
- —C(=O)OH, —C(=O)$OR^{1C1}$,
- —C(=O)$R^{1C1}$,
- —C(=O)$NH_2$, —C(=O)$NHR^{1C1}$, —C(=O)$NR^{1C1}_2$, 13 C(=O)$NR^{1C2}R^{1C3}$,
- —NHC(=O)$R^{1C1}$, —$NR^{1C1}$C(=O)$R^{1C1}$,
- —NHC(=O)$OR^{1C1}$, —$NR^{1C1}$C(=O)$OR^{1C1}$,
- —OC(=O)$NH_2$, —OC(=O)$NHR^{1C1}$, —OC(=O)$NR^{1C1}_2$, —OC(=O)$NR^{1C2}R^{1C3}$,
- —NHC(=O)$NH_2$, —NHC(=O)$NHR^{1C1}$,
- —NHC(=O)$NR^{1C1}_2$, —NHC(=O)$NR^{1C2}R^{1C3}$,
- —$NR^{1C1}$C(=O)$NH_2$, —$NR^{1C1}$C(=O)$NHR^{1C1}$,
- —$NR^{1C1}$C(=O)$NR^{1C1}_2$, —$NR^{1C1}$C(=O)$NR^{1C2}R^{1C3}$,
- —NHS(=O)$_2R^{1C1}$S(=O)$_2R^{1C1}$,
- —S(=O)$_2NH_2$, —S(=O)$_2NHR^{1C1}$, —S(=O)$_2NR^{1C1}_2$, —S(=O)$_2NR^{1C2}R^{1C3}$,
- —S(=O)$R^{1C1}$, —S(=O)$_2R^{1C1}$, —OS(=O)$_2R^{1C1}$, or —S(=O)$_2OR^{1C1}$;

wherein:
- each -$L^{1C}$- is independently saturated aliphatic $C_{1-5}$alkylene;
- in each group —$NR^{1C2}R^{1C3}$, $R^{1C2}$ and $R^{1C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{1C1}$ is independently:
- —$R^{1D1}$, —$R^{1D2}$, —$R^{1D3}$, —$R^{1D4}$, —$R^{1D5}$, —$R^{1D6}$, —$R^{1D7}$, —$R^{1D8}$,
- -$L^{1D}$-$R^{1D4}$, -$L^{1D}$-$R^{1D5}$, -$L^{1D}$-$R^{1D6}$, -$L^{1D}$-$R^{1D7}$, -$L^{1D}$-$R^{1D8}$, each —$R^{1D1}$ is independently saturated aliphatic $C_{1-6}$alkyl;
each —$R^{1D2}$ is independently aliphatic $C_{2-6}$alkenyl;
each —$R^{1D3}$ is independently aliphatic $C_{2-6}$alkynyl;
each —$R^{1D4}$ is independently saturated $C_{3-6}$cycloalkyl;
each —$R^{1D5}$ is independently $C_{3-6}$cycloalkenyl;
each —$R^{1D6}$ is independently non-aromatic $C_{3-8}$heterocyclyl;
each —$R^{1D7}$ is independently $C_{6-10}$carboaryl;
each —$R^{1D8}$ is independently $C_{5-10}$heteroaryl;
each -$L^{1D}$- is independently saturated aliphatic $C_{1-3}$alkylene;

wherein:
- each —$R^{1D4}$, —$R^{1D5}$, —$R^{1D6}$, —$R^{1D7}$, and —$R^{1D8}$ is optionally substituted with one or more substituents —$R^{1E1}$ and/or one or more substituents —$R^{1E2}$,
- each —$R^{1D1}$, —$R^{1D2}$, —$R^{1D3}$, and -$L^{1D}$- is optionally substituted with one or more substituents —$R^{1E2}$, and wherein:
each —$R^{1E1}$ is independently saturated aliphatic $C_{1-4}$alkyl, phenyl, or benzyl;
each —$R^{1E2}$ is independently:
- —F, —Cl, —Br, —I,
- —$CF_3$, —$OCF_3$,
- —OH, -$L^{1F}$-OH, —O-$L^{1F}$-OH,
- —$OR^{1F1}$, -$L^{1F}$-$OR^{1F1}$, —O-$L^{1F}$-$OR^{1F1}$,
- —SH, —$SR^{1F1}$,
- —CN,
- —$NO_2$,
- —$NH_2$, —$NHR^{1F1}$, —$NR^{1F1}_2$, —$NR^{1F2}R^{1F3}$,
- -$L^{1F}$-$NH_2$, -$L^{1F}$-$NHR^{1F1}$, -$L^{1F}$-$NR^{1F2}R^{1F3}$,
- —C(=O)OH, —C(=O)$OR^{1F1}$,
- —C(=O)$NH_2$, —C(=O)$NHR^{1F1}$, —C(=O)$NR^{1F1}_2$, or —C(=O)$NR^{1F2}R^{1F3}$;

wherein:
each —$R^{1F1}$ is independently saturated aliphatic $C_{1-4}$alkyl, phenyl, or benzyl;
each -$L^{1F}$- is independently saturated aliphatic $C_{1-5}$alkylene; and in each group —$NR^{1F2}R^{1F3}$, $R^{1F2}$ and $R^{1F3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

-$Q^{5A}$ is —$R^{2A7}$;

wherein:
each —$R^{2A7}$ is independently $C_{6-10}$carboaryl;
wherein:
each —$R^{2A7}$ is optionally substituted with one or more substituents —$R^{2B1}$ and/or one or more substituents —$R^{2B2}$, and
each
wherein:
each —$R^{2B1}$ is independently:
—$R^{2D1}$, —$R^{2D2}$, —$R^{2D3}$, —$R^{2D4}$, —$R^{2D5}$, —$R^{2D6}$, —$R^{2D7}$, —$R^{2D8}$,
-$L^{2D}$-$R^{2D4}$, -$L^{2D}$-$R^{2D5}$, -$L^{2D}$-$R^{2D6}$, -$L^{2D}$-$R^{2D7}$, -$L^{2D}$-$R^{2D8}$;
each —$R^{2B2}$ is independently:
—F, —Cl, —Br, —I,
—$CF_3$, —$OCF_3$,
—OH, -$L^{2C}$-OH, —O-$L^{2C}$-OH,
—$OR^{2C1}$, -$L^{2C}$-$OR^{2C1}$, —O-$L^{2C}$-$OR^{2C1}$,
—SH, —$SR^{2C1}$,
—CN,
—$NO_2$,
—$NH_2$, —$NHR^{2C1}$, —$NR^{2C1}{}_2$, —$NR^{2C2}R^{2C3}$,
-$L^{2C}$-$NH_2$, -$L^{2C}$-$NHR^{2C1}$, -$L^{2C}$-$NR^{2C1}{}_2$, -$L^{2C}$-$NR^{2C2}R^{2C3}$,
—O-$L^{2C}$-$NH_2$, —O-$L^{2C}$-$NHR^{2C1}$, —O-$L^{2C}$-$NR^{2C1}{}_2$, —O-$L^{2C}$-$NR^{2C2}R^{2C3}$,
—C(=O)OH, —C(=O)$OR^{2C1}$,
—C(=O)$R^{2C1}$,
—C(=O)$NH_2$, —C(=O)$NHR^{2C1}$, —C(=O)$NR^{2C1}{}_2$, —C(=O)$NR^{2C2}R^{2C3}$,
—NHC(=O)$R^{2C1}$, —$NR^{2C1}$C(=O)$R^{2C1}$,
—NHC(=O)$OR^{2C1}$, —$NR^{2C1}$C(=O)$OR^{2C1}$,
—OC(=O)$NH_2$, —OC(=O)$NHR^{2C1}$, —OC(=O)$NR^{2C1}{}_2$, —OC(=O)$NR^{2C2}R^{2C3}$,
—NHC(=O)$NH_2$, —NHC(=O)$NHR^{2C1}$,
—NHC(=O)$NR^{2C1}{}_2$, —NHC(=O)$NR^{2C2}R^{2C3}$,
—$NR^{2C1}$C(=O)$NH_2$, —$NR^{2C1}$C(=O)$NHR^{2C1}$,
—$NR^{2C1}$C(=O)$NR^{2C1}{}_2$, —$NR^{2C1}$C(=O)$NR^{2C2}R^{2C3}$,
—NHS(=O)$_2R^{2C1}$, —$NR^{1C1}$S(=O)$_2R^{2C1}$,
—S(=O)$_2NH_2$, —S(=O)$_2NHR^{2C1}$, —S(=O)$_2NR^{1C1}{}_2$, —S(=O)$_2NR^{1C2}R^{1C3}$,
—S(=O)$R^{2C1}$, —S(=O)$_2R^{2C1}$, —OS(=O)$_2R^{2C1}$, or —S(=O)$_2OR^{2C1}$;
wherein:
each -$L^{2C}$- is independently saturated aliphatic $C_{1-5}$alkylene;
in each group —$NR^{2C2}R^{2C3}$, $R^{2C2}$ and $R^{2C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{2C1}$ is independently:
—$R^{2D1}$, —$R^{2D2}$, —$R^{2D3}$, —$R^{2D4}$, —$R^{2D5}$, —$R^{2D6}$, —$R^{2D7}$, —$R^{2D8}$,
-$L^{2D}$-$R^{2D4}$, -$L^{2D}$-$R^{2D5}$, -$L^{2D}$-$R^{2D6}$, -$L^{2D}$-$R^{2D7}$, or -$L^{2D}$-$R^{2D8}$;
each —$R^{2D1}$ is independently saturated aliphatic $C_{1-6}$alkyl;
each —$R^{2D2}$ is independently aliphatic $C_{2-6}$alkenyl;
each —$R^{2D3}$ is independently aliphatic $C_{2-6}$alkynyl;
each —$R^{2D4}$ is independently saturated $C_{3-6}$cycloalkyl;
each —$R^{2D5}$ is independently $C_{3-6}$cycloalkenyl;
each —$R^{2D6}$ is independently non-aromatic $C_{3-8}$heterocyclyl;
each —$R^{2D7}$ is independently $C_{6-10}$carboaryl;
each —$R^{2D8}$ is independently $C_{5-10}$heteroaryl;
each -$L^{2D}$- is independently saturated aliphatic $C_{1-3}$alkylene;
wherein:
each —$R^{2D4}$, —$R^{2D5}$, —$R^{2D6}$, —$R^{2D7}$, and —$R^{2D8}$ is optionally substituted with one or more substituents —$R^{2E1}$ and/or one or more substituents —$R^{2E2}$,
each —$R^{2D1}$, —$R^{2D2}$, —$R^{2D3}$, and -$L^{2D}$- is optionally substituted with one or more substituents —$R^{2E2}$, and
wherein:
each —$R^{2E1}$ is independently saturated aliphatic $C_{1-4}$alkyl, phenyl, or benzyl;
each —$R^{2E2}$ is independently:
—F, —Cl, —Br, —I,
—$CF_3$, —$OCF_3$,
—OH, -$L^{2F}$-OH, —O-$L^{2F}$-OH,
—$OR^{2F1}$, -$L^{2F}$-$OR^{2F1}$, —O-$L^{2F}$-$OR^{2F1}$,
—SH, —$SR^{2F1}$,
—CN,
—$NO_2$,
—$NH_2$, —$NHR^{2F1}$, —$NR^{2F1}{}_2$, —$NR^{2F2}R^{2F3}$,
-$L^{2F}$-$NH_2$, -$L^{2F}$-$NHR^{2F1}$, -$L^{2F}$-$NR^{2F1}{}_2$, -$L^{2F}$-$NR^{2F2}R^{2F3}$,
—C(=O)OH, —C(=O)$OR^{2F1}$,
—C(=O)$NH_2$, —C(=O)$NHR^{2F1}$, —C(=O)$NR^{2F1}{}_2$, or —C(=O)$NR^{2F2}R^{2F3}$;
wherein:
each —$R^{2F1}$ is independently saturated aliphatic $C_{1-4}$alkyl, phenyl, or benzyl;
each -$L^{2F}$- is independently saturated aliphatic $C_{1-5}$alkylene; and
in each group —$NR^{2F2}R^{2F3}$, $R^{2F2}$ and $R^{2F3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

2. A compound according to claim 1, wherein —$R^{WA1}$, if present, is independently:
—$R^{1A1}$, —$R^{1A4}$, —$R^{1A6}$, —$R^{1A7}$, —$R^{1A8}$,
-$L^{1A}$-$R^{1A4}$, -$L^{1A}$-$R^{1A6}$, -$L^{1A}$-$R^{1A7}$, or -$L^{1A}$-$R^{1A8}$.

3. A compound according to claim 1, wherein —$R^{WA1}$, if present, is independently —$R^{1A7}$ or —$R^{1A8}$.

4. A compound selected from compounds of the following formula, or a pharmaceutically acceptable salt thereof:

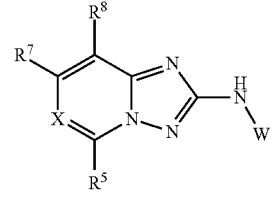

wherein:
—X= is —$CR^6$=;
and wherein:
—$R^5$ is independently —$R^{5A}$;
—$R^6$ is independently —$R^{6A}$;
—$R^7$ is independently —$R^{7A}$;
—$R^8$ is independently —$R^{8A}$; and
—W is independently —$W^A$;
wherein:
—$R^{5A}$ is independently -$Q^{5A}$;
—$R^{6A}$ is —H;

—$R^{7A}$ is —H;
—$R^{8A}$ is —H; and
—$W^A$ is independently —$C(=O)R^{WA2}$;
wherein:
—$R^{WA2}$ is independently:
—$R^{1A1}$, —$R^{1A2}$, —$R^{1A3}$, —$R^{1A4}$, —$R^{1A5}$, —$R^{1A6}$, —$R^{1A7}$, —$R^{1A8}$,
-$L^{1A}$-$R^{1A4}$, -$L^{1A}$-$R^{1A5}$, -$L^{1A}$-$R^{1A6}$, -$L^{1A}$-$R^{1A7}$, or -$L^{1A}$-$R^{1A8}$;
wherein:
  each —$R^{1A1}$ is independently saturated aliphatic $C_{1-6}$alkyl;
  each —$R^{1A2}$ is independently aliphatic $C_{2-6}$alkenyl;
  each —$R^{1A3}$ is independently aliphatic $C_{2-6}$alkynyl;
  each —$R^{1A4}$ is independently saturated $C_{3-6}$cycloalkyl;
  each —$R^{1A5}$ is independently $C_{3-6}$cycloalkenyl;
  each —$R^{1A6}$ is independently non-aromatic $C_{3-8}$heterocyclyl;
  each —$R^{1A7}$ is independently $C_{6-10}$carboaryl;
  each —$R^{1A8}$ is independently $C_{5-10}$heteroaryl;
  each -$L^{1A}$- is independently saturated aliphatic $C_{1-3}$alkylene;
wherein:
  each —$R^{1A4}$, —$R^{1A5}$, —$R^{1A6}$, —$R^{1A7}$, and —$R^{1A8}$ is optionally substituted with one or more substituents —$R^{1B1}$ and/or one or more substituents —$R^{1B2}$, and
  each —$R^{1A1}$, —$R^{1A2}$, —$R^{1A3}$, and -$L^{1A}$- is optionally substituted with one or more substituents —$R^{1B2}$,
wherein:
  each —$R^{1B1}$ is independently:
    —$R^{1D1}$, —$R^{1D2}$, —$R^{1D3}$, —$R^{1D4}$, —$R^{1D5}$, —$R^{1D6}$, —$R^{1D7}$, —$R^{1D8}$,
    -$L^{1D}$-$R^{1D4}$, -$L^{1D}$-$R^{1D5}$, -$L^{1D}$-$R^{1D6}$, -$L^{1D}$-$R^{1D7}$, or -$L^{1D}$-$R^{1D8}$;
  each —$R^{1B2}$ is independently:
    —F, —Cl, —Br, —I,
    —$CF_3$, —$OCF_3$,
    —OH, -$L^{1C}$-OH, —O-$L^{1C}$-OH,
    —$OR^{1C1}$, -$L^{1C}$-$OR^{1C1}$, —O-$L^{1C}$-$OR^{1C1}$,
    —SH, —$SR^{1C1}$,
    —CN,
    —$NO_2$,
    —$NH_2$, —$NHR^{1C1}$, —$NR^{1C1}_2$, —$NR^{1C2}R^{1C3}$,
    -$L^{1C}$-$NH_2$, -$L^{1C}$-$NHR^{1C1}$, -$L^{1C}$-$NR^{1C1}_2$, -$L^{1C}$-$NR^{1C2}R^{1C3}$,
    —O-$L^{1C}$-$NH_2$, —O-$L^{1C}$-$NHR^{1C1}$, —O-$L^{1C}$-$NR^{1C1}_2$, —O-$L^{1C}$-$NR^{1C2}R^{1C3}$,
    —C(=O)OH, —C(=O)$OR^{1C1}$,
    —C(=O)$R^{1C1}$,
    —C(=O)$NH_2$, —C(=O)$NHR^{1C1}$, —C(=O)$NR^{1C1}_2$, —C(=O)$NR^{1C2}R^{1C3}$,
    —NHC(=O)$R^{1C1}$, —$NR^{1C1}$C(=O)$R^{1C1}$,
    —NHC(=O)$OR^{1C1}$, —$NR^{1C1}$C(=O)$OR^{1C1}$,
    —OC(=O)$NH_2$, —OC(=O)$NHR^{1C1}$, —OC(=O)$NR^{1C1}_2$, —OC(=O)$NR^{1C2}R^{1C3}$,
    —NHC(=O)$NH_2$, —NHC(=O)$NHR^{1C1}$,
    —NHC(=O)$NR^{1C1}_2$, —NHC(=O)$NR^{1C2}R^{1C3}$,
    —$NR^{1C1}$C(=O)$NH_2$, —$NR^{1C1}$C(=O)$NHR^{1C1}$,
    —$NR^{1C1}$C(=O)$NR^{1C1}_2$, —$NR^{1C1}$C(=O)$NR^{1C2}R^{1C3}$,
    —NHS(=O)$_2R^{1C1}$, —$NR^{1C1}$S(=O)$_2R^{1C1}$,
    —S(=O)$_2NH_2$, —S(=O)$_2NHR^{1C1}$, —S(=O)$_2NR^{1C1}_2$, —S(=O)$_2NR^{1C2}R^{1C3}$,
    —S(=O)$R^{1C1}$, —S(=O)$_2R^{1C1}$, —OS(=O)$_2R^{1C1}$, or —S(=O)$_2OR^{1C1}$;
wherein:
  each -$L^{1C}$- is independently saturated aliphatic $C_{1-5}$alkylene;

in each group —$NR^{1C2}R^{1C3}$, $R^{1C2}$ and $R^{1C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{1C1}$ is independently:
  —$R^{1D1}$, —$R^{1D2}$, —$R^{1D3}$, —$R^{1D4}$, —$R^{1D5}$, —$R^{1D6}$, —$R^{1D7}$, —$R^{1D8}$,
  -$L^{1D}$-$R^{1D4}$, -$L^{1D}$-$R^{1D5}$, -$L^{1D}$-$R^{1D6}$, -$L^{1D}$-$R^{1D7}$, or -$L^{1D}$-$R^{1D8}$;
each —$R^{1D1}$ is independently saturated aliphatic $C_{1-6}$alkyl;
each —$R^{1D2}$ is independently aliphatic $C_{2-6}$alkenyl;
each —$R^{1D3}$ is independently aliphatic $C_{2-6}$alkynyl;
each —$R^{1D4}$ is independently saturated $C_{3-6}$cycloalkyl;
each —$R^{1D5}$ is independently $C_{3-6}$cycloalkenyl;
each —$R^{1D6}$ is independently non-aromatic $C_{3-8}$heterocyclyl;
each —$R^{1D7}$ is independently $C_{6-10}$carboaryl;
each —$R^{1D8}$ is independently $C_{5-10}$heteroaryl;
each -$L^{1D}$- is independently saturated aliphatic $C_{1-3}$alkylene;
wherein:
  each —$R^{1D4}$, —$R^{1D5}$, —$R^{1D6}$, —$R^{1D7}$, and —$R^{1D8}$ is optionally substituted with one or more substituents —$R^{1E1}$ and/or one or more substituents —$R^{1E2}$,
  each —$R^{1D1}$, $R^{1D2}$, —$R^{1D3}$, and -$L^{1D}$- is optionally substituted, for example, with one or more substituents —$R^{1E2}$, and
wherein:
  each —$R^{1E1}$ is independently saturated aliphatic $C_{1-4}$alkyl, phenyl, or benzyl;
  each —$R^{1E2}$ is independently:
    —F, —Cl, —Br, —I,
    —$CF_3$, —$OCF_3$,
    —OH, -$L^{1F}$-OH, —O-$L^{1F}$-OH,
    $OR^{1F1}$, $L^{1F}$-$OR^{1F1}$, —O-$L^{1F}$-$OR^{1F1}$,
    —SH, —$SR^{1F1}$,
    —CN,
    —$NO_2$,
    —$NH_2$, —$NHR^{1F1}$, —$NR^{1D1}_2$, —$NR^{1F2}R^{1F3}$,
    -$L^{1F}$-$NH_2$, -$L^{1F}$-$NHR^{1F1}$, -$L^{1F}$-$NR^{1F1}_2$, -$L^{1F}$-$NR^{1F2}R^{1F3}$,
    —C(=O)OH, —C(=O)$OR^{1F1}$,
    —C(=O)$NH_2$, —C(=O)$NHR^{1F1}$, —C(=O)$NR^{1F1}_2$, or —C(=O)$NR^{1F2}R^{1F3}$;
wherein:
  each —$R^{1F1}$ is independently saturated aliphatic $C_{1-4}$alkyl, phenyl, or benzyl;
  each -$L^{1F}$- is independently saturated aliphatic $C_{1-5}$alkylene; and
in each group —$NR^{1F2}R^{1F3}$, $R^{1F2}$ and $R^{1F3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
-$Q^{5A}$ is $R^{2A7}$;
wherein:
  each —$R^{2A7}$ is independently $C_{6-10}$carboaryl;

wherein:
  each —$R^{2A7}$ is substituted with one or more substituents —$R^{2B1}$ and/or one or more substituents —$R^{2B2}$, and
wherein:
  each —$R^{2B1}$ is independently:
    —$R^{2D1}$, —$R^{2D2}$, —$R^{2D3}$, —$R^{2D4}$, —$R^{2D5}$, —$R^{2D6}$, —$R^{2D7}$, —$R^{2D8}$,
    -$L^{2D}$-$R^{2D4}$, -$L^{2D}$-$R^{2D5}$, -$L^{2D}$-$R^{2D6}$, -$L^{2D}$-$R^{2D7}$, -$L^{2D}$-$R^{2D8}$,
  each —$R^{2B2}$ is independently:
    —F, —Cl, —Br, —I,
    —$CF_3$, —$OCF_3$,
    —OH, -$L^{2C}$-OH, —O-$L^{2C}$-OH,
    —$OR^{2C1}$, -$L^{2C}$-$OR^{2C1}$, —O-$L^{2C}$-$OR^{2C1}$,
    —SH, —$SR^{2C1}$,
    —CN,
    —$NO_2$,
    —$NH_2$, —$NHR^{2C1}$, —$NR^{2C1}_2$, —$NR^{2C2}R^{2C3}$,
    -$L^{2C}$-$NH_2$, -$L^{2C}$-$NHR^{2C1}$, —O-$L^{2C}$-$NR^{2C1}_2$, -$L^{2C}$-$NR^{2C2}R^{2C3}$,
    —O-$L^{2C}$-$NH_2$, —O-$L^{2C}$-$NHR^{2C1}$, —O-$L^{2C}$-$NR^{2C1}_2$, —O-$L^{2C}$-$NR^{2C2}R^{2C3}$,
    —C(=O)OH, —C(=O)$OR^{2C1}$,
    —C(=O)$R^{2C1}$,
    —C(=O)$NH_2$, —C(=O)$NHR^{2C1}$, —C(=O)$NR^{2C1}_2$, —C(=O)$NR^{2C2}R^{2C3}$,
    —NHC(=O)$R^{2C1}$, —$NR^{2C1}$C(=O)$R^{2C1}$,
    —NHC(=O)$OR^{2C1}$, —$NR^{2C1}$C(=O)$OR^{2C1}$,
    —OC(=O)$NH_2$, —OC(=O)$NHR^{2C1}$, —OC(=O)$NR^{2C1}_2$, —OC(=O)$NR^{2C2}R^{2C3}$,
    —NHC(=O)$NH_2$, —NHC(=O)$NHR^{2C1}$,
    —NHC(=O)$NR^{2C1}_2$, —NHC(=O)$NR^{2C2}R^{2C3}$,
    —$NR^{2C1}$C(=O)$NH_2$, —$NR^{2C1}$C(=O)$NHR^{2C1}$,
    —$NR^{2C1}$C(=O)$NR^{1C1}_2$, —$NR^{2C1}$C(=O)$NR^{2C2}R^{2C3}$,
    —NHS(=O)$_2$$R^{2C1}$, —$NR^{1C1}$S(=O)$_2$$R^{2C1}$,
    —S(=O)$_2$$NH_2$, —S(=O)$_2$$NHR^{2C1}$, —S(=O)$_2$$NR^{2C1}_2$, —S(=O)$_2$$NR^{2C2}R^{2C3}$,
    —S(=O)$R^{2C1}$, —S(=O)$_2$$R^{2C1}$, —OS(=O)$_2$$R^{2C1}$, or —S(=O)$_2$$OR^{2C1}$;
wherein:
  each -$L^{2C}$- is independently saturated aliphatic $C_{1-5}$alkylene;
  in each group —$NR^{2C2}R^{2C3}$, $R^{2C2}$ and $R^{2C3}$, taken together with the nitrogenatom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
  each —$R^{2C1}$ is independently:
    —$R^{2D1}$, —$R^{2D2}$, —$R^{2D3}$, —$R^{2D4}$, —$R^{2D5}$, —$R^{2D6}$, —$R^{2D7}$, —$R^{2D8}$,
    -$L^{2D}$-$R^{2D4}$, -$L^{2D}$-$R^{2D5}$, -$L^{2D}$-$R^{2D6}$, -$L^{2D}$-$R^{2D7}$, or -$L^{2D}$-$R^{2D8}$;
  each —$R^{2D1}$ is independently saturated aliphatic $C_{1-6}$alkyl;
  each —$R^{2D2}$ is independently aliphatic $C_{2-6}$alkenyl;
  each —$R^{2D3}$ is independently aliphatic $C_{2-6}$alkynyl;
  each —$R^{2D4}$ is independently saturated $C_{3-6}$cycloalkyl;
  each —$R^{2D5}$ is independently $C_{3-6}$cycloalkenyl;
  each —$R^{2D6}$ is independently non-aromatic $C_{3-8}$heterocyclyl;
  each —$R^{2D7}$ is independently $C_{6-10}$carboaryl;
  each —$R^{2D8}$ is independently $C_{5-10}$heteroaryl;
  each -$L^{2D}$- is independently saturated aliphatic $C_{1-3}$alkylene;

wherein:
  each —$R^{2D4}$, —$R^{2D5}$, —$R^{2D6}$, —$R^{2D7}$, and —$R^{2D8}$ is optionally substituted, with one or more substituents —$R^{2E1}$ and/or one or more substituents —$R^{2E2}$,
  each —$R^{2D1}$, —$R^{2D2}$, —$R^{2D3}$, and -$L^{2D}$- is optionally substituted, for example, with one or more substituents —$R^{2E2}$, and
wherein:
  each —$R^{2E1}$ is independently saturated aliphatic $C_{1-4}$alkyl, phenyl, or benzyl;
  each —$R^{2E2}$ is independently:
    —F, —Cl, —Br, —I,
    —$CF_3$, —$OCF_3$,
    —OH, -$L^{2F}$-OH, —O-$L^{2F}$-OH,
    —$OR^{2F1}$, -$L^{2F}$-$OR^{2F1}$, —O-$L^{2F}$-$OR^{2F1}$,
    —SH, —$SR^{2F1}$,
    —CN,
    —$NO_2$,
    —$NH_2$, —$NHR^{2F1}$, —$NR^{2F1}_2$, —$NR^{2F2}R^{2F3}$,
    -$L^{2F}$-$NH_2$, -$L^{2F}$-$NHR^{2F1}$, -$L^{2F}$-$NR^{2F1}_2$, -$L^{2F}$-$NR^{2F2}R^{2F3}$,
    —C(=O)OH, —C(=O)$OR^{2F1}$,
    —C(=O)$NH_2$, —C(=O)$NHR^{2F1}$, —C(=O)$NR^{2F1}_2$, or —C(=O)$NR^{2F2}R^{2F3}$;
wherein:
  each —$R^{2F1}$ is independently saturated aliphatic $C_{1-4}$alkyl, phenyl, or benzyl;
  each -$L^{2F}$- is independently saturated aliphatic $C_{1-5}$alkylene; and
  in each group —$NR^{2F2}R^{2F3}$, $R^{2F2}$ and $R^{2F3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
with the proviso that the compound is not a compound selected from the following compounds:
  Cyclopropanecarboxylic acid [5-(3-acetylamino-phenyl)-[1,2,4]triazolo[1,5-a]pyridin-2-yl]-amide (PP-002) (WW-002);
  Cyclopropanecarboxylic acid {5-[4-(4-methyl-piperazin-1-yl)-phenyl]-[1,2,4]triazolo[1,5-a]pyridin-2-yl}-amide (PP-003) (WW-003);
  Cyclopropanecarboxylic acid [5-(3-chloro-phenyl)-[1,2,4]triazolo[1,5-a]pyridin-2-yl]-amide (PP-004) (WW-004);
  Cyclopropanecarboxylic acid [5-(4-methoxy-phenyl)-[1,2,4]triazolo[1,5-a]pyridin-2-yl]-amide (PP-005) (WW-005);
  Cyclopropanecarboxylic acid [5-(3-fluoro-phenyl)-[1,2,4]triazolo[1,5-a]pyridin-2-yl]-amide (PP-007) (WW-007);
  Cyclopropanecarboxylic acid [5-(4-hydroxy-3,5-dimethyl-phenyl)-[1,2,4]triazolo[1,5-a]pyridin-2-yl]-amide (PP-008) (WW-008);
  4-[2-(Cyclopropanecarbonyl-amino)-[1,2,4]triazolo[1,5-a]pyridin-5-yl]-N-(2-dimethylamino-ethyl)-benzamide (PP-009) (WW-009);
  Cyclopropanecarboxylic acid [5-(2,4-dimethoxy-phenyl)-[1,2,4]triazolo[1,5-a]pyridin-2-yl]-amide (PP-010) (WW-010);
  Cyclopropanecarboxylic acid [5-(3-methanesulfonylamino-phenyl)-[1,2,4]triazolo[1,5-a]pyridin-2-yl]-amide (PP-011) (WW-011);

Cyclopropanecarboxylic acid [5-(2-dimethylamino-phenyl)-[1,2,4]triazolo[1,5-a]pyridin-2-yl]-amide (PP-012);

Cyclopropanecarboxylic acid [5-(3-chloro-4-fluoro-phenyl)-[1,2,4]triazolo[1,5-a]pyridin-2-yl]-amide (PP-013);

Cyclopropanecarboxylic acid [5-(3-trifluoromethoxy-phenyl)-[1,2,4]triazolo[1,5-a]pyridin-2-yl]-amide (PP-014);

3-Cyclohexyl-N-[5-(4-hydroxy-3,5-dimethyl-phenyl)-[1,2,4]triazolo[1,5-a]pyridin-2-yl]-propionamide (PP-017);

Furan-2-carboxylic acid [5-(3-fluoro-phenyl)-[1,2,4]triazolo[1,5-a]pyridin-2-yl]-amide (PP-019);

Furan-2-carboxylic acid [5-(4-hydroxy-3,5-dimethyl-phenyl)-[1,2,4]triazolo[1,5-a]pyridin-2-yl]-amide (PP-020);

4-[2-(Cyclopropanecarbonyl-amino)-[1,2,4]triazolo[1,5-a]pyridin-5-yl]-N-(2-hydroxy-ethyl)-benzamide (PP-022); and N-[5-(3-Amino-phenyl)-[1,2,4]triazolo[1,5-a]pyridin-2-yl]-3-pyridin-3-yl-propionamide (PP-024).

5. The compound according to claim 4, wherein —$R^{WA2}$, if present, is independently:
—$R^{1A1}$, —$R^{1A4}$, —$R^{1A6}$, —$R^{1A7}$, —$R^{1A8}$, -$L^{1A}$-$R^{1A4}$, -$L^{1A}$-$R^{1A6}$, $L^{1A}$-$R^{1A7}$, or -$L^{1A}$-$R^{1A8}$.

6. The compound according to claim 4, wherein —$R^{WA2}$, if present, is independently —$R^{1A1}$, —$R^{1A4}$, —$R^{1A6}$, -$L^{1A}$-$R^{1A4}$, or -$L^{1A}$-$R^{1A6}$.

7. The compound according to claim 4, wherein —$R^{WA2}$, if present, is independently —$R^{1A1}$, —$R^{1A4}$, or —$R^{1A6}$.

8. The compound according to claim 4, wherein —$R^{WA2}$, if present, is independently —$R^{1A1}$.

9. The compound according to claim 4, wherein —$R^{WA2}$, if present, is independently —$R^{1A4}$, —$R^{1A6}$, -$L^{1A}$-$R^{1A4}$, or -$L^{1A}$-$R^{1A6}$.

10. The compound according to claim 4, wherein —$R^{WA2}$, if present, is independently —$R^{1A4}$ or —$R^{1A6}$.

11. The compound according to claim 4, wherein —$R^{WA2}$, if present, is independently —$R^{1A4}$.

12. The compound according to claim 4, wherein —$R^{WA2}$, if present, is independently —$R^{1A6}$.

13. The compound according to claim 4, wherein —$R^{WA2}$, if present, is independently -$L^{1A}$-$R^{1A4}$ or -$L^{1A}$-$R^{1A6}$.

14. The compound according to claim 4, wherein —$R^{WA2}$, if present, is independently -$L^{1A}$-$R^{1A4}$.

15. The compound according to claim 4, wherein —$R^{WA2}$, if present, is independently -$L^{1A}$$R^{1A6}$.

16. The compound according to claim 4, wherein each -$L^{1A}$-, if present, is independently —$CH_2$—.

17. The compound according to claim 4, wherein each —$R^{1A1}$, if present, is independently saturated aliphatic $C_{1-3}$alkyl.

18. The compound according to claim 4, wherein each —$R^{1A4}$, if present, is independently saturated $C_{3-5}$cycloalkyl.

19. The compound according to claim 4, wherein each —$R^{1A4}$, if present, is independently saturated $C_3$cycloalkyl.

20. The compound according to claim 4, wherein each —$R^{1A6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

21. The compound according to claim 4, wherein each —$R^{1A7}$, if present, is independently phenyl or naphthyl, and is optionally substituted.

22. The compound according to claim 4, wherein each —$R^{1A8}$, if present, is independently $C_{5-6}$heteroaryl, and is optionally substituted.

23. The compound according to claim 4, wherein each —$R^{1A8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

24. The compound according to claim 4, wherein —$R^{2A7}$ is phenyl or naphthyl substituted with one or more substituents —$R^{2B1}$ and/or one or more substituents —$R^{2B2}$.

25. The compound according to claim 1, wherein each —$R^{2A7}$ is phenyl or naphthyl, and is optionally substituted.

26. The compound according to claim 24, wherein —$R^{2A7}$ is phenyl substituted with one or more substituents —$R^{2B1}$ and/or one or more substituents $R^{2B2}$.

27. The compound according to claim 26, wherein -$L^{2D}$- is —$CH_2$—.

28. The compound according to claim 26, wherein —$R^{2D6}$ is selected from azetidinyl, pyrrolidinyl, imidazolidinyl, pyrazolidinyl, piperidinyl, piperazinyl, morpholinyl, azepinmyl, diazepinyl, tetrahydrofuranyl, tetrahydropyranyl, dioxanyl, and is optionally substituted with one or more substituents —$R^{2E1}$ and/or one or more substituents —$R^{2E2}$.

29. The compound according to claim 26, wherein —$R^{WA2}$ is —$R^{1A4}$.

30. The compound according to claim 29, wherein —$R^{1A4}$ is saturated $C_3$-$C_5$cycloalkyl.

31. The compound according to claim 30, wherein —$R^{1A4}$ is saturated $C_3$cycloalkyl.

32. The compound according to claim 26, wherein —$R^{2B1}$ is $L^{2D}$-$R^{2D6}$.

33. The compound according to claim 26, wherein —$R^{2B2}$ is —$C(=O)R^{2C1}$.

* * * * *